US010537630B2

(12) United States Patent
Barbero Calzado et al.

(10) Patent No.: US 10,537,630 B2
(45) **Date of Patent: *Jan. 21, 2020**

(54) VIRUS PURIFICATION

(71) Applicant: Valneva SE, Nantes (FR)

(72) Inventors: Jana Barbero Calzado, Vienna (AT); Mario Nebenführ, Vienna (AT); Robert Schlegl, Siegenfeld (AT); Michael Weber, Vienna (AT); Jürgen Heindl-Wruss, Vienna (AT)

(73) Assignee: Valneva SE, Nantes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/062,245

(22) PCT Filed: Dec. 23, 2016

(86) PCT No.: PCT/EP2016/082662

§ 371 (c)(1),
(2) Date: Jun. 14, 2018

(87) PCT Pub. No.: WO2017/109223

PCT Pub. Date: Jun. 29, 2017

(65) Prior Publication Data

US 2018/0369359 A1 Dec. 27, 2018

(30) Foreign Application Priority Data

| | | | |
|---|---|---|---|
| Dec. 23, 2015 | (EP) | .................................... | 15202585 |
| Mar. 18, 2016 | (EP) | .................................... | 16161068 |
| Jun. 23, 2016 | (EP) | .................................... | 16176025 |
| Jun. 23, 2016 | (EP) | .................................... | 16176049 |
| Aug. 4, 2016 | (EP) | .................................... | 16182845 |

(51) Int. Cl.

| | |
|---|---|
| ***A61K 39/12*** | (2006.01) |
| ***A61P 31/14*** | (2006.01) |
| ***C07K 14/18*** | (2006.01) |
| ***C12N 7/02*** | (2006.01) |
| ***C12N 7/06*** | (2006.01) |
| ***C12N 7/00*** | (2006.01) |
| ***A61K 39/39*** | (2006.01) |
| *A61K 39/00* | (2006.01) |

(52) U.S. Cl.

CPC .............. *A61K 39/12* (2013.01); *A61K 39/39* (2013.01); *A61P 31/14* (2018.01); *C07K 14/18* (2013.01); *C07K 14/1825* (2013.01); *C12N 7/00* (2013.01); *C12N 7/02* (2013.01); *C12N 7/06* (2013.01); *A61K 2039/5252* (2013.01); *A61K 2039/5254* (2013.01); *A61K 2039/5258* (2013.01); *A61K 2039/55505* (2013.01); *C12N 2770/24134* (2013.01); *C12N 2770/24151* (2013.01); *C12N 2770/24163* (2013.01)

(58) Field of Classification Search

CPC .... A61K 2039/5258; A61K 2039/6068; A61K 2039/70; A61K 2039/5254; A61K 31/00; C12N 2770/24151; C12N 2770/24121; C12N 15/86; C12N 2710/24143; C12N 2770/24161; C12N 2840/203; C12N 15/113; C12N 2770/24111; C12N 2770/24221; C12N 2770/36151; Y02A 50/386; Y02A 50/53; Y02A 50/60; Y02A 50/385; Y02A 50/387; Y02A 50/393; Y02A 50/51; Y02A 50/389; Y02A 50/39

See application file for complete search history.

(56) References Cited

U.S. PATENT DOCUMENTS

| | | | | |
|---|---|---|---|---|
| 6,309,650 | B1 | 10/2001 | Kim et al. | |
| 7,871,814 | B2 * | 1/2011 | Andino-Pavlovsky ...................... | C07K 14/005 435/320.1 |
| 8,765,148 | B2 | 7/2014 | Wizel et al. | |
| 9,499,588 | B2 * | 11/2016 | Mason ................. | C07K 14/005 |
| 10,086,061 | B2 * | 10/2018 | Thomas ................. | A61K 39/12 |

FOREIGN PATENT DOCUMENTS

| | | | |
|---|---|---|---|
| CN | 105749268 | A | 7/2016 |
| WO | WO 1999/011762 | A1 | 3/1999 |
| WO | WO 2001/092552 | A2 | 12/2001 |
| WO | WO 2013/083726 | A1 | 6/2013 |
| WO | WO 2016/145149 | A1 | 9/2016 |

OTHER PUBLICATIONS

[No Author Listed] Centers for Disease Control and Prevention. Ingredients of vaccines fact sheet; continuously updated; https://www.cdc.gov/vaccines/vac-gen/additives.htm.
[No Author Listed] Japanese Encephalitis Vaccine. Centers for Disease Control and Prevention, 2016. Retrieved from https://www.cdc.gov/japaneseencephalitis/vaccine/ on Jun. 16, 2016.
[No Author Listed] Pan-American Health Organization, 2015. Number of Reported Cases of Chikungunya Fever in the Americas, by Country or Territory 2013-2014. Cumulative Cases (Updated Oct. 23, 2015).
[No Author Listed] Protamine sulfate. Wikimedia Foundation, Inc., 2015. Retrieved from https://en.wikipedia.org/wiki/Protamine_sulfate; updated Sep. 30, 2015 on Nov. 26, 2015.
[No Author Listed] Valneva Announces Successful Generation of a Highly-purified Zika Vaccine Candidate Using its FDA-EMA Approved Japanese Encephalitis Platform. Press release. Jul. 7, 2016.
[No Author Listed] World Health Organization, 2016 Zika Situation Report Feb. 5, 2016.
[No Author Listed] World Health Organization, 2016 Zika Virus Fact Sheet 2016. Retrieved from http://www.who.int/mediacentre/factsheets/zika/en/ on Mar. 11, 2016.

(Continued)

*Primary Examiner* — Bao Q Li
(74) *Attorney, Agent, or Firm* — Wolf, Greenfield & Sacks, P.C.

(57) ABSTRACT

Described herein are improved purification methods for virus vaccines and compositions. Also described are Zika, Chikungunya, dengue and yellow fever vaccines and methods of producing and administering said vaccines to subjects in need thereof.

12 Claims, 35 Drawing Sheets

Specification includes a Sequence Listing.

(56) References Cited

OTHER PUBLICATIONS

[No Author Listed] Zika virus, strain H/PF/2013. European virus archive, 2016.
Abbink et al., Durability and correlates of vaccine protection against Zika virus in rhesus monkeys. Sci. Transl. Med. 2017;9:eaao4163.
Altschul et al., Basic Local Alignment Search Tool. J. Mol. Biol. 1990;215:403-410.
Altschul et al., Gapped BLAST and PSI-BLAST: a new generation of protein database search programs. Nuc. Acids Res. 1997;25(17):3389-3402.
Baronti et al., Complete Coding Sequence of Zika Virus from a French Polynesia Outbreak in 2013. Genome Announc. May-Jun. 2014; 2(3):e00500-14. Abstract.
Bender et al., Zika Virus Vaccine Candidate VLA1601: Cooperation VALNEVA & EMERGENT. Presentation at World Vaccine Congress Apr. 4, 2018.
Cohen, Infectious Disease. The race for a Zika vaccine is on. Science. Feb. 5, 2016;351(6273):543-4. doi: 10.1126/science.351.6273.543.
Cox et al., Predicting Zika virus structural biology:Challenges and opportunities for intervention. Antivir Chem Chemother. Aug. 2015;24(3-4):118-26. doi: 10.1177/2040206616653873. Epub Jun. 13, 2016.
Dowall et al., A susceptible mouse model for Zika virus infection. PLOS Neglected Tropical Diseases.10(5):e0004658. May 5, 2016. DOI:10.1371/journal.pntd.0004658.
Fritsche et al., Vaccine hypersensitivity—update and overview. Swiss Med Wkly. 2010;140(17-18):238-246.
Gardner et al., Deliberate Attenuation of Chikungunya Virus by Adaptation to Heparan Sulfate-Dependent Infectivity: A Model of Rational Arboviral Vaccine Design. PLOS Neglected Tropical Diseases. 2014;8(2):e2719.
Geradin et al., Chikungunya virus-associated encephalitis: A cohort study on La Réunion Island. 2005-2009. Neurology. 86(1):94-102.
Gubler et al., Fields Virology. Knipe DM, Howley PM, editors. Lippincott-Raven Publishers; Philadelphia: 2007:1153-1252.
Haddow et al., Genetic Characterization of Zika Virus Strains: Geographic Expansion of the Asian Lineage. PLoS Negl Trop Dis 6(2): e1477. doi:10.1371/journal.pntd.0001477.
Hallengard et al., Novel Attenuated Chikungunya Vaccine Candidates Elicit Protective Immunity in C57BL/6 mice. J. Virology 88(5):2858-2866.
Hallengard et al., PrimeVirology. 88(22):13333-13343. Prime-Boost Immunization Strategies against Chikungunya Virus. J. Virology. 88(22):1333-13343.
Hombach et al., Report on a WHO consultation on immunological endpoints for evaluation of new Japanese encephalitis vaccines, WHO, Geneva, Sep. 2-3, 2004. Vaccine. 2005; 23(45):5205-5211.
Hutornojs et al., Comparison of ultracentrifugation methods for concentration of recombinant alphaviruses: sucrose and iodixanol cushions. Environmental Experimental Biology. 2012;10:117-123.
Katoh et al., Recent developments in the MAFFT multiple sequence alignment program. Briefings in Bioinformatics. 2008;9(4):286-298.
Kim et al., Design of Chimeric Alphaviruses with a Programmed, Attenuated, Cell Type-Restricted Phenotype. J Virol. 2011;85(9):4363-4376.
Konishi et al., Studies on structural proteins of Chikungunya Virus. I. Separation of three species of proteins and their preliminary characterization. Microbiol Immunol. 1980;24(5):419-28.
Larkin et al., Clustal W and Clustal X version 2.0. Bioinformatics. 2007;23(21):2947-2948.
Larocca et al., Vaccine protection against Zika virus from Brazil. Nature. 2016;536:474-478. doi:10.1038/nature18952. Methods.
Lindenbach et al., Fields Virology. Knipe DM, Howley PM, editors. Lippincott-Raven Publishers; Philadelphia: 2007;1101-1152.
Malone et al., Zika Virus: Medical Countermeasure Development Challenges. PLoS Negl Trop Dis. 2016;10(3):e0004530. doi:10.1371/journal.pntd.0004530.
Modjarrad et al., Preliminary aggregate safety and immunogenicity results from three trials of a purified inactivated Zika virus vaccine candidate: phase 1, randomised, double-blind, placebo-controlled clinical trials. Dec. 4, 2017.
Monath, Yellow fever: an update. Lancet Infect Dis. 2001;1(1):11-20.
Needleman et al., A general method applicable to the search for similarities in the amino acid sequence of two proteins. J. Mol. Biol. 1970;48(3):443-453.
Patkar et al., Yellow Fever virus NS3 plays an essential role in virus assembly independent of its known enzymatic functions. J Virol. Apr. 2008;82(7):3342-52. doi: 10.1128/JVI.02447-07. Epub Jan. 16, 2008.
Pearson et al., Improved tools for biological sequence comparison. Proc. Natl. Acad. Sci. USA. 1988;85(8):2444-8.
Pellerin, Walter Reed Scientists Test Zika Vaccine Candidate. U.S. Department of Defense. Jun. 9, 2016.
Pinto et al., A Temporal Role of Type I Interferon Signaling in CD8+ T Cell Maturation during Acute West Nile Virus Infection. PLoS Pathog. Dec. 2011;7(12):e1002407.
Plevka et al., Maturation of flaviviruses starts from one or more icosahedrally independent nucleation centres. EMBO reports. 2011;12(6):602-606.
Reed et al., A simple method of estimating fifty percent endpoints. American J Hygiene. May 1938;27:493-497.
Rocha et al., Microcephaly: normality parameters and its determinants in northeastern Brazil: a multicentre prospective cohort study. Bull World Health Organ, E-pub: Feb. 8, 2016. doi:http://dx.doi.org/10.2471/BLT.16.171215.
Rozen-Gagnon et al., Alphavirus Mutator Variants Present Host-Specific Defects and Attenuation in Mammalian and Insect Models, PLOS Pathogens, 10(1):e1003877.
Schlegl et al., Influence of elemental impurities in aluminum hydroxide adjuvant on the stability of inactivated Japanese Encephalitis vaccine, IXIARO®. Vaccine. 2015;33(44):5989-5996.
Shustov et al., Efficient, trans-complementing packaging systems for chimeric, pseudoinfectious dengue 2/yellow fever viruses. Virology. Apr. 25, 2010;400(1):8-17. doi: 10.1016/j.virol.2009.12.015.
Simizu et al., Structural Proteins of Chikungunya Virus, J Virol. 1984;51(1): 254-258.
Smith et al., Comparison of Biosequences. Adv. Appl. Math. 1981;2:482-489.
Srivastava et al., A purified inactivated Japanese encephalitis virus vaccine made in vero cells. Vaccine. 2001;19:4557-4565.
Tiwari et al., Assessment of immunogenic potential of Vero adapted formalin inactivated vaccine derived from novel ECSA genotype of Chikungunya virus. Vaccine. Apr. 21, 2009;27(18):2513-22. doi: 10.1016/j.vaccine.2009.02.062. Epub Feb. 27, 2009.
Vega-Rua et al., Chikungunya Virus Transmission Potential by Local Aedes Mosquitoes in the Americas and Europe. PLOS Neglected Tropical Diseases. 2015;9(5):e0003780.
Waterhouse et al., Jalview Version 2—a multiple sequence alignment editor and analysis workbench. Bioinformatics. 2009;25(9):1189-1191.
Way et al., Comparative Studies of some African Arboviruses in Cell Culture and in Mice, J Gen. Virol. 1976;30:123-130.
Weaver, Arrival of Chikungunya Virus in the New Word: Prospects for Spread and Impact on Public Health. PLoS Negl Trop Dis. 2014;8(6):e2921. doi:10.1371/journal.pntd.0002921.

* cited by examiner

| | | 0 | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|---|
| DVV_1.NC_001477.1 | 0 | 100.0 | 70.1 | 73.0 | 67.8 | 60.5 | 60.4 | 60.5 | 60.5 | 60.7 | 55.8 | 60.6 | 60.3 | 60.6 | 58.0 | 57.9 | 57.9 | 58.0 | 62.3 | 62.3 | 62.3 | 61.3 |
| DVV_16681.NC_001474.2 | 1 | 70.1 | 100.0 | 70.8 | 68.6 | 60.5 | 60.5 | 60.5 | 60.6 | 60.7 | 54.9 | 60.9 | 60.3 | 60.4 | 58.3 | 58.3 | 58.3 | 58.3 | 62.7 | 62.8 | 62.8 | 62.2 |
| DVV_3.NC_001475.2 | 2 | 73.0 | 70.8 | 100.0 | 68.9 | 60.2 | 60.1 | 60.1 | 60.1 | 60.1 | 55.8 | 60.3 | 60.0 | 60.1 | 57.5 | 57.6 | 57.5 | 57.5 | 62.6 | 62.7 | 62.7 | 62.5 |
| DVV_4.NC_002640.1 | 3 | 67.8 | 68.6 | 68.9 | 100.0 | 60.5 | 60.6 | 60.6 | 60.6 | 60.4 | 55.4 | 60.8 | 60.3 | 60.5 | 58.0 | 57.9 | 57.9 | 57.9 | 62.1 | 62.0 | 62.0 | 62.1 |
| JEV_SA14-14-2.AF315119.1 | 4 | 60.5 | 60.5 | 60.2 | 60.5 | 100.0 | 99.8 | 99.4 | 99.5 | 98.1 | 56.5 | 70.6 | 70.3 | 70.3 | 57.9 | 58.0 | 58.0 | 58.0 | 61.9 | 61.8 | 61.8 | 61.4 |
| JEV_SA14-14-2.D90195.1 | 5 | 60.4 | 60.5 | 60.1 | 60.6 | 99.8 | 100.0 | 99.4 | 99.5 | 98.2 | 56.6 | 70.6 | 70.4 | 70.3 | 57.9 | 58.0 | 57.9 | 58.0 | 61.9 | 61.8 | 61.8 | 61.5 |
| JEV_SA14.D90194.1 | 6 | 60.5 | 60.5 | 60.1 | 60.6 | 99.4 | 99.4 | 100.0 | 99.8 | 98.6 | 56.6 | 70.8 | 70.5 | 70.4 | 58.0 | 58.0 | 58.0 | 58.0 | 61.9 | 61.8 | 61.8 | 61.6 |
| JEV_virus.M55506.1 | 7 | 60.5 | 60.6 | 60.1 | 60.6 | 99.5 | 99.5 | 99.8 | 100.0 | 98.6 | 56.7 | 70.8 | 70.4 | 70.3 | 58.0 | 58.1 | 58.0 | 58.1 | 61.9 | 61.8 | 61.8 | 61.6 |
| JEV_virus.NC_001437.1 | 8 | 60.7 | 60.7 | 60.1 | 60.4 | 98.1 | 98.2 | 98.6 | 98.6 | 100.0 | 56.6 | 70.6 | 70.5 | 70.6 | 58.3 | 58.3 | 58.4 | 58.3 | 62.1 | 62.0 | 62.0 | 61.7 |
| TEV_virus.NC_001672.1 | 9 | 55.8 | 54.9 | 55.8 | 55.4 | 56.5 | 56.6 | 56.6 | 56.7 | 56.6 | 100.0 | 56.2 | 56.7 | 56.6 | 56.9 | 57.0 | 57.0 | 57.0 | 56.6 | 56.7 | 56.7 | 56.7 |
| WNV_956.NC_001563.2 | 10 | 60.6 | 60.9 | 60.3 | 60.8 | 70.6 | 70.6 | 70.8 | 70.8 | 70.6 | 56.2 | 100.0 | 79.6 | 79.6 | 58.1 | 58.0 | 58.1 | 58.2 | 62.4 | 62.3 | 62.3 | 62.2 |
| WNV_Chin-01.AY490240.2 | 11 | 60.3 | 60.3 | 60.0 | 60.3 | 70.3 | 70.4 | 70.5 | 70.4 | 70.5 | 56.7 | 79.6 | 100.0 | 95.3 | 58.2 | 58.2 | 58.2 | 58.2 | 62.0 | 62.1 | 62.1 | 62.7 |
| WNV_NY99_isol-385-99.NC_009942.1 | 12 | 60.6 | 60.4 | 60.1 | 60.5 | 70.3 | 70.3 | 70.4 | 70.3 | 70.6 | 56.6 | 79.6 | 95.3 | 100.0 | 57.8 | 57.8 | 57.8 | 57.8 | 62.0 | 62.0 | 62.0 | 62.4 |
| YFV_17D_vaccine_strain.NC_002031.1 | 13 | 58.0 | 58.3 | 57.5 | 58.0 | 57.9 | 57.9 | 58.0 | 58.0 | 58.3 | 56.9 | 58.1 | 58.2 | 57.8 | 100.0 | 99.4 | 99.9 | 99.9 | 58.5 | 58.5 | 58.5 | 58.2 |
| YFV_ASIB.AY640589.1 | 14 | 57.9 | 58.3 | 57.6 | 57.9 | 58.0 | 58.0 | 58.0 | 58.1 | 58.3 | 57.0 | 58.0 | 58.2 | 57.8 | 99.4 | 100.0 | 99.4 | 99.4 | 58.4 | 58.4 | 58.4 | 58.1 |
| YFV_Pasteur_17D-204.X15062.1 | 15 | 57.9 | 58.3 | 57.5 | 57.9 | 58.0 | 57.9 | 58.0 | 58.0 | 58.4 | 57.0 | 58.1 | 58.2 | 57.8 | 99.9 | 99.4 | 100.0 | 99.9 | 58.4 | 58.4 | 58.4 | 58.2 |
| YFV_vaccine_strain_17D-213.U17067.1 | 16 | 58.0 | 58.3 | 57.5 | 57.9 | 58.0 | 58.0 | 58.0 | 58.1 | 58.3 | 57.0 | 58.2 | 58.2 | 57.8 | 99.9 | 99.4 | 99.9 | 100.0 | 58.4 | 58.4 | 58.4 | 58.1 |
| ZVV_MR766-NIID.LC002520.1 | 17 | 62.3 | 62.7 | 62.6 | 62.1 | 61.9 | 61.9 | 61.9 | 61.9 | 62.1 | 56.6 | 62.4 | 62.0 | 62.0 | 58.5 | 58.4 | 58.4 | 58.4 | 100.0 | 99.7 | 99.7 | 88.9 |
| ZVV_MR_766.AY632535.2 | 18 | 62.3 | 62.8 | 62.7 | 62.0 | 61.8 | 61.8 | 61.8 | 61.8 | 62.0 | 56.7 | 62.3 | 62.1 | 62.0 | 58.5 | 58.4 | 58.4 | 58.4 | 99.7 | 100.0 | 100.0 | 88.8 |
| ZVV_MR_766.NC_012532.1 | 19 | 62.3 | 62.8 | 62.7 | 62.0 | 61.8 | 61.8 | 61.8 | 61.8 | 62.0 | 56.7 | 62.3 | 62.1 | 62.0 | 58.5 | 58.4 | 58.4 | 58.4 | 99.7 | 100.0 | 100.0 | 88.8 |
| ZVV_ZikaSPH2015.KU321639.1 | 20 | 61.3 | 62.2 | 62.5 | 62.1 | 61.4 | 61.5 | 61.6 | 61.6 | 61.7 | 56.7 | 62.2 | 62.7 | 62.4 | 58.2 | 58.1 | 58.2 | 58.1 | 88.9 | 88.8 | 88.8 | 100.0 |

60 % Identity and higher
70 % Identity and higher
80 % Identity and higher

Figure 3

| | | 0 | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|---|---|
| DVV_1.NC_001477.1 | 0 | 100.0 | 68.7 | 77.4 | 63.8 | 49.7 | 49.7 | 50.1 | 49.9 | 50.5 | 38.3 | 51.5 | 50.5 | 50.9 | 43.0 | 43.8 | 43.0 | 43.2 | 57.3 | 57.9 | 58.4 | 58.4 | 57.1 |
| DVV_16681.NC_001474.2 | 1 | 68.7 | 100.0 | 68.7 | 64.0 | 46.7 | 46.7 | 47.1 | 46.9 | 47.5 | 38.9 | 48.4 | 47.6 | 47.6 | 43.6 | 44.4 | 43.6 | 43.6 | 53.6 | 53.8 | 54.2 | 54.2 | 53.8 |
| DVV_3.NC_001475.2 | 2 | 77.4 | 68.7 | 100.0 | 62.8 | 48.0 | 48.0 | 48.2 | 48.2 | 48.6 | 38.2 | 46.8 | 46.7 | 46.3 | 41.6 | 42.2 | 41.6 | 41.7 | 57.3 | 57.7 | 58.2 | 58.2 | 57.1 |
| DVV_4.NC_002640.1 | 3 | 63.8 | 64.0 | 62.8 | 100.0 | 47.5 | 47.5 | 47.7 | 47.5 | 48.1 | 39.7 | 49.6 | 49.6 | 49.8 | 40.0 | 40.6 | 40.0 | 40.0 | 55.8 | 56.4 | 56.4 | 56.4 | 55.8 |
| JEV_SA14-14-2.AF315119.1 | 4 | 49.7 | 46.7 | 48.0 | 47.5 | 100.0 | 99.8 | 98.0 | 98.6 | 97.8 | 39.6 | 76.1 | 76.5 | 76.7 | 43.1 | 42.9 | 43.1 | 43.1 | 54.0 | 54.8 | 54.8 | 54.8 | 54.0 |
| JEV_SA14-14-2.D90195.1 | 5 | 49.7 | 46.7 | 48.0 | 47.5 | 99.8 | 100.0 | 98.2 | 98.8 | 98.0 | 39.8 | 76.3 | 76.7 | 76.9 | 43.1 | 42.9 | 43.1 | 43.1 | 54.0 | 54.8 | 54.8 | 54.8 | 54.0 |
| JEV_SA14.D90194.1 | 6 | 50.1 | 47.1 | 48.2 | 47.7 | 98.0 | 98.2 | 100.0 | 99.4 | 99.4 | 40.0 | 77.5 | 77.8 | 78.0 | 43.3 | 43.3 | 43.3 | 43.3 | 54.4 | 55.4 | 55.2 | 55.2 | 54.4 |
| JEV_virus.M55506.1 | 7 | 49.9 | 46.9 | 48.2 | 47.5 | 98.6 | 98.8 | 99.4 | 100.0 | 99.2 | 40.0 | 77.3 | 77.6 | 77.8 | 43.3 | 43.3 | 43.3 | 43.3 | 54.2 | 55.2 | 55.0 | 55.0 | 54.2 |
| JEV_virus.NC_001437.1 | 8 | 50.5 | 47.5 | 48.6 | 48.1 | 97.8 | 98.0 | 99.4 | 99.2 | 100.0 | 40.4 | 78.0 | 78.4 | 78.6 | 43.5 | 43.5 | 43.5 | 43.5 | 54.8 | 55.4 | 55.2 | 55.2 | 54.8 |
| TEV_virus.NC_001672.1 | 9 | 38.3 | 38.9 | 38.2 | 39.7 | 39.6 | 39.8 | 40.0 | 40.0 | 40.4 | 100.0 | 41.3 | 41.6 | 41.0 | 42.3 | 41.9 | 42.3 | 42.3 | 39.9 | 39.9 | 39.6 | 39.6 | 39.9 |
| WNV_956.NC_001563.2 | 10 | 51.5 | 48.4 | 46.8 | 49.6 | 76.1 | 76.3 | 77.5 | 77.3 | 78.0 | 41.3 | 100.0 | 94.6 | 94.0 | 43.8 | 43.6 | 43.8 | 43.8 | 55.0 | 55.0 | 54.8 | 54.8 | 55.0 |
| WNV_Chin-01.AY490240.2 | 11 | 50.5 | 47.6 | 46.7 | 49.6 | 76.5 | 76.7 | 77.8 | 77.6 | 78.4 | 41.6 | 94.6 | 100.0 | 98.8 | 43.9 | 43.5 | 43.9 | 43.9 | 54.4 | 54.2 | 54.0 | 54.0 | 54.4 |
| WNV_NY99_isol-385-99.NC_009942.1 | 12 | 50.9 | 47.6 | 45.3 | 49.8 | 76.7 | 76.9 | 78.0 | 77.8 | 78.6 | 41.0 | 94.0 | 98.8 | 100.0 | 43.9 | 43.5 | 43.9 | 43.9 | 54.0 | 53.8 | 53.8 | 53.8 | 54.0 |
| YFV_17D_vaccine_strain.NC_002031.1 | 13 | 43.0 | 43.6 | 41.6 | 40.0 | 43.1 | 43.1 | 43.3 | 43.3 | 43.5 | 42.3 | 43.8 | 43.9 | 43.9 | 100.0 | 97.6 | 100.0 | 99.8 | 42.0 | 43.4 | 43.5 | 43.5 | 42.0 |
| YFV_ASIB.AY640589.1 | 14 | 43.8 | 44.4 | 42.2 | 40.6 | 42.9 | 42.9 | 43.3 | 43.3 | 43.5 | 41.9 | 43.6 | 43.5 | 43.5 | 97.6 | 100.0 | 97.6 | 97.4 | 42.4 | 43.8 | 43.9 | 43.9 | 42.4 |
| YFV_isol-Pasteur_17D-204.X15062.1 | 15 | 43.0 | 43.6 | 41.6 | 40.0 | 43.1 | 43.1 | 43.3 | 43.3 | 43.5 | 42.3 | 43.8 | 43.9 | 43.9 | 100.0 | 97.6 | 100.0 | 99.8 | 42.0 | 43.4 | 43.5 | 43.5 | 42.0 |
| YFV_vaccine_strain_17D-213.U17067.1 | 16 | 43.2 | 43.6 | 41.7 | 40.0 | 43.1 | 43.1 | 43.3 | 43.3 | 43.5 | 42.3 | 43.8 | 43.9 | 43.9 | 99.8 | 97.4 | 99.8 | 100.0 | 42.0 | 43.4 | 43.5 | 43.5 | 42.0 |
| ZVVBeH818995.KU365777.1 | 17 | 57.3 | 53.6 | 57.3 | 55.8 | 54.0 | 54.0 | 54.4 | 54.2 | 54.8 | 39.9 | 55.0 | 54.4 | 54.0 | 42.0 | 42.4 | 42.0 | 42.0 | 100.0 | 96.8 | 96.4 | 96.4 | 99.8 |
| ZVV_MR766-NIID.LC002520.1 | 18 | 57.9 | 53.8 | 57.7 | 56.4 | 54.8 | 54.8 | 55.4 | 55.2 | 55.4 | 39.9 | 55.0 | 54.2 | 53.8 | 43.4 | 43.8 | 43.4 | 43.4 | 96.8 | 100.0 | 98.8 | 98.8 | 96.6 |
| ZVV_MR_766.AY632535.2 | 19 | 58.4 | 54.2 | 58.2 | 56.4 | 54.8 | 54.8 | 55.2 | 55.0 | 55.2 | 39.6 | 54.8 | 54.0 | 53.8 | 43.5 | 43.9 | 43.5 | 43.5 | 96.4 | 98.8 | 100.0 | 100.0 | 96.2 |
| ZVV_MR_766.NC_012532.1 | 20 | 58.4 | 54.2 | 58.2 | 56.4 | 54.8 | 54.8 | 55.2 | 55.0 | 55.2 | 39.6 | 54.8 | 54.0 | 53.8 | 43.5 | 43.9 | 43.5 | 43.5 | 96.4 | 98.8 | 100.0 | 100.0 | 96.2 |
| ZVV_ZikaSPH2015.KU321639.1 | 21 | 57.1 | 53.8 | 57.1 | 55.8 | 54.0 | 54.0 | 54.4 | 54.2 | 54.8 | 39.9 | 55.0 | 54.4 | 54.0 | 42.0 | 42.4 | 42.0 | 42.0 | 99.8 | 96.6 | 96.2 | 96.2 | 100.0 |

50 % Identity and higher
60 % Identity and higher
70 % Identity and higher

Figure 6

```
                                                      490       500       510
YFV_ASIBI.AY640589.1/292-784                      748 MGAVLIWVGINTRNMTMSMSMILVGVIMMFLSLGVGA
YFV_17D_vaccine_strain.NC_002031.1/292-784        748 MGAVLIWVGINTRNMTMSMSMILVGVIMMFLSLGVGA
YFV_vaccine_strain_17D-213.U17067.1/292-784       748 MGAVLIWVGINTRNMTMSMSMILVGVIMMFLSLGVGA
YFV_isol-Pasteur_17D-204.X15062.1/292-784         748 MGAVLIWVGINTRNMTMSMSMILVGVIMMFLSLGVGA
JEV_SA14.D90194.1/307-806                         770 MGALLLWMGVNARDRSIALAFLATGGVLVFLATNVHA
JEV_virus.NC_001437.1/307-806                     770 MGALLLWMGVNARDRSIALAFLATGGVLVFLATNVHA
JEV_virus.M55506.1/307-806                        770 MGALLLWMGVNARDRSIALAFLATGGVLVFLATNVHA
JEV_SA14-14-2.AF315119.1/307-806                  770 MGALLLWMGVNARDRSIALAFLATGGVLVFLATNVHA
JEV_SA14-14-2.D90195.1/307-806                    770 MGALLLWMGVNARDRSIALAFLATGGVLVFLATNVHA
DVV_1.NC_001477.1/294-788                         752 IGILLTWLGLNSRSTSLSMTCIAVGMVTLYLGVMVQA
DVV_16681.NC_001474.2/287-781                     745 IGVIITWIGMNSRSTSLSVTLVLVGIVTLYLGVMVQA
DVV_4.NC_002640.1/313-807                         771 IGFLVLWIGTNSRNTSMAMTCIAVGGITLFLGFTVQA
DVV_3.NC_001475.2/294-786                         750 IGVLLTWIGLNSKNTSMSFSCIAIGIITLYLGAVVQA
TEV_virus.NC_001672.1/292-787                     751 LGVALAWLGLNMRNPTMSMSFLLAGGLVLAMTLGVGA
WNV_956.NC_001563.2/306-802                       766 LGALLLWMGINARDRSIAMTFLAVGGVLLFLSVNVHA
WNV_NY99_isol-385-99.NC_009942.1/306-806          770 LGALLLWMGINARDRSIALTFLAVGGVLLFLSVNVHA
WNV_Chin-01.AY490240.2/306-806                    770 LGALLLWMGINARDRSIALTFLAIGGVLLFLSVNVHA
ZVV_MR766-NIID.LC002520.1/326-829                 793 IGTLLVWLGLNTKNGSISLTCLALGGVMIFLSTAVSA
ZVV_ZikaSPH2015.KU321639.1/326-829                793 IGTLLMWLGLNTKNGSISLMCLALGGVLIFLSTAVSA
ZVV_MR_766.NC_012532.1/326-825                    789 IGTLLVWLGLNTKNGSISLTCLALGGVMIFLSTAVSA
ZVV_MR_766.AY632535.2/326-825                     789 IGTLLVWLGLNTKNGSISLTCLALGGVMIFLSTAVSA
ZVV_BeH818995.KU365777.1/308-811                  775 IGTLLMWLGLNTKNGSISLMCLALGGVLIFLSTAVSA
```

Figure 7 (continued)

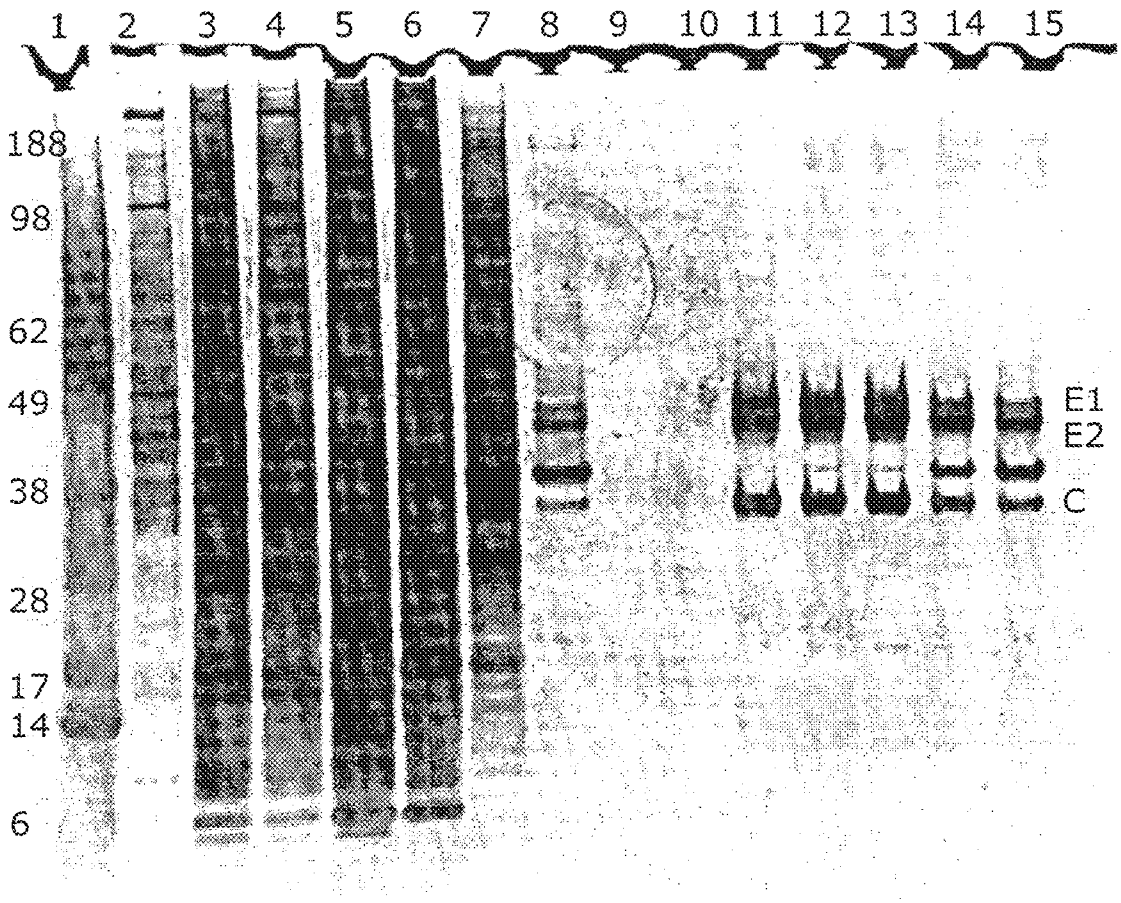

| Lane | Sample |
|---|---|
| 1 | Marker Seeblueplus2 |
| 2 | CHIKV lot20150812_WVB2015-01_Filtered harvest0.2µ_24hpi |
| 3 | CHIKV lot20150812_WVB2015-01_Filtered harvest0.2µ_48hpi |
| 4 | 20150812_CHIKV_DSP_UF/DF_Load |
| 5 | 20150812_CHIKV_DSP_UF/DF_conc.10x |
| 6 | 20150813_CHIKV_DSP_UF/DF_conc.&dia. 11x |
| 7 | 20150813_CHIKV_DSP_PStreatment |
| 8 | 20150813_CHIKV_DSP_PS&CC700treatment |
| 9 | 20150813_CHIKV_DSP_SGCFrac F5 |
| 10 | 20150813_CHIKV_DSP_SGCFrac F6 |
| 11 | 20150813_CHIKV_DSP_SGCPoolF7-F10 |
| 12 | 20150813_CHIKV_DSP_SGCPoolF7-F11 (final pool) |
| 13 | 20150813_CHIKV_DSP_SGCPoolF7-F12 |
| 14 | 20150813_CHIKV_DSP_SGCFrac F13 |
| 15 | 20150813_CHIKV_DSP_SGCFrac F14 |

Figure 11C

+ Similar virus concentration in harvests Day 2, Day3, Day 7; lower virus concentration in harvest Day 5

+ Day 2 and Day 3 harvests contained more HCP than Days 5/7 (correlates with observed CPE)

+ Minor amount of virus multimers observed

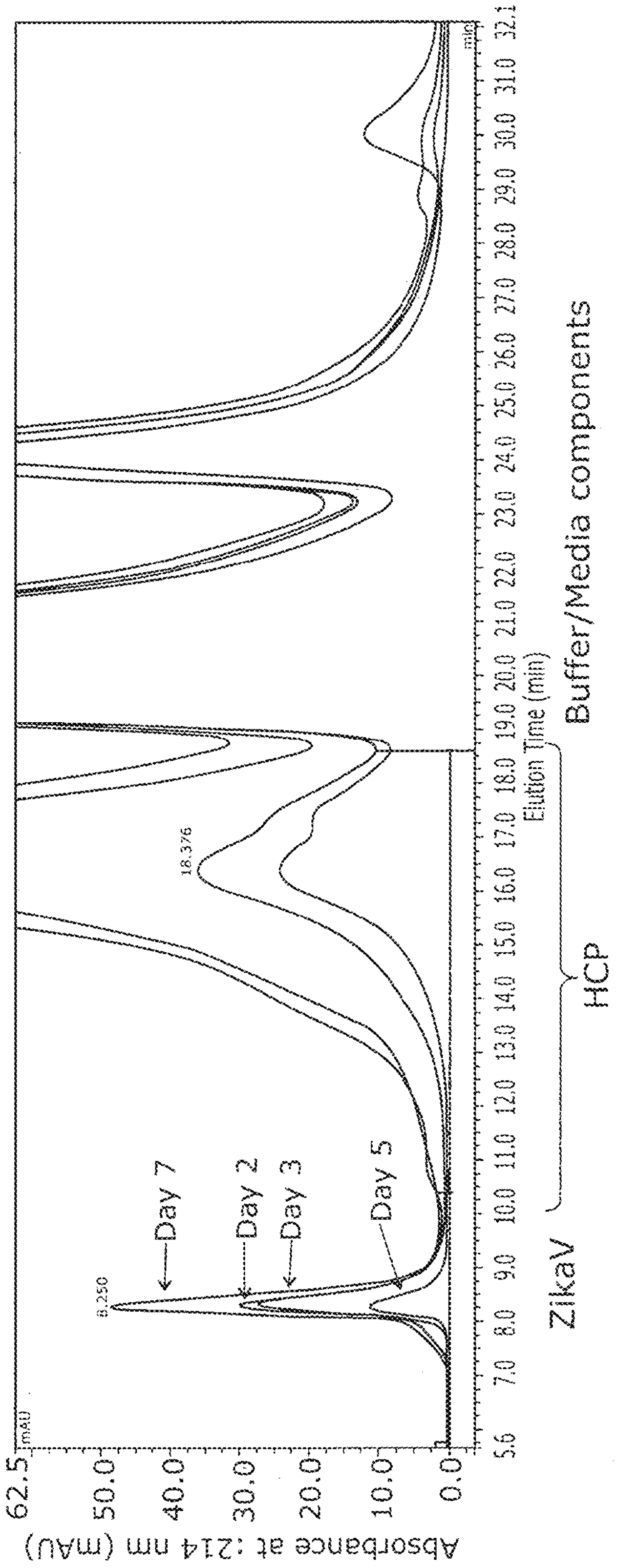
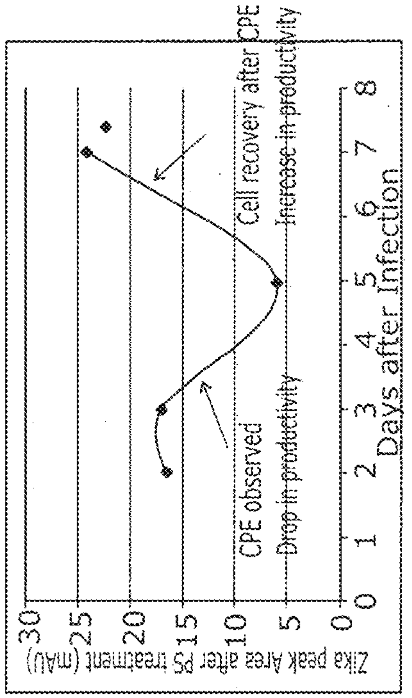
+ PS removes virus aggregates and partially host cell proteins (HCP)
+ Infectoius virus titer is not affected by PS treatment
+ Strong cytopathic effect (CPE) on day 3,drop in productivity
+ Remaining cells seem to recover well and increase in Zika productivity
Figure 20

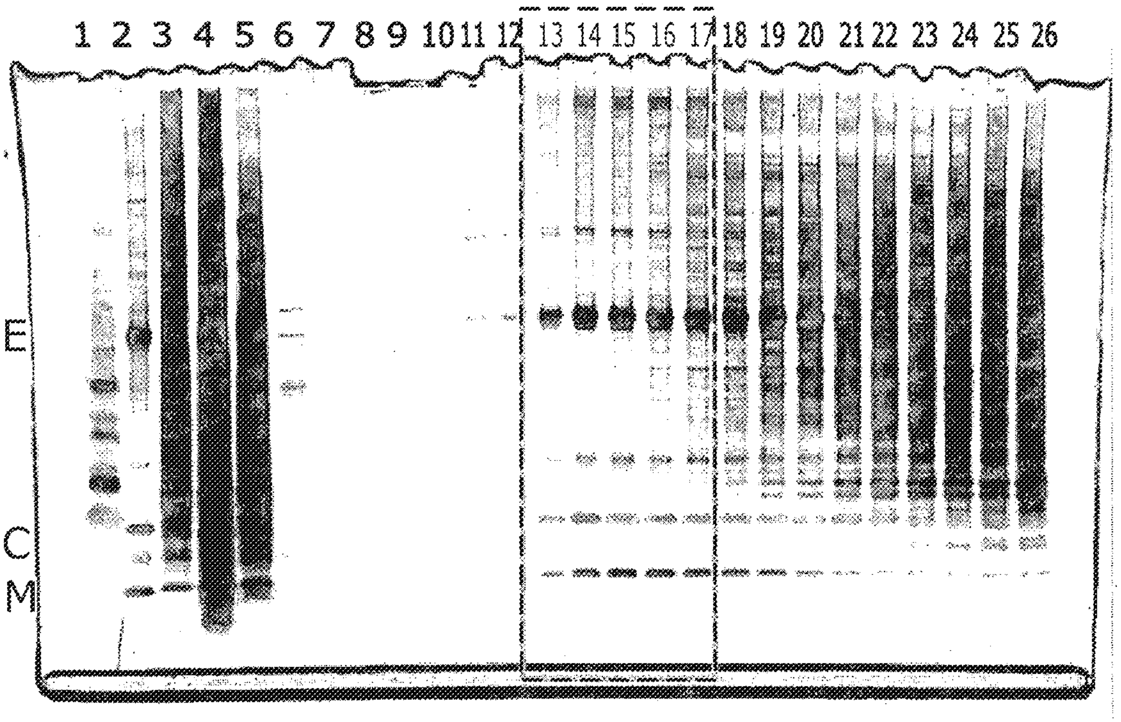

| Lane | Sample |
|---|---|
| 1 | Molecular weight Marker |
| 2 | JEV Sucrose Gradient Pool (Reference) |
| 3 | Zika Harvest pool (day 2,3,5,7) |
| 4 | Zika Harvest pool (day 2,3,5,7)concentrated 300x |
| 5 | Zika Harvest pool (day 2,3,5,7)concentrated 300x + Protamine sulfate |
| 6 | Ultrafiltration Permeate |
| 7 | SGC Bottle 1, Fraction 4 |
| 8 | SGC Bottle 1, Fraction 5 |
| 9 | SGC Bottle 1, Fraction 6 |
| 10 | SGC Bottle 1, Fraction 7 |
| 11 | SGC Bottle 1, Fraction 8 |
| 12 | SGC Bottle 1, Fraction 9 |
| 13 | SGC Bottle 1, Fraction 10 |
| 14 | SGC Bottle 1, Fraction 11 |
| 15 | SGC Bottle 1, Fraction 12 |
| 16 | SGC Bottle 1, Fraction 13 |
| 17 | SGC Bottle 1, Fraction 14 |
| 18 | SGC Bottle 1, Fraction 15 |
| 19 | SGC Bottle 1, Fraction 16 |
| 20 | SGC Bottle 1, Fraction 17 |
| 21 | SGC Bottle 1, Fraction 18 |
| 22 | SGC Bottle 1, Fraction 19 |
| 23 | SGC Bottle 1, Fraction 20 |
| 24 | SGC Bottle 1, Fraction 21 |
| 25 | SGC Bottle 1, Fraction 22 |
| 26 | SGC Bottle 1, Fraction 23 |

Pooled fractions F10-F14
(10mL total volume pere bottle)

Figure 21

| | 12 µg | 3.0 µg | 1.0 µg | 0.33 µg | 0.11 µg | 0.037 µg |
|---|---|---|---|---|---|---|
| EC50 | 1371 | 807.6 | 380.7 | 456.1 | 179.9 | 142.0 |

| | 12 µg | 3.0 µg | 1.0 µg | 0.33 µg | 0.11 µg | 0.037 µg |
|---|---|---|---|---|---|---|
| EC50 | 1029 | 819.1 | 556.9 | 477.3 | 158.1 | 118.0 |

VIRUS PURIFICATION

RELATED APPLICATION

This application is a national stage filing under 35 U.S.C. § 371 of International Patent Application Serial No. PCT/EP2016/082662, filed Dec. 23, 2016, the contents of which is incorporated herein by reference in its entirety.

FIELD OF INVENTION

The disclosure relates to methods for the purification of viruses for use in vaccines and in particular relates to an improved sucrose gradient process step allowing the separation of impurities such as protamine sulphate.

BACKGROUND OF THE INVENTION

Adverse responses to protamine sulfate have been known for many years. Previous exposure to protamine can induce a humoral immune response and predispose susceptible individuals to the development of untoward reactions from the subsequent use of this drug. Patients exposed to protamine through the use of protamine-containing insulin or during heparin neutralization may experience life-threatening reactions and fatal anaphylaxis upon receiving large doses of protamine intravenously. Severe reactions to intravenous protamine can occur in the absence of local or systemic allergic reactions to subcutaneous injection of protamine-containing insulin. Although there is no clear evidence for hypersensitivity reactions of protamine sulphate linked to vaccination, vaccines containing protamine impurities have a precaution and contraindication warning in their labels stating that a serious allergic reaction after a previous dose of such a protamine containing vaccine (e.g. IXIARO®, see CDC site http://www.cdc.gov/japaneseencephalitis/vaccine/) is a contraindication to further doses. Thus elimination of said impurity is a medical request for an improved safety profile. On the other hand protamine sulphate is an excellent tool (and often better than other reagents such as benzonase) to purify crude harvests of viruses grown on cell substrates.

Chikungunya virus (ChikV) is a positive-sense, single-stranded RNA virus from the genus Alphavirus, family Togaviridae. Chikungunya virus disease is mainly an outbreak disease and is associated with high attack rates. The virus is transmitted to humans via a mosquito vector and causes fever, rash, fatigue and severe polyarthralgia. Infections with ChikV generally resolve spontaneously and are not usually fatal, except in rare cases involving CNS infection, where the death rate is from 10-30%. Particularly at risk for ChikV CNS disease are infants under one year and adults over 65 years, with an infection rate of 25-fold and 6-fold higher than the general population, respectively, and with a rate of persistent disabilities estimated at between 30% and 45% (Gerardin, 2016). Furthermore, about 30 percent of all ChikV patients experience arthralgia for months to years after recovery. In some cases, neurological, renal, cardiac, respiratory or hepatic complications can also result.

There are currently no vaccines or medications available for the treatment or prevention of Chikungunya virus disease. Outbreaks in the past have occurred mainly in Africa, but the Central/East/South African (ECSA) genotype has recently expanded its geographical range, resulting in outbreaks in India, Asia, and even temperate Europe (Weaver, S., Arrival of Chikungunya Virus in the New World: Prospects for Spread and Impact on Public Health PLOS Neglected Tropical Diseases (2014) 8(6): e2921). Although ChikV has been repeatedly imported into the Americas since 1995, no autochthonous transmission was reported until 2013 in the Caribbean. By 2015, the epidemic had spread to the mainland and caused more than 1,000,000 suspected cases in 43 countries in the Americas (Pan-American Health Organization (2015) Number of Cumulative Cases of Chikungunya Fever in the Americas). Further epidemics may been aided in part by the spread of the ChikV mosquito vector into non-endemic regions, as well as the ability of ChikV to adapt to local mosquito species (Vega-Rua et al., Chikungunya Virus Transmission Potential by Local Aedes Mosquitoes in the Americas and Europe, May 20, 2015, PLOS Neglected Tropical Diseases DOI:10.1371/journal.pntd.0003780). The high rate of contagion of Chikungunya virus disease, its potential for long-lasting complications, as well as its geographical spread underscore the need for developing preventative measures, such as vaccines.

In 2007, Zika virus was detected for the first time outside of the endemic regions of Asia and Africa since its discovery in a Rhesus monkey in Uganda in 1947. Since then, the virus has caused a large epidemic in French Polynesia, spreading through islands in the Pacific and into South and Central America by 2015 (WHO "Zika Situation Report" Feb. 5, 2016). Evidence suggests that in addition to being transmitted by Aedes species mosquitoes, other vectors may exist, and the virus may be transmitted by blood transfusion, transplacentally, and through sexual transmission (WHO Zika Virus Fact Sheet, February 2016). Though the symptoms of Zika virus infection include mild fever, rash, and conjunctivitis, there is a likely correlation between infection and neurological disorders, including Guillain-Barré syndrome and microcephaly in fetuses/neonates subsequent to infection during pregnancy. There is currently no specific treatment or vaccine for Zika virus and the only preventative measures involve control of the mosquito vector. Zika virus presents a substantial public health threat due to the wide circulation of the Aedes mosquito, multiple routes of transmission, and potentially severe neurological effects of infection.

Yellow fever (YF) still represents a constant threat to public health in endemic regions of tropical Africa and South America. The World Health Organization (WHO) estimated that 200,000 cases occur annually with 30,000 fatalities (WHO 2009). Yellow fever virus (YFV), a single-stranded RNA virus, belongs to the family of the Flaviviridae and is transmitted by mosquitoes (Lindenbach B D, Thiel H J, and Rice C M 2007). Yellow fever disease can be divided into three stages. After an incubation period of three to six days, patients develop febrile illness with symptoms like fever, malaise, lower back pain, headache, myalgia, nausea, vomiting, and prostration lasting three to four days. Symptoms disappear for two to forty-eight hours before fifteen to twenty-five percent of the patients enter the third phase, the period of intoxication, characterized by fever, vomiting, epigastric pain, hemorrhagic diathesis, jaundice, and liver and renal failure. Death occurs in twenty to fifty percent of severe YF cases on the seventh to tenth day (Monath 2001; Monath 2004; Gubler, Kuno, and Markoff 2007).

SUMMARY OF THE INVENTION

During the course of virus purification, it was observed that addition of protamine sulfate to a virus harvest produced on a cell substrate removed not only contaminating DNA derived from host cells, as expected, but surprisingly also virtually eliminated immature and otherwise non-infectious virus particles from the preparation. This finding provided a streamlined, gentle, reproducible and broadly-applicable process for obtaining highly-purified infectious virus particles for applications such as vaccine preparation. In addition, it was surprisingly found that said protamine sulfate can be very efficiently separated from the virus fraction allowing for a safer vaccine produced at high yields.

Disclosed herein are virus vaccines and compositions comprising inactivated or attenuated viruses, and related methods of producing said vaccines and compositions. Also provided are methods of administering said virus vaccines for the prevention of virus infection and/or for the production of an anti-virus immune response in subjects, for example subjects at risk of being exposed to virus. In embodiments disclosed herein, "prevention" of a virus infection is equivalent to "protection from" a virus infection; i.e., the vaccine of the invention protects a vaccinated subject from noticeable or serious infection and/or mild or serious sequelae of infection. In particular, the invention is directed to a virus vaccine comprising an optimally inactivated virus particle, wherein the virus particle in an appropriate dose is able to seroconvert a subject that is administered the virus vaccine with at least a 70% probability, preferably an 80% probability; i.e., to confer seroprotection. Another advantage of the invention is that related methods of producing said vaccines and compositions are very efficient and provide pure compositions largely devoid of impurities, in particular protamine sulphate, allowing for high volume production of vaccines. Examples to the above are provided for Zika virus, Chikungunya virus and yellow fever virus.

The herein disclosed in vivo data regarding immunogenicity of the inactivated Zika virus vaccine of the current invention indicates that the virus is surprisingly potently immunogenic and also highly cross-protective (very similar immunogenicity in African and Asian strains). Data indicate that immunogenicity was unexpectedly higher than the recently reported inactivated Zika virus vaccine candidate (Larocca, et. al, 2016, Nature doi:10.1038/nature18952.). Inactivated viruses are among the safest vaccines and especially preferred for delivery to populations where safety is especially concerning, such as pregnant women, children and immunocompromised individuals, which makes the herein disclosed inactivated Zika virus particularly suitable. Obtaining a high titer of inactivated virus is a challenge in the field. The herein disclosed process for purifying inactivated Zika virus results in not only a high yield, but also a very pure drug substance.

Each of the limitations of the invention can encompass various embodiments of the invention. It is therefore anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF THE DRAWINGS

The accompanying drawings are not intended to be drawn to scale. The figures are illustrative only and are not required for enablement of the disclosure. For purposes of clarity, not every component may be labeled in every drawing, alignments were performed with the multi alignment package Jalview (Waterhouse et al., 2009, Bioinformatics 25 (9) 1189-1191). In the drawings:

FIG. 3: Pairwise alignment-Jalview (% identity, nt), complete genomes.

FIG. 6: Pairwise alignment-Jalview (% identity, aa), E-protein.

The sucrose gradient centrifugation (SGC) purified pool consisting of SGC fractions F7-F11 is shown in lane 12.

FIG. 12: SEC area (mAU*min; right axis) and $TCID_{50}$ results (log TCID50/mL; left axis) of attenuated Δ5nsP3 ChikV production harvests before and after PS treatment. The grey portions of the bars indicate large losses in SEC area following PS treatment, but no corresponding change in the total number of infectious particles (indicated by black portions of the bars) (A); SEC profile of virus preparation before and after PS addition, showing complete removal of large size virus aggregates by PS treatment as well as a reduction in host cell proteins (HCP) and low molecular weight (LMW) impurities (B).

Figure 13:
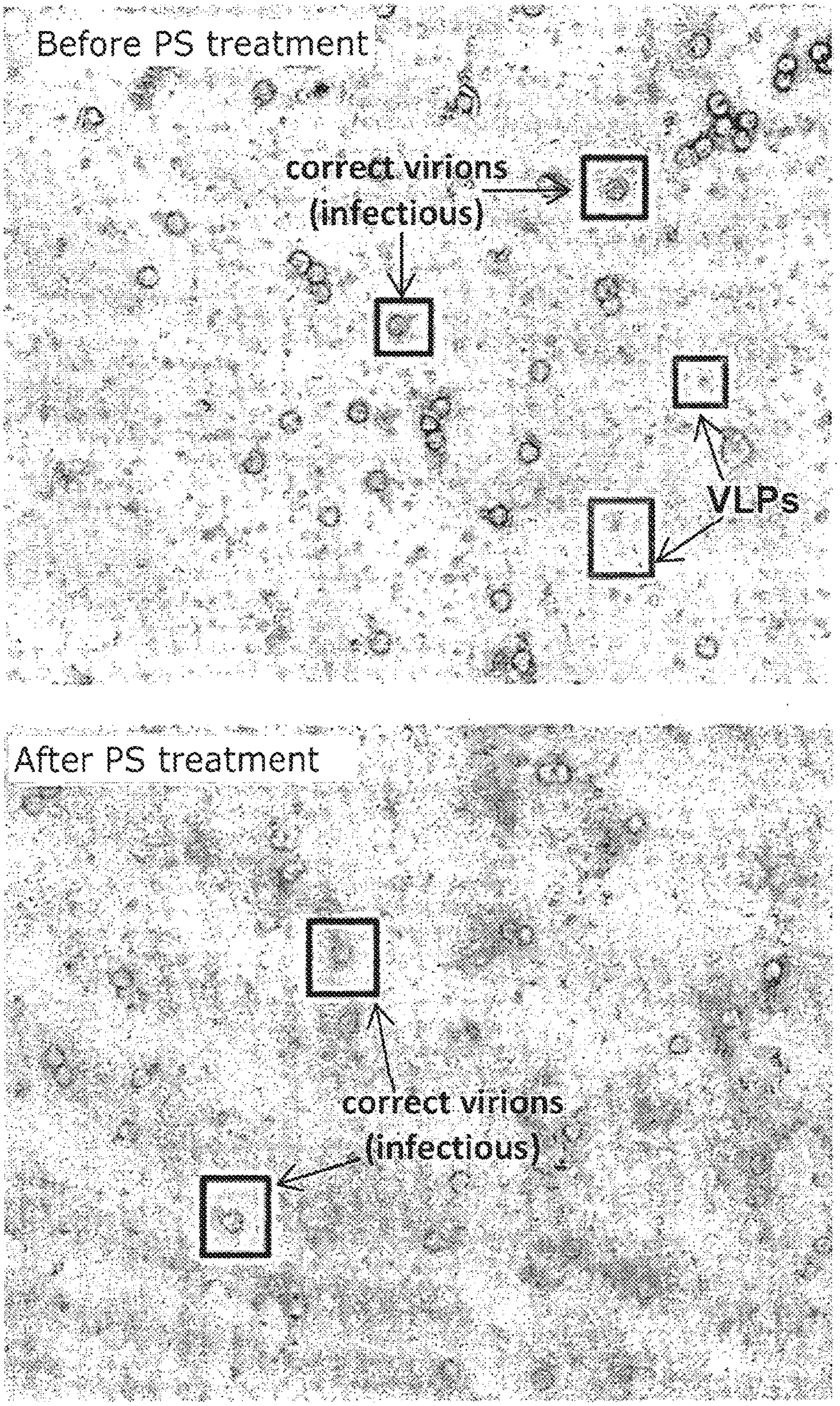

FIG. 13: Electron micrographs of attenuated Δ5nsP3 ChikV harvest before and after PS treatment.

Figure 14:
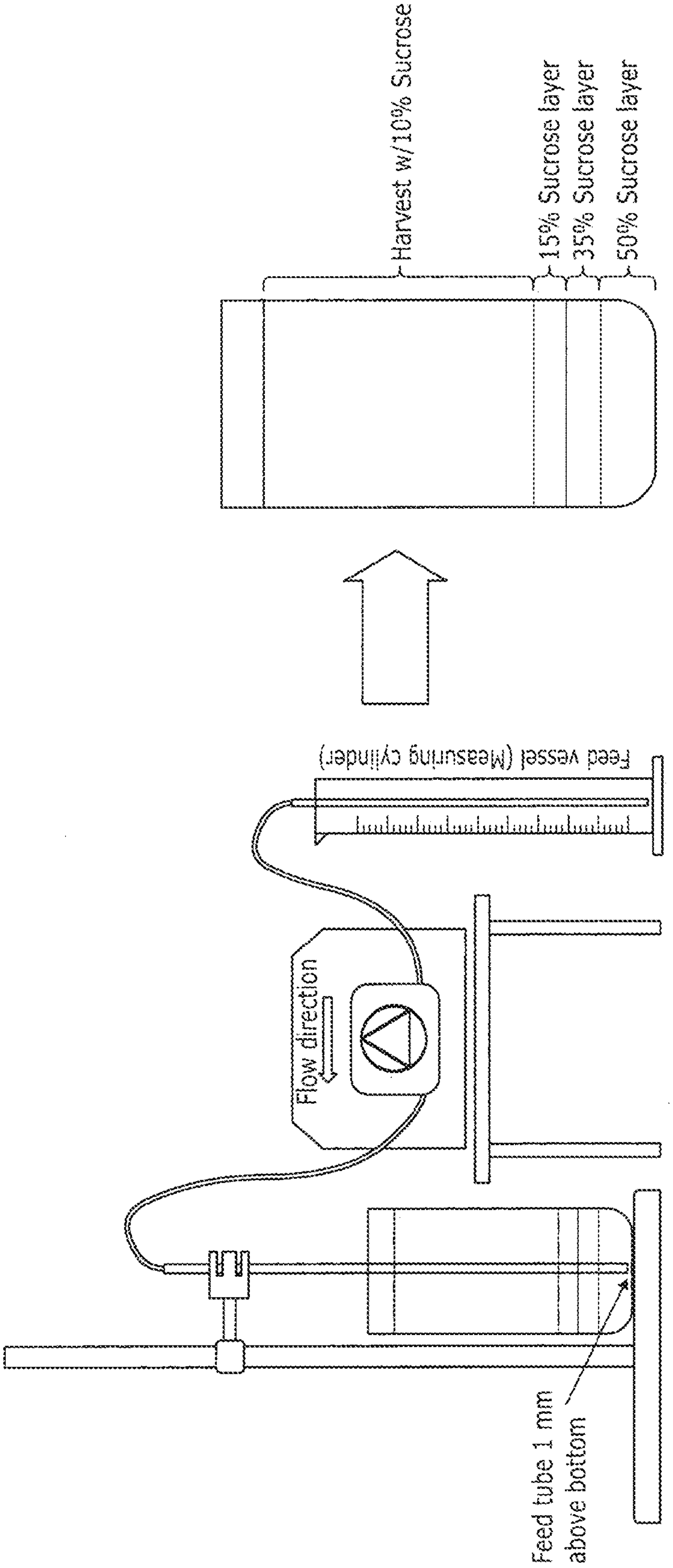

FIG. 14: Preparation of the optimized sucrose gradient of the invention.

FIG. 15: Comparison of four different sucrose gradient centrifugation experiments performed to empirically determine the optimal combination of sucrose layers for an exemplary purification of ChikV. The ChikV content in the gradient fractions was determined by SEC. The sucrose content in the gradient fractions was determined by refractometry as ° Bx (sucrose weight percentage). Protamine sulphate (PS) content was determined by SEC. PS was separated within the sucrose gradient alongside host cell derived residual contaminants and was therefore used to assess the quality of ChikV separation from residual contaminants in the tested gradients. A: ChikV load material containing 10% sucrose was loaded on top of one 50% (w/w) sucrose layer. Determination of sucrose content in the fractions showed the formation of a linear gradient. SEC showed concentration of ChikV within a sucrose concentration range from 40-30% (w/w) sucrose. PS SEC showed insufficient separation of PS from ChikV. B: ChikV load material containing 10% sucrose was loaded on top of a two layer system consisting of a 50% (w/w) sucrose bottom layer and a second 35% (w/w) sucrose layer. Determination of sucrose content in the fractions showed the formation of a linear gradient. SEC showed concentration of ChikV within a sucrose concentration range from 40-30% (w/w) sucrose. PS SEC showed acceptable separation of PS from ChikV, however a slight overlap is still present. C: ChikV load material containing 10% sucrose was loaded on top of a two layer system consisting of a 50% (w/w) sucrose bottom layer and a second 25% (w/w) sucrose layer. Determination of sucrose content in the fractions showed the formation of a linear gradient. SEC showed concentration of ChikV within a sucrose concentration range from 40-30% (w/w) sucrose. PS SEC showed a good separation of PS from ChikV. D: ChikV load material containing 10% sucrose was loaded on top of a three layer system consisting of a 50% (w/w) sucrose bottom layer as well as a 35% and a 15% (w/w) sucrose layer. Determination of sucrose content in the fractions showed the formation of a linear gradient and SEC showed concentration of ChikV within a sucrose concentration range from 40-30% (w/w) sucrose. PS SEC showed a very good separation of PS and residual contaminants from ChikV. Of the four tested sucrose layer systems the combination of 3 layers (shown in FIG. 16D) showed the best separation of the virus particles from residual contaminants and was therefore used for further DSP development.

Figure 16:
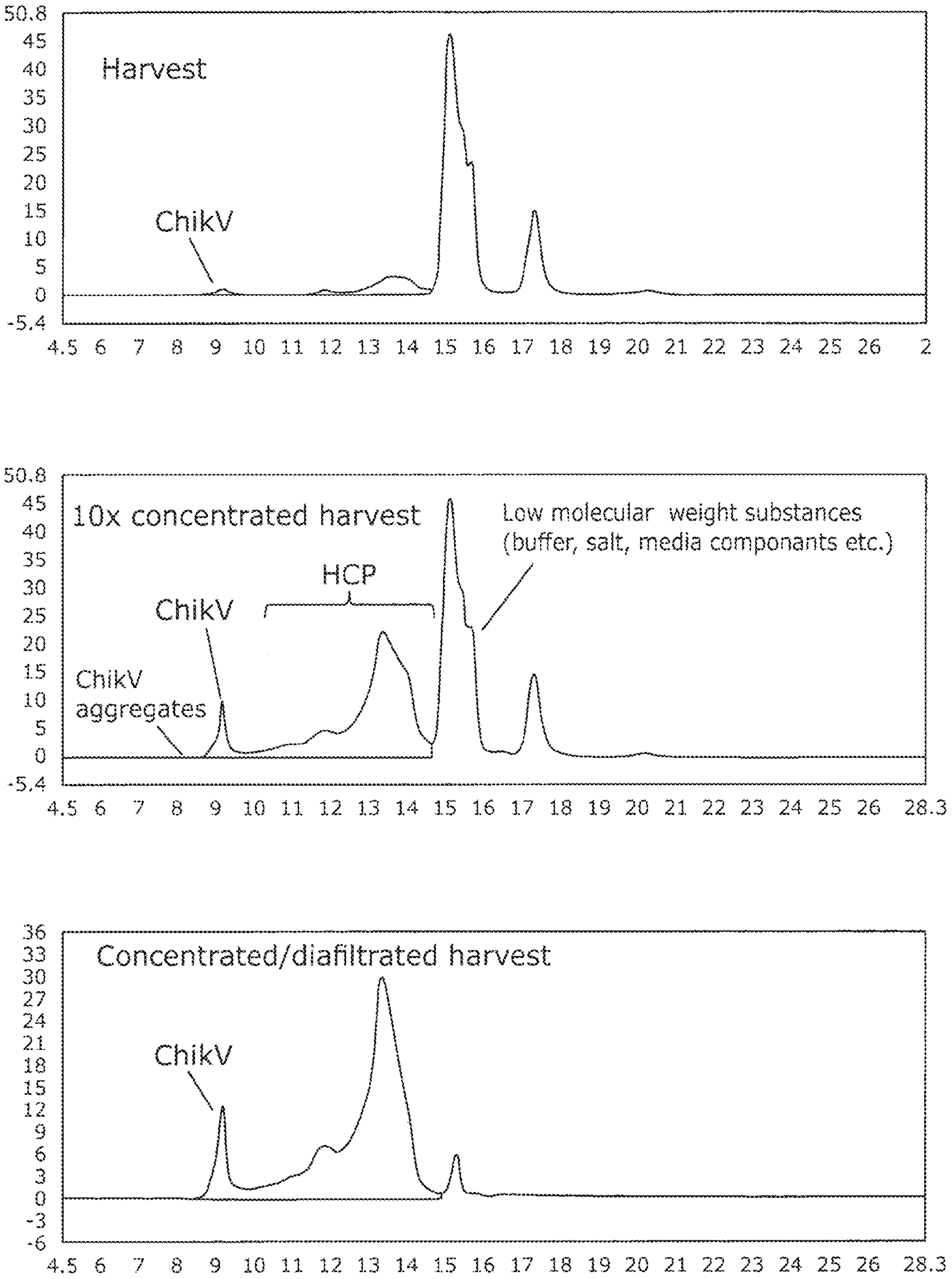
Figure 16:
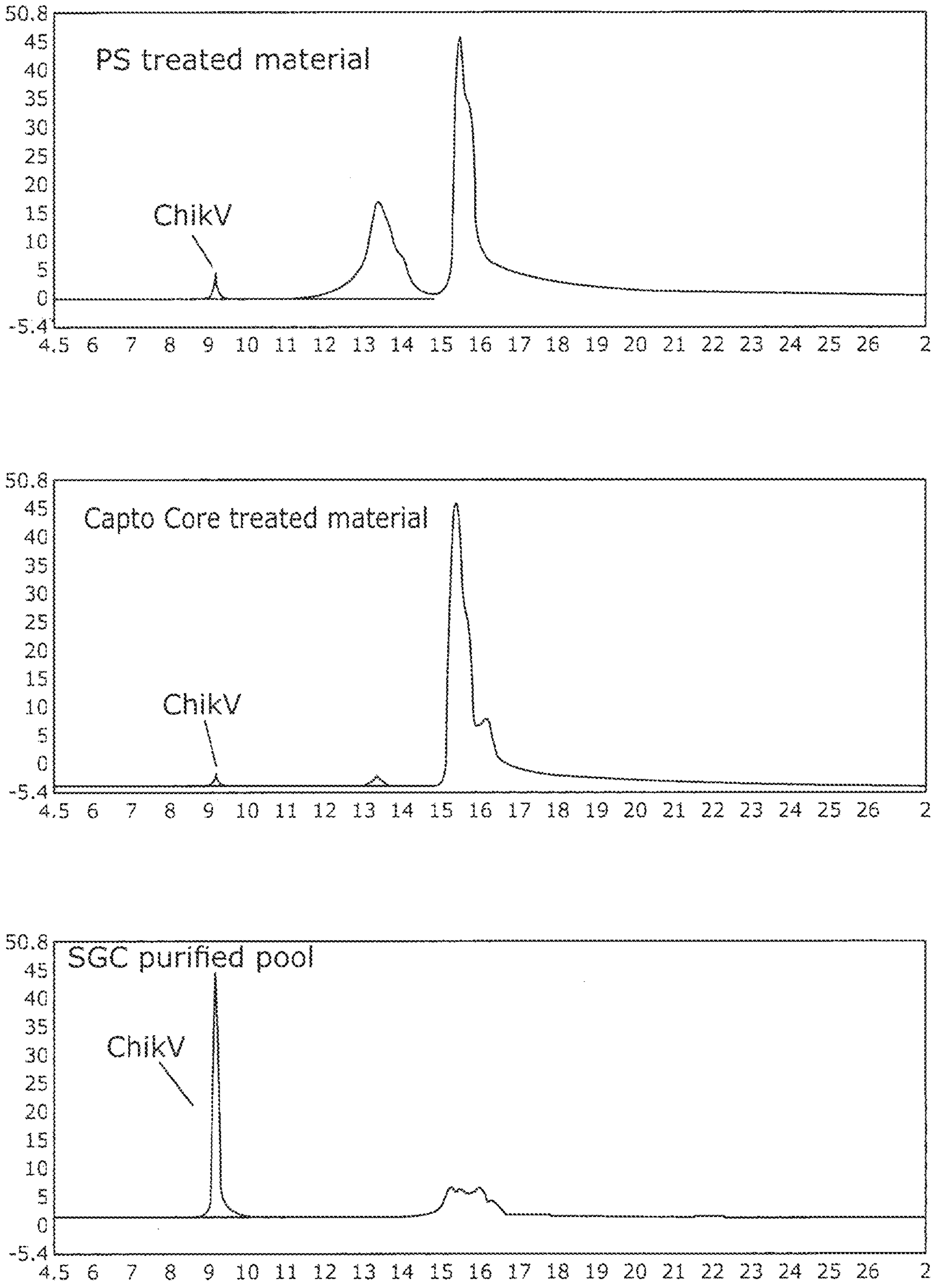

FIG. 16: Relative amounts of attenuated Δ5nsP3 ChikV particles and other components as measured by SEC-HPLC analysis at the different steps of the process of the invention including, from top to bottom: crude harvest (a); 10× concentrated harvest; diafiltrated concentrated harvest; PS treated material; CC700-treated material and SGC purified pool.

Figure 17A:
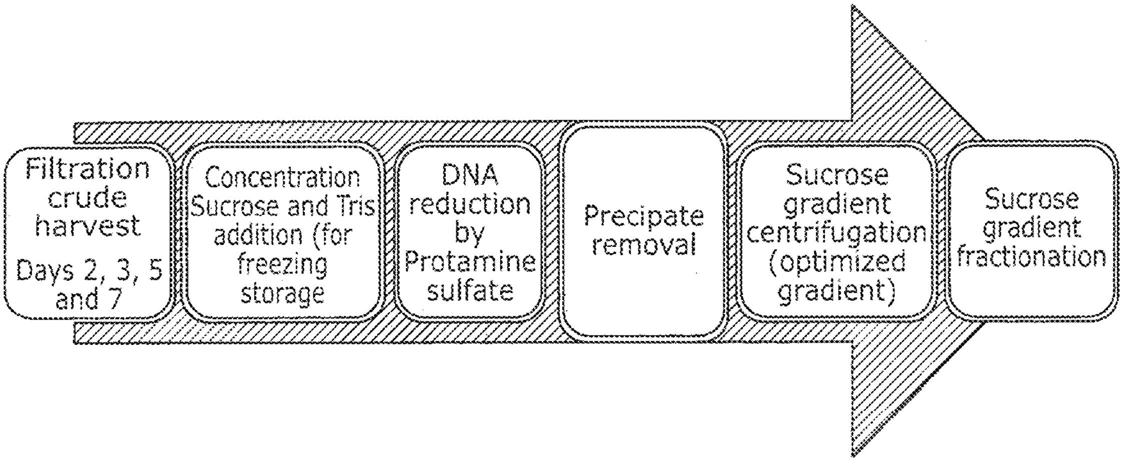
Figure 17B:
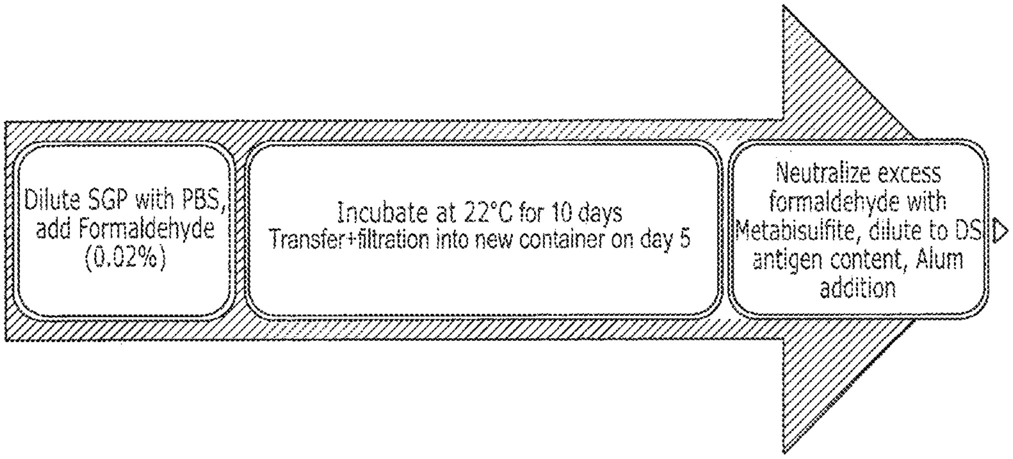

FIG. 17: An exemplary downstream virus purification process from the crude harvest to formulation of the drug substance (vaccine), a preferred embodiment of the process of the invention (A). A flow-chart of an exemplary virus inactivation process is shown in (B). Both processes were exemplified in detail with Zika virus.

Figure 18:
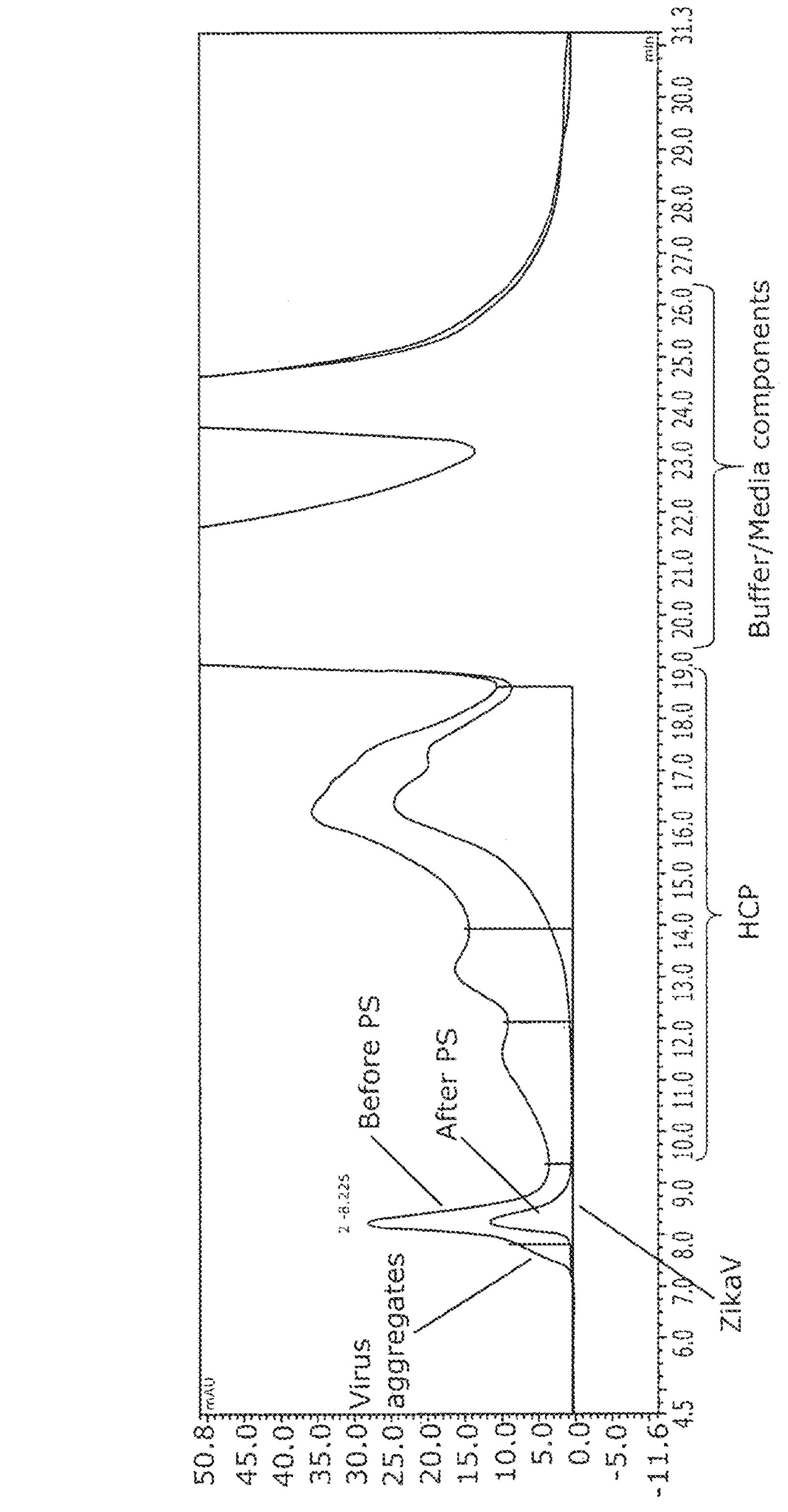

FIG. 18: PS treatment resulted in selective removal of Zika virus aggregates and Vero HCP and LMW impurities (SEC-HPLC of 30× concentrated Zika Virus harvest day 5).

Figure 19:
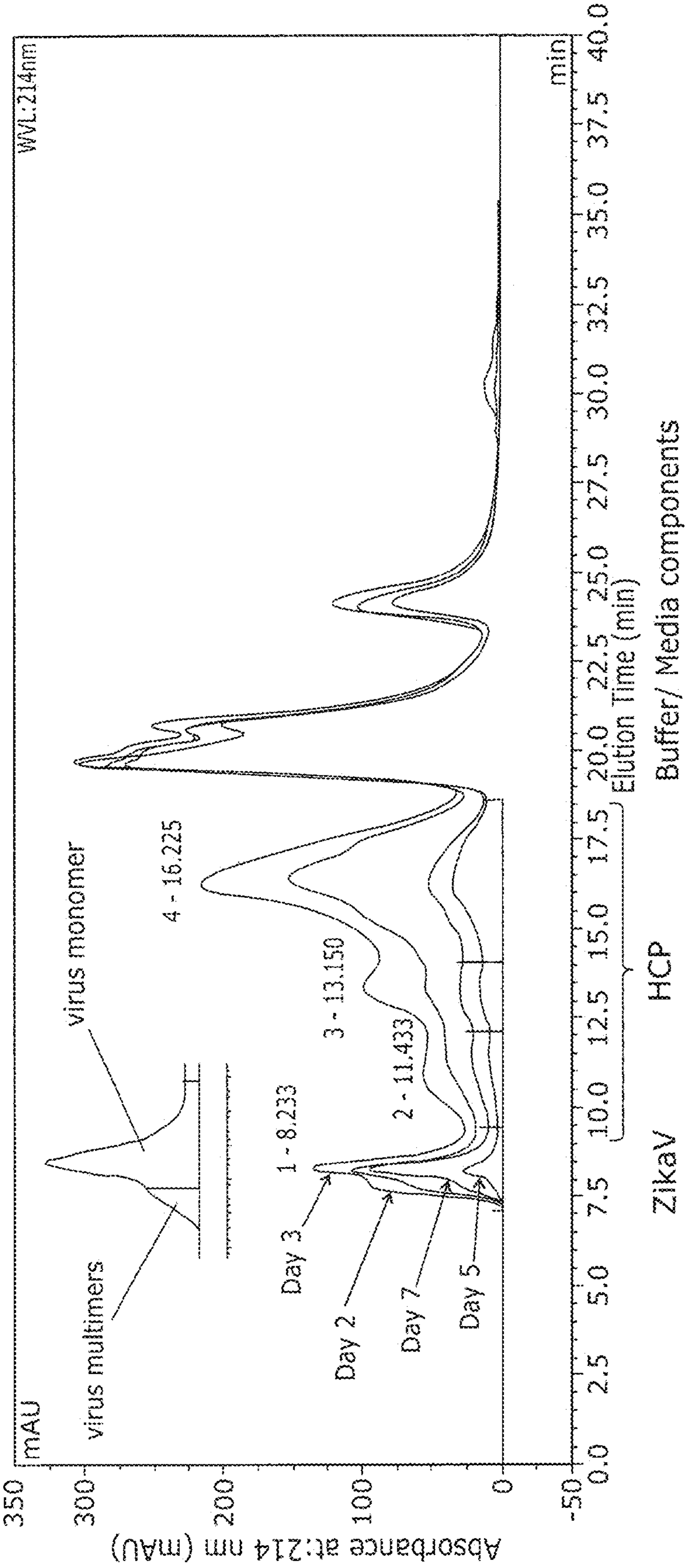

FIG. 19: SEC-HPLC of individual 30× concentrated Zika harvest prior PS treatment at different time points.

FIG. 20: SEC-HPLC of individual 30× concentrated Zika harvest post PS treatment at different time points. The smaller graph indicates the observed cytopathic effect (CPE) over time.

FIG. 21: Representative silver stained SDS-PAGE from the sucrose gradient harvest of a Zika virus purification is shown.

Figure 22:
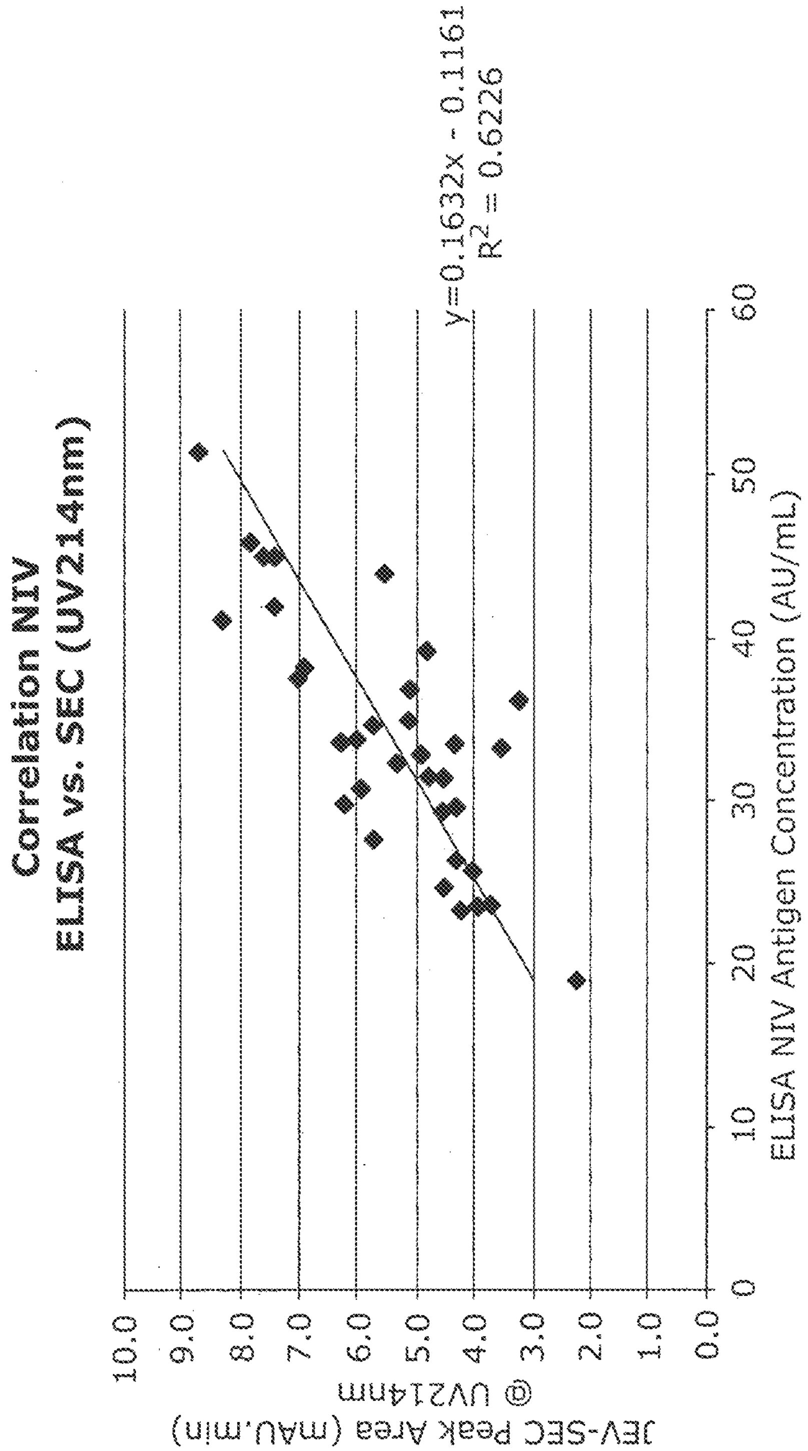

FIG. 22: Correlation between JEV antigen content in neutralized inactivated virus (NIV) analysed by ELISA and SEC-HPLC (Dionex Ultimate 3000, Superose 6 column).

Figure 23:
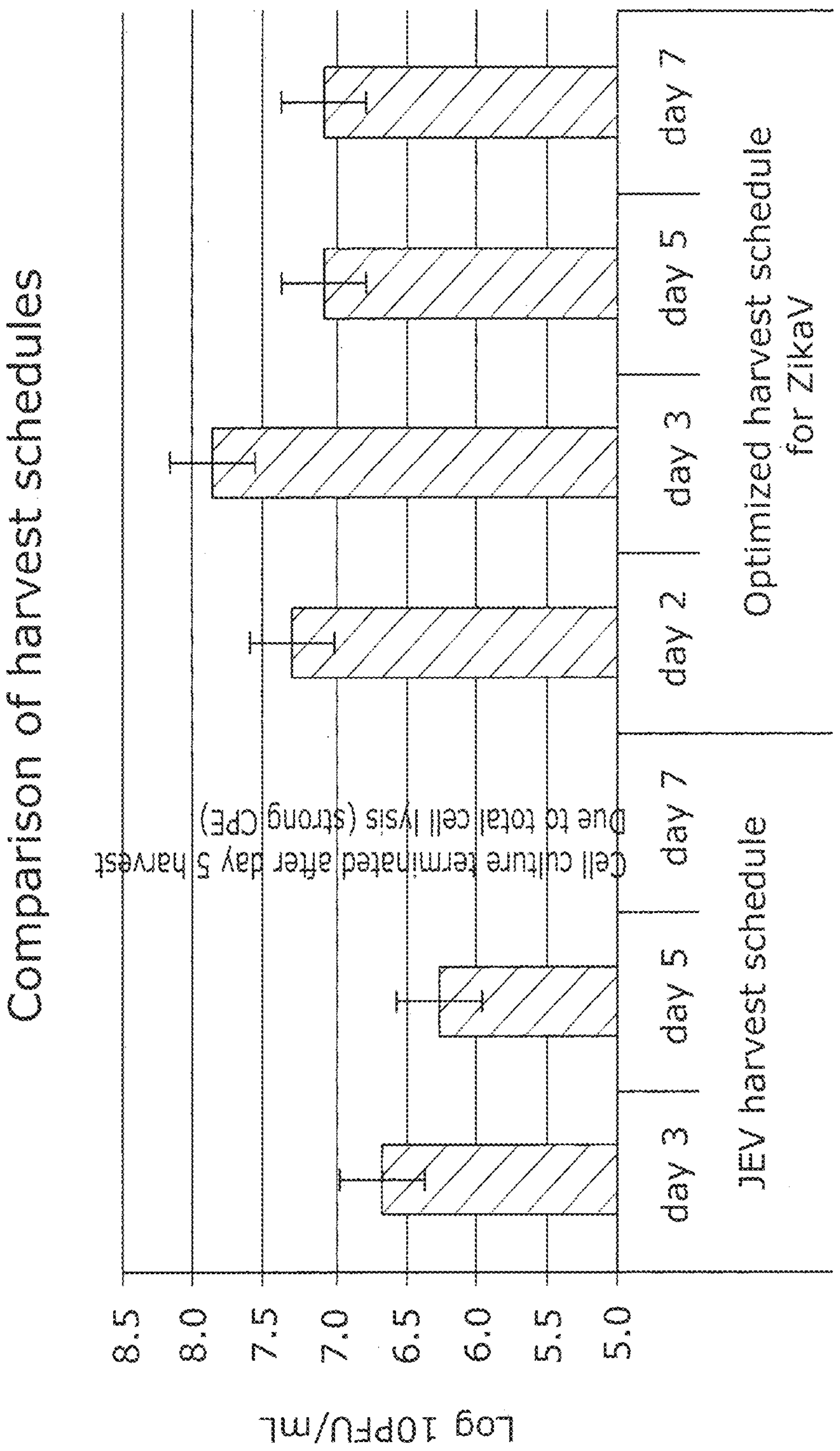

FIG. 23: Comparison of JEV and ZikaV harvest yields at different time points.

Figure 24:
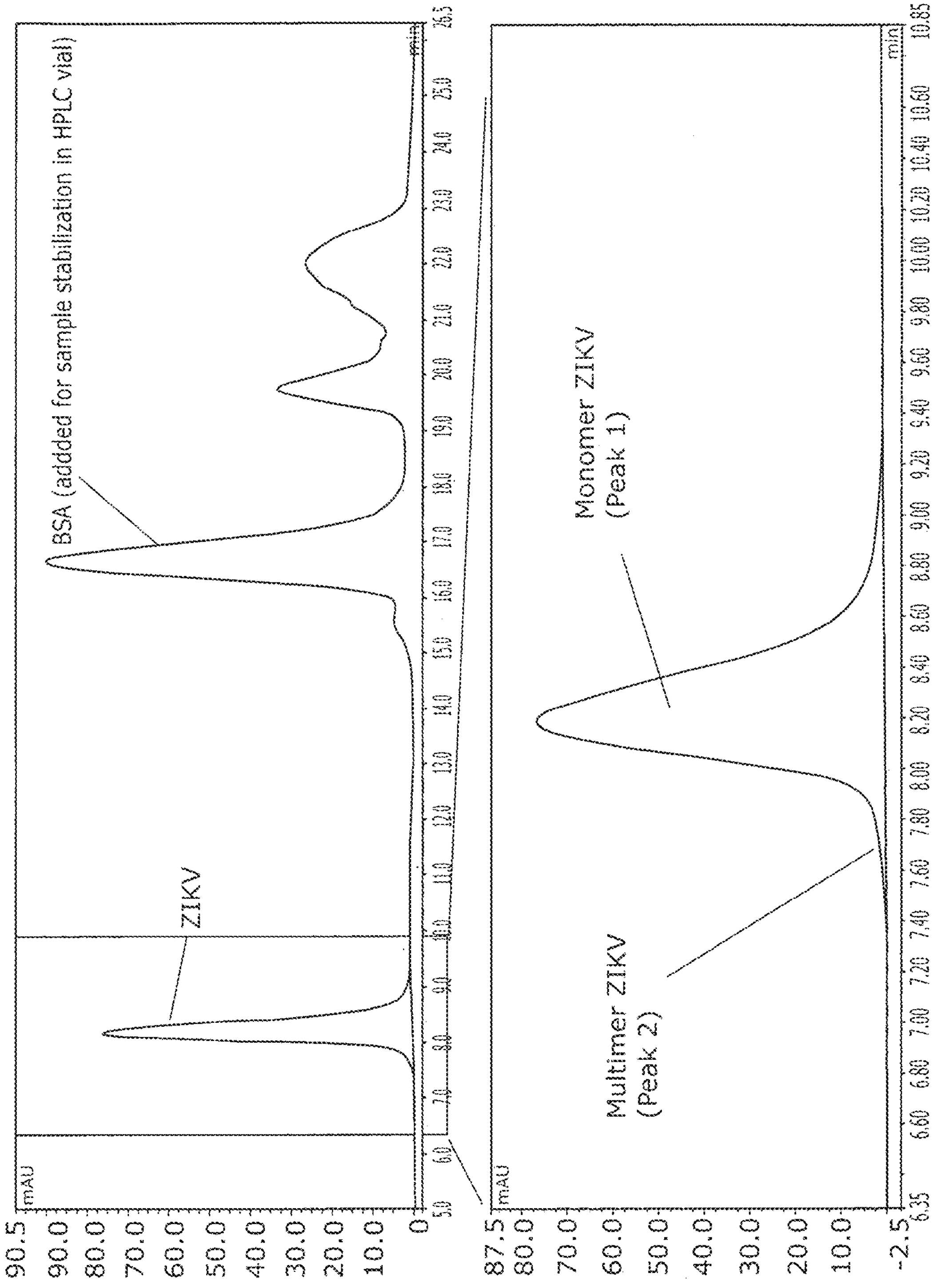

FIG. 24: SEC-HPLC elution profile of ZikaV NIV. Data were processed on Dionex Ultimate 3000/Superose 6 Increase column. Both panels are from the same chromatogram. The upper graph is the complete elution profile; the lower graph is an enlargement of the ZIKA virus elution peak.

Figure 25:
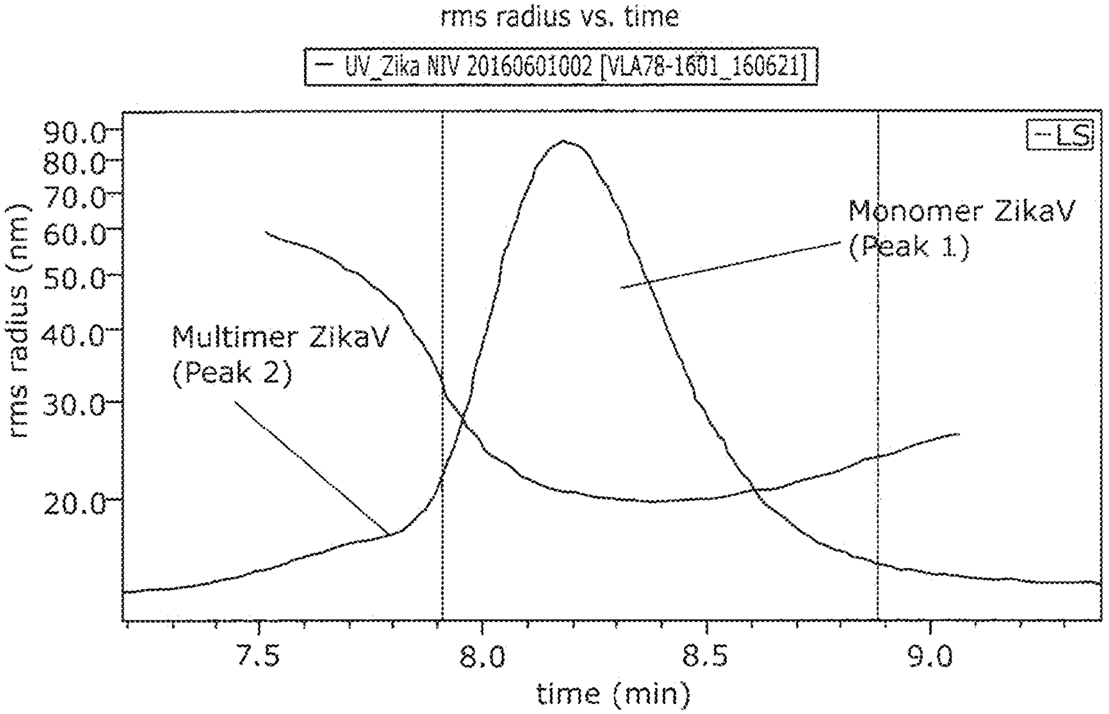

FIG. 25: SEC-MALLS analysis of inactivated ZikaV.

Figure 26:
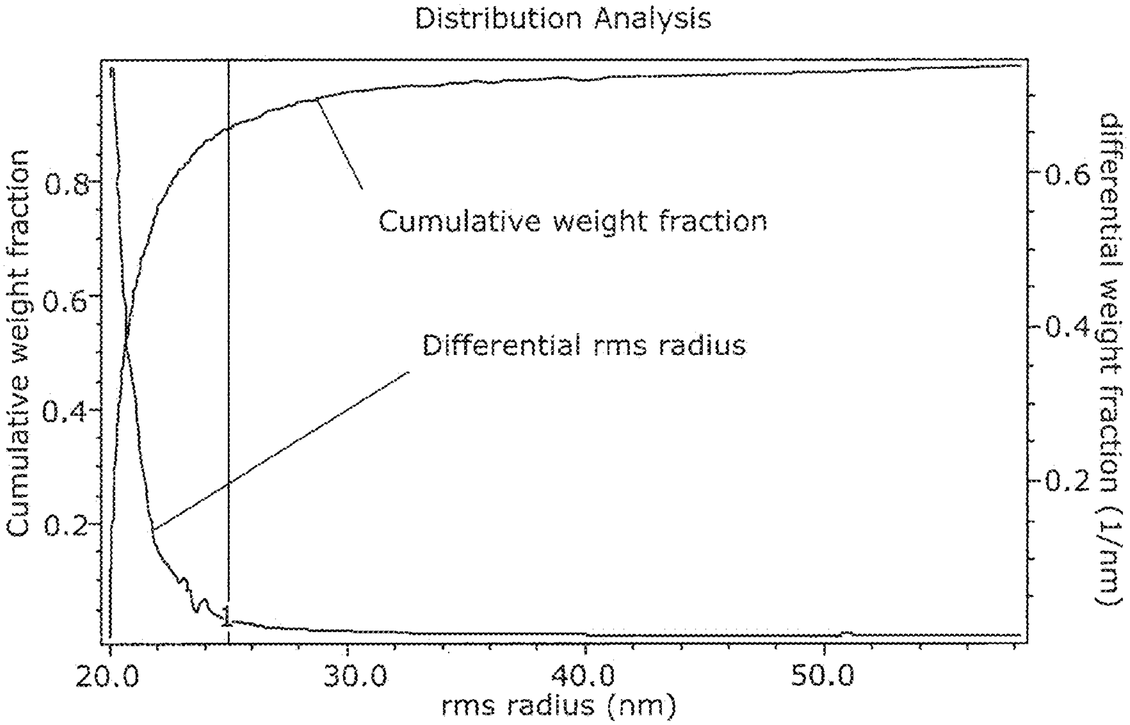

FIG. 26: Cumulative particle size distribution of Zika NIV.

Figure 27:
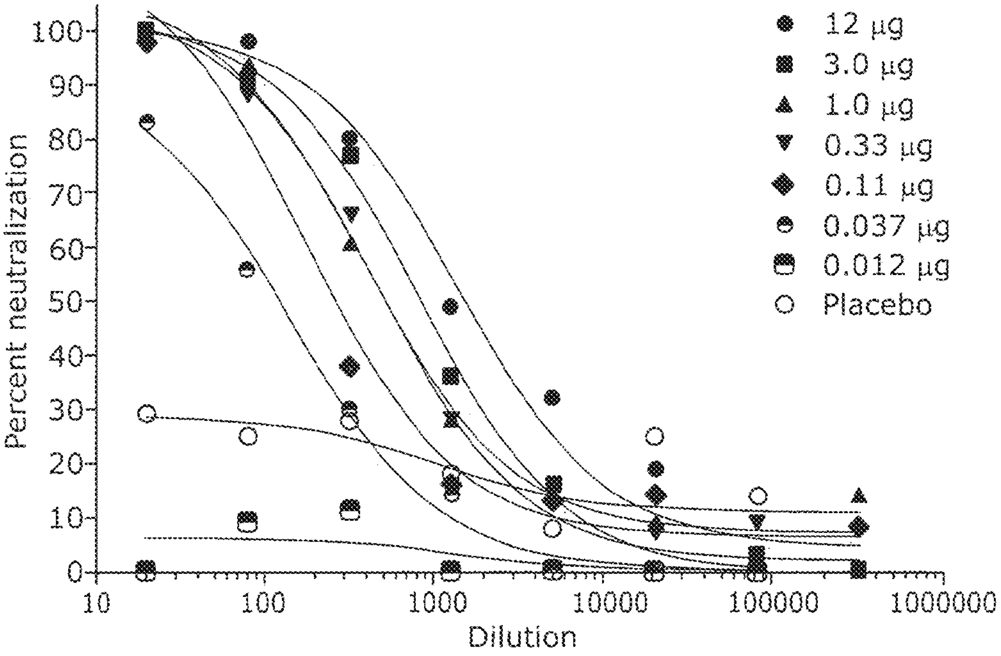

FIG. 27: Graphical representation of the neutralization of the Zika virus H/PF/2013 with pooled immunized mouse sera. The number of plaques without serum was set to 100%. The EC50 was calculated using the 3-parameter method.

Figure 28:
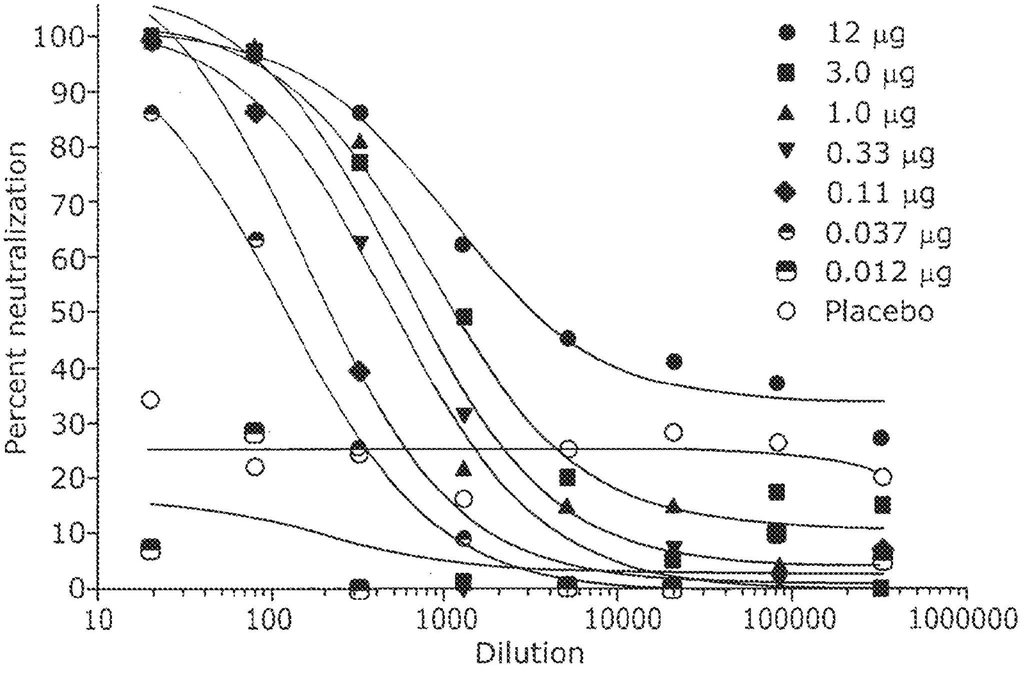

FIG. 28: Graphical representation of the neutralization of the Zika virus MR766 with pooled immunized mouse sera. The number of plaques without serum was set to 100%. The EC50 was calculated using the 3-parameter method.

Figure 29:
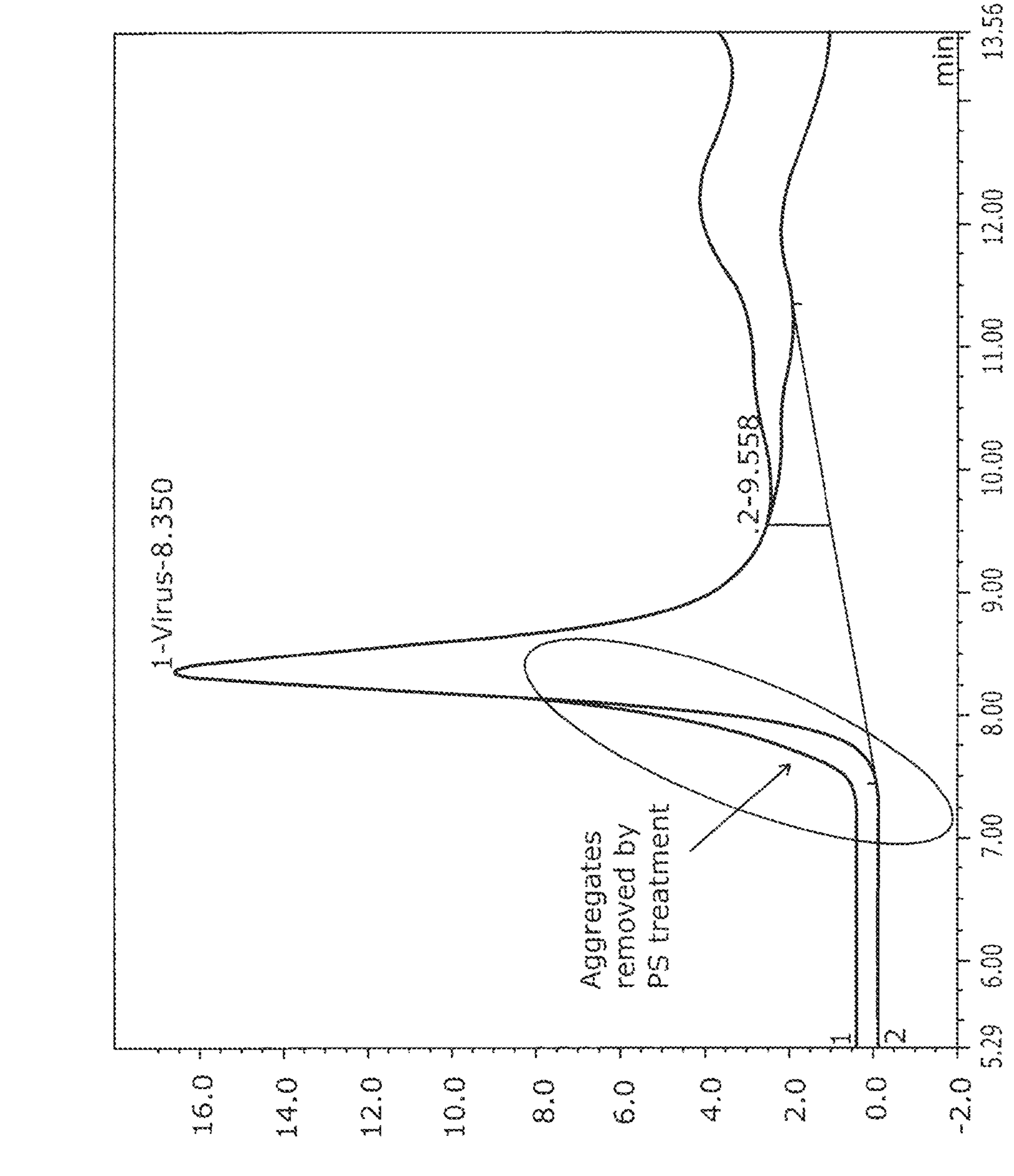

FIG. 29: Change in SEC profile of yellow fever virus peak after PS addition according to the invention showing a complete removal of large size aggregates and LMW impurities.

DETAILED DESCRIPTION OF THE INVENTION

Disclosed herein are virus vaccines and compositions comprising an inactivated or attenuated virus, and related methods of producing said vaccines and compositions. Also provided are methods of administering said virus vaccines for the prevention of virus infection and/or for the production of an anti-virus immune response in subjects, for example subjects at risk of being exposed to virus. In particular, the invention is directed to a virus vaccine comprising an optimally inactivated or attenuated virus particle, wherein the virus particle in an appropriate dose is able to seroconvert a subject that is administered the virus vaccine with at least a 70% probability, preferably an 80% probability, i.e., is able to confer seroprotection in at least 70% of vaccinated subjects. Another advantage of the invention is that related methods of producing said vaccines and compositions are very efficient and provide pure compositions largely devoid of impurities, in particular protamine sulphate, allowing for high volume production of vaccines. Examples to the above are provided for Zika virus, Chikungunya virus and yellow fever virus.

Disclosed herein are downstream processes for purifying virus particles from a crude preparation. The downstream process can be applied to either a virus which has not adapted for propagation on a particular cell substrate or for a partially/fully cell substrate adapted virus particle.

Aspects of the invention provide processes for the purification of infectious virus particles comprising the steps of (a) providing a crude harvest (a) comprising virus particles and impurities, wherein the impurities are generated from growing said virus particles on a cell substrate; (b) reducing impurities from the crude harvest (a) by precipitation with an agent comprising a protamine salt, preferably a protamine sulphate, to obtain a virus preparation (b); and further purifying the virus preparation (b) by an optimized sucrose density gradient centrifugation to obtain a virus preparation (c) comprising the infectious virus particles.

In some embodiments, the concentration of protamine sulphate in step (b) is about 1 to 10 mg/ml, more preferably about 1 to 5 mg/ml, more preferably about 1 to 2 mg/ml. In one embodiment, the concentration of protamine sulphate in step (b) is about 2 mg/mL. In one embodiment, the concentration of protamine sulphate is 1.2 to 1.8 mg/ml, more preferably 1.4 to 1.6 mg/ml. In a preferred embodiment, the concentration of protamine sulphate in step (b) is about 1.6 mg/ml (for e.g. Chikungunya) or about 2 mg/ml (for e.g. Zika).

In some embodiments, the residual host cell DNA of the virus preparation (c) is less than 1 mg/mL, especially less than 900, 800, 700, 600, 500, 400, 300 or 200 ng/mL, preferably less than 100 ng/mL. In a preferred embodiment, the residual host cell DNA of the virus preparation (c) is less than 10 ng/mL. In some embodiments, the residual host cell protein of the final virus preparation (c) is less than 10 mg/mL, especially less than 9, 8, 7, 6, 5, 4, 3 or 2 mg/mL, preferably less than 1 mg/mL. In a preferred embodiment, the residual host cell protein of the virus preparation (c) is less than 100 ng/mL. In some embodiments, the residual non-infectious virus particles of the final virus preparation (c) is less than 10 μg/mL, especially less than 9, 8, 7, 6, 5, 4, 3 or 2 mg/mL, preferably less than 1 mg/mL. In a preferred embodiment, the residual non-infectious virus particles of the virus preparation (c) is less than 100 ng/mL.

In some embodiments, the residual protamine is less than 1 μg/mL, especially less than 900, 800, 700, 600, 500, 400, 300 or 200 ng/mL, preferably less than 100 ng/mL, more preferably is below the detection limit of HPLC, in particular below the detection limit in the final drug substance. In some embodiments, the PS content is tested by HPLC or size exclusion chromatography (SEC). For example, HPLC is validated for PS determination in JEV sucrose gradient pool samples as a routine release assay and is very sensitive (i.e., LOQ 3 μg/mL; LOD 1 μg/mL). In the current invention, PS content in virus DS samples was <LOD. In one embodiment, the HPLC assessment of PS content can be performed on a Superdex Peptide 10/300GL column (GE: 17-5176-01) using 30% Acetonitrile, 0.1% Trifluoroacetic acid as solvent with a flow rate of 0.6 ml/min at 25° C. and detection at 214 nm. A more sensitive method of measurement for residual protamine in a purified virus preparation is mass spectrometry (MS). In some embodiments, the residual PS levels in a virus preparation are tested by MS or other such highly sensitive method, e.g. nuclear magnetic resonance (NMR). With this method, residual PS, as well as fragments and/or break-down products of PS, can be detected at trace amounts, such as levels as low as, for example, $10^6$, $10^7$ or $10^8$ molecules per typical sample load. In some embodiments, the PS levels are tested in the sucrose gradient pool. In some embodiments, the PS levels are tested in the drug product. In some embodiments, the PS levels are tested in the drug substance.

In some embodiments, the crude harvest (a) comprising the virus particles and impurities is subjected to one or more pre-purification step(s) prior to step (b). In some embodiments, the one or more pre-purification step(s) comprises digesting host cell genomic DNA in the crude harvest (a) comprising the virus particles and impurities by enzymatic treatment. In some embodiments, the one or more pre-purification step(s) comprises filtration, ultrafiltration, concentration, buffer exchange and/or diafiltration. In some embodiments, the one or more pre-purification steps is filtration using a filter having a pore size equal to or less than 1 μm. In some embodiments, the filter has a pore size equal to or less than 0.2 μm. In a preferred embodiment, the filter has a pore size of 0.2 μm. In some embodiments, the concentration and/or ultra/diafiltration and/or buffer exchange is performed by tangential flow filtration (TFF). In some embodiments, ultra/diafiltration of the crude harvest (a) comprising the virus particles and impurities is performed using a hollow fiber membrane having a cut-off of equal to or less than 300 kDa. In a preferred embodiment, the hollow fiber membrane has a cut-off of about 100 kDa.

The process according to the current invention may also comprise the use of a sucrose gradient, preferably an optimized sucrose gradient. The sucrose gradient is preferably optimized for the removal of protamine sulfate, also for the removal of immature viral particles or other viral particles which are non-infectious or host cell proteins or nucleic acids (DNA, RNA, mRNA, etc) or other host cell debris. In the current invention the optimized sucrose gradient comprises at least two, at least three, at least four layers of sucrose solutions with different densities. In one embodiment, the virus preparation to be purified is provided in a sucrose solution which has a density of about 8%, about 9%, about 10%, about 11%, about 12% sucrose (w/w), preferably about 10%. In one embodiment, one sucrose solution in the gradient has a density of about 45%, about 46%, about 47%, about 48%, about 49%, about 50%, about 51%, about 52%, about 53%, about 54%, about 55% sucrose (w/w), preferably about 50%. In one embodiment, one sucrose solution in the gradient has a density of about 30%, about 31%, about 32%, about 33%, about 34%, about 35%, about 36%, about 37%, about 38%, about 39%, about 40% sucrose (w/w), preferably about 35%. In one embodiment, one sucrose solution in the gradient has a density of about 10%, about 11%, about 12%, about 13%, about 14%, about 15%, about 16%, about 17%, about 18%, about 19%, about 20% sucrose (w/w), preferably about 15% sucrose. In a preferred embodiment, the sucrose gradient comprises three layers of sucrose solutions of about 50%, about 35% and about 15% (w/w) sucrose and the virus composition to be purified is contained in about 10% (w/w) sucrose. Because the invention provided for means to not only test for host cell DNA but also immature viral particles, the skilled person in the art is able to more precisely optimize the sucrose gradient for most efficient purification and include additional tools such as PRNT assay to monitor purification success.

In some embodiments, the virus particle is a live virus, a chimeric virus, an attenuated live virus, a modified live virus, or a recombinant live virus. In a further step, the virus particles of the invention may be optionally inactivated. In some embodiments, the virus particle is an attenuated form of the virus particle. For example, the virus may have reduced infectivity, virulence, and/or replication in a host, as compared to a wild-type virus. In some embodiments, the virus is a mutated or modified virus, for example the nucleic acid of the virus may contain at least one mutation relative to the wild-type virus. In some embodiments, the virus is a recombinant live virus, meaning a virus that is generated recombinantly and may contain nucleic acid from different sources.

In some embodiments, the virus particle is a live virus, an attenuated live virus, a modified live virus, or a recombinant live virus. In some embodiments, the virus belongs to a virus family selected from the group consisting of Paramyxoviridae, Orthomyxoviridae, Flaviviridae, Filoviridae, Arenaviridae, Rhabdoviridae, and Coronaviridae. In some embodiments, the virus belongs to a virus family selected from the group consisting of Togaviridae (being live or inactivated), such as alphaviruses, or Flaviviridae (being live or inactivated). In some embodiments, the virus is a virus of the family Flaviviridae, i.e. a flavivirus. In other embodiments, the virus is a Zika virus or yellow fever virus. In preferred embodiments, the virus is a Zika virus. In a most preferred embodiment, the Zika virus is a Zika virus from the Asian lineage. In a preferred embodiment, the virus is a Chikungunya virus, preferably an attenuated Chikungunya virus. In a most preferred embodiment, the attenuated Chikungunya virus contains a deletion in the non-structural protein 3, such as that provided by e.g. SEQ ID NO: 77. In a preferred embodiment, the virus is a yellow fever virus such as e.g. SEQ ID NO: 76.

In some embodiments, the relative reduction of impurity of the final virus preparation relative to the liquid medium (a) comprising the virus particles and impurities is in a range from 60 to 95%. In some embodiments, the residual impurity of the final virus preparation is less than 1%.

In some embodiments, the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line. In some embodiments, said cell line is a duck cell line. In some embodiments, said cell line is a diploid avian cell line. In some embodiments, said cell line is an EB66 cell line. In a preferred embodiment, said cell line is a Vero cell line.

Aspects of the invention provide a use of any of the processes described herein for manufacturing a composition for immunization against a viral infection. In a preferred embodiment, the composition is a vaccine. In one embodiment, the composition or vaccine is directed against Chikungunya virus, such as an attenuated Chikungunya virus. In one embodiment, the composition or vaccine is directed against a flavivirus. In one embodiment, the composition or vaccine is directed against yellow fever virus. In one embodiment, the composition or vaccine is directed against Zika virus such as e.g. a Zika virus of the Asian lineage.

Other aspects provide compositions comprising the virus particles obtainable by any of the processes described herein for treating and/or preventing a viral infection. In one embodiment, the viral infection is caused by Chikungunya virus. In one embodiment, the viral infection is caused by a flavivirus. In one embodiment, the viral infection is caused by yellow fever virus. In one embodiment, the viral infection is caused by Zika virus such as e.g. a Zika virus of the Asian lineage.

Furthermore, disclosed herein are vaccines and compositions comprising an inactivated Zika virus or yellow fever virus or an attenuated Chikungunya virus and related methods of producing said vaccines and compositions. Also provided are methods of administering the said vaccines for the prevention of Zika, yellow fever or Chikungunya virus infection and/or for the production of an anti-Zika, yellow fever or Chikungunya virus immune response in subjects, for example subjects at risk of being exposed to Zika, yellow fever or Chikungunya virus.

Zika virus is a flavivirus closely related to Dengue virus and is similarly transmitted by the Aedes species mosquito, although other arthropod vectors for Zika virus are possible. Since it was first isolated from a Rhesus monkey in the Zika forest of Uganda in 1947, there were very few reported incidents of human infection, especially outside of the endemic regions of Africa and Asia until a large outbreak in French Polynesia in 2007 (Haddow et al. *PLoS Neglected Tropical Diseases* (2012) 6(2), Malone et al. *PLoS Neglected Tropical Diseases* (2016) 10(3),). The virus has since spread through islands of the Pacific, including Oceania, and into South and Central America (WHO "Zika Situation Report" Feb. 5, 2016).

In addition to being spread by the bite of an infected mosquito, evidence also suggests transmission may occur between individuals, such as from the blood of an infected individual, in utero/transplacental transmission from an infected mother to the fetus, sexual transmission between sexual partners, and possibly by other local transmission routes. There is a possible association between Zika virus infection during pregnancy and microcephaly in the fetus/neonate. Microcephaly is a rare condition in which a baby's head circumference is significantly less than expected based on the average for their age, sex, and ethnicity. This is a result of the brain failing to undergo proper embryonic development, and in 90% of cases is associated with mental retardation (Rocha et al. (2016) *Bull World Health Organ* 8 Feb. 2016).

There is a probable association between individuals having had a prior Zika virus infection and the incidence of Guillain-Barré syndrome, a neurological disorder in which the individual's immune system destroys the myelin sheath surrounding axons of the peripheral nervous system (WHO "Zika Situation Report" Feb. 5, 2016).

No specific treatments or vaccines for Zika virus currently exist, and the only measures at this time to prevent infection are through vector control and avoiding travel to regions experiencing outbreaks.

Described herein are Zika virus vaccines and compositions comprising inactivated Zika virus that provide a safe method for generating an immune response to Zika virus, including virus-neutralizing antibodies, that may help prevent against Zika virus infection.

Any strain of Zika virus may be used in the methods and compositions described herein. In some embodiments, the Zika virus is an isolate from an infected subject during a Zika virus outbreak. In some embodiments, the Zika virus is a strain isolated from Africa or from the African virus lineage. In some embodiments, the Zika virus is a strain isolated from Asia or from the Asian lineage (includes also strains from French Polynesia). In some embodiments, the Zika virus is a strain isolated from the Americas (South America, Central America, or North America), such as a Suriname Zika virus strain.

In some embodiments, the Zika virus has an RNA genome corresponding (but not limited) to the DNA sequence provided by GenBank Accession No. AY632535.2, KU321639.1, KU497555.1, KU501215.1, KU509998.1, KU527068.1, KU681081.3, KU681082.3, KU707826.1, KU744693.1, or LC002520.1 or RNA genome disclosed partially or fully herein (SEQ ID NO: 2 to 69). In one embodiment, the Zika virus comprises the RNA sequence corresponding to the DNA sequence provided by SEQ ID NO: 78. In one embodiment, the DNA sequence has at least 95%, 96%, 97%, 98%, at least 99% sequence identity with SEQ ID NO: 78. In one embodiment, the Zika virus contains an RNA molecule encoding the entire polyprotein according to SEQ ID NO: 79 or a polyprotein with at 95%, 96%, 97%, 98%, at least 99% sequence identity with SEQ ID NO: 79. In one embodiment, the In some embodiments, the attenuated form of ChikV is derived from the LR2006-OPY1 ChikV infectious clone (La Reunion isolate). In some embodiments, the attenuated form of ChikV is a Δ5nsP3 mutant similar to the attenuated virus described by Hallengärd et al. (Novel Attenuated Chikungunya Vaccine Candidates Elicit Protective Immunity in C57BL/6 mice (2014) Journal of Virology 88(5):2858-2866) or an immunogenic variant thereof. The immunogenic variant of the Δ5nsP3 ChikV mutant is herein defined as having at least 80% sequence identity to the nucleotide sequence of the Δ5nsP3 mutant sequence (SEQ ID NO: 77), especially at least 81%, 82%, 83%, 84%, 85%, 86%, 87%, 88% 89%, 90%, 91%, 92%, 93%, 94%, 95%, 96%, 97%, 98% or at least 99% sequence identity.

In some embodiments, the process of the invention results in an enrichment of infectious virus particles from the crude harvest comprising infectious virus particles and non-infectious virus particles and other virus products such that the enrichment of the infectious virus particles is at least 50%, at least 60%, at least 70%, at least 80%, at least 90%, at least 95%, preferably at least 80%, especially at least 85% relative to the total virus particle content of the crude harvest (a) comprising the virus particles and impurities.

In some embodiments, the residual impurity of the final virus preparation with respect to all impurities in the crude harvest is less than 10%, 9%, 8%, 7%, 6%, 5%, 4%, 3%, 2%, 1%, preferably less than 5% as determined by SEC-HPLC (Size Exclusion Chromatography—HPLC).

A unique aspect of the current invention is the realization that know-how related to the vaccine design and purification approach used for the Japanese Encephalitis Vaccine (JEV) IXIARO® (see Srivastava A. K. et al., 2001, Vaccine 19, 4557-4565, WO99/11762) may be employed and improved upon in order to expedite the development of a Zika, (or e.g. Chikungunya or yellow fever) virus vaccine and provide it to the subjects in need as soon as possible. The industrial process as disclosed for IXIARO®, providing a very effective vaccine against JEV, was complemented by further significant improvements disclosed herein in order to provide a more efficient (higher yield) and safer (less or no protamine sulphate with its allergic potential) Zika vaccine compared to the available JEV vaccine. A particular innovation of the herein disclosed vaccines is their greatly reduced protamine salt (SEQ ID NO: 1) content in the final drug substance facilitated by the development of an improved sucrose gradient. Said sucrose gradient not only allowed the separation of protamine sulphate but also allowed for a very effective inactivation by formaldehyde and resulted in the case of Zika with over 90% yield with the improved process disclosed herein vs about 35% yield with the published JEV process, see experimental part for comparison). Interestingly, this very efficient process can also be applied to live vaccines as the herein disclosed Chikungunya vaccine. Herein disclosed preliminary results with a yellow fever vaccine are also supportive that this approach can be used. Thus, the invention provides for a robust and widely applicable process for viral vaccines.

Aspects of the disclosure relate to methods of producing a virus in Vero tissue culture cells. Vero cells are a commonly used tissue culture cell line derived from the kidney of an African green monkey. The Vero cells used in the methods described herein are the VERO (WHO) cell line, obtained from the Health Protection Agency general cell collection under catalogue number 88020401.

Vero cells can be grown to confluent monolayers, for example in tissue culture flasks; in suspension (on microcarriers), for example in roller bottles; or in any other cell culture system for viral production. In some embodiments, the Vero cells are grown in a bioreactor for viral production. For plaque assays or the plaque reduction neutralization test (PRNT), Vero cells are grown in monolayers in tissue culture flasks, dishes, or wells of a plate. To infect the Vero cells with the virus, the culture medium is inoculated with virus and the cells are incubated with the virus for a period of time. The cells may be washed after inoculation to remove any virus that did not adsorb to the cells in a given amount of time.

The methods provided herein involve passaging the virus in Vero cells. As used herein, the terms "passage" or "passaging" refer to infecting a population of Vero cells with virus and subsequently inoculating a second population of Vero cells with virus produced by infection of the first Vero cell population. In some embodiments, a portion of the culture medium from the infected Vero cells (containing virus that was released from the infected cells) is used to inoculate a second population of Vero cells. This is referred to as one passage or one round of passaging. The passaging may be performed serially, for example, a portion of the culture medium from the infected second population of Vero cells is used to inoculate a third population of Vero cells, and so on. In some embodiments, virus obtained from a single plaque is used to inoculate another population of cells.

In some embodiments, the virus is passaged in Vero cells several times, such as at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 times. In some embodiments, the virus is passaged in Vero cells at least 4 times or 5 times. In some embodiments, the virus is passaged in Vero cells at least 30 times. It is important that the virus population, i.e. the virus sequences, stays as much as possible constant over said passaging. If adaption of the virus occurs (i.e. appearance of mutated viruses in the original virus population), it is preferred that said passages are not used in the context of manufacturing of said virus, e.g. for Zika it was found that up to passage 3 and culturing to day 7 can be used without major shifts in virus population, i.e. introduction of virus population with mutations. However this observation needs to be done for each virus strain and may be different.

In some embodiments, the Vero cells are incubated for at least 2 days after inoculation with the virus at e.g. a typical 0.01 MOI (multiplicity of infection), to allow for viral production, prior to passaging. In some embodiments, the Vero cells are incubated for at least 3, 4, 5, 6, 7, 8, 9, 10 or more than 10 days e.g. at least 7 days after inoculation with the virus prior to passaging. The number of days the Vero cells are incubated after viral inoculation may depend on factors such as the multiplicity of infection used to inoculate the cells and the viral titer desired in the culture medium. Serial passaging of the virus in Vero cells may result in generation of a Vero cell adapted virus strain.

The culture medium from the infected Vero cells may be harvested (collected) to obtain the virus. In some embodiments, the culture medium is harvested from infected Vero cells and is replaced with fresh culture medium, which is then harvested after another period of time. In some embodiments, the culture medium harvested from infected Vero cells is pooled from independent Vero cell cultures and/or from independent days. Harvesting can be repeated up to 4 times by 7 or 9 days post infection, for example, and result in a high yield of virus per unit cell culture. In order to minimize the adoption of Zika virus strain to Vero cells, it was found that Vero cell could be incubated for at least 7 days, more preferably 5 days, prior to passaging and subsequently supernatants could be harvested at days 2, 3, 5 and 7 or 2, 3, and 5 (see also experimental part). The harvested culture medium can be stored at +4° C. prior to purification of the virus from the culture medium for up to 2 weeks.

In some embodiments, debris from infected and lysed Vero cells may be removed from the harvested culture medium, referred to as a "clarification" of the culture medium. The harvested culture medium may be clarified by common methods known in the art, such as low-speed centrifugation, for example, at 1500 g for 10 min, and/or by filtration through a filter of pore size of 0.45 μm. The harvested culture medium can be stored at +4° C. prior to concentration.

The inventive processes of this invention can also be applied to the purification of infectious virus particles grown on other cell substrates such as Chick embryo cell (CEF), Sf-9, high five, MRC-5, WI-38, MDCK, PER.C6, and avian cell lines, e.g. the duck cell line EB66 and many others.

To concentrate the titer of the virus in the harvested culture medium, it may be subjected to concentration by any method known in the art. For example, the harvested culture medium may be concentrated by methods including, without limitation, ultrafiltration, ultracentrifugation, centrifugal concentrator, vacuum centrifugation, and lyophilization. In some embodiments, the harvested culture medium is concentrated by ultrafiltration and the retentate containing the virus is collected. In some embodiments, the harvested culture medium is concentrated by precipitation in which polyethylene glycol (PEG) 8000 is dissolved in the culture medium (up to 10%) and the precipitate is dissolved in a buffer, for example phosphate-buffered saline (PBS, pH 7.0).

The harvested culture medium may be precipitated to produce a virus supernatant. In some embodiments, the harvested culture medium is precipitated to remove host cell DNA such as Vero cell DNA and other undesired material, such as Vero cell debris, from the harvested culture medium. In some embodiments, the harvested culture medium is concentrated prior to precipitation. In some embodiments, the harvested culture medium is precipitated by adding protamine sulfate (e.g. SEQ ID NO: 1) to the harvested culture medium and incubating the mixture, for example at +4° C. or on ice. In some embodiments, the harvested culture medium is treated with benzonase to remove host cell DNA e.g. Vero cell DNA and other undesired material, such as Vero cell debris, from the harvested culture medium. However, it was found that the treatment with protamine sulfate is preferred (see experimental part). In some embodiments, the precipitated culture medium is centrifuged to collect precipitated material and the supernatant containing the virus, referred to as a "virus supernatant," is collected.

The virus supernatant may be further purified after precipitation, for example density gradient ultracentrifugation. In some embodiments, the virus supernatant is further purified by sucrose gradient. Fractions may be collected from the sucrose gradients and assayed for presence of the virus. Methods for assaying for virus positive fractions include plaque assay, hemagglutination assay, polyacrylamide gel electrophoresis, and antigen assays such as Western blotting and ELISA. The fractions containing virus may be pooled based on titer of the virus and level of other impurities. The level or amount of impurities present in the virus supernatant can be estimated by testing for host cell DNA e.g. Vero cell DNA, virus aggregates and/or host cell protein e.g. Vero cell protein (see experimental part). A particular embodiment of the invention is the improved sucrose gradient that allows for an efficient protamine separation as shown in the experimental part. It was surprisingly found that the addition of a virus-containing fraction with 10% (w/w) sucrose to a simple three layer sucrose density gradient (e.g. a gradient comprising a 15% (w/w) sucrose solution, a 35% (w/w) sucrose solution, and a 50% (w/w) sucrose solution) resulted in efficient separation of protamine sulphate without much loss of virus. Thus a particularly preferred embodiment of the invention is the use of a sucrose density gradient that is able to efficiently separate protamine sulphate, wherein said sucrose density gradient is used in the purification of virus such as the viruses described herein, e.g. a Zika virus, yellow fever virus or Chikungunya virus.

To achieve a safe vaccine or composition for the administration to subjects, the virus supernatant may be inactivated (see experimental part for Zika virus). According to the current invention, the inactivation step or steps may be performed at any point in the process such as e.g., directly following harvest, before or after PS treatment or sucrose gradient centrifugation or any other permutation thereof. As used herein, the terms "inactivated" and "optimally inactivated" may be used interchangeably and refer to a process (or its result) by which the virus is rendered unable to infect a host cell (non-infectious), but that does not affect or substantially affect the antigenicity of the virus, for example, the immunogenic antigens exposed on the surface of the virus are able to stimulate an immune response in a subject (e.g., antigen-specific antibodies). By "does not affect or substantially affect the antigenicity of the virus" is meant that the inactivated virus retains at least 50%, at least 55%, at least 60%, at least 65%, at least 70%, at least 75%, at least 80%, at least 85%, at least 90%, at least 95%, at least 96%, at least 97%, at least 98%, at least 99%, or even essentially 100% of the antigenicity of a virus that is not subjected to inactivation.

A variety of methods are known in the art for inactivating viruses. In some embodiments, the virus is inactivated by chemical inactivation, thermal inactivation, pH inactivation, or UV inactivation.

In some embodiments, the inactivating is by chemical inactivation and involves contacting the virus with one or more chemical inactivation agents for a period of time under conditions such that the virus is inactivated but the antigenic epitopes are substantially intact. In some embodiments, the virus is inactivated for a period of time that is longer than is required to completely inactivate the virus. In some embodiments, the virus supernatant is inactivated for the number of days required to inactivate the virus plus at least one additional day. Samples of the virus supernatant may be taken at one or more times throughout the inactivation process and assessed for viral viability (infectivity) by any method known in the art, such as by infecting a monolayer of host cells (i.e., plaque assay). Using such a procedure, the period of time that is required to completely inactivate the virus can be determined, and a longer period of time is selected to ensure complete inactivation.

In some embodiments, the virus is contacted with a chemical inactivation agent for between 1 day and 50 days, between 2 days and 40 days, between 2 days and 30 days, between 2 days and 20 days, between 2 days and 10 days, between 3 days and 9 days, between 4 days and 8 days, between 5 days and 7 days, between 2 days and 5 days, or between 5 and 10 days. In some embodiments, the virus is contacted with one or more chemical inactivation agents for at least 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, or at least 50 days.

In some embodiments, the chemical inactivation is performed at about +5° C., +10° C., +15° C., +20° C., +25° C., +30° C., +35° C., +40° C., or about +45° C. In some embodiments, the chemical inactivation is performed at about +4° C. In some embodiments, the chemical inactivation is performed at about +22° C.

Any chemical inactivation agent known in the art may be suitable for inactivating the virus in the methods described herein. It will be appreciated by one of skill in the art that factors such as the chemical inactivation agent and the temperature at which inactivation is performed may affect the length of time (number of days) required to completely inactivate the virus. Examples of chemical inactivation agents include, without limitation, formaldehyde, enzymes, β-propiolactone, ethanol, trifluroacetic acid, acetonitrile, bleach, urea, guanidine hydrochloride, tri-n-butyl phosphate, ethylene-imine or a derivatives thereof, and organic solvents such as Tween, Triton, sodium deoxycholate, and sulfobetaine. A preferred inactivation is the inactivation with formaldehyde at 22° C.+/−2° C. for about 10 days.

In some embodiments, the inactivating agent is neutralized after chemical inactivation of the virus. In some embodiments, the inactivating agent is formaldehyde and is neutralized after chemical inactivation using sodium thiosulphate or sodium metabisulfite.

In some embodiments, the virus is inactivated by thermal inactivation. In some embodiments, the thermal inactivation involves exposing the virus to heat, such as dry heat or vapor heat, for a period of time. In some embodiments, the thermal inactivation involves exposing the virus to temperatures of about +40° C., +45° C., +50° C., +55° C., +60° C., +65° C., +70° C., +75° C., +80° C., +85° C., +90° C., +95° C., or about +100° C. In some embodiments, the virus is exposed to heat for at least 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, about 96 hours, or longer. A preferred thermal inactivation involves exposing the virus to temperatures of about +56° C. for 60 minutes.

In some embodiments, the virus is inactivated by exposing the virus to acidic or alkaline conditions for a period of time such that the virus is completely inactivated. The pH of a virus preparation may be adjusted to a desired pH, for example by the addition of an acid, a base, or a buffer with a particular pH to the virus preparation. In some embodiments, the virus is inactivated at an acidic pH of about 2, 2.5, 3, 3.5, 4, 4.5, 5 or about 5.5. In other embodiments, the virus is inactivated at an alkaline pH of about 8, 8.5, 9, 9.5, 10, or about 10.5.

In some embodiments, the virus is inactivated using UV inactivation. UV inactivation involves exposing the virus to energy-rich radiation, such as UV-A, UV-B, or UV-C light for a period of time.

It will be appreciated that any two or more methods of inactivation may be combined and performed concurrently or serially.

The inactivated virus may be subsequently dialyzed to remove any undesired material, including the inactivating agent and any neutralizing agent, and/or to replace the buffer with a buffer that is pharmaceutically acceptable for administration to subjects. In some embodiments, the inactivated virus is dialyzed with PBS. In addition or alternatively, the inactivated virus may be filtered, such as sterile filtered, through a 0.22 μm filter.

It is believed that the herein described improved process (comprising the PS treatment in combination with the optimized sucrose gradient) is applicable and efficient to any virus purification and in particular efficient for any RNA type virus (such as the herein described Zika and Chikungunya and yellow fever viruses) of similar size (i.e. about 50 to 100 nm). Furthermore, it is believed that the combination of the PS treatment with the optimized sucrose gradient allowing for a complete (or almost complete) separation of PS provides a very efficient virus purification in the very high range, e.g. above 70%, more preferably 75%, 80% or 90%, even more preferably 95%. It is believed that the complete reduction of PS in the virus fraction through the process of the invention allows a very efficient inactivation with almost no or very low viral loss e.g. below 30%, more preferably less than 25%, 20% or 10% loss, even more preferably less than 15% loss.

Any of the methods or uses described herein may be for the prevention of a virus infection in a subject. As used herein, the terms "prevent," and "preventing", include the administration of a virus vaccine or composition to a subject to reduce, or delay the onset of the manifestation of clinical or subclinical symptoms, complications, pathologies or biochemical indicia of a disease or infection, or to reduce or inhibit the spread/transmission of the virus. As used herein, "prevent" may also be construed as "protecting from". As used herein, antigen(s), such as an inactivated virus, that is administered to a subject prophylactically (e.g., prior to infection) may be referred to as a vaccine.

Zika Vaccine

As described herein Zika virus may cause any of a variety of symptoms upon infection of a subject, and is generally characterized by mild fever; rash (exanthema) on face, neck trunk, upper arms; headache; sensitivity to light; non-inflammatory joint pain; conjunctivitis; lack of appetite; diarrhea; abdominal pain; and/or dizziness. Zika virus infection during pregnancy is likely associated with microcephaly in the fetus/neonate. There is also a probable association between the onset of Guillain-Barré syndrome or symptoms thereof. Diagnosis of Zika virus infection in subjects exposed to Zika virus or suspected of being exposed to Zika virus involves detecting the presence of virus-specific antibodies and/or molecular testing, such as PCR or real-time PCR detection of Zika virus.

Provided herein are methods for administering a dose of a therapeutically effective amount of a Zika virus vaccine to a subject in need thereof. In some embodiments, the subject is a mammalian subject, such as a human, non-human primate, rodent, rabbit, sheep, dog, cat, horse, or cow. In some embodiments, the subject is a mouse. In some embodiments, the subject is a human subject, such as a child, an adult, or an elderly adult. In some embodiments, the subject is a female subject. In some embodiments, the subject is pregnant or planning on becoming pregnant. In some embodiments, the subject is at risk of being exposed to Zika virus. In some embodiments, the subject is living in or traveling to an area where Zika virus is present or is thought to be present. In some embodiments, the subject is living in or traveling to an area that is experiencing a Zika virus infection outbreak. In some embodiments, the subject is living in or traveling to an area where an arthropod vector capable of transmitting the Zika virus vector is present or is thought to be present.

Any of the Zika virus vaccines or compositions described herein may be administered to a subject in a therapeutically effective amount or a dose of a therapeutically effective amount. As used herein, a "therapeutically effective amount" of vaccine is any amount that results in a desired response or outcome in a subject, such as those described herein, including but not limited to prevention of infection, an immune response or an enhanced immune response to Zika virus, or prevention or reduction of symptoms associated with Zika disease.

In some embodiments, the therapeutically effective amount of a Zika virus vaccine or composition described herein is an amount sufficient to generate antigen-specific antibodies (e.g., anti-Zika virus antibodies). In some embodiments, the therapeutically effective amount is sufficient to seroconvert a subject with at least 70% probability. In some embodiments, the therapeutically effective amount is sufficient to seroconvert a subject with at least 75%, 80%, 85% 90%, 95%, 96%, 97%, 98%, or at least 99% probability. Whether a subject has been seroconverted can be assessed by any method known in the art, such as obtaining a serum sample from the subject and performing an assay to detect anti-Zika virus antibodies. In some embodiments, a subject is seroconverted if a serum sample from the subject contains an amount of anti-Zika virus antibodies that surpasses a threshold or predetermined baseline. A subject is generally considered seroconverted if there is at least a 4-fold increase in anti-Zika virus antibodies (i.e., anti-Zika E protein IgG antibodies) present in a serum sample from the subject as compared to a serum sample previously taken from the same subject.

In some embodiments, seroconversion of a subject is assessed by performing a plaque reduction neutralization test (PRNT). Briefly, PRNT is used to determine the serum titer required to reduce the number of Zika virus plaques by 50% (PRNT50) as compared to a control serum/antibody. The PRNT50 may be carried out using monolayers of Vero cells or any other cell type/line that can be infected with Zika virus. Sera from subjects are diluted and incubated with live, non-inactivated Zika virus. The serum/virus mixture may be applied to the Vero cells and incubated for a period of time. Plaques formed on the Vero cell monolayers are counted and compared to the number of plaques formed by the Zika virus in the absence of serum or a control antibody. A threshold of neutralizing antibodies of 1:10 dilution of serum in a PRNT50 is generally accepted as evidence of protection (Hombach et. al. Vaccine (2005) 23:5205-5211).

In some embodiments, the Zika virus may be formulated for administration in a composition, such as a pharmaceutical composition. The term "pharmaceutical composition" as used herein means a product that results from the mixing or combining of at least one active ingredient, such as an inactivated Zika virus, and one or more inactive ingredients, which may include one or more pharmaceutically acceptable excipient.

Pharmaceutical compositions of the invention, including vaccines, can be prepared in accordance with methods well known and routinely practiced in the art (see e.g., Remington: The Science and Practice of Pharmacy, Mack Publishing Co. 20th ed. 2000; and Ingredients of Vaccines—Fact Sheet from the Centers for Disease Control and Prevention, e.g., adjuvants and enhancers such as alum to help the vaccine improve its work, preservatives and stabilizers to help the vaccine remain unchanged (e.g., albumin, phenols, glycine)). Pharmaceutical compositions are preferably manufactured under GMP conditions. Typically a therapeutically effective dose of the inactivated Zika virus preparation is employed in the pharmaceutical composition of the invention. The inactivated Zika virus is formulated into pharmaceutically acceptable dosage forms by conventional methods known to those of skill in the art. Dosage regimens are adjusted to provide the optimum desired response (e.g., the prophylactic response).

Dosages of the active ingredients in the pharmaceutical compositions of the present invention can be varied so as to obtain an amount of the active ingredient which is effective to achieve the desired pharmaceutical response for a particular subject, composition, and mode of administration, without being toxic to the subject. The selected dosage level depends upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the subject being treated, and like factors.

A physician, veterinarian or other trained practitioner, can start doses of the inactivated Zika virus vaccine employed in the pharmaceutical composition at levels lower than that required to achieve the desired therapeutic effect and gradually increase the dosage until the desired effect (e.g., production of anti-Zika virus antibodies) is achieved. In general, effective doses of the compositions of the present invention, for the prophylactic treatment of groups of people as described herein vary depending upon many different factors, including means of administration, target site, physiological state of the patient, whether the patient is human or an animal, other medications administered, and the titer of anti-Zika virus antibodies desired. Dosages need to be titrated to optimize safety and efficacy. In some embodiments, the dosing regimen entails subcutaneous or intramuscular administration of a dose of inactivated Zika virus twice, once at day 0 and once at about day 7. In some embodiments, the dosing regimen entails subcutaneous administration of a dose of inactivated Zika virus twice, once at day 0 and once at about day 14. In some embodiments, the dosing regimen entails subcutaneous administration of a dose of inactivated Zika virus twice, once at day 0 and once at about day 28. In some embodiments, the inactivated Zika virus is administered to the subject once.

Any of the Zika virus vaccines or compositions described herein may be administered to a subject with, prior to, or after administration of one or more adjuvants. An adjuvant is a molecule that enhances a response in a subject, such as an immune response, to an antigen or other molecule. In some embodiments, an adjuvant may stabilize an antigen or other molecule. Determining whether a Zika virus vaccine or compositions thereof are administered with an adjuvant depends on various factors (e.g., type and extent of response desired) and will be evident to one of skill in the art. In some embodiments, administering any of the Zika virus vaccines or compositions described herein with, prior to, or after administration of an adjuvant may enhance the production of virus neutralizing (anti-Zika virus) antibodies. In some embodiments, a subject that is administered any of the Zika virus vaccines or compositions described herein with, prior to, or after administration of an adjuvant may only require a single administration of the Zika virus vaccine or composition to be seroconverted (produce a level of anti-Zika virus antibodies). Examples of adjuvants may include, without limitation, aluminium salt (aluminium hydroxide or aluminium phosphate), calcium phosphate hydroxide, paraffin oil, killed bacteria, bacterial toxins, toxoids, subunits of bacteria, squalene, thimerosal, detergents, IL-1, IL-2, IL-12, 2-component adjuvants, such as 2-component adjuvants containing an antibacterial peptide and a TLR9 agonist (e.g., IC310), and combinations such as Freund's complete adjuvant and Freund's incomplete adjuvant. In some embodiments, the Zika virus vaccines or compositions is administered with aluminium hydroxide. In some embodiments, the inactivated Zika virus vaccine or composition is administered with aluminium phosphate salt. A preferred aluminium salt is the aluminium hydroxide with reduced Cu content, e.g. lower than 1.25 ppb based on the weight of the Zika composition, an adjuvant described in detail in WO 2013/083726 or Schlegl et al., Vaccine 33 (2015) 5989-5996.

In some embodiments, the adjuvant is comprised of two components. In some embodiments, the 2-component adjuvant comprises an antibacterial peptide and a TLR9 agonist. In some embodiments, the antibacterial peptide is provided by the amino acid sequence $KLKL_5KLK$ (SEQ ID NO: 71). In some embodiments, the TLR9 agonist is a deoxyinosine-containing immunostimulatory oligodeoxynucleic acid molecule (I-ODN). In some embodiments, the I-ODN comprises the nucleic acid sequence $(dIdC)_{13}$ (SEQ ID NO: 70). In some embodiments, the adjuvant is IC31®. In some embodiments, the adjuvant is in nanoparticle form (See, e.g., U.S. Pat. No. 8,765,148 B2, incorporated by reference in its entirety). In some embodiments, the adjuvant is IC31®, i.e. $KLKL_5KLK$ (SEQ ID NO: 71) and the nucleic acid sequence $(dIdC)_{13}$ (SEQ ID NO: 70), in combination with an aluminium salt such as aluminium hydroxide.

The Zika virus vaccines or compositions described herein may be administered to a subject concomitantly with one or more vaccine to another infectious agent, such as another infectious agent is that present or thought to be present in the same geographic area as Zika virus. In some embodiments, the other infectious agent is one that the subject is also at risk of being in contact with. In some embodiments, the other infectious agent is transmitted by the same arthropod vector as Zika virus. In some embodiments, the other infectious agent is Japanese Encephalitis virus, Yellow Fever virus, Dengue virus and/or Chikungunya virus.

Also within the scope of the present disclosure are kits for use in prophylactically administering to a subject, for example to prevent or reduce the severity of Zika virus infection. Such kits can include one or more containers comprising a composition containing inactivated Zika virus, such as an inactivated Zika virus vaccine. In some embodiments, the kit may further include one or more additional containing comprising a second composition, such as a second vaccine. In some embodiments, the second vaccine is a vaccine for another arbovirus. In some embodiments, the second vaccine is a Dengue virus vaccine and/or a Chikungunya virus vaccine.

In some embodiments, the kit can comprise instructions for use in accordance with any of the methods described herein. The included instructions can comprise a description of administration of the composition containing inactivated Zika virus to prevent, delay the onset, or reduce the severity of Zika virus infection. The kit may further comprise a description of selecting a subject suitable for administration based on identifying whether that subject is at risk for exposure to Zika virus or contracting a Zika virus infection. In still other embodiments, the instructions comprise a description of administering a composition containing inactivated Zika virus to a subject at risk of exposure to Zika virus or contracting Zika virus infection.

The instructions relating to the use of the composition containing inactivated Zika virus generally include information as to the dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine readable instructions are also acceptable.

The kits of the present disclosure are in suitable packaging. Suitable packaging includes, but is not limited to, vials, bottles, jars, flexible packaging, and the like. Also contemplated are packages for use in combination with a specific device, such as a syringe or an infusion device. The container may have a sterile access port, for example the container may be a vial having a stopper pierceable by a hypodermic injection needle. At least one active agent in the composition is an inactivated Zika virus, as described herein.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

Unless otherwise defined herein, scientific and technical terms used in connection with the present disclosure shall have the meanings that are commonly understood by those of ordinary skill in the art. Further, unless otherwise required by context, singular terms shall include pluralities and plural terms hall include the singular. The methods and techniques of the present disclosure are generally performed according to conventional methods well-known in the art. Generally, nomenclatures used in connection with, and techniques of biochemistry, enzymology, molecular and cellular biology, microbiology, virology, cell or tissue culture, genetics and protein and nucleic chemistry described herein are those well-known and commonly used in the art. The methods and techniques of the present disclosure are generally performed according to conventional methods well known in the art and as described in various general and more specific references that are cited and discussed throughout the present specification unless otherwise indicated.

The present invention is further illustrated by the following examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove. However, the citation of any reference is not intended to be an admission that the reference is prior art.

TABLE 1

Overview of process buffers and stock solutions.

| Buffer | Composition | Final pH | Final conductivity [mS/cm] |
|---|---|---|---|
| A | 0.5M NaOH | | n.a. |
| B | 0.1M NaOH | | n.a. |
| C | 25 mM Tris, 150 mM NaCl | 7.4 ± 0.2 | 16.5 |
| D | 1M Tris | 7.4 ± 0.2 | n.a. |
| E | 4.5M NaCl | n.a. | n.a. |
| F | 1M NaCl | n.a. | n.a. |
| G | 1% SDS | n.a. | n.a. |
| H | 50% (w/w) Sucrose in 25 mM Tris, 150 mM NaCl | 7.4 ± 0.2 | n.a. |

TABLE 1-continued

| Overview of process buffers and stock solutions. | | | |
|---|---|---|---|
| Buffer | Composition | Final pH | Final conductivity [mS/cm] |
| I | 35% (w/w) Sucrose in 25 mM Tris, 150 mM NaCl | 7.4 ± 0.2 | n.a. |
| J | 15% (w/w) Sucrose in 25 mM Tris, 150 mM NaCl | 7.4 ± 0.2 | n.a. |
| K | 10 × PBS | 7.4 ± 0.2 | n.a. |
| L | 50 mg/mL Protamine sulphate | 7.4 ± 0.2 | n.a. |
| M | Drug substance formulation buffer (10 mM Tris(hydroxymethyl)-aminomethan, 5% Sucrose, 1% (10 mg/mL) rHSA) | 7.4 ± 0.2 | 1.3 |

TABLE 2

| Abbreviations. | |
|---|---|
| °Bx | Degrees Brix = sugar content (w/w) of an aqueous solution* |
| BSA | Bovine serum albumin |
| CC700 | Capto ™ Core 700 |
| ChikV | Chikungunya virus |
| CPE | Cytopathic effect |
| EtOH | Ethanol |
| EU | Endotoxin units |
| DS | Drug Substance |
| DP | Drug Product |
| DSP | Downstream Process |
| HCP | Host cell protein |
| hcDNA | Host cell DNA |
| hpi | Hours post infection |

TABLE 2-continued

| Abbreviations. | |
|---|---|
| HPLC | High Performance Liquid Chromatography |
| ID | Inner diameter |
| JEV | Japanese Encephalitis virus |
| LAL | Limulus amebocyte lysate |
| LDS buffer | Lithium dodecyl sulfate sample loading buffer |
| LOD | Limit of detection |
| LOQ | Limit of quantitation |
| MALLS | Multiangle light scattering |
| mAU | Milli absorbance units |
| MS | Mass spectroscopy |
| NIV | Neutralized inactivated virus |
| PBS | Phosphate buffered saline |
| PD | Process development |
| PFU | Plaque forming units |
| p.i. | Post-infection |
| PS | Protamine sulphate or protamine sulfate |
| rcf | Relative centrifugal force |
| rHSA | Recombinant human serum albumin |
| Rms radius | Root mean square radius |
| rMSB | Research master seed bank |
| RSD | Relative standard deviation |
| SEC | Size exclusion chromatography |
| SGC | Sucrose gradient centrifugation |
| SGP | Sucrose gradient purified |
| SDS | Sodium dodecyl sulphate |
| TBS | Tris buffered saline |
| TFF | Tangential flow filtration |
| TCID50 | Tissue culture infectious dose 50% |
| UF/DF | Ultrafiltration/diafiltration |
| WFI | Water for injection |
| ZikaV | Zika virus |

*Degrees Brix (°Bx) is the sugar content of an aqueous solution. One degree Brix is 1 gram of sucrose in 100 grams of solution and represents the strength of the solution as percentage by mass. °Bx corresponds to the sucrose content in percent (w/w), e.g., 45 °Bx equals 45% (w/w) sucrose.

TABLE A

Primers for Zika virus sequencing: lower case letters indicate bases not included in ZIKA but containing restriction sites for later cloning when needed (therefore, two Tms provided).

| Primer Pair | Oligoname | Primer sequence (5'-3') restriction sites (lower case) | Tm (gene-specific) | Tm (entire primer) | Amplicon size [bp] |
|---|---|---|---|---|---|
| 1 | 9320_Zika_PF_1F | SEQ ID NO: 80 ttaggatccGTTGTTGATCTGTGTGAAT | 69.9 | 74.6 | 707 |
| | 9321_Zika_PF_1R | SEQ ID NO: 81 taactcgagCGTACACAACCCAAGTT | 69.3 | 75.6 | |
| 2 | 9322_Zika_PF_2F | SEQ ID NO: 82 ttaggatccTCACTAGACGTGGGAGTG | 70 | 73.9 | 704 |
| | 9323_Zika_PF_2R | SEQ ID NO: 83 taactcgagAAGCCATGTCYGATATTGAT | 69.8 | 73.7 | |
| 3 | 9324_Zika_PF_3F | SEQ ID NO: 84 ttaggatccGCATACAGCATCAGGTG | 72.3 | 74.5 | 712 |
| | 9325_Zika_PF_3R | SEQ ID NO: 85 taactcgagTGTGGAGTTCCGGTGTCT | 72 | 76.4 | |
| 4 | 9326_Zika_PF_4F | SEQ ID NO: 86 ttaggatccGAATAGAGCGAARGTTGAGATA | 70.9 | 74 | 712 |
| | 9327_Zika_PF_4R | SEQ ID NO: 87 taactcgAGTGGTGGGTGATCTTCTTCT | 70.5 | 73.7 | |
| 5 | 9328_Zika_PF_5F | SEQ ID NO: 88 ttaggatcCAGTCACAGTGGAGGTACAGTAC | 70.3 | 75 | 704 |
| | 9329_Zika_PF_5R | SEQ ID NO: 89 taactcgagCRCAGATACCATCTTCCC | 71.5 | 77.3 | |

TABLE A-continued

Primers for Zika virus sequencing: lower case letters indicate bases not included in ZIKA but containing restriction sites for later cloning when needed (therefore, two Tms provided).

| Primer Pair | Oligoname | Primer sequence (5'-3') restriction sites (lower case) | Tm (gene-specific) | Tm (entire primer) | Amplicon size [bp] |
|---|---|---|---|---|---|
| 6 | 9330_Zika_PF_6F | SEQ ID NO: 90 ttaggatCCCTTATGTGCTTGGCCTTAG | 70.7 | 72.7 | 698 |
| | 9331_Zika_PF_6R | SEQ ID NO: 91 taactcgagTCTTCAGCCTCCATGTG | 70.4 | 76.9 | |
| 7 | 9332_Zika_PF_7F | SEQ ID NO: 92 ttaggatccAATGCCCACTCAAACATAGA | 71.9 | 75 | 716 |
| | 9333_Zika_PF_7R | SEQ ID NO: 93 taactcgagTCATTCTCTTCTTCAGCCCTT | 71 | 74 | |
| 8 | 9334_Zika_PF_8F | SEQ ID NO: 94 ttaggatccAAGGGTGATCGAGGAAT | 70.9 | 75.2 | 703 |
| | 9335_Zika_PF_8R | SEQ ID NO: 95 taactcgagTTCCCTTCAGAGAGAGGAGC | 71.9 | 73.4 | |
| 9 | 9336_Zika_PF_9F | SEQ ID NO: 96 ttaggatccTCTTTTGCAAACTGCGATC | 71.9 | 75 | 699 |
| | 9337_Zika_PF_9R | SEQ ID NO: 97 taactcgagTCCAGCTGCAAAGGGTAT | 71 | 74.9 | |
| 10 | 9338_Zika_PF_10F | SEQ ID NO: 98 ttaggatccGTGTGGACATGTACATTGA | 71.4 | 75.8 | 706 |
| | 9339_Zika_PF_10R | SEQ ID NO: 99 taactcgagCCCATTGCCATAAAGTC | 70.4 | 75.8 | |
| 11 | 9340_Zika_PF_11F | SEQ ID NO: 100 ttaggatccTCATACTGTGGTCCATGGA | 71.6 | 78.1 | 692 |
| | 9341_Zika_PF_11R | SEQ ID NO: 101 taactcgagGCCCATCTCAACCCTTG | 74 | 78 | |
| 12 | 9342_Zika_PF_12F | SEQ ID NO: 102 ttaggatccTAGAGGGCTTCCAGTGC | 70.9 | 74 | 707 |
| | 9343_Zika_PF_12R | SEQ ID NO: 103 taactcgAGATACTCATCTCCAGGTTTGTTG | 70.2 | 72.2 | |
| 13 | 9344_Zika_PF_13F | SEQ ID NO: 104 ttaggatccGAAAACAAAACATCAAGAGTG | 70.6 | 75.4 | 726 |
| | 9345_Zika_PF_13R | SEQ ID NO: 105 taactcgagGAATCTCTCTGTCATGTGTCCT | 71.9 | 75.6 | |
| 14 | 9346_Zika_PF_14F | SEQ ID NO: 106 ttaggatccTTGATGGCACGACCAAC | 73.1 | 75.6 | 715 |
| | 9347_Zika_PF_14R | SEQ ID NO: 107 ttaggatccGTTGTTGATCTGTGTGAAT | 70.8 | 77.9 | |
| 15 | 9348_Zika_PF_15F | SEQ ID NO: 108 taactcgagCAGGTCAATGTCCATTG | 71.9 | 75.4 | 719 |
| | 9349_Zika_PF_15R | SEQ ID NO: 109 ttaggatccTGTTGTGTTCCTATTGCTGGT | 73.9 | 77.2 | |
| 16 | 9350_Zika_PF_16F | SEQ ID NO: 110 taactcgaGTGATCAGRGCCCCAGC | 72.3 | 75.4 | 703 |
| | 9351_Zika_PF_16R | SEQ ID NO: 111 ttaggatccTGCTGCCCAGAAGAGAA | 72 | 76.3 | |
| 17 | 9352_Zika_PF_17F | SEQ ID NO: 112 taactcgaGCACCAACAYGGGTTCTT | 73.6 | 76 | 705 |
| | 9353_Zika_PF_17R | SEQ ID NO: 113 ttaggatcCTCAAGGACGGTGTGGC | 72 | 75.5 | |

TABLE A-continued

Primers for Zika virus sequencing: lower case letters indicate bases not included in ZIKA but containing restriction sites for later cloning when needed (therefore, two Tms provided).

| Primer Pair | Oligoname | Primer sequence (5'-3') restriction sites (lower case) | Tm (gene-specific) | Tm (entire primer) | Amplicon size [bp] |
|---|---|---|---|---|---|
| 18 | 9354_Zika_PF_18F | SEQ ID NO: 114 taactcgagCAATGATCTTCATGTTGGG | 71.7 | 75.8 | 699 |
| | 9355_Zika_PF_18R | SEQ ID NO: 115 ttaggatccTATGGGGGAGGACTGGT | 71 | 74.1 | |
| 19 | 9356_Zika_PF_19F | SEQ ID NO: 116 taactcGAGCCCAGAACCTTGGATC | 73.3 | 75.5 | 711 |
| | 9357_Zika_PF_19R | SEQ ID NO: 117 ttaggatcCAGACCCCCAAGAAGGC | 71.3 | 76.9 | |
| 20 | 9358_Zika_PF_20F | SEQ ID NO: 118 taactcgagCCCCTTTGGTCTTGTCT | 71.7 | 75 | 706 |
| | 9359_Zika_PF_20R | SEQ ID NO: 119 ttaggatccAGGAAGGATGTATGCAGATG | 71.9 | 73.9 | |
| 21 | 9360_Zika_PF_21F | SEQ ID NO: 120 taactcgagACATTTGCGCATATGATTTTG | 70.4 | 75.7 | 709 |
| | 9361_Zika_PF_21R | SEQ ID NO: 121 ttaggatccAGGAAGGACACACAAGAGT | 71.8 | 75 | |
| 22 | 9362_Zika_PF_22F | SEQ ID NO: 122 taactcgagACAGGCTGCACAGCTTT | 70 | 79.1 | 581 |
| | 9363_Zika_PF_22R | SEQ ID NO: 123 ttaggatccTCTCTCATAGGGCACAGAC | 74.8 | 81.1 | |

SEQUENCES

SEQ ID NO: 1
A typical form of protamine
PRRRRSSSRP VRRRRRPRVS RRRRRRGGRR RR

Provided below are examples of nucleic acid sequences of the genomes of_Zika_viruses that may be used in the methods, compositions, and/or vaccines described herein.

SEQ ID NO: 2
KU321639.1 Zika virus strain ZikaSPH2015, Brazil, complete genome (SEQ ID NO: 2)
GTTGTTACTGTTGCTGACTCAGACTGCGACAGTTCGAGTTTGAAGCGAAAGCTAGCAACAGTATCAACAGGTTTTATTTGG
ATTTGGAAACGAGAGTTTCTGGTCATGAAAAACCCAAAAAAGAAATCCGGAGGATTCCGGATTGTCAATATGCTAAAACG
CGGAGTAGCCCGTGTGAGCCCCTTTGGGGGCTTGAAGAGGCTGCCAGCCGGACTTCTGCTGGGTCATGGGCCCATCAGG
ATGGTCTTGGCAATTCTAGCCTTTTTGAGATTCACGGCAATCAAGCCATCACTGGGTCTCATCAATAGATGGGGTTCAGTG
GGGAAAAAAGAGGCTATGGAAATAATAAAGAAGTTCAAGAAAGATCTGGCTGCCATGCTGAGAATAATCAATGCTAGGA
AGGAGAAGAAGAGACGGGGCGCAGATACTAGTGTCGGAATTGTTGGCCTCCTGCTGACCACAGCTATGGCAGCGGAGG
TCACTAGACGTGGGAGTGCATACTATATGTACTTGGACAGAAACGATGCTGGGGAGGCCATATCTTTTCCAACCACATTG
GGGATGAATAAGTGTTATATACAGATCATGGATCTTGGACACATGTGTGATGCCACCATGAGCTATGAATGCCCTATGCT
GGATGAGGGGGTGGAACCAGATGACGTCGATTGTTGGTGCAACACGACGTCAACTTGGGTTGTGTACGGAACCTGCCAT
CACAAAAAAGGTGAAGCACGGAGATCTAGAAGAGCTGTGACGCTCCCCTCCCATTCCACTAGGAAGCTGCAAACGCGGT
CGCAAACCTGGTTGGAATCAAGAGAATACACAAAGCACTTGATTAGAGTCGAAAATTGGATATTCAGGAACCCTGGCTTC
GCGTTAGCAGCAGCTGCCATCGCTTGGCTTTTGGGAAGCTCAACGAGCCAAAAAGTCATATACTTGGTCATGATACTGCT
GATTGCCCCGGCATACAGCATCAGGTGCATAGGAGTCAGCAATAGGGACTTTGTGGAAGGTATGTCAGGTGGGACTTGG
GTTGATATTGTCTTGGAACATGGAGGTTGTGTCACCGTAATGGCACAGGACAAACCGACTGTCGACATAGAGCTGGTTAC
AACAACAGTCAGCAACATGGCGGAGGTAAGATCCTACTGCTATGAGGCATCAATATCAGACATGGCTTCGGACAGCCGCT
GCCCAACACAAGGTGAAGCCTACCTTGACAAGCAATCAGACACTCAATATGTCTGCAAAAGAACGTTAGTGGACAGAGGC
TGGGGAAATGGATGTGGACTTTTTGGCAAAGGGAGTCTGGTGACATGCGCTAAGTTTGCATGCTCCAAGAAAATGACCG
GGAAGAGCATCCAGCCAGAGAATCTGGAGTACCGGATAATGCTGTCAGTTCATGGCTCCCAGCACAGTGGGATGATCGT
TAATGACACAGGACATGAAACTGATGAGAATAGAGCGAAGGTTGAGATAACGCCCAATTCACCAAGAGCCGAAGCCACC
CTGGGGGGTTTTGGAAGCCTAGGACTTGATTGTGAACCGAGGACAGGCCTTGACTTTTCAGATTTGTATTACTTGACTATG
AATAACAAGCACTGGTTGGTTCACAAGGAGTGGTTCCACGACATTCCATTACCTTGGCACGCTGGGGCAGACACCGGAAC
TCCACACTGGAACAACAAAGAAGCACTGGTAGAGTTCAAGGACGCACATGCCAAAAGGCAAACTGTCGTGGTTCTAGGG
AGTCAAGAAGGAGCAGTTCACACGGCCCTTGCTGGAGCTCTGGAGGCTGAGATGGATGGTGCAAAGGGAAGGCTGTCCT
CTGGCCACTTGAAATGTCGCCTGAAAATGGATAAACTTAGATTGAAGGGCGTGTCATACTCCTTGTGTACCGCAGCGTTCA
CATTCACCAAGATCCCGGCTGAAACACTGCACGGGACAGTCACAGTGGAGGTACAGTACGCAGGGACAGATGGACCTTG
CAAGGTTCCAGCTCAGATGGCGGTGGACATGCAAACTCTGACCCCAGTTGGGAGGTTGATAACCGCTAACCCCGTAATCA
CTGAAAGCACTGAGAACTCTAAGATGATGCTGGAACTTGATCCACCATTTGGGGACTCTTACATTGTCATAGGAGTCGGG -continued

| SEQUENCES |
| --- |
| GAGAAGAAGATCACCCACCACTGGCACAGGAGTGGCAGCACCATTGGAAAAGCATTTGAAGCCACTGTGAGAGGTGCCA |
| AGAGAATGGCAGTCTTGGGAGACACAGCCTGGGACTTTGGATCAGTTGGAGGCGCTCTCAACTCATTGGGCAAGGGCAT |
| CCATCAAATTTTTGGAGCAGCTTTCAAATCATTGTTTGGAGGAATGTCCTGGTTCTCACAAATTCTCATTGGAACGTTGCTG |
| ATGTGGTTGGGTCTGAACACAAAGAATGGATCTATTTCCCTTATGTGCTTGGCCTTAGGGGGAGTGTTGATCTTCTTATCC |
| ACAGCCGTCTCTGCTGATGTGGGGTGCTCGGTGGACTTCTCAAAGAAGGAGACGAGATGCGGTACAGGGGTGTTCGTCT |
| ATAACGACGTTGAAGCCTGGAGGGACAGGTACAAGTACCATCCTGACTCCCCCCGTAGATTGGCAGCAGCAGTCAAGCA |
| AGCCTGGGAAGATGGTATCTGCGGGATCTCCTCTGTTTCAAGAATGGAAAACATCATGTGGAGATCAGTAGAAGGGGAG |
| CTCAACGCAATCCTGGAAGAGAATGGAGTTCAACTGACGGTCGTTGTGGGATCTGTAAAAAACCCCATGTGGAGAGGTC |
| CACAGAGATTGCCCGTGCCTGTGAACGAGCTGCCCCACGGCTGGAAGGCTTGGGGGAAATCGCACTTCGTCAGAGCAGC |
| AAAGACAAATAACAGCTTTGTCGTGGATGGTGACACACTGAAGGAATGCCCACTCAAACATAGAGCATGGAACAGCTTTC |
| TTGTGGAGGATCATGGGTTCGGGGTATTTCACACTAGTGTCTGGCTCAAGGTTAGAGAAGATTATTCATTAGAGTGTGAT |
| CCAGCCGTTATTGGAACAGCTGTTAAGGGAAAGGAGGCTGTACACAGTGATCTAGGCTACTGGATTGAGAGTGAGAAGA |
| ATGACACATGGAGGCTGAAGAGGGCCCATCTGATCGAGATGAAAACATGTGAATGGCCAAAGTCCCACACATTGTGGAC |
| AGATGGAATAGAAGAGAGTGATCTGATCATACCCAAGTCTTTAGCTGGGCCACTCAGCCATCACAATACCAGAGAGGGCT |
| ACAGGACCCAAATGAAAGGGCCATGGCACAGTGAAGAGCTTGAAATTCGGTTTGAGGAATGCCCAGGCACTAAGGTCCA |
| CGTGGAGGAAACATGTGGAACAAGAGGACCATCTCTGAGATCAACCACTGCAAGCGGAAGGGTGATCGAGGAATGGTG |
| CTGCAGGGAGTGCACAATGCCCCCACTGTCGTTCCGGGCTAAAGATGGCTGTTGGTATGGAATGGAGATAAGGCCCAGG |
| AAAGAACCAGAAAGCAACTTAGTAAGGTCAATGGTGACTGCAGGATCAACTGATCACATGGATCACTTCTCCCTTGGAGT |
| GCTTGTGATTCTGCTCATGGTGCAGGAAGGGCTGAAGAAGAGAATGACCACAAAGATCATCATAAGCACATCAATGGCA |
| GTGCTGGTAGCTATGATCCTGGGAGGATTTTCAATGAGTGACCTGGCTAAGCTTGCAATTTTGATGGGTGCCACCTTCGC |
| GGAAATGAACACTGGAGGAGATGTAGCTCATCTGGCGCTGATAGCGGCATTCAAAGTCAGACCAGCGTTGCTGGTATCTT |
| TCATCTTCAGAGCTAATTGGACACCCCGTGAAAGCATGCTGCTGGCCTTGGCCTCGTGTCTTTTGCAAACTGCGATCTCCG |
| CCTTGGAAGGCGACCTGATGGTTCTCATCAATGGTTTTGCTTTGGCCTGGTTGGCAATACGAGCGATGGTTGTTCCACGCA |
| CTGATAACATCACCTTGGCAATCCTGGCTGCTCTGACACCACTGGCCCGGGGCACACTGCTTGTGGCGTGGAGAGCAGGC |
| CTTGCTACTTGCGGGGGGTTTATGCTCCTCTCTCTGAAGGGAAAAGGCAGTGTGAAGAAGAACTTACCATTTGTCATGGC |
| CCTGGGACTAACCGCTGTGAGGCTGGTCGACCCCATCAACGTGGTGGGGCTGCTGTTGCTCACAAGGAGTGGGAAGCGG |
| AGCTGGCCCCCTAGCGAAGTACTCACAGCTGTTGGCCTGATATGCGCATTGGCTGGAGGGTTCGCCAAGGCAGATATAGA |
| GATGGCTGGGCCCATGGCCGCGGTCGGTCTGCTAATTGTCAGTTACGTGGTCTCAGGAAAGAGTGTGGACATGTACATTG |
| AAAGAGCAGGTGACATCACATGGGAAAAAGATGCGGAAGTCACTGGAAACAGTCCCCGGCTCGATGTGGCGCTAGATG |
| AGAGTGGTGATTTCTCCCTGGTGGAGGATGACGGTCCCCCCATGAGAGAGATCATACTCAAGGTGGTCCTGATGACCATC |
| TGTGGCATGAACCCAATAGCCATACCCTTTGCAGCTGGAGCGTGGTACGTATACGTGAAGACTGGAAAAAGGAGTGGTG |
| CTCTATGGGATGTGCCTGCTCCCAAGGAAGTAAAAAAGGGGGAGACCACAGATGGAGTGTACAGAGTAATGACTCGTAG |
| ACTGCTAGGTTCAACACAAGTTGGAGTGGGAGTTATGCAAGAGGGGGTCTTTCACACTATGTGGCACGTCACAAAAGGA |
| TCCGCGCTGAGAAGCGGTGAAGGGAGACTTGATCCATACTGGGGAGATGTCAAGCAGGATCTGGTGTCATACTGTGGTC |
| CATGGAAGCTAGATGCCGCCTGGGACGGGCACAGCGAGGTGCAGCTCTTGGCCGTGCCCCCCGGAGAGAGAGCGAGGA |
| ACATCCAGACTCTGCCCGGAATATTTAAGACAAAGGATGGGGACATTGGAGCGGTTGCGCTGGATTACCCAGCAGGAAC |
| TTCAGGATCTCCAATCCTAGACAAGTGTGGGAGAGTGATAGGACTTTATGGCAATGGGGTCGTGATCAAAAATGGGAGT |
| TATGTTAGTGCCATCACCCAAGGGAGGAGGGAGGAAGAGACTCCTGTTGAGTGCTTCGAGCCTTCGATGCTGAAGAAGA |
| AGCAGCTAACTGTCTTAGACTTGCATCCTGGAGCTGGGAAAACCAGGAGAGTTCTTCCTGAAATAGTCCGTGAAGCCATA |
| AAAACAAGACTCCGTACTGTGATCTTAGCTCCAACCAGGGTTGTCGCTGCTGAAATGGAGGAAGCCCTTAGAGGGCTTCC |
| AGTGCGTTATATGACAACAGCAGTCAATGTCACCCACTCTGGAACAGAAATCGTCGACTTAATGTGCCATGCCACCTTCAC |
| TTCACGTCTACTACAGCCAATCAGAGTCCCCAACTATAATCTGTATATTATGGATGAGGCCCACTTCACAGATCCCTCAAGT |
| ATAGCAGCAAGAGGATACATTTCAACAAGGGTTGAGATGGGCGAGGCGGCTGCCATCTTCATGACCGCCACGCCACCAG |
| GAACCCGTGACGCATTTCCGGACTCCAACTCACCAATTATGGACACCGAAGTGGAAGTCCCAGAGAGAGCCTGGAGCTCA |
| GGCTTTGATTGGGTGACGGATTATTCTGGAAAAACAGTTTGGTTTGTTCCAAGCGTGAGGAACGGCAATGAGATCGCAGC |
| TTGTCTGACAAAGGCTGGAAAACGGGTCATACAGCTCAGCAGAAAGACTTTTGAGACAGAGTTCCAGAAAACAAAACATC |
| AAGAGTGGGACTTTGTCGTGACAACTGACATTTCAGAGATGGGCGCCAACTTTAAAGCTGACCGTGTCATAGATTCCAGG |
| AGATGCCTAAAGCCGGTCATACTTGATGGCGAGAGAGTCATTCTGGCTGGACCCATGCCTGTCACACATGCCAGCGCTGC |
| CCAGAGGAGGGGGCGCATAGGCAGGAATCCCAACAAACCTGGAGATGAGTATCTGTATGGAGGTGGGTGCGCAGAGAC |
| TGACGAAGACCATGCACACTGGCTTGAAGCAAGAATGCTCCTTGACAATATTTACCTCCAAGATGGCCTCATAGCCTCGCT |
| CTATCGACCTGAGGCCGACAAAGTAGCAGCCATTGAGGGAGAGTTCAAGCTTAGGACGGAGCAAAGGAAGACCTTTGTG |
| GAACTCATGAAAAGAGGAGATCTTCCTGTTTGGCTGGCCTATCAGGTTGCATCTGCCGGAATAACCTACACAGATAGAAG |
| ATGGTGCTTTGATGGCACGACCAACAACACCATAATGGAAGACAGTGTGCCGGCAGAGGTGTGGACCAGACACGGAGA |
| GAAAAGAGTGCTCAAACCGAGGTGGATGGACGCCAGAGTTTGTTCAGATCATGCGGCCCTGAAGTCATTCAAGGAGTTT |
| GCCGCTGGGAAAAGAGGAGCGGCTTTTGGAGTGATGGAAGCCCTGGGAACACTGCCAGGACACATGACAGAGAGATTC |
| CAGGAAGCCATTGACAACCTCGCTGTGCTCATGCGGGCAGAGACTGGAAGCAGGCCTTACAAAGCCGCGGCGGCCCAAT |
| TGCCGGAGACCCTAGAGACCATTATGCTTTTGGGGTTGCTGGGAACAGTCTCGCTGGGAATCTTTTTCGTCTTGATGAGG |
| AACAAGGGCATAGGGAAGATGGGCTTTGGAATGGTGACTCTTGGGGCCAGCGCATGGCTCATGTGGCTCTCGGAAATTG |
| AGCCAGCCAGAATTGCATGTGTCCTCATTGTTGTGTTCCTATTGCTGGTGGTGCTCATACCTGAGCCAGAAAAGCAAAGAT |
| CTCCCCAGGACAACCAAATGGCAATCATCATCATGGTAGCAGTAGGTCTTCTGGGCTTGATTACCGCCAATGAACTCGGAT |
| GGTTGGAGAGAACAAAGAGTGACCTAAGCCATCTAATGGGAAGGAGAGAGGAGGGGGCAACCATGGGATTCTCAATGG |
| ACATTGACCTGCGGCCAGCCTCAGCTTGGGCCATCTATGCTGCCTTGACAACTTTCATTACCCCAGCCGTCCAACATGCAGT |
| GACCACTTCATACAACAACTACTCCTTAATGGCGATGGCCACGCAAGCTGGAGTGTTGTTTGGTATGGGCAAAGGGATGC |
| CATTCTACGCATGGGACTTTGGAGTCCCGCTGCTAATGATAGGTTGCTACTCACAATTAACGCCCCTGACCCTAATAGTGG |
| CCATCATTTTGCTCGTGGCGCACTACATGTACTTGATCCCAGGGCTGCAGGCAGCAGCTGCGCGTGCTGCCCAGAAGAGA |
| ACGGCAGCTGGCATCATGAAGAACCCTGTTGTGGATGGAATAGTGGTGACTGACATTGACACAATGACAATTGACCCCCA |
| AGTGGAGAAAAAGATGGGACAGGTGCTACTCATGGCAGTAGCCGTCTCCAGCGCCATACTGTCGCGGACCGCCTGGGGG |
| TGGGGGGAGGCTGGGGCCCTGATCACAGCCGCAACTTCCACTTTGTGGGAAGGCTCTCCGAACAAGTACTGGAACTCCTC |
| TACAGCCACTTCACTGTGTAACATTTTTAGGGGAAGTTACTTGGCTGGAGCTTCTCTAATCTACACAGTAACAAGAAACGC |
| TGGCTTGGTCAAGAGACGTGGGGGTGGAACAGGAGAGACCCTGGGAGAGAAATGGAAGGCCCGCTTGAACCAGATGTC |
| GGCCCTGGAGTTCTACTCCTACAAAAAGTCAGGCATCACCGAGGTGTGCAGAGAAGAGGCCCGCCGCGCCCTCAAGGAC |
| GGTGTGGCAACGGGAGGCCATGCTGTGTCCCGAGGAAGTGCAAAGCTGAGATGGTTGGTGGAGCGGGGATACCTGCAG |
| CCCTATGGAAAGGTCATTGATCTTGGATGTGGCAGAGGGGGCTGGAGTTACTACGCCGCCACCATCCGCAAAGTTCAAGA |
| AGTGAAAGGATACACAAAAGGAGGCCCTGGTCATGAAGAACCCGTGTTGGTGCAAAGCTATGGGTGGAACATAGTCCGT |
| CTTAAGAGTGGGGTGGACGTCTTTCATATGGCGGCTGAGCCGTGTGACACGTTGCTGTGTGACATAGGTGAGTCATCATC |
| TAGTCCTGAAGTGGAAGAAGCACGGACGCTCAGAGTCCTCTCCATGGTGGGGGATTGGCTTGAAAAAAGACCAGGAGCC |
| TTTTGTATAAAAGTGTTGTGCCCATACACCAGCACTATGATGGAAACCCTGGAGCGACTGCAGCGTAGGTATGGGGGAG |

-continued

| SEQUENCES |
| --- |

GACTGGTCAGAGTGCCACTCTCCCGCAACTCTACACATGAGATGTACTGGGTCTCTGGAGCGAAAAGCAACACCATAAAA
AGTGTGTCCACCACGAGCCAGCTCCTCTTGGGGCGCATGGACGGGCCTAGGAGGCCAGTGAAATATGAGGAGGATGTGA
ATCTCGGCTCTGGCACGCGGGCTGTGGTAAGCTGCGCTGAAGCTCCCAACATGAAGATCATTGGTAACCGCATTGAAAGG
ATCCGCAGTGAGCACGCGGAAACGTGGTTCTTTGACGAGAACCACCCATATAGGACATGGGCTTACCATGGAAGCTATGA
GGCCCCCACACAAGGGTCAGCGTCCTCTCTAATAAACGGGGTTGTCAGGCTCCTGTCAAAACCCTGGGATGTGGTGACTG
GAGTCACAGGAATAGCCATGACCGACACCACACCGTATGGTCAGCAAAGAGTTTTCAAGGAAAAAGTGGACACTAGGGT
GCCAGACCCCCAAGAAGGTACTCGTCAGGTTATGAGCATGGTCTCTTCCTGGTTGTGGAAAGAGCTAGGCAAACACAAAC
GGCCACGAGTCTGTACCAAAGAAGAGTTCATCAACAAGGTTCGTAGCAATGCAGCATTAGGGGCAATATTTGAAGAGGA
AAAAGAGTGGAAGACTGCAGTGGAAGCTGTGAACGATCCAAGGTTCTGGGCTCTAGTGGACAAGGAAAGAGAGCACCA
CCTGAGAGGAGAGTGCCAGAGTTGTGTGTACAACATGATGGGAAAAAGAGAAAAGAAACAAGGGGAATTTGGAAAGGC
CAAGGGCAGCCGCGCCATCTGGTATATGTGGCTAGGGGCTAGATTTCTAGAGTTCGAAGCCCTTGGATTCTTGAACGAGG
ATCACTGGATGGGGAGAGAGAACTCAGGAGGTGGTGTTGAAGGGCTGGGATTACAAAGACTCGGATATGTCCTAGAAG
AGATGAGTCGCATACCAGGAGGAAGGATGTATGCAGATGACACTGCTGGCTGGGACACCCGCATCAGCAGGTTTGATCT
GGAGAATGAAGCTCTAATCACCAACCAAATGGAGAAAGGGCACAGGGCCTTGGCATTGGCCATAATCAAGTACACATAC
CAAAACAAAGTGGTAAAGGTCCTTAGACCAGCTGAAAAAGGGAAAACAGTTATGGACATTATTTCGAGACAAGACCAAA
GGGGGAGCGGACAAGTTGTCACTTACGCTCTTAACACATTTACCAACCTAGTGGTGCAACTCATTCGGAATATGGAGGCT
GAGGAAGTCCTAGAGATGCAAGACTTGTGGCTGCTGCGGAGGTCAGAGAAAGTGACCAACTGGTTGCAGAGCAACGGA
TGGGATAGGCTCAAACGAATGGCAGTCAGTGGAGATGATTGCGTTGTGAAGCCAATTGATGATAGGTTTGCACATGCCCT
CAGGTTCTTGAATGATATGGGAAAAGTTAGGAAGGACACACAAGAGTGGAAACCCTCAACTGGATGGGACAACTGGGAA
GAAGTTCCGTTTTGCTCCCACCACTTCAACAAGCTCCATCTCAAGGACGGGAGGTCCATTGTGGTTCCCTGCCGCCACCAA
GATGAACTGATTGGCCGGGCCCGCGTCTCTCCAGGGGCGGGATGGAGCATCCGGGAGACTGCTTGCCTAGCAAAATCAT
ATGCGCAAATGTGGCAGCTCCTTTATTTCCACAGAAGGGACCTCCGACTGATGGCCAATGCCATTTGTTCATCTGTGCCAG
TTGACTGGGTTCCAACTGGGAGAACTACCTGGTCAATCCATGGAAAGGGAGAATGGATGACCACTGAAGACATGCTTGT
GGTGTGGAACAGAGTGTGGATTGAGGAGAACGACCACATGGAAGACAAGACCCCAGTTACGAAATGGACAGACATTCCC
TATTTGGGAAAAAGGGAAGACTTGTGGTGTGGATCTCTCATAGGGCACAGACCGCGCACCACCTGGGCTGAGAACATTA
AAAACACAGTCAACATGGTGCGCAGGATCATAGGTGATGAAGAAAAGTACATGGACTACCTATCCACCCAAGTTCGCTAC
TTGGGTGAAGAAGGGTCTACACCTGGAGTGCTGTAAGCACCAATCTTAATGTTGTCAGGCCTGCTAGTCAGCCACAGCTT
GGGGAAAGCTGTGCAGCCTGTGACCCCCCCAGGAGAAGCTGGGAAACCAAGCCTATAGTCAGGCCGAGAACGCCATGG
CACGGAAGAAGCCATGCTGCCTGTGAGCCCCTCAGAGGACACTGAGTCAAAAAACCCCACGCGCTTGGAGGCGCAGGAT
GGGAAAAGAAGGTGGCGACCTTCCCCACCCTTCAATCTGGGGCCTGAACTGGAGATCAGCTGTGGATCTCCAGAAGAGG
GACTAGTGGTTAGAGGAGA

SEQ ID NO: 3
KU497555.1 Zika virus isolate Brazil-ZKV2015, Brazil, complete genome
CCAATCTGTGAATCAGACTGCGACAGTTCGAGTTTGAAGCGAAAGCTAGCAACAGTATCAACAGGTTTTATTTTGGATTTG
GAAACGAGAGTTTCTGGTCATGAAAAACCCAAAAAAGAAATCCGGAGGATTCCGGATTGTCAATATGCTAAAACGCGGA
GTAGCCCGTGTGAGCCCCTTTGGGGGCTTGAAGAGGCTGCCAGCCGGACTTCTGCTGGGTCATGGGCCCATCAGGATGG
TCTTGGCGATTCTAGCCTTTTTGAGATTCACGGCAATCAAGCCATCACTGGGTCTCATCAATAGATGGGGTTCAGTGGGGA
AAAAAGAGGCTATGGAAATAATAAAGAAGTTCAAGAAAGATCTGGCTGCCATGCTGAGAATAATCAATGCCAGGAAGGA
GAAGAAGAGACGAGGCGCAGATACTAGTGTCGGAATCGTTGGCCTCCTGCTGACCACAGCTATGGCAGCGGAGGTCACT
AGACGTGGGAGTGCATACTATATGTACTTGGACAGAAACGATGCTGGGGAGGCCATATCTTTTCCAACCACATTGGGGAT
GAATAAGTGTTATATACAGATCATGGATCTTGGACACATGTGTGATGCCACCATGAGCTATGAATGCCCTATGCTGGATG
AGGGGGTGGAACCAGATGACGTCGATTGTTGGTGCAACACGACGTCAACTTGGGTTGTGTACGGAACCTGCCATCACAA
AAAAGGTGAAGCACGGAGATCTAGAAGAGCTGTGACGCTCCCCTCCCATTCCACTAGGAAGCTGCAAACGCGGTCGCAA
ACCTGGTTGGAATCAAGAGAATACACAAAGCACTTGATTAGAGTCGAAAATTGGATATTCAGGAACCCTGGCTTCGCGTT
AGCAGCAGCTGCCATCGCTTGGCTTTTGGGAAGCTCAACGAGCCAAAAAGTCATATACTTGGTCATGATACTGCTGATTGC
CCCGGCATACAGCATCAGGTGCATAGGAGTCAGCAATAGGGACTTTGTGGAAGGTATGTCAGGTGGGACTTGGGTTGAT
GTTGTCTTGGAACATGGGGGTTGTGTCACCGTAATGGCACAGGACAAACCGACTGTCGACATAGAGCTGGTTACAACAAC
AGTCAGCAACATGGCGGAGGTAAGATCCTACTGCTATGAGGCATCAATATCAGACATGGCTTCGGACAGCCGCTGCCCAA
CACAAGGTGAAGCCTACCTTGACAAGCAATCAGACACTCAATATGTCTGCAAAAGAACGTTAGTGGACAGAGGCTGGGG
AAATGGATGTGGACTTTTTGGCAAAGGGAGCCTGGTGACATGCGCTAAGTTTGCATGCTCCAAGAAAATGACCGGGAAG
AGCATCCAGCCAGAGAATCTGGAGTACCGGATAATGCTGTCAGTTCATGGCTCCCAGCACAGTGGGATGATCGTTAATGA
CACAGGACATGAAACTGATGAGAATAGAGCGAAGGTTGAGATAACGCCCAATTCACCAAGAGCCGAAGCCACCCTGGGG
GGTTTTGGAAGCTTAGGACTTGATTGTGAACCGAGGACAGGCCTTGACTTTTCAGATTTGTATTACTTGACTATGAATAAC
AAGCACTGGTTGGTTCACAAGGAGTGGTTCCACGACATTCCATTACCTTGGCACGCTGGGGCAGACACCGGAACTCCACA
CTGGAACAACAAAGAAGCACTGGTAGAGTTCAAGGACGCACATGCCAAAAGGCAAACTGTCGTGGTTCTAGGGACTCAA
GAAGGAGCAGTTCACACGGCCCTTGCTGGAGCTCTGGAGGCTGAGATGGATGGTGCAAAGGGAAGGCTGTCCTCTGGCC
ACTTGAAATGTCGCCTGAAAATGGATAAACTTAGATTGAAGGGCGTGTCATACTCCTTGTGTACCGCAGCGTTCACATTCA
CCAAGATCCCGGCTGAAACACTGCACGGGACAGTCACAGTGGAGGTACAGTACGCAGGGACAGATGGACCTTGCAAGGT
TCCAGCTCAGATGGCGGTGGACATGCAAACTCTGACCCCAGTTGGGAGGTTGATAACCGCTAACCCCGTAATCACTGAAA
GCACTGAGAACTCTAAGATGATGCTGGAACTTGATCCACCATTTGGGGACTCTTACATTGTCATAGGAGTCGGGGAGAAG
AAGATCACCCACCACTGGCACAGGAGTGGCAGCACCATTGGAAAAGCATTTGAAGCCACTGTGAGAGGTGCCAAGAGAA
TGGCAGTCTTGGGAGACACAGCCTGGGACTTTGGATCAGTTGGAGGCGCTCTCAACTCATTGGGCAAGGGCATCCATCAA
ATTTTTGGAGCAGCTTTCAAATCATTGTTTGGAGGAATGTCCTGGTTCTCACAAATTCTCATTGGAACGTTGCTGATGTGGT
TGGGTCTGAACACAAAGAATGGATCTATTTCCCTTATGTGCTTGGCCTTAGGGGGAGTGTTGATCTTCTTATCCACAGCCG
TCTCTGCTGATGTGGGGTGCTCGGTGGACTTCTCAAAGAAGGAGACGAGATGTGGTACAGGGGTGTTCGTCTATAACGA
CGTTGAAGCCTGGAGGGACAGGTACAAGTACCATCCTGACTCTCCCCGTAGATTGGCAGCAGCAGTCAAGCAAGCCTGG
GAAGATGGTATCTGCGGGATCTCCTCTGTTTCAAGAATGGAAAACATCATGTGGAGATCAGTAGAAGGGGAGCTTAACG
CAATCCTGGAAGAGAATGGAGTTCAACTGACGGTCGTTGTGGGATCTGTAAAAAACCCCATGTGGAGAGGTCCACAGAG
ATTGCCCGTGCCTGTGAACGAGCTGCCCCACGGCTGGAAGGCTTGGGGGAAATCGTACTTCGTCAGAGCAGCAAAGACA
AATAACAGCTTTGTCGTGGATGGTGACACACTGAAGGAATGCCCACTCAAACATAGAGCATGGAACAGCTTTCTTGTGGA
GGATCATGGGTTCGGGGTATTTCACACTAGTGTCTGGCTCAAGGTTAGAGAAGATTATTCATTAGAGTGTGATCCAGCCG
TTATTGGAACAGCTGTTAAGGGAAAGGAGGCTGTACACAGTGATCTAGGCTACTGGATTGAGAGTGAGAAGAATGACAC
ATGGAGGCTGAAGAGGGCCCATCTGATCGAGATGAAAACATGTGAATGGCCAAAGTCCCACACATTGTGGACAGATGGA
ATAGAAGAGAGTGATCTGATCATACCCAAGTCTTTAGCTGGGCCACTCAGCCATCACAATACCAGAGAGGGCTACAGGAC
CCAAATGAAAGGGCCATGGCACAGTGAAGAGCTTGAAATTCGGTTTGAGGAATGCCCAGGCACTAAGGTCCACGTGGAG
GAAACATGTGGAACAAGAGGACCATCTCTGAGATCAACCACTGCAAGCGGAAGGGTGATCGAGGAATGGTGCTGCAGG -continued

| SEQUENCES |
|---|
| GAGTGCACAATGCCCCCACTGTCGTTCCGGGCTAAAGATGGCTGTTGGTATGGAATGGAGATAAGGCCCAGGAAAGAAC<br>CAGAAAGCAACTTAGTAAGGTCAATGGTGACTGCAGGATCAACTGATCACATGGATCACTTCTCCCTTGGAGTGCTTGTG<br>ATTCTGCTCATGGTGCAGGAAGGGCTGAAGAAGAGAATGACCACAAAGATCATCATAAGCACATCAATGGCAGTGCTGG<br>TAGCTATGATCCTGGGAGGATTTTCAATGAGTGACCTGGCTAAGCTTGCAATTTTGATGGGTGCCACCTTCGCGGAAATG<br>AACACTGGAGGAGATGTAGCTCATCTGGCGCTGATAGCGGCATTCAAAGTCAGACCAGCGTTGCTGGTATCTTTCATCTTC<br>AGAGCTAATTGGACACCCCGTGAAAGCATGCTGCTGGCCTTGGCCTCGTGTTTTTTGCAAACTGCGATCTCCGCCTTGGAA<br>GGCGACCTGATGGTTCTCATCAATGGTTTTGCTTTGGCCTGGTTGGCAATACGAGCGATGGTTGTTCCACGCACTGACAAC<br>ATCACCTTGGCAATCCTGGCTGCTCTGACACCACTGGCCCGGGGCACACTGCTTGTGGCGTGGAGAGCAGGCCTTGCTAC<br>TTGCGGGGGGTTTATGCTCCTCTCTCTGAAGGGAAAAGGCAGTGTGAAGAAGAACTTACCATTTGTCATGGCCCTGGGAC<br>TAACCGCTGTGAGGCTGGTCGACCCCATCAACGTGGTGGGACTGCTGTTGCTCACAAGGAGTGGGAAGCGGAGCTGGCC<br>CCCTAGCGAAGTACTCACAGCTGTTGGCCTGATATGCGCATTGGCTGGAGGGTTCGCCAAGGCAGATATAGAGATGGCT<br>GGGCCCATGGCCGCGGTCGGTCTGCTAATTGTCAGTTACGTGGTCTCAGGAAAGAGTGTGGACATGTACATTGAAAGAG<br>CAGGTGACATCACATGGGAAAAAGATGCGGAAGTCACTGGAAACAGTCCCCGGCTCGATGTGGCGCTAGATGAGAGTG<br>GTGACTTCTCCCTGGTGGAGGATGACGGTCCCCCCATGAGAGAGATCATACTCAAGGTGGTCCTGATGACCATCTGTGGC<br>ATGAACCCAATAGCCATACCCTTTGCAGCTGGAGCGTGGTACGTATACGTGAAGACTGGAAAAAGGAGTGGTGCTCTATG<br>GGATGTGCCTGCTCCCAAGGAAGTAAAAAAGGGGGAGACCACAGATGGAGTGTACAGAGTAATGACTCGTAGACTGCTA<br>GGTTCAACACAAGTTGGAGTGGGAGTTATGCAAGAGGGGGTCTTTCACACTATGTGGCACGTCACAAAAGGATCCGCGC<br>TGAGAAGCGGTGAAGGGAGACTTGATCCATACTGGGGAGATGTCAAGCAGGATCTGGTGTCATACTGTGGTCCATGGAA<br>GCTAGATGCCGCCTGGGACGGGCACAGCGAGGTGCAGCTCTTGGCCGTGCCCCCCGGAGAGAGAGCGAGGAACATCCA<br>GACTCTGCCCGGAATATTTAAGACAAAGGATGGGGACATTGGAGCGGTTGCGCTGGATTACCCAGCAGGAACTTCAGGA<br>TCTCCAATCCTAGACAAGTGTGGGAGAGTGATAGGACTTTATGGCAATGGGGTCGTGATAAAAAATGGGAGTTATGTTA<br>GTGCCATCACCCAAGGGAGGAGGGAGGAAGAGACTCCTGTTGAGTGCTTCGAGCCTTCGATGCTGAAGAAGAAGCAGCT<br>AACTGTCTTAGACTTGCATCCTGGAGCTGGGAAAACCAGGAGAGTTCTTCCTGAAATAGTCCGTGAAGCCATAAAAACAA<br>GACTCCGTACTGTGATCTTAGCTCCAACCAGGGTTGTCGCTGCTGAAATGGAGGAAGCCCTTAGAGGGCTTCCAGTGCGT<br>TATATGACAACAGCAGTCAATGTCACCCACTCTGGAACAGAAATCGTCGACTTAATGTGCCATGCCACCTTCACTTCACGT<br>CTACTACAGCCAATCAGAGTCCCCAACTATAATCTGTATATTATGGATGAGGCCCACTTCACAGATCCCTCAAGCATAGCA<br>GCAAGAGGATACATTTCAACAAGGGTTGAGATGGGCGAGGCGGCTGCCATCTTCATGACCGCCACGCCACCAGGAACCC<br>GTGACGCATTTCCGGACTCCAACTCACCAATTATGGACACCGAAGTGGAAGTCCCAGAGAGAGCCTGGAGCTCAGGCTTT<br>GATTGGGTGACGGATCATTCTGGAAAAACAGTTTGGTTTGTTCCAAGCGTGAGGAACGGCAATGAGATCGCAGCTTGTCT<br>GACAAAGGCTGGAAAACGGGTCATACAGCTCAGCAGAAAGACTTTTGAGACAGAGTTCCAGAAAACAAAACATCAAGAG<br>TGGGACTTTGTCGTGACAACTGACATTTCAGAGATGGGCGCCAACTTTAAAGCTGACCGTGTCATAGATTCCAGGAGATG<br>CCTAAAGCCGGTCATACTTGATGGCGAGAGAGTCATTCTGGCTGGACCCATGCCTGTCACACATGCCAGCGCTGCCCAGA<br>GGAGGGGGCGCATAGGCAGGAATCCCAACAAACCTGGAGATGAGTACCTGTATGGAGGTGGGTGCGCAGAGACTGACG<br>AAGACCATGCACACTGGCTTGAAGCAAGAATGCTCCTTGACAATATTTACCTCCAAGATGGCCTCATAGCCTCGCTCTATC<br>GACCTGAGGCCGACAAAGTAGCAGCCATTGAGGGAGAGTTCAAGCTTAGGACGGAGCAAAGGAAGACCTTTGTGGAAC<br>TCATGAAAAGAGGAGATCTTCCTGTTTGGCTGGCCTATCAGGTTGCATCTGCCGGAATAACCTACACAGATAGAAGATGG<br>TGCTTTGATGGCACGACCAACAACACCATAATGGAAGACAGTGTGCCGGCAGAGGTGTGGACCAGACACGGAGAGAAA<br>AGAGTGCTCAAACCGAGGTGGATGGACGCCAGAGTTTGTTCAGATCATGCGGCCCTGAAGTCATTCAAGGAGTTTGCCGC<br>TGGGAAAAGAGGAGCGGCTTTTGGAGTGATGGAAGCCCTGGGAACACTGCCAGGACACATGACAGAGAGATTCCAGGA<br>AGCCATTGACAACCTCGCTGTGCTCATGCGGGCAGAGACTGGAAGCAGGCCTTACAAAGCCGCGGCGGCCCAATTGCCG<br>GAGACCCTAGAGACCATTATGCTTTTGGGGTTGCTGGGAACAGTCTCGCTGGGAATCTTTTTCGTCTTGATGAGGAACAA<br>GGGCATAGGGAAGATGGGCTTTGGAATGGTGACTCTTGGGGCCAGCGCATGGCTCATGTGGCTCTCGGAAATTGAGCCA<br>GCCAGAATTGCATGTGTCCTCATTGTTGTGTTCCTATTGCTGGTGGTGCTCATACCTGAGCCAGAAAAGCAAAGATCTCCC<br>CAGGACAACCAAATGGCAATCATCATCATGGTAGCAGTAGGTCTTCTGGGCTTGATTACCGCCAATGAACTCGGATGGTT<br>GGAGAGAACAAAGAGTGACCTAAGCCATCTAATGGGAAGGAGAGAGGAGGGGGCAACCATAGGATTCTCAATGGACAT<br>TGACCTGCGGCCAGCCTCAGCTTGGGCCATCTATGCTGCCTTGACAACTTTCATTACCCCAGCCGTCCAACATGCAGTGAC<br>CACTTCATACAACAACTACTCCTTAATGGCGATGGCCACGCAAGCTGGAGTGTTGTTTGGTATGGGCAAAGGGATGCCAT<br>TCTACGCATGGGACTTTGGAGTCCCGCTGCTAATGATAGGTTGCTACTCACAATTAACACCCCTGACCCTAATAGTGGCCA<br>TCATTTTGCTCGTGGCGCACTACATGTACTTGATCCCAGGGCTGCAGGCAGCAGCTGCGCGTGCTGCCCAGAAGAGAACG<br>GCAGCTGGCATCATGAAGAACCCTGTTGTGGATGGAATAGTGGTGACTGACATTGACACAATGACAATTGACCCCCAAGT<br>GGAGAAAAAGATGGGACAGGTGCTACTCATAGCAGTAGCCGTCTCCAGCGCCATACTGTCGCGGACCGCCTGGGGGTGG<br>GGGGAGGCTGGGGCCCTGATCACAGCCGCAACTTCCACTTTGTGGGAAGGCTCTCCGAACAAGTACTGGAACTCCTCTAC<br>AGCCACTTCACTGTGTAACATTTTTAGGGGAAGTTACTTGGCTGGAGCTTCTCTAATCTACACAGTAACAAGAAACGCTGG<br>CTTGGTCAAGAGACGTGGGGGTGGAACAGGAGAGACCCTGGGAGAGAAATGGAAGGCCCGCTTGAACCAGATGTCGGC<br>CCTGGAGTTCTACTCCTACAAAAAGTCAGGCATCACCGAGGTGTGCAGAGAAGAGGCCCGCCGCGCCCTCAAGGACGGT<br>GTGGCAACGGGAGGCCATGCTGTGTCCCGAGGAAGTGCAAAGCTGAGATGGTTGGTGGAGCGGGGATACCTGCAGCCC<br>TATGGAAAGGTCATTGATCTTGGATGTGGCAGAGGGGGCTGGAGTTACTACGCCGCCACCATCCGCAAAGTTCAAGAAG<br>TGAAAGGATACACAAAAGGAGGCCCTGGTCATGAAGAACCCGTGTTGGTGCAAAGCTATGGGTGGAACATAGTCCGTCT<br>TAAGAGTGGGGTGGACGTCTTTCATATGGCGGCTGAGCCGTGTGACACGTTGCTGTGTGACATAGGTGAGTCATCATCTA<br>GTCCTGAAGTGGAAGAAGCACGGACGCTCAGAGTCCTCTCCATGGTGGGGGATTGGCTTGAAAAAAGACCAGGAGCCTT<br>TTGCATAAAAGTGTTGTGCCCATACACCAGCACTATGATGGAAACCCTGGAGCGACTGCAGCGTAGGTATGGGGGAGGA<br>CTGGTCAGAGTGCCACTCTCCCGCAACTCTACACATGAGATGTACTGGGTCTCTGGAGCGAAAAGCAACACCATAAAAAG<br>TGTGTCCACCACGAGCCAGCTCCTCTTGGGGCGCATGGACGGGCCTAGGAGGCCAGTGAAATATGAGGAGGATGTGAAT<br>CTCGGCTCTGGCACGCGGGCTGTGGTAAGCTGCGCTGAAGCTCCCAACATGAAGATCATTGGTAACCGCATTGAAAGGAT<br>CCGCAGTGAGCACGCGGAAACGTGGTTCTTTGACGAAAACCACCCATATAGGACATGGGCTTACCATGGAAGCTATGTG<br>GCCCCCACACAAGGGTCAGCGTCCTCTCTAATAAACGGGGTTGTCAGGCTCCTGTCAAAACCCTGGGATGTGGTGACTGG<br>AGTCACAGGAATAGCCATGACCGACACCACACCGTATGGTCAGCAAAGAGTTTTCAAGGAAAAAGTGGACACTAGGGTG<br>CCAGACCCCCAAGAAGGCACTCGTCAGGTTATGAGCATGGTCTCTTCCTGGTTGTGGAAAGAGCTAGGCAAACACAAACG<br>ACCACGAGTCTGTACCAAAGAAGAGTTCATCAACAAGGTTCGTAGCAATGCAGCATTAGGGGCAATATTTGAAGAGGAA<br>AAAGAGTGGAAGACTGCAGTGGAAGCTGTGAACGATCCAAGGTTCTGGGCTCTAGTGGACAAGGAAAGAGAGCACCAC<br>CTGAGAGGAGAGTGCCAGAGTTGTGTGTACAACATGATGGGAAAAAGAGAAAAGAAACAAGGGGAATTTGGAAAGGCC<br>AAGGGCAGCCGCGCCATCTGGTATATGTGGCTAGGGGCTAGATTTCTAGAGTTCGAAGCCCTTGGATTCTTGAACGAGGA<br>TCACTGGATGGGGAGAGAGAACTCAGGAGGTGGTGTTGAAGGGCTGGGATTACAAAGACTCGGATATGTCCTAGAAGA<br>GATGAGTCGCATACCAGGAGGAAGGATGTATGCAGATGACACTGCTGGCTGGGACACCCGCATCAGCAGGTTTGATCTG<br>GAGAATGAAGCTCTAATCACCAACCAAATGGAGAAAGGGCACAGGGCCTTGGCATTGGCCATAATCAAGTACACATACC<br>AAAACAAAGTGGTAAAGGTCCTTAGACCAGCTGAAAAAGGGAAAACAGTTATGGACATTATTTCGAGACAAGACCAAAG<br>GGGGAGCGGACAAGTTGTCACTTACGCTCTTAACACATTTACCAACCTAGTGGTGCAACTCATTCGGAATATGGAGGCTG |

-continued

SEQUENCES

AGGAAGTTCTAGAGATGCAAGACTTGTGGCTGCTGCGGAGGTCAGAGAAAGTGACCAACTGGTTGCAGAGCAACGGAT
GGGATAGGCTCAAACGAATGGCAGTCAGTGGAGATGATTGCGTTGTGAAGCCAATTGATGATAGGTTTGCACATGCCCTC
AGGTTCTTGAATGATATGGGAAAAGTTAGGAAGGACACACAAGAGTGGAAACCCTCAACTGGATGGGACAACTGGGAA
GAAGTTCCGTTTTGCTCCCACCACTTCAACAAGCTCCATCTCAAGGACGGGAGGTCCATTGTGGTTCCCTGCCGCCACCAA
GATGAACTGATTGGCCGGGCCCGCGTCTCTCCAGGGGCGGGATGGAGCATCCGGGAGACTGCTTGCCTAGCAAAATCAT
ATGCGCAAATGTGGCAGCTCCTTTATTTCCACAGAAGGGACCTCCGACTGATGGCCAATGCCATTTGTTCATCTGTGCCAG
TTGACTGGGTTCCAACTGGGAGAACTACCTGGTCAATCCATGGAAAGGGAGAATGGATGACCACTGAAGACATGCTTGT
GGTGTGGAACAGAGTGTGGATTGAGGAGAACGACCACATGGAAGACAAGACCCCAGTTACGAAATGGACAGACATTCCC
TATTTGGGAAAAAGGGAAGACTTGTGGTGTGGATCTCTCATAGGGCACAGACCGCGCACCACCTGGGCTGAGAACATTA
AAAATACAGTCAACATGGTGCGCAGGATCATAGGTGATGAAGAAAAGTACATGGACTACCTATCCACCCAAGTTCGCTAC
TTGGGTGAAGAAGGGTCTACACCTGGAGTGCTGTGAGCACCAATCTTAATGTTGTCAGGCCTGCTAGTCAGCCACAGCTT
GGGGAAAGCTGTGCAGCCTGTGACCCCTCCAGGAGAAGCTGGGTAACCAAGCCTATAGTCAGGCCGAGAACGCCATGGC
ACGGAAGAAGCCATGCTGCCTGTGAGCCCCTCAGAGGACACTGAGTCAAAAAACCCCACGCGCTTGGAGGCGCAGGATG
GGAAAAGAAGGTGGCGACCTTCCCCACCCTTCAATCTGGGGCCTGAACTGGAGATCAGCTGTGGATCTCCAGAAGAGGG
ACTAGTGGTTAGAGGAGACCCCCCGGAAAACGCAAAACAGCATATTGACGCTGGGAAAGACCAGAGACTCCATGAGTTT
CCACCACGCTGGCCGCCAGGCACAGATCGCCGAATAGCGGCGGCCGGTGTGGGGAAATCCA

SEQ ID NO: 4
KU501215.1 Zika virus strain PRVABC59, Puerto Rico, complete genome
GTTGTTGATCTGTGTGAATCAGACTGCGACAGTTCGAGTTTGAAGCGAAAGCTAGCAACAGTATCAACAGGTTTTATTTTG
GATTTGGAAACGAGAGTTTCTGGTCATGAAAAACCCAAAAAAGAAATCCGGAGGATTCCGGATTGTCAATATGCTAAAAC
GCGGAGTAGCCCGTGTGAGCCCCTTTGGGGGCTTGAAGAGGCTGCCAGCCGGACTTCTGCTGGGTCATGGGCCCATCAG
GATGGTCTTGGCGATTCTAGCCTTTTTGAGATTCACGGCAATCAAGCCATCACTGGGTCTCATCAATAGATGGGGTTCAGT
GGGGAAAAAAGAGGCTATGGAAACAATAAAGAAGTTCAAGAAAGATCTGGCTGCCATGCTGAGAATAATCAATGCTAGG
AAGGAGAAGAAGAGACGAGGCGCAGATACTAGTGTCGGAATTGTTGGCCTCCTGCTGACCACAGCTATGGCAGCGGAG
GTCACTAGACGTGGGAGTGCATACTATATGTACTTGGACAGAAACGATGCTGGGGAGGCCATATCTTTTCCAACCACATT
GGGGATGAATAAGTGTTATATACAGATCATGGATCTTGGACACATGTGTGATGCCACCATGAGCTATGAATGCCCTATGC
TGGATGAGGGGGTGGAACCAGATGACGTCGATTGTTGGTGCAACACGACGTCAACTTGGGTTGTGTACGGAACCTGCCA
TCACAAAAAAGGTGAAGCACGGAGATCTAGAAGAGCTGTGACGCTCCCCTCCCATTCCACCAGGAAGCTGCAAACGCGG
TCGCAAACCTGGTTGGAATCAAGAGAATACACAAAGCACTTGATTAGAGTCGAAAATTGGATATTCAGGAACCCTGGCTT
CGCGTTAGCAGCAGCTGCCATCGCTTGGCTTTTGGGAAGCTCAACGAGCCAAAAAGTCATATACTTGGTCATGATACTGCT
GATTGCCCCGGCATACAGCATCAGGTGCATAGGAGTCAGCAATAGGGACTTTGTGGAAGGTATGTCAGGTGGGACTTGG
GTTGATGTTGTCTTGGAACATGGAGGTTGTGTCACCGTAATGGCACAGGACAAACCGACTGTCGACATAGAGCTGGTTAC
AACAACAGTCAGCAACATGGCGGAGGTAAGATCCTACTGCTATGAGGCATCAATATCAGACATGGCTTCTGACAGCCGCT
GCCCAACACAAGGTGAAGCCTACCTTGACAAGCAATCAGACACTCAATATGTCTGCAAAAGAACGTTAGTGGACAGAGGC
TGGGGAAATGGATGTGGACTTTTTGGCAAAGGGAGCCTGGTGACATGCGCTAAGTTTGCATGCTCCAAGAAAATGACCG
GGAAGAGCATCCAGCCAGAGAATCTGGAGTACCGGATAATGCTGTCAGTTCATGGCTCCCAGCACAGTGGGATGATCGT
TAATGACACAGGACATGAAACTGATGAGAATAGAGCGAAAGTTGAGATAACGCCCAATTCACCGAGAGCCGAAGCCACC
CTGGGGGGTTTTGGAAGCCTAGGACTTGATTGTGAACCGAGGACAGGCCTTGACTTTTCAGATTTGTATTACTTGACTATG
AATAACAAGCACTGGTTGGTTCACAAGGAGTGGTTCCACGACATTCCATTACCTTGGCACGCTGGGGCAGACACCGGAAC
TCCACACTGGAACAACAAAGAAGCACTGGTAGAGTTCAAGGACGCACATGCCAAAAGGCAAACTGTCGTGGTTCTAGGG
AGTCAAGAAGGAGCAGTTCACACGGCCCTTGCTGGAGCTCTGGAGGCTGAGATGGATGGTGCAAAGGGAAGGCTGTCCT
CTGGCCACTTGAAATGTCGCCTGAAAATGGATAAACTTAGATTGAAGGGCGTGTCATACTCCTTGTGTACTGCAGCGTTCA
CATTCACCAAGATCCCGGCTGAAACACTGCACGGGACAGTCACAGTGGAGGTACAGTACGCAGGGACAGATGGACCTTG
CAAGGTTCCAGCTCAGATGGCGGTGGACATGCAAACTCTGACCCCAGTTGGGAGGTTGATAACCGCTAACCCCGTAATCA
CTGAAAGCACTGAGAACTCTAAGATGATGCTGGAACTTGATCCACCATTTGGGGACTCTTACATTGTCATAGGAGTCGGG
GAGAAGAAGATCACCCACCACTGGCACAGGAGTGGCAGCACCATTGGAAAAGCATTTGAAGCCACTGTGAGAGGTGCCA
AGAGAATGGCAGTCTTGGGAGACACAGCCTGGGACTTTGGATCAGTTGGAGGCGCTCTCAACTCATTGGGCAAGGGCAT
CCATCAAATTTTTGGAGCAGCTTTCAAATCATTGTTTGGAGGAATGTCCTGGTTCTCACAAATTCTCATTGGAACGTTGCTG
ATGTGGTTGGGTCTGAACACAAAGAATGGATCTATTTCCCTTATGTGCTTGGCCTTAGGGGGAGTGTTGATCTTCTTATCC
ACAGCCGTCTCTGCTGATGTGGGGTGCTCGGTGGACTTCTCAAAGAAGGAGACGAGATGCGGTACAGGGGTGTTCGTCT
ATAACGACGTTGAAGCCTGGAGGGACAGGTACAAGTACCATCCTGACTCCCCCCGTAGATTGGCAGCAGCAGTCAAGCA
AGCCTGGGAAGATGGTATCTGCGGGATCTCCTCTGTTTCAAGAATGGAAAACATCATGTGGAGATCAGTAGAAGGGGAG
CTCAACGCAATCCTGGAAGAGAATGGAGTTCAACTGACGGTCGTTGTGGGATCTGTAAAAAACCCCATGTGGAGAGGTC
CACAGAGATTGCCCGTGCCTGTGAACGAGCTGCCCCACGGCTGGAAGGCTTGGGGGAAATCGTATTTCGTCAGAGCAGC
AAAGACAAATAACAGCTTTGTCGTGGATGGTGACACACTGAAGGAATGCCCACTCAAACATAGAGCATGGAACAGCTTTC
TTGTGGAGGATCATGGGTTCGGGGTATTTCACACTAGTGTCTGGCTCAAGGTTAGAGAAGATTATTCATTAGAGTGTGAT
CCAGCCGTTATTGGAACAGCTGTTAAGGGAAAGGAGGCTGTACACAGTGATCTAGGCTACTGGATTGAGAGTGAGAAGA
ATGACACATGGAGGCTGAAGAGGGCCCATCTGATCGAGATGAAAACATGTGAATGGCCAAAGTCCCACACATTGTGGAC
AGATGGAATAGAAGAGAGTGATCTGATCATACCCAAGTCTTTAGCTGGGCCACTCAGCCATCACAATACCAGAGAGGGCT
ACAGGACCCAAATGAAAGGGCCATGGCACAGTGAAGAGCTTGAAATTCGGTTTGAGGAATGCCCAGGCACTAAGGTCCA
CGTGGAGGAAACATGTGGAACAAGAGGACCATCTCTGAGATCAACCACTGCAAGCGGAAGGGTGATCGAGGAATGGTG
CTGCAGGGAGTGCACAATGCCCCCACTGTCGTTCCGGGCTAAAGATGGCTGTTGGTATGGAATGGAGATAAGGCCCAGG
AAAGAACCAGAAAGCAACTTAGTAAGGTCAATGGTGACTGCAGGATCAACTGATCACATGGACCACTTCTCCCTTGGAGT
GCTTGTGATCCTGCTCATGGTGCAGGAAGGGCTGAAGAAGAGAATGACCACAAAGATCATCATAAGCACATCAATGGCA
GTGCTGGTAGCTATGATCCTGGGAGGATTTTCAATGAGTGACCTGGCTAAGCTTGCAATTTTGATGGGTGCCACCTTCGC
GGAAATGAACACTGGAGGAGATGTAGCTCATCTGGCGCTGATAGCGGCATTCAAAGTCAGACCAGCGTTGCTGGTATCTT
TCATCTTCAGAGCTAATTGGACACCCCGTGAAAGCATGCTGCTGGCCTTGGCCTCGTGTCTTTTGCAAACTGCGATCTCCG
CCTTGGAAGGCGACCTGATGGTTCTCATCAATGGTTTTGCTTTGGCCTGGTTGGCAATACGAGCGATGGTTGTTCCACGCA
CTGATAACATCACCTTGGCAATCCTGGCTGCTCTGACACCACTGGCCCGGGGCACACTGCTTGTGGCGTGGAGAGCAGGC
CTTGCTACTTGCGGGGGGTTTATGCTCCTCTCTCTGAAGGGAAAAGGCAGTGTGAAGAAGAACTTACCATTTGTCATGGC
CCTGGGACTAACCGCTGTGAGGCTGGTCGACCCCATCAACGTGGTGGGACTGCTGTTGCTCACAAGGAGTGGGAAGCGG
AGCTGGCCCCCTAGCGAAGTACTCACAGCTGTTGGCCTGATATGCGCATTGGCTGGAGGGTTCGCCAAGGCAGATATAGA
GATGGCTGGGCCCATGGCCGCGGTCGGTCTGCTAATTGTCAGTTACGTGGTCTCAGGAAAGAGTGTGGACATGTACATTG
AAAGAGCAGGTGACATCACATGGGAAAAAGATGCGGAAGTCACTGGAAACAGTCCCCGGCTCGATGTGGCGCTAGATG
AGAGTGGTGATTTCTCCCTGGTGGAGGATGACGGTCCCCCCATGAGAGAGATCATACTCAAGGTGGTCCTGATGACCATC
TGTGGCATGAACCCAATAGCCATACCCTTTGCAGCTGGAGCGTGGTACGTATACGTGAAGACTGGAAAAAGGAGTGGTG -continued

| SEQUENCES |
|---|
| CTCTATGGGATGTGCCTGCTCCCAAGGAAGTAAAAAAGGGGGAGACCACAGATGGAGTGTACAGAGTAATGACTCGTAG<br>ACTGCTAGGTTCAACACAAGTTGGAGTGGGAGTTATGCAAGAGGGGGTCTTTCACACTATGTGGCACGTCACAAAAGGA<br>TCCGCGCTGAGAAGCGGTGAAGGGAGACTTGATCCATACTGGGGAGATGTCAAGCAGGATCTGGTGTCATACTGTGGTC<br>CATGGAAGCTAGATGCCGCCTGGGATGGGCACAGCGAGGTGCAGCTCTTGGCCGTGCCCCCCGGAGAGAGAGCGAGGA<br>ACATCCAGACTCTGCCCGGAATATTTAAGACAAAGGATGGGGACATTGGAGCGGTTGCGCTGGATTACCCAGCAGGAAC<br>TTCAGGATCTCCAATCCTAGACAAGTGTGGGAGAGTGATAGGACTTTATGGCAATGGGGTCGTGATCAAAAACGGGAGT<br>TATGTTAGTGCCATCACCCAAGGGAGGAGGGAGGAAGAGACTCCTGTTGAGTGCTTCGAGCCCTCGATGCTGAAGAAGA<br>AGCAGCTAACTGTCTTAGACTTGCATCCTGGAGCTGGGAAAACCAGGAGAGTTCTTCCTGAAATAGTCCGTGAAGCCATA<br>AAAACAAGACTCCGTACTGTGATCTTAGCTCCAACCAGGGTTGTCGCTGCTGAAATGGAGGAGGCCCTTAGAGGGCTTCC<br>AGTGCGTTATATGACAACAGCAGTCAATGTCACCCACTCTGGAACAGAAATCGTCGACTTAATGTGCCATGCCACCTTCAC<br>TTCACGTCTACTACAGCCAATCAGAGTCCCCAACTATAATCTGTATATTATGGATGAGGCCCACTTCACAGATCCCTCAAGT<br>ATAGCAGCAAGAGGATACATTTCAACAAGGGTTGAGATGGGCGAGGCGGCTGCCATCTTCATGACCGCCACGCCACCAG<br>GAACCCGTGACGCATTTCCGGACTCCAACTCACCAATTATGGACACCGAAGTGGAAGTCCCAGAGAGAGCCTGGAGCTCA<br>GGCTTTGATTGGGTGACGGATCATTCTGGAAAAACAGTTTGGTTTGTTCCAAGCGTGAGGAACGGCAATGAGATCGCAGC<br>TTGTCTGACAAAGGCTGGAAAACGGGTCATACAGCTCAGCAGAAAGACTTTTGAGACAGAGTTCCAGAAAACAAAACATC<br>AAGAGTGGGACTTTGTCGTGACAACTGACATTTCAGAGATGGGCGCCAACTTTAAAGCTGACCGTGTCATAGATTCCAGG<br>AGATGCCTAAAGCCGGTCATACTTGATGGCGAGAGAGTCATTCTGGCTGGACCCATGCCTGTCACACATGCCAGCGCTGC<br>CCAGAGGAGGGGGCGCATAGGCAGGAATCCCAACAAACCTGGAGATGAGTATCTGTATGGAGGTGGGTGCGCAGAGAC<br>TGACGAAGACCATGCACACTGGCTTGAAGCAAGAATGCTCCTTGACAATATTTACCTCCAAGATGGCCTCATAGCCTCGCT<br>CTATCGACCTGAGGCCGACAAAGTAGCAGCCATTGAGGGAGAGTTCAAGCTTAGGACGGAGCAAAGGAAGACCTTTGTG<br>GAACTCATGAAAAGAGGAGATCTTCCTGTTTGGCTGGCCTATCAGGTTGCATCTGCCGGAATAACCTACACAGATAGAAG<br>ATGGTGCTTTGATGGCACGACCAACAACACCATAATGGAAGACAGTGTGCCGGCAGAGGTGTGGACCAGACACGGAGA<br>GAAAAGAGTGCTCAAACCGAGGTGGATGGACGCCAGAGTTTGTTCAGATCATGCGGCCCTGAAGTCATTCAAGGAGTTT<br>GCCGCTGGGAAAAGAGGAGCGGCTTTTGGAGTGATGGAAGCCCTGGGAACACTGCCAGGACACATGACAGAGAGATTC<br>CAGGAAGCCATTGACAACCTCGCTGTGCTCATGCGGGCAGAGACTGGAAGCAGGCCTTACAAAGCCGCGGCGGCCCAAT<br>TGCCGGAGACCCTAGAGACCATAATGCTTTTGGGGTTGCTGGGAACAGTCTCGCTGGGAATCTTCTTCGTCTTGATGAGG<br>AACAAGGGCATAGGGAAGATGGGCTTTGGAATGGTGACTCTTGGGGCCAGCGCATGGCTCATGTGGCTCTCGGAAATTG<br>AGCCAGCCAGAATTGCATGTGTCCTCATTGTTGTGTTCCTATTGCTGGTGGTGCTCATACCTGAGCCAGAAAAGCAAAGAT<br>CTCCCCAGGACAACCAAATGGCAATCATCATCATGGTAGCAGTAGGTCTTCTGGGCTTGATTACCGCCAATGAACTCGGAT<br>GGTTGGAGAGAACAAAGAGTGACCTAAGCCATCTAATGGGAAGGAGAGAGGAGGGGGCAACCATAGGATTCTCAATGG<br>ACATTGACCTGCGGCCAGCCTCAGCTTGGGCCATCTATGCTGCCTTGACAACTTTCATTACCCCAGCCGTCCAACATGCAGT<br>GACCACCTCATACAACAACTACTCCTTAATGGCGATGGCCACGCAAGCTGGAGTGTTGTTTGGCATGGGCAAAGGGATGC<br>CATTCTACGCATGGGACTTTGGAGTCCCGCTGCTAATGATAGGTTGCTACTCACAATTAACACCCCTGACCCTAATAGTGG<br>CCATCATTTTGCTCGTGGCGCACTACATGTACTTGATCCCAGGGCTGCAGGCAGCAGCTGCGCGTGCTGCCCAGAAGAGA<br>ACGGCAGCTGGCATCATGAAGAACCCTGTTGTGGATGGAATAGTGGTGACTGACATTGACACAATGACAATTGACCCCCA<br>AGTGGAGAAAAAGATGGGACAGGTGCTACTCATAGCAGTAGCCGTCTCCAGCGCCATACTGTCGCGGACCGCCTGGGGG<br>TGGGGGGAGGCTGGGGCTCTGATCACAGCCGCAACTTCCACTTTGTGGGAAGGCTCTCCGAACAAGTACTGGAACTCCTC<br>TACAGCCACTTCACTGTGTAACATTTTTAGGGGAAGTTACTTGGCTGGAGCTTCTCTAATCTACACAGTAACAAGAAACGC<br>TGGCTTGGTCAAGAGACGTGGGGGTGGAACAGGAGAGACCCTGGGAGAGAAATGGAAGGCCCGCTTGAACCAGATGTC<br>GGCCCTGGAGTTCTACTCCTACAAAAAGTCAGGCATCACCGAGGTGTGCAGAGAAGAGGCCCGCCGCGCCCTCAAGGAC<br>GGTGTGGCAACGGGAGGCCATGCTGTGTCCCGAGGAAGTGCAAAGCTGAGATGGTTGGTGGAGCGGGGATACCTGCAG<br>CCCTATGGAAAGGTCATTGATCTTGGATGTGGCAGAGGGGGCTGGAGTTACTACGTCGCCACCATCCGCAAAGTTCAAGA<br>AGTGAAAGGATACACAAAAGGAGGCCCTGGTCATGAAGAACCCGTGTTGGTGCAAAGCTATGGGTGGAACATAGTCCGT<br>CTTAAGAGTGGGGTGGACGTCTTTCATATGGCGGCTGAGCCGTGTGACACGTTGCTGTGTGACATAGGTGAGTCATCATC<br>TAGTCCTGAAGTGGAAGAAGCACGGACGCTCAGAGTCCTCTCCATGGTGGGGGATTGGCTTGAAAAAAGACCAGGAGCC<br>TTTTGTATAAAAGTGTTGTGCCCATACACCAGCACTATGATGGAAACCCTGGAGCGACTGCAGCGTAGGTATGGGGGAG<br>GACTGGTCAGAGTGCCACTCTCCCGCAACTCTACACATGAGATGTACTGGGTCTCTGGAGCGAAAAGCAACACCATAAAA<br>AGTGTGTCCACCACGAGCCAGCTCCTCTTGGGGCGCATGGACGGGCCTAGGAGGCCAGTGAAATATGAGGAGGATGTGA<br>ATCTCGGCTCTGGCACGCGGGCTGTGGTAAGCTGCGCTGAAGCTCCCAACATGAAGATCATTGGTAACCGCATTGAAAGG<br>ATCCGCAGTGAGCACGCGGAAACGTGGTTCTTTGACGAGAACCACCCATATAGGACATGGGCTTACCATGGAAGCTATGA<br>GGCCCCCACACAAGGGTCAGCGTCCTCTCTAATAAACGGGGTTGTCAGGCTCCTGTCAAAACCCTGGGATGTGGTGACTG<br>GAGTCACAGGAATAGCCATGACCGACACCACACCGTATGGTCAGCAAAGAGTTTTCAAGGAAAAAGTGGACACTAGGGT<br>GCCAGACCCCCAAGAAGGCACTCGTCAGGTTATGAGCATGGTCTCTTCCTGGTTGTGGAAAGAGCTAGGCAAACACAAAC<br>GGCCACGAGTCTGCACCAAAGAAGAGTTCATCAACAAGGTTCGTAGCAATGCAGCATTAGGGGCAATATTTGAAGAGGA<br>AAAAGAGTGGAAGACTGCAGTGGAAGCTGTGAACGATCCAAGGTTCTGGGCTCTAGTGGACAAGGAAAGAGAGCACCA<br>CCTGAGAGGAGAGTGCCAGAGCTGTGTGTACAACATGATGGGAAAAAGAGAAAAGAAACAAGGGGAATTTGGAAAGGC<br>CAAGGGCAGCCGCGCCATCTGGTATATGTGGCTAGGGGCTAGATTTCTAGAGTTCGAAGCCCTTGGATTCTTGAACGAGG<br>ATCACTGGATGGGGAGAGAGAACTCAGGAGGTGGTGTTGAAGGGCTGGGATTACAAAGACTCGGATATGTCCTAGAAG<br>AGATGAGTCGTATACCAGGAGGAAGGATGTATGCAGATGACACTGCTGGCTGGGACACCCGCATTAGCAGGTTTGATCT<br>GGAGAATGAAGCTCTAATCACCAACCAAATGGAGAAAGGGCACAGGGCCTTGGCATTGGCCATAATCAAGTACACATAC<br>CAAAACAAAGTGGTAAAGGTCCTTAGACCAGCTGAAAAAGGGAAAACAGTTATGGACATTATTTCGAGACAAGACCAAA<br>GGGGGAGCGGACAAGTTGTCACTTACGCTCTTAACACATTTACCAACCTAGTGGTGCAACTCATTCGGAATATGGAGGCT<br>GAGGAAGTTCTAGAGATGCAAGACTTGTGGCTGCTGCGGAGGTCAGAGAAAGTGACCAACTGGTTGCAGAGCAACGGA<br>TGGGATAGGCTCAAACGAATGGCAGTCAGTGGAGATGATTGCGTTGTGAAGCCAATTGATGATAGGTTTGCACATGCCCT<br>CAGGTTCTTGAATGATATGGGAAAAGTTAGGAAGGACACACAAGAGTGGAAACCCTCAACTGGATGGGACAACTGGGAA<br>GAAGTTCCGTTTTGCTCCCACCACTTCAACAAGCTCCATCTCAAGGACGGGAGGTCCATTGTGGTTCCCTGCCGCCACCAA<br>GATGAACTGATTGGCCGGGCCCGCGTCTCTCCAGGGGCGGATGGAGCATCCGGGAGACTGCTTGCCTAGCAAAATCAT<br>ATGCGCAAATGTGGCAGCTCCTTTATTTCCACAGAAGGGACCTCCGACTGATGGCCAATGCCATTTGTTCATCTGTGCCAG<br>TTGACTGGGTTCCAACTGGGAGAACTACCTGGTCAATCCATGGAAAGGGAGAATGGATGACCACTGAAGACATGCTTGT<br>GGTGTGGAACAGAGTGTGGATTGAGGAGAACGACCACATGGAAGACAAGACCCCAGTTACGAAATGGACAGACATTCCC<br>TATTTGGGAAAAAGGGAAGACTTGTGGTGTGGATCTCTCATAGGGCACAGACCGCGCACCACCTGGGCTGAGAACATTA<br>AAAACACAGTCAACATGGTGCGCAGGATCATAGGTGATGAAGAAAAGTACATGGACTACCTATCCACCCAAGTTCGCTAC<br>TTGGGTGAAGAAGGGTCTACACCTGGAGTGCTGTAAGCACCAATCTTAATGTTGTCAGGCCTGCTAGTCAGCCACAGCTT<br>GGGGAAAGCTGTGCAGCCTGTGACCCCCCCAGGAGAAGCTGGGAAACCAAGCCTATAGTCAGGCCGAGAACGCCATGG<br>CACGGAAGAAGCCATGCTGCCTGTGAGCCCCTCAGAGGACACTGAGTCAAAAAACCCCACGCGCTTGGAGGCGCAGGAT<br>GGGAAAAGAAGGTGGCGACCTTCCCCACCCTTCAATCTGGGGCCTGAACTGGAGATCAGCTGTGGATCTCCAGAAGAGG<br>GACTAGTGGTTAGAGGA |

-continued

SEQUENCES

SEQ ID NO: 5
KU509998.1 Zika virus strain Haiti/1225/2014, Haiti, complete genome
GTTGTTACTGTTGCTGACTCAGACTGCGACAGTTCGAGTTTGAAGCGAAAGCTAGCAACAGTATCAACAGGTTTTATTTGG
ATTTGGAAACGAGAGTTTCTGGTCATGAAAAACCCAAAAAAGAAATCCGGAGGATTCCGGATTGTCAATATGCTAAAACG
CGGAGTAGCCCGTGTGAGCCCCTTTGGGGGCTTGAAGAGGCTGCCAGCCGGACTTCTGCTGGGTCATGGGCCCATCAGG
ATGGTCTTGGCAATTCTAGCCTTTTTGAGATTCACGGCAATCAAGCCATCACTGGGTCTCATCAATAGATGGGGTTCAGTG
GGGAAAAAAGAGGCTATGGAAATAATAAAGAAGTTCAAGAAAGATCTGGCTGCCATGCTGAGAATAATCAATGCTAGGA
AGGAGAAGAAGAGACGAGGCGCAGATACTAGTGTCGGAATTGTTGGCCTCCTGCTGACCACAGCTATGGCAGCGGAGG
TCACTAGACGTGGGAGTGCATACTATATGTACTTGGACAGAAACGATGCTGGGGAGGCCATATCTTTTCCAACCACATTG
GGGATGAATAAGTGTTATATACAGATCATGGATCTTGGACACATGTGTGATGCCACCATGAGCTATGAATGCCCTATGCT
GGATGAGGGGGTGGAACCAGATGACGTCGATTGTTGGTGCAACACGACGTCAACTTGGGTTGTGTACGGAACCTGCCAT
CACAAAAAAGGTGAAGCACGGAGATCTAGAAGAGCTGTGACGCTCCCCTCCCATTCCACTAGGAAGCTGCAAACGCGGT
CGCAAACCTGGTTGGAATCAAGAGAATACACAAAGCACTTGATTAGAGTCGAAAATTGGATATTCAGGAACCCTGGCTTC
GCGTTAGCAGCAGCTGCCATCGCTTGGCTTTTGGGAAGCTCAACGAGCCAAAAAGTCATATACTTGGTCATGATACTGCT
GATTGCCCCGGCATACAGCATCAGGTGCATAGGAGTCAGCAATAGGGACTTTGTGGAAGGTATGTCAGGTGGGACTTGG
GTTGATGTTGTCTTGGAACATGGAGGTTGTGTCACCGTAATGGCACAGGACAAACCGACTGTCGACATAGAGCTGGTTAC
AACAACAGTCAGCAACATGGCGGAGGTAAGATCCTACTGCTATGAGGCATCAATATCAGACATGGCTTCGGACAGCCGCT
GCCCAACACAAGGTGAAGCCTACCTTGACAAGCAATCAGACACTCAATATGTCTGCAAAAGAACGTTAGTGGACAGAGGC
TGGGGAAATGGATGTGGACTTTTTGGCAAAGGGAGTCTGGTGACATGCGCTAAGTTTGCATGCTCCAAGAAAATGACCG
GGAAGAGCATCCAGCCAGAGAATCTGGAGTACCGGATAATGCTGTCAGTTCATGGCTCCCAGCACAGTGGGATGATCGT
TAATGACACAGGACATGAAACTGATGAGAATAGAGCGAAGGTTGAGATAACGCCCAATTCACCAAGAGCCGAAGCCACC
CTGGGGGGTTTTGGAAGCCTAGGACTTGATTGTGAACCGAGGACAGGCCTTGACTTTTCAGATTTGTATTACTTGACTATG
AATAACAAGCACTGGTTGGTTCACAAGGAGTGGTTCCACGACATTCCATTACCTTGGCACGCTGGGGCAGACACCGGAAC
TCCACACTGGAACAACAAAGAAGCACTGGTAGAGTTCAAGGACGCACATGCCAAAAGGCAAACTGTCGTGGTTCTAGGG
AGTCAAGAAGGAGCAGTTCACACGGCCCTTGCTGGAGCTCTGGAGGCTGAGATGGATGGTGCAAAGGGAAGGCTGTCCT
CTGGCCACTTGAAATGTCGCCTGAAAATGGATAAACTTAGATTGAAGGGCGTGTCATACTCCTTGTGTACCGCAGCGTTCA
CATTCACCAAGATCCCGGCTGAAACACTGCACGGGACAGTCACAGTGGAGGTACAGTACGCAGGGACAGATGGACCTTG
CAAGGTTCCAGCTCAGATGGCGGTGGACATGCAAACTCTGACCCCAGTTGGGAGGTTGATAACCGCTAACCCCGTAATCA
CTGAAAGCACTGAGAACTCTAAGATGATGCTGGAACTTGATCCACCATTTGGGGACTCTTACATTGTCATAGGAGTCGGG
GAGAAGAAGATCACCCACCACTGGCACAGGAGTGGCAGCACCATTGGAAAAGCATTTGAAGCCACTGTGAGAGGTGCCA
AGAGAATGGCAGTCTTGGGAGACACAGCCTGGGACTTTGGATCAGTTGGAGGCGCTCTCAACTCATTGGGCAAGGGCAT
CCATCAAATTTTTGGAGCAGCTTTCAAATCATTGTTTGGAGGAATGTCCTGGTTCTCACAAATTCTCATTGGAACGTTGCTG
ATGTGGTTGGGTCTGAACACAAAGAATGGATCTATTTCCCTTATGTGCTTGGCCTTAGGGGGAGTGTTGATCTTCTTATCC
ACAGCCGTCTCTGCTGATGTGGGGTGCTCGGTGGACTTCTCAAAGAAGGAGACGAGATGCGGTACAGGGGTGTTCGTCT
ATAACGACGTTGAAGCCTGGAGGGACAGGTACAAGTACCATCCTGACTCCCCCCGTAGATTGGCAGCAGCAGTCAAGCA
AGCCTGGGAAGATGGTATCTGCGGGATCTCCTCTGTTTCAAGAATGGAAAACATCATGTGGAGATCAGTAGAAGGGGAG
CTCAACGCAATCCTGGAAGAGAATGGAGTTCAACTGACGGTCGTTGTGGGATCTGTAAAAAACCCCATGTGGAGAGGTC
CACAGAGATTGCCCGTGCCTGTGAACGAGCTGCCCCACGGCTGGAAGGCTTGGGGGAAATCGCACTTCGTCAGAGCAGC
AAAGACAAATAACAGCTTTGTCGTGGATGGTGACACACTGAAGGAATGCCCACTCAAACATAGAGCATGGAACAGCTTTC
TTGTGGAGGATCATGGGTTCGGGGTATTTCACACTAGTGTCTGGCTCAAGGTTAGAGAAGATTATTCATTAGAGTGTGAT
CCAGCCGTTATTGGAACAGCTGTTAAGGGAAAGGAGGCTGTACACAGTGATCTAGGCTACTGGATTGAGAGTGAGAAGA
ATGACACATGGAGGCTGAAGAGGGCCCATCTGATCGAGATGAAAACATGTGAATGGCCAAAGTCCCACACATTGTGGAC
AGATGGAATAGAAGAGAGTGATCTGATCATACCCAAGTCTTTAGCTGGGCCACTCAGCCATCACAATACCAGAGAGGGCT
ACAGGACCCAAATGAAAGGGCCATGGCACAGTGAAGAGCTTGAAATTCGGTTTGAGGAATGCCCAGGCACTAAGGTCCA
CGTGGAGGAAACATGTGGAACAAGAGGACCATCTCTGAGATCAACCACTGCAAGCGGAAGGGTGATCGAGGAATGGTG
CTGCAGGGAGTGCACAATGCCCCCACTGTCGTTCCGGGCTAAAGATGGCTGTTGGTATGGAATGGAGATAAGGCCCAGG
AAAGAACCAGAAAGCAACTTAGTAAGGTCAATGGTGACTGCAGGATCAACTGATCACATGGATCACTTCTCCCTTGGAGT
GCTTGTGATTCTGCTCATGGTGCAGGAAGGGCTGAAGAAGAGAATGACCACAAAGATCATCATAAGCACATCAATGGCA
GTGCTGGTAGCTATGATCCTGGGAGGATTTTCAATGAGTGACCTGGCTAAGCTTGCAATTTTGATGGGTGCCACCTTCGC
GGAAATGAACACTGGAGGAGATGTAGCTCATCTGGCGCTGATAGCGGCATTCAAAGTCAGACCAGCGTTGCTGGTATCTT
TCATCTTCAGAGCTAATTGGACACCCCGTGAAAGCATGCTGCTGGCCTTGGCCTCGTGTCTTTTGCAAACTGCGATCTCCG
CCTTGGAAGGCGACCTGATGGTTCTCATCAATGGTTTTGCTTTGGCCTGGTTGGCAATACGAGCGATGGTTGTTCCACGCA
CTGATAACATCACCTTGGCAATCCTGGCTGCTCTGACACCACTGGCCCGGGGCACACTGCTTGTGGCGTGGAGAGCAGGC
CTTGCTACTTGCGGGGGGTTTATGCTCCTCTCTCTGAAGGGAAAAGGCAGTGTGAAGAAGAACTTACCATTTGTCATGGC
CCTGGGACTAACCGCTGTGAGGCTGGTCGACCCCATCAACGTGGTGGGGCTGCTGTTGCTCACAAGGAGTGGGAAGCGG
AGCTGGCCCCCTAGCGAAGTACTCACAGCTGTTGGCCTGATATGCGCATTGGCTGGAGGGTTCGCCAAGGCAGATATAGA
GATGGCTGGGCCCATGGCCGCGGTCGGTCTGCTAATTGTCAGTTACGTGGTCTCAGGAAAGAGTGTGGACATGTACATTG
AAAGAGCAGGTGACATCACATGGGAAAAAGATGCGGAAGTCACTGGAAACAGTCCCCGGCTCGATGTGGCGCTAGATG
AGAGTGGTGATTTCTCCCTGGTGGAGGATGACGGTCCCCCCATGAGAGAGATCATACTCAAGGTGGTCCTGATGACCATC
TGTGGCATGAACCCAATAGCCATACCCTTTGCAGCTGGAGCGTGGTACGTATACGTGAAGACTGGAAAAAGGAGTGGTG
CTCTATGGGATGTGCCTGCTCCCAAGGAAGTAAAAAAGGGGGAGACCACAGATGGAGTGTACAGAGTAATGACTCGTAG
ACTGCTAGGTTCAACACAAGTTGGAGTGGGAGTTATGCAAGAGGGGGTCTTTCACACTATGTGGCACGTCACAAAAGGA
TCCGCGCTGAGAAGCGGTGAAGGGAGACTTGATCCATACTGGGGAGATGTCAAGCAGGATCTGGTGTCATACTGTGGTC
CATGGAAGCTAGATGCCGCCTGGGACGGGCACAGCGAGGTGCAGCTCTTGGCCGTGCCCCCCGGAGAGAGAGCGAGGA
ACATCCAGACTCTGCCCGGAATATTTAAGACAAAGGATGGGGACATTGGAGCGGTTGCGCTGGATTACCCAGCAGGAAC
TTCAGGATCTCCAATCCTAGACAAGTGTGGGAGAGTGATAGGACTTTATGGCAATGGGGTCGTGATCAAAAATGGGAGT
TATGTTAGTGCCATCACCCAAGGGAGGAGGGAGGAAGAGACTCCTGTTGAGTGCTTCGAGCCTTCGATGCTGAAGAAGA
AGCAGCTAACTGTCTTAGACTTGCATCCTGGAGCTGGGAAAACCAGGAGAGTTCTTCCTGAAATAGTCCGTGAAGCCATA
AAAACAAGACTCCGTACTGTGATCTTAGCTCCAACCAGGGTTGTCGCTGCTGAAATGGAGGAAGCCCTTAGAGGGCTTCC
AGTGCGTTATATGACAACAGCAGTCAATGTCACCCACTCTGGAACAGAAATCGTCGACTTAATGTGCCATGCCACCTTCAC
TTCACGTCTACTACAGCCAATCAGAGTCCCCAACTATAATCTGTATATTATGGATGAGGCCCACTTCACAGATCCCTCAAGT
ATAGCAGCAAGAGGATACATTTCAACAAGGGTTGAGATGGGCGAGGCGGCTGCCATCTTCATGACCGCCACGCCACCAG
GAACCCGTGACGCATTTCCGGACTCCAACTCACCAATTATGGACACCGAAGTGGAAGTCCCAGAGAGAGCCTGGAGCTCA
GGCTTTGATTGGGTGACGGATTATTCTGGAAAAACAGTTTGGTTTGTTCCAAGCGTGAGGAACGGCAATGAGATCGCAGC
TTGTCTGACAAAGGCTGGAAAACGGGTCATACAGCTCAGCAGAAAGACTTTTGAGACAGAGTTCCAGAAAACAAAACATC
AAGAGTGGGACTTTGTCGTGACAACTGACATTTCAGAGATGGGCGCCAACTTTAAAGCTGACCGTGTCATAGATTCCAGG -continued

SEQUENCES

AGATGCCTAAAGCCGGTCATACTTGATGGCGAGAGAGTCATTCTGGCTGGACCCATGCCTGTCACACATGCCAGCGCTGC
CCAGAGGAGGGGGCGCATAGGCAGGAATCCCAACAAACCTGGAGATGAGTATCTGTATGGAGGTGGGTGCGCAGAGAC
TGACGAAGACCATGCACACTGGCTTGAAGCAAGAATGCTCCTTGACAATATTTACCTCCAAGATGGCCTCATAGCCTCGCT
CTATCGACCTGAGGCCGACAAAGTAGCAGCCATTGAGGGAGAGTTCAAGCTTAGGACGGAGCAAAGGAAGACCTTTGTG
GAACTCATGAAAAGAGGAGATCTTCCTGTTTGGCTGGCCTATCAGGTTGCATCTGCCGGAATAACCTACACAGATAGAAG
ATGGTGCTTTGATGGCACGACCAACAACACCATAATGGAAGACAGTGTGCCGGCAGAGGTGTGGACCAGACACGGAGA
GAAAAGAGTGCTCAAACCGAGGTGGATGGACGCCAGAGTTTGTTCAGATCATGCGGCCCTGAAGTCATTCAAGGAGTTT
GCCGCTGGGAAAAGAGGAGCGGCTTTTGGAGTGATGGAAGCCCTGGGAACACTGCCAGGACACATGACAGAGAGATTC
CAGGAAGCCATTGACAACCTCGCTGTGCTCATGCGGGCAGAGACTGGAAGCAGGCCTTACAAAGCCGCGGCGGCCCAAT
TGCCGGAGACCCTAGAGACCATTATGCTTTTGGGGTTGCTGGGAACAGTCTCGCTGGGAATCTTTTTCGTCTTGATGAGG
AACAAGGGCATAGGGAAGATGGGCTTTGGAATGGTGACTCTTGGGGCCAGCGCATGGCTCATGTGGCTCTCGGAAATTG
AGCCAGCCAGAATTGCATGTGTCCTCATTGTTGTGTTCCTATTGCTGGTGGTGCTCATACCTGAGCCAGAAAAGCAAAGAT
CTCCCCAGGACAACCAAATGGCAATCATCATCATGGTAGCAGTAGGTCTTCTGGGCTTGATTACCGCCAATGAACTCGGAT
GGTTGGAGAGAACAAAGAGTGACCTAAGCCATCTAATGGGAAGGAGAGAGGAGGGGGCAACCATGGGATTCTCAATGG
ACATTGACCTGCGGCCAGCCTCAGCTTGGGCCATCTATGCTGCCTTGACAACTTTCATTACCCCAGCCGTCCAACATGCAGT
GACCACTTCATACAACAACTACTCCTTAATGGCGATGGCCACGCAAGCTGGAGTGTTGTTTGGTATGGGCAAAGGGATGC
CATTCTACGCATGGGACTTTGGAGTCCCGCTGCTAATGATAGGTTGCTACTCACAATTAACGCCCCTGACCCTAATAGTGG
CCATCATTTTGCTCGTGGCGCACTACATGTACTTGATCCCAGGGCTGCAGGCAGCAGCTGCGCGTGCTGCCCAGAAGAGA
ACGGCAGCTGGCATCATGAAGAACCCTGTTGTGGATGGAATAGTGGTGACTGACATTGACACAATGACAATTGACCCCCA
AGTGGAGAAAAAGATGGGACAGGTGCTACTCATGGCAGTAGCCGTCTCCAGCGCCATACTGTCGCGGACCGCCTGGGGG
TGGGGGGAGGCTGGGGCCCTGATCACAGCCGCAACTTCCACTTTGTGGGAAGGCTCTCCGAACAAGTACTGGAACTCCTC
TACAGCCACTTCACTGTGTAACATTTTTAGGGGAAGTTACTTGGCTGGAGCTTCTCTAATCTACACAGTAACAAGAAACGC
TGGCTTGGTCAAGAGACGTGGGGGTGGAACAGGAGAGACCCTGGGAGAGAAATGGAAGGCCCGCTTGAACCAGATGTC
GGCCCTGGAGTTCTACTCCTACAAAAAGTCAGGCATCACCGAGGTGTGCAGAGAAGAGGCCCGCCGCGCCCTCAAGGAC
GGTGTGGCAACGGGAGGCCATGCTGTGTCCCGAGGAAGTGCAAAGCTGAGATGGTTGGTGGAGCGGGGATACCTGCAG
CCCTATGGAAAGGTCATTGATCTTGGATGTGGCAGAGGGGGCTGGAGTTACTACGCCGCCACCATCCGCAAAGTTCAAGA
AGTGAAAGGATACACAAAAGGAGGCCCTGGTCATGAAGAACCCGTGTTGGTGCAAAGCTATGGGTGGAACATAGTCCGT
CTTAAGAGTGGGGTGGACGTCTTTCATATGGCGGCTGAGCCGTGTGACACGTTGCTGTGTGACATAGGTGAGTCATCATC
TAGTCCTGAAGTGGAAGAAGCACGGACGCTCAGAGTCCTCTCCATGGTGGGGGATTGGCTTGAAAAAAGACCAGGAGCC
TTTTGTATAAAAGTGTTGTGCCCATACACCAGCACTATGATGGAAACCCTGGAGCGACTGCAGCGTAGGTATGGGGGAG
GACTGGTCAGAGTGCCACTCTCCCGCAACTCTACACATGAGATGTACTGGGTCTCTGGAGCGAAAAGCAACACCATAAAA
AGTGTGTCCACCACGAGCCAGCTCCTCTTGGGGCGCATGGACGGGCCTAGGAGGCCAGTGAAATATGAGGAGGATGTGA
ATCTCGGCTCTGGCACGCGGGCTGTGGTAAGCTGCGCTGAAGCTCCCAACATGAAGATCATTGGTAACCGCATTGAAAGG
ATCCGCAGTGAGCACGCGGAAACGTGGTTCTTTGACGAGAACCACCCATATAGGACATGGGCTTACCATGGAAGCTATGA
GGCCCCCACACAAGGGTCAGCGTCCTCTCTAATAAACGGGGTTGTCAGGCTCCTGTCAAAACCCTGGGATGTGGTGACTG
GAGTCACAGGAATAGCCATGACCGACACCACACCGTATGGTCAGCAAAGAGTTTTCAAGGAAAAAGTGGACACTAGGGT
GCCAGACCCCCAAGAAGGCACTCGTCAGGTTATGAGCATGGTCTCTTCCTGGTTGTGGAAAGAGCTAGGCAAACACAAAC
GGCCACGAGTCTGTACCAAAGAAGAGTTCATCAACAAGGTTCGTAGCAATGCAGCATTAGGGGCAATATTTGAAGAGGA
AAAAGAGTGGAAGACTGCAGTGGAAGCTGTGAACGATCCAAGGTTCTGGGCTCTAGTGGACAAGGAAAGAGAGCACCA
CCTGAGAGGAGAGTGCCAGAGTTGTGTGTACAACATGATGGGAAAAAGAGAAAAGAAACAAGGGGAATTTGGAAAGGC
CAAGGGCAGCCGCGCCATCTGGTATATGTGGCTAGGGGCTAGATTTCTAGAGTTCGAAGCCCTTGGATTCTTGAACGAGG
ATCACTGGATGGGGAGAGAGAACTCAGGAGGTGGTGTTGAAGGGCTGGGATTACAAAGACTCGGATATGTCCTAGAAG
AGATGAGTCGCATACCAGGAGGAAGGATGTATGCAGATGACACTGCTGGCTGGGACACCCGCATCAGCAGGTTTGATCT
GGAGAATGAAGCTCTAATCACCAACCAAATGGAGAAAGGGCACAGGGCCTTGGCATTGGCCATAATCAAGTACACATAC
CAAAACAAAGTGGTAAAGGTCCTTAGACCAGCTGAAAAAGGGAAGACAGTTATGGACATTATTTCGAGACAAGACCAAA
GGGGGAGCGGACAAGTTGTCACTTACGCTCTTAACACATTTACCAACCTAGTGGTGCAACTCATTCGGAATATGGAGGCT
GAGGAAGTTCTAGAGATGCAAGACTTGTGGCTGCTGCGGAGGTCAGAGAAAGTGACCAACTGGTTGCAGAGCAACGGA
TGGGATAGGCTCAAACGAATGGCAGTCAGTGGAGATGATTGCGTTGTGAAGCCAATTGATGATAGGTTTGCACATGCCCT
CAGGTTCTTGAATGATATGGGAAAAGTTAGGAAGGACACACAAGAGTGGAAACCCTCAACTGGATGGGACAACTGGGAA
GAAGTTCCGTTTTGCTCCCACCACTTCAACAAGCTCCATCTCAAGGACGGGAGGTCCATTGTGGTTCCCTGCCGCCACCAA
GATGAACTGATTGGCCGGGCCCGCGTCTCTCCAGGGGCGGGATGGAGCATCCGGGAGACTGCTTGCCTAGCAAAATCAT
ATGCGCAAATGTGGCAGCTCCTTTATTTCCACAGAAGGGACCTCCGACTGATGGCCAATGCCATTTGTTCATCTGTGCCAG
TTGACTGGGTTCCAACTGGGAGAACTACCTGGTCAATCCATGGAAAGGGAGAATGGATGACCACTGAAGACATGCTTGT
GGTGTGGAACAGAGTGTGGATTGAGGAGAACGACCACATGGAAGACAAGACCCCAGTTACGAAATGGACAGACATTCCC
TATTTGGGAAAAAGGGAAGACTTGTGGTGTGGATCTCTCATAGGGCACAGACCGCGCACCACCTGGGCTGAGAACATTA
AAAACACAGTCAACATGGTGCGCAGGATCATAGGTGATGAAGAAAAGTACATGGACTACCTATCCACCCAAGTTCGCTAC
TTGGGTGAAGAAGGGTCTACACCTGGAGTGCTGTAAGCACCAATCTTAATGTTGTCAGGCCTGCTAGTCAGCCACAGCTT
GGGGAAAGCTGTGCAGCCTGTGACCCCCCCAGGAGAAGCTGGGAAACCAAGCCTATAGTCAGGCCGAGAACGCCATGG
CACGGAAGAAGCCATGCTGCCTGTGAGCCCCTCAGAGGACACTGAGTCAAAAAACCCCACGCGCTTGGAGGCGCAGGAT
GGGAAAAGAAGGTGGCGACCTTCCCCACCCTTCAATCTGGGGCCTGAACTGGAGATCAGCTGTGGATCTCCAGAAGAGG
GACTAGTGGTTAGAGGAGA

SEQ ID NO: 6
KU527068.1 Zika virus strain Natal RGN, Brazil: Rio Grande do Norte, Natal, complete genome
AGTTGTTGATCTGTGTGAATCAGACTGCGACAGTTCGAGTTTGAAGCGAAAGCTAGCAACAGTATCAACAGGTTTTATTTT
GGATTTGGAAACGAGAGTTTCTGGTCATGAAAAACCCAAAAAAGAAATCCGGAGGATTCCGGATTGTCAATATGCTAAAA
CGCGGAGTAGCCCGTGTGAGCCCCTTTGGGGGCTTGAAGAGGCTGCCAGCCGGACTTCTGCTGGGTCATGGGCCCATCA
GGATGGTCTTGGCAATTCTAGCCTTTTTGAGATTCACGGCAATCAAGCCATCACTGGGTCTCATCAATAGATGGGGTTCAG
TGGGGAAAAAAGAGGCTATGGAAATAATAAAGAAGTTCAAGAAAGATCTGGCTGCCATGCTGAGAATAATCAATGCTAG
GAAGGAGAAGAAGAGACGAGGCGCAGATACTAGTGTCGGAATTGTTGGCCTCCTGCTGACCACAGCTATGGCAGCGGA
GGTCACTAGACGTGGGAGTGCATACTATATGTACTTGGACAGAAACGATGCTGGGGAGGCCATATCTTTTCCAACCACAT
TGGGGATGAATAAGTGTTATATACAGATCATGGATCTTGGACACATGTGTGATGCCACCATGAGCTATGAATGCCCTATG
CTGGATGAGGGGGTGGAACCAGATGACGTCGATTGTTGGTGCAACACGACGTCAACTTGGGTTGTGTACGGAACCTGCC
ATCACAAAAAAGGTGAAGCACGGAGATCTAGAAGAGCTGTGACGCTCCCCTCCCATTCCACTAGGAAGCTGCAAACGCG
GTCGCAAACCTGGTTGGAATCAAGAGAATACACAAAGCACTTGATTAGAGTCGAAAATTGGATATTCAGGAACCCTGGCT
TCGCGTTAGCAGCAGCTGCCATCGCTTGGCTTTTGGGAAGCTCAACGAGCCAAAAAGTCATATACTTGGTCATGATACTGC
TGATTGCCCCGGCATACAGCATCAGGTGCATAGGAGTCAGCAATAGGGACTTTGTGGAAGGTATGTCAGGTGGGACTTG -continued

| SEQUENCES |
| --- |

GGTTGATGTTGTCTTGGAACATGGAGGTTGTGTCACCGTAATGGCACAGGACAAACCGACTGTCGACATAGAGCTGGTTA
CAACAACAGTCAGCAACATGGCGGAGGTAAGATCCTACTGCTATGAGGCATCAATATCAGACATGGCTTCGGACAGCCGC
TGCCCAACACAAGGTGAAGCCTACCTTGACAAGCAATCAGACACTCAATATGTCTGCAAAAGAACGTTAGTGGACAGAGG
CTGGGGAAATGGATGTGGACTTTTTGGCAAAGGGAGCCTGGTGACATGCGCTAAGTTTGCATGCTCCAAGAAAATGACC
GGGAAGAGCATCCAGCCAGAGAATCTGGAGTACCGGATAATGCTGTCAGTTCATGGCTCCCAGCACAGTGGGATGATCG
TTAATGACACAGGACATGAAACTGATGAGAATAGAGCGAAGGTTGAGATAACGCCCAATTCACCAAGAGCCGAAGCCAC
CCTGGGGGGTTTTGGAAGCCTAGGACTTGATTGTGAACCGAGGACAGGCCTTGACTTTTCAGATTTGTATTACTTGACTAT
GAATAACAAGCACTGGTTGGTCCACAAGGAGTGGTTCCACGACATTCCATTACCTTGGCACGCTGGGGCAGACACCGGAA
CTCCACACTGGAACAACAAAGAAGCACTGGTAGAGTTCAAGGACGCACATGCCAAAAGGCAAACTGTCGTGGTTCTAGG
GAGTCAAGAAGGAGCAGTTCACACGGCCCTTGCTGGAGCTCTGGAGGCTGAGATGGATGGTGCAAAGGGAAGGCTGTC
CTCTGGCCACTTGAAATGTCGCCTGAAAATGGATAAACTTAGATTGAAGGGCGTGTCATACTCCTTGTGTACCGCAGCGTT
CACATTCACCAAGATCCCGGCTGAAACACTGCACGGGACAGTCACAGTGGAGGTACAGTACGCAGGGACAGATGGACCT
TGCAAGGTTCCAGCTCAGATGGCGGTGGACATGCAAACTCTGACCCCAGTTGGGAGGTTGATAACCGCTAACCCCGTAAT
CACTGAAAGCACTGAGAACTCTAAGATGATGCTGGAACTTGATCCACCATTTGGGGACTCTTACATTGTCATAGGAGTCG
GGGAGAAGAAGATCACCCACCACTGGCACAGGAGTGGCAGCACCATTGGAAAAGCATTTGAAGCCACTGTGAGAGGTG
CCAAGAGAATGGCAGTCTTGGGAGACACAGCCTGGGACTTTGGATCAGTTGGAGGCGCTCTCAACTCATTGGGCAAGGG
CATCCATCAAATTTTTGGAGCAGCTTTCAAATCATTGTTTGGAGGAATGTCCTGGTTCTCACAAATCCTCATTGGAACGTTG
CTGATGTGGTTGGGTCTGAACACAAAGAATGGATCTATTTCCCTTATGTGCTTGGCCTTAGGGGGAGTGTTGATCTTCTTA
TCCACAGCCGTCTCTGCTGATGTGGGGTGCTCGGTGGACTTCTCAAAGAAGGAGACGAGATGCGGTACAGGGGTGTTCG
TCTATAACGACGTTGAAGCCTGGAGGGACAGGTACAAGTACCATCCTGACTCCCCCCGTAGATTGGCAGCAGCAGTCAAG
CAAGCCTGGGAAGATGGTATCTGCGGGATCTCCTCTGTTTCAAGAATGGAGAACATCATGTGGAGATCAGTAGAAGGGG
AGCTCAACGCAATCTTGGAAGAGAATGGAGTTCAACTGACGGTCGTTGTGGGATCTGTAAAAAACCCCATGTGGAGAGG
TCCACAGAGATTGCCCGTGCCTGTGAACGAGCTGCCCCACGGCTGGAAGGCTTGGGGGAAATCGTACTTCGTCAGAGCA
GCAAAGACAAATAACAGCTTTGTCGTGGATGGTGACACACTGAAGGAATGCCCACTCGAACATAGAGCATGGAACAGCT
TTCTTGTGGAGGATCATGGGTTCGGGGTATTTCACACTAGTGTCTGGCTCAAGGTTAGAGAAGATTATTCATTAGAGTGT
GATCCAGCCGTTATTGGAACAGCTGTTAAGGGGAAGGAGGCTGTACACAGTGATCTAGGCTACTGGATTGAGAGTGAGA
AGAATGACACATGGAGGCTGAAGAGGGCCCATCTAATCGAGATGAAAACATGTGAATGGCCAAAGTCCCACACATTGTG
GGCAGATGGAATAGAAGAGAGTGATCTGATCATTCCCAAGTCTTTAGCTGGGCCACTCAGCCATCACAATACCAGAGAGG
GCTACAGGACCCAAATGAAAGGGCCATGGCACAGTGAAGAGCTTGAAATTCGGTTTGAGGAATGCCCGGGCACTAAGGT
CCACGTGGAGGAAACATGTGGAACAAGAGGACCATCTCTGAGATCAACCACTGCAAGCGGAAGGGTGATCGAGGAATG
GTGCTGCAGGGAGTGCACAATGCCCCCACTGTCGTTCCGGGCTAAAGATGGCTGTTGGTATGGAATGGAGATAAGGCCC
AGGAAAGAACCAGAAAGCAACTTAGTAAGGTCAGTGGTGACTGCAGGATCAACTGATCACATGGATCACTTCTCCCTTGG
AGTGCTTGTGATTCTGCTCATGGTGCAGGAAGGGCTGAAGAAGAGAATGACCACAAAGATCATCATAAGCACATCAATG
GCAGTGCTGGTAGCTATGATCCTGGGAGGATTTTCAATGAGTGACCTGGCTAAGCTTGCAATTTTGATGGGCGCCACCTT
CGCGGAAATGAACACTGGAGGAGATGTAGCTCATCTGGCGCTGATAGCGGCATTCAAAGTCAGACCAGCGTTGCTGGTA
TCTTTCATCTTCAGAGCTAATTGGACACCCCGTGAAAGCATGCTGCTGGCCTTGGCCTCGTGTCTTTTGCAAACTGCGATCT
CCGCCTTGGAAGGCGACCTGATGGTTCTCATCAATGGTTTTGCTTTGGCCTGGTTGGCAATACGAGCGATGGTTGTTCCAC
GCACTGATAACATCACCTTGGCAATCCTGGCTGCTCTGACACCACTGGCCCGGGGCACACTGCTTGTGGCGTGGAGAGCA
GGCCTTGCTACTTGCGGGGGGTTTATGCTCCTCTCTCTGAAGGGAAAAGGCAGTGTGAAGAAGAACTTACCATTTGTCAT
GGCCCTGGGACTAACCGCTGTGAGGCTGGTCGACCCCATCAACGTGGTGGGACTGCTGTTGCTCACAAGGAGTGGGAAG
CGGAGCTGGCCCCCTAGCGAAGTACTCACAGCTGTTGGCCTGATATGCGCATTGGCTGGAGGGTTCGCCAAGGCAGATAT
AGAGATGGCTGGGCCCATGGCCGCGGTCGGTCTGCTAATTGTCAGTTACGTGGTCTCAGGAAAGAGTGTGGACATGTAC
ATTGAAAGAGCAGGTGACATCACATGGGAAAAAGATGCGGAAGTCACTGGAAACAGTCCCCGGCTCGATGTGGCGCTAG
ATGAGAGTGGTGATTTCTCCCTGGTGGAGGATGACGGTCCCCCCATGAGAGAGATCATACTCAAGGTGGTCCTGATGACC
ATCTGTGGCATGAACCCAATAGCCATACCCTTTGCAGCTGGAGCGTGGTACGTATACGTGAAGACTGGAAAAAGGAGTG
GTGCTCTATGGGATGTGCCTGCTCCCAAGGAAGTAAAAAAGGGGGAGACCACAGATGGAGTGTACAGAGTAATGACTCG
TAGACTGCTAGGTTCAACACAAGTTGGAGTGGGAGTTATGCAAGAGGGGGTCTTTCACACTATGTGGCACGTCACAAAA
GGATCCGCGCTGAGAAGCGGTGAAGGGAGACTTGATCCATACTGGGGAGATGTCAAGCAGGATCTGGTGTCATACTGTG
GTCCATGGAAGCTAGATGCCGCCTGGGACGGGCACAGCGAGGTGCAGCTCTTGGCCGTGCCCCCCGGAGAGAGAGCGA
GGAACATCCAGACTCTGCCCGGAATATTTAAGACAAAGGATGGGGACATTGGAGCGGTTGCGCTGGATTACCCAGCAGG
AACTTCAGGATCTCCAATCCTAGACAAGTGTGGGAGAGTGATAGGACTTTATGGCAATGGGGTCGTGATCAAAAATGGG
AGTTATGTTAGTGCCATCACCCAAGGGAGGAGGGAGGAAGAGACTCCTGTTGAGTGCTTCGAGCCTTCGATGCTGAAGA
AGAAGCAGCTAACTGTCTTAGACTTGCATCCTGGAGCTGGGAAAACCAGGAGAGTTCTTCCTGAAATAGTCCGTGAAGCC
ATAAAAACAAGACTCCGTACTGTGATCTTAGCTCCAACCAGGGTTGTCGCTGCTGAAATGGAGGAAGCCCTTAGAGGGCT
TCCAGTGCGTTATATGACAACAGCAGTCAATGTCACCCACTCTGGAACAGAAATCGTCGACTTAATGTGCCATGCCACCTT
CACTTCACGTCTACTACAGCCAATCAGAGTCCCCAACTATAATCTGTATATTATGGATGAGGCCCACTTCACAGATCCCTCA
AGTATAGCAGCAAGAGGATACATTTCAACAAGGGTTGAGATGGGCGAGGCGGCTGCCATCTTCATGACCGCCACGCCAC
CAGGAACCCGTGACGCATTTCCGGACTCCAACTCACCAATTATGGACACCGAAGTGGAAGTCCCAGAGAGAGCCTGGAG
CTCAGGCTTTGATTGGGTGACGGATCATTCTGGAAAAACAGTTTGGTTTGTTCCAAGCGTGAGGAACGGCAATGAGATCG
CAGCTTGTCTGACAAAGGCTGGAAAACGGGTCATACAGCTCAGCAGAAAGACTTTTGAGACAGAGTTCCAGAAAACAAA
ACATCAAGAGTGGGACTTTGTCGTGACAACTGACATTTCAGAGATGGGCGCCAACTTTAAAGCTGACCGTGTCATAGATT
CCAGGAGATGCCTAAAGCCGGTCATACTTGATGGCGAGAGAGTCATTTTGGCTGGACCCATGCCTGTCACACATGCCAGC
GCTGCCCAGAGGAGGGGGCGCATAGGCAGGAATCCCAACAAACCTGGAGATGAGTATCTGTATGGAGGTGGGTGCGCA
GAGACTGACGAAGACCATGCACACTGGCTTGAAGCAAGAATGCTCCTTGACAATATTTACCTCCAAGATGGCCTCATAGC
CTCGCTCTATCGACCTGAGGCCGACAAAGTAGCAGCCATTGAGGGAGAGTTCAAGCTTAGGACGGAGCAAAGGAAGACC
TTTGTGGAACTCATGAAAAGAGGAGATCTTCCTGTTTGGCTGGCCTATCAGGTTGCATCTGCCGGAATAACCTACACAGAT
AGAAGATGGTGCTTTGATGGCACGACCAACAACACCATAATGGAAGACAGTGTGCCGGCAGAGGTGTGGACCAGACAC
GGAGAGAAAAGAGTGCTCAAACCGAGGTGGATGGACGCCAGAGTTTGTTCAGATCATGCGGCCCTGAAGTCATTCAAGG
AGTTTGCCGCTGGGAAAAGAGGAGCGGCTTTTGGAGTGATGGAAGCCCTGGGAACACTGCCAGGACACATGACAGAGA
GATTCCAGGAAGCCATTGACAACCTCGCTGTGCTCATGCGGGCAGAGACTGGAAGCAGGCCTTACAAAGCCGCGGCGGC
CCAATTGCCGGAGACCCTAGAGACCATTATGCTTTTGGGGTTGCTGGGAACAGTCTCGCTGGGAATCTTTTTCGTCTTGAT
GAGGAACAAGGGCATAGGGAAGATGGGCTTTGGAATGGTGACTCTTGGGGCCAGCGCATGGCTCATGTGGCTCTCGGA
AATTGAGCCAGCCAGAATTGCATGTGTCCTCATTGTTGTGTTCCTATTGCTGGTGGTGCTCATACCTGAGCCAGAAAAGCA
AAGATCTCCCCAGGACAACCAAATGGCAATCATCATCATGGTAGCAGTAGGTCTTCTGGGCTTGATTACCGCCAATGAACT
CGGATGGTTGGAGAGAACAAAGAGTGACCTAAGCCATCTAATGGGAAGGAGAGAGGAGGGAGCAACCATAGGATTCTC
AATGGACATTGACCTGCGGCCAGCCTCAGCTTGGGCCATCTATGCTGCCTTGACAACTTTCATTACCCCAGCCGTCCAACA
TGCAGTGACCACTTCATACAACAACTACTCCTTAATGGCGATGGCCACGCAAGCTGGAGTGTTGTTTGGTATGGGCAAAG

-continued

SEQUENCES

GGATGCCATTCTACGCATGGGACTTTGGAGTCCCGCTGCTAATGATAGGTTGCTACTCACAATTAACACCCCTGACCCTAA
TAGTGGCCATCATTTTGCTCGTGGCGCACTACATGTACTTGATCCCAGGGCTGCAGGCAGCAGCTGCGCGTGCTGCCCAG
AAGAGAACGGCAGCTGGCATCATGAAGAACCCTGTTGTGGATGGAATAGTGGTGACTGACATTGACACAATGACAATTG
ACCCCCAAGTGGAGAAAAAGATGGGACAGGTGCTACTCATAGCAGTAGCAGTCTCCAGCGCCATACTGTCGCGGACCGC
CTGGGGGTGGGGGGAGGCTGGGGCCCTGATCACAGCCGCAACTTCCACTTTGTGGGAAGGCTCTCCGAACAAGTACTGG
AACTCCTCTACAGCCACTTCACTGTGTAACATTTTTAGGGGAAGTTACTTGGCTGGAGCTTCTCTAATCTACATAGTAACAA
GAAACGCTGGCTTGGTCAAGAGACGTGGGGGTGGAACAGGAGAGACCCTGGGAGAGAAATGGAAGGCCCGCTTGAAC
CAGATGTCGGCCCTGGAGTTCTACTCCTACAAAAAGTCAGGCATCACCGAGGTGTGCAGAGAAGAGGCCCGCCGCGCCC
TCAAGGATGGTGTGGCAACGGGAGGCCATGCTGTGTCCCGAGGAAGTGCAAAGCTGAGATGGTTGGTGGAGCGGGGAT
ACCTGCAGCCCTATGGAAAGGTCATTGATCTTGGATGTGGCAGAGGGGGCTGGAGTTACTACGCCGCCACCATCCGCAAA
GTTCAAGAAGTGAAAGGATACACAAAAGGAGGCCCTGGTCATGAAGAACCCGTGTTGGTGCAAAGCTATGGGTGGAAC
ATAGTCCGTCTTAAGAGTGGGGTGGACGTCTTTCATATGGCGGCTGAGCCGTGTGACACGTTGCTGTGTGACATAGGTGA
GTCATCATCTAGTCCTGAAGTGGAAGAAGCACGGACGCTCAGAGTCCTCTCCATGGTGGGGGATTGGCTTGAAAAAAGA
CCAGGAGCCTTTTGTATAAAAGTGTTGTGCCCATACACCAGCACTATGATGGAAACCCTGGAGCGACTGCAGCGTAGGTA
TGGGGGAGGACTGGTCAGAGTGCCACTCTCCCGCAACTCTACACATGAGATGTACTGGGTCTCTGGAGCGAAAAGCAAC
ACCATAAAAAGTGTGTCCACCACGAGCCAGCTCCTCTTGGGGCGCATGGACGGGCCTAGGAGGCCAGTGAAATATGAGG
AGGATGTGAATCTCGGCTCTGGCACGCGGGCTGTGGTAAGCTGCGCTGAAGCTCCCAACATGAAGATCATTGGTAACCGC
ATTGAAAGGATCCGCAGTGAGCACGCGGAAACGTGGTTCTTTGACGAGAACCACCCATATAGGACATGGGCTTACCATG
GAAGCTATGAGGCCCCCACACAAGGGTCAGCGTCCTCTCTAATAAACGGGGTTGTCAGGCTCCTGTCAAAACCCTGGGAT
GTGGTGACTGGAGTCACAGGAATAGCCATGACCGACACCACACCGTATGGTCAGCAAAGAGTTTTCAAGGAAAAAGTGG
ACACTAGGGTGCCAGACCCCCAAGAAGGCACTCGTCAGGTTATGAGCATGGTCTCTTCCTGGTTGTGGAAAGAGCTAGGC
AAACACAAACGGCCACGAGTCTGTACCAAAGAAGAGTTCATCAACAAGGTTCGTAGCAATGCAGCATTAGGGGCAATATT
TGAAGAGGAAAAAGAGTGGAAGACTGCAGTGGAAGCTGTGAACGATCCAAGGTTCTGGGCTCTAGTGGACAAGGAAAG
AGAGCACCACCTGAGAGGAGAGTGCCAGAGTTGTGTGTACAACATGATGGGAAAAAGAGAAAAGAAACAAGGGGAATT
TGGAAAGGCCAAGGGCAGCCGCGCCATCTGGTATATGTGGCTAGGGGCTAGATTTCTAGAGTTCGAAGCCCTTGGATTCT
TGAACGAGGATCACTGGATGGGGAGAGAGAACTCAGGAGGTGGTGTTGAAGGGCTGGGATTACAAAGACTCGGATATG
TCCTAGAAGAGATGAGTCGCATACCAGGAGGAAGGATGTATGCAGATGACACTGCTGGCTGGGACACCCGCATCAGCAG
GTTCGATCTGGAGAATGAAGCTCTAATCACCAACCAAATGGAGAAAGGGCATAGGGCCTTGGCATTGGCCATAATCAAGT
ACACATACCAAAACAAAGTGGTAAAGGTCCTTAGACCAGCTGAAAAAGGGAAAACAGTTATGGACATTATTTCGAGACAA
GACCAAAGGGGGAGCGGACAAGTTGTCACTTACGCTCTTAACACATTTACCAACCTAGTGGTGCAACTCATTCGGAATAT
GGAGGCTGAGGAAGTTCTAGAGATGCAAGACTTGTGGCTGCTGCGGAGGTCAGAGAAAGTGACCAACTGGTTGCAGAG
CAACGGATGGGATAGGCTCAAACGAATGGCAGTCAGTGGAGATGATTGCGTTGTGAAGCCAATTGATGATAGGTTTGCA
CATGCCCTCAGGTTCTTGAATGATATGGGAAAAGTTAGGAAGGACACACAAGAGTGGAAACCCTCAACTGGATGGGACA
ACTGGGAAGAAGTTCCGTTTTGCTCCCACCACTTCAACAAGCTCCATCTCAAGGACGGGAGGTCCATTGTGGTTCCCTGCC
GCCACCAAGATGAACTGATTGGCCGGGCCCGCGTCTCTCCAGGGGCGGGATGGAGCATCCGGGAGACTGCTTGCCTAGC
AAAATCATATGCGCAAATGTGGCAGCTCCTTTATTTCCACAGAAGGGACCTCCGACTGATGGCCAATGCCATTTGTTCATC
TGTGCCAGTTGACTGGGTTCCAACTGGGAGAACTACCTGGTCAATCCATGGAAAGGGAGAATGGATGACCACTGAAGAC
ATGCTTGTGGTGTGGAACAGAGTGTGGATTGAGGAGAACGACCACATGGAAGACAAGACCCCAGTTACGAAATGGACA
GACATTCCCTATTTGGGAAAAAGGGAAGACTTGTGGTGTGGATCTCTCATAGGGCACAGACCGCGCACCACCTGGGCTGA
GAACATTAAAAACACAGTCAACATGGTGCGCAGGATCATAGGTGATGAAGAAAAGTACATGGACTACCTATCCACCCAAG
TTCGCTACTTGGGTGAAGAAGGGTCTACACCTGGAGTGCTGTAAGCACCAATCTTAATGTTGTCAGGCCTGCTAGTCAGC
CACAGCTTGGGGAAAGCTGTGCAGCCTGTGACCCCCCCAGGAGAAGCTGGGAAACCAAGCCTATAGTCAGGCCGAGAAC
GCCATGGCACGGAAGAAGCCATGCTGCCTGTGAGCCCCTCAGAGGACACTGAGTCAAAAAACCCCATGCGCTTGGAGGC
GCAGGATGGGAAAAGAAGGTGGCGACCTTCCCCACCCTTCAATCTGGGGCCTGAACTGGAGATCAGCTGTGGATCTCCA
GAAGAGGGACTAGTGGTTAGAGGAGACCCCCCGGAAAACGCAAAACAGCATATTGACGCTGGGAAAGACCAGAGACTC
CATGAGTTTCCACCACGCTGGCCGCCAGGCACAGATCGCCGAATAGCGGCGGCCGGTGTGGGGAAATCCATGGGTCTT

SEQ ID NO: 7
KU681081.3 Zika virus isolate Zika virus/*H. sapiens*-tc/THA/2014/SV0127- 14, Thailand, complete genome
AGTTGTTGATCTGTGTGAATCAGACTGCGACAGTTCGAGTTTGAAGCGAAAGCTAGCAACAGTATCAACAGGTTTTATTTT
GGATTTGGAAACGAGAGTTTCTGGTCATGAAAAACCCAAAAAAGAAATCCGGAGGATTCCGGATTGTCAATATGCTAAAA
CGCGGAGTAGCCCGTGTGAGCCCCTTTGGGGGCTTGAAGAGGCTGCCAGCCGGACTTCTGCTGGGTCATGGGCCCATCA
GGATGGTCTTGGCGATTCTAGCCTTTTTGAGATTCACGGCAATCAAGCCATCACTGGGTCTCATCAATAGATGGGGTTCAG
TGGGAAAAAAAGAGGCTATGGAAATAATAAAGAAGTTCAAGAAAGATCTGGCTGCCATGCTGAGAATAATCAATGCTAG
GAAGGAGAAGAAGAGACGAGGCACAGATACTAGTGTCGGAATTGTTGGCCTCCTGCTGACCACAGCTATGGCAGCGGA
GGTCACTAGACGTGGGAGTGCATACTATATGTACTTGGACAGAAGCGATGCTGGGGAGGCCATATCTTTTCCAACCACAC
TGGGGATGAATAAGTGTTATATACAGATCATGGATCTTGGACACATGTGTGATGCCACCATGAGCTATGAATGCCCTATG
CTGGATGAGGGGGTAGAACCAGATGACGTCGATTGTTGGTGCAACACGACGTCAACTTGGGTTGTGTACGGAACCTGCC
ATCACAAAAAAGGTGAAGCACGGAGATCCAGAAGAGCTGTGACGCTCCCCTCCCATTCCACTAGGAAGCTGCAAACGCG
GTCGCAGACCTGGTTGGAATCAAGAGAATACACAAAGCACTTGATTAGAGTCGAAAATTGGATATTCAGGAACCCTGGCT
TCGCGTTAGCAGCAGCTGCCATCGCTTGGCTTTTGGGAAGCTCAACGAGCCAAAAAGTCATATACTTGGTCATGATACTGC
TGATTGCCCCGGCATACAGCATCAGGTGCATAGGAGTCAGTAATAGGGACTTTGTGGAAGGTATGTCAGGTGGGACTTG
GGTTGATGTTGTCTTGGAACATGGAGGTTGTGTCACCGTAATGGCACAGGACAAACCGACTGTCGACATAGAGCTGGTTA
CAACAACAGTCAGCAACATGGCGGAGGTAAGATCCTACTGCTATGAGGCATCAATATCGGACATGGCTTCGGACAGCCG
CTGCCCAACACAAGGTGAAGCCTACCTTGACAAGCAATCAGACACTCAATATGTCTGCAAAAGAACGTTAGTGGACAGAG
GCTGGGGAAATGGATGTGGACTTTTTGGCAAAGGGAGCCTGGTGACATGCGCTAAGTTTGCATGCTCCAAGAAAATGAC
CGGGAAGAGCATCCAGCCAGAGAATCTGGAGTACCGGATAATGCTGTCAGTTCATGGCTCCCAGCACAGTGGGATGATC
GTTAATGACACAGGACATGAAACTGATGAGAATAGAGCGAAGGTTGAGATAACGCCCAATTCACCAAGAGCCGAAGCCA
CCCTGGGGGGTTTTGGAAGCCTAGGACTTGATTGTGAACCGAGGACAGGCCTTGACTTTTCAGATTTGTATTACTTGACTA
TGAACAACAAGCACTGGTTGGTTCACAAGGAGTGGTTCCACGACATTCCATTACCTTGGCACACTGGGGCAGACACCGGA
ACTCCACACTGGAACAACAAAGAAGCACTGGTAGAGTTCAAGGACGCACATGCCAAAAGGCAAACTGTCGTGGTTCTAG
GGAGTCAAGAAGGAGCAGTTCACACGGCCCTTGCTGGAGCTCTGGAGGCTGAGATGGATGGTGCAAAGGGAAGGCTGT
CCTCTGGCCACTTGAAATGTCGCCTGAAAATGGATAAACTTAGATTGAAGGGCGTGTCATACTCCTTGTGTACCGCAGCGT
TCACATTCACCAAGATCCCGGCTGAAACACTGCACGGGACAGTCACAGTGGAGGTACAGTACGCAGGGACAGATGGACC
TTGCAAGGTTCCAGCTCAGATGGCGGTGGACATGCAAACTCTGACCCCAGTTGGGAGGTTGATAACCGCTAACCCCGTAA
TCACTGAAGGCACTGAGAACTCTAAGATGATGCTGGAACTTGATCCACCATTTGGGGACTCTTACATTGTCATAGGAGTCG -continued

| SEQUENCES |
|---|
| GGGAGAAGAAGATCACCCACCACTGGCACAGGAGTGGCAGCACCATTGGAAAAGCATTTGAAGCCACTGTGAGAGGTG<br>CCAAGAGAATGGCAGTCTTGGGAGACACAGCCTGGGACTTTGGATCAGTTGGAGGCGTTCTTAACTCATTGGGCAAGGG<br>CATCCATCAAATTTTTGGAGCAGCTTTCAAATCATTGTTTGGAGGAATGTCCTGGTTCTCACAAATTCTCATTGGAACGTTG<br>CTGATGTGGTTGGGTCTGAATACAAAGAATGGATCTATTTCCCTTATGTGCTTGGCCTTAGGGGGAGTGTTGATCTTCTTA<br>TCCACAGCCGTCTCCGCTGATGTGGGGTGCTCGGTGGACTTCTCAAAGAAGGAAACGAGATGCGGTACAGGGGTGTTCG<br>TCTATAACGACGTTGAAGCCTGGAGGGACAGGTACAAGTACCATCCTGACTCCCCTCGTAGATTGGCAGCAGTAGTCAAG<br>CAAGCCTGGGAAGATGGTATCTGTGGGATCTCCTCTGTTTCAAGAATGGAAAACATCATGTGGAGATCAGTAGAAGGGG<br>AGCTCAACGCAATCCTGGAAGAGAATGGAGTTCAACTGACGGTCGTTGTGGGATCTGTAAAAAACCCCATGTGGAGAGG<br>TCCACAGAGATTGCCCGTGCCTGTGAACGAGCTGCCCCACGGCTGGAAGGCTTGGGGGAAATCGTACTTCGTCAGAGCA<br>GCAAAGACAAATAACAGCTTTGTCGTGGATGGTGACACACTGAAGGAATGCCCACTCAAACATAGAGCATGGAACAGCTT<br>TCTTGTGGAGGATCATGGGTTCGGGGTATTTCACACTAGTGTCTGGCTCAAGGTTAGAGAAGATTATTCACTAGAGTGTG<br>ATCCAGCCGTCATTGGAACAGCTGTTAAGGGAAAGGAGGCTGTACACAGTGATCTAGGCTACTGGATTGAGAGTGAGAA<br>GAACGACACATGGAGGCTGAGGAGGGCCCACCTGATCGAGATGAAAACATGTGAATGGCCAAAGTCCCACACATTGTGG<br>ACAGATGGAATAGAAGAGAGTGATCTGATCATACCCAAGTCTTTAGCTGGGCCACTCAGCCATCACAACACCAGAGAGG<br>GCTACAGGACCCAAATGAAAGGGCCATGGCACAGTGAAGAGCTTGAAATTCGGTTTGAGGAATGCCCAGGCACTAAGGT<br>CCACGTGGAGGAAACATGTGGAACAAGAGGACCATCTCTGAGATCAACCACTGCAAGCGGAAGGGTGATCGAGGAATG<br>GTGCTGCAGGGAGTGCACAATGCCCCCACTGTCGTTCCGGGCTAAAGATGGCTGTTGGTATGGAATGGAGATAAGGCCC<br>AGGAAAGAACCAGAAAGTAACTTAGTAAGGTCAATGGTGACTGCAGGATCAACTGATCACATGGATCACTTTTCCCTTGG<br>AGTGCTTGTGATTCTGCTCATGGTGCAGGAAGGGCTGAAGAAGAGAATGACCACAAAGATCATCATAAGCACATCAATG<br>GCAGTGCTGGTAGCTATGATCCTGGGAGGATTTTCAATGAGTGATCTGGCTAAGCTTGCAATTTTGATGGGTGCCACCTTT<br>GCGGAAATGAACACTGGAGGAGATGTAGCTCATCTGGCGCTGGTAGCGGCATTCAAAGTCAGACCAGCGTTGCTGGTAT<br>CTTTCATCTTCAGAGCTAATTGGACACCCCGTGAAAGCATGCTGCTGGCCTTGGCCTCGTGTCTTTTGCAAACTGCGATCTC<br>CGCCTTGGAAGGCGACCTGATGGTTCTCATCAATGGTTTTGCTTTGGCCTGGTTGGCAATACGAGCGATGGTTGTTCCACG<br>CACTGACAATATCACCTTGGCAATCCTGGCTGCTCTGACACCACTGGCCCGGGGCACACTGCTTGTGGCGTGGAGAGCAG<br>GCCTTGCTACTTGCGGGGGGTTCATGCTCCTCTCTCTGAAGGGGAAAGGCAGTGTGAAGAAGAACTTACCATTTGTCATG<br>GCCCTGGGACTAACCGCTGTGAGGCTGGTCGACCCCATCAACGTGGTGGGACTGCTGTTGCTCACAAGGAGTGGGAAGC<br>GGAGCTGGCCCCCTAGCGAAGTACTCACAGCTGTTGGCCTGATATGCGCATTGGCTGGAGGGTTCGCCAAGGCAGATAT<br>AGAGATGGCTGGGCCCATGGCCGCGGTCGGTCTGCTAATTGTCAGTTACGTGGTCTCAGGAAAGAGTGTGGACATGTAC<br>ATTGAAAGAGCAGGTGACATCACATGGGAAAAAGATGCGGAAGTTACTGGAAACAGTCCCCGGCTCGATGTGGCACTAG<br>ATGAGAGTGGTGATTTCTCCCTGGTGGAGGATGACGGTCCCCCCATGAGAGAGATCATACTCAAAGTGGTCCTGATGACC<br>ATCTGTGGCATGAACCCAATAGCCATACCCTTTGCAGCTGGAGCGTGGTACGTATACGTGAAAACTGGAAAAAGGAGTG<br>GTGCTCTATGGGATGTGCCTGCTCCCAAGGAAGTAAAAAAGGGGGAGACCACAGATGGAGTGTACAGAGTAATGACTCG<br>TAGACTGCTAGGTTCAACACAAGTTGGAGTGGGAGTTATGCAAGAGGGGGTCTTTCACACTATGTGGCATGTCACAAAAG<br>GATCCGCGCTGAGAAGCGGTGAAGGGAGACTTGATCCATACTGGGGAGATGTCAAGCAGGATCTGGTGTCATACTGTGG<br>TCCATGGAAGCTAGATGCCGCCTGGGACGGGCACAGCGAGGTGCAGCTCTTGGCCGTGCCCCCCGGAGAGAGAGCGAG<br>GAACATCCAGACTCTGCCCGGAATATTTAAGACAAAGGATGGGGACATTGGAGCGGTTGCGCTGGACTATCCAGCAGGA<br>ACTTCAGGATCTCCAATCCTAGACAAGTGTGGGAGAGTGATAGGACTCTATGGCAATGGGGTCGTGATCAAGAATGGGA<br>GTTATGTCAGTGCCATCACCCAAGGGAGGAGGGAGGAAGAGACTCCTGTTGAGTGCTTCGAGCCTTCGATGCTGAAGAA<br>GAAGCAGCTAACTGTCTTAGACTTGCATCCTGGAGCTGGGAAAACCAGGAGAGTTCTTCCTGAAATAGTCCGTGAAGCCA<br>TAAAAACGAGACTCCGTACTGTGATCTTAGCTCCAACCAGGGTTGTCGCTGCTGAAATGGAGGAAGCCCTTAGAGGGCTT<br>CCAGTGCGTTATATGACAACAGCAGTCAATGTCACCCATTCTGGGACAGAAATCGTTGACTTAATGTGCCATGCCACCTTC<br>ACTTCACGTCTACTACAGCCAATCAGAGTCCCCAACTATAATCTGTATATTATGGATGAGGCCCACTTCACAGATCCCTCAA<br>GTATAGCAGCAAGAGGATACATTTCAACAAGGGTTGAGATGGGCGAGGCAGCTGCCATCTTCATGACCGCCACGCCACC<br>AGGAACCCGTGACGCATTCCCGGACTCCAACTCACCAATTATGGACACCGAAGTGGAAGTCCCAGAGAGAGCCTGGAGC<br>TCAGGCTTTGATTGGGTGACGGATCATTCTGGAAAAACAGTTTGGTTTGTCCCAAGCGTGAGGAACGGCAATGAGATCGC<br>AGCTTGTCTGACAAAGGCTGGAAAACGGGTCATACAGCTCAGCAGAAAGACTTTTGAGACAGAGTTCCAGAAAACAAAA<br>CATCAAGAGTGGGACTTCGTCGTGACAACTGACATTTCAGAGATGGGCGCCAACTTTAAAGCTGACCGTGTCATAGATTC<br>CAGGAGATGCCTAAAGCCGGTCATACTTGATGGCGAGAGAGTCATTCTGGCTGGACCCATGCCTGTCACACATGCCAGCG<br>CTGCCCAGAGGAGGGGGCGCATAGGCAGGAATCCCAACAAACCTGGAGATGAGTATCTGTATGGAGGTGGGTGCGCAG<br>AGACTGATGAAGACCATGCACACTGGCTTGAAGCAAGAATGCTCCTTGACAATATTTACCTCCAAGATGGCCTCATAGCCT<br>CGCTCTATCGACCTGAGGCCGACAAAGTAGCAGCCATTGAGGGAGAGTTCAAGCTTAGGACGGAGCAAAGGAAGACCTT<br>TGTGGAACTCATGAAAAGAGGAGATCTTCCTGTTTGGCTGGCCTATCAGGTTGCATCTGCCGGAATAACCTACACAGATA<br>GAAGATGGTGCTTTGATGGCATGACCAACAACACCATAATGGAAGACAGTGTGCCGGCAGAGGTGTGGACCAGACACG<br>GAGAGAAAAGAGTGCTCAAACCGAGGTGGATGGACGCCAGAGTTTGTTCAGATCATGCGGCCCTGAAGTCATTCAAGGA<br>GTTTGCCGCTGGGAAAAGAGGAGCGGCTTTTGGAGTGATGGAAGCCCTGGGAACACTGCCAGGACACATGACGGAGAG<br>ATTCCAGGAAGCCATTGACAACCTCGCTGTGCTCATGCGGGCAGAGACTGGAAGCAGGCCTTACAAAGCCGCGGCGGCC<br>CAATTGCCGGAGACCCTAGAGACCATTATGCTTTTGGGGTTGCTGGGAACAGTCTCGCTGGGAATCTTTTTCGTCTTGATG<br>CGGAACAAGGGCATAGGGAAGATGGGCTTTGGAATGGTGACTCTTGGGGCCAGCGCATGGCTCATGTGGCTCTCGGAAA<br>TTGAGCCAGCCAGAATTGCATGCGTCCTCATTGTTGTGTTCCTATTGCTGGTGGTGCTCATACCTGAGCCAGAAAAGCAAA<br>GATCCCCCCAGGACAACCAAATGGCAATCATCATCATGGTAGCAGTAGGTCTTCTGGGCTTGATTACCGCCAATGAACTCG<br>GATGGTTGGAGAGAACAAAGAGTGACCTAAGCCATCTAATGGGAAGGAGAGAGGAGGGGGCAACCATAGGATTCTCAA<br>TGGACATTGACCTGCGGCCAGCCTCGGCCTGGGCCATCTATGCTGCCCTGACAACTTTCATTACCCCAGCCGTCCAACATG<br>CAGTGACCACTTCATACAACAACTACTCCTTAATGGCGATGGCCACGCAAGCTGGAGTGTTGTTTGGTATGGGCAAAGGG<br>ATGCCATTCTACGCATGGGACTTTGGAGTCCCGCTGCTAATGATAGGTTGCTACTCACAATTAACACCCCTGACCCTAATA<br>GTGGCTATCATTTTGCTCGTGGCGCACTACATGTACTTGATCCCAGGGCTGCAGGCAGCAGCTGCGCGTGCTGCCCAGAA<br>GAGAACGGCAGCTGGCATCATGAAGAACCCTGTTGTGGATGGAATAGTGGTGACTGACATTGACACAATGACTATTGAC<br>CCCCAAGTGGAGAAAAAGATGGGACAGGTGCTACTCATAGCAGTAGCCGTCTCCAGCGCCATACTGTCGCGGACCGCCT<br>GGGGGTGGGGGGAAGCTGGGGCCCTGATCACAGCTGCAACTTCCACTTTGTGGGAAGGCTCTCCGAACAAGTACTGGAA<br>CTCCTCTACAGCCACTTCACTGTGCAACATTTTTAGGGGAAGTTACTTGGCTGGAGCTTCTCTAATCTACACAGTAACAAGA<br>AACGCTGGCTTGGTCAAGAGACGTGGGGGTGGAACAGGAGAGACCCTGGGAGAGAAATGGAAGGCCCGCTTGAACCA<br>GATGTCGGCCCTGGAGTTCTACTCCTACAAAAAGTCAGGCATCACCGAGGTGTGCAGAGAAGAGGCCCGCCGCGCCCTC<br>AAGGACGGTGTGGCAACGGGAGGCCATGCTGTGTCCCGAGGAAGTGCAAAGCTGAGATGGTTGGTGGAGCGGGGATAC<br>CTGCAGCCCTATGGAAAGGTCATTGATCTTGGATGTGGCAGAGGGGGCTGGAGTTACTACGCCGCCACCATCCGCAAAGT<br>TCAAGAAGTGAAAGGATACACAAAAGGAGGCCCTGGTCATGAAGAACCCATGTTGGTGCAAAGCTATGGGTGGAACATA<br>GTCCGTCTTAAGAGTGGGGTGGACGTCTTTCATATGGCGGCTGAGCCGTGTGACACGTTGCTGTGTGACATAGGTGAGTC<br>ATCATCTAGTCCTGAAGTGGAAGAAGCACGGACGCTCAGAGTCCTCTCCATGGTGGGGGATTGGCTTGAAAAAAGACCA<br>GGAGCCTTTTGTGTAAAAGTGTTGTGCCCATACACCAGCACTATGATGGAAACCCTGGAGCGACTGCAGCGTAGGTATGG |

-continued

SEQUENCES

GGGAGGACTGGTCAGAGTGCCACTCTCCCGCAACTCTACACATGAGATGTACTGGGTCTCTGGAGCGAAAAGCAACACC
ATAAAAAGTGTGTCCACCACGAGCCAGCTCCTCTTGGGGCGCATGGACGGGCCCAGGAGGCCAGTGAAATATGAGGAG
GATGTGAATCTCGGCTCTGGCACGCGGGCTGTGGTAAGCTGCGCTGAAGCTCCCAACATGAAGATCATTGGTAACCGCAT
TGAAAGGATCCGCAGTGAGCACGCGGAAACGTGGTTCTTTGACGAGAACCACCCATATAGGACATGGGCTTACCATGGA
AGCTATGAGGCCCCTACACAAGGGTCAGCGTCCTCTCTAATAAACGGGGTTGTCAGGCTCCTGTCAAAACCCTGGGATGT
GGTGACTGGAGTCACAGGAATAGCCATGACCGACACCACACCGTATGGTCAGCAAAGAGTTTTCAAGGAAAAAGTGGAC
ACCAGGGTGCCAGACCCCCAAGAAGGCACTCGTCAGGTTATGAGCATGGTCTCTTCCTGGTTGTGGAAAGAGCTAGGCA
AACACAAACGGCCACGAGTCTGTACCAAAGAAGAGTTCATCAACAAGGTTCGTAGCAATGCAGCATTAGGGGCAATATTT
GAAGAGGAAAAAGAGTGGAAGACCGCAGTGGAAGCTGTGAACGATCCAAGGTTCTGGGCTCTAGTGGACAAGGAAAGA
GAGCACCACCTGAGAGGAGAGTGCCAGAGCTGTGTGTACAACATGATGGGAAAAAGAGAAAAGAAACAAGGGGAATTT
GGAAAGGCCAAGGGCAGCCGCGCCATCTGGTATATGTGGCTAGGGGCTAGATTTCTAGAGTTCGAAGCCCTTGGATTCTT
AAATGAGGATCACTGGATGGGGAGAGAGAACTCAGGAGGTGGTGTTGAAGGGCTGGGATTACAAAGACTCGGATATGT
CCTAGAAGAGATGAGTCGCATACCAGGAGGAAGGATGTATGCAGATGACACTGCTGGCTGGGACACCCGCATCAGCAG
GTTTGATCTGGAGAATGAAGCTTTAATCACCAACCAAATGGAGAAAGGGCACAGGGCCTTAGCATTGGCCATAATCAAGT
ACACATACCAAAACAAAGTGGTAAAGGTCCTTAGACCAGCTGAAAAAGGGAAGACAGTTATGGACATTATTTCAAGACAA
GACCAAAGGGGGAGCGGACAAGTTGTCACTTACGCTCTTAACACATTTACCAACCTAGTGGTGCAACTCATTCGGAATAT
GGAGGCTGAGGAAGTTCTAGAGATGCAAGACTTGTGGCTGCTGCGGAGGTCAGAGAAAGTGACCAACTGGTTGCAGAG
CAACGGATGGGATAGGCTCAAACGAATGGCAGTCAGTGGAGATGATTGCGTTGTGAAGCCAATTGATGATAGGTTTGCA
CATGCCCTCAGGTTCTTGAATGATATGGGAAAAGTTAGGAAGGACACACAAGAGTGGAAACCCTCAACTGGATGGGACA
ACTGGGAAGAAGTTCCGTTTTGTTCCCACCACTTCAACAAGCTCCATCTCAAGGACGGGAGGTCCATTGTGGTTCCCTGCC
GCCACCAAGATGAACTGATTGGCCGGGCCCGTGTCTCTCCAGGGGCGGGATGGAGCATCCGGGAGACTGCTTGCCTAGC
AAAGTCATATGCGCAAATGTGGCAGCTCCTTTATTTCCACAGAAGGGACCTCCGACTGATGGCCAATGCCATCTGTTCATC
TGTGCCAGTTGACTGGGTTCCAACTGGGAGAACTACCTGGTCAATCCATGGAAAGGGAGAATGGATGACCACTGAAGAC
ATGCTTGTGGTGTGGAACAGAGTGTGGATTGAGGAGAACGACCACATGGAAGACAAGACCCCAGTTACGAAATGGACA
GACATTCCCTATCTGGGAAAAAGGGAAGACTTGTGGTGTGGATCTCTCATAGGGCACAGACCGCGCACCACCTGGGCTG
AGAACATTAAAAACACAGTCAACATGGTGCGCAGGATCATAGGTGATGAAGAAAAGTACATGGACTACCTATCCACCCAA
GTTCGCTACTTGGGTGAAGAAGGGTCTACACCTGGAGTGCTATAAGCACCAATCTTAGTGTTGTCAGGCCTGCTAGTCAG
CCACAGCTTGGGGAAAGCTGTGCAGCCTGTGACCCCCCCAGGAGAGGCTGGGAAACCAAGCCCATAGTCAGGCCGAGAA
CGCCATGGCACGGAAGAAGCCATGCTGCCTGTGAGCCCCTCAGAGGACACTGAGTCAAAAAACCCCACGCGCTTGGAGG
CGCAGGATGGGAAAAGAAGGTGGCGACCTTCCCCACCCTTCAATCTGGGGCCTGAACTGGAGATCAGCTGTGGATCTCC
AGAAGAGGGACTAGTGGTTAGAGGAGACCCCCCGGAAAACGCAAAACAGCATATTGACGCTGGGAAAGACCAGAGACT
CCATGAGTTTCCACCACGCTGGCCGCCAGGCACAGATCGCCGAATAGCGGCGGCCGGTGTGGGGAAATCCATGGGTCT

SEQ ID NO: 8
KU681082.3 Zika virus isolate Zika virus/*H. sapiens*-tc/PHL/2012/CPC-0740, Philippines, complete genome
AGTTGTTGATCTGTGTGAATCAGACTGCGACAGTTCGAGTTTGAAGCGAAAGCTAGCAACAGTATCAACAGGTTTTATTTT
GGATTTGGAAACGAGAGTTTCTGGTCATGAAAAACCCAAAAAAGAAATCCGGAGGATTCCGGATTGTCAATATGCTAAAA
CGCGGAGTAGCCCGTGTGAGCCCCTTTGGGGGCTTGAAGAGGCTGCCAGCCGGACTTCTGCTGGGCCATGGGCCCATCA
GGATGGTCTTGGCGATACTAGCCTTTTTGAGATTCACGGCAATCAAGCCATCACTGGGTCTCATCAATAGATGGGGTTCA
GTGGGGAAAAAAGAGGCTATGGAAATAATAAAGAAGTTCAAGAAAGATCTGGCTGCCATGCTGAGAATAATCAATGCTA
GGAAGGAGAAGAAGAGACGAGGCGCAGATACTAGCGTCGGAATTGTTGGCCTCCTCCTGACCACAGCCATGGCAGTAG
AGGTCACTAGACGTGGGAGTGCATACTATATGTACTTGGACAGAAGCGATGCTGGGGAGGCCATATCTTTTCCAACCACA
CTGGGGATGAATAAGTGTTACATACAAATCATGGATCTTGGACACATGTGTGATGCCACCATGAGCTATGAATGCCCTAT
GTTGGATGAGGGGGTAGAACCAGATGACGTCGATTGCTGGTGCAACACGACATCAACTTGGGTTGTGTATGGAACCTGC
CACCACAAAAAAGGTGAAGCACGGAGATCTAGAAGAGCTGTGACGCTCCCCTCCCATTCCACTAGGAAGCTGCAAACGC
GGTCGCAGACCTGGTTGGAATCAAGAGAATACACAAAGCACCTGATTAGAGTTGAAAATTGGATATTCAGGAACCCTGG
CTTCGCGTTAGCAGCAGCTGTCATCGCTTGGCTTTTGGGAAGTTCAACGAGCCAAAAAGTCATATATCTGGTCATGATACT
GCTGATTGCCCCGGCATACAGCATCAGGTGCATAGGAGTCAGCAATAGGGACTTTGTGGAAGGTATGTCAGGTGGGACT
TGGGTTGATGTTGTCTTGGAACATGGAGGTTGTGTTACCGTAATGGCACAGGACAAACCGACTGTCGACATAGAGCTGGT
TACAACAACAGTCAGCAACATGGCGGAGGTAAGATCCTACTGCTATGAGGCATCAATATCGGATATGGCTTCGGACAGCC
GCTGCCCAACACAAGGTGAGGCCTACCTTGACAAGCAGTCAGACACTCAATATGTCTGCAAAAGAACGTTAGTGGACAGA
GGCTGGGGAAATGGATGTGGACTTTTTGGCAAAGGGAGCCTGGTGACATGCGCTAAGTTTGCATGCTCCAAGAAAATGA
CCGGGAAGAGCATCCAGCCAGAGAATCTGGAGTACCGGATAATGCTGTCAGTTCATGGCTCCCAGCACAGTGGGATGAT
CGTTAATGACACAGGACATGAAACTGATGAGAATAGAGCGAAGGTTGAGATAACGCCCAATTCACCAAGAGCCGAAGCC
ACCCTGGGGGGTTTTGGGAGCCTAGGACTTGATTGTGAACCGAGGACAGGCCTTGACTTTTCAGATTTGTATTACCTGACT
ATGAATAACAAGCACTGGTTGGTTCACAAGGAGTGGTTCCACGACATTCCATTACCTTGGCATGCTGGGGCAGACACTGG
AACTCCACATTGGAACAACAAAGAAGCACTGGTAGAGTTCAAGGACGCACATGCAAAAAGGCAAACTGTCGTGGTTCTA
GGGAGTCAAGAAGGAGCAGTTCACACGGCCCTTGCTGGAGCTCTGGAGGCTGAGATGGATGGAGCCAAGGGAAGGCTG
TCCTCTGGCCACTTGAAATGTCGCCTGAAAATGGATAAACTTAGATTGAAGGGCGTGTCATACTCCTTGTGCACTGCAGCG
TTCACATTCACCAAGATCCCGGCTGAAACACTGCACGGGACAGTCACAGTGGAGGTACAGTACGCAGGGACAGATGGAC
CTTGCAAGGTTCCAGCTCAGATGGCGGTGGATATGCAAACTCTGACCCCAGTTGGGAGGTTGATAACCGCTAACCCTGTA
ATCACTGAAAGCACCGAGAACTCTAAGATGATGCTGGAACTTGATCCACCATTTGGGGACTCTTACATTGTCATAGGAGTC
GGGGAGAAGAAGATCACCCATCACTGGCACAGGAGTGGCAGCACCATTGGAAAAGCATTTGAAGCCACTGTGAGAGGT
GCCAAGAGAATGGCAGTCTTGGGAGACACAGCCTGGGACTTTGGATCAGTTGGGGGTGCTCTCAACTCATTGGGCAAGG
GCATCCATCAAATTTTTGGAGCAGCTTTCAAATCATTGTTCGGAGGAATGTCCTGGTTCTCACAAATTCTCATTGGAACGTT
GCTGGTGTGGTTGGGTCTGAATACAAAGAATGGATCTATTTCCCTTACGTGCTTGGCCTTAGGGGGAGTGTTGATCTTCTT
ATCCACAGCCGTTTCTGCTGATGTGGGGTGCTCGGTGGACTTCTCAAAGAAGGAAACGAGATGCGGTACAGGGGTGTTC
GTCTATAACGACGTTGAAGCCTGGAGGGACAGGTACAAGTACCATCCTGACTCCCCTCGTAGATTGGCAGCAGCAGTCAA
GCAAGCCTGGGAAGATGGGATCTGTGGGATCTCCTCTGTCTCAAGAATGGAAAACATCATGTGGAGATCAGTAGAAGGG
GAGCTCAACGCAATCCTGGAAGAGAATGGAGTTCAACTGACGGTCGTTGTGGGATCTGTAAAAAACCCCATGTGGAGAG
GTCCACAGAGATTGCCCGTGCCTGTGAACGAGCTGCCCCACGGCTGGAAGGCTTGGGGGAAATCGTACTTCGTCAGAGC
AGCAAAGACAAATAACAGCTTTGTCGTGGATGGTGACACACTGAAGGAATGCCCACTCAAACATAGAGCATGGAACAGC
TTTCTTGTGGAGGATCATGGGTTTGGGGTATTTCACACTAGTGTCTGGCTCAAGGTTAGAGAAGATTATTCATTAGAGTGT
GATCCAGCCGTCATTGGAACAGCTGCTAAGGGAAAGGAGGCTGTGCACAGCGATCTAGGCTACTGGATTGAGAGTGAGA
AGAACGACACATGGAGGCTGAAGAGGGCCCACCTGATCGAGATGAAAACATGTGAATGGCCAAAGTCCCACACATTGTG
GACAGATGGAGTAGAAGAAAGTGATCTGATCATACCCAAGTCTTTAGCTGGGCCACTCAGCCATCACAACACCAGAGAG -continued

| SEQUENCES |
| --- |
| GGCTACAGGACTCAAATGAAAGGGCCATGGCACAGTGAAGAGCTTGAAATTCGGTTTGAGGAATGCCCAGGCACTAAGG<br>TCCACGTGGAGGAAACATGTGGGACAAGAGGACCATCCCTGAGATCAACCACTGCAAGCGGAAGGGTGATCGAGGAAT<br>GGTGCTGCAGGGAATGCACAATGCCCCCACTGTCGTTCCGAGCTAAAGATGGCTGTTGGTATGGAATGGAGATAAGGCC<br>CAGGAAAGAACCAGAAAGTAACTTAGTAAGGTCAATGGTGACTGCAGGATCAACTGATCACATGGATCACTTCTCTCTTG<br>GAGTGCTTGTGATTTTGCTCATGGTGCAGGAAGGGCTGAAGAAGAGAATGACCACAAAGATCATCATAAGCACATCAAT<br>GGCAGTGCTGGTAGCCATGATCCTGGGAGGATTTTCAATGAGTGACCTGGCTAAGCTTGCAATTTTGATGGGTGCCACCT<br>TCGCGGAAATGAACACTGGAGGAGATGTAGCTCATTTGGCGCTGATAGCGGCATTCAAAGTCAGACCTGCGTTGCTGGTA<br>TCTTTCATCTTCAGAGCTAATTGGACACCCCGTGAGAGCATGCTGCTGGCCTTGGCCTCGTGTCTTCTGCAAACTGCGATCT<br>CCGCCTTGGAAGGCGACCTGATGGTTCTCATCAATGGTTTTGCTTTGGCCTGGTTGGCAATACGAGCGATGGTTGTTCCAC<br>GCACTGACAACATCACCTTGGCAATCCTGGCTGCTCTGACACCACTGGCCCGGGGCACACTGCTTGTGGCGTGGAGAGCA<br>GGCCTTGCTACTTGCGGGGGGTTCATGCTCCTCTCTCTGAAGGGGAAAGGCAGTGTGAAGAAGAACCTACCATTTGTCAT<br>GGCCTTGGGACTAACTGCTGTGAGGCTGGTCGACCCCATCAACGTGGTGGGACTGCTGTTGCTCACAAGGAGTGGGAAG<br>CGGAGCTGGCCCCCTAGTGAAGTACTCACAGCTGTTGGCCTGATATGCGCATTGGCTGGAGGGTTCGCCAAGGCGGATA<br>TAGAGATGGCTGGGCCCATGGCCGCGGTCGGTCTGCTAATTGTCAGTTACGTGGTCTCAGGAAAGAGTGTGGACATGTA<br>CATTGAAAGAGCAGGTGACATCACATGGGAAAAAGATGCGGAAATCACTGGAAACAGTCCCCGGCTCGATGTGGCACTA<br>GATGAGAGTGGTGATTTCTCCCTAGTGGAGGATGATGGTCCACCCATGAGAGAGATCATACTCAAAGTGGTCCTGATGAC<br>CATCTGCGGCATGAACCCAATAGCCATACCCTTTGCAGCTGGAGCGTGGTACGTGTATGTGAAGACTGGAAAAAGGAGT<br>GGTGCTCTATGGGATGTGCCTGCTCCCAAGGAAGTAAAAAAGGGGGAGACCACAGATGGAGTGTACAGAGTAATGACTC<br>GTAGACTGCTTGGTTCAACACAAGTTGGAGTGGGAGTCATGCAAGAGGGGGTCTTCCACACTATGTGGCACGTCACAAA<br>AGGATCCGCGCTGAGAAGCGGTGAAGGGAGACTTGATCCATACTGGGGAGATGTCAAGCAGGATCTGGTGTCATACTGT<br>GGTCCGTGGAAGCTAGACGCCGCCTGGGACGGGCACAGCGAGGTGCAGCTCTTGGCCGTGCCCCCCGGAGAGAGAGCG<br>AGGAACATCCAGACTCTGCCCGGAACATTTAAGACAAAGGATGGGGACATTGGAGCAGTTGCGCTGGACTACCCAGCAG<br>GAACTTCAGGATCTCCAATCCTAGACAAGTGTGGGAGAGTGATAGGACTCTATGGTAATGGGGTCGTGATAAAAAATGG<br>GAGTTATGTTAGTGCCATCACCCAAGGGAGGAGGGAGGAAGAGACTCCTGTTGAGTGCTTCGAGCCTTCGATGCTGAAG<br>AAGAAGCAGCTAACTGTCTTAGACCTGCATCCTGGAGCCGGGAAAACCAGGAGAGTTCTTCCTGAAATAGTCCGTGAAGC<br>CATAAAAACAAGACTCCGTACTGTGATCTTAGCTCCAACCAGGGTCGTCGCTGCTGAAATGGAGGAAGCCCTTAGAGGGC<br>TTCCAGTTCGTTATATGACAACAGCAGTCAATGTCACCCATTCTGGGACAGAAATCGTTGACTTAATGTGCCATGCTACCTT<br>CACTTCACGCCTACTACAACCAATCAGAGTCCCCAACTATAATTTGTATATTATGGATGAGGCCCACTTCACAGATCCCTCA<br>AGTATAGCAGCAAGAGGATACATTTCAACAAGGGTTGAGATGGGCGAGGCGGCTGCCATCTTCATGACCGCCACGCCAC<br>CAGGAACCCGTGACGCATTCCCGGACTCCAACTCACCAATTATGGACACCGAGGTGGAAGTCCCAGAGAGAGCCTGGAG<br>CACAGGCTTTGATTGGGTGACGGATCATTCTGGGAAAACAGTCTGGTTTGTTCCAAGCGTGAGGAACGGCAATGAGATC<br>GCAGCTTGTCTGACAAAGGCTGGAAAACGGGTCATACAGCTCAGCAGAAAGACTTTTGAGACAGAGTTCCAGAAAACGA<br>AAAATCAAGAGTGGGACTTCGTCGTGACAACCGACATTTCAGAGATGGGCGCCAACTTTAAAGCTGACCGTGTCATAGAT<br>TCCAGGAGATGCTTAAAGCCGGTCATACTTGATGGCGAGAGAGTCATTTTGGCTGGACCCATGCCTGTCACACATGCCAG<br>CGCTGCTCAGAGGAGGGGGCGCATAGGCAGGAATCCCAACAAACCTGGAGATGAGTATCTGTATGGAGGTGGGTGCGC<br>AGAGACTGATGAAGATCACGCACACTGGCTTGAAGCAAGAATGCTTCTTGACAACATTTACCTCCAAGATGGCCTCATAG<br>CTTCGCTCTATCGACCTGAGGCCGACAAAGTAGCAGCTATTGAGGGAGAGTTCAAGCTTAGGACGGAGCAAAGGAAGAC<br>CTTTGTGGAACTCATGAAAAGAGGAGATCTTCCGGTTTGGTTGGCCTATCAGGTTGCATCTGCCGGAATAACCTACACAG<br>ATAGAAGATGGTGCTTTGATGGCATGACCAACAACACCATAATGGAAGACAGTGTGCCGGCAGAGGTGTGGACCAGATA<br>CGGAGAGAAAAGAGTGCTCAAACCGAGGTGGATGGACGCCAGAGTTTGTTCAGATCATGCGGCCCTGAAGTCATTCAAA<br>GAGTTTGCCGCTGGGAAAAGAGGAGCGGCCTTTGGAGTGATAGAAGCCCTGGGAACACTGCCAGGACACATGACAGAG<br>AGATTCCAGGAAGCCATTGACAACCTCGCTGTGCTCATGCGGGCAGAGACTGGAAGCAGGCCTTACAAAGCCGCGGCGG<br>CCCAATTGCCGGAGACCCTAGAGACCATTATGCTTTTGGGGTTGCTGGGAACAGTCTCGCTGGGAATCTTTTTCGTCTTGA<br>TGCGGAACAAGGGCATGGGGAAGATGGGCTTTGGAATGGTGACTCTTGGGGCCAGCGCATGGCTTATGTGGCTCTCGGA<br>AATTGAGCCAGCCAGAATTGCATGTGTCCTCATTGTCGTGTTCCTATTGCTGGTGGTGCTCATACCTGAGCCAGAAAAGCA<br>AAGATCTCCTCAGGACAACCAAATGGCAATCATCATCATGGTAGCAGTGGGTCTTCTGGGCTTGATTACCGCCAATGAACT<br>CGGATGGTTGGAGAGAACAAAAAGTGACCTAAGCCATCTAATGGGAAGGAGAGAGGAGGGGGCAACCACAGGATTCTC<br>AATGGACATTGACCTGCGGCCAGCCTCAGCTTGGGCTATCTATGCTGCTCTGACAACTTTCATCACCCCAGCCGTCCAACA<br>TGCGGTGACCACTTCATACAACAACTACTCCTTAATGGCGATGGCCACGCAAGCTGGGGTGTTGTTTGGTATGGGCAAAG<br>GGATGCCATTCTACGCATGGGACTTTGGAGTCCCGCTGCTAATGATGGGTTGCTACTCACAATTAACACCTCTGACCCTAA<br>TAGTGGCCATCATTTTGCTCGTGGCGCACTACATGTACTTGATCCCAGGGCTGCAGGCAGCAGCTGCGCGGGCTGCCCAG<br>AAGAGAACGGCAGCTGGCATCATGAAGAACCCTGTTGTGGATGGAATAGTGGTGACTGACATTGACACAATGACAATTG<br>ACCCCCAAGTGGAAAAAAAGATGGGGCAGGTGCTACTCATAGCAGTAGCCGTCTCCAGCGCCATACTGTCGCGGACCGC<br>CTGGGGGTGGGGGGAGGCTGGGGCCCTGATCACAGCTGCAACTTCCACCTTGTGGGAAGGCTCTCCGAACAAGTACTGG<br>AACTCCTCCACAGCCACTTCACTGTGTAACATTTTTAGGGGAAGTTACTTGGCTGGAGCTTCTCTAATCTACACAGTAACAA<br>GAAACGCTGGCTTGGTCAAGAGACGTGGGGGTGGAACGGGAGAGACCCTGGGAGAGAAATGGAAGGCCCGCCTGAAC<br>CAGATGTCGGCCCTGGAGTTCTACTCCTACAAAAAGTCAGGCATCACCGAGGTGTGCAGAGAAGAGGCCCGCCGTGCCCT<br>CAAGGACGGTGTGGCAACAGGAGGCCATGCTGTGTCCCGAGGAAGTGCAAAGCTTAGATGGCTGGTGGAGAGAGGATA<br>CCTGCAGCCCTATGGAAAGGTCATTGATCTTGGATGTGGCAGAGGGGGCTGGAGTTACTATGCCGCCACCATCCGCAAAG<br>TTCAGGAAGTGAAAGGATACACAAAAGGAGGCCCTGGTCATGAAGAACCCATGTTGGTGCAAAGCTATGGGTGGAACAT<br>AGTCCGTCTTAAGAGTGGGGTGGACGTCTTTCACATGGCGGCTGAGCCGTGTGACACTTTGCTGTGTGATATAGGTGAGT<br>CATCATCTAGTCCTGAAGTGGAAGAAGCACGGACGCTCAGAGTCCTCTCCATGGTGGGGGATTGGCTTGAAAAAAGACC<br>AGGAGCCTTTTGTATAAAAGTGTTGTGCCCATACACCAGCACTATGATGGAAACCCTGGAGCGACTGCAGCGTAGGTATG<br>GGGGAGGACTGGTCAGGGTGCCACTCTCCCGCAACTCTACACATGAGATGTACTGGGTCTCTGGAGCGAAAAGCAACAC<br>CATAAAAAGTGTGTCCACCACGAGCCAGCTCCTCTTGGGGCGCATGGACGGGCCCAGGAGGCCAGTGAAATATGAGGAG<br>GATGTGAATCTCGGCTCTGGCACGCGGGCTGTGGTAAGCTGCGCTGAAGCTCCCAACATGAAGATCATTGGTAACCGCAT<br>TGAGAGGATCCGCAGTGAGCACGCGGAAACGTGGTTCTTTGACGAGAACCACCCATATAGGACATGGGCTTACCATGGA<br>AGCTATGAGGCCCCTACACAAGGGTCAGCGTCCTCTCTAATAAACGGGGTTGTCAGGCTCCTGTCAAAACCCTGGGATGT<br>GGTGACTGGAGTCACAGGAATAGCCATGACTGACACCACACCGTATGGTCAGCAAAGAGTTTTCAAGGAAAAAGTGGAC<br>ACTAGGGTGCCAGACCCCCAAGAAGGCACTCGTCAGGTTATGAGCATGGTCTCTTCCTGGTTATGGAAGGAGCTAGGCAA<br>ACACAAACGGCCACGAGTCTGTACCAAAGAAGAGTTCATCAACAAGGTTCGTAGCAATGCAGCATTAGGGGCAATATTTG<br>AAGAGGAAAAAGAGTGGAAGACTGCAGTGGAAGCTGTGAATGATCCAAGGTTCTGGGCTCTAGTGGACAAGGAAAGAG<br>AGCATCACCTGAGAGGAGAGTGTCAGAGCTGTGTGTACAACATGATGGGAAAAAGAGAAAAGAAACAAGGGGAATTTG<br>GAAAGGCCAAGGGCAGCCGCGCCATCTGGTATATGTGGCTAGGGGCTAGATTCCTAGAGTTCGAAGCCCTTGGATTCTTG<br>AATGAGGATCATTGGATGGGGAGAGAGAATTCAGGAGGTGGTGTTGAAGGACTGGGATTACAAAGACTCGGATATGTC<br>CTAGAAGAGATGAGTCGCATACCAGGAGGAAGGATGTATGCAGATGATACTGCTGGCTGGGACACCCGCATCAGCAGGT<br>TTGATCTGGAGAATGAAGCTCTAATCACCAACCAAATGGAGAAAGGGCACAGGGCCTTGGCATTGGCCATAATCAAGTAC |

-continued

SEQUENCES

ACATACCAAAACAAAGTGGTAAAGGTCCTTAGACCAGCTGAAAAAGGGAAGACAGTTATGGACATTATTTCAAGACAAG
ACCAAAGGGGGAGCGGACAAGTTGTCACTTACGCTCTTAATACATTCACCAACCTGGTGGTGCAGCTCATTCGGAATATG
GAGGCTGAGGAAGTTCTAGAGATGCAAGACTTGTGGCTGCTGCGGAGGCCAGAGAAAGTGACCAACTGGTTGCAAAGC
AACGGATGGGATAGGCTCAAAAGAATGGCAGTCAGTGGAGATGATTGCGTTGTGAAACCAATTGATGATAGGTTTGCAC
ATGCCCTCAGGTTCTTGAATGATATGGGAAAAGTTAGGAAGGACACACAAGAGTGGAAACCCTCAACTGGATGGGACAA
CTGGGAAGAAGTTCCGTTTTGCTCCCACCACTTCAACAAACTCCATCTTAAGGACGGGAGGTCCATTGTGGTTCCCTGCCG
CCACCAAGATGAACTGATTGGCCGAGCCCGCGTATCACCAGGGGCGGGATGGAGCATCCGGGAGACTGCTTGCCTAGCA
AAATCATATGCGCAAATGTGGCAGCTCCTTTATTTCCACAGAAGGGACCTCCGACTGATGGCCAATGCCATTTGTTCATCT
GTGCCAGTTGATTGGGTTCCAACTGGGAGAACTACCTGGTCAATCCATGGAAAGGGAGAATGGATGACCACTGAAGACA
TGCTTGTGGTATGGAACAGAGTGTGGATTGAGGAAAACGACCACATGGAAGACAAGACCCCAGTTACAAAATGGACAGA
CATTCCCTATTTGGGAAAAAGAGAAGACTTGTGGTGTGGATCTCTCATAGGGCACAGACCGCGTACTACCTGGGCTGAGA
ACATCAAAAATACAGTCAACATGATGCGCAGGATCATAGGTGATGAAGAAAAGTACATGGACTACCTATCCACCCAGGTT
CGCTACTTGGGTGAAGAAGGGTCCACACCTGGAGTGCTGTAAGCACCAATCTTAGTGTTGTCAGGCCTGCTAGTCAGCCA
CAGCTTGGGGAAAGCTGTGCAGCCTGTGACCCCCCCAGGAGAAGCTGGGAAACCAAGCCTATAGTCAGGCCGAGAACGC
CATGGCACGGAAGAAGCCATGCTGCCTGTGAGCCCCTCAGAGGACACTGAGTCAAAAAACCCCACGCGCTTGGAGGCGC
AGGATGGGAAAAGAAGGTGGCGACCTTCCCCACCCTTCAATCTGGGGCCTGAACTGGAGATCAGCTGTGGATCTCCAGA
AGAGGGACTAGTGGTTAGAGGAGACCCCCCGGAAAACGCAAAACAGCATATTGACGCTGGGAAAGACCAGAGACTCCA
TGAGTTTCCACCACGCTGGCCGCCAGGCACAGATCGCCGAATAGCGGCGGCCGGTGTGGGGAAATCCATGGGTCT

SEQ ID NO: 9
KU707826.1 Zika virus isolate SSABR1, Brazil, complete genome
GACAGTTCGAGTTTGAAGCGAAAGCTAGCAACAGTATCAACAGGTTTTATTTGGATTTGGAAACGAGAGTTTCTGGTCAT
GAAAAACCCAAAAAAGAAATCCGGAGGATTCCGGATTGTCAATATGCTAAAACGCGGAGTAGCCCGTGTGAGCCCCTTT
GGGGGCTTGAAGAGGCTGCCAGCCGGACTTCTGCTGGGTCATGGGCCCATCAGGATGGTCTTGGCGATTCTAGCCTTTTT
GAGATTCACGGCAATCAAGCCATCACTGGGTCTCATCAATAGATGGGGTTCAGTGGGGAAAAAAGAGGCTATGGAAATA
ATAAAGAAGTTCAAGAAAGATCTGGCTGCCATGCTGAGAATAATCAATGCTAGGAAGGAGAAGAAGAGACGAGGCGCA
GATACTAGTGTCGGAATTGTTGGCCTCCTGCTGACCACAGCTATGGCAGCGGAGGTCACTAGACGTGGGAGTGCATACTA
TATGTACTTGGACAGAAACGATGCTGGGGAGGCCATATCTTTTCCAACCACATTGGGGATGAATAAGTGTTATATACAGA
TCATGGATCTTGGACACATGTGTGATGCCACCATGAGCTATGAATGCCCTATGCTGGATGAGGGGGTGGAACCAGATGAC
GTCGATTGTTGGTGCAACACGACGTCAACTTGGGTTGTGTACGGAACCTGCCATCACAAAAAAGGTGAAGCACGGAGAT
CTAGAAGAGCTGTGACGCTCCCCTCCCATTCCACTAGGAAGCTGCAAACGCGGTCGCAAACCTGGTTGGAATCAAGAGAA
TACACAAAGCACTTGATTAGAGTCGAAAATTGGATATTCAGGAACCCTGGCTTCGCGTTAGCAGCAGCTGCCATCGCTTG
GCTTTTGGGAAGCTCAACGAGCCAAAAAGTCATATACTTGGTCATGATACTGCTGATTGCCCCGGCATACAGCATCAGGT
GCATAGGAGTCAGCAATAGGGACTTTGTGGAAGGTATGTCAGGTGGGACCTGGGTTGATGTTGTCTTGGAACATGGAGG
TTGTGTCACCGTAATGGCACAGGACAAACCGACTGTCGACATAGAGCTGGTTACAACAACAGTCAGCAACATGGCGGAG
GTAAGATCCTACTGCTATGAGGCATCAATATCAGACATGGCTTCGGACAGCCGCTGCCCAACACAAGGTGAAGCCTACCT
TGACAAGCAATCAGACACTCAATATGTCTGCAAAAGAACGTTAGTGGACAGAGGCTGGGGAAATGGATGTGGACTTTTT
GGCAAAGGGAGCCTGGTGACATGCGCTAAGTTTGCATGCTCCAAGAAAATGACCGGGAAGAGCATCCAGCCAGAGAATC
TGGAGTACCGGATAATGCTGTCAGTTCATGGCTCCCAGCACAGTGGGATGATTGTTAATGACACAGGACATGAAACTGAT
GAGAATAGAGCGAAAGTTGAGATAACGCCCAATTCACCAAGAGCCGAAGCCACCCTGGGGGGTTTTGGAAGCCTAGGAC
TTGATTGTGAACCGAGGACAGGCCTTGACTTTTCAGATTTGTATTACTTGACTATGAATAACAAGCACTGGTTGGTTCACA
AGGAGTGGTTCCACGACATTCCATTACCTTGGCACGCTGGGGCAGACACCGGAACTCCACACTGGAACAACAAAGAAGC
ACTGGTAGAGTTCAAGGACGCACATGCCAAAAGGCAAACTGTCGTGGTTCTAGGGAGTCAAGAAGGAGCAGTTCACACG
GCCCTTGCTGGAGCTCTGGAGGCTGAGATGGATGGTGCAAAGGGAAGGCTGTCCTCTGGCCACTTGAAATGTCGCCTGA
AAATGGATAAACTTAGATTGAAGGGCGTGTCATACTCCTTGTGTACTGCAGCGTTCACATTCACCAAGATCCCGGCTGAAA
CACTGCACGGGACAGTCACAGTGGAGGTACAGTACGCAGGGACAGATGGACCTTGCAAGGTTCCAGCTCAGATGGCGGT
GGACATGCAAACTCTGACCCCAGTTGGGAGGTTGATAACCGCTAACCCCGTAATCACTGAAAGCACTGAGAACTCTAAGA
TGATGCTGGAACTTGATCCACCATTTGGGGACTCTTACATTGTCATAGGAGTCGGGGAGAAGAAGATCACCCACCACTGG
CACAGGAGTGGCAGCACCATTGGAAAAGCATTTGAAGCCACTGTGAGAGGTGCCAAGAGAATGGCAGTCTTGGGAGAC
ACAGCCTGGGACTTTGGATCAGTTGGAGGCGCTCTCAACTCATTGGGCAAGGGCATCCATCAAATTTTTGGAGCAGCTTT
CAAATCATTGTTTGGAGGAATGTCCTGGTTCTCACAAATTCTCATTGGAACGTTGCTGATGTGGTTGGGTCTGAACACAAA
GAATGGATCTATTTCCCTTATGTGCTTGGCCTTAGGGGGAGTGTTGATCTTCTTATCCACAGCCGTCTCTGCTGATGTGGG
GTGCTCGGTGGACTTCTCAAAGAAGGAGACGAGATGCGGTACAGGGGTGTTCGTCTATAACGACGTTGAAGCCTGGAGG
GACAGGTACAAGTACCATCCTGACTCCCCCCGTAGATTGGCAGCAGCAGTCAAGCAAGCCTGGGAAGATGGTATCTGCG
GGATCTCCTCTGTTTCAAGAATGGAAAACATCATGTGGAGATCAGTAGAAGGGGAGCTCAACGCAATCCTGGAAGAGAA
TGGAGTTCAACTGACGGTCGTTGTGGGATCTGTAAAAAACCCCATGTGGAGAGGTCCACAGAGATTGCCCGTGCCTGTGA
ACGAGCTGCCCCACGGCTGGAAGGCTTGGGGGAAATCGTACTTCGTCAGAGCAGCAAAGACAAATAACAGCTTTGTCGT
GGATGGTGACACACTGAAGGAATGCCCACTCAAACATAGAGCATGGAACAGCTTTCTTGTGGAGGATCATGGGTTCGGG
GTATTTCACACTAGTGTCTGGCTCAAGGTTAGAGAAGATTATTCATTAGAGTGTGATCCAGCCGTTATTGGAACAGCTGTT
AAGGGAAAGGAGGCTGTACACAGTGATCTAGGCTACTGGATTGAGAGTGAGAAGAATGACACATGGAGGCTGAAGAGG
GCCCATCTGATCGAGATGAAAACATGTGAATGGCCAAAGTCCCACACATTGTGGACAGATGGAATAGAAGAGAGTGATC
TGATCATACCCAAGTCTTTAGCTGGGCCACTCAGCCATCACAATACCAGAGAGGGCTACAGGACCCAAATGAAAGGGCCA
TGGCACAGTGAAGAGCTTGAAATTCGGTTTGAGGAATGCCCAGGCACTAAGGTCCACGTGGAGGAAACATGTGGAACAA
GAGGACCATCTCTGAGATCAACCACTGCAAGCGGAAGGGTGATCGAGGAATGGTGCTGCAGGGAGTGCACAATGCCCCC
ACTGTCGTTCCGGGCTAAAGATGGCTGTTGGTATGGAATGGAGATAAGGCCCAGGAAAGAACCAGAAAGCAACTTAGTA
AGGTCAATGGTGACTGCAGGATCAACTGATCACATGGACCACTTCTCCCTTGGAGTGCTTGTGATTCTGCTCATGGTGCAG
GAAGGGCTGAAGAAGAGAATGACCACAAAGATCATCATAAGCACATCAATGGCAGTGCTGGTAGCTATGATCCTGGGAG
GATTTTCAATGAGTGACCTGGCTAAGCTTGCAATTTTGATGGGTGCCACCTTCGCGGAAATGAACACTGGAGGAGATGTA
GCTCATCTGGCGCTGATAGCGGCATTCAAAGTCAGACCAGCGTTGCTGGTATCTTTCATCTTCAGAGCTAATTGGACACCC
CGTGAAAGCATGCTGCTGGCCTTGGCCTCGTGTCTTTTGCAAACTGCGATCTCCGCCTTGGAAGGCGACCTGATGGTTCTC
ATCAATGGTTTTGCTTTGGCCTGGTTGGCAATACGAGCGATGGTTGTTCCACGCACTGATAACATCACCTTGGCAATCCTG
GCTGCTCTGACACCACTGGCCCGGGGCACACTGCTTGTGGCGTGGAGAGCAGGCCTTGCTACTTGCGGGGGGTTTATGCT
CCTCTCTCTGAAGGGAAAAGGCAGTGTGAAGAAGAACTTACCATTTGTCATGGCCCTGGGACTAACCGCTGTGAGGCTGG
TCGACCCCATCAACGTGGTGGGACTGCTGTTGCTCACAAGGAGTGGGAAGCGGAGCTGGCCCCCTAGCGAAGTACTCAC
AGCTGTTGGCCTGATATGCGCATTGGCTGGAGGGTTCGCCAAGGCAGATATAGAGATGGCTGGGCCCATGGCCGCGGTC
GGTCTGCTAATTGTCAGTTACGTGGTCTCAGGAAAGAGTGTGGACATGTACATTGAAAGAGCAGGTGACATCACATGGG
AAAAAGATGCGGAAGTCACTGGAAACAGTCCCCGGCTCGATGTGGCGCTAGATGAGAGTGGTGATTTCTCCCTGGTGGA -continued

| SEQUENCES |
| --- |
| GGATGACGGTCCCCCCATGAGAGAGATCATACTCAAGGTGGTCCTGATGACCATCTGTGGCATGAACCCAATAGCCATAC<br>CCTTTGCAGCTGGAGCGTGGTACGTATACGTGAAGACTGGAAAAAGGAGTGGTGCTCTATGGGATGTGCCTGCTCCCAA<br>GGAAGTAAAAAAGGGGGAGACCACAGATGGAGTGTACAGAGTAATGACTCGTAGACTGCTAGGTTCAACACAAGTTGG<br>AGTGGGAGTTATGCAAGAGGGGGTCTTTCACACTATGTGGCACGTCACAAAAGGATCCGCGCTGAGAAGCGGTGAAGG<br>GAGACTTGATCCATACTGGGGAGATGTCAAGCAGGATCTGGTGTCATACTGTGGTCCATGGAAGCTAGATGCCGCCTGG<br>GACGGGCACAGCGAGGTGCAGCTCTTGGCCGTGCCCCCCGGAGAGAGAGCGAGGAACATCCAGACTCTGCCCGGAATAT<br>TTAAGACAAAGGATGGGGACATTGGAGCGGTTGCGCTGGATTACCCAGCAGGAACTTCAGGATCTCCAATCCTAGACAA<br>GTGTGGGAGAGTGATAGGACTTTATGGCAATGGGGTCGTGATCAAAAATGGGAGTTATGTTAGTGCCATCACCCAAGGG<br>AGGAGGGAGGAAGAGACTCCTGTTGAGTGCTTCGAGCCTTCGATGCTGAAGAAGAAGCAGCTAACTGTCTTAGACTTGC<br>ATCCTGGAGCTGGGAAAACCAGGAGAGTTCTTCCTGAAATAGTCCGTGAAGCCATAAAAACAAGACTCCGTACTGTGATC<br>TTAGCTCCAACCAGGGTTGTCGCTGCTGAAATGGAGGAGGCCCTTAGAGGGCTTCCAGTGCGTTATATGACAACAGCAGT<br>CAATGTCACCCACTCTGGAACAGAAATCGTCGACTTAATGTGCCATGCCACCTTCACTTCACGTCTACTACAGCCAATCAGA<br>GTCCCCAACTATAATCTGTATATTATGGATGAGGCCCACTTCACAGATCCCTCAAGTATAGCAGCAAGAGGATACATTTCA<br>ACAAGGGTTGAGATGGGCGAGGCGGCTGCCATCTTCATGACCGCCACGCCACCAGGAACCCGTGACGCATTTCCGGACT<br>CCAACTCACCAATTATGGACACCGAAGTGGAAGTCCCAGAGAGAGCCTGGAGCTCAGGCTTTGATTGGGTGACGGATCA<br>TTCTGGAAAAACAGTTTGGTTTGTTCCAAGCGTGAGGAACGGCAATGAGATCGCAGCTTGTCTGACAAAGGCTGGAAAAC<br>GGGTCATACAGCTCAGCAGAAAGACTTTTGAGACAGAGTTCCAGAAAACAAAACATCAAGAGTGGGACTTTGTCGTGAC<br>AACTGACATTTCAGAGATGGGCGCCAACTTTAAAGCTGACCGTGTCATAGATTCCAGGAGATGCCTAAAGCCGGTCATAC<br>TTGATGGCGAGAGAGTCATTCTGGCTGGACCCATGCCTGTCACACATGCCAGCGCTGCCCAGAGGAGGGGGCGCATAGG<br>CAGGAATCCCAACAAACCTGGAGATGAGTATCTGTATGGAGGTGGGTGCGCAGAGACTGACGAAGACCATGCACACTGG<br>CTTGAAGCAAGAATGCTCCTTGACAATATTTACCTCCAAGATGGCCTCATAGCCTCGCTCTATCGACCTGAGGCCGACAAA<br>GTAGCAGCCATTGAGGGAGAGTTCAAGCTTAGGACGGAGCAAAGGAAGACCTTTGTGGAACTCATGAAAAGAGGAGAT<br>CTTCCTGTTTGGCTGGCCTATCAGGTTGCATCTGCCGGAATAACCTACACAGATAGAAGATGGTGCTTTGATGGCACGACC<br>AACAACACCATAATGGAAGACAGTGTGCCGGCAGAGGTGTGGACCAGACACGGAGAGAAAAGAGTGCTCAAACCGAGG<br>TGGATGGACGCCAGAGTTTGTTCAGATCATGCGGCCCTGAAGTCATTCAAGGAGTTTGCCGCTGGGAAAAGAGGAGCGG<br>CTTTTGGAGTGATGGAAGCCCTGGGAACACTGCCAGGACACATGACAGAGAGATTCCAGGAAGCCATTGACAACCTCGC<br>TGTGCTCATGCGGGCAGAGACTGGAAGCAGGCCTTACAAAGCCGCGGCGGCCCAATTGCCGGAGACCCTAGAGACCATT<br>ATGCTTTTGGGGTTGCTGGGAACAGTCTCGCTGGGAATCTTCTTCGTCTTGATGAGGAACAAGGGCATAGGGAAGATGG<br>GCTTTGGAATGGTGACTCTTGGGGCCAGCGCATGGCTCATGTGGCTCTCGGAAATTGAGCCAGCCAGAATTGCATGTGTC<br>CTCATTGTTGTGTTTCTATTGCTGGTGGTGCTCATACCTGAGCCAGAAAAGCAAAGATCTCCCCAGGACAACCAAATGGCA<br>ATCATCATCATGGTAGCAGTAGGTCTTCTGGGCTTGATTACCGCCAATGAACTCGGATGGTTGGAGAGAACAAAGAGTGA<br>CCTAAGCCATCTAATGGGAAGGAGAGAGGAGGGGGCAACCATAGGATTCTCAATGGACATTGACCTGCGGCCAGCCTCA<br>GCTTGGGCCATCTATGCTGCCTTGACAACTTTCATTACCCCAGCCGTCCAACATGCAGTGACCACTTCATACAACAACTACT<br>CCTTAATGGCGATGGCCACGCAAGCTGGAGTGTTGTTTGGTATGGGCAAAGGGATGCCATTCTACGCATGGGACTTTGGA<br>GTCCCGCTGCTAATGATAGGTTGCTACTCACAATTAACACCCCTGACCCTAATAGTGGCCATCATTTTGCTCGTGGCGCACT<br>ACATGTACTTGATCCCAGGGCTGCAGGCAGCAGCTGCGCGTGCTGCCCAGAAGAGAACGGCAGCTGGCATCATGAAGAA<br>CCCTGTTGTGGATGGAATAGTGGTGACTGACATTGACACAATGACAATTGACCCCCAAGTGGAGAAAAAGATGGGACAG<br>GTGCTACTCATAGCAGTAGCCGTCTCCAGCGCCATACTGTCGCGGACCGCCTGGGGGTGGGGGGAGGCTGGGGCCCTGA<br>TCACAGCCGCAACTTCCACTTTGTGGGAAGGCTCTCCGAACAAGTACTGGAACTCCTCTACAGCCACTTCACTGTGTAACA<br>TTTTTAGGGGAAGTTACTTGGCTGGAGCTTCTCTAATCTACACAGTAACAAGAAACGCTGGCTTGGTCAAGAGACGTGGG<br>GGTGGAACAGGAGAGACCCTGGGAGAGAAATGGAAGGCCCGCTTGAACCAGATGTCGGCCCTGGAGTTCTACTCCTACA<br>AAAAGTCAGGCATCACCGAGGTGTGCAGAGAAGAGGCCCGCCGCGCCCTCAAGGACGGTGTGGCAACGGGAGGCCATG<br>CTGTGTCCCGAGGAAGTGCAAAGCTGAGATGGTTGGTGGAGCGGGGATACCTGCAGCCCTATGGAAAGGTCATTGATCT<br>TGGATGTGGCAGAGGGGGCTGGAGTTACTACGCCGCCACCATCCGCAAAGTTCAAGAAGTGAAAGGATACACAAAAGG<br>AGGCCCTGGTCATGAAGAACCCGTGTTGGTGCAAAGCTATGGGTGGAACATAGTCCGTCTTAAGAGTGGGGTGGACGTC<br>TTTCATATGGCGGCTGAGCCGTGTGACACGTTGCTGTGTGACATAGGTGAGTCATCATCTAGTCCTGAAGTGGAAGAAGC<br>ACGGACGCTCAGAGTCCTCTCCATGGTGGGGGATTGGCTTGAAAAAAGACCAGGAGCCTTTTGTATAAAGGTGTTGTGCC<br>CATACACCAGCACTATGATGGAAACCCTGGAGCGACTGCAGCGTAGGTATGGGGGAGGACTGGTCAGAGTGCCACTCTC<br>CCGCAACTCTACACATGAGATGTATTGGGTCTCTGGAGCGAAAAGCAACACCATAAAAAGTGTGTCCACCACGAGCCAGC<br>TCCTCTTGGGGCGCATGGACGGGCCTAGGAGGCCAGTGAAATATGAGGAGGATGTGAATCTCGGCTCTGGCACGCGGGC<br>TGTGGTAAGCTGCGCTGAAGCTCCCAACATGAAGATCATTGGTAACCGCATTGAAAGGATCCGCAGTGAGCACGCGGAA<br>ACGTGGTTCTTTGACGAGAACCACCCATATAGGACATGGGCTTACCATGGAAGCTATGAGGCCCCCACACAAGGGTCAGC<br>GTCCTCTCTAATAAACGGGGTTGTCAGGCTCCTGTCAAAACCCTGGGATGTGGTGACTGGAGTCACAGGAATAGCCATGA<br>CCGACACCACACCGTATGGTCAGCAAAGAGTTTTCAAGGAAAAAGTGGACACTAGGGTGCCAGACCCCCAAGAAGGCAC<br>TCGTCAGGTTATGAGCATGGTCTCTTCCTGGTTGTGGAAAGAGCTAGGCAAACACAAACGGCCACGAGTCTGTACCAAAG<br>AAGAGTTCATCAACAAGGTTCGTAGCAATGCAGCATTAGGGGCAATATTTGAAGAGGAAAAAGAGTGGAAGACTGCAGT<br>GGAAGCTGTGAACGATCCAAGGTTCTGGGCTCTAGTGGATAAGGAAAGAGAGCACCACCTGAGAGGAGAGTGCCAGAG<br>TTGTGTGTACAACATGATGGGAAAAAGAGAAAAGAAACAAGGGGAATTTGGAAAGGCCAAGGGCAGCCGCGCCATCTG<br>GTATATGTGGCTAGGGGCTAGATTTCTAGAGTTCGAAGCCCTTGGATTCTTGAACGAGGATCACTGGATGGGGAGAGAG<br>AACTCAGGAGGTGGTGTTGAAGGGCTGGGATTACAAAGACTCGGATATGTCCTAGAAGAGATGAGTCGTATACCAGGAG<br>GAAGGATGTATGCAGATGACACTGCTGGCTGGGACACCCGCATCAGCAGGTTTGATCTGGAGAATGAAGCTCTAATCACC<br>AACCAAATGGAAAAAGGGCACAGGGCCTTGGCATTGGCCATAATCAAGTACACATACCAAAACAAAGTGGTAAAGGTCC<br>TTAGACCAGCTGAAAAAGGGAAAACAGTTATGGACATTATTTCGAGACAAGACCAAAGGGGGAGCGGACAAGTTGTCAC<br>TTACGCTCTTAACACATTTACCAACCTAGTGGTGCAACTCATTCGGAATATGGAGGCTGAGGAAGTTCTAGAGATGCAAG<br>ACTTGTGGCTGCTGCGGAGGTCAGAGAAAGTGACCAACTGGTTGCAGAGCAACGGATGGGATAGGCTCAAACGAATGG<br>CAGTCAGTGGAGATGATTGCGTTGTGAAGCCAATTGATGATAGGTTTGCACATGCCCTCAGGTTCTTGAATGATATGGGA<br>AAAGTTAGGAAGGACACACAAGAGTGGAAACCCTCAACTGGATGGGACAACTGGGAAGAAGTTCCGTTTTGCTCCCACC<br>ACTTCAACAAGCTCCATCTCAAGGACGGGAGGTCCATTGTGGTTCCCTGCCGCCACCAAGATGAACTGATTGGCCGGGCC<br>CGCGTCTCTCCAGGGGCGGGATGGAGCATCCGGGAGACTGCTTGCCTAGCAAAATCATATGCGCAAATGTGGCAGCTCCT<br>TTATTTCCACAGAAGGGACCTCCGACTGATGGCCAATGCCATTTGTTCATCTGTGCCAGTTGACTGGGTTCCAACTGGGAG<br>AACTACCTGGTCAATCCATGGAAAGGGAGAATGGATGACCACTGAAGACATGCTTGTGGTGTGGAACAGAGTGTGGATT<br>GAGGAGAACGACCACATGGAAGACAAGACCCCAGTTACGAAATGGACAGACATCCCCTATTTGGGAAAAAGGGAAGACT<br>TGTGGTGTGGATCTCTCATAGGGCACAGACCGCGCACCACCTGGGCTGAGAACATTAAAAACACAGTCAACATGGTGCGC<br>AGGATCATAGGTGATGAAGAAAAGTACATGGACTACCTATCCACCCAAGTTCGCTACTTGGGTGAAGAAGGGTCTACACC<br>TGGAGTGCTGTAAGCACCAGTCTTAATGTTGTCAGGCCTGCTAGTCAGCCACAGCTTGGGGAAAGCTGTGCAGCCTGTGA<br>CCCCCCCAGGAGAAGCTGGGAAACCAAGCCTATAGTCAGGCCGAGAACGCCATGGCACGGAAGAAGCCATGCTGCCTGT |

-continued

| SEQUENCES |
| --- |

GAGCCCCTCAGAGGACACTGAGTCAAAAAACCCCACGCGCTTGGAGGCGCAGGATGGGAAAAGAAGGTGGCGACCTTC
CCCACCCTTCAATCTGGGGCCTGAACTGGAGATCAGCTGTGGATCTCCAGAAGAGGGACTAGTGGTTAGAGGAG

SEQ ID NO: 10
KU744693.1 Zika virus isolate VE_Ganxian, China, complete genome
GTTGTTACTGTTGCTGACTCAGACTGCGACAGTTCGAGTTTGAAGCGAAAGCTAGCAACAGTATCAACAGGTTTTATTTGG
ATTTGGAAACGAGAGTTTCTGGTCATGAAAAACCCAAAAAAGAAATCCGGAGGATTCCGGATTGTCAATATGCTAAAACG
CGGAGTAGCCCGTGTGAGCCCCTTTGGGGGCTTGAAGAGGCTGCCAGCCGGACTTCTGCTGGGTCATGGGCCCATCAGG
ATGGTCTTGGCAATTCTAGCCTTTTTGAGATTCACGGCAATCAAGCCATCACTGGGTCTCATCAATAGATGGGGTTCAGTG
GGGAAAAAAGATGCTATGGAAATAATAAAGAAGTTCAAGAAAGATCTGGCTGCCATGCTGAGAATAATCAATGCTAGGA
AGGAGAAGAAGAGACGAGGCGCAGATACTAGTGTCGGAATTGTTGGCCTCCTGCTGACCACAGCTATGGCAGCGGAGG
TCACTAGACGTGGGAGTGCATACTATATGTACTTGGACAGAAACGATGCTGGGGAGGCCATATCTTTTCCAACCACATTG
GGGATGAATAAGTGTTATATACAGATCATGGATCTTGGACACATGTGTGATGCCACCATGAGCTATGAATGCCCTATGCT
GGATGAGGGGGTGGAACCAGATGACGTCGATTGTTGGTGCAACACGACGTCAACTTGGGTTGTGTACGGAACCTGCCAT
CACAAAAAAGGTGAAGCACGGAGATCTAGAAGAGCTGTGACGCTCCCTTCCCATTCCACTAGGAAGCTGCAAACGCGGT
CGCAAACCTGGTTGGAATCAAGAGAATACACAAAGCACTTGATTAGAGTCGAAAATTGGATATTCAGGAACCCTGGCTTC
GCGTTAGCAGCAGCTGCCATCGCTTGGCTTTTGGGAAGCTCAACGAGCCAAAAAGTCATATACTTGGTCATGATACTGCT
GATTGCCCCGGCATACAGCATCAGGTGCATAGGAGTCAGCAATAGGGACTTTGTGGAAGGTATGTCAGGTGGGACTTGG
GTTGATGTTGTCTTGGAACATGGAGGTTGTGTCACCGCAATGGCACAGGACAAACCGACTGTCGACATAGAGCTGGTTAC
AACAACAGTCAGCAACATGGCGGAGGTAAGATCCTACTGCTATGAGGCATCAATATCAGACATGGCTTCGGACAGCCGCT
GCCCAACACAAGGTGAAGCCTACCTTGACAAGCAATCAGACACTCAATATGTTTGCAAAAGAACGTTAGTGGACAGAGGC
TGGGGAAATGGATGTGGACTTTTTGGCAAAGGGAGTCTGGTGACATGCGCTAAGTTTGCATGCTCCAAGAAAATGACCG
GGAAGAGCATCCAGCCAGAGAATCTGGAGTACCGGATAATGCTGTCAGTTCATGGCTCCCAGCACAGTGGGATGCTCGTT
AATGACACAGGACATGAAACTGATGAGAATAGAGCGAAGGTTGAGATAACGCCCAATTCACCAAGAGCCGAAGCCACCC
TGGGGGGTTTTGGAAGCCTAGGACTTGATTGTGAACCGAGGACAGGCCTTGACTTTTCAGATTTGTATTACTTGACTATGA
ATAACAAGCACTGGTTGGCTCACAAGGAGTGGTTCCACGACATTCCATTACCTTGGCACGCTGGGGCAGCCACCGGAACT
CCACACTGGAACAACAAAGAAGCACTGGTAGAGTTCAAGGACGCACATGCCAAAAGGCAAACTGTCGTGGTTCTAGGGA
GTCAAGAAGGAGCAGTTCACACGGCCCTTGCTGGAGCTCTGGAGGCTGAGATGGATGGTGCAAAGGGAAGGCTGTCCTC
TGGCCACTTGAAATGTCGCCTGAAAATGGATAAACTTAGATTGAAGGGCGTGTCATACTCCTTGTGTACCGCAGCGTTCAC
ATTCACCAAGATCCCGGCTGAAACAGTGGACGGGACAGTCACAGTGGAGGGACAGTACGGAGGGACAGATGGACCTTG
CAAGGTTCCAGCTCAGATGGCGGTGGACATGCAGACTCTGACCCCAGTTGGGAGGTTGATAACCGCTAACCCCGTAATCA
CTGAAAGCACTGAGAACTCTAAGATGATGCTGGAACTTGATCCACCATTTGGGGACTCTTACATTGTCATAGGAGTCGGG
GAGAAGAAGATCACCCACCACTGGCACAGGAGTGGCAGCACCATTGGAAAAGCATTTGAAGCCACTGTGAGAGGTGCCA
AGAGAATGGCAGTCTTGGGAGACACAGCCTGGGACTTTGGATCAGTTGGAGGCGCTCTCAACTCATTGGGCAAGGGCAT
CCATCAAATTATTGGAGCAGCTTTCAAATCATTGTTTGGAGGAATGTCCTGGTTCTCACAAATTCTCATTGGGACGTTGCTG
ATGTGGTTGGGTCTGAACACAAAGAATGGATCTATTTCCCTTATGTGCTTGGCCTTAGGGGGAGTGTTGATCTTCTTATCC
ACAGCCGTCTCAGGTGGTGTGGGGTGCTCGGTGGACTTCTCAAAGAAGGAGACGAGATGCGGTACAGGGGTGTTCGTCT
ATAACGATGTTGAAGCCTGGAGGGACAGGTACAAGTACCATCCTGACTCCCCCCGTAGATTGGCAGCAGCAGTCAAGCA
AGCCTGGGAAGATGGTATCTGCGGGATCTCCTCTGTTTCAAGAATGGAAAACATCATGTGGAGATCAGTAGAAGGGGAG
CTCAACGCAATCCTGGAAGAGAATGGAGTTCAACTGACGGTCGTTGTGGGATCTGTAAAAAACCCCATGTGGAGAGGTC
CACAGAGATTGCCCGTGCCTGTGAACGAGCTGCCCCACGGCTGGAAGGCTTGGGGGAAATCGTACTTCGTCAGAGCAGC
AAAGACAAATAACAGCTTTGTCGTGGATGGTGACACACTGAAGGAATGCCCACTCAAACATAGAGCATGGAACAGCTTTC
TTGTGGAGGATCATGGGTTCGGGGTATTTCACACTAGTGTCTGGCTCAAGGTTAGAGAAGACTATTGGTTAGAGTGTGAT
CCAGCCGTTATTGGAACAGCTGTTAAGGGAAAGGAGGCTGTACACAGTGATCTAGGCTACTGGATTGAGAGTGAGAAGA
ATGACACATGGTGGCTGAAGAGGGCCCATCTGATCGAGATGAAAACATGTGAATGGCCAAAGTCCCACACATTGTGGAC
AGATGGAATAGAAGAGAGTGATCTGATCATACCCAAGTCTTTAGCTGGGCCACTCAGCCATCACAATGCCAGAGAGGGCT
ACAGGACCCAAATGAAAGGGCCATGGCACAGTGAAGAGCTTGAAATTCGGTTTGAGGAATGCCCAGGCACTAAGGTCCA
CGTGGAGGAAACATGTGGAACAAGAGGACCATCTCTGAGATCAACCACTGCAAGCGGAAGGGTGATCGAGGAATGGTG
CTCCAGGGAGTGCACAATGCCCCCACTGTCCTTCCAGGCTAAAGATGGCTGTTGGTATGGAATGGAGATAAGGCCCAGG
AAAGAACCAGAAAGCAACTTAGTAAGGTCAATGGTGACTGCAGGATCAACTGATCACATGGATCACTTCTCCCTTGGAGT
GCTTGTGATTCTGCTCATGGTGCAGGAAGGGCTGAAGAAGAGAATGACCACAAAGATCATCATAAGCACATCAATGGCA
GTGCTGGTAGCTATGATCCTGGGAGGATTTTCAATGAGTGACCTGGCTAAGCTTGCAATTTTGATGGGTGCCACCTTCGC
GGAAATGAACACTGGAGGAGATGTAGCTCATCTGGCGCTGATAGCGGCATTCAAAGTCAGACCAGCGTTGCTGGTATCTT
TCATCTTCAGAGCTAATTGGACACCCCGTGAAAGCATGCTGCTGGCCTTGGCCTCGTGTCTTTTGCAAACTGCGATCTCCG
CCTTGGAAGGCGACCTGATGGTTCTCATCAATGGTTTTGCTTTGGCCTGGTTGGCAATACGAGCGATGGTTGTTCCACGCA
CTGATAACATCACCTTAGCAATCCTGGCTGCTCTGACACCACTGGCCCGGGGCACACTGCTTGTGGCGTGGAGAGCAGGC
CTTGCTACTTGCGGGGGGTTTATGCTCCTCTCTCTGAAGGGAAAAGGCAGTGTGAAGAAGAACTTACCATTTGTCATGGC
CCTGGGACTAACCGCTGTGAGGCTGGTCGACCCCATCAACGTGGTGGGACTGCTGTTGCTCACAAGGAGTGGGAAGCGG
AGCTGGCCCCCTAGCGAAGTACTCACAGCTGTTGGCCTGATATGCGCATTGGCTGGAGGGTTCGCCAAGGCAGATATAGA
GATGGCTGGGCCCATGGCCGCGGTCGGTCTGCTAATTGTCAGTTACGTGGTCTCAGGAAAGAGTGTGGACATGTACATTG
AAAGAGCAGGTGACATCACATGGGAAAAAGATGCGGAAGTCACTGGAAACAGTCCCCGGCTCGATGTGGCGCTAGATG
AGAGTGGTGATTTCTCCCTGGTGGAGGATGACGGTCCCCCCATGAGAGAGATCATACTCAAGGTGGTCCTGATGACCATC
TGTGGCATGAACCCAATAGCCATACCCTTTGCAGCTGGAGCGTGGTACGTATACGTGAAGACTGGAAAAAGGAGTGGTG
CTCTATGGGATGTGCCTGCTCCCAAGGAAGTAAAAAAGGGGGAGACCACAGATGGAGTGTACAGAGTAATGACTCGCAG
ACTGCTAGGTTCAACACAAGTTGGAGTGGGAGTTATGCAAGAGGGGGTCTTTCACACTATGTGGCACGTCACAAAAGGA
TCCGCGCTGAGAAGCGGTGAAGGGAGACTTGATCCATACTGGGGAGATGTCAAGCAGGATCTGGTGTCATACTGTGGTC
CATGGAAGCTAGATGCCGCCTGGGACGGGCACAGCGAGGTGCAGCTCTTGGCCGTGCCCCCCGGAGAGAGAGCGAGGA
ACATCCAGACTCTGCCCGGAATATTTAAGACAAAGGATGGGGACATTGGAGCGGTTGCACTGGATTACCCAGCAGGAAC
TTCAGGATCTCCAATCCTAGACAAGTGTGGGAGAGTGATAGGACTTTATGGCAATGGGGTCGTGATCAAAAATGGGAGT
TATGTTAGTGCCATCACCCAAGGGAGGAGGGAGGAAGAGACTCCTGTTGAGTGCTTCGAGCCTTCGATGCTGAAGAAGA
AGCAGCTAACTGTCTTAGACTTGCATCCTGGAGCTGGGAAAACCAGGAGAGTTCTTCCTGAAATAGTCCGTGAAGCCATA
AAAACAAGACTCCGTACTGTGATCTTGGCTCCAACCAGGGTTGTCGCTGCTGAAATGGAGGAGGCCCTTAGAGGGCTTCC
AGTGCGTTATATGACAACAGCAGTCAATGTCACCCACTCTGGAACAGAAATCGTCGACTTAATGTGCCATGCCACCTTCAC
TTCACGTCTACTACAGCCAATTAGAGTCCCCAACTATAATCTGTATATTATGGATGAGGCCCACTTCACAGATCCCTCAAGT
ATAGCAGCAAGAGGATACATTTCAACAAGGGTTGAGATGGGCGAGGCGGCTGCCATCTTCATGACCGCCACGCCACCAG
GAACCCGTGACGCATTTCCGGACTCCAACTCACCAATTATGGACACCGAAGTGGAAGTCCCAGAGAGAGCCTGGAGCTCA
GGCTTTGATTGGGTGACGGAGTATTCTGGAAAAACAGTTTGGTTTGTTCCACGCGTGAGGAACGGCAATGAGATCGCAG -continued

SEQUENCES

CTTGTCTGACAAAGGCTGGAAAACGGGTCATACAGCTCAGCAGAAAGACTTTTGAGACAGAGTTCCAGAAAACAAAACAT
CAAGAGTGGGACTTTGTCGTGACAACTGACATTTCAGAGATGGGCGCCAACTTTAAAGCTGACCGTGTCATAGATTCCAG
GAGATGCCTAAAGCCGGTCATACTTGGTGGCGAGAGAGTCATTCTGGCTGGACCCATGCCTGTCACACATGCCAGCGCTG
CCCAGAGGAGGGGGCGCATAGGCAGGAATCCCAACAAACCTGGAGATGAGTATCTGTATGGAGGTGGGTGCGCAGAGA
CTGACGAAGACCATGCACACTGGCTTGAAGCAAGAATGCTCCTTGACAATATTTACCTCCAAGATGGCCTCATAGCCTCGC
TCTATCGACCTGAGGCCGACAAAGTAGCAGCCATTGAGGGAGAGTTCAAGCTTAGGACGGAGCAAAGGAAGACCTTTGT
GGAACTCATGAAAAGAGGAGATCTTCCTGTTTGGCTGGCCTATCAGGTTGCATCTGCCGGAATAACCTACACAGATAGAA
GATGGTGCTTTGATGGCACGACCAACAACACCATAATGGAAGACAGTGTGCCGGCAGAGGTGTGGACCAGACACGGAG
AGAAAAGAGTGCTCAAACCGAGGTGGATGGACGCCAGAGTTTGTTCAGATCATGCGGCCCTGAAGTCATTCAAGGAGTT
TGCCGCTGGGAAAAGAGGAGCGGCTTTTGGAGTGATGGAAGCCCTGGGAACACTGCCAGGACACATGACAGAGAGATT
CCAGGAAGCCATTGACAACCTCGCTGTGCTCATGCGGGCAGAGACTGGAAGCAGGCCTTACAAAGCCGCGGCGGCCCAA
TTGCCGGAGACCCTAGAGACCATTATGCTTTTGGGGTTGCTGGGAACAGTCTCGCTGGGAATCTTTTTCGTCTTGATGAGG
AACAAGGGCATAGGGAAGATGGGCTTTGGAATGGTGACTCTTGGGGCCAGCGCATGGCTCATGTGGCTCTCGGAAATTG
AGCCAGCCAGAATTGCATGTGTCCTCATTGTTGTGTTCCTATTGCTGGTGGTGCTCATACCTGAGCCAGAAAAGCAAAGAT
CTCCCCAGGACAACCAAATGGCCATCATCATCATGGTAGCAGTAGGTCTTCTGGGCTTGATTACCGCCAATGAACTCGGAT
GGTTGGAGAGAACAAAGAGTGACCTAAGCCATCTAATGGGAAGGAGAGAGGAGGGGGCAACCATGGGATTCTCAATGG
ACATTGACCTGCGGCCAGCCTCAGCTTGGGCCATCTATCCTGCCTTGACATCTTTCATTACCCCAGCCGTCCAACATGCAGT
GACCACTTCATACAACAACTACTCCTTAATGGCGATGGCCACGCAAGCTGGAGTGTTGTTTGGTATGGGCAAAGGGATGC
CATTCTACGCATGGGACTTTGGAGTCCCGCTGCTAATGATAGGTTGCTACTCACAATTAACGCCCCTGACCCTAATAGTGG
CCATCATTTTGCTCGTGGCGCACTACATGTACTTGATCCCAGGGCTGCAGGCAGCAGCTGCGCGTGCTGCCCAGAAGAGA
ACGGCAGCTGGCATCATGAAGAACCCTGTTGTGGAGGGAATAGTGGTGACTGACATTGACACAATGACAATTGACCCCC
AAGTGGAGAAAAAGATGGGACAGGTGCTACTCATGGCAGTAGCCGTCTCCAGCGCCATACTGTCGAGGACCGCCTGGGG
GTGGGGGGAGGCTGGGGCCCTGATCACAGCCGCAACTTCCACTTTGTGGGAAGGCTCTCCGAACAAGTACTGGAACTCC
TCTACAGCCACCTCACTGTGTAACATTTTTAGGGGAAGTTACTTGGCTGGAGCTTCTCTAATCTACACAGTAACAAGAAAC
GCTGGCTTGGTCAAGAGACGTGGGGGTGGAACAGGAGAGACCCTGGGAGAGAAATGGAAGGCCCGCTTGAACCAGAT
GTCGGCCCTGGAGTTCTACTCCTACAAAAAGTCAGGCATCACCGAGGTGTGCAGAGAAGAGGCCCGCCGCGCCCTCAAG
GACGGTGTGGCAACGGGAGGCCATGCTGTGTCCCGAGGAAGTGCAAAGCTGAGATGGTTGGTGGAGCGGGGATACCTG
CAGCCCTATGGAAAGGTCATTGATCTTGGATGTGGCAGAGGGGGCTGGAGTTACTACGCCGCCACCATCCGCAAAGTTCA
AGAAGTGAAAGGATACACAAAAGGAGGCCCTGGTCATGAAGAACCCGTGTTGGTGCAAAGCTATGGGTGGAACATAGT
CCGTCTTAAGAGTGGGGTGGACGTCTTTCATATGGCGGCTGAGCCGTGTGACACGTTGCTGTGTGACATAGGTGAGTCAT
CATCTAGTCCTGAAGTGGAAGAAGCACGGACGCTCAGAGTCCTCTCCATGGTGGGGGATTGGCTTGAAAAAAGACCAGG
AGCCTTTTGTATAAAAGTGTTGTGCCCATACACCAGCACTATGATGGAAACCCTGGAGCGACTGCAGCGTAGGTATGGGG
GAGGACTGGTCAGAGTGCCACTCTCCCGCAACTCTACACATGAGATGTACTGGGTCTCTGGAGCGAAAAGCAACACCATA
AAAAGTGTGTCCACCACGAGCCAGCTCCTCTTGGGGCGCATGGACGGGCCTAGGAGGCCAGTGAAATATGAGGAGGAT
GTGAATCTCGGCTCTGGCACGCGGGCTGTGGTAAGCTGCGCTGAAGCTCCCAACATGAAGATCATTGGTAACCGCATTGA
AAGGATCCGCGCTGAGAAAGCGGAAACGTGGTTCTTTGACGAGAACCACCCATATAGGACATGGGCTTACCATGGAAGC
TATGATGCCGCCACACAAGGGTCAGCGTCCTCTCTAATAAACGGGGTTGTCAGGCTCCTGTCAAAACCCTGGGATGTGGT
GACTGGAGTCACAGGAATAGCCATGACCGACACCACACCGTATGGTCAGCAAAGAGTTTTCAAGGAAAAAGTGGACACT
AGGGTGCCAGACCCCCAAGAAGGCACTCGTCAGGTTATGAGCATGGTCTCTTCCTGGTTGTGGAAAGAGCTAGGCAAAC
ACAAACGGCCACGAGTCTGTACCAAAGAAGAGTTCATCAACAAGGTTCGTAGCAATGCAGCATTAGGGGCAATATTTGAA
GAGGAAAAAGAGTGGAAGACTGCAGTGGAAGCTGTGAACGATCCAAGGTTCTGGGCTCTAGTGGACAAGGAAAGAGAG
CACCACCTGAGAGGAGAGTGCCAGAGTTGTGTGTACATCACAATGGGAAAAAGAGAAAAGAAACAAGGGGAATTTGGA
AAGGCCAAGGGCAGCCGCGCCATCTGGTATATGTGGCTAGGGGCTAGATTTCTAGAGTTCGAAGCCCTTGGATTCTTGAA
CGAGGATCACTGGATGGGGAGAGAGAACTCAGGAGGTGGTGTTGAAGGGCTGGGATTACAAAGACTCGGATATGTCCT
AGAAGAGATGAGTCGCATACCAGGAGGAAGGATGTATGCAGATGACACTGCTGGCTGGGACACCCGCATCAGCAGGTTT
GATCTGGAGAATGAAGCTCTAATCACCAACCAAATGGAGAAAGGGCACAGGGCCTTGGCATTGGCCATAATCAAGTACA
CATACCAAAACAAAGTGGTAAAGGTCCTTAGACCAGCTGAAAAAGGGAAGACAGTTATGGACATTATTTCGAGACAAGA
CCAAAGGGGGAGCGGACAAGTTGTCACTTACGCTCTCAACACATTTACCAACCTAGTGGTGCAACTCATTCGGAATATGG
AGGCTGAGGAAGTTCTAGAGATGCAAGACTTGTGGCTGCTGCGGAGGTCAGAGAAAGTGACCAACTGGTTGCAGAGCA
ACGGATGGGATAGGCTCAAACGAATGGCGGTCAGTGGAGATGATTGCGTTGTGAAACCAATTGATGATAGGTTTGCACA
TGCCCTCAGGTTCTTGAATGATATGGGAAAAGTTAGGAAGGACACACAAGAGTGGAAACCCTCAACTGGATGGGACAAC
TGGGAAGAAGTTCCCTTCTGCTCCCACCACTTCAACAAGCTCCATCTCAAGGACGGGAGGTCCATTGTGGTTCCCTGCCGC
CACCAAGATGAACTGATTGGCCGGGCCCGCGTCTCTCCAGGGGCGGGATGGAGCATCCGGGAGACTGCTTGCCTAGCAA
AATCATATGCGCAAATGTGGCAGCTCCTTTATTTCCACAGAAGGGACCTCCGACTGATGGCCAATGCCATTTGTTCATCTG
TGCCAGTTGACTGGGTTCCAACTGGGAGAACTACCTGGTCAATCCATGGAAAGGGAGAATGGATGACCACTGAAGACAT
GCTTGTGGCGTGGAACAGAGTGTGGATTGAGGAGAACGACCACATGGAAGACAAGACCCCAGTCACGAAATGGACAGA
CATTCCCTATTTGGGAAAAAGGGAAGACTTGTGGTGTGGATCTCTCATAGGGCACAGACCGCGCACCACCTGGGCTGAGA
ACATTAAAAACACAGTCAACATGGTGCGCAGGATCATAGGTGATGAAGAAAAGTACATGGACTACCTATCCACCCAAGTT
CGCTACTTGGGTGAAGAAGGGTCTACACCTGGAGTGCTGTAAGCACCAATCTTAATGTTGTCAGGCCTGCTAGTCAGCCA
CAGCTTGGGGAAAGCTGTGCAGCCTGTGACCCCCCCAGGAGAAGCTGGGAAACCAAGCCTATAGTCAGGCCGAGAACGC
CATGGCACGGAAGAAGCCATGCTGCCTGTGAGCCCCTCAGAGGACACTGAGTCAAAAAACCCCACGCGCTTGGAGGCGC
AGGATGGGAAAAGAAGGTGGCGACCTTCCCCACCCTTCAATCTGGGGCCTGAACTGGAGATCAGCTGTGGATCTCCAGA
AGAGGGACTAGTGGTTAGAGGAGA

SEQ ID NO: 11
LC002520.1 Zika virus genomic RNA, strain: MR766-NIID, Uganda, complete genome
AGTTGTTGATCTGTGTGAGTCAGACTGCGACAGTTCGAGTCTGAAGCGAGAGCTAACAACAGTATCAACAGGTTTAATTT
GGATTTGGAAACGAGAGTTTCTGGTCATGAAAAACCCAAAGAAGAAATCCGGAGGATTCCGGATTGTCAATATGCTAAA
ACGCGGAGTAGCCCGTGTAAACCCCTTGGGAGGTTTGAAGAGGTTGCCAGCCGGACTTCTGCTGGGTCATGGACCCATCA
GAATGGTTTTGGCGATACTAGCCTTTTTGAGATTTACAGCAATCAAGCCATCACTGGGCCTTATCAACAGATGGGGTTCCG
TGGGGAAAAAAGAGGCTATGGAAATAATAAAGAAGTTCAAGAAAGATCTTGCTGCCATGTTGAGAATAATCAATGCTAG
GAAAGAGAGGAAGAGACGTGGCGCAGACACCAGCATCGGAATCATTGGCCTCCTGCTGACTACAGCCATGGCAGCAGA
GATCACTAGACGCGGGAGTGCATACTACATGTACTTGGATAGGAGCGATGCCGGGAAGGCCATTTCGTTTGCTACCACAT
TGGGAGTGAACAAGTGCCACGTACAGATCATGGACCTCGGGCACATGTGTGACGCCACCATGAGTTATGAGTGCCCTATG
CTGGATGAGGGAGTGGAACCAGATGATGTCGATTGCTGGTGCAACACGACATCAACTTGGGTTGTGTACGGAACCTGTC
ATCACAAAAAAGGTGAGGCACGGCGATCTAGAAGAGCCGTGACGCTCCCTTCTCACTCTACAAGGAAGTTGCAAACGCG
GTCGCAGACCTGGTTAGAATCAAGAGAATACACGAAGCACTTGATCAAGGTTGAAAACTGGATATTCAGGAACCCCGGG -continued

SEQUENCES

TTTGCGCTAGTGGCCGTTGCCATTGCCTGGCTTTTGGGAAGCTCGACGAGCCAAAAAGTCATATACTTGGTCATGATACTG
CTGATTGCCCCGGCATACAGTATCAGGTGCATTGGAGTCAGCAATAGAGACTTCGTGGAGGGCATGTCAGGTGGGACCT
GGGTTGATGTTGTCTTGGAACATGGAGGCTGCGTTACCGTGATGGCACAGGACAAGCCAACAGTTGACATAGAGTTGGT
CACGACGACGGTTAGTAACATGGCCGAGGTAAGATCCTATTGCTACGAGGCATCGATATCGGACATGGCTTCGGACAGTC
GTTGCCCAACACAAGGTGAAGCCTACCTTGACAAGCAATCAGACACTCAATATGTCTGCAAAAGAACATTAGTGGACAGA
GGTTGGGGAAACGGTTGTGGACTTTTTGGCAAAGGGAGCTTGGTGACATGTGCCAAGTTTACGTGTTCTAAGAAGATGA
CCGGGAAGAGCATTCAACCGGAAAATCTGGAGTATCGGATAATGCTATCAGTGCATGGCTCCCAGCATAGCGGGATGAC
TGTCAATGATATAGGATATGAAACTGACGAAAATAGAGCGAAAGTCGAGGTTACGCCTAATTCACCAAGAGCGGAAGCA
ACCTTGGGAGGCTTTGGAAGCTTAGGACTTGACTGTGAACCAAGGACAGGCCTTGACTTTTCAGATCTGTATTACCTGACC
ATGAACAATAAGCATTGGTTGGTGCACAAAGAGTGGTTTCATGACATCCCATTGCCTTGGCATGCTGGGGCAGACACTGG
AACTCCACACTGGAACAACAAAGAGGCATTGGTAGAATTCAAGGATGCCCACGCCAAGAGGCAAACCGTCGTCGTTCTG
GGGAGCCAGGAAGGAGCCGTTCACACGGCTCTCGCTGGAGCTCTAGAGGCTGAGATGGATGGTGCAAAGGGAAAGCTG
TTCTCTGGCCATTTGAAATGCCGCCTAAAAATGGACAAGCTTAGATTGAAGGGCGTGTCATATTCCTTGTGCACTGCGGCA
TTCACATTCACCAAGGTCCCAGCTGAAACACTGCATGGAACAGTCACAGTGGAGGTGCAGTATGCAGGGACAGATGGAC
CCTGCAAGATCCCAGTCCAGATGGCGGTGGACATGCAGACCCTGACCCCAGTTGGAAGGCTGATAACCGCCAACCCCGTG
ATTACTGAAAGCACTGAGAACTCAAAGATGATGTTGGAGCTTGACCCACCATTTGGGGATTCTTACATTGTCATAGGAGTT
GGGGACAAGAAAATCACCCACCACTGGCATAGGAGTGGTAGCACCATCGGAAAGGCATTTGAGGCCACTGTGAGAGGC
GCCAAGAGAATGGCAGTCCTGGGGGATACAGCCTGGGACTTCGGATCAGTCGGGGGTGTGTTCAACTCACTGGGTAAGG
GCATTCACCAGATTTTTGGAGCAGCCTTCAAATCACTGTTTGGAGGAATGTCCTGGTTCTCACAGATCCTCATAGGCACGC
TGCTAGTGTGGTTAGGTTTGAACACAAAGAATGGATCTATCTCCCTCACATGCTTGGCCCTGGGGGGAGTGATGATCTTCC
TCTCCACGGCTGTTTCTGCTGACGTGGGGTGCTCAGTGGACTTCTCAAAAAAGGAAACGAGATGTGGCACGGGGGTATTC
ATCTATAATGATGTTGAAGCCTGGAGGGACCGGTACAAGTACCATCCTGACTCCCCCCGCAGATTGGCAGCAGCAGTCAA
GCAGGCCTGGGAAGAGGGGATCTGTGGGATCTCATCCGTTTCAAGAATGGAAAACATCATGTGGAAATCAGTAGAAGGG
GAGCTCAATGCTATCCTAGAGGAGAATGGAGTTCAACTGACAGTTGTTGTGGGATCTGTAAAAAACCCCATGTGGAGAG
GTCCACAAAGATTGCCAGTGCCTGTGAATGAGCTGCCCCATGGCTGGAAAGCCTGGGGGAAATCGTATTTTGTTAGGGCG
GCAAAGACCAACAACAGTTTTGTTGTCGACGGTGACACACTGAAGGAATGTCCGCTTGAGCACAGAGCATGGAATAGTTT
TCTTGTGGAGGATCACGGGTTTGGAGTCTTCCACACCAGTGTCTGGCTTAAGGTCAGAGAAGATTACTCATTAGAATGTG
ACCCAGCCGTCATAGGAACAGCTGTTAAGGGAAGGGAGGCCGCGCACAGTGATCTGGGCTATTGGATTGAAAGTGAAAA
GAATGACACATGGAGGCTGAAGAGGGCCCACCTGATTGAGATGAAAACATGTGAATGGCCAAAGTCTCACACATTGTGG
ACAGATGGAGTAGAAGAAAGTGATCTTATCATACCCAAGTCTTTAGCTGGTCCACTCAGCCACCACAACACCAGAGAGGG
TTACAGAACCCAAGTGAAAGGGCCATGGCACAGTGAAGAGCTTGAAATCCGGTTTGAGGAATGTCCAGGCACCAAGGTT
TACGTGGAGGAGACATGCGGAACTAGAGGACCATCTCTGAGATCAACTACTGCAAGTGGAAGGGTCATTGAGGAATGGT
GCTGTAGGGAATGCACAATGCCCCCACTATCGTTTCGAGCAAAAGACGGCTGCTGGTATGGAATGGAGATAAGGCCCAG
GAAAGAACCAGAGAGCAACTTAGTGAGGTCAATGGTGACAGCGGGGTCAACCGATCATATGGACCACTTCTCTCTTGGA
GTGCTTGTGATTCTACTCATGGTGCAGGAGGGGTTGAAGAAGAGAATGACCACAAAGATCATCATGAGCACATCAATGG
CAGTGCTGGTAGTCATGATCTTGGGAGGATTTTCAATGAGTGACCTGGCCAAGCTTGTGATCCTGATGGGTGCTACTTTCG
CAGAAATGAACACTGGAGGAGATGTAGCTCACTTGGCATTGGTAGCGGCATTTAAAGTCAGACCAGCCTTGCTGGTCTCC
TTCATTTTCAGAGCCAATTGGACACCCCGTGAGAGCATGCTGCTAGCCCTGGCTTCGTGTCTTCTGCAAACTGCGATCTCT
GCTCTTGAAGGTGACTTGATGGTCCTCATTAATGGATTTGCTTTGGCCTGGTTGGCAATTCGAGCAATGGCCGTGCCACGC
ACTGACAACATCGCTCTACCAATCTTGGCTGCTCTAACACCACTAGCTCGAGGCACACTGCTCGTGGCATGGAGAGCGGG
CCTGGCTACTTGTGGAGGGATCATGCTCCTCTCCCTGAAAGGGAAAGGTAGTGTGAAGAAGAACCTGCCATTTGTCATGG
CCCTGGGATTGACAGCTGTGAGGGTAGTAGACCCTATTAATGTGGTAGGACTACTGTTACTCACAAGGAGTGGGAAGCG
GAGCTGGCCCCCTAGTGAAGTTCTCACAGCCGTTGGCCTGATATGTGCACTGGCCGGAGGGTTTGCCAAGGCAGACATTG
AGATGGCTGGACCCATGGCTGCAGTAGGCTTGCTAATTGTCAGCTATGTGGTCTCGGGAAAGAGTGTGGACATGTACATT
GAAAGAGCAGGTGACATCACATGGGAAAAGGACGCGGAAGTCACTGGAAACAGTCCTCGGCTTGACGTGGCACTGGAT
GAGAGTGGTGATTTCTCCTTGGTAGAGGAAGATGGTCCACCCATGAGAGAGATCATACTTAAGGTGGTCCTGATGGCCAT
CTGTGGCATGAACCCAATAGCTATACCTTTTGCTGCAGGAGCGTGGTATGTGTATGTGAAGACTGGGAAAAGGAGTGGC
GCCCTCTGGGACGTGCCTGCTCCCAAAGAAGTGAAGAAAGGAGAGACCACAGATGGAGTGTACAGAGTGATGACTCGCA
GACTGCTAGGTTCAACACAGGTTGGAGTGGGAGTCATGCAAGAGGGAGTCTTCCACACCATGTGGCACGTTACAAAAGG
AGCCGCACTGAGGAGCGGTGAGGGAAGACTTGATCCATACTGGGGGGATGTCAAGCAGGACTTGGTGTCATACTGTGG
GCCTTGGAAGTTGGATGCAGCTTGGGATGGACTCAGCGAGGTACAGCTTTTGGCCGTACCTCCCGGAGAGAGGGCCAGA
AACATTCAGACCCTGCCTGGAATATTCAAGACAAAGGACGGGGACATCGGAGCAGTTGCTCTGGACTACCCTGCAGGGA
CCTCAGGATCTCCGATCCTAGACAAATGTGGAAGAGTGATAGGACTCTATGGCAATGGGGTTGTGATCAAGAATGGAAG
CTATGTTAGTGCTATAACCCAGGGAAAGAGGGAGGAGGAGACTCCGGTTGAATGTTTCGAACCCTCGATGCTGAAGAAG
AAGCAGCTAACTGTCTTGGATCTGCATCCAGGAGCCGGAAAAACCAGGAGAGTTCTTCCTGAAATAGTCCGTGAAGCCAT
AAAAAAGAGACTCCGGACAGTGATCTTGGCACCAACTAGGGTTGTCGCTGCTGAGATGGAGGAGGCCTTGAGAGGACTT
CCGGTGCGTTACATGACAACAGCAGTCAACGTCACCCATTCTGGGACAGAAATCGTTGATTTGATGTGCCATGCCACTTTC
ACTTCACGCTTACTACAACCCATCAGAGTCCCTAATTACAATCTCTACATCATGGATGAAGCCCACTTCACAGACCCCTCAA
GTATAGCTGCAAGAGGATATATATCAACAAGGGTTGAAATGGGCGAGGCGGCTGCCATTTTTATGACTGCCACACCACCA
GGAACCCGTGATGCGTTTCCTGACTCTAACTCACCAATCATGGACACAGAAGTGGAAGTCCCAGAGAGAGCCTGGAGCTC
AGGCTTTGATTGGGTGACAGACCATTCTGGGAAAACAGTTTGGTTCGTTCCAAGCGTGAGAAACGGAAATGAAATCGCA
GCCTGTCTGACAAAGGCTGGAAAGCGGGTCATACAGCTCAGCAGGAAGACTTTTGAGACAGAATTTCAGAAAACAAAAA
ATCAAGAGTGGGACTTTGTCATAACAACTGACATCTCAGAGATGGGCGCCAACTTCAAGGCTGACCGGGTCATAGACTCT
AGGAGATGCCTAAAACCAGTCATACTTGATGGTGAGAGAGTCATCTTGGCTGGGCCCATGCCTGTCACGCATGCTAGTGC
TGCTCAGAGGAGAGGACGTATAGGCAGGAACCCTAACAAACCTGGAGATGAGTACATGTATGGAGGTGGGTGTGCAGA
GACTGATGAAGGCCATGCACACTGGCTTGAAGCAAGAATGCTTCTTGACAACATCTACCTCCAGGATGGCCTCATAGCCTC
GCTCTATCGGCCTGAGGCCGATAAGGTAGCCGCCATTGAGGGAGAGTTTAAGCTGAGGACAGAGCAAAGGAAGACCTTC
GTGGAACTCATGAAGAGAGGAGACCTTCCCGTCTGGCTAGCCTATCAGGTTGCATCTGCCGGAATAACTTACACAGACAG
AAGATGGTGCTTTGATGGCACAACCAACAACACCATAATGGAAGACAGCGTACCAGCAGAGGTGTGGACAAAGTATGGA
GAGAAGAGAGTGCTCAAACCGAGATGGATGGATGCTAGGGTCTGTTCAGACCATGCGGCCCTGAAGTCGTTCAAAGAAT
TCGCCGCTGGAAAAAGAGGAGCGGCTTTGGGAGTAATGGAGGCCCTGGGAACACTGCCAGGACACATGACAGAGAGGT
TTCAGGAAGCCATTGACAACCTCGCCGTGCTCATGCGAGCAGAGACTGGAAGCAGGCCTTATAAGGCAGCGGCAGCCCA
ACTGCCGGAGACCCTAGAGACCATTATGCTCTTAGGTTTGCTGGGAACAGTTTCACTGGGGATCTTCTTCGTCTTGATGCG
GAATAAGGGCATCGGGAAGATGGGCTTTGGAATGGTAACCCTTGGGGCCAGTGCATGGCTCATGTGGCTTTCGGAAATT
GAACCAGCCAGAATTGCATGTGTCCTCATTGTTGTGTTTTTATTACTGGTGGTGCTCATACCCGAGCCAGAGAAGCAAAGA
TCTCCCCAAGATAACCAGATGGCAATTATCATCATGGTGGCAGTGGGCCTTCTAGGTTTGATAACTGCAAACGAACTTGGA
TGGCTGGAAAGAACAAAAAATGACATAGCTCATCTAATGGGAAGGAGAGAAGAAGGAGCAACCATGGGATTCTCAATG

-continued

SEQUENCES

GACATTGATCTGCGGCCAGCCTCCGCCTGGGCTATCTATGCCGCATTGACAACTCTCATCACCCCAGCTGTCCAACATGCG
GTAACCACTTCATACAACAACTACTCCTTAATGGCGATGGCCACACAAGCTGGAGTGCTGTTTGGCATGGGCAAAGGGAT
GCCATTTTATGCATGGGACCTTGGAGTCCCGCTGCTAATGATGGGTTGCTATTCACAATTAACACCCCTGACTCTGATAGT
AGCTATCATTCTGCTTGTGGCGCACTACATGTACTTGATCCCAGGCCTACAAGCGGCAGCAGCGCGTGCTGCCCAGAAAA
GGACAGCAGCTGGCATCATGAAGAATCCCGTTGTGGATGGAATAGTGGTAACTGACATTGACACAATGACAATAGACCC
CCAGGTGGAGAAGAAGATGGGACAAGTGTTACTCATAGCAGTAGCCATCTCCAGTGCTGTGCTGCTGCGGACCGCCTGG
GGATGGGGGGAGGCTGGAGCTCTGATCACAGCAGCGACCTCCACCTTGTGGGAAGGCTCTCCAAACAAATACTGGAACT
CCTCTACAGCCACCTCACTGTGCAACATCTTCAGAGGAAGCTATCTGGCAGGAGCTTCCCTTATCTATACAGTGACGAGAA
ACGCTGGCCTGGTTAAGAGACGTGGAGGTGGGACGGGAGAGACTCTGGGAGAGAAGTGGAAAGCTCGTCTGAATCAGA
TGTCGGCCCTGGAGTTCTACTCTTATAAAAAGTCAGGTATCACTGAAGTGTGTAGAGAGGAGGCTCGCCGTGCCCTCAAG
GATGGAGTGGCCACAGGAGGACATGCCGTATCCCGGGGAAGTGCAAAGCTCAGATGGTTGGTGGAGAGAGGATATCTG
CAGCCCTATGGGAAGGTTGTTGACCTCGGATGTGGCAGAGGGGGCTGGAGCTATTATGCCGCCACCATCCGCAAAGTGC
AGGAGGTGAGAGGATACACAAAGGGAGGTCCCGGTCATGAAGAACCCATGCTGGTGCAAAGCTATGGGTGGAACATAG
TTCGTCTCAAGAGTGGAGTGGACGTCTTCCACATGGCGGCTGAGCCGTGTGACACTCTGCTGTGTGACATAGGTGAGTCA
TCATCTAGTCCTGAAGTGGAAGAGACACGAACACTCAGAGTGCTCTCTATGGTGGGGGACTGGCTTGAAAAAAGACCAG
GGGCCTTCTGTATAAAGGTGCTGTGCCCATACACCAGCACTATGATGGAAACCATGGAGCGACTGCAACGTAGGCATGG
GGGAGGATTAGTCAGAGTGCCATTGTCTCGCAACTCCACACATGAGATGTACTGGGTCTCTGGGGCAAAGAGCAACATCA
TAAAAAGTGTGTCCACCACAAGTCAGCTCCTCCTGGGACGCATGGATGGCCCCAGGAGGCCAGTGAAATATGAGGAGGA
TGTGAACCTCGGCTCGGGTACACGAGCTGTGGCAAGCTGTGCTGAGGCTCCTAACATGAAAATCATCGGCAGGCGCATTG
AGAGAATCCGCAATGAACATGCAGAAACATGGTTTCTTGATGAAAACCACCCATACAGGACATGGGCCTACCATGGGAGC
TACGAAGCCCCCACGCAAGGATCAGCGTCTTCCCTCGTGAACGGGGTTGTTAGACTCCTGTCAAAGCCTTGGGACGTGGT
GACTGGAGTTACAGGAATAGCCATGACTGACACCACACCATACGGCCAACAAAGAGTCTTCAAAGAAAAAGTGGACACC
AGGGTGCCAGATCCCCAAGAAGGCACTCGCCAGGTAATGAACATAGTCTCTTCCTGGCTGTGGAAGGAGCTGGGGAAAC
GCAAGCGGCCACGCGTCTGCACCAAAGAAGAGTTTATCAACAAGGTGCGCAGCAATGCAGCACTGGGAGCAATATTTGA
AGAGGAAAAAGAATGGAAGACGGCTGTGGAAGCTGTGAATGATCCAAGGTTTTGGGCCCTAGTGGATAGGGAGAGAGA
ACACCACCTGAGAGGAGAGTGTCACAGCTGTGTGTACAACATGATGGGAAAAAGAGAAAAGAAGCAAGGAGAGTTCGG
GAAAGCAAAAGGTAGCCGCGCCATCTGGTACATGTGGTTGGGAGCCAGATTCTTGGAGTTTGAAGCCCTTGGATTCTTGA
ACGAGGACCATTGGATGGGAAGAGAAAACTCAGGAGGTGGAGTCGAAGGGTTAGGATTGCAAAGACTTGGATACATTC
TAGAAGAAATGAATCGGGCACCAGGAGGAAAGATGTACGCAGATGACACTGCTGGCTGGGACACCCGCATTAGTAAGTT
TGATCTGGAGAATGAAGCTCTGATTACCAACCAAATGGAGGAAGGGCACAGAACTCTGGCGTTGGCCGTGATTAAATAC
ACATACCAAAACAAAGTGGTGAAGGTTCTCAGACCAGCTGAAGGAGGAAAAACAGTTATGGACATCATTTCAAGACAAG
ACCAGAGAGGGAGTGGACAAGTTGTCACTTATGCTCTCAACACATTCACCAACTTGGTGGTGCAGCTTATCCGGAACATG
GAAGCTGAGGAAGTGTTAGAGATGCAAGACTTATGGTTGTTGAGGAAGCCAGAGAAAGTGACCAGATGGTTGCAGAGC
AATGGATGGGATAGACTCAAACGAATGGCGGTCAGTGGAGATGACTGCGTTGTGAAGCCAATCGATGATAGGTTTGCAC
ATGCCCTCAGGTTCTTGAATGACATGGGAAAAGTTAGGAAAGACACACAGGAGTGGAAACCCTCGACTGGATGGAGCAA
TTGGGAAGAAGTCCCGTTCTGCTCCCACCACTTCAACAAGCTGTACCTCAAGGATGGGAGATCCATTGTGGTCCCTTGCCG
CCACCAAGATGAACTGATTGGCCGAGCTCGCGTCTCACCAGGGGCAGGATGGAGCATCCGGGAGACTGCCTGTCTTGCA
AAATCATATGCGCAGATGTGGCAGCTCCTTTATTTCCACAGAAGAGACCTTCGACTGATGGCTAATGCCATTTGCTCGGCT
GTGCCAGTTGACTGGGTACCAACTGGGAGAACCACCTGGTCAATCCATGGAAAGGGAGAATGGATGACCACTGAGGACA
TGCTCATGGTGTGGAATAGAGTGTGGATTGAGGAGAACGACCATATGGAGGACAAGACTCCTGTAACAAAATGGACAGA
CATTCCCTATCTAGGAAAAAGGGAGGACTTATGGTGTGGATCCCTTATAGGGCACAGACCCCGCACCACTTGGGCTGAAA
ACATCAAAGACACAGTCAACATGGTGCGCAGGATCATAGGTGATGAAGAAAAGTACATGGACTATCTATCCACCCAAGTC
CGCTACTTGGGTGAGGAAGGGTCCACACCCGGAGTGTTGTAAGCACCAATTTTAGTGTTGTCAGGCCTGCTAGTCAGCCA
CAGTTTGGGGAAAGCTGTGCAGCCTGTAACCCCCCCAGGAGAAGCTGGGAAACCAAGCTCATAGTCAGGCCGAGAACGC
CATGGCACGGAAGAAGCCATGCTGCCTGTGAGCCCCTCAGAGGACACTGAGTCAAAAAACCCCACGCGCTTGGAAGCGC
AGGATGGGAAAAGAAGGTGGCGACCTTCCCCACCCTTCAATCTGGGGCCTGAACTGGAGACTAGCTGTGAATCTCCAGC
AGAGGGACTAGTGGTTAGAGGAGACCCCCCGGAAAACGCAAAACAGCATATTGACGCTGGGAAAGACCAGAGACTCCA
TGAGTTTCCACCACGCTGGCCGCCAGGCACAGATCGCCGAACAGCGGCGGCCGGTGTGGGGAAATCCATGGTTTCT

SEQ ID NO: 12
AY632535.2 NC_012532.1 Zika virus strain MR 766, Uganda, complete genome
AGTTGTTGATCTGTGTGAGTCAGACTGCGACAGTTCGAGTCTGAAGCGAGAGCTAACAACAGTATCAACAGGTTTAATTT
GGATTTGGAAACGAGAGTTTCTGGTCATGAAAAACCCCAAAGAAGAAATCCGGAGGATCCGGATTGTCAATATGCTAAA
ACGCGGAGTAGCCCGTGTAAACCCCTTGGGAGGTTTGAAGAGGTTGCCAGCCGGACTTCTGCTGGGTCATGGACCCATCA
GAATGGTTTTGGCGATACTAGCCTTTTTGAGATTTACAGCAATCAAGCCATCACTGGGCCTTATCAACAGATGGGGTTCCG
TGGGGAAAAAAGAGGCTATGGAAATAATAAAGAAGTTCAAGAAAGATCTTGCTGCCATGTTGAGAATAATCAATGCTAG
GAAAGAGAGGAAGAGACGTGGCGCAGACACCAGCATCGGAATCATTGGCCTCCTGCTGACTACAGCCATGGCAGCAGA
GATCACTAGACGCGGGAGTGCATACTACATGTACTTGGATAGGAGCGATGCCGGGAAGGCCATTTCGTTTGCTACCACAT
TGGGAGTGAACAAGTGCCACGTACAGATCATGGACCTCGGGCACATGTGTGACGCCACCATGAGTTATGAGTGCCCTATG
CTGGATGAGGGAGTGGAACCAGATGATGTCGATTGCTGGTGCAACACGACATCAACTTGGGTTGTGTACGGAACCTGTC
ATCACAAAAAAGGTGAGGCACGGCGATCTAGAAGAGCCGTGACGCTCCCTTCTCACTCTACAAGGAAGTTGCAAACGCG
GTCGCAGACCTGGTTAGAATCAAGAGAATACACGAAGCACTTGATCAAGGTTGAAAACTGGATATTCAGGAACCCCGGG
TTTGCGCTAGTGGCCGTTGCCATTGCCTGGCTTTTGGGAAGCTCGACGAGCCAAAAAGTCATATACTTGGTCATGATACTG
CTGATTGCCCCGGCATACAGTATCAGGTGCATTGGAGTCAGCAATAGAGACTTCGTGGAGGGCATGTCAGGTGGGACCT
GGGTTGATGTTGTCTTGGAACATGGAGGCTGCGTTACCGTGATGGCACAGGACAAGCCAACAGTCGACATAGAGTTGGT
CACGACGACGGTTAGTAACATGGCCGAGGTAAGATCCTATTGCTACGAGGCATCGATATCGGACATGGCTTCGGACAGTC
GTTGCCCAACACAAGGTGAAGCCTACCTTGACAAGCAATCAGACACTCAATATGTCTGCAAAAGAACATTAGTGGACAGA
GGTTGGGGAAACGGTTGTGGACTTTTTGGCAAAGGGAGCTTGGTGACATGTGCCAAGTTTACGTGTTCTAAGAAGATGA
CCGGGAAGAGCATTCAACCGGAAAATCTGGAGTATCGGATAATGCTATCAGTGCATGGCTCCCAGCATAGCGGGATGAT
TGGATATGAAACTGACGAAGATAGAGCGAAAGTCGAGGTTACGCCTAATTCACCAAGAGCGGAAGCAACCTTGGGAGGC
TTTGGAAGCTTAGGACTTGACTGTGAACCAAGGACAGGCCTTGACTTTTCAGATCTGTATTACCTGACCATGAACAATAAG
CATTGGTTGGTGCACAAAGAGTGGTTTCATGACATCCCATTGCCTTGGCATGCTGGGGCAGACACCGGAACTCCACACTG
GAACAACAAAGAGGCATTGGTAGAATTCAAGGATGCCCACGCCAAGAGGCAAACCGTCGTCGTTCTGGGGAGCCAGGAA
GGAGCCGTTCACACGGCTCTCGCTGGAGCTCTAGAGGCTGAGATGGATGGTGCAAAGGGAAGGCTGTTCTCTGGCCATT
TGAAATGCCGCCTAAAAATGGACAAGCTTAGATTGAAGGGCGTGTCATATTCCTTGTGCACTGCGGCATTCACATTCACCA
AGGTCCCAGCTGAAACACTGCATGGAACAGTCACAGTGGAGGTGCAGTATGCAGGGACAGATGGACCCTGCAAGATCCC
AGTCCAGATGGCGGTGGACATGCAGACCCTGACCCCAGTTGGAAGGCTGATAACCGCCAACCCCGTGATTACTGAAAGC -continued

| SEQUENCES |
| --- |
| ACTGAGAACTCAAAGATGATGTTGGAGCTTGACCCACCATTTGGGGATTCTTACATTGTCATAGGAGTTGGGGACAAGAA<br>AATCACCCACCACTGGCATAGGAGTGGTAGCACCATCGGAAAGGCATTTGAGGCCACTGTGAGAGGCGCCAAGAGAATG<br>GCAGTCCTGGGGGATACAGCCTGGGACTTCGGATCAGTCGGGGGTGTGTTCAACTCACTGGGTAAGGGCATTCACCAGA<br>TTTTTGGAGCAGCCTTCAAATCACTGTTTGGAGGAATGTCCTGGTTCTCACAGATCCTCATAGGCACGCTGCTAGTGTGGT<br>TAGGTTTGAACACAAAGAATGGATCTATCTCCCTCACATGCTTGGCCCTGGGGGGAGTGATGATCTTCCTCTCCACGGCTG<br>TTTCTGCTGACGTGGGGTGCTCAGTGGACTTCTCAAAAAAGGAAACGAGATGTGGCACGGGGGTATTCATCTATAATGAT<br>GTTGAAGCCTGGAGGGACCGGTACAAGTACCATCCTGACTCCCCCCGCAGATTGGCAGCAGCAGTCAAGCAGGCCTGGG<br>AAGAGGGGATCTGTGGGATCTCATCCGTTTCAAGAATGGAAAACATCATGTGGAAATCAGTAGAAGGGGAGCTCAATGC<br>TATCCTAGAGGAGAATGGAGTTCAACTGACAGTTGTTGTGGGATCTGTAAAAAACCCCATGTGGAGAGGTCCACAAAGAT<br>TGCCAGTGCCTGTGAATGAGCTGCCCCATGGCTGGAAAGCCTGGGGGAAATCGTATTTTGTTAGGGCGGCAAAGACCAA<br>CAACAGTTTTGTTGTCGACGGTGACACACTGAAGGAATGTCCGCTTGAGCACAGAGCATGGAATAGTTTTCTTGTGGAGG<br>ATCACGGGTTTGGAGTCTTCCACACCAGTGTCTGGCTTAAGGTCAGAGAAGATTACTCATTAGAATGTGACCCAGCCGTCA<br>TAGGAACAGCTGTTAAGGGAAGGGAGGCCGCGCACAGTGATCTGGGCTATTGGATTGAAAGTGAAAAGAATGACACAT<br>GGAGGCTGAAGAGGGCCCACCTGATTGAGATGAAAACATGTGAATGGCCAAAGTCTCACACATTGTGGACAGATGGAGT<br>AGAAGAAAGTGATCTTATCATACCCAAGTCTTTAGCTGGTCCACTCAGCCACCACAACACCAGAGAGGGTTACAGAACCC<br>AAGTGAAAGGGCCATGGCACAGTGAAGAGCTTGAAATCCGGTTTGAGGAATGTCCAGGCACCAAGGTTTACGTGGAGG<br>AGACATGCGGAACTAGAGGACCATCTCTGAGATCAACTACTGCAAGTGGAAGGGTCATTGAGGAATGGTGCTGTAGGGA<br>ATGCACAATGCCCCCACTATCGTTTCGAGCAAAAGACGGCTGCTGGTATGGAATGGAGATAAGGCCCAGGAAAGAACCA<br>GAGAGCAACTTAGTGAGGTCAATGGTGACAGCGGGGTCAACCGATCATATGGACCACTTCTCTCTTGGAGTGCTTGTGAT<br>TCTACTCATGGTGCAGGAGGGGTTGAAGAAGAGAATGACCACAAAGATCATCATGAGCACATCAATGGCAGTGCTGGTA<br>GTCATGATCTTGGGAGGATTTTCAATGAGTGACCTGGCCAAGCTTGTGATCCTGATGGGTGCTACTTTCGCAGAAATGAA<br>CACTGGAGGAGATGTAGCTCACTTGGCATTGGTAGCGGCATTTAAAGTCAGACCAGCCTTGCTGGTCTCCTTCATTTTCAG<br>AGCCAATTGGACACCCCGTGAGAGCATGCTGCTAGCCCTGGCTTCGTGTCTTCTGCAAACTGCGATCTCTGCTCTTGAAGG<br>TGACTTGATGGTCCTCATTAATGGATTTGCTTTGGCCTGGTTGGCAATTCGAGCAATGGCCGTGCCACGCACTGACAACAT<br>CGCTCTACCAATCTTGGCTGCTCTAACACCACTAGCTCGAGGCACACTGCTCGTGGCATGGAGAGCGGGCCTGGCTACTT<br>GTGGAGGGATCATGCTCCTCTCCCTGAAAGGGAAAGGTAGTGTGAAGAAGAACCTGCCATTTGTCATGGCCCTGGGATT<br>GACAGCTGTGAGGGTAGTAGACCCTATTAATGTGGTAGGACTACTGTTACTCACAAGGAGTGGGAAGCGGAGCTGGCCC<br>CCTAGTGAAGTTCTCACAGCCGTTGGCCTGATATGTGCACTGGCCGGAGGGTTTGCCAAGGCAGACATTGAGATGGCTG<br>GACCCATGGCTGCAGTAGGCTTGCTAATTGTCAGCTATGTGGTCTCGGGAAAGAGTGTGGACATGTACATTGAAAGAGCA<br>GGTGACATCACATGGGAAAAGGACGCGGAAGTCACTGGAAACAGTCCTCGGCTTGACGTGGCACTGGATGAGAGTGGT<br>GACTTCTCCTTGGTAGAGGAAGATGGTCCACCCATGAGAGAGATCATACTCAAGGTGGTCCTGATGGCCATCTGTGGCAT<br>GAACCCAATAGCTATACCTTTTGCTGCAGGAGCGTGGTATGTGTATGTGAAGACTGGGAAAAGGAGTGGCGCCCTCTGG<br>GACGTGCCTGCTCCCAAAGAAGTGAAGAAAGGAGAGACCACAGATGGAGTGTACAGAGTGATGACTCGCAGACTGCTA<br>GGTTCAACACAGGTTGGAGTGGGAGTCATGCAAGAGGGAGTCTTCCACACCATGTGGCACGTTACAAAAGGAGCCGCAC<br>TGAGGAGCGGTGAGGGAAGACTTGATCCATACTGGGGGGATGTCAAGCAGGACTTGGTGTCATACTGTGGGCCTTGGAA<br>GTTGGATGCAGCTTGGGATGGACTCAGCGAGGTACAGCTTTTGGCCGTACCTCCCGGAGAGAGGGCCAGAAACATTCAG<br>ACCCTGCCTGGAATATTCAAGACAAAGGACGGGGACATCGGAGCAGTTGCTCTGGACTACCCTGCAGGGACCTCAGGAT<br>CTCCGATCCTAGACAAATGTGGAAGAGTGATAGGACTCTATGGCAATGGGGTTGTGATCAAGAATGGAAGCTATGTTAGT<br>GCTATAACCCAGGGAAAGAGGGAGGAGGAGACTCCGGTTGAATGTTTCGAACCCTCGATGCTGAAGAAGAAGCAGCTA<br>ACTGTCTTGGATCTGCATCCAGGAGCCGGAAAAACCAGGAGAGTTCTTCCTGAAATAGTCCGTGAAGCCATAAAAAAGAG<br>ACTCCGGACAGTGATCTTGGCACCAACTAGGGTTGTCGCTGCTGAGATGGAGGAGGCCTTGAGAGGACTTCCGGTGCGT<br>TACATGACAACAGCAGTCAACGTCACCCATTCTGGGACAGAAATCGTTGATTTGATGTGCCATGCCACTTTCACTTCACGC<br>TTACTACAACCCATCAGAGTCCCTAATTACAATCTCAACATCATGGATGAAGCCCACTTCACAGACCCCTCAAGTATAGCTG<br>CAAGAGGATACATATCAACAAGGGTTGAAATGGGCGAGGCGGCTGCCATTTTTATGACTGCCACACCACCAGGAACCCGT<br>GATGCGTTTCCTGACTCTAACTCACCAATCATGGACACAGAAGTGGAAGTCCCAGAGAGAGCCTGGAGCTCAGGCTTTGA<br>TTGGGTGACAGACCATTCTGGGAAAACAGTTTGGTTCGTTCCAAGCGTGAGAAACGGAAATGAAATCGCAGCCTGTCTGA<br>CAAAGGCTGGAAAGCGGGTCATACAGCTCAGCAGGAAGACTTTTGAGACAGAATTTCAGAAAACAAAAAATCAAGAGTG<br>GGACTTTGTCATAACAACTGACATCTCAGAGATGGGCGCCAACTTCAAGGCTGACCGGGTCATAGACTCTAGGAGATGCC<br>TAAAACCAGTCATACTTGATGGTGAGAGAGTCATCTTGGCTGGGCCCATGCCTGTCACGCATGCTAGTGCTGCTCAGAGG<br>AGAGGACGTATAGGCAGGAACCCTAACAAACCTGGAGATGAGTACATGTATGGAGGTGGGTGTGCAGAGACTGATGAA<br>GGCCATGCACACTGGCTTGAAGCAAGAATGCTTCTTGACAACATCTACCTCCAGGATGGCCTCATAGCCTCGCTCTATCGG<br>CCTGAGGCCGATAAGGTAGCCGCCATTGAGGGAGAGTTTAAGCTGAGGACAGAGCAAAGGAAGACCTTCGTGGAACTC<br>ATGAAGAGAGGAGACCTTCCCGTCTGGCTAGCCTATCAGGTTGCATCTGCCGGAATAACTTACACAGACAGAAGATGGTG<br>CTTTGATGGCACAACCAACAACACCATAATGGAAGACAGTGTACCAGCAGAGGTTTGGACAAAGTATGGAGAGAAGAGA<br>GTGCTCAAACCGAGATGGATGGATGCTAGGGTCTGTTCAGACCATGCGGCCCTGAAGTCGTTCAAAGAATTCGCCGCTGG<br>AAAAAGAGGAGCGGCTTTGGGAGTAATGGAGGCCCTGGGAACACTGCCAGGACACATGACAGAGAGGTTTCAGGAAGC<br>CATTGACAACCTCGCCGTGCTCATGCGAGCAGAGACTGGAAGCAGGCCTTATAAGGCAGCGGCAGCCCAACTGCCGGAG<br>ACCCTAGAGACCATTATGCTCTTAGGTTTGCTGGGAACAGTTTCACTGGGGATCTTCTTCGTCTTGATGCGGAATAAGGGC<br>ATCGGGAAGATGGGCTTTGGAATGGTAACCCTTGGGGCCAGTGCATGGCTCATGTGGCTTTCGGAAATTGAACCAGCCA<br>GAATTGCATGTGTCCTCATTGTTGTGTTTTTATTACTGGTGGTGCTCATACCCGAGCCAGAGAAGCAAAGATCTCCCCAAG<br>ATAACCAGATGGCAATTATCATCATGGTGGCAGTGGGCCTTCTAGGTTTGATAACTGCAAACGAACTTGGATGGCTGGAA<br>AGAACAAAAAATGACATAGCTCATCTAATGGGAAGGAGAGAAGAAGGAGCAACCATGGGATTCTCAATGGACATTGATC<br>TGCGGCCAGCCTCCGCCTGGGCTATCTATGCCGCATTGACAACTCTCATCACCCCAGCTGTCCAACATGCGGTAACCACTT<br>CATACAACAACTACTCCTTAATGGCGATGGCCACACAAGCTGGAGTGCTGTTTGGCATGGGCAAAGGGATGCCATTTATG<br>CATGGGGACCTTGGAGTCCCGCTGCTAATGATGGGTTGCTATTCACAATTAACACCCCTGACTCTGATAGTAGCTATCATT<br>CTGCTTGTGGCGCACTACATGTACTTGATCCCAGGCCTACAAGCGGCAGCAGCGCGTGCTGCCCAGAAAAGGACAGCAG<br>CTGGCATCATGAAGAATCCCGTTGTGGATGGAATAGTGGTAACTGACATTGACACAATGACAATAGACCCCCAGGTGGA<br>GAAGAAGATGGGACAAGTGTTACTCATAGCAGTAGCCATCTCCAGTGCTGTGCTGCTGCGGACCGCCTGGGGATGGGGG<br>GAGGCTGGAGCTCTGATCACAGCAGCGACCTCCACCTTGTGGGAAGGCTCTCCAAACAAATACTGGAACTCCTCTACAGC<br>CACCTCACTGTGCAACATCTTCAGAGGAAGCTATCTGGCAGGAGCTTCCCTTATCTATACAGTGACGAGAAACGCTGGCCT<br>GGTTAAGAGACGTGGAGGTGGGACGGGAGAGACTCTGGGAGAGAAGTGGAAAGCTCGTCTGAATCAGATGTCGGCCCT<br>GGAGTTCTACTCTTATAAAAAGTCAGGTATCACTGAAGTGTGTAGAGAGGAGGCTCGCCGTGCCCTCAAGGATGGAGTG<br>GCCACAGGAGGACATGCCGTATCCCGGGGAAGTGCAAAGATCAGATGGTTGGAGGAGAGAGGATATCTGCAGCCCTAT<br>GGGAAGGTTGTTGACCTCGGATGTGGCAGAGGGGGCTGGAGCTATTATGCCGCCACCATCCGCAAAGTGCAGGAGGTG<br>AGAGGATACACAAAGGGAGGTCCCGGTCATGAAGAACCCATGCTGGTGCAAAGCTATGGGTGGAACATAGTTCGTCTCA<br>AGAGTGGAGTGGACGTCTTCCACATGGCGGCTGAGCCGTGTGACACTCTGCTGTGTGACATAGGTGAGTCATCATCTAGT<br>CCTGAAGTGGAAGAGACACGAACACTCAGAGTGCTCTCTATGGTGGGGGACTGGCTTGAAAAAGACCAGGGGCCTTCT |

-continued

SEQUENCES

GTATAAAGGTGCTGTGCCCATACACCAGCACTATGATGGAAACCATGGAGCGACTGCAACGTAGGCATGGGGGAGGATT
AGTCAGAGTGCCATTGTGTCGCAACTCCACACATGAGATGTACTGGGTCTCTGGGGCAAAGAGCAACATCATAAAAAGTG
TGTCCACCACAAGTCAGCTCCTCCTGGGACGCATGGATGGCCCCAGGAGGCCAGTGAAATATGAGGAGGATGTGAACCT
CGGCTCGGGTACACGAGCTGTGGCAAGCTGTGCTGAGGCTCCTAACATGAAAATCATCGGCAGGCGCATTGAGAGAATC
CGCAATGAACATGCAGAAACATGGTTTCTTGATGAAAACCACCCATACAGGACATGGGCCTACCATGGGAGCTACGAAGC
CCCCACGCAAGGATCAGCGTCTTCCCTCGTGAACGGGGTTGTTAGACTCCTGTCAAAGCCTTGGGACGTGGTGACTGGAG
TTACAGGAATAGCCATGACTGACACCACACCATACGGCCAACAAAGAGTCTTCAAAGAAAAAGTGGACACCAGGGTGCC
AGATCCCCAAGAAGGCACTCGCCAGGTAATGAACATAGTCTCTTCCTGGCTGTGGAAGGAGCTGGGGAAACGCAAGCGG
CCACGCGTCTGCACCAAAGAAGAGTTTATCAACAAGGTGCGCAGCAATGCAGCACTGGGAGCAATATTTGAAGAGGAAA
AAGAATGGAAGACGGCTGTGGAAGCTGTGAATGATCCAAGGTTTTGGGCCCTAGTGGATAGGGAGAGAGAACACCACC
TGAGAGGAGAGTGTCACAGCTGTGTGTACAACATGATGGGAAAAAGAGAAAAGAAGCAAGGAGAGTTCGGGAAAGCA
AAAGGTAGCCGCGCCATCTGGTACATGTGGTTGGGAGCCAGATTCTTGGAGTTTGAAGCCCTTGGATTCTTGAACGAGGA
CCATTGGATGGGAAGAGAAAACTCAGGAGGTGGAGTCGAAGGGTTAGGATTGCAAAGACTTGGATACATTCTAGAAGA
AATGAATCGGGCACCAGGAGGAAAGATGTACGCAGATGACACTGCTGGCTGGGACACCCGCATTAGTAAGTTTGATCTG
GAGAATGAAGCTCTGATTACCAACCAAATGGAGGAAGGGCACAGAACTCTGGCGTTGGCCGTGATTAAATACACATACC
AAAACAAAGTGGTGAAGGTTCTCAGACCAGCTGAAGGAGGAAAAACAGTTATGGACATCATTTCAAGACAAGACCAGAG
AGGGAGTGGACAAGTTGTCACTTATGCTCTCAACACATTCACCAACTTGGTGGTGCAGCTTATCCGGAACATGGAAGCTG
AGGAAGTGTTAGAGATGCAAGACTTATGGTTGTTGAGGAAGCCAGAGAAAGTGACCAGATGGTTGCAGAGCAATGGAT
GGGATAGACTCAAACGAATGGCGGTCAGTGGAGATGACTGCGTTGTGAAGCCAATCGATGATAGGTTTGCACATGCCCT
CAGGTTCTTGAATGACATGGGAAAAGTTAGGAAAGACACACAGGAGTGGAAACCCTCGACTGGATGGAGCAATTGGGA
AGAAGTCCCGTTCTGCTCCCACCACTTCAACAAGCTGTACCTCAAGGATGGGAGATCCATTGTGGTCCCTTGCCGCCACCA
AGATGAACTGATTGGCCGAGCTCGCGTCTCACCAGGGGCAGGATGGAGCATCCGGGAGACTGCCTGTCTTGCAAAATCA
TATGCGCAGATGTGGCAGCTCCTTTATTTCCACAGAAGAGACCTTCGACTGATGGCTAATGCCATTTGCTCGGCTGTGCCA
GTTGACTGGGTACCAACTGGGAGAACCACCTGGTCAATCCATGGAAAGGGAGAATGGATGACCACTGAGGACATGCTCA
TGGTGTGGAATAGAGTGTGGATTGAGGAGAACGACCATATGGAGGACAAGACTCCTGTAACAAAATGGACAGACATTCC
CTATCTAGGAAAAAGGGAGGACTTATGGTGTGGATCCCTTATAGGGCACAGACCCCGCACCACTTGGGCTGAAAACATCA
AAGACACAGTCAACATGGTGCGCAGGATCATAGGTGATGAAGAAAAGTACATGGACTATCTATCCACCCAAGTCCGCTAC
TTGGGTGAGGAAGGGTCCACACCCGGAGTGTTGTAAGCACCAATTTTAGTGTTGTCAGGCCTGCTAGTCAGCCACAGTTT
GGGGAAAGCTGTGCAGCCTGTAACCCCCCCAGGAGAAGCTGGGAAACCAAGCTCATAGTCAGGCCGAGAACGCCATGG
CACGGAAGAAGCCATGCTGCCTGTGAGCCCCTCAGAGGACACTGAGTCAAAAAACCCCACGCGCTTGGAAGCGCAGGAT
GGGAAAAGAAGGTGGCGACCTTCCCCACCCTTCAATCTGGGGCCTGAACTGGAGACTAGCTGTGAATCTCCAGCAGAGG
GACTAGTGGTTAGAGGAGACCCCCCGGAAAACGCAAAACAGCATATTGACGTGGGAAAGACCAGAGACTCCATGAGTTT
CCACCACGCTGGCCGCCAGGCACAGATCGCCGAACTTCGGCGGCCGGTGTGGGGAAATCCATGGTTTCT

SEQ ID NO: 13
KJ776791.1, Zika virus strain H/PF/2013 polyprotein gene, complete cds
AGTATCAACAGGTTTTATTTTGGATTTGGAAACGAGAGTTTCTGGTCATGAAAAACCCAAAAAAGAAATCCGGAGGATTC
CGGATTGTCAATATGCTAAAACGCGGAGTAGCCCGTGTGAGCCCCTTTGGGGGCTTGAAGAGGCTGCCAGCCGGACTTCT
GCTGGGTCATGGGCCCATCAGGATGGTCTTGGCGATTCTAGCCTTTTTGAGATTCACGGCAATCAAGCCATCACTGGGTCT
CATCAATAGATGGGGTTCAGTGGGGAAAAAAGAGGCTATGGAAATAATAAAGAAGTTCAAGAAAGATCTGGCTGCCATG
CTGAGAATAATCAATGCTAGGAAGGAGAAGAAGAGACGAGGCGCAGATACTAGTGTCGGAATTGTTGGCCTCCTGCTGA
CCACAGCTATGGCAGCGGAGGTCACTAGACGTGGGAGTGCATACTATATGTACTTGGACAGAAACGACGCTGGGGAGGC
CATATCTTTTCCAACCACATTGGGGATGAATAAGTGTTATATACAGATCATGGATCTTGGACACATGTGTGATGCCACCAT
GAGCTATGAATGCCCTATGCTGGATGAGGGGGTGGAACCAGATGACGTCGATTGTTGGTGCAACACGACGTCAACTTGG
GTTGTGTACGGAACCTGCCATCACAAAAAAGGTGAAGCACGGAGATCTAGAAGAGCTGTGACGCTCCCCTCCCATTCCAC
TAGGAAGCTGCAAACGCGGTCGCAAACCTGGTTGGAATCAAGAGAATACACAAAGCACTTGATTAGAGTCGAAAATTGG
ATATTCAGGAACCCTGGCTTCGCGTTAGCAGCAGCTGCCATCGCTTGGCTTTTGGGAAGCTCAACGAGCCAAAAAGTCAT
ATACTTGGTCATGATACTGCTGATTGCCCCGGCATACAGCATCAGGTGCATAGGAGTCAGCAATAGGGACTTTGTGGAAG
GTATGTCAGGTGGGACTTGGGTTGATGTTGTCTTGGAACATGGAGGTTGTGTCACCGTAATGGCACAGGACAAACCGACT
GTCGACATAGAGCTGGTTACAACAACAGTCAGCAACATGGCGGAGGTAAGATCCTACTGCTATGAGGCATCAATATCGG
ACATGGCTTCGGACAGCCGCTGCCCAACACAAGGTGAAGCCTACCTTGACAAGCAATCAGACACTCAATATGTCTGCAAA
AGAACGTTAGTGGACAGAGGCTGGGGAAATGGATGTGGACTTTTTGGCAAAGGGAGCCTGGTGACATGCGCTAAGTTTG
CATGCTCCAAGAAAATGACCGGGAAGAGCATCCAGCCAGAGAATCTGGAGTACCGGATAATGCTGTCAGTTCATGGCTCC
CAGCACAGTGGGATGATCGTTAATGACACAGGACATGAAACTGATGAGAATAGAGCGAAGGTTGAGATAACGCCCAATT
CACCAAGAGCCGAAGCCACCCTGGGGGGTTTTGGAAGCCTAGGACTTGATTGTGAACCGAGGACAGGCCTTGACTTTTCA
GATTTGTATTACTTGACTATGAATAACAAGCACTGGTTGGTTCACAAGGAGTGGTTCCACGACATTCCATTACCTTGGCAC
GCTGGGGCAGACACCGGAACTCCACACTGGAACAACAAAGAAGCACTGGTAGAGTTCAAGGACGCACATGCCAAAAGG
CAAACTGTCGTGGTTCTAGGGAGTCAAGAAGGAGCAGTTCACACGGCCCTTGCTGGAGCTCTGGAGGCTGAGATGGATG
GTGCAAAGGGAAGGCTGTCCTCTGGCCACTTGAAATGTCGCCTGAAAATGGATAAACTTAGATTGAAGGGCGTGTCATAC
TCCTTGTGTACCGCAGCGTTCACATTCACCAAGATCCCGGCTGAAACACTGCACGGGACAGTCACAGTGGAGGTACAGTA
CGCAGGGACAGATGGACCTTGCAAGGTTCCAGCTCAGATGGCGGTGGACATGCAAACTCTGACCCCAGTTGGGAGGTTG
ATAACCGCTAACCCCGTAATCACTGAAAGCACTGAGAACTCTAAGATGATGCTGGAACTTGATCCACCATTTGGGGACTCT
TACATTGTCATAGGAGTCGGGGAGAAGAAGATCACCCACCACTGGCACAGGAGTGGCAGCACCATTGGAAAAGCATTTG
AAGCCACTGTGAGAGGTGCCAAGAGAATGGCAGTCTTGGGAGACACAGCCTGGGACTTTGGATCAGTTGGAGGCGCTCT
CAACTCATTGGGCAAGGGCATCCATCAAATTTTTGGAGCAGCTTTCAAATCATTGTTTGGAGGAATGTCCTGGTTCTCACA
AATTCTCATTGGAACGTTGCTGATGTGGTTGGGTCTGAACACAAAGAATGGATCTATTTCCCTTATGTGCTTGGCCTTAGG
GGGAGTGTTGATCTTCTTATCCACAGCTGTCTCTGCTGATGTGGGGTGCTCGGTGGACTTCTCAAAGAAGGAGACGAGAT
GCGGTACAGGGGTGTTCGTCTATAACGACGTTGAAGCCTGGAGGGACAGGTACAAGTACCATCCTGACTCCCCCCGTAGA
TTGGCAGCAGCAGTCAAGCAAGCCTGGGAAGATGGTATCTGTGGGATCTCCTCTGTTTCAAGAATGGAAAACATCATGTG
GAGATCAGTAGAAGGGGAGCTCAACGCAATCCTGGAAGAGAATGGAGTTCAACTGACGGTCGTTGTGGGATCTGTAAAA
AACCCCATGTGGAGAGGTCCACAGAGATTGCCCGTGCCTGTGAACGAGCTGCCCCACGGCTGGAAGGCTTGGGGGAAAT
CGTACTTCGTCAGAGCAGCAAAGACAAATAACAGCTTTGTCGTGGATGGTGACACACTGAAGGAATGCCCACTCAAACAT
AGAGCATGGAACAGCTTTCTTGTGGAGGATCATGGGTTCGGGGTATTTCACACTAGTGTCTGGCTCAAGGTTAGAGAAGA
TTATTCATTAGAGTGTGATCCAGCCGTTATTGGAACAGCTGTTAAGGGAAAGGAGGCTGTACACAGTGATCTAGGCTACT
GGATTGAGAGTGAGAAGAATGACACATGGAGGCTGAAGAGGGCCCATCTGATCGAGATGAAAACATGTGAATGGCCAA
AGTCCCACACATTGTGGACAGATGGAATAGAAGAGAGTGATCTGATCATACCCAAGTCTTTAGCTGGGCCACTCAGCCAT
CACAATACCAGAGAGGGCTACAGGACCCAAATGAAAGGGCCATGGCACAGTGAAGAGCTTGAAATTCGGTTTGAGGAAT -continued

| SEQUENCES |
| --- |
| GCCCAGGCACTAAGGTCCACGTGGAGGAAACATGTGGAACAAGAGGACCATCTCTGAGATCAACCACTGCAAGCGGAAG |
| GGTGATCGAGGAATGGTGCTGCAGGGAGTGCACAATGCCCCCACTGTCGTTCCGGGCTAAAGATGGCTGTTGGTATGGA |
| ATGGAGATAAGGCCCAGGAAAGAACCAGAAAGTAACTTAGTAAGGTCAATGGTGACTGCAGGATCAACTGATCACATGG |
| ATCACTTCTCCCTTGGAGTGCTTGTGATTCTGCTCATGGTGCAGGAAGGGCTGAAGAAGAGAATGACCACAAAGATCATC |
| ATAAGCACATCGATGGCAGTGCTGGTAGCTATGATCCTGGGAGGATTTTCAATGAGTGACCTGGCTAAGCTTGCAATTTT |
| GATGGGTGCCACCTTCGCGGAAATGAACACTGGAGGAGATGTAGCTCATCTGGCGCTGATAGCGGCATTCAAAGTCAGA |
| CCAGCGTTGCTGGTATCTTTCATCTTCAGAGCTAATTGGACACCCCGTGAAAGCATGCTGCTGGCCTTGGCCTCGTGTCTTT |
| TGCAAACTGCGATCTCCGCCTTGGAAGGCGACCTGATGGTTCTCATCAATGGTTTTGCTTTGGCCTGGTTGGCAATACGAG |
| CGATGGTTGTTCCACGCACTGATAACATCACCTTGGCAATCCTGGCTGCTCTGACACCACTGGCCCGGGGCACACTGCTTG |
| TGGCGTGGAGAGCAGGCCTTGCTACTTGCGGGGGGTTTATGCTCCTCTCTCTGAAGGGAAAAGGCAGTGTGAAGAAGAA |
| CTTACCATTTGTCATGGCCCTGGGACTAACCGCTGTGAGGCTGGTCGACCCCATCAACGTGGTGGGACTGCTGTTGCTCAC |
| AAGGAGTGGGAAGCGGAGCTGGCCCCCTAGCGAAGTACTCACAGCTGTTGGCCTGATATGCGCATTGGCTGGAGGGTTC |
| GCCAAGGCAGATATAGAGATGGCTGGGCCCATGGCCGCGGTCGGTCTGCTAATTGTCAGTTACGTGGTCTCAGGAAAGA |
| GTGTGGACATGTACATTGAAAGAGCAGGTGACATCACATGGGAAAAAGATGCGGAAGTCACTGGAAACAGTCCCCGGCT |
| CGATGTGGCGCTAGATGAGAGTGGTGATTTCTCCCTGGTGGAGGATGACGGTCCCCCCATGAGAGAGATCATACTCAAG |
| GTGGTCCTGATGACCATCTGTGGCATGAACCCAATAGCCATACCCTTTGCAGCTGGAGCGTGGTACGTATACGTGAAGAC |
| TGGAAAAAGGAGTGGTGCTCTATGGGATGTGCCTGCTCCCAAGGAAGTAAAAAAGGGGGAGACCACAGATGGAGTGTA |
| CAGAGTAATGACTCGTAGACTGCTAGGTTCAACACAAGTTGGAGTGGGAGTTATGCAAGAGGGGGTCTTTCACACTATGT |
| GGCACGTCACAAAAGGATCCGCGCTGAGAAGCGGTGAAGGGAGACTTGATCCATACTGGGGAGATGTCAAGCAGGATC |
| TGGTGTCATACTGTGGTCCATGGAAGCTAGATGCCGCCTGGGACGGGCACAGCGAGGTGCAGCTCTTGGCCGTGCCCCC |
| CGGAGAGAGAGCGAGGAACATCCAGACTCTGCCCGGAATATTTAAGACAAAGGATGGGGACATTGGAGCGGTTGCGCT |
| GGATTACCCAGCAGGAACTTCAGGATCTCCAATCCTAGACAAGTGTGGGAGAGTGATAGGACTTTATGGCAATGGGGTC |
| GTGATCAAAAATGGGAGTTATGTTAGTGCCATCACCCAAGGGAGGAGGGAGGAAGAGACTCCTGTTGAGTGCTTCGAGC |
| CTTCGATGCTGAAGAAGAAGCAGCTAACTGTCTTAGACTTGCATCCTGGAGCTGGGAAAACCAGGAGAGTTCTTCCTGAA |
| ATAGTCCGTGAAGCCATAAAAACAAGACTCCGTACTGTGATCTTAGCTCCAACCAGGGTTGTCGCTGCTGAAATGGAGGA |
| AGCCCTTAGAGGGCTTCCAGTGCGTTATATGACAACAGCAGTCAATGTCACCCACTCTGGAACAGAAATCGTCGACTTAAT |
| GTGCCATGCCACCTTCACTTCACGTCTACTACAGCCAATCAGAGTCCCCAACTATAATCTGTATATTATGGATGAGGCCCAC |
| TTCACAGATCCCTCAAGTATAGCAGCAAGAGGATACATTTCAACAAGGGTTGAGATGGGCGAGGCGGCTGCCATCTTCAT |
| GACCGCCACGCCACCAGGAACCCGTGACGCATTTCCGGACTCCAACTCACCAATTATGGACACCGAAGTGGAAGTCCCAG |
| AGAGAGCCTGGAGCTCAGGCTTTGATTGGGTGACGGATCATTCTGGAAAAACAGTTTGGTTTGTTCCAAGCGTGAGGAAC |
| GGCAATGAGATCGCAGCTTGTCTGACAAAGGCTGGAAAACGGGTCATACAGCTCAGCAGAAAGACTTTTGAGACAGAGT |
| TCCAGAAAACAAAACATCAAGAGTGGGACTTTGTCGTGACAACTGACATTTCAGAGATGGGCGCCAACTTTAAAGCTGAC |
| CGTGTCATAGATTCCAGGAGATGCCTAAAGCCGGTCATACTTGATGGCGAGAGAGTCATTCTGGCTGGACCCATGCCTGT |
| CACACATGCCAGCGCTGCCCAGAGGAGGGGGCGCATAGGCAGGAATCCCAACAAACCTGGAGATGAGTATCTGTATGGA |
| GGTGGGTGCGCAGAGACTGACGAAGACCATGCACACTGGCTTGAAGCAAGAATGCTCCTTGACAATATTTACCTCCAAGA |
| TGGCCTCATAGCCTCGCTCTATCGACCTGAGGCCGACAAAGTAGCAGCCATTGAGGGAGAGTTCAAGCTTAGGACGGAG |
| CAAAGGAAGACCTTTGTGGAACTCATGAAAAGAGGAGATCTTCCTGTTTGGCTGGCCTATCAGGTTGCATCTGCCGGAAT |
| AACCTACACAGATAGAAGATGGTGCTTTGATGGCACGACCAACAACACCATAATGGAAGACAGTGTGCCGGCAGAGGTG |
| TGGACCAGACACGGAGAGAAAAGAGTGCTCAAACCGAGGTGGATGGACGCCAGAGTTTGTTCAGATCATGCGGCCCTGA |
| AGTCATTCAAGGAGTTTGCCGCTGGGAAAAGAGGAGCGGCTTTTGGAGTGATGGAAGCCCTGGGAACACTGCCAGGACA |
| CATGACAGAGAGATTCCAGGAAGCCATTGACAACCTCGCTGTGCTCATGCGGGCAGAGACTGGAAGCAGGCCTTACAAA |
| GCCGCGGCGGCCCAATTGCCGGAGACCCTAGAGACCATTATGCTTTTGGGGTTGCTGGGAACAGTCTCGCTGGGAATCTT |
| TTTCGTCTTGATGAGGAACAAGGGCATAGGGAAGATGGGCTTTGGAATGGTGACTCTTGGGGCCAGCGCATGGCTCATG |
| TGGCTCTCGGAAATTGAGCCAGCCAGAATTGCATGTGTCCTCATTGTTGTGTTCCTATTGCTGGTGGTGCTCATACCTGAG |
| CCAGAAAAGCAAAGATCTCCCCAGGACAACCAAATGGCAATCATCATCATGGTAGCAGTAGGTCTTCTGGGCTTGATTAC |
| CGCCAATGAACTCGGATGGTTGGAGAGAACAAAGAGTGACCTAAGCCATCTAATGGGAAGGAGAGAGGAGGGGGCAAC |
| CATAGGATTCTCAATGGACATTGACCTGCGGCCAGCCTCAGCTTGGGCCATCTATGCTGCCTTGACAACTTTCATTACCCCA |
| GCCGTCCAACATGCAGTGACCACTTCATACAACAACTACTCCTTAATGGCGATGGCCACGCAAGCTGGAGTGTTGTTTGGT |
| ATGGGCAAAGGGATGCCATTCTACGCATGGGACTTTGGAGTCCCGCTGCTAATGATAGGTTGCTACTCACAATTAACACC |
| CCTGACCCTAATAGTGGCCATCATTTTGCTCGTGGCGCACTACATGTACTTGATCCCAGGGCTGCAGGCAGCAGCTGCGC |
| GTGCTGCCCAGAAGAGAACGGCAGCTGGCATCATGAAGAACCCTGTTGTGGATGGAATAGTGGTGACTGACATTGACAC |
| AATGACAATTGACCCCCAAGTGGAGAAAAAGATGGGACAGGTGCTACTCATAGCAGTAGCCGTCTCCAGCGCCATACTGT |
| CGCGGACCGCCTGGGGGTGGGGGAGGCTGGGGCCCTGATCACAGCGGCAACTTCCACTTTGTGGGAAGGCTCTCCGA |
| ACAAGTACTGGAACTCCTCTACAGCCACTTCACTGTGTAACATTTTTAGGGGAAGTTACTTGGCTGGAGCTTCTCTAATCTA |
| CACAGTAACAAGAAACGCTGGCTTGGTCAAGAGACGTGGGGGTGGAACAGGAGAGACCCTGGGAGAGAAATGGAAGG |
| CCCGCTTGAACCAGATGTCGGCCCTGGAGTTCTACTCCTACAAAAAGTCAGGCATCACCGAGGTGTGCAGAGAAGAGGCC |
| CGCCGCGCCCTCAAGGACGGTGTGGCAACGGGAGGCCATGCTGTGTCCCGAGGAAGTGCAAAGCTGAGATGGTTGGTG |
| GAGCGGGGATACCTGCAGCCCTATGGAAAGGTCATTGATCTTGGATGTGGCAGAGGGGGCTGGAGTTACTACGCCGCCA |
| CCATCCGCAAAGTTCAAGAAGTGAAAGGATACACAAAAGGAGGCCCTGGTCATGAAGAACCCATGTTGGTGCAAAGCTA |
| TGGGTGGAACATAGTCCGTCTTAAGAGTGGGGTGGACGTCTTTCATATGGCGGCTGAGCCGTGTGACACGTTGCTGTGTG |
| ACATAGGTGAGTCATCATCTAGTCCTGAAGTGGAAGAAGCACGGACGCTCAGAGTCCTCTCCATGGTGGGGGATTGGCTT |
| GAAAAAAGACCAGGAGCCTTTTGTATAAAAGTGTTGTGCCCATACACCAGCACTATGATGGAAACCCTGGAGCGACTGCA |
| GCGTAGGTATGGGGGAGGACTGGTCAGAGTGCCACTCTCCCGCAACTCTACACATGAGATGTACTGGGTCTCTGGAGCG |
| AAAAGCAACACCATAAAAAGTGTGTCCACCACGAGCCAGCTCCTCTTGGGGCGCATGGACGGGCCCAGGAGGCCAGTGA |
| AATATGAGGAGGATGTGAATCTCGGCTCTGGCACGCGGGCTGTGGTAAGCTGCGCTGAAGCTCCCAACATGAAGATCAT |
| TGGTAACCGCATTGAAAGGATCCGCAGTGAGCACGCGGAAACGTGGTTCTTTGACGAGAACCACCCATATAGGACATGG |
| GCTTACCATGGAAGCTATGAGGCCCCCACACAAGGGTCAGCGTCCTCTCTAATAAACGGGGTTGTCAGGCTCCTGTCAAA |
| ACCCTGGGATGTGGTGACTGGAGTCACAGGAATAGCCATGACCGACACCACACCGTATGGTCAGCAAAGAGTTTTCAAG |
| GAAAAAGTGGACACTAGGGTGCCAGACCCCCAAGAAGGCACTCGTCAGGTTATGAGCATGGTCTCTTCCTGGTTGTGGA |
| AAGAGCTAGGCAAACACAAACGGCCACGAGTCTGTACCAAAGAAGAGTTCATCAACAAGGTTCGTAGCAATGCAGCATT |
| AGGGGCAATATTTGAAGAGGAAAAAGAGTGGAAGACTGCAGTGGAAGCTGTGAACGATCCAAGGTTCTGGGCTCTAGT |
| GGACAAGGAAAGAGAGCACCACCTGAGAGGAGAGTGCCAGAGTTGTGTGTACAACATGATGGGAAAAAGAGAAAAGA |
| AACAAGGGGAATTTGGAAAGGCCAAGGGCAGCCGCGCCATCTGGTATATGTGGCTAGGGGCTAGATTTCTAGAGTTCGA |
| AGCCCTTGGATTCTTGAACGAGGATCACTGGATGGGGAGAGAGAACTCAGGAGGTGGTGTTGAAGGGCTGGGATTACA |
| AAGACTCGGATATGTCCTAGAAGAGATGAGTCGCATACCAGGAGGAAGGATGTATGCAGATGACACTGCTGGCTGGGAC |
| ACCCGCATCAGCAGGTTTGATCTGGAGAATGAAGCTCTAATCACCAACCAAATGGAGAAAGGGCACAGGGCCTTGGCAT |
| TGGCCATAATCAAGTACACATACCAAAACAAAGTGGTAAAGGTCCTTAGACCAGCTGAAAAAGGGAAGACAGTTATGGA |

-continued

SEQUENCES

CATTATTTCGAGACAAGACCAAAGGGGGAGCGGACAAGTTGTCACTTACGCTCTTAACACATTTACCAACCTAGTGGTGC
AACTCATTCGGAATATGGAGGCTGAGGAAGTTCTAGAGATGCAAGACTTGTGGCTGCTGCGGAGGTCAGAGAAAGTGAC
CAACTGGTTGCAGAGCAACGGATGGGATAGGCTCAAACGAATGGCAGTCAGTGGAGATGATTGCGTTGTGAAGCCAATT
GATGATAGGTTTGCACATGCCCTCAGGTTCTTGAATGATATGGGAAAAGTTAGGAAGGACACACAAGAGTGGAAACCCT
CAACTGGATGGGACAACTGGGAAGAAGTTCCGTTTTGCTCCCACCACTTCAACAAGCTCCATCTCAAGGACGGGAGGTCC
ATTGTGGTTCCCTGCCGCCACCAAGATGAACTGATTGGCCGGGCCCGCGTCTCTCCAGGGGCGGGATGGAGCATCCGGG
AGACTGCTTGCCTAGCAAAATCATATGCGCAAATGTGGCAGCTCCTTTATTTCCACAGAAGGGACCTCCGACTGATGGCCA
ATGCCATTTGTTCATCTGTGCCAGTTGACTGGGTTCCAACTGGGAGAACTACCTGGTCAATCCATGGAAAGGGAGAATGG
ATGACCACTGAAGACATGCTTGTGGTGTGGAACAGAGTGTGGATTGAGGAGAACGACCACATGGAAGACAAGACCCCA
GTTACGAAATGGACAGACATTCCCTATTTGGGAAAAAGGGAAGACTTGTGGTGTGGATCTCTCATAGGGCACAGACCGC
GCACCACCTGGGCTGAGAACATTAAAAACACAGTCAACATGGTGCGCAGGATCATAGGTGATGAAGAAAAGTACATGGA
CTACCTATCCACCCAAGTTCGCTACTTGGGTGAAGAAGGGTCTACACCTGGAGTGCTGTAAGCACCAATCTTAGTGTTGTC
AGGCCTGCTAGTCAGCCACAGCTTGGGGAAAGCTGTGCAGCCTGTGACCCCCCCAGGAGAAGCTGGGAAACCAAGCCTA
TAGTCAGGCCGAGAACGCCATGGCACGGAAGAAGCCATGCTGCCTGTGAGCCCCTCAGAGGACACTGAGTCAAAAAACC
CCACGCGCTTGGAGGCGCAGGATGGGAAAAGAAGGTGGCGACCTTCCCCACCCTTCAATCTGGGGCCTGAACTGGAGAT
CAGCTGTGGATCTCCAGAAGAGGGACTAGTGGTTAGAGGAG

In some embodiments, the Zika virus has a RNA genome corresponding to the DNA sequence provided by the nucleic acid sequence of any one of SEQ ID NOs: 2-13 or 78. In some embodiments, the Zika virus has a variant genome that is at least 80%, 81%, 82%, 83%, 84%, 85%, 86%, 87%, 88%, 89%, 90%, 91%, 92%. 93%, 94%, 95%, 96%, 97%, 98%, 99%, 99.5%, 99.6%, 99.7%, 99.8% or 99.9% identical to any one of SEQ ID NOs: 2-13 or 78.

Provided below are amino acid sequences of the E-proteins of Zika strains that may be used in the methods, compositions, and/or vaccines described herein.

SEQ ID NO: 14 isol-ARB15076.AHF49784.1.Central_African_Republic/291-788 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFTCSKKMTGKSIQPENLEYRIMLSVHGSQHSGMIVNDENRAKVEVT PNSPRAEATLGGFGSLGLDCEPRTGLDFSDLYYLTMNNKHWLVHKEWFHDIPLPWHAGADTGTPHWNNKEALVEFKDAHAK RQTVVVLGSQEGAVHTALAGALEAEMDGAKGRLFSGHLKCRLKMDKLRLKGVSYSLCTAAFTFTKVPAETLHGTVTVEVQYAG TDGPCKVPAQMAVDMQTLTPVGRLITANPVITESTENSKMMLELDPPFGDSYIVIGVGDKKITHHWHRSGSTIGKAFEATVRG AKRMAVLGDTAWDFGSVGGVFNSLGKGIHQIFGAAFKSLFGGMSWFSQILIGTLLVWLGLNTKNGSISLTCLALGGVMIFLSTA

VSA

SEQ ID NO: 15 isol-IbH_30656.AEN75265.1.Nigeria/291-788 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFTCSKKMTGKSIQPENLEYRIMLSVHGSQHSGMIVNDENRAKVEVT PNSPRAEATLGGFGSLGLDCEPRTGLDFSDLYYLTMNNKHWLVHKEWFHDIPLPWHSGADTETPHWNNKEALVEFKDAHAK RQTVVVLGSQEGAVHTALAGALEAEMDGAKGRLSSGHLKCRLKMDKLRLKGVSYSLCTAAFTFTKVPAETLHGTVTVEVQYAG RDGPCKVPAQMAVDMQTLTPVGRLITANPVITESTENSKMMLELDPPFGDSYIVIGVGDKKITHHWHRSGSIIGKAFEATVRG AKRMAVLGDTAWDFGSVGGVFNSLGKGIHQIFGAAFKSLFGGMSWFSQILIGTLLVWLGLNTKNGSISLTCLALGGVMIFLSTA

VSA

SEQ ID NO: 16

ArB1362.AHL43500.1.-/291-794 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFTCSKKMTGKSIQPENLEYRIMLSVHGSQHSGMIVNDXXXXXXXNR AEVEVTPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLFSGHLKCRLKMDKLRLKGVSYSLCTAAFTFTKVPAETLHGTVTV EVQYAGTDGPCKVPAQMAVDMQTLTPVGRLITANPVITESTENSKMMLELDPPFGDSYIVIGVGDKKITHHWHRSGSTIGKAF EATVRGAKRMAVLGDTAWDFGSVGGVFNSLGKGIHQIFGAAFKSLFGGMSWFSQILIGTLLVWLGLNTKNGSISLTCLALGGV

MIFLSTAVSA

-continued

SEQ ID NO: 17
ArD128000.AHL43502.1.-/291-794 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFTCSKKMTGKSIQPENLEYRIMLSVHGSQHSGMXXXXXGHETDEN RAKVEVTPNSPRAEATLGGFGSLGLDCEPRTGLDFSDLYYLTMNNKHRLVRKEWFHDIPLPWHAGADTGTPHWNNKEALVEF KDAHAKRQTVVVLGSQEGAVHTALAGALEAEMDGAKGRLFSGHLKCRLKMDKLRLKGVSYSLCTAAFTFTKVPAETLHGTVTV EVQYAGTDGPCKVPAQMAVDMQTLTPVGRLITANPVITESTENSKMMLELDPPFGDSYIVIGVGDKKITHHWLKKGSSIGKAF EATVRGAKRMAVLGDTAWDFGSVGGVFNSLGKGVHQIFGAAFKSLFGGMSWFSQILIGTLLVWLGLNTKNGSISLTCLALGG

VMIFLSTAVSA

SEQ ID NO: 18
ArD158095.AHL43505.1.-/291-794 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFTCSKKMTGKSIQPENLEYRIMLSVHGSQHSGMIVNDIGHETDENR AKVEVTPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLFSGHLKCRLKMDKLRLKGVSYSLCTAAFTFTKVPAETLHGTVTV EVQYAGTDGPCKVPAQMAVDMQTLTPVGRLITANPVITESTENSKMMLELDPPFGDSYIVIGVGDKKITHHWHRSGSTIGKAF EATVRGAKRMAVLGDTAWDFGSVGGVFNSLGKGIHQIFGAAFKSLFGGMSWFSQILIGTLLVWLGLNTKNGSISLTCLALGGV

MIFLSTAVSA

SEQ ID NO: 19
ArD158084.AHL43504.1.-/291-794 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFTCSKKMTGKSIQPENLEYRIMLSVHGSQHSGMIVNDIGHETDENR AKVEVTPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLFSGHLKCRLKMDKLRLKGVSYSLCTAAFTFTKVPAETLHGTVTV EVQYAGTDGPCKVPAQMAVDMQTLTPVGRLITANPVITESTENSKMMLELDPPFGDSYIVIGVGDKKITHHWHRSGSTIGKAF EATVRGAKRMAVLGDTAWDFGSVGGVFNSLGKGIHQIFGAAFKSLFGGMSWFSQILIGTLLVWLGLNTKNGSISLTCLALGGV

MIFLSTAVSA

SEQ ID NO: 20
isol-ARB13565.AHF49783.1.Central_African_Republic/291-794 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFTCSKKMTGKSIQPENLEYRIMLSVHGSQHSGMIVNDIGHETDENR AKVEVTPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLFSGHLKCRLKMDKLRLKGVSYSLCTAAFTFTKVPAETLHGTVTV EVQYAGTDGPCKVPAQMAVDMQTLTPVGRLITANPVITESTENSKMMLELDPPFGDSYIVIGVGDKKITHHWHRSGSTIGKAF EATVRGAKRMAVLGDTAWDFGSVGGVFNSLGKGVHQIFGAAFKSLFGGMSWFSQILIGTLLVWLGLNTKNGSISLTCLALGG

VMIFLSTAVSA

SEQ ID NO: 21
isol-ARB7701.AHF49785.1.Central_African_Republic/291-794 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFTCSKKMTGKSIQPENLEYRIMLSVHGSQHSGMIVNDIGHETDENR AKVEVTPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLFSGHLKCRLKMDKLRLKGVSYSLCTAAFTFTKVPAETLHGTVTV EVQYAGTDGPCKVPAQMAVDMQTLTPVGRLITANPVITESTENSKMMLELDPPFGDSYIVIGVGDKKITHHWHRSGSTIGKAF EATVRGAKRMAVLGDTAWDFGSVGGVFNSLGKGVHQIFGAAFKSLFGGMSWFSQILIGTLLVWLGLNTKNGSISLTCLALGG

VMIFLSTAVSA

-continued

SEQ ID NO: 22
isol-ArD_41519.AEN75266.1.Senegal/291-794 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFTCSKKMTGKSIQPENLEYRIMLSVHGSQHSGMIVNDTGHETDEN RAKVEVTPNSPRAEATLGGFGSLGLDCEPRTGLDFSDLYYLTMNNKHWLVHKEWFHDIPLPWHAGADTGTPHWNNKEALVE FKDAHAKRQTVVVLGSQEGAVHTALAGALEAEMDGAKGRLFSGHLKCRLKMDKLRLKGVSYSLCTAAFTFTKVPAETLHGTVT VEVQYAGTDGPCKVPAQMAVDMQTLTPVGRLITANPVITESTENSKMMLELDPPFGDSYIVIGVGDKKITHHWHRSGSTIGKA FEATVRGAKRMAVLGDTAWDFGSVGGVFNSLGKGIHQIFGAAFKSLFGGMSWFSQILIGTLLVWLGLNTKNGSISLTCLALGG

VMIFLSTAVSA

SEQ ID NO: 23
MR766-NIID. BAP47441.1.Uganda/291-794 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFTCSKKMTGKSIQPENLEYRIMLSVHGSQHSGMTVNDIGYETDENR AKVEVTPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGKLFSGHLKCRLKMDKLRLKGVSYSLCTAAFTFTKVPAETLHGTVTV EVQYAGTDGPCKIPVQMAVDMQTLTPVGRLITANPVITESTENSKMMLELDPPFGDSYIVIGVGDKKITHHWHRSGSTIGKAF EATVRGAKRMAVLGDTAWDFGSVGGVFNSLGKGIHQIFGAAFKSLFGGMSWFSQILIGTLLVWLGLNTKNGSISLTCLALGGV

MIFLSTAVSA

SEQ ID NO: 24
LC002520.1/326-829 Zika virus genomic RNA, strain: MR766-NIID, Uganda, Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFTCSKKMTGKSIQPENLEYRIMLSVHGSQHSGMTVNDIGYETDENR AKVEVTPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGKLFSGHLKCRLKMDKLRLKGVSYSLCTAAFTFTKVPAETLHGTVTV EVQYAGTDGPCKIPVQMAVDMQTLTPVGRLITANPVITESTENSKMMLELDPPFGDSYIVIGVGDKKITHHWHRSGSTIGKAF EATVRGAKRMAVLGDTAWDFGSVGGVFNSLGKGIHQIFGAAFKSLFGGMSWFSQILIGTLLVWLGLNTKNGSISLTCLALGGV

MIFLSTAVSA

SEQ ID NO: 25
isol-MR_766.AEN75263.1.Uganda/291-794 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFTCSKKMTGKSIQPENLEYRIMLSVHGSQHSGMIVNDTGYETDENR AKVEVTPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGKLFSGHLKCRLKMDKLRLKGVSYSLCTAAFTFTKVPAETLHGTVTV EVQYAGTDGPCKIPVQMAVDMQTLTPVGRLITANPVITESTENSKMMLELDPPFGDSYIVIGVGDKKITHHWHRSGSTIGKAF EATVRGAKRMAVLGDTAWDFGSVGGVFNSLGKGIHQIFGAAFKSLFGGMSWFSQILIGTLLVWLGLNTKNGSISLTCLALGGV

MIFLSTAVSA

SEQ ID NO: 26
ArD7117.AHL43501.1.-/291-794 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFTCSKKMTGKSIQPENLEYRIMLSVHGSQHSGMIVNDIGHETDENR AKVEVTPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLFSGHLKCRLKMDKLRLKGVSYSLCTAVCTAAKVPAETLHGTVT VEVQYAGTDGPCKVPAQMAVDMQTLTPVGRLITANPVITESTENSKMMLELDPPFGDSYIVIGVGDKKITHHWHRSGSTIGKA FEATVRGAKRMAVLGDTAWDFGSVGGVFNSLGKGIHQIFGAAFKSLFGGMSWFSQILIGTLLVWLGLNTKNGSISLTCLALGG

VMIFLSTAVSA

-continued

SEQ ID NO: 27

AY632535.2/326-825 NC_012532.1 Zika virus strain MR 766, Uganda, Flavivirus envelope glycoprotein E.

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFTCSKKMTGKSIQPENLEYRIMLSVHGSQHSGMIGYETDEDRAKVE

VTPNSPRAEATLGGFGSLGLDCEPRTGLDFSDLYYLTMNNKHWLVHKEWFHDIPLPWHAGADTGTPHWNNKEALVEFKDAH

AKRQTVVVLGSQEGAVHTALAGALEAEMDGAKGRLFSGHLKCRLKMDKLRLKGVSYSLCTAAFTFTKVPAETLHGTVTVEVQY

AGTDGPCKIPVQMAVDMQTLTPVGRLITANPVITESTENSKMMLELDPPFGDSYIVIGVGDKKITHHWHRSGSTIGKAFEATV

RGAKRMAVLGDTAWDFGSVGGVFNSLGKGIHQIFGAAFKSLFGGMSWFSQILIGTLLVWLGLNTKNGSISLTCLALGGVMIFL

STAVSA

SEQ ID NO: 28

MR_766.AAV34151.1.Uganda/291-790 Flavivirus envelope glycoprotein E. |Q32ZE1|Q32ZE1_9FL IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFTCSKKMTGKSIQPENLEYRIMLSVHGSQHSGMIGYETDEDRAKVE VTPNSPRAEATLGGFGSLGLDCEPRTGLDFSDLYYLTMNNKHWLVHKEWFHDIPLPWHAGADTGTPHWNNKEALVEFKDAH AKRQTVVVLGSQEGAVHTALAGALEAEMDGAKGRLFSGHLKCRLKMDKLRLKGVSYSLCTAAFTFTKVPAETLHGTVTVEVQY AGTDGPCKIPVQMAVDMQTLTPVGRLITANPVITESTENSKMMLELDPPFGDSYIVIGVGDKKITHHWHRSGSTIGKAFEATV RGAKRMAVLGDTAWDFGSVGGVFNSLGKGIHQIFGAAFKSLFGGMSWFSQILIGTLLVWLGLNTKNGSISLTCLALGGVMIFL

STAVSA

SEQ ID NO: 29

MR_766.YP_009227198.1.Uganda/1-500 envelope protein E[Zika virus]

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFTCSKKMTGKSIQPENLEYRIMLSVHGSQHSGMIGYETDEDRAKVE

VTPNSPRAEATLGGFGSLGLDCEPRTGLDFSDLYYLTMNNKHWLVHKEWFHDIPLPWHAGADTGTPHWNNKEALVEFKDAH

AKRQTVVVLGSQEGAVHTALAGALEAEMDGAKGRLFSGHLKCRLKMDKLRLKGVSYSLCTAAFTFTKVPAETLHGTVTVEVQY

AGTDGPCKIPVQMAVDMQTLTPVGRLITANPVITESTENSKMMLELDPPFGDSYIVIGVGDKKITHHWHRSGSTIGKAFEATV

RGAKRMAVLGDTAWDFGSVGGVFNSLGKGIHQIFGAAFKSLFGGMSWFSQILIGTLLVWLGLNTKNGSISLTCLALGGVMIFL

STAVSA

SEQ ID NO: 30

KU681081.3/308-811 Zika virus isolate Zika virus/*H. sapiens*-tc/THA/2014/SV0127- 14, Thailand, Flavivirus envelope glycoprotein E.

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHTGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITEGTENSKMMLELDPPFGDSYIVIGVGEKKITHHWHRSGSTIGKAF

EATVRGAKRMAVLGDTAWDFGSVGGVLNSLGKGIHQIFGAAFKSLFGGMSWFSQILIGTLLMWLGLNTKNGSISLMCLALGG

VLIFLSTAVSA

SEQ ID NO: 31 isol-Zika_virus % *H. sapiens*-tc % THA% 2014 % SV0127-_14.AMD61710.1.Thailand/291-794 Flavivirus envelope glycoprotein E.

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHTGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITEGTENSKMMLELDPPFGDSYIVIGVGEKKITHHWHRSGSTIGKAF

EATVRGAKRMAVLGDTAWDFGSVGGVLNSLGKGIHQIFGAAFKSLFGGMSWFSQILIGTLLMWLGLNTKNGSISLMCLALGG

VLIFLSTAVSA

-continued

SEQ ID NO: 32
CK-ISL_2014.AIC06934.1.Cook_Islands/1-504 Flavivirus envelope glycoprotein E. (Fragment) OS = Zika virus GN = E PE = 4 SV = 1
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 33
Natal_RGN.AMB18850.1.Brazil:_Rio_Grande_do_Norte,_Natal/291-794 Flavivirus envelope glycoprotein E.]
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 34
isol-Si323.AMC37200.1.Colombia/1-504 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 35
KU707826.1/317-820 Zika virus isolate SSABR1, Brazil, Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 36
KU509998.1/326-829 Zika virus strain Haiti/1225/2014, Haiti, Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF -continued EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 37 isol-GDZ16001.AML82110.1.China/291-794 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 38

BeH819015.AMA12085.1.Brazil/291-794 Flavivirus envelope glycoprotein E.]
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 39

MRS_OPY_Martinique_PaRi_2015.AMC33116.1.Martinique/291-794 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 40

KU501215.1/308-811 Zika virus strain PRVABC59, Puerto Rico, Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 41

Haiti % 1225 % 2014.AMB37295.1.Haiti/291-794 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF -continued EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 42

KU527068.1/308-811 Zika virus strain Natal RGN, Brazil: Rio Grande do Norte, Natal, Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 43 isol-Z1106027.ALX35662.1.Suriname/5-508 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 44 isol-FLR.AMM39804.1.Colombia:_Barranquilla/291-794 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 45

PLCal_ZV_isol-From_Vero_E6_cells.AHL37808.1.Canada/254-757 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 46

BeH818995.AMA12084.1.Brazil/291-794 Flavivirus envelope glycoprotein E. [Zika virus].
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF -continued EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 47
H/PF/2013.AHZ13508.1.French_Polynesia/291-794 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 48
PRVABC59.AMC13911.1.Puerto_Rico/291-794 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 49
KU321639.1/326-829 Zika virus strain ZikaSPH2015, Brazil, Flavivirus envelope glycoprotein E.
IRCIGVSNRDFVEGMSGGTWVDIVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 50
ZikaSPH2015.ALU33341.1.Brazil/291-794 Flavivirus envelope glycoprotein E.
IRCIGVSNRDFVEGMSGGTWVDIVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 51
103344.AMC13912.1.Guatemala/291-794 polyprotein [Zika virus]. 103344.AMC13912.1.Guatemala
Flavivirus envelope glycoprotein E.
IRCIGVSNRDFVEGMSGGTWVDVVLEHGGCVTVMAQDKPTVDIELVTTTVSNMAEIRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF -continued EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 52
isol-Brazil-ZKV2015.AMD16557.1.Brazil/291-794 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGTQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 53
KU497555.1/308-811 Zika virus isolate Brazil-ZKV2015, Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGTQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 54
isol-ZJ03.AMM39806.1.China/291-794 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF EATVRGARRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 55
isol-FSS13025.AFD30972.1.Cambodia/291-794 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF EATVRGAKRMAVLGDTAWDFGSVGGALNSLGKGIHQIFGAAFKSLFGGMSWFSQILIGTLLVWLGLNTKNGSISLMCLALGG

VLIFLSTAVSA

SEQ ID NO: 56
isol-Z1106032.ALX35660.1.Suriname/291-794 Flavivirus envelope glycoprotein E. [Zika virus]
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF -continued EATVRGAKRMAVLGDTAWDFGSVGGALNSLGKGIHQIFGAAFKSLFGGMSWFSQILIGTLLMWLGLNAKNGSISLMCLALGG

VLIFLSTAVSA

SEQ ID NO: 57
isol-Z1106033.ALX35659.1.Suriname/291-794 Flavivirus envelope glycoprotein E. [Zika virus]
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF EATVRGAKRMAVLGDTAWDFGSVGGALNSLGKGIHQIFGAAFKSLFGGMSWFSQILIGTLLMWLGLNAKNGSISLMCLALGG

VLIFLSTAVSA

SEQ ID NO: 58
isol-BeH828305.AMK49165.1.Brazil/291-794 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDTQTLTPVGRLITANPVITESTENSKMMLELDPPFGDSYIVIGVGEKKITHHWHRSGSTIGKAFE ATVRGAKRMAVLGDTAWDFGSVGGALNSLGKGIHQIFGAAFKSLFGGMSWFSQILIGTLLMWLGLNTKNGSISLMCLALGGV

LIFLSTAVSA

SEQ ID NO: 59
isol-GD01.AMK79468.1.China/291-794 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNGTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 60
isol-Z1106031.ALX35661.1.Suriname/291-794 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVLAQMAVDMQTLTPVGRLITANPVITESTENSKMMLELDPPFGDSYIVIGVGEKKITHHWHRSGSTIGKAF EATVRGAKRMAVLGDTAWDFGSVGGALNSLGKGIHQIFGAAFKSLFGGMSWFSQILIGTLLMWLGLNTKNGSISLMCLALGG

VLIFLSTAVSA

SEQ ID NO: 61
ACD75819.1.Micronesia/291-794 Flavivirus envelope glycoprotein E.
IRCIGVSNRDFVEGMSGGTWVDVVLEHGGCVTVMAQDKPAVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMIVNDTGHETDEN RAKVEITPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLSSGHLKCRLKMDKLRLKGVSYSLCTAAFTFTKIPAETLHGTVTV EVQYAGTDGPCKVPAQMAVDMQTLTPVGRLITANPVITESTENSKMMLELDPPFGDSYIVIGVGEKKITHHWHRSGSTIGKAF -continued EATVRGAKRMAVLGDTAWDFGSVGGALNSLGKGIHQIFGAAFKSLFGGMSWFSQILIGTLLVWLGLNTKNGSISLTCLALGGV

LIFLSTAVSA

SEQ ID NO: 62

KU681082.3/308-811 Zika virus isolate Zika virus/*H. sapiens*-tc/PHL/2012/CPC-0740, Philippines, Flavivirus envelope glycoprotein E.

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLVWLGLNTKNGSISLTCLALGGV

LIFLSTAVSA

SEQ ID NO: 63 isol-Zika_virus % *H. sapiens*-tc % PHL % 2012 % CPC-0740.AMD61711.1.Philippines/291-794 Flavivirus envelope glycoprotein E.

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDTGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLVWLGLNTKNGSISLTCLALGGV

LIFLSTAVSA

SEQ ID NO: 64 isol-BeH823339.AMK49164.2.Brazil/291-794 Flavivirus envelope glycoprotein E.

IRCIGVSNRDFVEGMSGGTWVDVVLEHGGCVTVMAQDKPTVDIELVSTTVSNMAEVRSYCYEATISDIASDSRCPTQGEAYLD

KQSDTQYVCKRTLVDRGWGNGCGLFGKGSLVTCAKFACSKKMTGKSIQPENLEYRIMLSVHGSQHSGMIVNDTGHETDENR

AKVEITPNSPRAEATLGGFGSLGLDCEPRTGLDFSDLYYLTMNNKHWLVHKEWFHDIPLPWHAGADTGTPHWNNKEALVEFK

DAHAKRQTAVVLGSQEGAVHTALAGALEAEMDGAKGRLSSGHLKCRLKMDKLRLKGVSYSLCTAAFTFTKIPAETLHGTVTVE

VQYAGTDGPCKVPAQMAVDMQTLTPVGRLITANPVITESTENSKMMLELDPPFGDSYIVIGVGEKKITHHWHRSGSTIGKAFE

ATVRGAKRMAVLGDTAWDFGSVGGALNSLGKGIHQIFGAAFKSLFGGMSWFSQILIGTLLMWLGLNTKNGSISLMCLALGGV

LIFLSTAVSA

SEQ ID NO: 65 isol-P6-740.AEN75264.1.Malaysia/291-794 Flavivirus envelope glycoprotein E.

IRCIGVSNRDFVEGMSGGTWVDVVLEHGGCVTVMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMIVNDXGHETDEN

RAKVEITPNSPRAEATLGGFGSLGLDCEPRTGLDFSDLYYLTMNNKHWLVHKEWFHDIPLPWHAGADTGTPHWNNKEALVEF

KDAHAKRQTVVVLGSQEGAVHTALAGALEAEMDGAKGRLSSGHLKCRLKMDKLRLKGVSYSLCTAAFTFTKIPAETLHGTVTV

EVQYAGTDGPCKVPAQMAVDMQTLTPVGRLITANPVITESTENSKMMLELDPPFGDSYIVIGVGDKKITHHWXRSGSTIGKAF

EATVRGAKRMAVLGDTAWDFGSVGGALNSLGKGIHQIFGAAFKSLFGGMSWFSQILIGTLLVWLGLNTKNGSISLTCLALGGV

LIFLSTAVSA

SEQ ID NO: 66

KU744693.1/326-829 Zika virus isolate VE_Ganxian, China, Flavivirus envelope glycoprotein E.

IRCIGVSNRDFVEGMSGGTWVDVVLEHGGCVTAMAQDKPTVDIELVTTTVSNMAEVRSYCYEASISDMASDSRCPTQGEAYL

DKQSDTQYVCKRTLVDRGWGNGCGLFGKGSLVTCAKFACSKKMTGKSIQPENLEYRIMLSVHGSQHSGMLVNDTGHETDEN

RAKVEITPNSPRAEATLGGFGSLGLDCEPRTGLDFSDLYYLTMNNKHWLAHKEWFHDIPLPWHAGAATGTPHWNNKEALVEF

KDAHAKRQTVVVLGSQEGAVHTALAGALEAEMDGAKGRLSSGHLKCRLKMDKLRLKGVSYSLCTAAFTFTKIPAETVDGTVTV

EGQYGGTDGPCKVPAQMAVDMQTLTPVGRLITANPVITESTENSKMMLELDPPFGDSYIVIGVGEKKITHHWHRSGSTIGKAF

-continued

EATVRGAKRMAVLGDTAWDFGSVGGALNSLGKGIHQIIGAAFKSLFGGMSWFSQILIGTLLMWLGLNTKNGSISLMCLALGG

VLIFLSTAVSG

SEQ ID NO: 67
isol-VE_Ganxian.AMK79469.1.China/291-794 Flavivirus envelope glycoprotein E.
IRCIGVSNRDFVEGMSGGTWVDVVLEHGGCVTAMAQDKPTVDIELVTTTVSNMAEVRSYCYEASISDMASDSRCPTQGEAYL DKQSDTQYVCKRTLVDRGWGNGCGLFGKGSLVTCAKFACSKKMTGKSIQPENLEYRIMLSVHGSQHSGMLVNDTGHETDEN RAKVEITPNSPRAEATLGGFGSLGLDCEPRTGLDFSDLYYLTMNNKHWLAHKEWFHDIPLPWHAGAATGTPHWNNKEALVEF KDAHAKRQTVVVLGSQEGAVHTALAGALEAEMDGAKGRLSSGHLKCRLKMDKLRLKGVSYSLCTAAFTFTKIPAETVDGTVTV EGQYGGTDGPCKVPAQMAVDMQTLTPVGRLITANPVITESTENSKMMLELDPPFGDSYIVIGVGEKKITHHWHRSGSTIGKAF EATVRGAKRMAVLGDTAWDFGSVGGALNSLGKGIHQIIGAAFKSLFGGMSWFSQILIGTLLMWLGLNTKNGSISLMCLALGG

VLIFLSTAVSG

SEQ ID NO: 68
ArD157995.AHL43503.1.-1291-794 Flavivirus envelope glycoprotein E.
ISCIGVSNRDLVEGMSGGTWVDVVLEHGGCVTEMAQDKPTVDIELVTMTVSNMAEVRSYCYEASLSDMASASRCPTQGEPSL DKQSDTQSVCKRTLGDRGWGNGCGIFGKGSLVTCSKFTCCKKMPGKSIQPENLEYRIMLPVHGSQHSGMIVNDIGHETDENR AKVEVTPNSPRAEATLGGFGSLGLDCEPRTGLDFSDLYYLTMNNKHWLVHKEWFHDIPLPWHAGADTGTPHWNNKEALVEF KDAHAKRQTVVVLGSQEGAVHTALAGALEAEMDGAKGRLFSGHLKCRLKMDKLRLKGVSYSLCTAAFTFTKVPAETLHGTVTV EVQSAGTDGPCKVPAQMAVDMQTLTPVGRLITANPVITESTENSKMMLELDPPFGDSYIVIGVGDKKITHHWHRSGSTIGKAF EATVRGAKRMAVLGDTAWDFGSVGGVFNSLGKGIHQIFGAAFKSLFGGMSWFSQILIGTLLVWLGLNTKNGSISLTCLALGGV

MIFLSTAVSA

SEQ ID NO: 69
MR_766.ABI54475.1.Uganda/291-788 Flavivirus envelope glycoprotein E.
IRCIGVSNRDFVEGMSGGTWVDVVLEHGGCVTVMAQDKPTVDIELVTTTVSNMAEVRSYCYEASISDMASDSRCPTQGEAYL DKQSDTQYVCKRTLVDRGWGNGCGLFGKGSLVTCAKFTCSKKMTGKSIQPENLEYRIMLSVHGSQHSGMIVNDENRAKVEVT PNSPRAEATLGGFGSLGLDCEPRTGLDFSDLYYLTMNNKHWLVHKEWFHDIPLPWHAGADTGTPHWNNKEALVEFKDAHAK RQTVVVLGSQEGAVHTALAGALEAEMDGAKGRLFSGHLKCRLKMDKLRLKGVSYSLCTAAFTFTKVPAETLHGTVTVEVQYAG TDGPCKVPAQMAVDMQTLTPVGRLITANPVITESTENSKMMLELDPPFGDSYIVIGVGDKKITHHWHRSGSTIGKAFEATVRG AKRMAVLGDTAWDFGSVGGVFNSLGKGIHQIFGAAFKSLFGGMSWFSQILIGTLLVWLGLNTKNGSISLTCLALGGVMIFLSTA

VSA

SEQ ID NO: 70
5'-(dIdC)$_{13}$-3'
dIdCdIdCdIdCdIdCdIdCdIdCdIdCdIdCdIdCdIdCdIdCdIdCdIdC

SEQ ID NO: 71
KLK peptide
KLKLLLLLKLK

Provided below are examples of nucleic acid sequences of the genomes of Chikungunya, Japanese Encephalitis and yellow fever viruses that may be used in the methods, compositions, and/or vaccines described herein.

SEQ ID NO: 72
Chikungunya virus strain LR2006_OPY1, complete genome ACCESSION: DQ443544
ATGGCTGCGTGAGACACACGTAGCCTACCAGTTTCTTACTGCTCTACTCTGCAAAGCAAGAGATTAATAACCCATCATG

GATCCTGTGTACGTGGACATAGACGCTGACAGCGCCTTTTTGAAGGCCCTGCAACGTGCGTACCCCATGTTTGAGGTGG

AACCAAGGCAGGTCACACCGAATGACCATGCTAATGCTAGAGCGTTCTCGCATCTAGCTATAAAACTAATAGAGCAGG

AAATTGACCCCGACTCAACCATCCTGGATATCGGCAGTGCGCCAGCAAGGAGGATGATGTCGGACAGGAAGTACCACT

GCGTCTGCCCGATGCGCAGTGCGGAAGATCCCGAGAGACTCGCCAATTATGCGAGAAAGCTAGCATCTGCCGCAGGAA

AAGTCCTGGACAGAAACATCTCTGGAAAGATCGGGGACTTACAAGCAGTAATGGCCGTGCCAGACACGGAGACGCCA

-continued

ACATTCTGCTTACACACAGACGTCTCATGTAGACAGAGAGCAGACGTCGCTATATACCAAGACGTCTATGCTGTACACG

CACCCACGTCGCTATACCACCAGGCGATTAAAGGGGTCCGAGTGGCGTACTGGGTTGGGTTCGACACAACCCCGTTCAT

GTACAATGCCATGGCGGGTGCCTACCCCTCATACTCGACAAACTGGGCAGATGAGCAGGTACTGAAGGCTAAGAACAT

AGGATTATGTTCAACAGACCTGACGGAAGGTAGACGAGGCAAGTTGTCTATTATGAGAGGGAAAAAGCTAAAACCGT

GCGACCGTGTGCTGTTCTCAGTAGGGTCAACGCTCTACCCGGAAAGCCGCAAGCTACTTAAGAGCTGGCACCTGCCATC

GGTGTTCCATTTAAAGGGCAAACTCAGCTTCACATGCCGCTGTGATACAGTGGTTTCGTGTGAGGGCTACGTCGTTAAG

AGAATAACGATGAGCCCAGGCCTTTATGGAAAAACCACAGGGTATGCGGTAACCCACCACGCAGACGGATTCCTGATG

TGCAAGACTACCGACACGGTTGACGGCGAAAGARTGTCATTCTCGGTGTGCACATACGTGCCGGCGACCATTTGTGATC

AAATGACCGGCATCCTTGCTACAGAAGTCACGCCGGAGGATGCACAGAAGCTGTTGGTGGGGCTGAACCAGAGAATA

GTGGTTAACGGCAGAACGCAACGGAATACGAACACCATGAAAAATTATCTGCTTCCCGTGGTCGCCCAAGCCTTCAGTA

AGTGGGCAAAGGAGTGCCGGAAAGACATGGAAGATGAAAAACTCCTGGGGGTCAGAGAAAGAACACTGACCTGCTG

CTGTCTATGGGCATTCAAGAAGCAGAAAACACACACGGTCTACAAGAGGCCTGATACCCAGTCAATTCAGAAGGTTCA

GGCCGAGTTTGACAGCTTTGTGGTACCGAGTCTGTGGTCGTCCGGGTTGTCAATCCCTTTGAGGACTAGAATCAAATGG

TTGTTAAGCAAGGTGCCAAAAACCGACCTGATCCCATACAGCGGAGACGCCCGAGAAGCCCGGGACGCAGAAAAAGA

AGCAGAGGAAGAACGAGAAGCAGAACTGACTCGCGAAGCCCTACCACCTCTACAGGCAGCACAGGAAGATGTTCAGG

TCGAAATCGACGTGGAACAGCTTGAGGACAGAGCGGGCGCAGGAATAATAGAGACTCCGAGAGGAGCTATCAAAGTT

ACTGCCCAACCAACAGACCACGTCGTGGGAGAGTACCTGGTACTCTCCCCGCAGACCGTACTACGTAGCCAGAAGCTCA

GTCTGATTCACGCTTTGGCGGAGCAAGTGAAGACGTGCACGCACAACGGACGAGCAGGGAGGTATGCGGTCGAAGCG

TACGACGGCCGAGTCCTAGTGCCCTCAGGCTATGCAATCTCGCCTGAAGACTTCCAGAGTCTAAGCGAAAGCGCAACG

ATGGTGTATAACGAAAGAGAGTTCGTAAACAGAAAGCTACACCATATTGCGATGCACGGACCAGCCCTGAACACCGAC

GAAGAGTCGTATGAGCTGGTGAGGGCAGAGAGGACAGAACACGAGTACGTCTACGACGTGGATCAGAGAAGATGCT

GTAAGAAGGAAGAAGCCGCAGGACTGGTACTGGTGGGCGACTTGACTAATCCGCCCTACCACGAATTCGCATATGAAG

GGCTAAAAATCCGCCCTGCCTGCCCATACAAAATTGCAGTCATAGGAGTCTTCGGAGTACCGGGATCTGGCAAGTCAGC

TATTATCAAGAACCTAGTTACCAGGCAGGACCTGGTGACTAGCGGAAAGAAAGAAAACTGCCAAGAAATCACCACCGA

CGTGATGAGACAGAGAGGTCTAGAGATATCTGCACGTACGGTTGACTCGCTGCTCTTGAATGGATGCAACAGACCAGT

CGACGTGTTGTACGTAGACGAGGCGTTTGCGTGCCACTCTGGAACGCTACTTGCTTTGATCGCCTTGGTGAGACCAAGG

CAGAAAGTTGTACTTTGTGGTGACCCGAAGCAGTGCGGCTTCTTCAATATGATGCAGATGAAAGTCAACTATAATCACA

ACATCTGCACCCAAGTGTACCACAAAAGTATCTCCAGGCGGTGTACACTGCCTGTGACCGCCATTGTGTCATCGTTGCAT

TACGAAGGCAAAATGCGCACTACGAATGAGTACAACAAGCCGATTGTAGTGGACACTACAGGCTCAACAAAACCTGAC

CCTGGAGACCTCGTGTTAACGTGCTTCAGAGGGTGGGTTAAACAACTGCAAATTGACTATCGTGGATACGAGGTCATG

ACAGCAGCCGCATCCCAAGGGTTAACCAGAAAAGGAGTTTACGCAGTTAGACAAAAAGTTAATGAAAACCCGCTCTAT

GCATCAACGTCAGAGCACGTCAACGTACTCCTAACGCGTACGGAAGGTAAACTGGTATGGAAGACACTTTCCGGCGAC

CCGTGGATAAAGACGCTGCAGAACCCACCGAAAGGAAACTTCAAAGCAACTATTAAGGAGTGGGAGGTGGAGCATGC

ATCAATAATGGCGGGCATCTGCAGTCACCAAATGACCTTCGATACATTCCAAAATAAAGCCAACGTTTGTTGGGCTAAG

AGCTTGGTCCCTATCCTCGAAACAGCGGGGATAAAACTAAATGATAGGCAGTGGTCTCAGATAATTCAAGCCTTCAAAG

AAGACAAAGCATACTCACCTGAAGTAGCCCTGAATGAAATATGTACGCGCATGTATGGGGTGGATCTAGACAGCGGGC

TATTTTCTAAACCGTTGGTGTCTGTGTATTACGCGGATAACCACTGGGATAATAGGCCTGGAGGGAAAATGTTCGGATT

TAACCCCGAGGCAGCATCCATTCTAGAAAGAAAGTATCCATTCACAAAAGGGAAGTGGAACATCAACAAGCAGATCTG

CGTGACTACCAGGAGGATAGAAGACTTTAACCCTACCACCAACATCATACCGGCCAACAGGAGACTACCACACTCATTA

GTGGCCGAACACCGCCCAGTAAAAGGGGAAAGAATGGAATGGCTGGTTAACAAGATAAACGGCCACCACGTGCTCCT

GGTCAGTGGCTATAACCTTGCACTGCCTACTAAGAGAGTCACTTGGGTAGCGCCGTTAGGTGTCCGCGGAGCGGACTA

-continued

CACATACAACCTAGAGTTGGGTCTGCCAGCAACGCTTGGTAGGTATGACCTAGTGGTCATAAACATCCACACACCTTTTC

GCATACACCATTACCAACAGTGCGTCGACCACGCAATGAAACTGCAAATGCTCGGGGGTGACTCATTGAGACTGCTCAA

ACCGGGCGGCTCTCTATTGATCAGAGCATATGGTTACGCAGATAGAACCAGTGAACGAGTCATCTGCGTATTGGGACG

CAAGTTTAGATCGTCTAGAGCGTTGAAACCACCATGTGTCACCAGCAACACTGAGATGTTTTTCCTATTCAGCAACTTTG

ACAATGGCAGAAGGAATTTCACAACTCATGTCATGAACAATCAACTGAATGCAGCCTTCGTAGGACAGGTCACCCGAG

CAGGATGTGCACCGTCGTACCGGGTAAAACGCATGGACATCGCGAAGAACGATGAAGAGTGCGTAGTCAACGCCGCT

AACCCTCGCGGGTTACCGGGTGRCGGTGTTTGCAAGGCAGTATACAAAAAATGGCCGGAGTCCTTTAAGAACAGTGCA

ACACCAGTGGGAACCGCAAAAACAGTTATGTGCGGTACGTATCCAGTAATCCACGCTGTTGGACCAAACTTCTCTAATT

ATTCGGAGTCTGAAGGGGACCGGGAATTGGCAGCTGCCTATCGAGAAGTCGCAAAGGAAGTAACTAGGCTGGGAGTA

AATAGTGTAGCTATACCTCTCCTCTCCACAGGTGTATACTCAGGAGGGAAAGACAGGCTGACCCAGTCACTGAACCACC

TCTTTACAGCCATGGACTCGACGGATGCAGACGTGGTCATCTACTGCCGCGACAAAGAATGGGAGAAGAAAATATCTG

AGGCCATACAGATGCGGACCCAAGTAGAGCTGCTGGATGAGCACATCTCCATAGACTGCGATATTGTTCGCGTGCACC

CTGACAGCAGCTTGGCAGGCAGAAAAGGATACAGCACCACGGAAGGCGCACTGTACTCATATCTAGAAGGGACCCGTT

TTCATCAGACGGCTGTGGATATGGCGGAGATACATACTATGTGGCCAAAGCAAACAGAGGCCAATGAGCAAGTCTGCC

TATATGCCCTGGGGGAAAGTATTGAATCGATCAGGCAGAAATGCCCGGTGGATGATGCAGACGCATCATCTCCCCCCA

AAACTGTCCCGTGCCTTTGCCGTTACGCTATGACTCCAGAACGCGTCACCCGGCTTCGCATGAACCACGTCACAAGCATA

ATTGTGTGTTCTTCGTTTCCCCTCCCAAAGTACAAAATAGAAGGAGTGCAAAAAGTCAAATGCTCTAAGGTAATGCTATT

TGACCACAACGTGCCATCGCGCGTAAGTCCAAGGGAATATAKATCTTCCCAGGAGTCTGCACAGGAGGCGAGTACAAT

CACGTCACTGACGCATAGTCAATTCGACCTAAGCGTTGATGGCGAGATACTGCCCGTCCCGTCAGACCTGGATGCTGAC

GCCCCAGCCCTAGAACCAGCACTAGACGACGGGGCGACACACACGCTGCCATCCACAACCGGAAACCTTGCGGCCGTG

TCTGATTGGGTAATGAGCACCGTACCTGTCGCGCCGCCCAGAAGAAGGCGAGGGAGAAACCTGACTGTGACATGTGAC

GAGAGAGAAGGGAATATAACACCCATGGCTAGCGTCCGATTCTTTAGGGCAGAGCTGTGTCCGGTCGTACAAGAAACA

GCGGAGACGCGTGACACAGCAATGTCTCTTCAGGCACCACCGAGTACCGCCACGGAACCGAATCATCCGCCGATCTCCT

TCGGAGCATCAAGCGAGACGTTCCCCATTACATTTGGGGACTTCAACGAAGGAGAAATCGAAAGCTTGTCTTCTGAGCT

ACTAACTTTCGGAGACTTCTTACCAGGAGAAGTGGATGACTTGACAGACAGCGACTGGTCCACGTGCTCAGACACGGA

CGACGAGTTATGACTAGACAGGGCAGGTGGGTATATATTCTCGTCGGACACCGGTCCAGGTCATTTACAACAGAAGTC

AGTACGCCAGTCAGTGCTGCCGGTGAACACCCTGGAGGAAGTCCACGAGGAGAAGTGTTACCCACCTAAGCTGGATGA

AGCAAAGGAGCAACTATTACTTAAGAAACTCCAGGAGAGTGCATCCATGGCCAACAGAAGCAGGTATCAGTCGCGCAA

AGTAGAAAACATGAAAGCAGCAATCATCCAGAGACTAAAGAGAGGCTGTAGACTATACTTAATGTCAGAGACCCCAAA

AGTCCCTACTTACCGGACTACATATCCGGCGCCTGTGTACTCGCCTCCGATCAACGTCCGATTGTCCAATCCCGAGTCCG

CAGTGGCAGCATGCAATGAGTTCTTAGCTAGAAACTATCCAACTGTCTCATCATACCAAATTACCGACGAGTATGATGC

ATATCTAGACATGGTGGACGGGTCGGAGAGTTGCCTGGACCGAGCGACATTCAATCCGTCAAAACTCAGGAGCTACCC

GAAACAGCACGCTTACCACGCGCCCTCCATCAGAAGCGCTGTACCGTCCCCATTCCAGAACACACTACAGAATGTACTG

GCAGCAGCCACGAAAAGAAACTGCAACGTCACACAGATGAGGGAATTACCCACTTTGGACTCAGCAGTATTCAACGTG

GAGTGTTTCAAAAAATTCGCATGCAACCAAGAATACTGGGAAGAATTTGCTGCCAGCCCTATTAGGATAACAACTGAGA

ATTTAGCAACCTATGTTACTAAACTAAAAGGGCCAAAAGCAGCAGCGCTATTCGCAAAAACCCATAATCTACTGCCACT

ACAGGAAGTACCAATGGATAGGTTCACAGTAGATATGAAAAGGGACGTAAAGGTGACTCCTGGTACAAAGCATACAG

AGGAAAGACCTAAGGTGCAGGTTATACAGGCGGCTGAACCCTTGGCGACAGCATACCTATGTGGGATTCACAGAGAG

CTGGTTAGGAGGCTGAACGCCGTCCTCCTACCCAATGTACATACACTATTTGACATGTCTGCCGAGGATTTCGATGCCAT

CATAGCCGCACACTTTAAGCCAGGAGACACTGTTTTGGAAACGGACATAGCCTCCTTTGATAAGAGCCAAGATGATTCA

-continued

CTTGCGCTTACTGCTTTGATGCTGTTAGAGGATTTAGGGGTGGATCACTCCCTGCTGGACTTGATAGAGGCTGCTTTCG

GAGAGATTTCCAGCTGTCACCTACCGACAGGTACGCGCTTCAAGTTCGGCGCCATGATGAAATCAGGTATGTTCCTAAC

TCTGTTCGTCAACACATTGTTAAACATCACCATCGCCAGCCGAGTGCTGGAAGATCGTCTGACAAAATCCGCGTGCGCG

GCCTTCATCGGCGACGACAACATAATACATGGAGTCGTCTCCGATGAATTGATGGCAGCCAGATGTGCCACTTGGATGA

ACATGGAAGTGAAGATCATAGATGCAGTTGTATCCTTGAAAGCCCCTTACTTTTGTGGAGGGTTTATACTGCACGATAC

TGTGACAGGAACAGCTTGCAGAGTGGCAGACCCGCTAAAAAGGCTTTTTAAACTGGGCAAACCGCTAGCGGCAGGTG

ACGAACAAGATGAAGATAGAAGACGAGCGCTGGCTGACGAAGTGATCAGATGGCAACGAACAGGGCTAATTGATGAG

CTGGAGAAAGCGGTATACTCTAGGTACGAAGTGCAGGGTATATCAGTTGTGGTAATGTCCATGGCCACCTTTGCAAGCT

CCAGATCCAACTTCGAGAAGCTCAGAGGACCCGTCATAACTTTGTACGGCGGTCCTAAATAGGTACGCACTACAGCTAC

CTATTTTGCAGAAGCCGACAGCAAGTATCTAAACACTAATCAGCTACAATGGAGTTCATCCCAACCCAAACTTTTTACAA

TAGGAGGTACCAGCCTCGACCCTGGACTCCGCGCCCTACTATCCAAGTCATCAGGCCCAGACCGCGCCCTCAGAGGCAA

GCTGGGCAACTTGCCCAGCTGATCTCAGCAGTTAATAAACTGACAATGCGCGCGGTACCCCAACAGAAGCCACGCAGG

AATCGGAAGAATAAGAAGCAAAAGCAAAAACAACAGGCGCCACAAAACAACACAAATCAAAAGAAGCAGCCACCTAA

AAAGAAACCGGCTCAAAAGAAAAAGAAGCCGGGCCGCAGAGAGAGGATGTGCATGAAAATCGAAAATGATTGTATTT

TCGAAGTCAAGCACGAAGGTAAGGTAACAGGTTACGCGTGCCTGGTGGGGGACAAAGTAATGAAACCAGCACACGTA

AAGGGGACCATCGATAACGCGGACCTGGCCAAACTGGCCTTTAAGCGGTCATCTAAGTATGACCTTGAATGCGCGCAG

ATACCCGTGCACATGAAGTCCGACGCTTCGAAGTTCACCCATGAGAAACCGGAGGGGTACTACAACTGGCACCACGGA

GCAGTACAGTACTCAGGAGGCCGGTTCACCATCCCTACAGGTGCTGGCAAACCAGGGGACAGCGGCAGACCGATCTTC

GACAACAAGGGACGCGTGGTGGCCATAGTCTTAGGAGGAGCTAATGAAGGAGCCCGTACAGCCCTCTCGGTGGTGAC

CTGGAATAAAGACATTGTCACTAAAATCACCCCCGAGGGGGCCGAAGAGTGGAGTCTTGCCATCCCAGTTATGTGCCT

GTTGGCAAACACCACGTTCCCCTGCTCCCAGCCCCCTTGCACGCCCTGCTGCTACGAAAAGGAACCGGAGGAAACCCTA

CGCATGCTTGAGGACAACGTCATGAGACCTGGGTACTATCAGCTGCTACAAGCATCCTTAACATGTTCTCCCCACCGCCA

GCGACGCAGCACCAAGGACAACTTCAATGTCTATAAAGCCACAAGACCATACTTAGCTCACTGTCCCGACTGTGGAGAA

GGGCACTCGTGCCATAGTCCCGTAGCACTAGAACGCATCAGAAATGAAGCGACAGACGGGACGCTGAAAATCCAGGT

CTCCTTGCAAATCGGAATAAAGACGGATGACAGCCACGATTGGACCAAGCTGCGTTATATGGACAACCACATGCCAGC

AGACGCAGAGAGGGCGGGGCTATTTGTAAGAACATCAGCACCGTGTACGATTACTGGAACAATGGGACACTTCATCCT

GGCCCGATGTCCAAAAGGGGAAACTCTGACGGTGGGATTCACTGACAGTAGGAAGATTAGTCACTCATGTACGCACCC

ATTTCACCACGACCCTCCTGTGATAGGTCGGGAAAAATTCCATTCCCGACCGCAGCACGGTAAAGAGCTACCTTGCAGC

ACGTACGTGCAGAGCACCGCCGCAACTACCGAGGAGATAGAGGTACACATGCCCCCAGACACCCCTGATCGCACATTA

ATGTCACAACAGTCCGGCAACGTAAAGATCACAGTCAATGGCCAGACGGTGCGGTACAAGTGTAATTGCGGTGGCTCA

AATGAAGGACTAACAACTACAGACAAAGTGATTAATAACTGCAAGGTTGATCAATGTCATGCCGCGGTCACCAATCACA

AAAAGTGGCAGTATAACTCCCCTCTGGTCCCGCGTAATGCTGAACTTGGGGACCGAAAAGGAAAAATTCACATCCCGTT

TCCGCTGGCAAATGTAACATGCAGGGTGCCTAAAGCAAGGAACCCCACCGTGACGTACGGGAAAAACCAAGTCATCAT

GCTACTGTATCCTGACCACCCAACACTCCTGTCCTACCGGAATATGGGAGAAGAACCAAACTATCAAGAAGAGTGGGT

GATGCATAAGAAGGAAGTCGTGCTAACCGTGCCGACTGAAGGGCTCGAGGTCACGTGGGGCAACAACGAGCCGTATA

AGTATTGGCCGCAGTTATCTACAAACGGTACAGCCCATGGCCACCCGCATGAGATAATTCTGTATTATTATGAGCTGTAC

CCCACTATGACTGTAGTAGTTGTGTCAGTGGCCACGTTCATACTCCTGTCGATGGTGGGTATGGCAGCGGGGATGTGCA

TGTGTGCACGACGCAGATGCATCACACCGTATGAACTGACACCAGGAGCTACCGTCCCTTTCCTGCTTAGCCTAATATGC

TGCATCAGAACAGCTAAAGCGGCCACATACCAAGAGGCTGCGATATACCTGTGGAACGAGCAGCAACCTTTGTTTTGG

CTACAAGCCCTTATTCCGCTGGCAGCCCTGATTGTTCTATGCAACTGTCTGAGACTCTTACCATGCTGCTGTAAAACGTT

GGCTTTTTTAGCCGTAATGAGCGTCGGTGCCCACACTGTGAGCGCGTACGAACACGTAACAGTGATCCCGAACACGGT

-continued

GGGAGTACCGTATAAGACTCTAGTCAATAGACCTGGCTACAGCCCCATGGTATTGGAGATGGAACTACTGTCAGTCACT

TTGGAGCCAACACTATCGCTTGATTACATCACGTGCGAGTACAAAACCGTCATCCCGTCTCCGTACGTGAAGTGCTGCG

GTACAGCAGAGTGCAAGGACAAAAACCTACCTGACTACAGCTGTAAGGTCTTCACCGGCGTCTACCCATTTATGTGGGG

CGGCGCCTACTGCTTCTGCGACGCTGAAAACACGCAGTTGAGCGAAGCACACGTGGAGAAGTCCGAATCATGCAAAAC

AGAATTTGCATCAGCATACAGGGCTCATACCGCATCTGCATCAGCTAAGCTCCGCGTCCTTTACCAAGGAAATAACATC

ACTGTAACTGCCTATGCAAACGGCGACCATGCCGTCACAGTTAAGGACGCCAAATTCATTGTGGGGCCAATGTCTTCAG

CCTGGACACCTTTCGACAACAAAATTGTGGTGTACAAAGGTGACGTCTATAACATGGACTACCCGCCCTTTGGCGCAGG

AAGACCAGGACAATTTGGCGATATCCAAAGTCGCACACCTGAGAGTAAAGACGTCTATGCTAATACACAACTGGTACT

GCAGAGACCGGCTGTGGGTACGGTACACGTGCCATACTCTCAGGCACCATCTGGCTTTAAGTATTGGCTAAAAGAACG

CGGGGCGTCGCTGCAGCACACAGCACCATTTGGCTGCCAAATAGCAACAAACCCGGTAAGAGCGGTGAACTGCGCCGT

AGGGAACATGCCCATCTCCATCGACATACCGGAAGCGGCCTTCACTAGGGTCGTCGACGCGCCCTCTTTAACGGACATG

TCGTGCGAGGTACCAGCCTGCACCCATTCCTCAGACTTTGGGGGCGTCGCCATTATTAAATATGCAGCCAGCAAGAAAG

GCAAGTGTGCGGTGCATTCGATGACTAACGCCGTCACTATTCGGGAAGCTGAGATAGAAGTTGAAGGGAATTCTCAGC

TGCAAATCTCTTTCTCGACGGCCTTAGCCAGCGCCGAATTCCGCGTACAAGTCTGTTCTACACAAGTACACTGTGCAGCC

GAGTGCCACCCCCCGAAGGACCACATAGTCAACTACCCGGCGTCACATACCACCCTCGGGGTCCAGGACATCTCCGCTA

CGGCGATGTCATGGGTGCAGAAGATCACGGGAGGTGTGGGACTGGTTGTTGCTGTTGCCGCACTGATTCTAATCGTGG

TGCTATGCGTGTCGTTCAGCAGGCACTAACTTGACAATTAAGTATGAAGGTATATGTGTCCCCTAAGAGACACACTGTA

CATAGCAAATAATCTATAGATCAAAGGGCTACGCAACCCCTGAATAGTAACAAAATACAAAATCACTAAAAATTATAAA

AACAGAAAAATACATAAATAGGTATACGTGTCCCCTAAGAGACACATTGTATGTAGGTGATAAGTATAGATCAAAGGG

CCGAATAACCCCTGAATAGTAACAAAATATGAAAATCAATAAAAATCATAAAATAGAAAAACCATAAACAGAAGTAGTT

CAAAGGGCTATAAAACCCCTGAATAGTAACAAAACATAAAATTAATAAAAATCAAATGAATACCATAATTGGCAAACGG

AAGAGATGTAGGTACTTAAGCTTCCTAAAAGCAGCCGAACTCACTTTGAGAAGTAGGCATAGCATACCGAACTCTTCCA

CGATTCTCCGAACCCACAGGGACGTAGGAGATGTTATTTTGTTTTTAATATTTCAAAAAAAAAAAAAAAAAAAAAAAAA

AAAA

SEQ ID NO: 73

Japanese encephalitis virus strain SA14-14-2, complete genome, ACCESSION: KC517497

TTTAAACAGTTTTTTAGAACGGAAGATAACCATGACTAAAAAACCAGGAGGGCCCGGTAAAAACCGGGCTATCAATAT

GCTGAAACGCGGCCTACCCCGCGTATTCCCACTAGTGGGAGTGAAGAGGGTAGTAATGAGCTTGTTGGACGGCAGAG

GGCCAGTACGTTTCGTGCTGGCTCTTATCACGTTCTTCAAGTTTACAGCATTAGCCCCGACCAAGGCGCTTTTAGGCCGA

TGGAAAGCAGTGGAAAAGAGTGTGGCAATGAAACATCTTACTAGTTTCAAACGAGAACTTGGAACACTCATTGACGCC

GTGAACAAGCGGGGCAGAAAGCAAAACAAAAGAGGAGGAAATGAAGGCTCAATCATGTGGCTCGCGAGCTTGGCAG

TTGTCATAGCTTGTGCAGGAGCCATGAAGTTGTCGAATTTCCAGGGGAAGCTTTTGATGACCATCAACAACACGGACAT

TGCAGACGTTATCGTGATTCCCACCTCAAAAGGAGAGAACAGATGCTGGGTCCGGGCAATCGACGTCGGCTACATGTG

TGAGGACACTATCACGTACGAATGTCCTAAGCTTACCATGGGCAATGATCCAGAGGATGTGGATTGCTGGTGTGACAA

CCAAGAAGTCTACGTCCAATATGGACGGTGCACGCGGACCAGGCATTCCAAGCGAAGCAGGAGATCCGTGTCGGTCCA

AACACATGGGGAGAGTTCACTAGTGAATAAAAAAGAGGCTTGGCTGGATTCAACGAAAGCCACACGATATCTCATGAA

AACTGAGAACTGGATCATAAGGAATCCTGGCTATGCTTTCCTGGCGGCGGTACTTGGCTGGATGCTTGGCAGTAACAAC

GGTCAACGCGTGGTATTTACCATCCTCCTGCTGTTGGTCGCTCCGGCTTACAGTTTTAATTGTCTGGGAATGGGCAATCG

TGACTTCATAGAAGGAGCCAGTGGAGCCACTTGGGTGGACTTGGTGCTAGAAGGAGATAGCTGCTTGACAATCATGGC

AAACGACAAACCAACATTGGACGTCCGCATGATTAACATCGAAGCTAGCCAACTTGCTGAGGTCAGAAGTTACTGCTAT

CATGCTTCAGTCACTGACATCTCGACGGTGGCTCGGTGCCCCACGACTGGAGAAGCCCACAACGAGAAGCGAGCTGAT

-continued

AGTAGCTATGTGTGCAAACAAGGCTTCACTGACCGTGGGTGGGGCAACGGATGTGGACTTTTCGGGAAGGGAAGCAT

TGACACATGTGCAAAATTCTCCTGCACCAGTAAAGCGATTGGGAGAACAATCCAGCCAGAAAACATCAAATACGAAGTT

GGCATTTTTGTGCATGGAACCACCACTTCGGAAAACCATGGGAATTATTCAGCGCAAGTTGGGGCGTCCCAGGCGGCA

AAGTTTACAGTAACACCCAATGCTCCTTCGATAACCCTCAAACTTGGTGACTACGGAGAAGTCACACTGGACTGTGAGC

CAAGGAGTGGACTGAACACTGAAGCGTTTTACGTCATGACCGTGGGGTCAAAGTCATTTCTGGTCCATAGGGAGTGGT

TTCATGACCTCGCTCTCCCCTGGACGTCCCCTTCGAGCACAGCGTGGAGAAACAGAGAACTCCTCATGGAATTTGAAGG

GGCGCACGCCACAAAACAGTCCGTTGTTGCTCTTGGGTCACAGGAAGGAGGCCTCCATCAGGCGTTGGCAGGAGCCAT

CGTGGTGGAGTACTCAAGCTCAGTGAAGTTAACATCAGGCCACCTGAAATGTAGGCTGAAAATGGACAAACTGGCTCT

GAAAGGCACAACCTATGGCATGTGTACAGAAAAATTCTCGTTCGCGAAAAATCCGGCGGACACTGGTCACGGAACAGT

TGTCATTGAACTCTCCTACTCTGGGAGTGATGGCCCCTGCAAAATTCCGATTGTTTCCGTTGCGAGCCTCAATGACATGA

CCCCCGTTGGGCGGCTGGTGACAGTGAACCCCTTCGTCGCGACTTCCAGTGCCAACTCAAAGGTGCTGGTCGAGATGG

AACCCCCCTTCGGAGACTCCTACATCGTAGTTGGAAGGGGAGACAAGCAGATCAACCACCATTGGCACAAAGCTGGAA

GCACGCTGGGCAAGGCCTTTTCAACAACTTTGAAGGGAGCTCAAAGACTGGCAGCGTTGGGCGACACAGCCTGGGACT

TTGGCTCTATTGGAGGGGTCTTCAACTCCATAGGAAAAGCCGTTCACCAAGTGTTTGGTGGTGCCTTCAGAACACTCTTT

GGGGGAATGTCTTGGATCACACAAGGGCTAATGGGTGCCCTACTGCTCTGGATGGGCGTCAACGCACGAGACCGATCA

ATTGCTTTGGCCTTCTTAGCCACAGGGGGTGTGCTCGTGTTCTTAGCGACCAATGTGCATGCTGACACTGGATGTGCCA

TTGACATCACAAGAAAAGAGATGAGATGTGGAAGTGGCATCTTCGTGCACAACGACGTGGAAGCCTGGGTGGATAGG

TATAAATATTTGCCAGAAACGCCCAGATCCCTAGCGAAGATCGTCCACAAAGCGCACAAGGAAGGCGTGTGCGGAGTC

AGATCTGTCACTAGACTGGAGCACCAAATGTGGGAAGCCGTACGGGACGAATTGAACGTCCTGCTCAAAGAGAATGCA

GTGGACCTCAGTGTGGTTGTGAACAAGCCCGTGGGAAGATATCGCTCAGCCCCTAAACGCCTATCCATGACGCAAGAG

AAGTTTGAAATGGGCTGGAAAGCATGGGGAAAAAGCATTCTCTTTGCCCCGGAATTGGCTAACTCCACATTTGTCGTAG

ATGGACCTGAGACAAAGGAATGCCCTGATGAGCACAGAGCTTGGAACAGCATGCAAATCGAAGACTTCGGCTTTGGCA

TCACATCAACCCGTGTGTGGCTGAAAATTAGAGAGGAGAGCACTGACGAGTGTGATGGAGCGATCATAGGCACGGCT

GTCAAAGGACATGTGGCAGTCCATAGTGACTTGTCGTACTGGATTGAGAGTCGCTACAACGACACATGGAAACTTGAG

AGGGCAGTCTTTGGAGAGGTCAAATCTTGCACTTGGCCAGAGACACACACCCTTTGGGGAGATGATGTTGAGGAAAGT

GAACTCATCATTCCGCACACCATAGCCGGACCAAAAAGCAAGCACAATCGGAGGGAAGGGTATAAGACACAAAACCA

GGGACCTTGGGATGAGAATGGCATAGTCTTGGACTTTGATTATTGCCCAGGGACAAAAGTCACCATTACAGAGGATTG

TGGCAAGAGAGGCCCTTCGGTCAGAACCACTACTGACAGTGGAAAGTTGATCACTGACTGGTGCTGTCGCAGTTGCTC

CCTTCCGCCCCTACGATTCCGGACAGAAAATGGCTGCTGGTACGGAATGGAAATCAGACCTGTTAGGCATGATGAAAC

AACACTCGTCAGATCACAGGTTGATGCTTTCAATGGTGAAATGGTTGACCCTTTTCAGCTGGGCCTTCTGGTGATGTTTC

TGGCCACCCAGGAGGTCCTTCGCAAGAGGTGGACGGCCAGATTGACCATTCCTGCGGTTTTGGGGGCCCTACTTGTGC

TGATGCTTGGGGGCATCACTTACACTGATTTGGCGAGGTATGTGGTGCTAGTCGCTGCTGCTTTCGCAGAGGCCAACAG

TGGAGGAGACGTCCTGCACCTTGCTTTGATTGCCGTTTTTAAGATCCAACCAGCATTTCTAGTGATGAACATGCTTAGCA

CGAGATGGACGAACCAAGAAAACGTGGTTCTGGTCCTAGGGGCTGCCTTTTTCCAATTGGCCTCAGTAGATCTGCAAAT

AGGAGTCCACGGAATCCTGAATGCCGCCGCTATAGCATGGATGATTGTCCGAGCGATCACCTTCCCCACAACCTCCTCC

GTCACCATGCCAGTCTTAGCGCTTCTAACTCCGGGGATGAGGGCTCTATACCTAGACACTTACAGAATCATCCTCCTCGT

CATAGGGATTTGCTCCCTGCTGCACGAGAGGAAAAAGACCATGGCAAAAAAGAAAGGAGCTGTACTCTTGGGCTTAGC

GCTCACATCCACTGGATGGTTCTCGCCCACCACTATAGCTGCCGGACTAATGGTCTGCAACCCAAACAAGAAGAGAGG

GTGGCCAGCTACTGAGTTTTTGTCGGCAGTTGGATTGATGTTTGCCATCGTAGGTGGTTTGGCCGAGTTGGATATTGAA

TCCATGTCAATACCCTTCATGCTGGCAGGTCTCATGGCAGTGTCCTACGTGGTGTCAGGAAAAGCAACAGATATGTGGC

TTGAACGGGCCGCCGACATCAGCTGGGAGATGGATGCTGCAATCACAGGAAGCAGTCGGAGGCTGGATGTGAAACTG

-continued

GATGATGACGGAGATTTTCACTTGATTGATGATCCCGGTGTTCCATGGAAGGTCTGGGTCCTGCGCATGTCTTGCATTG

GCTTAGCCGCCCTCACGCCTTGGGCCATCGTTCCCGCCGCTTTCGGTTATTGGCTCACTTTAAAAACAACAAAAAGAGG

GGGCGTGTTTTGGGACACGCCATCCCCAAAACCTTGCTCAAAAGGAGACACCACTACAGGAGTCTACCGAATTATGGCT

AGAGGGATTCTTGGCACTTACCAGGCCGGCGTCGGAGTCATGTACGAGAATGTTTTCCACACACTATGGCACACAACTA

GAGGAGCAGCCATTATGAGTGGAGAAGGAAAATTGACGCCATACTGGGGTAGTGTGAGAGAAGACCGCATAGCTTAC

GGAGGCCCATGGAGGTTTGACCGAAAATGGAATGGAACAGATGACGTGCAAGTGATCGTGGTAGAACCGGGGAAGG

CTGCAGTAAACATCCAGACAAAACCAGGAGTGTTTCGGACTCCCTTCGGGGAGGTTGGGGCTGTTAGTCTGGATTACCC

GCGAGGAACATCCGGCTCACCCATTCTGGATTCCAATGGAGACATTATAGGCCTATACGGCAATGGAGTTGAGCTTGG

CGATGGCTCATACGTCAGCGCCATCGTGCAGGGTGACCGTCAGGAGGAACCAGTCCCAGAAGCTTACACCCCAAACAT

GTTGAGAAAGAGACAGATGACTGTGCTAGATTTGCACCCTGGTTCAGGGAAAACCAGGAAAATTCTGCCACAAATAAT

TAAGGACGCTATCCAGCAGCGCCTAAGAACAGCTGTGTTGGCACCGACGCGGGTGGTAGCAGCAGAAATGGCAGAAG

CTTTGAGAGGGCTCCCAGTACGATATCAAACTTCAGCAGTGCAGAGAGAGCACCAAGGGAATGAAATAGTGGATGTG

ATGTGCCACGCCACTCTGACCCATAGACTGATGTCACCGAACAGAGTGCCCAACTACAACCTATTTGTCATGGATGAAG

CTCATTTCACCGACCCAGCCAGTATAGCCGCACGAGGATACATTGCTACCAAGGTGGAATTAGGGGAGGCAGCAGCCA

TCTTTATGACAGCGACCCCGCCTGGAACCACGGATCCTTTTCCTGACTCAAATGCCCCAATCCATGATTTGCAAGATGAG

ATACCAGACAGGGCATGGAGCAGTGGATACGAATGGATCACAGAATATGCGGGTAAAACCGTGTGGTTTGTGGCGAG

CGTAAAAATGGGGAATGAGATTGCAATGTGCCTCCAAAGAGCGGGGAAAAAGGTCATCCAACTCAACCGCAAGTCCTA

TGACACAGAATACCCAAAATGTAAGAATGGAGACTGGGATTTTGTCATTACCACCGACATCTCTGAAATGGGGGCCAA

CTTCGGTGCGAGCAGGGTCATCGACTGTAGAAAGAGCGTGAAACCCACCATCTTAGAAGAGGGAGAAGGCAGAGTCA

TCCTCGGAAACCCATCTCCCATAACCAGTGCAAGCGCAGCTCAACGGAGGGGCAGAGTAGGCAGAAACCCCAACCAAG

TTGGAGATGAATACCACTATGGGGGGGCTACCAGTGAAGATGACAGTAACCTAGCCCATTGGACAGAGGCAAAGATC

ATGTTAGACAACATACACATGCCCAATGGACTGGTGGCCCAGCTCTATGGACCAGAGAGGGAAAAGGCTTTCACAATG

GATGGCGAATACCGTCTCAGAGGTGAAGAAAAGAAAAACTTCTTAGAGCTGCTTAGGACGGCTGACCTCCCGGTGTGG

CTGGCCTACAAGGTGGCGTCCAATGGCATTCAGTACACCGACAGAAAGTGGTGTTTTGATGGGCCGCGTACGAATGCC

ATACTGGAGGACAACACCGAGGTAGAGATAGTCACCCGGATGGGTGAGAGGAAAATCCTCAAGCCGAGATGGCTTGA

TGCAAGAGTTTATGCAGATCACCAAGCCCTCAAGTGGTTCAAAGACTTTGCAGCAGGGAAGAGATCAGCCGTTAGCTTC

ATAGAGGTGCTCGGTCGCATGCCTGAGCATTTCATGGGAAAGACGCGGGAAGCTTTAGACACCATGTACTTGGTTGCA

ACGGCTGAGAAAGGTGGGAAAGCACACCGAATGGCTCTCGAAGAGCTGCCAGATGCACTGGAAACCATCACACTTATT

GTCGCCATTACTGTGATGACAGGAGGATTCTTCCTACTAATGATGCAGCGAAAGGGTATAGGGAAGATGGGTCTTGGA

GCTCTAGTGCTCACGCTAGCTACCTTCTTCCTGTGGGCGGCAGAGGTTCCTGGAACCAAAATAGCAGGGACCCTGCTGA

TCGCCCTGCTGCTGATGGTGGTTCTCATCCCAGAACCGGAAAAACAGAGGTCACAGACAGATAACCAACTGGCGGTGT

TTCTCATCTGTGTCTTGACCGTGGTTGGAGTGGTGGCAGCAAACGAGTACGGGATGCTAGAAAAAACCAAAGCAGATC

TCAAGAGCATGTTTGGCGGAAAGACGCAGGCATCAGGACTGACTGGATTGCCAAGCATGGCACTGGACCTGCGTCCAG

CCACAGCCTGGGCACTGTATGGGGGGAGCACAGTCGTGCTAACCCCTCTTCTGAAGCACCTGATCACGTCGGAATACGT

CACCACATCGCTAGCCTCAATTAACTCACAAGCTGGCTCATTATTCGTCTTGCCACGAGGCGTGCCTTTTACCGACCTAG

ACTTGACCGTTGGCCTCGTCTTCCTTGGCTGTTGGGGTCAAATCACCCTCACAACGTTTCTGACAGCCATGGTTCTGGCG

ACACTTCACTATGGGTACATGCTCCCTGGATGGCAAGCAGAAGCACTCAGGGCTGCCCAGAGAAGGACAGCGGCTGG

AATAATGAAGAATGCCGTTGTTGACGGAATGGTCGCCACTGATGTGCCTGAACTGGAAAGGACTACTCCTCTGATGCA

AAAGAAAGTCGGACAGGTGCTCCTCATAGGGGTAAGCGTGGCAGCGTTCCTCGTCAACCCTAATGTCACCACTGTGAG

AGAAGCAGGGGTGTTGGTGACGGCGGCTACGCTTACTTTGTGGGACAATGGAGCCAGTGCCGTTTGGAATTCCACCAC

-continued

AGCCACGGGACTCTGCCATGTCATGCGAGGTAGCTACCTGGCTGGAGGCTCCATTGCTTGGACTCTCATCAAGAACGCT

GATAAGCCCTCCTTGAAAAGGGGAAGGCCTGGGGGCAGGACGCTAGGGGAGCAGTGGAAGGAAAAACTAAATGCCA

TGAGCAGAGAAGAGTTTTTTAAATACCGGAGAGAGGCCATAATCGAGGTGGACCGCACTGAAGCACGCAGGGCCAGA

CGTGAAAATAACATAGTGGGAGGACATCCGGTTTCGCGAGGCTCAGCAAAACTCCGTTGGCTCGTGGAGAAAGGATTT

GTCTCGCCAATAGGAAAAGTCATTGATCTAGGGTGTGGGCGTGGAGGATGGAGCTACTACGCAGCAACCCTGAAGAA

GGTCCAGGAAGTCAGAGGATACACGAAAGGTGGGGCGGGACATGAAGAACCGATGCTCATGCAGAGCTACGGCTGG

AACCTGGTCTCCCTGAAGAGTGGAGTGGACGTGTTTTACAAACCTTCAGAGCCCAGTGACACCCTGTTCTGTGACATAG

GGGAATCCTCCCCAAGTCCAGAAGTAGAAGAACAACGCACACTACGCGTCCTAGAGATGACATCTGACTGGTTGCACC

GAGGACCTAGAGAGTTCTGCATTAAAGTTCTCTGCCCTTACATGCCCAAGGTTATAGAAAAAATGGAAGTTCTGCAGCG

CCGCTTCGGAGGTGGGCTAGTGCGTCTCCCCCTGTCCCGAAACTCCAATCACGAGATGTATTGGGTTAGTGGAGCCGCT

GGCAATGTGGTGCACGCTGTGAACATGACCAGCCAGGTACTACTGGGGCGAATGGATCGCACAGTGTGGAGAGGGCC

AAAGTATGAGGAAGATGTCAACCTAGGGAGCGGAACAAGAGCCGTGGGAAAGGGAGAAGTCCATAGCAATCAGGAG

AAAATCAAGAAGAGAATCCAGAAGCTTAAAGAAGAATTCGCCACAACGTGGCACAAAGACCCTGAGCATCCATACCGC

ACTTGGACATACCACGGAAGCTATGAAGTGAAGGCTACTGGCTCAGCCAGCTCTCTCGTCAACGGAGTGGTGAAGCTC

ATGAGCAAACCTTGGGACGCCATTGCCAACGTCACCACCATGGCCATGACTGACACCACCCCTTTTGGACAGCAAAGAG

TTTTCAAGGAGAAAGTTGACACGAAGGCTCCTGAGCCACCAGCTGGAGCCAAGGAAGTGCTCAACGAGACCACCAACT

GGCTGTGGGCCCACTTGTCACGGGAAAAAAGACCCCGCTTGTGCACCAAGGAAGAATTCATAAAGAAAGTCAACAGCA

ACGCGGCTCTTGGAGCAGTGTTCGCTGAACAGAATCAATGGAGCACGGCGCGTGAGGCTGTGGATGACCCGCGGTTTT

GGGAGATGGTTGATGAAGAGAGGGAAAACCATCTGCGAGGAGAGTGTCACACATGTATCTACAACATGATGGGAAAA

AGAGAGAAGAAGCCTGGAGAGTTTGGAAAAGCTAAAGGAAGCAGGGCCATTTGGTTCATGTGGCTTGGAGCACGGTA

TCTAGAGTTTGAAGCTTTGGGGTTCCTGAATGAAGACCATTGGCTGAGCCGAGAGAATTCAGGAGGTGGAGTGGAAG

GCTCAGGCGTCCAAAAGCTGGGATACATCCTCCGTGACATAGCAGGAAAGCAAGGAGGGAAAATGTACGCTGATGAT

ACCGCCGGGTGGGACACTAGAATTACCAGAACTGATTTAGAAAATGAAGCTAAGGTACTGGAGCTCCTAGACGGTGAA

CACCGCATGCTCGCCCGAGCCATAATTGAACTGACTTACAGGCACAAAGTGGTCAAGGTCATGAGACCTGCAGCAGAA

GGAAAGACCGTGATGGACGTGATATCAAGAGAAGATCAAAGGGGGAGTGGACAGGTGGTCACTTATGCTCTTAACAC

TTTCACGAACATCGCTGTCCAGCTCGTCAGGCTGATGGAGGCTGAGGGGGTCATTGGACCACAACACTTGGAACAGCT

ACCTAGGAAAAACAAGATAGCTGTCAGGACCTGGCTCTTTGAGAATGGAGAGGAGAGAGTGACCAGGATGGCGATCA

GCGGAGACGACTGTGTCGTCAAGCCGCTGGACGACAGATTCGCCACAGCCCTCCACTTCCTCAACGCAATGTCAAAGGT

CAGAAAAGACATCCAGGAATGGAAGCCTTCGCATGGCTGGCACGATTGGCAGCAAGTTCCCTTCTGCTCTAACCATTTT

CAGGAGATTGTGATGAAAGATGGAAGGAGTATAGTTGTCCCGTGCAGAGGACAGGATGAGCTGATAGGCAGGGCTCG

CATCTCTCCAGGAGCTGGATGGAATGTGAAGGACACAGCTTGCCTGGCCAAAGCATATGCACAGATGTGGCTACTCCT

ATACTTCCATCGCAGGGACTTGCGTCTCATGGCAAATGCGATTTGCTCAGCAGTGCCAGTGGATTGGGTGCCCACAGGC

AGGACATCCTGGTCAATACACTCGAAAGGAGAGTGGATGACCACGGAAGACATGCTGCAGGTCTGGAACAGAGTCTG

GATTGAAGAAAATGAATGGATGATGGACAAGACTCCAATCACAAGCTGGACAGACGTTCCGTATGTGGGAAAGCGTG

AGGACATCTGGTGTGGCAGCCTCATCGGAACGCGATCCAGAGCAACCTGGGCTGAGAACATCTATGCGGCGATAAACC

AGGTTAGAGCTGTCATTGGGAAAGAAAATTATGTTGACTACATGACCTCACTCAGGAGATACGAAGACGTCTTGATCCA

GGAAGACAGGGTCATCTAGTGTGATTTAAGGTAGAAAAGTAGACTATGTAAATAATGTAAATGAGAAAATGCATGCAT

ATGGAGTCAGGCCAGCAAAAGCTGCCACCGGATACTGGGTAGACGGTGCTGCCTGCGTCTCAGTCCCAGGAGGACTG

GGTTAACAAATCTGACAACAGAAAGTGAGAAAGCCCTCAGAACCGTCTCGGAAGTAGGTCCCTGCTCACTGGAAGTTG

AAAGACCAACGTCAGGCCACAAATTTGTGCCACTCCGCTAGGGAGTGCGGCCTGCGCAGCCCCAGGAGGACTGGGTTA

CCAAAGCCGTTGAGGCCCCCACGGCCCAAGCCTCGTCTAGGATGCAATAGACGAGGTGTAAGGACTAGAGGTTAGAG

-continued

GAGACCCCGTGGAAACAACAACATGCGGCCCAAGCCCCCTCGAAGCTGTAGAGGAGGTGGAAGGACTAGAGGTTAGA

GGAGACCCCGCATTTGCATCAAACAGCATATTGACACCTGGGAATAGACTGGGAGATCTTCTGCTCTATCTCAACATCA

GCTACTAG

SEQ ID NO: 74

Japanese encephalitis virus strain SA14-14-2, complete genome, ACCESSION: JN604986

AGAAGTTTATCTGTGTGAACTTCTTGGCTTAGTATCGTAGAGAAGAATCGAGAGATTAGTGCAGTTTAAACAGTTTTTTA

GAACGGAAGATAACCATGACTAAAAAACCAGGAGGGCCCGGTAAAAACCGGGCTATCAATATGCTGAAACGCGGCCT

ACCCCGCGTATTCCCACTAGTGGGAGTGAAGAGGGTAGTAATGAGCTTGTTGGACGGCAGAGGGCCAGTACGTTTCGT

GCTGGCTCTTATCACGTTCTTCAAGTTTACAGCATTAGCCCCGACCAAGGCGCTTTCAGGCCGATGGAAAGCAGTGGAA

AAGAGTGTGGCAATGAAACATCTTACTAGTTTCAAACGAGAACTTGGAACACTCATTGACGCCGTGAACAAGCGGGGC

AGAAAGCAAAACAAAAGAGGAGGAAATGAAGGCTCAATCATGTGGCTCGCGAGCTTGGCAGTTGTCATAGCTTGTGC

AGGAGCCATGAAGTTGTCGAATTTCCAGGGGAAGCTTTTGATGACCATCAACAACACGGACATTGCAGACGTTATCGT

GATTCCCACCTCAAAAGGAGAGAACAGATGCTGGGTCCGGGCAATCGACGTCGGCTACATGTGTGAGGACACTATCAC

GTACGAATGTCCTAAGCTTACCATGGGCAATGATCCAGAGGATGTGGATTGCTGGTGTGACAACCAAGAAGTCTACGT

CCAATATGGACGGTGCACGCGGACCAGGCATTCCAAGCGAAGCAGGAGATCCGTGTCGGTCCAAACACATGGGGAGA

GTTCACTAGTGAATAAAAAAGAGGCTTGGCTGGATTCAACGAAAGCCACACGATATCTCATGAAAACTGAGAACTGGA

TCATAAGGAATCCTGGCTATGCTTTCCTGGCGGCGGTACTTGGCTGGATGCTTGGCAGTAACAACGGTCAACGCGTGGT

ATTTACCATCCTCCTGCTGTTGGTCGCTCCGGCTTACAGTTTTAATTGTCTGGGAATGGGCAATCGTGACTTCATAGAAG

GAGCCAGTGGAGCCACTTGGGTGGACTTGGTGCTAGAAGGAGACAGCTGCTTGACAATCATGGCAAACGACAAACCA

ACATTGGACGTCCGCATGATTAACATCGAAGCTAGCCAACTTGCTGAGGTCAGAAGTTACTGCTATCATGCTTCAGTCA

CTGACATCTCGACGGTGGCTCGGTGCCCCACGACTGGAGAAGCCCACAACGAGAAGCGAGCTGATAGTAGCTATGTGT

GCAAACAAGGCTTCACTGACCGTGGGTGGGGCAACGGATGTGGATTTTTCGGGAAGGGAAGCATTGACACATGTGCA

AAATTCTCCTGCACCAGTAAAGCGATTGGGAGAACAATCCAGCCAGAAAACATCAAATACAAAGTTGGCATTTTTGTGC

ATGGAACCACCACTTCGGAAAACCATGGGAATTATTCAGCGCAAGTTGGGGCGTCCCAGGCGGCAAAGTTTACAGTAA

CACCCAATGCTCCTTCGGTAGCCCTCAAACTTGGTGACTACGGAGAAGTCACACTGGACTGTGAGCCAAGGAGTGGAC

TGAACACTGAAGCGTTTTACGTCATGACCGTGGGGTCAAAGTCATTTCTGGTCCATAGGGAGTGGTTTCATGACCTCGC

TCTCCCCTGGACGTCCCCTTCGAGCACAGCGTGGAGAAACAGAGAACTCCTCATGGAATTTGAAGGGGCGCACGCCAC

AAAACAGTCCGTTGTTGCTCTTGGGTCACAGGAAGGAGGCCTCCATCATGCGTTGGCAGGAGCCATCGTGGTGGAGTA

CTCAAGCTCAGTGATGTTAACATCAGGCCACCTGAAATGTAGGCTGAAAATGGACAAACTGGCTCTGAAAGGCACAAC

CTATGGCATGTGTACAGAAAAATTCTCGTTCGCGAAAAATCCGGTGGACACTGGTCACGGAACAGTTGTCATTGAACTC

TCCTACTCTGGGAGTGATGGCCCCTGCAAAATTCCGATTGTTTCCGTTGCGAGCCTCAATGACATGACCCCCGTTGGGC

GGCTGGTGACAGTGAACCCCTTCGTCGCGACTTCCAGTGCCAACTCAAAGGTGCTGGTCGAGATGGAACCCCCCTTCG

GAGACTCCTACATCGTAGTTGGAAGGGGAGACAAGCAGATCAACCACCATTGGCACAAAGCTGGAAGCACGCTGGGC

AAGGCCTTTTCAACAACTTTGAAGGGAGCTCAAAGACTGGCAGCGTTGGGCGACACAGCCTGGGACTTTGGCTCTATT

GGAGGGGTCTTCAACTCCATAGGAAGAGCCGTTCACCAAGTGTTTGGTGGTGCCTTCAGAACACTCTTTGGGGGAATG

TCTTGGATCACACAAGGGCTAATGGGTGCCCTACTGCTCTGGATGGGCGTCAACGCACGAGACCGATCAATTGCTTTGG

CCTTCTTAGCCACAGGAGGTGTGCTCGTGTTCTTAGCGACCAATGTGCATGCTGACACTGGATGTGCCATTGACATCAC

AAGAAAAGAGATGAGATGTGGAAGTGGCATCTTCGTGCACAACGACGTGGAAGCCTGGGTGGATAGGTATAAATATT

TGCCAGAAACGCCCAGATCCCTAGCGAAGATCGTCCACAAAGCGCACAAGGAAGGCGTGTGCGGAGTCAGATCTGTCA

CTAGACTGGAGCACCAAATGTGGGAAGCCGTAAGGGACGAATTGAACGTCCTGCTCAAAGAGAATGCAGTGGACCTC

AGTGTGGTTGTGAACAAGCCCGTGGGAAGATATCGCTCAGCCCCTAAACGCCTATCCATGACGCAAGAGAAGTTTGAA

-continued

ATGGGCTGGAAAGCATGGGGAAAAAGCATCCTCTTTGCCCCGGAATTGGCTAACTCCACATTTGTCGTAGATGGACCTG

AGACAAAGGAATGCCCTGATGAGCACAGAGCTTGGAACAGCATGCAAATCGAAGACTTCGGCTTTGGCATCACATCAA

CCCGTGTGTGGCTGAAAATTAGAGAGGAGAGCACTGACGAGTGTGATGGAGCGATCATAGGCACGGCTGTCAAAGGA

CATGTGGCAGTCCATAGTGACTTGTCGTACTGGATTGAGAGTCGCTACAACGACACATGGAAACTTGAGAGGGCAGTC

TTTGGAGAGGTCAAATCTTGCACTTGGCCAGAGACACACACCCTTTGGGGAGATGATGTTGAGGAAAGTGAACTCATC

ATTCCGCACACCATAGCCGGACCAAAAAGCAAGCACAATCGGAGGGAAGGGTATAAGACACAAAACCAGGGACCTTG

GGATGAGAATGGCATAGTCTTGGACTTTGATTATTGCCCAGGGACAAAAGTCACCATTACAGAGGATTGTAGCAAGAG

AGGCCCTTCGGTCAGAACCACTACTGACAGTGGAAAGTTGATCACTGACTGGTGCTGTCGCAGTTGCTCCCTTCCGCCC

CTACGATTCCGGACAGAAAATGGCTGCTGGTACGGAATGGAAATCAGACCTGTTATGCATGATGAAACAACACTCGTC

AGATCACAGGTTCATGCTTTCAAAGGTGAAATGGTTGACCCTTTTCAGCTGGGCCTTCTGGTGATGTTTCTGGCCACCCA

GGAAGTCCTTCGCAAGAGGTGGACGGCCAGATTGACCATTCCTGCGGTTTTGGGGGTCCTACTTGTGCTGATGCTTGG

GGGTATCACTTACACTGATTTGGCGAGGTATGTGGTGCTAGTCGCTGCTGCTTTCGCAGAGGCCAACAGTGGAGGAGA

CGTCCTGCACCTTGCTTTGATTGCTGTTTTTAAGATCCAACCAGCATTTTTAGTGATGAACATGCTTAGCACGAGATGGA

CGAACCAAGAAAACGTGGTTCTGGTCCTAGGGGCTGCCTTTTTCCAATTGGCCTCAGTAGATCTGCAAATAGGAGTCCA

CGGAATCCTGAATGCCGCCGCTATAGCATGGATGATTGTCCGAGCGATCACCTTCCCCACAACCTCCTCCGTCACCATGC

CAGTCTTAGCGCTTCTAACTCCGGGGATGAGGGCTCTATACCTAGACACTTACAGAATCATCCTCCTCGTCATAGGGATT

TGCTCCCTGCTGCACGAGAGGAAAAAGACCATGGCGAAAAAGAAAGGAGCTGTACTCTTGGGCTTAGCGCTCACATCC

ACTGGATGGTTCTCGCCCACCACTATAGCTGCCGGACTAATGGTCTGCAACCCAAACAAGAAGAGAGGGTGGCCAGCT

ACTGAGTTTTTGTCGGCAGTTGGATTGATGTTTGCCATCGTAGGTGGTTTGGCCGAGTTGGATATTGAATCCATGTCAAT

ACCCTTCATGCTGGCAGGTCTCATGGCAGTGTCCTACGTGGTGTCAGGAAAAGCAACAGATATGTGGCTTGAACGGGC

CGCCGACATCAGCTGGGATATGGGTGCTGCAATCACAGGAAGCAGTCGGAGGCTGGATGTGAAACTGGATGATGACG

GAGATTTTCACTTGATTGATGATCCCGGTGTTCCATGGAAGGTCTGGGTCCTGCGCATGTCTTGCATTGGCTTAGCCGCC

CTCACGCCTTGGGCCATCGTTCCCGCCGCTTTCGGTTATTGGCTCACTTTAAAAACAACAAAAAGAGGGGGCGTGTTTT

GGGACACGCCATCCCCAAAACCTTGCTCAAAAGGAGACACCACTACAGGAGTCTACCGAATTATGGCTAGAGGGATTC

TTGGCACTTACCAGGCCGGCGTCGGAGTCATGTACGAGAATGTTTTCCACACACTATGGCACACAACTAGAGGAGCAG

CCATTGTGAGTGGAGAAGGAAAATTGACGCCATACTGGGGTAGTGTGAAAGAAGACCGCATAGCTTACGGAGGCCCA

TGGAGGTTTGACCGAAAATGGAATGGAACAGATGACGTGCAAGTGATCGTGGTAGAACCGGGGAAGGGCGCAGTAA

ACATCCAGACAAAACCAGGAGTGTTTCGGACTCCCTTCGGGGAGGTTGGGGCTGTTAGTCTGGATTACCCGCGAGGAA

CATCCGGCTCACCCATTCTGGATTCCAATGGAGACATTATAGGCCTATACGGCAATGGAGTTGAGCTTGGCGATGGCTC

ATACGTCAGCGCCATCGTGCAGGGTGACCGTCAGGAGGAACCAGTCCCAGAAGCTTACACCCCAAACATGTTGAGAAA

GAGACAGATGACTGTGCTAGATTTGCACCCTGGTTCAGGGAAAACCAGGAAAATTCTGCCACAAATAATTAAGGACGC

TATCCAGCAGCGCCTAAGAACAGCTGTGTTGGCACCGACGCGGGTGGTAGCAGCAGAAATGGCAGAAGCTTTGAGAG

GGCTCCCAGTACGATATCAAACTTCAGCAGTGCAGAGAGAGCACCAAGGGAATGAAATAGTGGATGTGATGTGCCAC

GCCACTCTGACCCATAGACTGATGTCACCGAACAGAGTGCCCAACTACAACCTATTTGTCATGGATGAAGCTCATTTCAC

CGACCCAGCCAGTATAGCCGCACGAGGATACATTGCTACCAAGGTGGAATTAGGGGAGGCAGCAGCCATCTTTATGAC

AGCGACCCCGCCTGGAACCACGGATCCTTTTCCTGACTCAAATGCCCCAATCCATGATTTGCAAGATGAGATACCAGAC

AGGGCATGGAGCAGTGGATACGAATGGATCACAGAATATGCGGGTAAAACCGTGTGGTTTGTGGCGAGCGTAAAAAT

GGGGAATGAGATTGCAATGTGCCTCCAAAGAGCGGGGAAAAAGGTCATCCAACTCAACCGCAAGTCCTATGACACAG

AATACCCAAAATGTAAGAATGGAGACTGGGATTTTGTCATTACCACCGACATCTCTGAAATGGGGGCCAACTTCGGTGC

GAGCAGGGTCATCGACTGTAGAAAGAGCGTGAAACCCACCATCTTAGAAGAGGGAGAAGGCAGAGTCATCCTCGGAA

ACCCATCTCCCATAACCAGTGCAAGCGCAGCTCAACGGAGGGGCAGAGTAGGCAGAAACCCCAATCAAGTTGGAGAT

-continued

GAATACCACTATGGGGGGGCTACCAGTGAAGATGACAGTAACCTAGCCCATTGGACAGAGGCAAAGATCATGTTAGAC

AACATACACATGCCCAATGGACTGGTGGCCCAGCTCTATGGACCAGAGAGGGAAAAGGCTTTCACAATGGATGGCGAA

TACCGTCTCAGAGGTGAAGAAAAGAAAAACTTCTTAGAGCTGCTTAGGACGGCTGACCTCCCGGTGTGGCTGGCCTAC

AAGGTGGCGTCCAATGGCATTCAGTACACCGACAGAAAGTGGTGTTTTGATGGGCCGCGTACGAATGCCATACTGGAG

GACAACACCGAGGTAGAGATAGTCACCCGGATGGGTGAGAGGAAAATCCTCAAGCCGAGATGGCTTGATGCAAGAGT

TTATGCAGATCACCAGGCCCTCAAGTGGTTCAAAGACTTTGCAGCAGGGAAGAGATCAGCCGTTAGCTTCATAGAGGT

GCTCGGTCGCATGCCTGAGCATTTCATGGGAAAGACGCGGGAAGCTTTAGACACCATGTACTTGGTTGCAACGGCTGA

GAAAGGTGGGAAAGCACACCGAATGGCTCTCGAAGAGCTGCCAGATGCACTGGAAACCATCACACTTATTGTCGCCAT

TACTGTGATGACAGGAGGATTCTTCCTACTAATGATGCAGCGAAAGGGTATAGGGAAGATGGGTCTTGGAGCTCTAGT

GCTCACACTAGCTACCTTCTTCCTGTGGGCGGCAGAGGTTCCTGGAACCAAAATAGCAGGGACCCTGCTGATCGCCCTG

CTGCTGATGGTGGTTCTCATCCCAGAACCGGAAAAACAGAGGTCACAGACAGATAACCAACTGGCGGTGTTTCTCATCT

GTGTCTTGACCGTGGTTGGAGTGGTGGCAGCAAACGAGTACGGGATGCTAGAAAAAACCAAAGCGGATCTCAAGAGC

ATGTTTGGCGGAAAGACGCAGGCATCAGGACTGACTGGATTGCCAAGCATGGCACTGGACCTGCGTCCAGCCACAGCC

TGGGCACTGTATGGGGGGAGCACAGTCGTGCTAACCCCTCTTCTGAAGCACCTGATCACGTCGGAATACGTCACCACAT

CGCTAGCTTCAATTAACTCACAAGCTGGCTCATTATTCGTCTTGCCACGAGGCGTGCCTTTTACCGACCTAGACTTGACT

GTTGGCCTCGTCTTCCTTGGCTGTTGGGGTCAAGTCACCCTCACAACGTTTCTGACAGCCATGGTTCTGGCGACACTTCA

CTATGGGTACATGCTCCCTGGATGGCAAGCAGAAGCACTCAGGGCTGCCCAGAGAAGGACAGCGGCTGGAATAATGA

AGAATGCCGTTGTTGACGGAATGGTCGCCACTGATGTGCCTGAACTGGAAAGGACTACTCCTCTGATGCAAAAGAAAG

TCGGACAGGTGCTCCTCATAGGGGTAAGCGTGGCAGCGTTCCTCGTCAACCCTAATGTCACCACTGTGAGAGAAGCAG

GGGTGTTGGTGACGGCGGCTACGCTTACTTTGTGGGACAATGGAGCCAGTGCCGTTTGGAATTCCACCACAGCCACGG

GACTCTGCCATGTCATGCGAGGTAGCTACCTGGCTGGAGGCTCCATTGCTTGGACTCTCATCAAGAACGCTGATAAGCC

CTCCTTGAAAAGGGGAAGGCCTGGGGGCAGGACGCTAGGGGAGCAGTGGAAGGAAAAACTAAATGCCATGAGTAGA

GAAGAGTTTTTTAAATACCGGAGAGAGGCCATAATCGAGGTGGACCGCACTGAAGCACGCAGGGCCAGACGTGAAAA

TAACATAGTGGGAGGACATCCGGTTTCGCGAGGCTCAGCAAAACTCCGTTGGCTCGTGGAGAAAGGATTTGTCTCGCC

AATAGGAAAAGTCATTGATCTAGGGTGTGGGCGTGGAGGATGGAGCTACTACGCAGCAACCCTGAAGAAGGTCCAGG

AAGTCAGAGGATACACGAAAGGTGGGGCGGGACATGAAGAACCGATGCTCATGCAGAGCTACGGCTGGAACCTGGTC

TCCCTGAAGAGTGGAGTGGACGTGTTTTACAAACCTTCAGAGCCCAGTGATACCCTGTTCTGTGACATAGGGGAATCCT

CCCCAAGTCCAGAAGTAGAAGAACAACGCACACTACGCGTCCTAGAGATGACATCTGACTGGTTGCACCGAGGACCTA

GAGAGTTCTGCATTAAAGTTCTCTGCCCTTACATGCCCAAGGTTATAGAAAAAATGGAAGTTCTGCAGCGTCGCTTCGG

AGGTGGGCTAGTGCGTCTCCCCCTGTCCCGAAACTCCAATCACGAGATGTATTGGGTTAGTGGAGCCGCTGGCAATGT

GGTGCACGCTGTGAACATGACCAGCCAGGTATTACTGGGGCGAATGGATCGCACAGTGTGGAGAGGGCCAAAGTATG

AGGAAGATGTCAACCTAGGGAGCGGAACAAGAGCCGTGGGAAAGGGAGAAGTCCATAGCAATCAGGAGAAAATCAA

GAAGAGAATCCAGAAGCTTAAAGAAGAATTCGCCACAACGTGGCACAAAGACCCTGAGCATCCATACCGCACTTGGAC

ATACCACGGAAGCTATGAAGTGAAGGCTACTGGCTCAGCCAGCTCTCTCGTCAACGGAGTGGTGAAGCTCATGAGCAA

ACCTTGGGACGCCATTGCCAACGTCACCACCATGGCCATGACTGACACCACCCCTTTTGGACAGCAAAGAGTTTTCAAG

GAGAAAGTTGACACGAAGGCTCCTGAGCCACCAGCTGGAGCCAAGGAAGTGCTCAACGAGACCACCAACTGGCTGTG

GGCCTACTTGTCACGGGAAAAAAGACCCCGCTTGTGCACCAAGGAAGAATTCATTAAGAAAGTTAACAGCAACGCGGC

TCTTGGAGCAGTGTTCGCTGAACAGAATCAATGGAGCACGGCGCGTGAGGCTGTGGATGACCCGCGGTTTTGGGAGA

TGGTTGATGAAGAGAGGGAAAACCATCTGCGAGGAGAGTGTCACACATGTATCTACAACATGATGGGAAAAAGAGAG

AAGAAGCCTGGAGAGTTTGGAAAAGCTAAAGGAAGCAGGGCCATTTGGTTCATGTGGCTTGGAGCACGGTATCTAGA

-continued

GTTTGAAGCTTTGGGGTTCCTGAATGAAGACCATTGGCTGAGCCGAGAGAATTCAGGAGGTGGAGTGGAAGGCTCAG

GCGTCCAAAAGCTGGGATACATCCTCCGTGACATAGCAGGAAAGCAAGGAGGGAAAATGTACGCTGATGATACCGCC

GGGTGGGACACTAGAATTACCAGAACTGATTTAGAAAATGAAGCTAAGGTACTGGAGCTCCTAGACGGTGAACACCGC

ATGCTCGCCCGAGCCATAATTGAACTGACTTACAGGCACAAAGTGGTCAAGGTCATGAGACCTGCAGCAGAAGGAAAG

ACCGTGATGGACGTGATATCAAGAGAAGATCAAAGGGGGAGTGGACAGGTGGTCACTTATGCTCTTAACACTTTCACG

AACATCGCTGTCCAGCTCGTCAGGCTGATGGAGGCTGAGGGGGTCATTGGACCACAACACTTGGAACATCTACCTAGG

AAAAACAAGATAGCTGTCAGGACCTGGCTCTTTGAGAATGGAGAGGAGAGAGTGACCAGGATGGCGATCAGCGGAG

ACGACTGTGCCGTCAAACCGCTGGACGACAGATTCGCCACAGCCCTCCACTTCCTCAACGCAATGTCAAAGGTCAGAAA

AGACATCCAGGAATGGAAGCCTTCGCATGGCTGGCACGATTGGCAGCAAGTTCCCTTCTGTTCTAACCATTTTCAGGAG

ATTGTGATGAAAGATGGAAGGAGTATAGTTGTCCCGTGCAGAGGACAGGATGAGCTGATAGGCAGGGCTCGCATCTC

TCCTGGAGCTGGATGGAATGTGAAGGACACAGCTTGCCTGGCCAAAGCATATGCACAGATGTGGCTACTCCTATACTTC

CATCGCAGGGACTTGCGTCTCATGGCAAATGCGATTTGCTCAGCAGTGCCAGTAGATTGGGTGCCCACAGGCAGGACA

TCCTGGTCAATACACTCGAAAGGAGAGTGGATGACCACGGAAGACATGCTGCAGGTCTGGAACAGAGTTTGGATTGAA

GAAAATGAATGGATGATGGACAAGACTCCAATCACAAGCTGGACAGACGTTCCGTATGTGGGAAAGCGCGAGGACAT

CTGGTGTGGCAGCCTCATCGGAACGCGATCCAGAGCAACCTGGGCTGAGAACATCTATGCGGCGATAAACCAGGTTAG

AGCTGTCATTGGGAAAGAAAATTATGTTGACTACATGACCTCACTCAGGAGATACGAAGACGTCTTGATCCAGGAAGA

CAGGGTCATCTAGTGTGATTTAAGGTAGAAAAGTAGACTATGTAAACAATGTAAATGAGAAAATGCATGCATATGGAG

TCAGGCCAGCAAAAGCTGCCACCGGATACTGGGTAGACGGTGCTGCCTGCGTCTCAGTCCCAGGAGGACTGGGTTAAC

AAATCTGACAACAGAAAGTGAGAAAGCCCTCAGAACCGTCTCGGAAGTAGGTCCCTGCTCACTGGAAGTTGAAAGACC

AACGTCAGGCCACAAATTTGTGCCACTCCGCTAGGGAGTGCGGCCTGCGCAGCCCCAGGAGGACTGGGTTACCAAAGC

CGTTGAGGCCCCCACGGCCCAAGCCTCGTCTAGGATGCAATAGACGAGGTGTAAGGACTAGAGGTTAGAGGAGACCC

CGTGGAAACAACAACATGCGGCCCAAGCCCCCTCGAAGCTGTAGAGGAGGTGGAAGGACTAGAGGTTAGAGGAGACC

CCGCATTTGCATCAAACAGCATATTGACACCTGGGAATAGACTGGGAGATCTTCTGCTCTATCTCAACATCAGCTACTAG

GCACAGAGCGCCGAAGTATGTAGCTGGTGGTGAGGAAGAACACAGGATCT

SEQ ID NO: 75

Japanese encephalitis virus strain SA14-14-2, complete genome, ACCESSION: AF315119

AGAAGTTTATCTGTGTGAACTTCTTGGCTTAGTATCGTAGAGAAGAATCGAGAGATTAGTGCAGTTTAAACAGTTTTTA

GAACGGAAGATAACCATGACTAAAAAACCAGGAGGGCCCGGTAAAAACCGGGCTATCAATATGCTGAAACGCGGCCT

ACCCCGCGTATTCCCACTAGTGGGAGTGAAGAGGGTAGTAATGAGCTTGTTGGACGGCAGAGGGCCAGTACGTTTCGT

GCTGGCTCTTATCACGTTCTTCAAGTTTACAGCATTAGCCCCGACCAAGGCGCTTTCAGGCCGATGGAAAGCAGTGGAA

AAGAGTGTGGCAATGAAACATCTTACTAGTTTCAAACGAGAACTTGGAACACTCATTGACGCCGTGAACAAGCGGGGC

AGAAAGCAAAACAAAAGAGGAGGAAATGAAGGCTCAATCATGTGGCTCGCGAGCTTGGCAGTTGTCATAGCTTGTGC

AGGAGCCATGAAGTTGTCGAATTTCCAGGGGAAGCTTTTGATGACCATCAACAACACGGACATTGCAGACGTTATCGT

GATTCCCACCTCAAAAGGAGAGAACAGATGCTGGGTCCGGGCAATCGACGTCGGCTACATGTGTGAGGACACTATCAC

GTACGAATGTCCTAAGCTTACCATGGGCAATGATCCAGAGGATGTGGATTGCTGGTGTGACAACCAAGAAGTCTACGT

CCAATATGGACGGTGCACGCGGACCAGGCATTCCAAGCGAAGCAGGAGATCCGTGTCGGTCCAAACACATGGGGAGA

GTTCACTAGTGAATAAAAAAGAGGCTTGGCTGGATTCAACGAAAGCCACACGATATCTCATGAAAACTGAGAACTGGA

TCATAAGGAATCCTGGCTATGCTTTCCTGGCGGCGGTACTTGGCTGGATGCTTGGCAGTAACAACGGTCAACGCGTGGT

ATTTACCATCCTCCTGCTGTTGGTCGCTCCGGCTTACAGTTTTAATTGTCTGGGAATGGGCAATCGTGACTTCATAGAAG

GAGCCAGTGGAGCCACTTGGGTGGACTTGGTGCTAGAAGGAGACAGCTGCTTGACAATCATGGCAAACGACAAACCA

ACATTGGACGTCCGCATGATTAACATCGAAGCTAGCCAACTTGCTGAGGTCAGAAGTTACTGCTATCATGCTTCAGTCA

CTGACATCTCGACGGTGGCTCGGTGCCCCACGACTGGAGAAGCCCACAACGAGAAGCGAGCTGATAGTAGCTATGTGT

-continued

GCAAACAAGGCTTCACTGACCGTGGGTGGGGCAACGGATGTGGATTTTTCGGGAAGGGAAGCATTGACACATGTGCA

AAATTCTCCTGCACCAGTAAAGCGATTGGGAGAACAATCCAGCCAGAAAACATCAAATACAAAGTTGGCATTTTTGTGC

ATGGAACCACCACTTCGGAAAACCATGGGAATTATTCAGCGCAAGTTGGGGCGTCCCAGGCGGCAAAGTTTACAGTAA

CACCCAATGCTCCTTCGGTAGCCCTCAAACTTGGTGACTACGGAGAAGTCACACTGGACTGTGAGCCAAGGAGTGGAC

TGAACACTGAAGCGTTTTACGTCATGACCGTGGGGTCAAAGTCATTTCTGGTCCATAGGGAGTGGTTTCATGACCTCGC

TCTCCCCTGGACGTCCCCTTCGAGCACAGCGTGGAGAAACAGAGAACTCCTCATGGAATTTGAAGGGGCGCACGCCAC

AAAACAGTCCGTTGTTGCTCTTGGGTCACAGGAAGGAGGCCTCCATCATGCGTTGGCAGGAGCCATCGTGGTGGAGTA

CTCAAGCTCAGTGATGTTAACATCAGGCCACCTGAAATGTAGGCTGAAAATGGACAAACTGGCTCTGAAAGGCACAAC

CTATGGCATGTGTACAGAAAAATTCTCGTTCGCGAAAAATCCGGTGGACACTGGTCACGGAACAGTTGTCATTGAACTC

TCCTACTCTGGGAGTGATGGCCCCTGCAAAATTCCGATTGTTTCCGTTGCGAGCCTCAATGACATGACCCCCGTTGGGC

GGCTGGTGACAGTGAACCCCTTCGTCGCGACTTCCAGTGCCAACTCAAAGGTGCTGGTCGAGATGGAACCCCCCTTCG

GAGACTCCTACATCGTAGTTGGAAGGGGAGACAAGCAGATCAACCACCATTGGCACAAAGCTGGAAGCACGCTGGGC

AAGGCCTTTTCAACAACTTTGAAGGGAGCTCAAAGACTGGCAGCGTTGGGCGACACAGCCTGGGACTTTGGCTCTATT

GGAGGGGTCTTCAACTCCATAGGAAGAGCCGTTCACCAAGTGTTTGGTGATGCCTTCAGAACACTCTTTGGGGGAATG

TCTTGGATCACACAAGGGCTAATGGGTGCCCTACTGCTCTGGATGGGCGTCAACGCACGAGACCGATCAATTGCTTTGG

CCTTCTTAGCCACAGGAGGTGTGCTCGTGTTCTTAGCGACCAATGTGCATGCTGACACTGGATGTGCCATTGACATCAC

AAGAAAAGAGATGAGATGTGGAAGTGGCATCTTCGTGCACAACGACGTGGAAGCCTGGGTGGATAGGTATAAATATT

TGCCAGAAACGCCCAGATCCCTAGCGAAGATCGTCCACAAAGCGCACAAGGAAGGCGTGTGCGGAGTCAGATCTGTCA

CTAGACTGGAGCACCAAATGTGGGAAGCCGTAAGGGACGAATTGAACGTCCTGCTCAAAGAGAATGCAGTGGACCTC

AGTGTGGTTGTGAACAAGCCCGTGGGAAGATATCGCTCAGCCCCTAAACGCCTATCCATGACGCAAGAGAAGTTTGAA

ATGGGCTGGAAAGCATGGGGAAAAAGCATCCTCTTTGCCCCGGAATTGGCTAACTCCACATTTGTCGTAGATGGACCTG

AGACAAAGGAATGCCCTGATGAGCACAGAGCTTGGAACAGCATGCAAATCGAAGACTTCGGCTTTGGCATCACATCAA

CCCGTGTGTGGCTGAAAATTAGAGAGGAGAGCACTGACGAGTGTGATGGAGCGATCATAGGCACGGCTGTCAAAGGA

CATGTGGCAGTCCATAGTGACTTGTCGTACTGGATTGAGAGTCGCTACAACGACACATGGAAACTTGAGAGGGCAGTC

TTTGGAGAGGTCAAATCTTGCACTTGGCCAGAGACACACACCCTTTGGGGAGATGATGTTGAGGAAAGTGAACTCATC

ATTCCGCACACCATAGCCGGACCAAAAAGCAAGCACAATCGGAGGGAAGGGTATAAGACACAAAACCAGGGACCTTG

GGATGAGAATGGCATAGTCTTGGACTTTGATTATTGCCCAGGGACAAAAGTCACCATTACAGAGGATTGTAGCAAGAG

AGGCCCTTCGGTCAGAACCACTACTGACAGTGGAAAGTTGATCACTGACTGGTGCTGTCGCAGTTGCTCCCTTCCGCCC

CTACGATTCCGGACAGAAAATGGCTGCTGGTACGGAATGGAAATCAGACCTGTTATGCATGATGAAACAACACTCGTC

AGATCACAGGTTCATGCTTTCAAAGGTGAAATGGTTGACCCTTTTCAGCTGGGCCTTCTGGTGATGTTTCTGGCCACCCA

GGAAGTCCTTCGCAAGAGGTGGACGGCCAGATTGACCATTCCTGCGGTTTTGGGGGTCCTACTTGTGCTGATGCTTGG

GGGTATCACTTACACTGATTTGGCGAGGTATGTGGTGCTAGTCGCTGCTGCTTTCGCAGAGGCCAACAGTGGAGGAGA

CGTCCTGCACCTTGCTTTGATTGCTGTTTTTAAGATCCAACCAGCATTTTTAGTGATGAACATGCTTAGCACGAGATGGA

CGAACCAAGAAAACGTGGTTCTGGTCCTAGGGGCTGCCTTTTTCCAATTGGCCTCAGTAGATCTGCAAATAGGAGTCCA

CGGAATCCTGAATGCCGCCGCTATAGCATGGATGATTGTCCGAGCGATCACCTTCCCCACAACCTCCTCCGTCACCATGC

CAGTCTTAGCGCTTCTAACTCCGGGGATGAGGGCTCTATACCTAGACACTTACAGAATCATCCTCCTCGTCATAGGGATT

TGCTCCCTGCTGCACGAGAGGAAAAAGACCATGGCGAAAAAGAAAGGAGCTGTACTCTTGGGCTTAGCGCTCACATCC

ACTGGATGGTTCTCGCCCACCACTATAGCTGCCGGACTAATGGTCTGCAACCCAAACAAGAAGAGAGGGTGGCCAGCT

ACTGAGTTTTTGTCGGCAGTTGGATTGATGTTTGCCATCGTAGGTGGTTTGGCCGAGTTGGATATTGAATCCATGTCAAT

ACCCTTCATGCTGGCAGGTCTCATGGCAGTGTCCTACGTGGTGTCAGGAAAAGCAACAGATATGTGGCTTGAACGGGC

-continued

CGCCGACATCAGCTGGGATATGGGTGCTGCAATCACAGGAAGCAGTCGGAGGCTGGATGTGAAACTGGATGATGACG

GAGATTTTCACTTCATTGATGATCCCGGTGTTCCATGGAAGGTCTGGGTCCTGCGCATGTCTTGCATTGGCTTAGCCGCC

CTCACGCCTTGGGCCATCGTTCCCGCCGCTTTCGGTTATTGGCTCACTTTAAAAACAACAAAAAGAGGGGGCGTGTTTT

GGGACACGCCATCCCCAAAACCTTGCTCAAAAGGAGACACCACTACAGGAGTCTACCGAATTATGGCTAGAGGGATTC

TTGGCACTTACCAGGCCGGCGTCGGAGTCATGTACGAGAATGTTTTCCACACACTATGGCACACAACTAGAGGAGCAG

CCATTGTGAGTGGAGAAGGAAAATTGACGCCATACTGGGGTAGTGTGAAAGAAGACCGCATAGCTTACGGAGGCCCA

TGGAGGTTTGACCGAAAATGGAATGGAACAGATGACGTGCAAGTGATCGTGGTAGAACCGGGGAAGGGCGCAGTAA

ACATCCAGACAAAACCAGGAGTGTTTCGGACTCCCTTCGGGGAGGTTGGGGCTGTTAGTCTGGATTACCCGCGAGGAA

CATCCGGCTCACCCATTCTGGATTCCAATGGAGACATTATAGGCCTATACGGCAATGGAGTTGAGCTTGGCGATGGCTC

ATACGTCAGCGCCATCGTGCAGGGTGACCGTCAGGAGGAACCAGTCCCAGAAGCTTACACCCCAAACATGTTGAGAAA

GAGACAGATGACTGTGCTAGATTTGCACCCTGGTTCAGGGAAAACCAGGAAAATTCTGCCACAAATAATTAAGGACGC

TATCCAGCAGCGCCTAAGAACAGCTGTGTTGGCACCGACGCGGGTGGTAGCAGCAGAAATGGCAGAAGTTTTGAGAG

GGCTCCCAGTACGATATCAAACTTCAGCAGTGCAGAGAGAGCACCAAGGGAATGAAATAGTGGATGTGATGTGCCAC

GCCACTCTGACCCATAGACTGATGTCACCGAACAGAGTGCCCAACTACAACCTATTTGTCATGGATGAAGCTCATTTCAC

CGACCCAGCCAGTATAGCCGCACGAGGATACATTGCTACCAAGGTGGAATTAGGGGAGGCAGCAGCCATCTTTATGAC

AGCGACCCCGCCTGGAACCACGGATCCTTTTCCTGACTCAAATGCCCCAATCCATGATTTGCAAGATGAGATACCAGAC

AGGGCATGGAGCAGTGGATACGAATGGATCACAGAATATGCGGGTAAAACCGTGTGGTTTGTGGCGAGCGTAAAAAT

GGGGAATGAGATTGCAATGTGCCTCCAAAGAGCGGGGAAAAAGGTCATCCAACTCAACCGCAAGTCCTATGACACAG

AATACCCAAAATGTAAGAATGGAGACTGGGATTTTGTCATTACCACCGACATCTCTGAAATGGGGGCCAACTTCGGTGC

GAGCAGGGTCATCGACTGTAGAAAGAGCGTGAAACCCACCATCTTAGAAGAGGGAGAAGGCAGAGTCATCCTCGGAA

ACCCATCTCCCATAACCAGTGCAAGCGCAGCTCAACGGAGGGGCAGAGTAGGCAGAAACCCCAATCAAGTTGGAGAT

GAATACCACTATGGGGGGGCTACCAGTGAAGATGACAGTAACCTAGCCCATTGGACAGAGGCAAAGATCATGTTAGAC

AACATACACATGCCCAATGGACTGGTGGCCCAGCTCTATGGACCAGAGAGGGAAAAGGCTTTCACAATGGATGGCGAA

TACCGTCTCAGAGGTGAAGAAAAGAAAAACTTCTTAGAGCTGCTTAGGACGGCTGACCTCCCGGTGTGGCTGGCCTAC

AAGGTGGCGTCCAATGGCATTCAGTACACCGACAGAAAGTGGTGTTTTGATGGGCCGCGTACGAATGCCATACTGGAG

GACAACACCGAGGTAGAGATAGTCACCCGGATGGGTGAGAGGAAAATCCTCAAGCCGAGATGGCTTGATGCAAGAGT

TTATGCAGATCACCAGGCCCTCAAGTGGTTCAAAGACTTTGCAGCAGGGAAGAGATCAGCCGTTAGCTTCATAGAGGT

GCTCGGTCGCATGCCTGAGCATTTCATGGGAAAGACGCGGGAAGCTTTAGACACCATGTACTTGGTTGCAACGGCTGA

GAAAGGTGGGAAAGCACACCGAATGGCTCTCGAAGAGCTGCCAGATGCACTGGAAACCATCACACTTATTGTCGCCAT

TACTGTGATGACAGGAGGATTCTTCCTACTAATGATGCAGCGAAAGGGTATAGGGAAGATGGGTCTTGGAGCTCTAGT

GCTCACACTAGCTACCTTCTTCCTGTGGGCGGCAGAGGTTCCTGGAACCAAAATAGCAGGGACCCTGCTGATCGCCCTG

CTGCTGATGGTGGTTCTCATCCCAGAACCGGAAAAACAGAGGTCACAGACAGATAACCAACTGGCGGTGTTTCTCATCT

GTGTCTTGACCGTGGTTGGAGTGGTGGCAGCAAACGAGTACGGGATGCTAGAAAAAACCAAAGCGGATCTCAAGAGC

ATGTTTGGCGGAAAGACGCAGGCATCAGGACTGACTGGATTGCCAAGCATGGCACTGGACCTGCGTCCAGCCACAGCC

TGGGCACTGTATGGGGGGAGCACAGTCGTGCTAACCCCTCTTCTGAAGCACCTGATCACGTCGGAATACGTCACCACAT

CGCTAGCTTCAATTAACTCACAAGCTGGCTCATTATTCGTCTTGCCACGAGGCGTGCCTTTTACCGACCTAGACTTGACT

GTTGGCCTCGTCTTCCTTGGCTGTTGGGGTCAAGTCACCCTCACAACGTTTCTGACAGCCATGGTTCTGGCGACACTTCA

CTATGGGTACATGCTCCCTGGATGGCAAGCAGAAGCACTCAGGGCTGCCCAGAGAAGGACAGCGGCTGGAATAATGA

AGAATGCCGTTGTTGACGGAATGGTCGCCACTGATGTGCCTGAACTGGAAAGGACTACTCCTCTGATGCAAAAGAAAG

TCGGACAGGTGCTCCTCATAGGGGTAAGCGTGGCAGCGTTCCTCGTCAACCCTAATGTCACCACTGTGAGAGAAGCAG

GGGTGTTGGTGACGGCGGCTACGCTTACTTTGTGGGACAATGGAGCCAGTGCCGTTTGGAATTCCACCACAGCCACGG

-continued

GACTCTGCCATGTCATGCGAGGTAGCTACCTGGCTGGAGGCTCCATTGCTTGGACTCTCATCAAGAACGCTGATAAGCC

CTCCTTGAAAAGGGGAAGGCCTGGGGGCAGGACGCTAGGGGAGCAGTGGAAGGAAAAACTAAATGCCATGAGTAGA

GAAGAGTTTTTTAAATACCGGAGAGAGGGCATAATCGAGGTGGACCGCACTGAAGCACGCAGGGCCAGAAGTGAAAA

TAACATAGTGGGAGGACATCCGGTTTCGCGAGGCTCAGCAAAACTCCGTTGGCTTGTGGAGAAAGGATTTGTCTCGCC

AATAGGAAAAGTCATTGATCTAGGGTGTGGGCGTGGAGGATGGAGCTACTACGCAGCAACCCTGAAGAAGGTCCAGG

AAGTCAGAGGATACACGAAAGGTGGGGCGGGACATGAAGAACCGATGCTCATGCAGAGCTACGGCTGGAACCTGGTC

TCCCTGAAGAGTGGAGTGGACGTGTTTTACAAACCTTCAGAGCCCAGTGATACCCTGTTCTGTGACATAGGGGAATCCT

CCCCAAGTCCAGAAGTAGAAGAACAACGCACACTACGCGTCCTAGAGATGACATCTGACTGGTTGCACCGAGGACCTA

GAGAGTTCTGCATTAAAGTTCTCTGCCCTTACATGCCCAAGGTTATAGAAAAAATTGAAGTTCTGCAGCGCCGCTTCGG

AGGTGGGCTAGTGCGTCTCCCCCTGTCCCGAAACTCCAATCACGAGATGTATTGGGTTAGTGGAGCCGCTGGCAATGT

GGTGCACGCTGTGAACATGACCAGCCAGGTATTACTGGGGCGAATGGATCGCACAGTGTGGAGAGGGCCAAAGTATG

AGGAAGATGTCAACCTAGGGAGCGGAACAAGAGCCGTGGGAAAGGGAGAAGTCCATAGCAATCAGGAGAAAATCAA

GAAGAGAATCCAGAAGCTTAAAGAAGAATTCGCCACAACGTGGCACAAAGACCCTGAGCATCCATACCGCACTTGGAC

ATACCACGGAAGCTATGAAGTGAAGGCTACTGGCTCAGCCAGCTCTCTCGTCAACGGAGTGGTGAAGCTCATGAGCAA

ACCTTGGGACGCCATTGCCAACGTCACCACCATGGCCATGACTGACACCACCCCTTTTGGACAGCAAAGAGTTTTCAAG

GAGAAAGTTGACACGAAGGCTCCTGAGCCACCAGCTGGAGCCAAGGAAGTGCTCAACGAGACCACCAACTGGCTGTG

GGCCTACTTGTCACGGGAAAAAAGACCCCGCTTGTGCACCAAGGAAGAATTCATTAAGAAAGTTAACAGCAACGCGGC

TCTTGGAGCAGTGTTCGCTGAACAGAATCAATGGAGCACGGCGCGTGAGGCTGTGGATGACCCGCGGTTTTGGGAGA

TGGTTGATGAAGAGAGGGAAAACCATCTGCGAGGAGAGTGTCACACATGTATCTACAACATGATGGGAAAAAGAGAG

AAGAAGCCTGGAGAGTTTGGAAAAGCTAAAGGAAGCAGGGCCATTTGGTTCATGTGGCTTGGAGCACGGTATCTAGA

GTTTGAAGCTTTGGGGTTCCTGAATGAAGACCATTGGCTGAGCCGAGAGAATTCAGGAGGTGGAGTGGAAGGCTCAG

GCGTCCAAAAGCTGGGATACATCCTCCGTGACATAGCAGGAAAGCAAGGAGGGAAAATGTACGCTGATGATACCGCC

GGGTGGGACACTAGAATTACCAGAACTGATTTAGAAAATGAAGCTAAGGTACTGGAGCTCCTAGACGGTGAACACCGC

ATGCTCGCCCGAGCCATAATTGAACTGACTTACAGGCACAAAGTGGTCAAGGTCATGAGACCTGCAGCAGAAGGAAAG

ACCGTGATGGACGTGATATCAAGAGAAGATCAAAGGGGGAGTGGACAGGTGGTCACTTATGCTCTTAACACTTTCACG

AACATCGCTGTCCAGCTCGTCAGGCTGATGGAGGCTGAGGGGGTCATTGGACCACAACACTTGGAACATCTACCTAGG

AAAAACAAGATAGCTGTCAGGACCTGGCTCTTTGAGAATGGAGAGGAGAGAGTGACCAGGATGGCGATCAGCGGAG

ACGACTGTGCCGTCAAACCGCTGGACGACAGATTCGCCACAGCCCTCCACTTCCTCAACGCAATGTCAAAGGTCAGAAA

AGACATCCAGGAATGGAAGCCTTCGCATGGCTGGCACGATTGGCAGCAAGTTCCCTTCTGTTCTAACCATTTTCAGGAG

ATTGTGATGAAAGATGGAAGGAGTATAGTTGTCCCGTGCAGAGGACAGGATGAGCTGATAGGCAGGGCTCGCATCTC

TCCAGGAGCTGGATGGAATGTGAAGGACACAGCTTGCCTGCCCAAAGCATATGCACAAATGTGGGTACTCCTATACTTC

CACCGCAGGGACTTGCGTCTCATGGCAAATGCGATTTGCTCAGCAGTGCCAGTAGATTGGGTGCCCACAGGCAGGACA

TCCTGGTCAATACACTCGAAAGGAGAGTGGATGACCACGGAAGACATGCTGCAGGTCTGGAACAGAGTTTGGATTGAA

GAAAATGAATGGATGATGGACAAGACTCCAATCACAAGCTGGACAGACGTTCCGTATGTGGGAAAGCGCGAGGACAT

CTGGTGTGGCAGCCTCATCGGAACGCGATCCAGAGCAACCTGGGCTGAGAACATCTATGCGGCGATAAACCAGGTTAG

AGCTGTCATTGGGAAAGAAAATTATGTTGACTACATGACCTCACTCAGGAGATACGAAGACGTCTTGATCCAGGAAGA

CAGGGTCATCTAGTGTGATTTAAGGTAGAAAAGTAGACTATGTAAACAATGTAAATGAGAAAATGCATGCATATGGAG

TCAGGCCAGCAAAAGCTGCCACCGGATACTGGGTAGACGGTGCTGCCTGCGTCTCAGTCCCAGGAGGACTGGGTTAAC

AAATCTGACAACAGAAAGTGAGAAAGCCCTCAGAACTGTCTCGGAAGTAGGTCCCTGCTCACTGGAAGTTGAAAGACC

AACGTCAGGCCACAAATTTGTGCCACTCCGCTAGGGAGTGCGGCCTGCGCAGCCCCAGGAGGACTGGGTTACCAAAGC

-continued

CGTTGAGCCCCCACGGCCCAAGCCTCGTCTAGGATGCAATAGACGAGGTGTAAGGACTAGAGGTTAGAGGAGACCCC

GTGGAAACAACAACATGCGGCCCAAGCCCCCTCGAAGCTGTAGAGGAGGTGGAAGGACTAGAGGTTAGAGGAGACCC

CGCATTTGCATCAAACAGCATATTGACACCTGGGAATAGACTGGGAGATCTTCTGCTCTATCTCAACATCAGCTACTAGG

CACAGAGCGCCGAAGTATGTACGTGGTGGTGAGGAAGAACACAGGATCT

SEQ ID NO: 76

>gi|564014614|gb|KF769015.1| Yellow fever virus strain 17D-204, complete genome

GTGCTAATTGAGGTGCATTGGTCTGCAAATCGAGTTGCTAGGCAATAAACACATTTGGATTAATTTTAATCGTTCGTTGAG

CGATTAGCAGAGAACTGACCAGAACATGTCTGGTCGTAAAGCTCAGGGAAAAACCCTGGGCGTCAATATGGTACGACGA

GGAGTTCGCTCCTTGTCAAACAAAATAAAACAAAAAACAAAACAAATTGGAAACAGACCTGGACCTTCAAGAGGTGTTCA

AGGATTTATCTTTTTCTTTTTGTTCAACATTTTGACTGGAAAAAAGATCACAGCCCACCTAAAGAGGTTGTGGAAAATGCTG

GACCCAAGACAAGGCTTGGCTGTTCTAAGGAAAGTCAAGAGAGTGGTGGCCAGTTTGATGAGAGGATTGTCCTCAAGGA

AACGCCGTTCCCATGATGTTCTGACTGTGCAATTCCTAATTTTGGGAATGCTGTTGATGACGGGTGGAGTGACCTTGGTGC

GGAAAAACAGATGGTTGCTCCTAAATGTGACATCTGAGGACCTCGGGAAAACATTCTCTGTGGGCACAGGCAACTGCACA

ACAAACATTTTGGAAGCCAAGTACTGGTGCCCAGACTCAATGGAATACAACTGTCCCAATCTCAGTCCAAGAGAGGAGCC

AGATGACATTGATTGCTGGTGCTATGGGGTGGAAAACGTTAGAGTCGCATATGGTAAGTGTGACTCAGCAGGCAGGTCT

AGGAGGTCAAGAAGGGCCATTGACTTGCCTACGCATGAAAACCATGGTTTGAAGACCCGGCAAGAAAAATGGATGACTG

GAAGAATGGGTGAAAGGCAACTCCAAAAGATTGAGAGATGGTTCGTGAGGAACCCCTTTTTTGCAGTGACGGCTCTGAC

CATTGCCTACCTTGTGGGAAGCAACATGACGCAACGAGTCGTGATTGCCCTACTGGTCTTGGCTGTTGGTCCGGCCTACTC

AGCTCACTGCATTGGAATTACTGACAGGGATTTCATTGAGGGGGTGCATGGAGGAACTTGGGTTTCAGCTACCCTGGAGC

AAGACAAGTGTGTCACTGTTATGGCCCCTGACAAGCCTTCATTGGACATCTCACTAGAGACAGTAGCCATTGATAGACCTG

CTGAGGTGAGGAAAGTGTGTTACAATGCAGTTCTCACTCATGTGAAGATTAATGACAAGTGCCCCAGCACTGGAGAGGCC

CACCTAGCTGAAGAGAACGAAGGGGACAATGCGTGCAAGCGCACTTATTCTGATAGAGGCTGGGGCAATGGCTGTGGCC

TATTTGGGAAAGGGAGCATTGTGGCATGCGCCAAATTCACTTGTGCCAAATCCATGAGTTTGTTTGAGGTTGATCAGACC

AAAATTCAGTATGTCATCAGAGCACAATTGCATGTAGGGGCCAAGCAGGAAAATTGGACTACCGACATTAAGACTCTCAA

GTTTGATGCCCTGTCAGGCTCCCAGGAAGTCGAGTTCATTGGGTATGGAAAAGCTACACTGGAATGCCAGGTGCAAACTG

CGGTGGACTTTGGTAACAGTTACATCGCTGAGATGGAAACAGAGAGCTGGATAGTGGACAGACAGTGGGCCCAGGACTT

GACCCTGCCATGGCAGAGTGGAAGTGGCGGGGTGTGGAGAGAGATGCATCATCTTGTCGAATTTGAACCTCCGCATGCC

GCCACTATCAGAGTACTGGCCCTGGGAAACCAGGAAGGCTCCTTGAAAACAGCTCTTACTGGCGCAATGAGGGTTACAAA

GGACACAAATGACAACAACCTTTACAAACTACATGGTGGACATGTTTCTTGCAGAGTGAAATTGTCAGCTTTGACACTCAA

GGGGACATCCTACAAAATATGCACTGACAAAATGTTTTTTGTCAAGAACCCAACTGACACTGGCCATGGCACTGTTGTGAT

GCAGGTGAAAGTGTCAAAAGGAGCCCCCTGCAGGATTCCAGTGATAGTAGCTGATGATCTTACAGCGGCAATCAATAAA

GGCATTTTGGTTACAGTTAACCCCATCGCCTCAACCAATGATGATGAAGTGCTGATTGAGGTGAACCCACCTTTTGGAGAC

AGCTACATTATCGTTGGGAGAGGAGATTCACGTCTCACTTACCAGTGGCACAAAGAGGGAAGCTCAATAGGAAAGTTGTT

CACTCAGACCATGAAAGGCGTGGAACGCCTGGCCGTCATGGGAGACACCGCCTGGGATTTCAGCTCCGCTGGAGGGTTC

TTCACTTCGGTTGGGAAAGGAATTCATACGGTGTTTGGCTCTGCCTTTCAGGGGCTATTTGGCGGCTTGAACTGGATAACA

AAGGTCATCATGGGGGCGGTACTTATATGGGTTGGCATCAACACAAGAAACATGACAATGTCCATGAGCATGATCTTGGT

AGGAGTGATCATGATGTTTTTGTCTCTAGGAGTTGGGGCGGATCAAGGATGCGCCATCAACTTTGGCAAGAGAGAGCTCA

AGTGCGGAGATGGTATCTTCATATTTAGAGACTCTGATGACTGGCTGAACAAGTACTCATACTATCCAGAAGATCCTGTGA

AGCTTGCATCAATAGTGAAAGCCTCTTTTGAAGAAGGGAAGTGTGGCCTAAATTCAGTTGACTCCCTTGAGCATGAGATG

TGGAGAAGCAGGGCAGATGAGATCAATGCCATTTTTGAGGAAAACGAGGTGGACATTTCTGTTGTCGTGCAGGATCCAA

AGAATGTTTACCAGAGAGGAACTCATCCATTTTCCAGAATTCGGGATGGTCTGCAGTATGGTTGGAAGACTTGGGGTAAG

AACCTTGTGTTCTCCCCAGGGAGGAAGAATGGAAGCTTCATCATAGATGGAAAGTCCAGGAAAGAATGCCCGTTTTCAAA

-continued

CCGGGTCTGGAATTCTTTCCAGATAGAGGAGTTTGGGACGGGAGTGTTCACCACACGCGTGTACATGGACGCAGTCTTTG

AATACACCATAGACTGCGATGGATCTATCTTGGGTGCAGCGGTGAACGGAAAAAAGAGTGCCCATGGCTCTCCAACATTT

TGGATGGGAAGTCATGAAGTAAATGGGACATGGATGATCCACACCTTGGAGGCATTAGATTACAAGGAGTGTGAGTGGC

CACTGACACATACGATTGGAACATCAGTTGAAGAGAGTGAAATGTTCATGCCGAGATCAATCGGAGGCCCAGTTAGCTCT

CACAATCATATCCCTGGATACAAGGTTCAGACGAACGGACCTTGGATGCAGGTACCACTAGAAGTGAAGAGAGAAGCTT

GCCCAGGGACTAGCGTGATCATTGATGGCAACTGTGATGGACGGGGAAAATCAACCAGATCCACCACGGATAGCGGGAA

AGTTATTCCTGAATGGTGTTGCCGCTCCTGCACAATGCCGCCTGTGAGCTTCCATGGTAGTGATGGGTGTTGGTATCCCAT

GGAAATTAGGCCAAGGAAAACGCATGAAAGCCATCTGGTGCGCTCCTGGGTTACAGCTGGAGAAATACATGCTGTCCCTT

TTGGTTTGGTGAGCATGATGATAGCAATGGAAGTGGTCCTAAGGAAAAGACAGGGACCAAAGCAAATGTTGGTTGGAG

GAGTAGTGCTCTTGGGAGCAATGCTGGTCGGGCAAGTAACTCTCCTTGATTTGCTGAAACTCACAGTGGCTGTGGGATTG

CATTTCCATGAGATGAACAATGGAGGAGACGCCATGTATATGGCGTTGATTGCTGCCTTTTCAATCAGACCAGGGCTGCTC

ATCGGCTTTGGGCTCAGGACCCTATGGAGCCCTCGGGAACGCCTTGTGCTGACCCTAGGAGCAGCCATGGTGGAGATTG

CCTTGGGTGGCGTGATGGGCGGCCTGTGGAAGTATCTAAATGCAGTTTCTCTCTGCATCCTGACAATAAATGCTGTTGCTT

CTAGGAAAGCATCAAATACCATCTTGCCCCTCATGGCTCTGTTGACACCTGTCACTATGGCTGAGGTGAGACTTGCCGCAA

TGTTCTTTTGTGCCGTGGTTATCATAGGGGTCCTTCACCAGAATTTCAAGGACACCTCCATGCAGAAGACTATACCTCTGGT

GGCCCTCACACTCACATCTTACCTGGGCTTGACACAACCTTTTTTGGGCCTGTGTGCATTTCTGGCAACCCGCATATTTGGG

CGAAGGAGTATCCCAGTGAATGAGGCACTCGCAGCAGCTGGTCTAGTGGGAGTGCTGGCAGGACTGGCTTTTCAGGAGA

TGGAGAACTTCCTTGGTCCGATTGCAGTTGGAGGACTCCTGATGATGCTGGTTAGCGTGGCTGGGAGGGTGGATGGGCT

AGAGCTCAAGAAGCTTGGTGAAGTTTCATGGGAAGAGGAGGCGGAGATCAGCGGGAGTTCCGCCCGCTATGATGTGGC

ACTCAGTGAACAAGGGGAGTTCAAGCTGCTTTCTGAAGAGAAAGTGCCATGGGACCAGGTTGTGATGACCTCGCTGGCC

TTGGTTGGGGCTGCCCTCCATCCATTTGCTCTTCTGCTGGTCCTTGCTGGGTGGCTGTTTCATGTCAGGGGAGCTAGGAGA

AGTGGGGATGTCTTGTGGGATATTCCCACTCCTAAGATCATCGAGGAATGTGAACATCTGGAGGATGGGATTTATGGCAT

ATTCCAGTCAACCTTCTTGGGGGCCTCCCAGCGAGGAGTGGGAGTGGCACAGGGAGGGGTGTTCCACACAATGTGGCAT

GTCACAAGAGGAGCTTTCCTTGTCAGGAATGGCAAGAAGTTGATTCCATCTTGGGCTTCAGTAAAGGAAGACCTTGTCGC

CTATGGTGGCTCATGGAAGTTGGAAGGCAGATGGGATGGAGAGGAAGAGGTCCAGTTGATCGCGGCTGTTCCAGGAAA

GAACGTGGTCAACGTCCAGACAAAACCGAGCTTGTTCAAAGTGAGGAATGGGGGAGAAATCGGGGCTGTCGCTCTTGAC

TATCCGAGTGGCACTTCAGGATCTCCTATTGTTAACAGGAACGGAGAGGTGATTGGGCTGTACGGCAATGGCATCCTTGT

CGGTGACAACTCCTTCGTGTCCGCCATATCCCAGACTGAGGTGAAGGAAGAAGGAAAGGAGGAGCTCCAAGAGATCCCG

ACAATGCTAAAGAAAGGAATGACAACTGTCCTTGATTTTCATCCTGGAGCTGGGAAGACAAGACGTTTCCTCCCACAGAT

CTTGGCCGAGTGCGCACGGAGACGCTTGCGCACTCTTGTGTTGGCCCCCACCAGGGTTGTTCTTTCTGAAATGAAGGAGG

CTTTTCACGGCCTGGACGTGAAATTCCACACACAGGCTTTTTCCGCTCACGGCAGCGGGAGAGAAGTCATTGATGCTATGT

GCCATGCCACCCTAACTTACAGGATGTTGGAACCAACTAGGGTTGTTAACTGGGAAGTGATCATTATGGATGAAGCCCAT

TTTTTGGATCCAGCTAGCATAGCCGCTAGAGGTTGGGCAGCGCACAGAGCTAGGGCAAATGAAAGTGCAACAATCTTGAT

GACAGCCACACCGCCTGGGACTAGTGATGAATTTCCACATTCAAATGGTGAAATAGAAGATGTTCAAACGGACATACCCA

GTGAGCCCTGGAACACAGGGCATGACTGGATCCTGGCTGACAAAAGGCCCACGGCATGGTTCCTTCCATCCATCAGAGCT

GCAAATGTCATGGCTGCCTCTTTGCGTAAGGCTGGAAAGAGTGTGGTGGTCCTGAACAGGAAAACCTTTGAGAGAGAAT

ACCCCACGATAAAGCAGAAGAAACCTGACTTTATATTGGCCACTGACATAGCTGAAATGGGAGCCAACCTTTGCGTGGAG

CGAGTGCTGGATTGCAGGACGGCTTTTAAGCCTGTGCTTGTGGATGAAGGGAGGAAGGTGGCAATAAAAGGGCCACTTC

GTATCTCCGCATCCTCTGCTGCTCAAAGGAGGGGGCGCATTGGGAGAAATCCCAACAGAGATGGAGACTCATACTACTAT

TCTGAGCCTACAAGTGAAAATAATGCCCACCACGTCTGCTGGTTGGAGGCCTCAATGCTCTTGGACAACATGGAGGTGAG

-continued

GGGTGGAATGGTCGCCCCACTCTATGGCGTTGAAGGAACTAAAACACCAGTTTCCCCTGGTGAAATGAGACTGAGGGAT

GACCAGAGGAAAGTCTTCAGAGAACTAGTGAGGAATTGTGACCTGCCCGTTTGGCTTTCGTGGCAAGTGGCCAAGGCTG

GTTTGAAGACGAATGATCGTAAGTGGTGTTTTGAAGGCCCTGAGGAACATGAGATCTTGAATGACAGCGGTGAAACAGT

GAAGTGCAGGGCTCCTGGAGGAGCAAAGAAGCCTCTGCGCCCAAGGTGGTGTGATGAAAGGGTGTCATCTGACCAGAG

TGCGCTGTCTGAATTTATTAAGTTTGCTGAAGGTAGGAGGGGAGCTGCTGAAGTGCTAGTTGTGCTGAGTGAACTCCCTG

ATTTCCTGGCTAAAAAAGGTGGAGAGGCAATGGATACCATCAGTGTGTTTCTCCACTCTGAGGAAGGCTCTAGGGCTTAC

CGCAATGCACTATCAATGATGCCTGAGGCAATGACAATAGTCATGCTGTTTATACTGGCTGGACTACTGACATCGGGAAT

GGTCATCTTTTTCATGTCTCCCAAAGGCATCAGTAGAATGTCTATGGCGATGGGCACAATGGCCGGCTGTGGATATCTCAT

GTTCCTTGGAGGCGTCAAACCCACTCACATCTCCTATATCATGCTCATATTCTTTGTCCTGATGGTGGTTGTGATCCCCGAG

CCAGGGCAACAAAGGTCCATCCAAGACAACCAAGTGGCATACCTCATTATTGGCATCCTGACGCTGGTTTCAGCGGTGGC

AGCCAACGAGCTAGGCATGCTGGAGAAAACCAAAGAGGACCTCTTTGGGAAGAAGAACTTAATTCCATCTAGTGCTTCAC

CCTGGAGTTGGCCGGATCTTGACCTGAAGCCAGGAGCTGCCTGGACAGTGTACGTTGGCATTGTTACAATGCTCTCTCCA

ATGTTGCACCACTGGATCAAAGTCGAATATGGCAACCTGTCTCTGTCTGGAATAGCCCAGTCAGCCTCAGTCCTTTCTTTCA

TGGACAAGGGGATACCATTCATGAAGATGAATATCTCGGTCATAATGCTGCTGGTCAGTGGCTGGAATTCAATAACAGTG

ATGCCTCTGCTCTGTGGCATAGGGTGCGCCATGCTCCACTGGTCTCTCATTTTACCTGGAATCAAAGCGCAGCAGTCAAAG

CTTGCACAGAGAAGGGTGTTCCATGGCGTTGCCAAGAACCCTGTGGTTGATGGGAATCCAACAGTTGACATTGAGGAAG

CTCCTGAAATGCCTGCCCTTTATGAGAAGAAACTGGCTCTATATCTCCTTCTTGCTCTCAGCCTAGCTTCTGTTGCCATGTGC

AGAACGCCCTTTTCATTGGCTGAAGGCATTGTCCTAGCATCAGCTGCCCTAGGGCCGCTCATAGAGGGAAACACCAGCCT

TCTTTGGAATGGACCCATGGCTGTCTCCATGACAGGAGTCATGAGGGGGAATCACTATGCTTTTGTGGGAGTCATGTACA

ATCTATGGAAGATGAAAACTGGACGCCGGGGGAGCGCGAATGGAAAAACTTTGGGTGAAGTCTGGAAGAGGGAACTGA

ATCTGTTGGACAAGCGACAGTTTGAGTTGTATAAAAGGACCGACATTGTGGAGGTGGATCGTGATACGGCACGCAGGCA

TTTGGCCGAAGGGAAGGTGGACACCGGGGTGGCGGTCTCCAGGGGGACCGCAAAGTTAAGGTGGTTCCATGAGCGTGG

CTATGTCAAGCTGGAAGGTAGGGTGATTGACCTGGGGTGTGGCCGCGGAGGCTGGTGTTACTACGCTGCTGCGCAAAAG

GAAGTGAGTGGGGTCAAAGGATTTACTCTTGGAAGAGACGGCCATGAGAAACCCATGAATGTGCAAAGTCTGGGATGG

AACATCATCACCTTCAAGGACAAAACTGATATCCACCGCCTAGAACCAGTGAAATGTGACACCCTTTTGTGTGACATTGGA

GAGTCATCATCGTCATCGGTCACAGAGGGGGAAAGGACCGTGAGAGTTCTTGATACTGTAGAAAAATGGCTGGCTTGTG

GGGTTGACAACTTCTGTGTGAAGGTGTTAGCTCCATACATGCCAGATGTTCTCGAGAAACTGGAATTGCTCCAAAGGAGG

TTTGGCGGAACAGTGATCAGGAACCCTCTCTCCAGGAATTCCACTCATGAAATGTACTACGTGTCTGGAGCCCGCAGCAAT

GTCACATTTACTGTGAACCAAACATCCCGCCTCCTGATGAGGAGAATGAGGCGTCCAACTGGAAAAGTGACCCTGGAGGC

TGACGTCATCCTCCCAATTGGGACACGCAGTGTTGAGACAGACAAGGGACCCCTGGACAAAGAGGCCATAGAAGAAAGG

GTTGAGAGGATAAAATCTGAGTACATGACCTCTTGGTTTTATGACAATGACAACCCCTACAGGACCTGGCACTACTGTGGC

TCCTATGTCACAAAAACCTCAGGAAGTGCGGCGAGCATGGTAAATGGTGTTATTAAAATTCTGACATATCCATGGGACAG

GATAGAGGAGGTCACAAGAATGGCAATGACTGACACAACCCCTTTTGGACAGCAAAGAGTGTTTAAAGAAAAAGTTGAC

ACCAGAGCAAAGGATCCACCAGCGGGAACTAGGAAGATCATGAAAGTTGTCAACAGGTGGCTGTTCCGCCACCTGGCCA

GAGAAAAGAACCCCAGACTGTGCACAAAGGAAGAATTTATTGCAAAAGTCCGAAGTCATGCAGCCATTGGAGCTTACCTG

GAAGAACAAGAACAGTGGAAGACTGCCAATGAGGCTGTCCAAGACCCAAAGTTCTGGGAACTGGTGGATGAAGAAAGG

AAGCTGCACCAACAAGGCAGGTGTCGGACTTGTGTGTACAACATGATGGGGAAAAGAGAGAAGAAGCTGTCAGAGTTT

GGGAAAGCAAAGGGAAGCCGTGCCATATGGTATATGTGGCTGGGAGCGCGGTATCTTGAGTTTGAGGCCCTGGGATTCC

TGAATGAGGACCATTGGGCTTCCAGGGAAAACTCAGGAGGAGGAGTGGAAGGCATTGGCTTACAATACCTAGGATATGT

GATCAGAGACCTGGCTGCAATGGATGGTGGTGGATTCTACGCGGATGACACCGCTGGATGGGACACGCGCATCACAGAG

GCAGACCTTGATGATGAACAGGAGATCTTGAACTACATGAGCCCACATCACAAAAAACTGGCACAAGCAGTGATGGAAA

-continued

TGACATACAAGAACAAAGTGGTGAAAGTGTTGAGACCAGCCCCAGGAGGGAAAGCCTACATGGATGTCATAAGTCGACG

AGACCAGAGAGGATCCGGGCAGGTAGTGACTTATGCTCTGAACACCATCACCAACTTGAAAGTCCAATTGATCAGAATGG

CAGAAGCAGAGATGGTGATACATCACCAACATGTTCAAGATTGTGATGAATCAGTTCTGACCAGGCTGGAGGCATGGCTC

ACTGAGCACGGATGTAACAGACTGAAGAGGATGGCGGTGAGTGGAGACGACTGTGTGGTCCGGCCCATCGATGACAGG

TTCGGCCTGGCCCTGTCCCATCTCAACGCCATGTCCAAGGTTAGAAAGGACATATCTGAATGGCAGCCATCAAAAGGGTG

GAATGATTGGGAGAATGTGCCCTTCTGTTCCCACCACTTCCATGAACTACAGCTGAAGGATGGCAGGAGGATTGTGGTGC

CTTGCCGAGAACAGGACGAGCTCATTGGGAGAGGAAGGGTGTCTCCAGGAAACGGCTGGATGATCAAGGAAACAGCTT

GCCTCAGCAAAGCCTATGCCAACATGTGGTCACTGATGTATTTTCACAAAAGGGACATGAGGCTACTGTCATTGGCTGTTT

CCTCAGCTGTTCCCACCTCATGGGTTCCACAAGGACGCACAACATGGTCGATTCATGGGAAAGGGGAGTGGATGACCACG

GAAGACATGCTTGAGGTGTGGAACAGAGTATGGATAACCAACAACCCACACATGCAGGACAAGACAATGGTGAAAAAAT

GGAGAGATGTCCCTTATCTAACCAAGAGACAAGACAAGCTGTGCGGATCACTGATTGGAATGACCAATAGGGCCACCTG

GGCCTCCCACATCCATTTGGTCATCCATCGTATCCGAACGCTGATTGGACAGGAGAAATACACTGACTACCTAACAGTCAT

GGACAGGTATTCTGTGGATGCTGACCTGCAACTGGGTGAGCTTATCTGAAACACCATCTAACAGGAATAACCGGGATACA

AACCACGGGTGGAGAACCGGACTCCCCACAACCTGAAACCGGGATATAAACCACGGCTGGAGAACCGGACTCCGCACTT

AAAATGAAACAGAAACCGGGATAAAAACTACGGATGGAGAACCGGACTCCACACATTGAGACAGAAGAAGTTGTCAGCC

CAGAACCCCACACGAGTTTTGCCACTGCTAAGCTGTGAGGCAGTGCAGGCTGGGACAGCCGACCTCCAGGTTGCGAAAA

ACCTGGTTTCTGGGACCTCCCACCCCAGAGTAAAAAGAACGGAGCCTCCGCTACCACCCTCCCACGTGGTGGTAGAAAGA

CGGGGTCTAGAGGTTAGAGGAGACCCTCCAGGGAACAAATAGTGGGACCATATTGACGCCAGGGAAAGACCGGAGTGG

TTCTCTGCTTTTCCTCCAGAGGTCTGTGAGCACAGTTTGCTCAAGAATAAGCAGACCTTTGGATGACAAA

SEQ ID NO: 77

Attenuated Chikungunya "Delta5nsP3" sequence

GATGGCTGCGTGAGACACACGTAGCCTACCAGTTTCTTACTGCTCTACTCTGCAAAGCAAGAGATTAATAACCCATCATGG

ATCCTGTGTACGTGGACATAGACGCTGACAGCGCCTTTTTGAAGGCCCTGCAACGTGCGTACCCCATGTTTGAGGTGGAA

CCAAGGCAGGTCACACCGAATGACCATGCTAATGCTAGAGCGTTCTCGCATCTAGCTATAAAACTAATAGAGCAGGAAAT

TGACCCCGACTCAACCATCCTGGATATCGGCAGTGCGCCAGCAAGGAGGATGATGTCGGACAGGAAGTACCACTGCGTC

TGCCCGATGCGCAGTGCGGAAGATCCCGAGAGACTCGCCAATTATGCGAGAAAGCTAGCATCTGCCGCAGGAAAAGTCC

TGGACAGAAACATCTCTGGAAAGATCGGGGACTTACAAGCAGTAATGGCCGTGCCAGACACGGAGACGCCAACATTCTG

CTTACACACAGACGTCTCATGTAGACAGAGAGCAGACGTCGCTATATACCAAGACGTCTATGCTGTACACGCACCCACGTC

GCTATACCACCAGGCGATTAAAGGGGTCCGAGTGGCGTACTGGGTTGGGTTCGACACAACCCCGTTCATGTACAATGCCA

TGGCGGGTGCCTACCCCTCATACTCGACAAACTGGGCAGATGAGCAGGTACTGAAGGCTAAGAACATAGGATTATGTTCA

ACAGACCTGACGGAAGGTAGACGAGGCAAGTTGTCTATTATGAGAGGGAAAAAGCTAAAACCGTGCGACCGTGTGCTGT

TCTCAGTAGGGTCAACGCTCTACCCGGAAAGCCGCAAGCTACTTAAGAGCTGGCACCTGCCATCGGTGTTCCATTTAAAG

GGCAAACTCAGCTTCACATGCCGCTGTGATACAGTGGTTTCGTGTGAGGGCTACGTCGTTAAGAGAATAACGATGAGCCC

AGGCCTTTATGGAAAAACCACAGGGTATGCGGTAACCCACCACGCAGACGGATTCCTGATGTGCAAGACTACCGACACG

GTTGACGGCGAAAGAATGTCATTCTCGGTGTGCACATACGTGCCGGCGACCATTTGTGATCAAATGACCGGCATCCTTGC

TACAGAAGTCACGCCGGAGGATGCACAGAAGCTGTTGGTGGGGCTGAACCAGAGAATAGTGGTTAACGGCAGAACGCA

ACGGAATACGAACACCATGAAAAATTATCTGCTTCCCGTGGTCGCCCAAGCCTTCAGTAAGTGGGCAAAGGAGTGCCGGA

AAGACATGGAAGATGAAAAACTCCTGGGGGTCAGAGAAAGAACACTGACCTGCTGCTGTCTATGGGCATTCAAGAAGCA

GAAAACACACACGGTCTACAAGAGGCCTGATACCCAGTCAATTCAGAAGGTTCAGGCCGAGTTTGACAGCTTTGTGGTAC

CGAGTCTGTGGTCGTCCGGGTTGTCAATCCCTTTGAGGACTAGAATCAAATGGTTGTTAAGCAAGGTGCCAAAAACCGAC

CTGATCCCATACAGCGGAGACGCCCGAGAAGCCCGGGACGCAGAAAAAGAAGCAGAGGAAGAACGAGAAGCAGAACT

-continued
GACTCGCGAAGCCCTACCACCTCTACAGGCAGCACAGGAAGATGTTCAGGTCGAAATCGACGTGGAACAGCTTGAGGAC

AGAGCGGGCGCAGGAATAATAGAGACTCCGAGAGGAGCTATCAAAGTTACTGCCCAACCAACAGACCACGTCGTGGGA

GAGTACCTGGTACTCTCCCCGCAGACCGTACTACGTAGCCAGAAGCTCAGTCTGATTCACGCTTTGGCGGAGCAAGTGAA

GACGTGCACGCACAACGGACGAGCAGGGAGGTATGCGGTCGAAGCGTACGACGGCCGAGTCCTAGTGCCCTCAGGCTA

TGCAATCTCGCCTGAAGACTTCCAGAGTCTAAGCGAAAGCGCAACGATGGTGTATAACGAAAGAGAGTTCGTAAACAGA

AAGCTACACCATATTGCGATGCACGGACCAGCCCTGAACACCGACGAAGAGTCGTATGAGCTGGTGAGGGCAGAGAGG

ACAGAACACGAGTACGTCTACGACGTGGATCAGAGAAGATGCTGTAAGAAGGAAGAAGCCGCAGGACTGGTACTGGTG

GGCGACTTGACTAATCCGCCCTACCACGAATTCGCATATGAAGGGCTAAAAATCCGCCCTGCCTGCCCATACAAAATTGCA

GTCATAGGAGTCTTCGGAGTACCGGGATCTGGCAAGTCAGCTATTATCAAGAACCTAGTTACCAGGCAGGACCTGGTGAC

TAGCGGAAAGAAAGAAAACTGCCAAGAAATCACCACCGACGTGATGAGACAGAGAGGTCTAGAGATATCTGCACGTACG

GTTGACTCGCTGCTCTTGAATGGATGCAACAGACCAGTCGACGTGTTGTACGTAGACGAGGCGTTTGCGTGCCACTCTGG

AACGCTACTTGCTTTGATCGCCTTGGTGAGACCAAGGCAGAAAGTTGTACTTTGTGGTGACCCGAAGCAGTGCGGCTTCT

TCAATATGATGCAGATGAAAGTCAACTATAATCACAACATCTGCACCCAAGTGTACCACAAAAGTATCTCCAGGCGGTGTA

CACTGCCTGTGACCGCCATTGTGTCATCGTTGCATTACGAAGGCAAAATGCGCACTACGAATGAGTACAACAAGCCGATT

GTAGTGGACACTACAGGCTCAACAAAACCTGACCCTGGAGACCTCGTGTTAACGTGCTTCAGAGGGTGGGTTAAACAACT

GCAAATTGACTATCGTGGATACGAGGTCATGACAGCAGCCGCATCCCAAGGGTTAACCAGAAAAGGAGTTTACGCAGTT

AGACAAAAAGTTAATGAAAACCCGCTCTATGCATCAACGTCAGAGCACGTCAACGTACTCCTAACGCGTACGGAAGGTAA

ACTGGTATGGAAGACACTTTCCGGCGACCCGTGGATAAAGACGCTGCAGAACCCACCGAAAGGAAACTTCAAAGCAACT

ATTAAGGAGTGGGAGGTGGAGCATGCATCAATAATGGCGGGCATCTGCAGTCACCAAATGACCTTCGATACATTCCAAAA

TAAAGCCAACGTTTGTTGGGCTAAGAGCTTGGTCCCTATCCTCGAAACAGCGGGGATAAAACTAAATGATAGGCAGTGGT

CTCAGATAATTCAAGCCTTCAAAGAAGACAAAGCATACTCACCTGAAGTAGCCCTGAATGAAATATGTACGCGCATGTAT

GGGGTGGATCTAGACAGCGGGCTATTTTCTAAACCGTTGGTGTCTGTGTATTACGCGGATAACCACTGGGATAATAGGCC

TGGAGGGAAAATGTTCGGATTTAACCCCGAGGCAGCATCCATTCTAGAAAGAAAGTATCCATTCACAAAAGGGAAGTGG

AACATCAACAAGCAGATCTGCGTGACTACCAGGAGGATAGAAGACTTTAACCCTACCACCAACATCATACCGGCCAACAG

GAGACTACCACACTCATTAGTGGCCGAACACCGCCCAGTAAAAGGGGAAAGAATGGAATGGCTGGTTAACAAGATAAAC

GGCCACCACGTGCTCCTGGTCAGTGGCTATAACCTTGCACTGCCTACTAAGAGAGTCACTTGGGTAGCGCCGTTAGGTGT

CCGCGGAGCGGACTACACATACAACCTAGAGTTGGGTCTGCCAGCAACGCTTGGTAGGTATGACCTAGTGGTCATAAACA

TCCACACACCTTTTCGCATACACCATTACCAACAGTGCGTCGACCACGCAATGAAACTGCAAATGCTCGGGGGTGACTCAT

TGAGACTGCTCAAACCGGGCGGCTCTCTATTGATCAGAGCATATGGTTACGCAGATAGAACCAGTGAACGAGTCATCTGC

GTATTGGGACGCAAGTTTAGATCGTCTAGAGCGTTGAAACCACCATGTGTCACCAGCAACACTGAGATGTTTTTCCTATTC

AGCAACTTTGACAATGGCAGAAGGAATTTCACAACTCATGTCATGAACAATCAACTGAATGCAGCCTTCGTAGGACAGGT

CACCCGAGCAGGATGTGCACCGTCGTACCGGGTAAAACGCATGGACATCGCGAAGAACGATGAAGAGTGCGTAGTCAAC

GCCGCTAACCCTCGCGGGTTACCGGGTGGCGGTGTTTGCAAGGCAGTATACAAAAAATGGCCGGAGTCCTTTAAGAACA

GTGCAACACCAGTGGGAACCGCAAAAACAGTTATGTGCGGTACGTATCCAGTAATCCACGCTGTTGGACCAAACTTCTCT

AATTATTCGGAGTCTGAAGGGGACCGGGAATTGGCAGCTGCCTATCGAGAAGTCGCAAAGGAAGTAACTAGGCTGGGA

GTAAATAGTGTAGCTATACCTCTCCTCTCCACAGGTGTATACTCAGGAGGGAAAGACAGGCTGACCCAGTCACTGAACCA

CCTCTTTACAGCCATGGACTCGACGGATGCAGACGTGGTCATCTACTGCCGCGACAAAGAATGGGAGAAGAAAATATCTG

AGGCCATACAGATGCGGACCCAAGTAGAGCTGCTGGATGAGCACATCTCCATAGACTGCGATATTGTTCGCGTGCACCCT

GACAGCAGCTTGGCAGGCAGAAAAGGATACAGCACCACGGAAGGCGCACTGTACTCATATCTAGAAGGGACCCGTTTTC

ATCAGACGGCTGTGGATATGGCGGAGATACATACTATGTGGCCAAAGCAAACAGAGGCCAATGAGCAAGTCTGCCTATA

TGCCCTGGGGGAAAGTATTGAATCGATCAGGCAGAAATGCCCGGTGGATGATGCAGACGCATCATCTCCCCCCAAAACTG

-continued

TCCCGTGCCTTTGCCGTTACGCTATGACTCCAGAACGCGTCACCCGGCTTCGCATGAACCACGTCACAAGCATAATTGTGT

GTTCTTCGTTTCCCCTCCCAAAGTACAAAATAGAAGGAGTGCAAAAAGTCAAATGCTCTAAGGTAATGCTATTTGACCACA

ACGTGCCATCGCGCGTAAGTCCAAGGGCTTATAGAGGTGCCGCTGCCGGTAACCTTGCGGCCGTGTCTGATTGGGTAATG

AGCACCGTACCTGTCGCGCCGCCCAGAAGAAGGCGAGGGAGAAACCTGACTGTGACATGTGACGAGAGAGAAGGGAAT

ATAACACCCATGGCTAGCGTCCGATTCTTTAGGGCAGAGCTGTGTCCGGTCGTACAAGAAACAGCGGAGACGCGTGACA

CAGCAATGTCTCTTCAGGCACCACCGAGTACCGCCACGGAACCGAATCATCCGCCGATCTCCTTCGGAGCATCAAGCGAG

ACGTTCCCCATTACATTTGGGGACTTCAACGAAGGAGAAATCGAAAGCTTGTCTTCTGAGCTACTAACTTTCGGAGACTTC

TTACCAGGAGAAGTGGATGACTTGACAGACAGCGACTGGTCCACGTGCTCAGACACGGACGACGAGTTAAGACTAGACA

GGGCAGGTGGGTATATATTCTCGTCGGACACCGGTCCAGGTCATTTACAACAGAAGTCAGTACGCCAGTCAGTGCTGCCG

GTGAACACCCTGGAGGAAGTCCACGAGGAGAAGTGTTACCCACCTAAGCTGGATGAAGCAAAGGAGCAACTATTACTTA

AGAAACTCCAGGAGAGTGCATCCATGGCCAACAGAAGCAGGTATCAGTCGCGCAAAGTAGAAAACATGAAAGCAGCAAT

CATCCAGAGACTAAAGAGAGGCTGTAGACTATACTTAATGTCAGAGACCCCAAAAGTCCCTACTTACCGGACTACATATCC

GGCGCCTGTGTACTCGCCTCCGATCAACGTCCGATTGTCCAATCCCGAGTCCGCAGTGGCAGCATGCAATGAGTTCTTAGC

TAGAAACTATCCAACTGTCTCATCATACCAAATTACCGACGAGTATGATGCATATCTAGACATGGTGGACGGGTCGGAGA

GTTGCCTGGACCGAGCGACATTCAATCCGTCAAAACTCAGGAGCTACCCGAAACAGCACGCTTACCACGCGCCCTCCATC

AGAAGCGCTGTACCGTCCCCATTCCAGAACACACTACAGAATGTACTGGCAGCAGCCACGAAAAGAAACTGCAACGTCAC

ACAGATGAGGGAATTACCCACTTTGGACTCAGCAGTATTCAACGTGGAGTGTTTCAAAAAATTCGCATGCAACCAAGAAT

ACTGGGAAGAATTTGCTGCCAGCCCTATTAGGATAACAACTGAGAATTTAGCAACCTATGTTACTAAACTAAAAGGGCCA

AAAGCAGCAGCGCTATTCGCAAAAACCCATAATCTACTGCCACTACAGGAAGTACCAATGGATAGGTTCACAGTAGATAT

GAAAAGGGACGTAAAGGTGACTCCTGGTACAAAGCATACAGAGGAAAGACCTAAGGTGCAGGTTATACAGGCGGCTGA

ACCCTTGGCGACAGCATACCTATGTGGGATTCACAGAGAGCTGGTTAGGAGGCTGAACGCCGTCCTCCTACCCAATGTAC

ATACACTATTTGACATGTCTGCCGAGGATTTCGATGCCATCATAGCCGCACACTTTAAGCCAGGAGACACTGTTTTGGAAA

CGGACATAGCCTCCTTTGATAAGAGCCAAGATGATTCACTTGCGCTTACTGCTTTGATGCTGTTAGAGGATTTAGGGGTGG

ATCACTCCCTGCTGGACTTGATAGAGGCTGCTTTCGGAGAGATTTCCAGCTGTCACCTACCGACAGGTACGCGCTTCAAGT

TCGGCGCCATGATGAAATCAGGTATGTTCCTAACTCTGTTCGTCAACACATTGTTAAACATCACCATCGCCAGCCGAGTGC

TGGAAGATCGTCTGACAAAATCCGCGTGCGCGGCCTTCATCGGCGACGACAACATAATACATGGAGTCGTCTCCGATGAA

TTGATGGCAGCCAGATGTGCCACTTGGATGAACATGGAAGTGAAGATCATAGATGCAGTTGTATCCTTGAAAGCCCCTTA

CTTTTGTGGAGGGTTTATACTGCACGATACTGTGACAGGAACAGCTTGCAGAGTGGCAGACCCGCTAAAAAGGCTTTTTA

AACTGGGCAAACCGCTAGCGGCAGGTGACGAACAAGATGAAGATAGAAGACGAGCGCTGGCTGACGAAGTGATCAGAT

GGCAACGAACAGGGCTAATTGATGAGCTGGAGAAAGCGGTATACTCTAGGTACGAAGTGCAGGGTATATCAGTTGTGGT

AATGTCCATGGCCACCTTTGCAAGCTCCAGATCCAACTTCGAGAAGCTCAGAGGACCCGTCATAACTTTGTACGGCGGTCC

TAAATAGGTACGCACTACAGCTACCTATTTTGCAGAAGCCGACAGCAAGTATCTAAACACTAATCAGCTACAATGGAGTTC

ATCCCAACCCAAACTTTTTACAATAGGAGGTACCAGCCTCGACCCTGGACTCCGCGCCCTACTATCCAAGTCATCAGGCCC

AGACCGCGCCCTCAGAGGCAAGCTGGGCAACTTGCCCAGCTGATCTCAGCAGTTAATAAACTGACAATGCGCGCGGTACC

ACAACAGAAGCCACGCAGGAATCGGAAGAATAAGAAGCAAAAGCAAAAACAACAGGCGCCACAAAACAACACAAATCA

AAAGAAGCAGCCACCTAAAAAGAAACCGGCTCAAAAGAAAAAGAAGCCGGGCCGCAGAGAGAGGATGTGCATGAAAAT

CGAAAATGATTGTATTTTCGAAGTCAAGCACGAAGGTAAGGTAACAGGTTACGCGTGCCTGGTGGGGGACAAAGTAATG

AAACCAGCACACGTAAAGGGGACCATCGATAACGCGGACCTGGCCAAACTGGCCTTTAAGCGGTCATCTAAGTATGACCT

TGAATGCGCGCAGATACCCGTGCACATGAAGTCCGACGCTTCGAAGTTCACCCATGAGAAACCGGAGGGGTACTACAACT

GGCACCACGGAGCAGTACAGTACTCAGGAGGCCGGTTCACCATCCCTACAGGTGCTGGCAAACCAGGGGACAGCGGCA

-continued

GACCGATCTTCGACAACAAGGGACGCGTGGTGGCCATAGTCTTAGGAGGAGCTAATGAAGGAGCCCGTACAGCCCTCTC

GGTGGTGACCTGGAATAAAGACATTGTCACTAAAATCACCCCCGAGGGGGCCGAAGAGTGGAGTCTTGCCATCCCAGTT

ATGTGCCTGTTGGCAAACACCACGTTCCCCTGCTCCCAGCCCCCTTGCACGCCCTGCTGCTACGAAAAGGAACCGGAGGA

AACCCTACGCATGCTTGAGGACAACGTCATGAGACCTGGGTACTATCAGCTGCTACAAGCATCCTTAACATGTTCTCCCCA

CCGCCAGCGACGCAGCACCAAGGACAACTTCAATGTCTATAAAGCCACAAGACCATACTTAGCTCACTGTCCCGACTGTG

GAGAAGGGCACTCGTGCCATAGTCCCGTAGCACTAGAACGCATCAGAAATGAAGCGACAGACGGGACGCTGAAAATCCA

GGTCTCCTTGCAAATCGGAATAAAGACGGATGACAGCCACGATTGGACCAAGCTGCGTTATATGGACAACCACATGCCAG

CAGACGCAGAGAGGGCGGGGCTATTTGTAAGAACATCAGCACCGTGTACGATTACTGGAACAATGGGACACTTCATCCT

GGCCCGATGTCCAAAAGGGGAAACTCTGACGGTGGGATTCACTGACAGTAGGAAGATTAGTCACTCATGTACGCACCCAT

TTCACCACGACCCTCCTGTGATAGGTCGGGAAAAATTCCATTCCCGACCGCAGCACGGTAAAGAGCTACCTTGCAGCACG

TACGTGCAGAGCACCGCCGCAACTACCGAGGAGATAGAGGTACACATGCCCCCAGACACCCCTGATCGCACATTAATGTC

ACAACAGTCCGGCAACGTAAAGATCACAGTCAATGGCCAGACGGTGCGGTACAAGTGTAATTGCGGTGGCTCAAATGAA

GGACTAACAACTACAGACAAAGTGATTAATAACTGCAAGGTTGATCAATGTCATGCCGCGGTCACCAATCACAAAAAGTG

GCAGTATAACTCCCCTCTGGTCCCGCGTAATGCTGAACTTGGGGACCGAAAAGGAAAAATTCACATCCCGTTTCCGCTGGC

AAATGTAACATGCAGGGTGCCTAAAGCAAGGAACCCCACCGTGACGTACGGGAAAAACCAAGTCATCATGCTACTGTATC

CTGACCACCCAACACTCCTGTCCTACCGGAATATGGGAGAAGAACCAAACTATCAAGAAGAGTGGGTGATGCATAAGAA

GGAAGTCGTGCTAACCGTGCCGACTGAAGGGCTCGAGGTCACGTGGGGCAACAACGAGCCGTATAAGTATTGGCCGCAG

TTATCTACAAACGGTACAGCCCATGGCCACCCGCATGAGATAATTCTGTATTATTATGAGCTGTACCCCACTATGACTGTA

GTAGTTGTGTCAGTGGCCACGTTCATACTCCTGTCGATGGTGGGTATGGCAGCGGGGATGTGCATGTGTGCACGACGCA

GATGCATCACACCGTATGAACTGACACCAGGAGCTACCGTCCCTTTCCTGCTTAGCCTAATATGCTGCATCAGAACAGCTA

AAGCGGCCACATACCAAGAGGCTGCGATATACCTGTGGAACGAGCAGCAACCTTTGTTTTGGCTACAAGCCCTTATTCCG

CTGGCAGCCCTGATTGTTCTATGCAACTGTCTGAGACTCTTACCATGCTGCTGTAAAACGTTGGCTTTTTTAGCCGTAATGA

GCGTCGGTGCCCACACTGTGAGCGCGTACGAACACGTAACAGTGATCCCGAACACGGTGGGAGTACCGTATAAGACTCT

AGTCAATAGACCTGGCTACAGCCCCATGGTATTGGAGATGGAACTACTGTCAGTCACTTTGGAGCCAACACTATCGCTTGA

TTACATCACGTGCGAGTACAAAACCGTCATCCCGTCTCCGTACGTGAAGTGCTGCGGTACAGCAGAGTGCAAGGACAAAA

ACCTACCTGACTACAGCTGTAAGGTCTTCACCGGCGTCTACCCATTTATGTGGGGCGGCGCCTACTGCTTCTGCGACGCTG

AAAACACGCAGTTGAGCGAAGCACACGTGGAGAAGTCCGAATCATGCAAAACAGAATTTGCATCAGCATACAGGGCTCA

TACCGCATCTGCATCAGCTAAGCTCCGCGTCCTTTACCAAGGAAATAACATCACTGTAACTGCCTATGCAAACGGCGACCA

TGCCGTCACAGTTAAGGACGCCAAATTCATTGTGGGGCCAATGTCTTCAGCCTGGACACCTTTCGACAACAAAATTGTGGT

GTACAAAGGTGACGTCTATAACATGGACTACCCGCCCTTTGGCGCAGGAAGACCAGGACAATTTGGCGATATCCAAAGTC

GCACACCTGAGAGTAAAGACGTCTATGCTAATACACAACTGGTACTGCAGAGACCGGCTGTGGGTACGGTACACGTGCC

ATACTCTCAGGCACCATCTGGCTTTAAGTATTGGCTAAAAGAACGCGGGGCGTCGCTGCAGCACACAGCACCATTTGGCT

GCCAAATAGCAACAAACCCGGTAAGAGCGGTGAACTGCGCCGTAGGGAACATGCCCATCTCCATCGACATACCGGAAGC

GGCCTTCACTAGGGTCGTCGACGCGCCCTCTTTAACGGACATGTCGTGCGAGGTACCAGCCTGCACCCATTCCTCAGACTT

TGGGGGCGTCGCCATTATTAAATATGCAGCCAGCAAGAAAGGCAAGTGTGCGGTGCATTCGATGACTAACGCCGTCACTA

TTCGGGAAGCTGAGATAGAAGTTGAAGGGAATTCTCAGCTGCAAATCTCTTTCTCGACGGCCTTAGCCAGCGCCGAATTC

CGCGTACAAGTCTGTTCTACACAAGTACACTGTGCAGCCGAGTGCCACCCCCCGAAGGACCACATAGTCAACTACCCGGC

GTCACATACCACCCTCGGGGTCCAGGACATCTCCGCTACGGCGATGTCATGGGTGCAGAAGATCACGGGAGGTGTGGGA

CTGGTTGTTGCTGTTGCCGCACTGATTCTAATCGTGGTGCTATGCGTGTCGTTCAGCAGGCACTAACTTGACAATTAAGTA

TGAAGGTATATGTGTCCCCTAAGAGACACACTGTACATAGCAAATAATCTATAGATCAAAGGGCTACGCAACCCCTGAAT

AGTAACAAAATACAAAATCACTAAAAATTATAAAAACAGAAAAATACATAAATAGGTATACGTGTCCCCTAAGAGACACA

-continued

TTGTATGTAGGTGATAAGTATAGATCAAAGGGCCGAATAACCCCTGAATAGTAACAAAATATGAAAATCAATAAAAATCA

TAAAATAGAAAAACCATAAACAGAAGTAGTTCAAAGGGCTATAAAACCCCTGAATAGTAACAAAACATAAAATTAATAAA

AATCAAATGAATACCATAATTGGCAAACGGAAGAGATGTAGGTACTTAAGCTTCCTAAAAGCAGCCGAACTCACTTTGAG

AAGTAGGCATAGCATACCGAACTCTTCCACGATTCTCCGAACCCACAGGGACGTAGGAGATGTTATTTTGTTTTTAATATTT

CAAAAAAAAAAAAAAAAAAAAAAA

SEQ ID NO: 78

ZIKV Sequence H/PF/2013 as sequenced

CAGACTGCGACAGTTCGAGTTTGAAGCGAAAGCTAGCAACAGTATCAACAGGTTTTATTTTGGATTTGGAAACGAGAGTT

TCTGGTCATGAAAAACCCAAAAAAGAAATCCGGAGGATTCCGGATTGTCAATATGCTAAAACGCGGAGTAGCCCGTGTG

AGCCCCTTTGGGGGCTTGAAGAGGCTGCCAGCCGGACTTCTGCTGGGTCATGGGCCCATCAGGATGGTCTTGGCGATTCT

AGCCTTTTTGAGATTCACGGCAATCAAGCCATCACTGGGTCTCATCAATAGATGGGGTTCAGTGGGGAAAAAAGAGGCTA

TGGAAATAATAAAGAAGTTCAAGAAAGATCTGGCTGCCATGCTGAGAATAATCAATGCTAGGAAGGAGAAGAAGAGAC

GAGGCGCAGATACTAGTGTCGGAATTGTTGGCCTCCTGCTGACCACAGCTATGGCAGCGGAGGTCACTAGACGTGGGAG

TGCATACTATATGTACTTGGACAGAAACGACGCTGGGGAGGCCATATCTTTTCCAACCACATTGGGGATGAATAAGTGTT

ATATACAGATCATGGATCTTGGACACATGTGTGATGCCACCATGAGCTATGAATGCCCTATGCTGGATGAGGGGGTGGAA

CCAGATGACGTCGATTGTTGGTGCAACACGACGTCAACTTGGGTTGTGTACGGAACCTGCCATCACAAAAAAGGTGAAGC

ACGGAGATCTAGAAGAGCTGTGACGCTCCCCTCCCATTCCACTAGGAAGCTGCAAACGCGGTCGCAAACCTGGTTGGAAT

CAAGAGAATACACAAAGCACTTGATTAGAGTCGAAAATTGGATATTCAGGAACCCTGGCTTCGCGTTAGCAGCAGCTGCC

ATCGCTTGGCTTTTGGGAAGCTCAACGAGCCAAAAAGTCATATACTTGGTCATGATACTGCTGATTGCCCCGGCATACAGC

ATCAGGTGCATAGGAGTCAGCAATAGGGACTTTGTGGAAGGTATGTCAGGTGGGACTTGGGTTGATGTTGTCTTGGAAC

ATGGAGGTTGTGTCACCGTAATGGCACAGGACAAACCGACTGTCGACATAGAGCTGGTTACAACAACAGTCAGCAACAT

GGCGGAGGTAAGATCCTACTGCTATGAGGCATCAATATCGGACATGGCTTCGGACAGCCGCTGCCCAACACAAGGTGAA

GCCTACCTTGACAAGCAATCAGACACTCAATATGTCTGCAAAAGAACGTTAGTGGACAGAGGCTGGGGAAATGGATGTG

GACTTTTTGGCAAAGGGAGCCTGGTGACATGCGCTAAGTTTGCATGCTCCAAGAAAATGACCGGGAAGAGCATCCAGCC

AGAGAATCTGGAGTACCGGATAATGCTGTCAGTTCATGGCTCCCAGCACAGTGGGATGATCGTTAATGACACAGGACATG

AAACTGATGAGAATAGAGCGAAGGTTGAGATAACGCCCAATTCACCAAGAGCCGAAGCCACCCTGGGGGGTTTTGGAAG

CCTAGGACTTGATTGTGAACCGAGGACAGGCCTTGACTTTTCAGATTTGTATTACTTGACTATGAATAACAAGCACTGGTT

GGTTCACAAGGAGTGGTTCCACGACATTCCATTACCTTGGCACGCTGGGGCAGACACCGGAACTCCACACTGGAACAACA

AAGAAGCACTGGTAGAGTTCAAGGACGCACATGCCAAAAGGCAAACTGTCGTGGTTCTAGGGAGTCAAGAAGGAGCAG

TTCACACGGCCCTTGCTGGAGCTCTGGAGGCTGAGATGGATGGTGCAAAGGGAAGGCTGTCCTCTGGCCACTTGAAATG

TCGCCTGAAAATGGATAAACTTAGATTGAAGGGCGTGTCATACTCCTTGTGTACCGCAGCGTTCACATTCACCAAGATCCC

GGCTGAAACACTGCACGGGACAGTCACAGTGGAGGTACAGTACGCAGGGACAGATGGACCTTGCAAGGTTCCAGCTCAG

ATGGCGGTGGACATGCAAACTCTGACCCCAGTTGGGAGGTTGATAACCGCTAACCCCGTAATCACTGAAAGCACTGAGAA

CTCTAAGATGATGCTGGAACTTGATCCACCATTTGGGGACTCTTACATTGTCATAGGAGTCGGGGAGAAGAAGATCACCC

ACCACTGGCACAGGAGTGGCAGCACCATTGGAAAAGCATTTGAAGCCACTGTGAGAGGTGCCAAGAGAATGGCAGTCTT

GGGAGACACAGCCTGGGACTTTGGATCAGTTGGAGGCGCTCTCAACTCATTGGGCAAGGGCATCCATCAAATTTTTGGAG

CAGCTTTCAAATCATTGTTTGGAGGAATGTCCTGGTTCTCACAAATTCTCATTGGAACGTTGCTGATGTGGTTGGGTCTGA

ACACAAAGAATGGATCTATTTCCCTTATGTGCTTGGCCTTAGGGGGAGTGTTGATCTTCTTATCCACAGCTGTCTCTGCTGA

TGTGGGGTGCTCGGTGGACTTCTCAAAGAAGGAGACGAGATGCGGTACAGGGGTGTTCGTCTATAACGACGTTGAAGCC

TGGAGGGACAGGTACAAGTACCATCCTGACTCCCCCCGTAGATTGGCAGCAGCAGTCAAGCAAGCCTGGGAAGATGGTA

TCTGTGGGATCTCCTCTGTTTCAAGAATGGAAAACATCATGTGGAGATCAGTAGAAGGGGAGCTCAACGCAATCCTGGAA

-continued

GAGAATGGAGTTCAACTGACGGTCGTTGTGGGATCTGTAAAAAACCCCATGTGGAGAGGTCCACAGAGATTGCCCGTGC

CTGTGAACGAGCTGCCCCACGGCTGGAAGGCTTGGGGGAAATCGTACTTCGTCAGAGCAGCAAAGACAAATAACAGCTT

TGTCGTGGATGGTGACACACTGAAGGAATGCCCACTCAAACATAGAGCATGGAACAGCTTTCTTGTGGAGGATCATGGGT

TCGGGGTATTTCACACTAGTGTCTGGCTCAAGGTTAGAGAAGATTATTCATTAGAGTGTGATCCAGCCGTTATTGGAACAG

CTGTTAAGGGAAAGGAGGCTGTACACAGTGATCTAGGCTACTGGATTGAGAGTGAGAAGAATGACACATGGAGGCTGA

AGAGGGCCCATCTGATCGAGATGAAAACATGTGAATGGCCAAAGTCCCACACATTGTGGACAGATGGAATAGAAGAGAG

TGATCTGATCATACCCAAGTCTTTAGCTGGGCCACTCAGCCATCACAATACCAGAGAGGGCTACAGGACCCAAATGAAAG

GGCCATGGCACAGTGAAGAGCTTGAAATTCGGTTTGAGGAATGCCCAGGCACTAAGGTCCACGTGGAGGAAACATGTGG

AACAAGAGGACCATCTCTGAGATCAACCACTGCAAGCGGAAGGGTGATCGAGGAATGGTGCTGCAGGGAGTGCACAAT

GCCCCCACTGTCGTTCCGGGCTAAAGATGGCTGTTGGTATGGAATGGAGATAAGGCCCAGGAAAGAACCAGAAAGTAAC

TTAGTAAGGTCAATGGTGACTGCAGGATCAACTGATCACATGGATCACTTCTCCCTTGGAGTGCTTGTGATTCTGCTCATG

GTGCAGGAAGGGCTGAAGAAGAGAATGACCACAAAGATCATCATAAGCACATCGATGGCAGTGCTGGTAGCTATGATCC

TGGGAGGATTTTCAATGAGTGACCTGGCTAAGCTTGCAATTTTGATGGGTGCCACCTTCGCGGAAATGAACACTGGAGGA

GATGTAGCTCATCTGGCGCTGATAGCGGCATTCAAAGTCAGACCAGCGTTGCTGGTATCTTTCATCTTCAGAGCTAATTGG

ACACCCCGTGAAAGCATGCTGCTGGCCTTGGCCTCGTGTCTTTTGCAAACTGCGATCTCCGCCTTGGAAGGCGACCTGATG

GTTCTCATCAATGGTTTTGCTTTGGCCTGGTTGGCAATACGAGCGATGGTTGTTCCACGCACTGATAACATCACCTTGGCA

ATCCTGGCTGCTCTGACACCACTGGCCCGGGGCACACTGCTTGTGGCGTGGAGAGCAGGCCTTGCTACTTGCGGGGGGTT

TATGCTCCTCTCTCTGAAGGGAAAAGGCAGTGTGAAGAAGAACTTACCATTTGTCATGGCCCTGGGACTAACCGCTGTGA

GGCTGGTCGACCCCATCAACGTGGTGGGACTGCTGTTGCTCACAAGGAGTGGGAAGCGGAGCTGGCCCCCTAGCGAAGT

ACTCACAGCTGTTGGCCTGATATGCGCATTGGCTGGAGGGTTCGCCAAGGCAGATATAGAGATGGCTGGGCCCATGGCC

GCGGTCGGTCTGCTAATTGTCAGTTACGTGGTCTCAGGAAAGAGTGTGGACATGTACATTGAAAGAGCAGGTGACATCAC

ATGGGAAAAAGATGCGGAAGTCACTGGAAACAGTCCCCGGCTCGATGTGGCGCTAGATGAGAGTGGTGATTTCTCCCTG

GTGGAGGATGACGGTCCCCCCATGAGAGAGATCATACTCAAGGTGGTCCTGATGACCATCTGTGGCATGAACCCAATAGC

CATACCCTTTGCAGCTGGAGCGTGGTACGTATACGTGAAGACTGGAAAAAGGAGTGGTGCTCTATGGGATGTGCCTGCTC

CCAAGGAAGTAAAAAAGGGGGAGACCACAGATGGAGTGTACAGAGTAATGACTCGTAGACTGCTAGGTTCAACACAAGT

TGGAGTGGGAGTTATGCAAGAGGGGGTCTTTCACACTATGTGGCACGTCACAAAAGGATCCGCGCTGAGAAGCGGTGAA

GGGAGACTTGATCCATACTGGGGAGATGTCAAGCAGGATCTGGTGTCATACTGTGGTCCATGGAAGCTAGATGCCGCCT

GGGACGGGCACAGCGAGGTGCAGCTCTTGGCCGTGCCCCCCGGAGAGAGAGCGAGGAACATCCAGACTCTGCCCGGAA

TATTTAAGACAAAGGATGGGGACATTGGAGCGGTTGCGCTGGATTACCCAGCAGGAACTTCAGGATCTCCAATCCTAGAC

AAGTGTGGGAGAGTGATAGGACTTTATGGCAATGGGGTCGTGATCAAAAATGGGAGTTATGTTAGTGCCATCACCCAAG

GGAGGAGGGAGGAAGAGACTCCTGTTGAGTGCTTCGAGCCTTCGATGCTGAAGAAGAAGCAGCTAACTGTCTTAGACTT

GCATCCTGGAGCTGGGAAAACCAGGAGAGTTCTTCCTGAAATAGTCCGTGAAGCCATAAAAACAAGACTCCGTACTGTGA

TCTTAGCTCCAACCAGGGTTGTCGCTGCTGAAATGGAGGAAGCCCTTAGAGGGCTTCCAGTGCGTTATATGACAACAGCA

GTCAATGTCACCCACTCTGGAACAGAAATCGTCGACTTAATGTGCCATGCCACCTTCACTTCACGTCTACTACAGCCAATCA

GAGTCCCCAACTATAATCTGTATATTATGGATGAGGCCCACTTCACAGATCCCTCAAGTATAGCAGCAAGAGGATACATTT

CAACAAGGGTTGAGATGGGCGAGGCGGCTGCCATCTTCATGACCGCCACGCCACCAGGAACCCGTGACGCATTTCCGGA

CTCCAACTCACCAATTATGGACACCGAAGTGGAAGTCCCAGAGAGAGCCTGGAGCTCAGGCTTTGATTGGGTGACGGATC

ATTCTGGAAAAACAGTTTGGTTTGTTCCAAGCGTGAGGAACGGCAATGAGATCGCAGCTTGTCTGACAAAGGCTGGAAA

ACGGGTCATACAGCTCAGCAGAAAGACTTTTGAGACAGAGTTCCAGAAAACAAAACATCAAGAGTGGGACTTTGTCGTG

ACAACTGACATTTCAGAGATGGGCGCCAACTTTAAAGCTGACCGTGTCATAGATTCCAGGAGATGCCTAAAGCCGGTCAT

ACTTGATGGCGAGAGAGTCATTCTGGCTGGACCCATGCCTGTCACACATGCCAGCGCTGCCCAGAGGAGGGGGCGCATA

-continued

GGCAGGAATCCCAACAAACCTGGAGATGAGTATCTGTATGGAGGTGGGTGCGCAGAGACTGACGAAGACCATGCACACT

GGCTTGAAGCAAGAATGCTCCTTGACAATATTTACCTCCAAGATGGCCTCATAGCCTCGCTCTATCGACCTGAGGCCGACA

AAGTAGCAGCCATTGAGGGAGAGTTCAAGCTTAGGACGGAGCAAAGGAAGACCTTTGTGGAACTCATGAAAAGAGGAG

ATCTTCCTGTTTGGCTGGCCTATCAGGTTGCATCTGCCGGAATAACCTACACAGATAGAAGATGGTGCTTTGATGGCACGA

CCAACAACACCATAATGGAAGACAGTGTGCCGGCAGAGGTGTGGACCAGACACGGAGAGAAAAGAGTGCTCAAACCGA

GGTGGATGGACGCCAGAGTTTGTTCAGATCATGCGGCCCTGAAGTCATTCAAGGAGTTTGCCGCTGGGAAAAGAGGAGC

GGCTTTTGGAGTGATGGAAGCCCTGGGAACACTGCCAGGACACATGACAGAGAGATTCCAGGAAGCCATTGACAACCTC

GCTGTGCTCATGCGGGCAGAGACTGGAAGCAGGCCTTACAAAGCCGCGGCGGCCCAATTGCCGGAGACCCTAGAGACCA

TTATGCTTTTGGGGTTGCTGGGAACAGTCTCGCTGGGAATCTTTTTCGTCTTGATGAGGAACAAGGGCATAGGGAAGATG

GGCTTTGGAATGGTGACTCTTGGGGCCAGCGCATGGCTCATGTGGCTCTCGGAAATTGAGCCAGCCAGAATTGCATGTGT

CCTCATTGTTGTGTTCCTATTGCTGGTGGTGCTCATACCTGAGCCAGAAAAGCAAAGATCTCCCCAGGACAACCAAATGGC

AATCATCATCATGGTAGCAGTAGGTCTTCTGGGCTTGATTACCGCCAATGAACTCGGATGGTTGGAGAGAACAAAGAGTG

ACCTAAGCCATCTAATGGGAAGGAGAGAGGAGGGGGCAACCATAGGATTCTCAATGGACATTGACCTGCGGCCAGCCTC

AGCTTGGGCCATCTATGCTGCCTTGACAACTTTCATTACCCCAGCCGTCCAACATGCAGTGACCACTTCATACAACAACTAC

TCCTTAATGGCGATGGCCACGCAAGCTGGAGTGTTGTTTGGTATGGGCAAAGGGATGCCATTCTACGCATGGGACTTTGG

AGTCCCGCTGCTAATGATAGGTTGCTACTCACAATTAACACCCCTGACCCTAATAGTGGCCATCATTTTGCTCGTGGCGCAC

TACATGTACTTGATCCCAGGGCTGCAGGCAGCAGCTGCGCGTGCTGCCCAGAAGAGAACGGCAGCTGGCATCATGAAGA

ACCCTGTTGTGGATGGAATAGTGGTGACTGACATTGACACAATGACAATTGACCCCCAAGTGGAGAAAAAGATGGGACA

GGTGCTACTCATAGCAGTAGCCGTCTCCAGCGCCATACTGTCGCGGACCGCCTGGGGGTGGGGGGAGGCTGGGGCCCTG

ATCACAGCGGCAACTTCCACTTTGTGGGAAGGCTCTCCGAACAAGTACTGGAACTCCTCTACAGCCACTTCACTGTGTAAC

ATTTTTAGGGGAAGTTACTTGGCTGGAGCTTCTCTAATCTACACAGTAACAAGAAACGCTGGCTTGGTCAAGAGACGTGG

GGGTGGAACAGGAGAGACCCTGGGAGAGAAATGGAAGGCCCGCTTGAACCAGATGTCGGCCCTGGAGTTCTACTCCTAC

AAAAAGTCAGGCATCACCGAGGTGTGCAGAGAAGAGGCCCGCCGCGCCCTCAAGGACGGTGTGGCAACGGGAGGCCAT

GCTGTGTCCCGAGGAAGTGCAAAGCTGAGATGGTTGGTGGAGCGGGGATACCTGCAGCCCTATGGAAAGGTCATTGATC

TTGGATGTGGCAGAGGGGGCTGGAGTTACTACGCCGCCACCATCCGCAAAGTTCAAGAAGTGAAAGGATACACAAAAGG

AGGCCCTGGTCATGAAGAACCCATGTTGGTGCAAAGCTATGGGTGGAACATAGTCCGTCTTAAGAGTGGGGTGGACGTC

TTTCATATGGCGGCTGAGCCGTGTGACACGTTGCTGTGTGACATAGGTGAGTCATCATCTAGTCCTGAAGTGGAAGAAGC

ACGGACGCTCAGAGTCCTCTCCATGGTGGGGGATTGGCTTGAAAAAAGACCAGGAGCCTTTTGTATAAAAGTGTTGTGCC

CATACACCAGCACTATGATGGAAACCCTGGAGCGACTGCAGCGTAGGTATGGGGGAGGACTGGTCAGAGTGCCACTCTC

CCGCAACTCTACACATGAGATGTACTGGGTCTCTGGAGCGAAAAGCAACACCATAAAAAGTGTGTCCACCACGAGCCAGC

TCCTCTTGGGGCGCATGGACGGGCCCAGGAGGCCAGTGAAATATGAGGAGGATGTGAATCTCGGCTCTGGCACGCGGG

CTGTGGTAAGCTGCGCTGAAGCTCCCAACATGAAGATCATTGGTAACCGCATTGAAAGGATCCGCAGTGAGCACGCGGA

AACGTGGTTCTTTGACGAGAACCACCCATATAGGACATGGGCTTACCATGGAAGCTATGAGGCCCCCACACAAGGGTCAG

CGTCCTCTCTAATAAACGGGGTTGTCAGGCTCCTGTCAAAACCCTGGGATGTGGTGACTGGAGTCACAGGAATAGCCATG

ACCGACACCACACCGTATGGTCAGCAAAGAGTTTTCAAGGAAAAAGTGGACACTAGGGTGCCAGACCCCCAAGAAGGCA

CTCGTCAGGTTATGAGCATGGTCTCTTCCTGGTTGTGGAAAGAGCTAGGCAAACACAAACGGCCACGAGTCTGTACCAAA

GAAGAGTTCATCAACAAGGTTCGTAGCAATGCAGCATTAGGGGCAATATTTGAAGAGGAAAAAGAGTGGAAGACTGCAG

TGGAAGCTGTGAACGATCCAAGGTTCTGGGCTCTAGTGGACAAGGAAAGAGAGCACCACCTGAGAGGAGAGTGCCAGA

GTTGTGTGTACAACATGATGGGAAAAAGAGAAAAGAAACAAGGGGAATTTGGAAAGGCCAAGGGCAGCCGCGCCATCT

GGTATATGTGGCTAGGGGCTAGATTTCTAGAGTTCGAAGCCCTTGGATTCTTGAACGAGGATCACTGGATGGGGAGAGA

-continued

GAACTCAGGAGGTGGTGTTGAAGGGCTGGGATTACAAAGACTCGGATATGTCCTAGAAGAGATGAGTCGCATACCAGGA

GGAAGGATGTATGCAGATGACACTGCTGGCTGGGACACCCGCATCAGCAGGTTTGATCTGGAGAATGAAGCTCTAATCA

CCAACCAAATGGAGAAAGGGCACAGGGCCTTGGCATTGGCCATAATCAAGTACACATACCAAAACAAAGTGGTAAAGGT

CCTTAGACCAGCTGAAAAAGGGAAGACAGTTATGGACATTATTTCGAGACAAGACCAAAGGGGGAGCGGACAAGTTGTC

ACTTACGCTCTTAACACATTTACCAACCTAGTGGTGCAACTCATTCGGAATATGGAGGCTGAGGAAGTTCTAGAGATGCAA

GACTTGTGGCTGCTGCGGAGGTCAGAGAAAGTGACCAACTGGTTGCAGAGCAACGGATGGGATAGGCTCAAACGAATG

GCAGTCAGTGGAGATGATTGCGTTGTGAAGCCAATTGATGATAGGTTTGCACATGCCCTCAGGTTCTTGAATGATATGGG

AAAAGTTAGGAAGGACACACAAGAGTGGAAACCCTCAACTGGATGGGACAACTGGGAAGAAGTTCCGTTTTGCTCCCAC

CACTTCAACAAGCTCCATCTCAAGGACGGGAGGTCCATTGTGGTTCCCTGCCGCCACCAAGATGAACTGATTGGCCGGGC

CCGCGTCTCTCCAGGGGCGGGATGGAGCATCCGGGAGACTGCTTGCCTAGCAAAATCATATGCGCAAATGTGGCAGCTC

CTTTATTTCCACAGAAGGGACCTCCGACTGATGGCCAATGCCATTTGTTCATCTGTGCCAGTTGACTGGGTTCCAACTGGG

AGAACTACCTGGTCAATCCATGGAAAGGGAGAATGGATGACCACTGAAGACATGCTTGTGGTGTGGAACAGAGTGTGGA

TTGAGGAGAACGACCACATGGAAGACAAGACCCCAGTTACGAAATGGACAGACATTCCCTATTTGGGAAAAAGGGAAGA

CTTGTGGTGTGGATCTCTCATAGGGCACAGACCGCGCACCACCTGGGCTGAGAACATTAAAAACACAGTCAACATGGTGC

GCAGGATCATAGGTGATGAAGAAAAGTACATGGACTACCTATCCACCCAAGTTCGCTACTTGGGTGAAGAAGGGTCTACA

CCTGGAGTGCTGTAAGCACCAATCTTAGTGTTGTCAGGCCTGCTAGTCAGCCACAGCTTGGGGAAAGCTGTGCAGCCTGT

GACCCCCCCAGGAGAAGCTGGGAAACCAAGCCTATAGTCAGGCCGAGAACGCCATGGCACGGAAGAAGCCATGCTGCCT

GTGAGCCCCTCAGAGGACACTGAGTCAAAAAACCCCACGCGCTTGGAGGCGCAGGATGGGAAAAGAAGGTGGCGACCT

TCCCCACCCTTCAATCTGGGGCCTGAACTGGAGATCAGCTGTGGATCTCCAGAAGAGGGACTAGTGGTTAGAGGAGACCC

CCCGGAAAACGCAAAACAGCATATTGACGCTGGGAAAGACCAGAGACTCCATGAGTTTCCACCACGCTGGCCGCCAGGC

ACAGATCGCCGAATAGCGGCGGCCGGTGTGGGG

SEQ ID NO: 79

AHZ13508.1, Zika virus polyprotein from Polynesian outbreak (H/PF/2013)

MKNPKKKSGGFRIVNMLKRGVARVSPFGGLKRLPAGLLLGHGPIRMVLAILAFLRFTAIKPSLGLINRWGSVGKKEAMEIIKKFK

KDLAAMLRIINARKEKKRRGADTSVGIVGLLLTTAMAAEVTRRGSAYYMYLDRNDAGEAISFPTTLGMNKCYIQIMDLGHMCD

ATMSYECPMLDEGVEPDDVDCWCNTTSTWVVYGTCHHKKGEARRSRRAVTLPSHSTRKLQTRSQTWLESREYTKHLIRVEN

WIFRNPGFALAAAAIAWLLGSSTSQKVIYLVMILLIAPAYSIRCIGVSNRDFVEGMSGGTWVDVVLEHGGCVTVMAQDKPTVD

IELVTTTVSNMAEVRSYCYEASISDMASDSRCPTQGEAYLDKQSDTQYVCKRTLVDRGWGNGCGLFGKGSLVTCAKFACSKKM

TGKSIQPENLEYRIMLSVHGSQHSGMIVNDTGHETDENRAKVEITPNSPRAEATLGGFGSLGLDCEPRTGLDFSDLYYLTMNNK

HWLVHKEWFHDIPLPWHAGADTGTPHWNNKEALVEFKDAHAKRQTVVVLGSQEGAVHTALAGALEAEMDGAKGRLSSGH

LKCRLKMDKLRLKGVSYSLCTAAFTFTKIPAETLHGTVTVEVQYAGTDGPCKVPAQMAVDMQTLTPVGRLITANPVITESTENS

KMMLELDPPFGDSYIVIGVGEKKITHHWHRSGSTIGKAFEATVRGAKRMAVLGDTAWDFGSVGGALNSLGKGIHQIFGAAFK

SLFGGMSWFSQILIGTLLMWLGLNTKNGSISLMCLALGGVLIFLSTAVSADVGCSVDFSKKETRCGTGVFVYNDVEAWRDRYK

YHPDSPRRLAAAVKQAWEDGICGISSVSRMENIMWRSVEGELNAILEENGVQLTVVVGSVKNPMWRGPQRLPVPVNELPHG

WKAWGKSYFVRAAKTNNSFVVDGDTLKECPLKHRAWNSFLVEDHGFGVFHTSVWLKVREDYSLECDPAVIGTAVKGKEAVH

SDLGYWIESEKNDTWRLKRAHLIEMKTCEWPKSHTLWTDGIEESDLIIPKSLAGPLSHHNTREGYRTQMKGPWHSEELEIRFEE

CPGTKVHVEETCGTRGPSLRSTTASGRVIEEWCCRECTMPPLSFRAKDGCWYGMEIRPRKEPESNLVRSMVTAGSTDHMDHF

SLGVLVILLMVQEGLKKRMTTKIIISTSMAVLVAMILGGFSMSDLAKLAILMGATFAEMNTGGDVAHLALIAAFKVRPALLVSFIF

RANWTPRESMLLALASCLLQTAISALEGDLMVLINGFALAWLAIRAMVVPRTDNITLAILAALTPLARGTLLVAWRAGLATCGG

FMLLSLKGKGSVKKNLPFVMALGLTAVRLVDPINVVGLLLLTRSGKRSWPPSEVLTAVGLICALAGGFAKADIEMAGPMAAVGL

LIVSYVVSGKSVDMYIERAGDITWEKDAEVTGNSPRLDVALDESGDFSLVEDDGPPMREIILKVVLMTICGMNPIAIPFAAGAW

YVYVKTGKRSGALWDVPAPKEVKKGETTDGVYRVMTRRLLGSTQVGVGVMQEGVFHTMWHVTKGSALRSGEGRLDPYWG

-continued

DVKQDLVSYCGPWKLDAAWDGHSEVQLLAVPPGERARNIQTLPGIFKTKDGDIGAVALDYPAGTSGSPILDKCGRVIGLYGNG

VVIKNGSYVSAITQGRREEETPVECFEPSMLKKKQLTVLDLHPGAGKTRRVLPEIVREAIKTRLRTVILAPTRVVAAEMEEALRGLP

VRYMTTAVNVTHSGTEIVDLMCHATFTSRLLQPIRVPNYNLYIMDEAHFTDPSSIAARGYISTRVEMGEAAAIFMTATPPGTRD

AFPDSNSPIMDTEVEVPERAWSSGFDWVTDHSGKTVWFVPSVRNGNEIAACLTKAGKRVIQLSRKTFETEFQKTKHQEWDFV

VTTDISEMGANFKADRVIDSRRCLKPVILDGERVILAGPMPVTHASAAQRRGRIGRNPNKPGDEYLYGGGCAETDEDHAHWLE

ARMLLDNIYLQDGLIASLYRPEADKVAAIEGEFKLRTEQRKTFVELMKRGDLPVWLAYQVASAGITYTDRRWCFDGTTNNTIME

DSVPAEVWTRHGEKRVLKPRWMDARVCSDHAALKSFKEFAAGKRGAAFGVMEALGTLPGHMTERFQEAIDNLAVLMRAET

GSRPYKAAAAQLPETLETIMLLGLLGTVSLGIFFVLMRNKGIGKMGFGMVTLGASAWLMWLSEIEPARIACVLIVVFLLLVVLIPE

PEKQRSPQDNQMAIIIMVAVGLLGLITANELGWLERTKSDLSHLMGRREEGATIGFSMDIDLRPASAWAIYAALTTFITPAVQH

AVTTSYNNYSLMAMATQAGVLFGMGKGMPFYAWDFGVPLLMIGCYSQLTPLTLIVAIILLVAHYMYLIPGLQAAAARAAQKR

TAAGIMKNPVVDGIVVTDIDTMTIDPQVEKKMGQVLLIAVAVSSAILSRTAWGWGEAGALITAATSTLWEGSPNKYWNSSTA

TSLCNIFRGSYLAGASLIYTVTRNAGLVKRRGGGTGETLGEKWKARLNQMSALEFYSYKKSGITEVCREEARRALKDGVATGGH

AVSRGSAKLRWLVERGYLQPYGKVIDLGCGRGGWSYYAATIRKVQEVKGYTKGGPGHEEPMLVQSYGWNIVRLKSGVDVFH

MAAEPCDTLLCDIGESSSSPEVEEARTLRVLSMVGDWLEKRPGAFCIKVLCPYTSTMMETLERLQRRYGGGLVRVPLSRNSTHE

MYWVSGAKSNTIKSVSTTSQLLLGRMDGPRRPVKYEEDVNLGSGTRAVVSCAEAPNMKIIGNRIERIRSEHAETWFFDENHPY

RTWAYHGSYEAPTQGSASSLINGVVRLLSKPWDVVTGVTGIAMTDTTPYGQQRVFKEKVDTRVPDPQEGTRQVMSMVSSW

LWKELGKHKRPRVCTKEEFINKVRSNAALGAIFEEEKEWKTAVEAVNDPRFWALVDKEREHHLRGECQSCVYNMMGKREKK

QGEFGKAKGSRAIWYMWLGARFLEFEALGFLNEDHWMGRENSGGGVEGLGLQRLGYVLEEMSRIPGGRMYADDTAGWDT

RISRFDLENEALITNQMEKGHRALALAIIKYTYQNKVVKVLRPAEKGKTVMDIISRQDQRGSGQVVTYALNTFTNLVVQLIRNM

EAEEVLEMQDLWLLRRSEKVTNWLQSNGWDRLKRMAVSGDDCVVKPIDDRFAHALRFLNDMGKVRKDTQEWKPSTGWD

NWEEVPFCSHHFNKLHLKDGRSIVVPCRHQDELIGRARVSPGAGWSIRETACLAKSYAQMWQLLYFHRRDLRLMANAICSSV

PVDWVPTGRTTWSIHGKGEWMTTEDMLVVWNRVWIEENDHMEDKTPVTKWTDIPYLGKREDLWCGSLIGHRPRTTWAE

NIKNTVNMVRRIIGDEEKYMDYLSTQVRYLGEEGSTPGVL

SEQ ID NO: 80

9320_Zika_PF_1F
ttaggatccGTTGTTGATCTGTGTGAAT

SEQ ID NO: 81

9321_Zika_PF_1R
taactcgagCGTACACAACCCAAGTT

SEQ ID NO: 82

9322_Zika_PF_2F
ttaggatccTCACTAGACGTGGGAGTG

SEQ ID NO: 83

9323_Zika_PF_2R
taactcgagAAGCCATGTCYGATATTGAT

SEQ ID NO: 84

9324_Zika_PF_3F
ttaggatccGCATACAGCATCAGGTG

SEQ ID NO: 85

9325_Zika_PF_3R
taactcgagTGTGGAGTTCCGGTGTCT

SEQ ID NO: 86

9326_Zika_PF_4F
ttaggatccGAATAGAGCGAARGTTGAGATA

SEQ ID NO: 87

9327_Zika_PF_4R
taactcgAGTGGTGGGTGATCTTCTTCT

-continued

SEQ ID NO: 88
9328_Zika_PF_5F
ttaggatcCAGTCACAGTGGAGGTACAGTAC

SEQ ID NO: 89
9329_Zika_PF_5R
taactcgagCRCAGATACCATCTTCCC

SEQ ID NO: 90
9330_Zika_PF_6F
ttaggatCCCTTATGTGCTTGGCCTTAG

SEQ ID NO: 91
9331_Zika_PF_6R
taactcgagTCTTCAGCCTCCATGTG

SEQ ID NO: 92
9332_Zika_PF_7F
ttaggatccAATGCCCACTCAAACATAGA

SEQ ID NO: 93
9333_Zika_PF_7R
taactcgagTCATTCTCTTCTTCAGCCCTT

SEQ ID NO: 94
9334_Zika_PF_8F
ttaggatccAAGGGTGATCGAGGAAT

SEQ ID NO: 95
9335_Zika_PF_8R
taactcgagTTCCCTTCAGAGAGAGGAGC

SEQ ID NO: 96
9336_Zika_PF_9F
ttaggatccTCTTTTGCAAACTGCGATC

SEQ ID NO: 97
9337_Zika_PF_9R
taactcgagTCCAGCTGCAAAGGGTAT

SEQ ID NO: 98
9338_Zika_PF_10F
ttaggatccGTGTGGACATGTACATTGA

SEQ ID NO: 99
9339_Zika_PF_10R
taactcgagCCCATTGCCATAAAGTC

SEQ ID NO: 100
9340_Zika_PF_11F
ttaggatccTCATACTGTGGTCCATGGA

SEQ ID NO: 101
9341_Zika_PF_11R
taactcgagGCCCATCTCAACCCTTG

SEQ ID NO: 102
9342_Zika_PF_12F
ttaggatccTAGAGGGCTTCCAGTGC

SEQ ID NO: 103
9343_Zika_PF_12R
taactcgAGATACTCATCTCCAGGTTTGTTG

SEQ ID NO: 104
9344_Zika_PF_13F
ttaggatccGAAAACAAAACATCAAGAGTG

SEQ ID NO: 105
9345_Zika_PF_13R
taactcgagGAATCTCTCTGTCATGTGTCCT

SEQ ID NO: 106
9346_Zika_PF_14F
ttaggatccTTGATGGCACGACCAAC

SEQ ID NO: 107
9347_Zika_PF_14R
ttaggatccGTTGTTGATCTGTGTGAAT

-continued

SEQ ID NO: 108
9348_Zika_PF_15F
taactcgagCAGGTCAATGTCCATTG

SEQ ID NO: 109
9349_Zika_PF_15R
ttaggatccTGTTGTGTTCCTATTGCTGGT

SEQ ID NO: 110
9350_Zika_PF_16F
taactcgaGTGATCAGRGCCCCAGC

SEQ ID NO: 111
9351_Zika_PF_16R
ttaggatccTGCTGCCCAGAAGAGAA

SEQ ID NO: 112
9352_Zika_PF_17F
taactcgaGCACCAACAYGGGTTCTT

SEQ ID NO: 113
9353_Zika_PF_17R
ttaggatcCTCAAGGACGGTGTGGC

SEQ ID NO: 114
9354_Zika_PF_18F
taactcgagCAATGATCTTCATGTTGGG

SEQ ID NO: 115
9355_Zika_PF_18R
ttaggatccTATGGGGGAGGACTGGT

SEQ ID NO: 116
9356_Zika_PF_19F
taactcGAGCCCAGAACCTTGGATC

SEQ ID NO: 117
9357_Zika_PF_19R
ttaggatcCAGACCCCCAAGAAGGC

SEQ ID NO: 118
9358_Zika_PF_20F
taactcgagCCCCTTTGGTCTTGTCT

SEQ ID NO: 119
9359_Zika_PF_20R
ttaggatccAGGAAGGATGTATGCAGATG

SEQ ID NO: 120
9360_Zika_PF_21F
taactcgagACATTTGCGCATATGATTTTG

SEQ ID NO: 121
9361_Zika_PF_21R
ttaggatccAGGAAGGACACACAAGAGT

SEQ ID NO: 122
9362_Zika_PF_22F
taactcgagACAGGCTGCACAGCTTT

SEQ ID NO: 123
9363_Zika_PF_22R
ttaggatccTCTCTCATAGGGCACAGAC

In some embodiments, the Zika virus has a polyprotein including an envelope (E) protein with an amino acid sequence provided by any one of SEQ ID NOs: 14-69. In some embodiments, the polyprotein or E protein sequence is at least 80%, 81%, 82%, 83%, 84%, 85%, 86%, 87%, 88%, 89%, 90%, 91%, 92%. 93%, 94%, 95%, 96%, 97%, 98%, 99%, 99.5%, 99.6%, 99.7%, 99.8% or 99.9% identical to any one of SEQ ID NOs: 2-69.

The terms “identical” or “percent identity” in the context of two or more nucleic acids or amino acid sequences refer to two or more sequences or subsequences that are the same. Two sequences are “substantially identical” if two sequences have a specified percentage of amino acid residues or nucleotides that are the same (e.g., at least 80%, 85%, 90%, 95%, 96%, 97%, 98%, or 99% identity) over a specified region or over the entire sequence, when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length. In some embodiments, the identity exists over the length of a protein, such as the E protein.

For sequence comparison, typically one sequence acts as a reference sequence, to which test sequences are compared.

Methods of alignment of sequences for comparison are well known in the art. See, e.g., by the local homology algorithm of Smith and Waterman (1970) Adv. Appl. Math. 2:482c, by the homology alignment algorithm of Needleman and Wunsch, J. MoI. Biol. 48:443, 1970, by the search for similarity method of Pearson and Lipman. Proc. Natl. Acad. Sci. USA 85:2444, 1988, by computerized implementations of these algorithms (GAP, BESTFIT, FASTA, Jalview and TFASTA in the Wisconsin Genetics Software Package, Genetics Computer Group. 575 Science Dr., Madison. Wis.), by multi sequence alignment implementation using e.g. CLUSTALW (Larkin et al., (2007). Bioinformatics, 23, 2947-2948.) or MAFFT (Katoh & Toh, 2008, Briefings in Bioinformatics 9:286-298), or by manual alignment and visual inspection (see. e.g., Brent et al., Current Protocols in Molecular Biology, John Wiley & Sons, Inc. (Ringbou ed., 2003)). Two examples of algorithms that are suitable for determining percent sequence identity and sequence similarity are the BLAST and BLAST 2.0 algorithms, which are described in Altschul et al., Nuc. Acids Res. 25:3389-3402, 1977 and Altschul et al., J. Mol. Biol. 215:403-410, 1990, respectively.

EXAMPLES

Example 1: Development of a Purification Process for Live Attenuated Chikungunya Virus Vaccine Produced in Vero Cells A downstream process was developed for the purification of infectious Chikungunya virus particles whereby non-infectious virus particles and aggregates are removed by the addition of protamine sulphate. The unexpected and novel purification properties of protamine sulphate (PS) were evaluated in purification processes for Chikungunya Virus (ChikV) as follows:

A downstream purification process for the attenuated Chikungunya virus mutant "Δ5nsP3" (as described by Hallengard et al., 2014, supra) produced under standard cell culture conditions in Vero cells was developed. The attenuated Δ5nsP3 Chikungunya virus was derived from the strain LR2006-OPY1, the complete genome of which is provided herein as SEQ ID NO: 72. Briefly, the downstream process consists of crude harvest filtration followed by concentration and diafiltration on a tangential flow filtration (TFF) system. Host cell DNA and host cell proteins were reduced by precipitation with protamine sulphate and by batch adsorption, respectively. Sucrose density gradient centrifugation was done as a final polishing step. Out of 16 roller bottles $1\times10^{12}$ total PFU were purified with an overall DSP process yield of 10-15% (~1 log 10 TCID50 loss). Sucrose gradient pool samples were characterized with regard to product-related impurities, such as hcDNA, HCP and endotoxins and met safety criteria.

Harvest of Vero Cell Culture Medium Containing ChikV Δ5nsP3

ChikV Δ5nsP3 was grown on Vero cells in roller bottles. A first harvest was performed after 24 hours post infection (hpi; day 1 harvest) and stored at 2-8° C. until further processing. After the first harvest, fresh medium was added and the roller bottles were returned to the incubator. A second harvest was done after 48 hours post infection (day 2 harvest) and stored at 2-8° C.

Filtration of Crude Cell Culture Harvest

At both harvest timepoints, the crude harvest was immediately filtered using a 0.2 μm filter capsule (GE ULTA™ CG, 2 inch). The filtered harvest after 48 hpi was pooled together with the 24 hpi harvest and the pooled filtered harvest material was immediately further processed by ultrafiltration.

Purification of ChikV Δ5nsP3 by Tangential Flow Filtration (TFF)

The pooled filtered harvest material was further processed by tangential flow filtration (TFF) in order to concentrate the harvest, reduce host cell proteins and replace the depleted cell culture medium with a defined buffer system (buffer exchange). A Millipore TFF system (Millipore Pellicon II mini membrane holder) equipped with a 100 kDa cutoff PES membrane module (Pellicon2 Biomax, 1000 $cm^2$) was used for concentration and buffer exchange. A Pellicon2 Biomax membrane module was mounted on the Pellicon II mini filter holder and the device was connected to a peristaltic pump. The system was first rinsed with ultra-pure water and then sanitized by recirculation of 0.1 M NaOH for 60 min. In case the system was not used immediately, it was stored in 0.1 M NaOH until use. Prior to use the system was rinsed with 1 L of RO-water followed by buffer A until the permeate pH value was constant at pH 7.4±0.2.

Adjustment of the ChikV Δ5nsP3 Harvest (pH, Salt)

The pooled filtered harvest material was adjusted to a final concentration of 25 mM Tris and 150 mM NaCl using stock solutions of both components (see Table 1). This adjustment was done to increase buffering capacity and to reduce unspecific adsorption to the membrane. The necessary volumes of stock solutions D (1 M Tris, pH 7.4) and E (4.5 M NaCl) were calculated as follows:

Volume of stock solution D (1 M Tris,pH 7.4) added to pooled harvest=Volume of pooled filtered harvest/40

Volume of stock solution E(4.5 M NaCl) added to pooled harvest=Volume of pooled filtered harvest/30

Example: 4 L harvest obtained from 20 RB (850 $cm^2$) would require addition of 100 mL stock solution D (1 M Tris, pH 7.4) and 133 mL stock solution E (4.5 M NaCl).

The calculated volumes of stock solution D and Buffer E were added to the pooled filtered harvest under gentle stirring. The adjusted harvest was then stirred using a magnetic stirrer for 5 minutes at room temperature.

Concentration and Diafiltration of the ChikV Δ5nsP3 Harvest by TFF

In a first step, the adjusted harvest material was concentrated approximately 10 fold. The feed flowrate was approximately 220 mL/min. The transmembrane flux at a transmembrane pressure of approximately 0.6 bar was in the range of 90±5 mL/min per 1000 $cm^2$ membrane. After concentration, the cell culture medium was exchanged against 25 mM Tris, 150 mM NaCl, pH 7.5, by continuous diafiltration with 6 volume exchanges. The diafiltration buffer was supplied to the feed vessel from a measuring cylinder by a second peristaltic pump set to a flowrate of approximately 90 mL/min. Minor flowrate adjustments of the second peristaltic pump in the range of ±10 mL/min were done manually to ensure a constant volume of harvest in the feed vessel. After 6 volume exchanges, diafiltration was stopped. The liquid remaining in the membrane module was recovered by pumping the module empty with air.

Sucrose Addition to Diafiltrated ChikV Δ5nsP3 Material

After diafiltration, sucrose stock solution H (50% (w/w) sucrose solution) was added to the diafiltrated material to achieve a final sucrose concentration of 10% (w/w). The volume of buffer H was calculated as follows:

Volume of stock solution H added (mL)=Volume (mL) of diafiltrated ChikV material×0.25 (dilution factor=1:4)(i.e., final sucrose concentration is 10%)

Example: 400 mL diafiltrated ChikV solution would require addition of 100 mL stock solution H (50% sucrose).

The calculated volume of solution H was added to the diafiltrated ChikV Δ5nsP3 material under gentle stirring and the solution was then stirred using a magnetic stirrer for a further 5 minutes at room temperature. (At this stage of the process the material can be either immediately further processed or stored frozen (<−65° C., hold step).)

DNA Reduction by Protamine Sulphate Precipitation

A DNA precipitation step using protamine sulphate (PS) was performed to reduce hcDNA. Protamine sulphate stock solution L (50 mg/mL PS in PBS) was added to the diafiltrated ChikV Δ5nsP3 material to a final nominal concentration of ~1.6 mg/mL. The necessary volume of stock solution L was calculated as follows:

Volume of stock solution L(50 mg/mL PS) added=Volume of diafiltrated ChikV Δ5nsP3 material in 10% sucrose/31

Example: 500 mL diafiltrated ChikV Δ5nsP3 solution in 10% sucrose would require addition of 16 mL stock solution L (50 mg/mL PS in PBS).

The protamine sulphate stock solution was added while stirring the ChikV Δ5nsP3 material using a magnetic stirrer followed by incubation at 2-8° C. for 30 minutes. After incubation, the precipitate was not removed. The material was immediately further processed by batch adsorption with Capto™ Core 700 chromatography media.

Batch Adsorption with Capto™ Core 700

To reduce HCPs, a batch adsorption step with Capto™ Core 700 (CC700) chromatography medium was performed after DNA precipitation. CC700 slurry (50% slurry in buffer A) was added directly to the protamine sulphate treated material. The required slurry volume was determined based on the volume of Δ5nsP3 ChikV harvest material (d1+d2) and was calculated as follows:

Volume of CC700 slurry added to PS-treated concentrated harvest (mL)=Volume of Δ5nsP3 ChikV harvest material (mL)×0.02(dilution factor=1:50)(i.e., final concentration of CC700 is 1%)

After slurry addition, the material was incubated at 4° C. for 15 minutes under constant agitation using a magnetic stirrer. After incubation, the CC700 solid matter was allowed to settle by gravity for 10 minutes. The Δ5nsP3 ChikV material was then removed from the top of the solution in order to avoid blocking of the filter by the CaptoCore particles. The remaining CaptoCore particles and the DNA precipitate were then removed from the solution by filtration using a 0.2 μm Mini Kleenpak EKV filter capsule (Pall). The resulting filtrate was further processed by sucrose density gradient centrifugation.

Sucrose Density Gradient Centrifugation

Sucrose density gradient centrifugation (SGC) was used for final concentration and polishing of the Δ5nsP3 ChikV material. The Δ5nsP3 ChikV material was loaded on top of a solution consisting of three layers of sucrose with different densities. The three sucrose layers were selected based on a preliminary study which showed the formation of a linear sucrose gradient and good separation of the virus particles from residual contaminants. The optimal volumes of the sucrose solutions were determined empirically. The volumes of individual layers for a centrifugation at 500 mL scale are shown in Table 3.

TABLE 3

Sucrose concentrations and volumes (500 mL scale).

| Solution | Volume (mL) |
|---|---|
| Harvest with 10% sucrose | 360 |
| 15% sucrose | 40 |
| 35% sucrose | 40 |
| 50% sucrose | 60 |
| Total volume | 500 |

Preparation of the Sucrose Gradient

The sucrose gradient bottles (500 mL) were prepared by underlaying the individual sucrose layers. A 3.5 mm ID plastic tube was attached to 60 cm of peristaltic pump tubing. The plastic tube was mounted on a laboratory stand using a clamp and placed into the centrifuge bottle. The nozzle of the plastic tube was placed at the bottom of the bottle. Using a peristaltic pump set to a flow rate of 25 mL per minute, the Δ5nsP3 ChikV material and the sucrose solutions were pumped into the cylinder. A measuring cylinder was used as a feed vessel. The first solution pumped was the Δ5nsP3 ChikV material as it had the lowest density (10% sucrose (w/w)). Following the addition of the Δ5nsP3 ChikV material, the sucrose solutions were pumped in ascending order starting with the lowest (15%), followed by the 35% sucrose solution and finishing with the highest density sucrose solution (50%). After all sucrose solutions were transferred, the plastic tubing was carefully removed in order not to disturb the layers. An illustration of a completed gradient is shown in FIG. 14.

Centrifugation

Prior to centrifugation a Beckman Avanti JXN-26 centrifuge equipped with rotor Beckman 10.500 was pre-cooled to 4° C. The prepared SG bottles were carefully transferred into the pre-cooled (4° C.) rotor so as to not to disturb the sucrose layers. The bottles were centrifuged at 10,000 rpm (~18,500 rcf) at 4° C. for 17-20 hours. (In case a different centrifuge system with a different rotor would be used, the necessary speed and centrifugation times would need to be calculated based on the k-factor in order to achieve comparable centrifugation efficiency.)

Sucrose Gradient Harvest

Harvesting of the sucrose gradient following centrifugation was done manually using a peristaltic pump. A 3.5 mm ID plastic tube attached to 60 cm of peristaltic pump tubing was used for harvesting the sucrose gradient. The 500 mL bottle containing the centrifuged gradient was mounted onto a laboratory stand in a tilted position (~12°) using a clamp. The plastic tubing was then placed into the bottle touching the bottom edge of the bottle and was fastened in position using a clamp. This resulted in a small gap of 1-2 mm between the tubing inlet and the bottom of the bottle (see FIG. 14). Using a peristaltic pump set to a flow rate of 60 mL per minute, the gradient was harvested and manually split into 5 mL fractions. A third of the bottle volume was harvested and the rest was discarded. The fractions were immediately tested by measuring UV absorbance in a plate reader as described below.

Analysis of Fractions by UV Absorbance and SEC-HPLC

Figure 1:
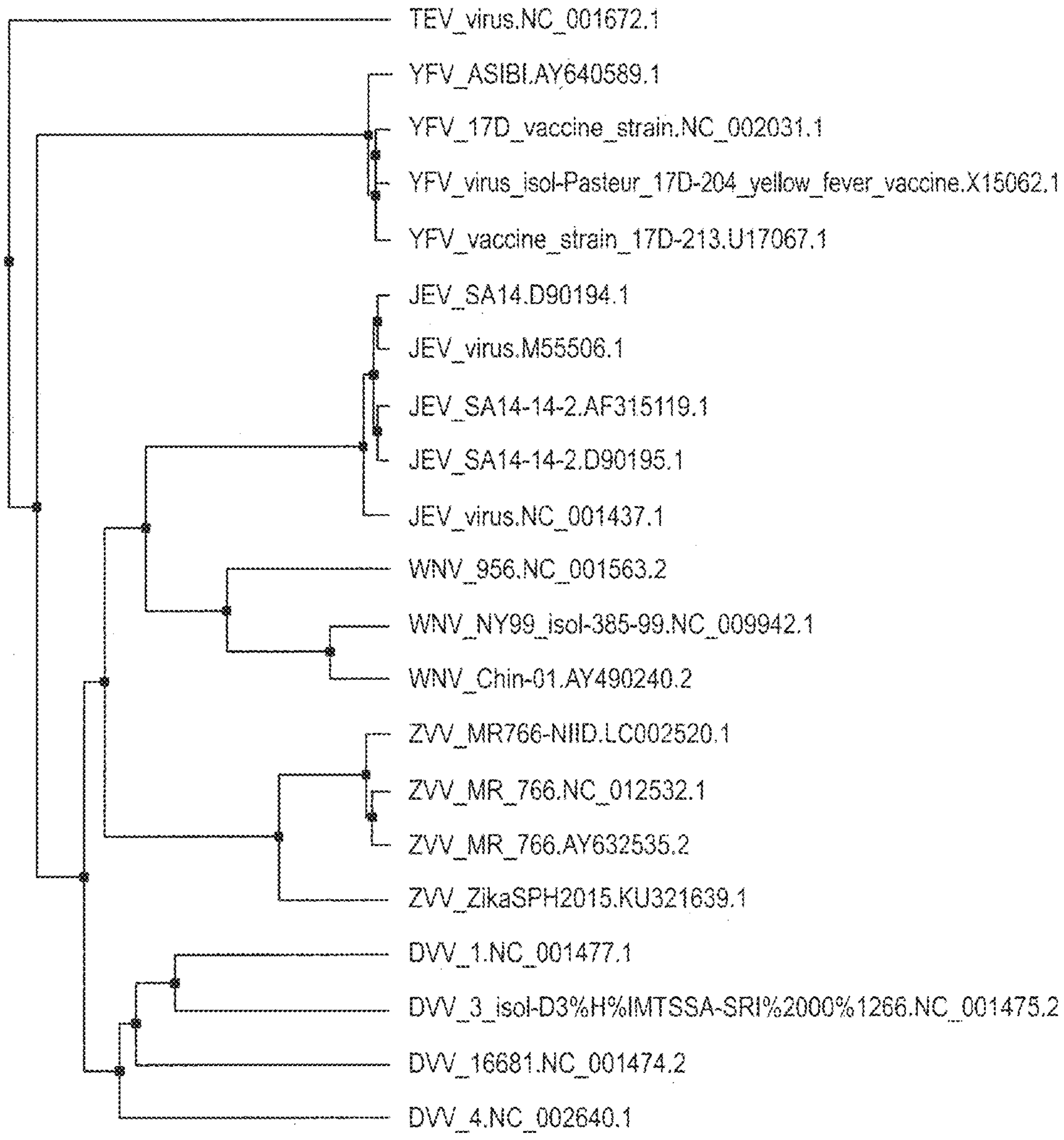
FIG. 1: Average distance tree (by % identity, nt), complete genomes.
Figure 2:
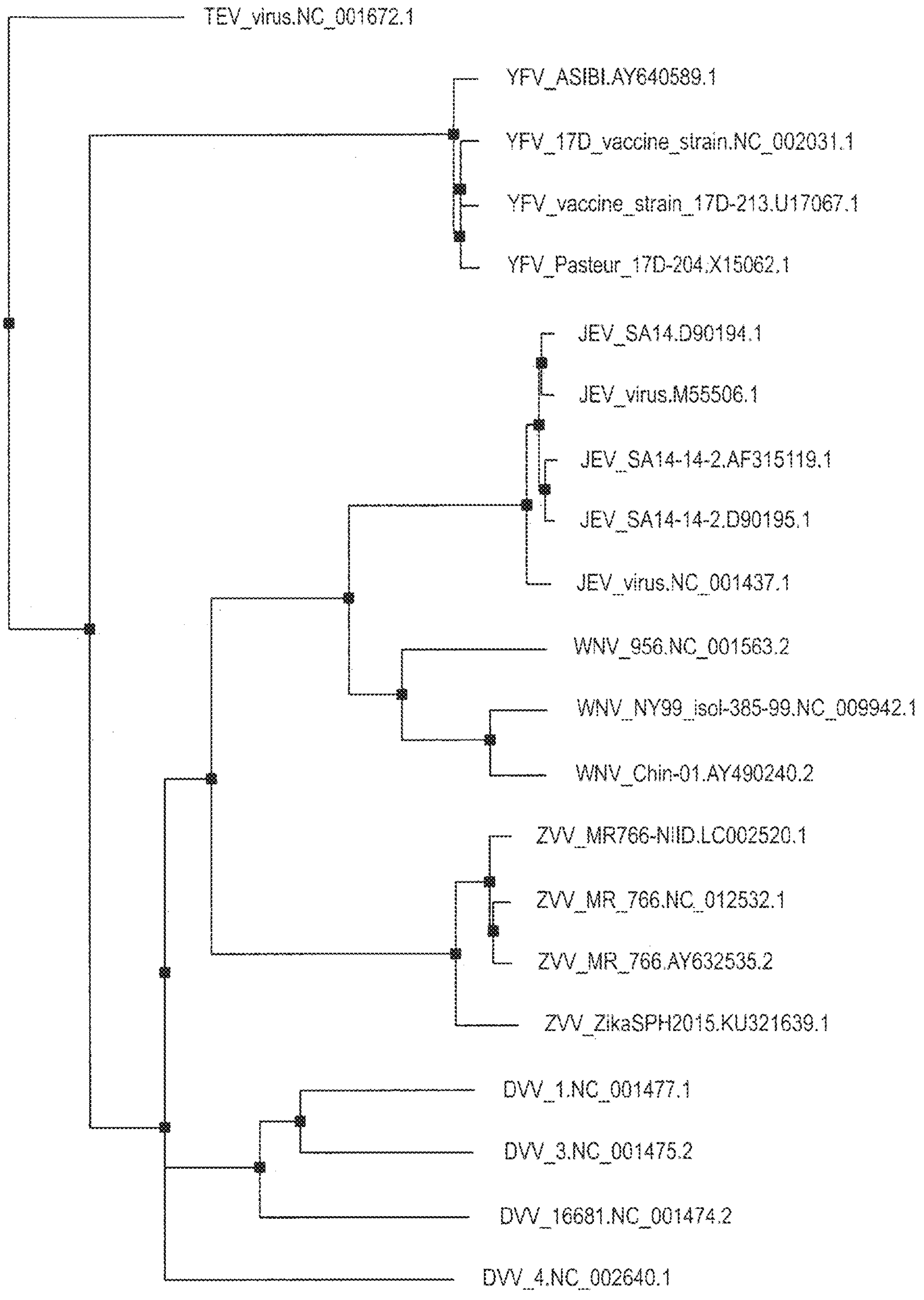
FIG. 2: Neighbor joining tree (by % identity, nt), complete genomes.
Figure 4:
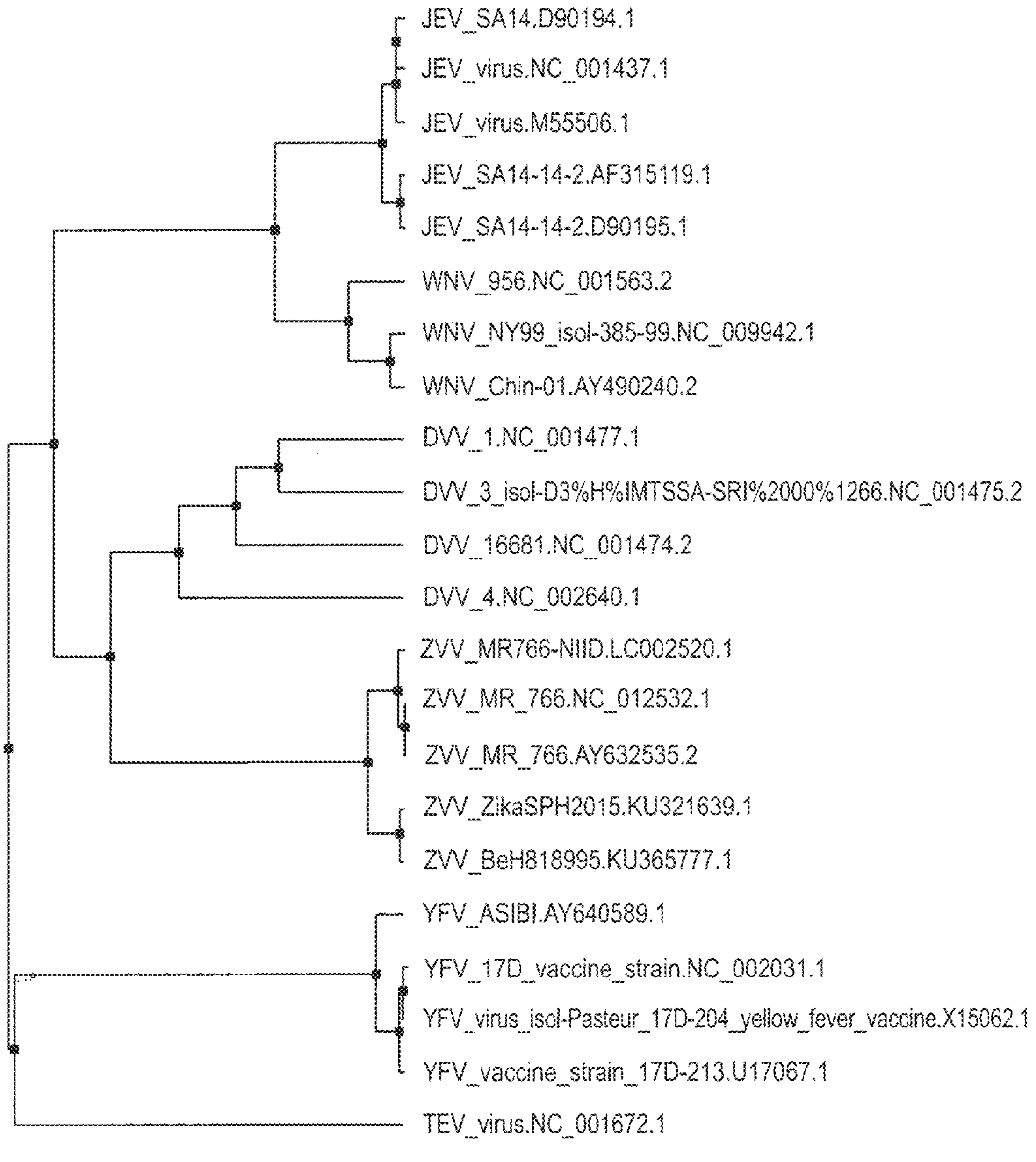
FIG. 4: Average distance tree (by % identity, aa), E-protein.
Figure 5:
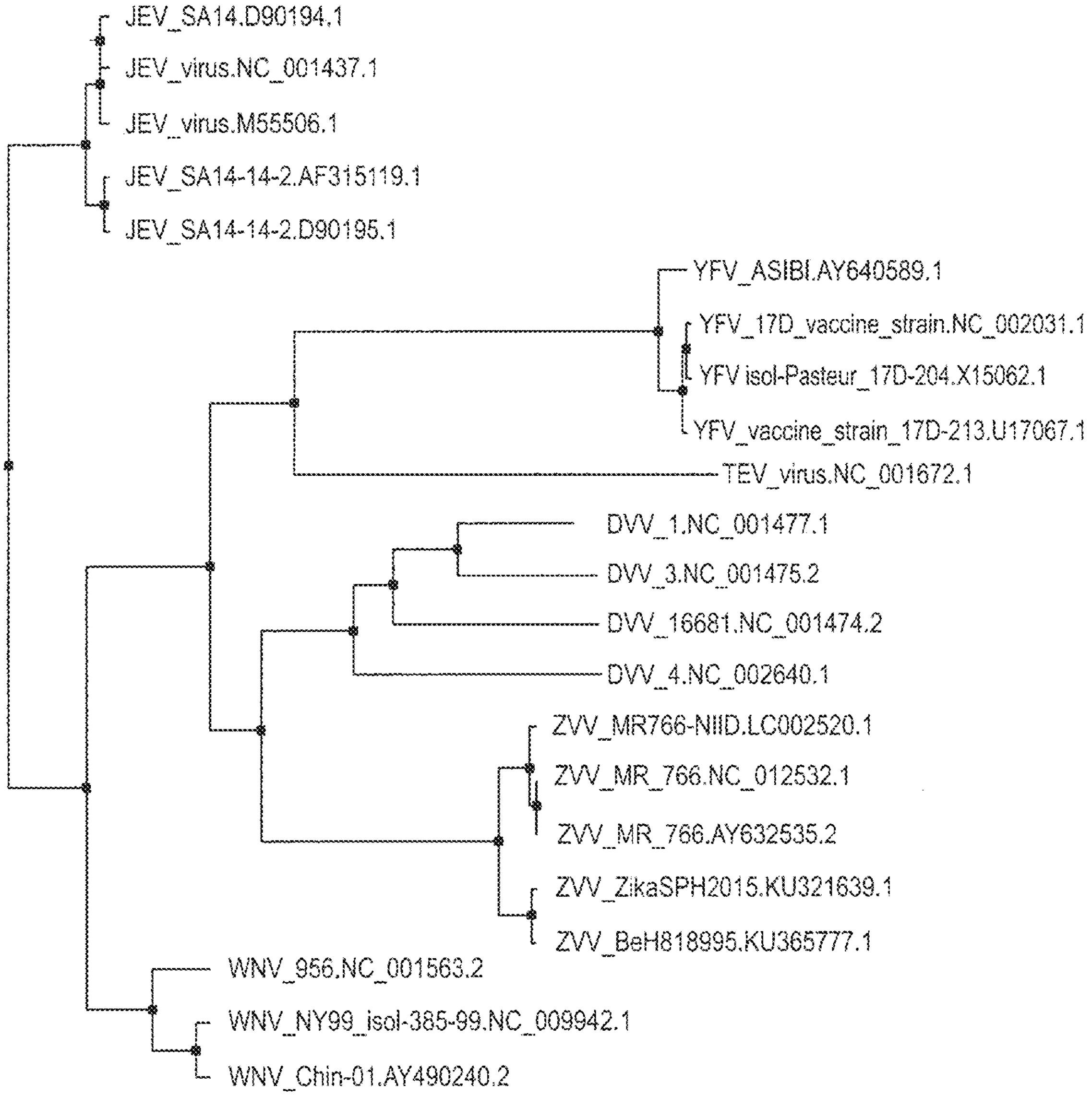
FIG. 5: Neighbor joining tree (by % identity. aa), E-protein.
Figure 7:
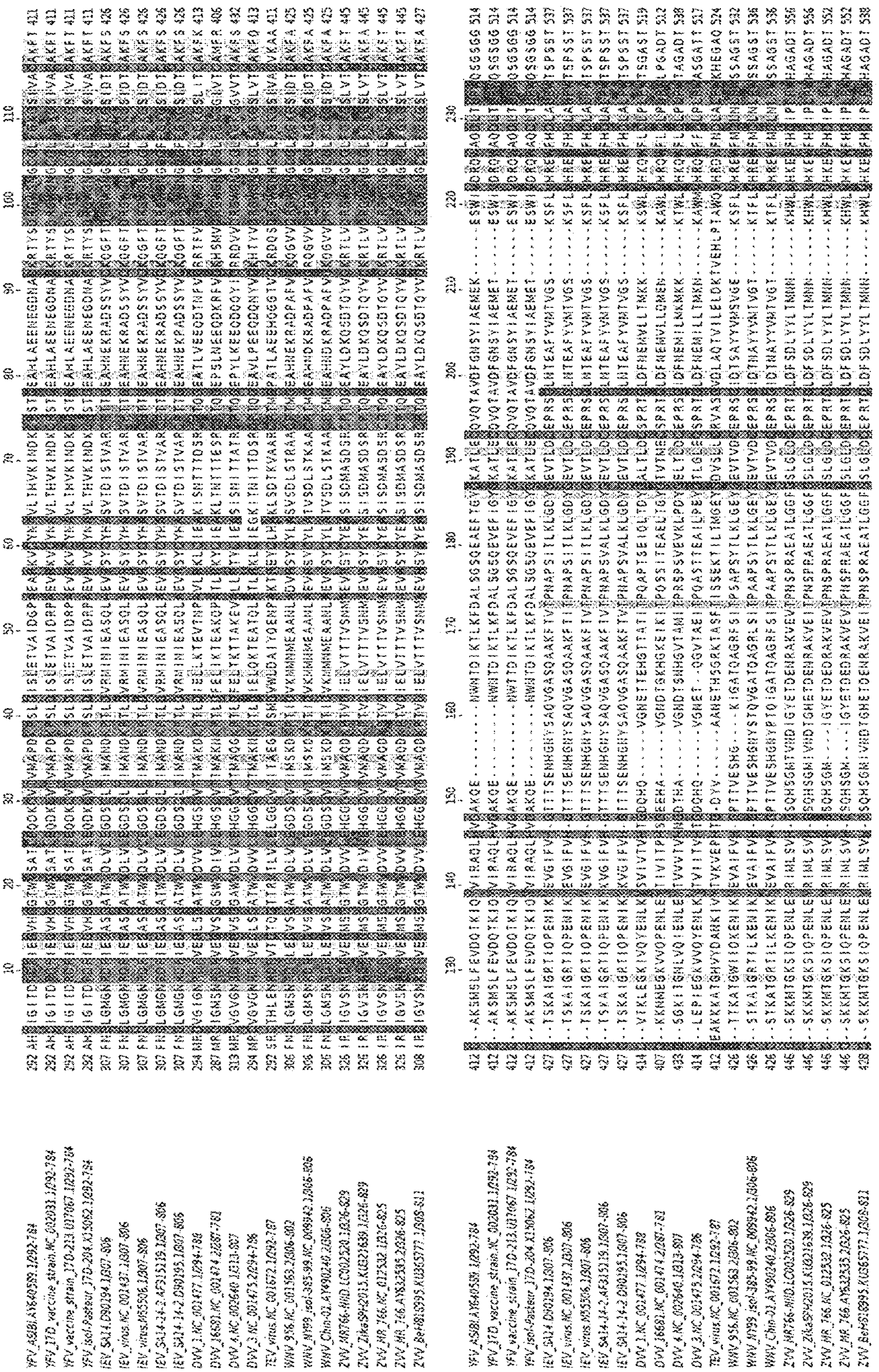
FIG. 7: Alignment (shading: % identity, aa), E-protein.
Figure 7:
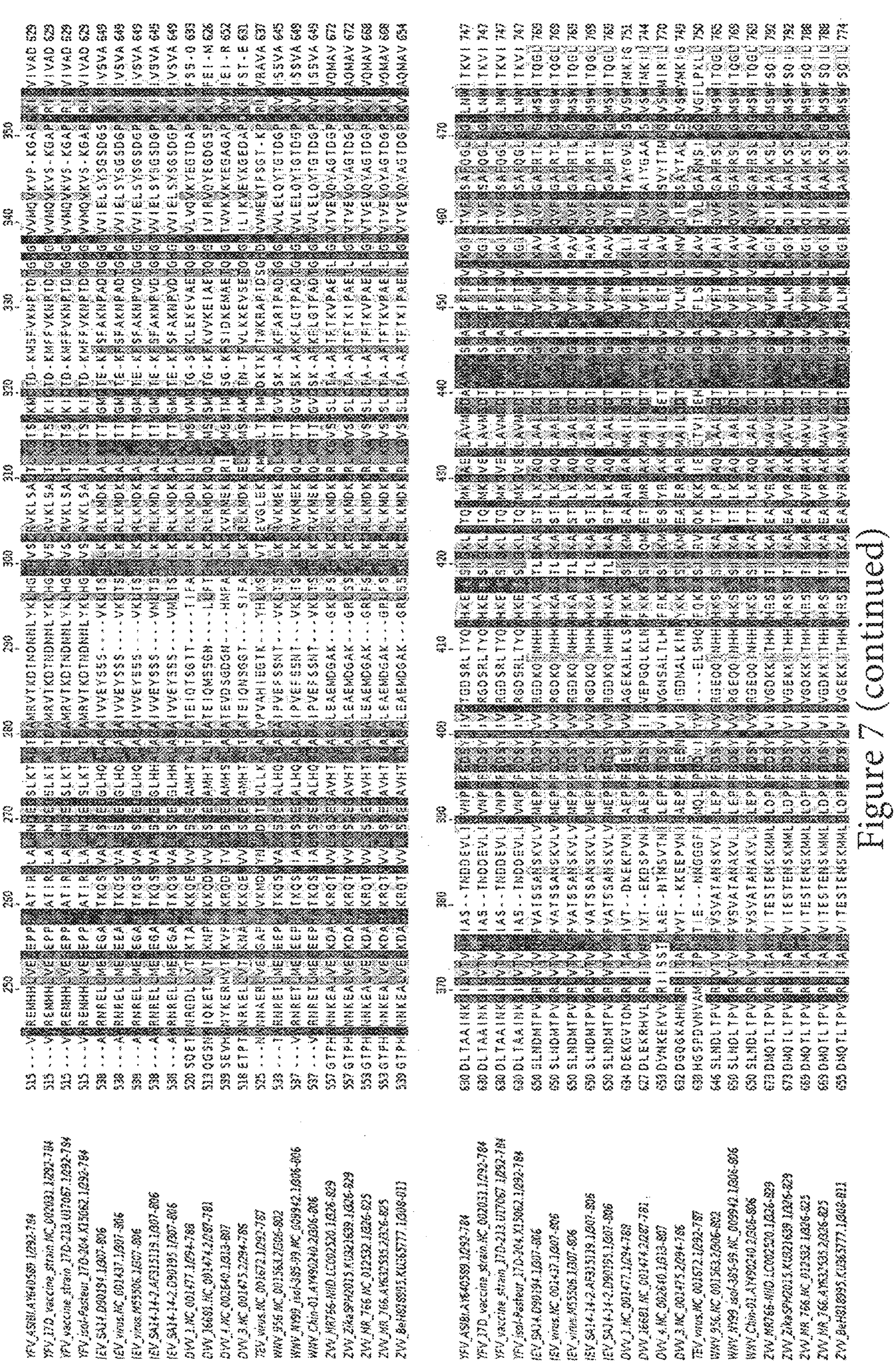
Figure 8:
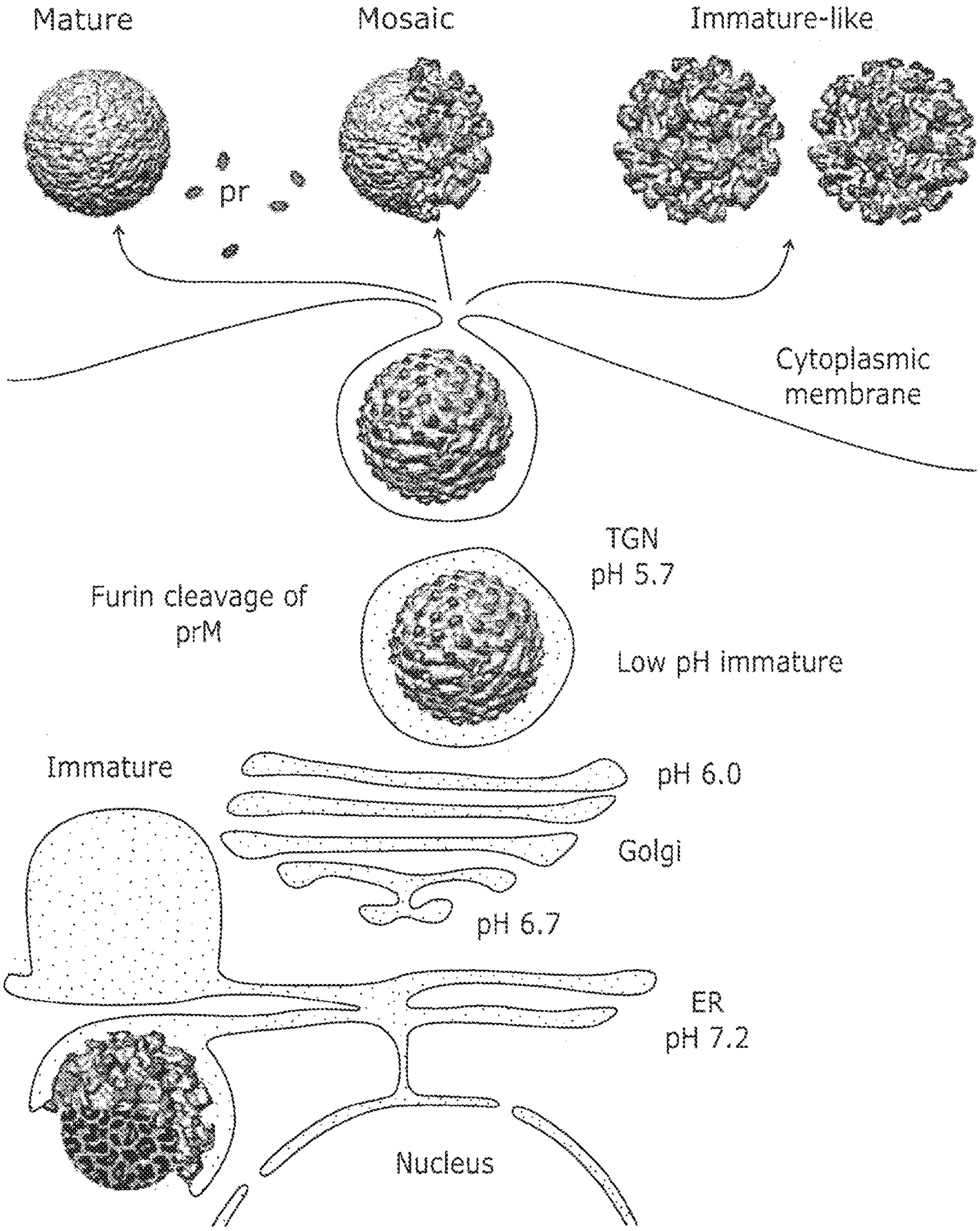
FIG. 8: An example of virus particle maturation in the host cell. As observed in flaviviruses, full maturation of the particles requires proteolytic cleavage of the precursor membrane glycoprotein (prM) by the host protease furin. Not all prM molecules are cleaved, resulting in the release of mature, mosaic or immature-like conformations from the cells. Mosaic and immature forms are generally not infectious—only mature virions are infective and have hemagglutinin (HA)/TCID50 activity. (Figure adapted from Plevka, et al., Maturation of flaviviruses starts from one or more icosahedrally independent nucleation centres, EMBO reports (2011) 12, 602-606).
Figure 9:
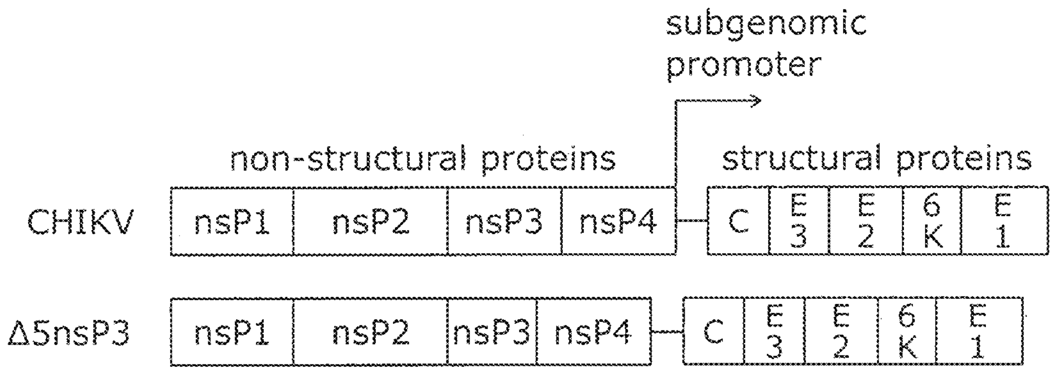
FIG. 9: Chikungunya virus schematic genome ("CHIKV"), including non-structural (nsP1-4) and structural proteins (C, E3, E2, 6K and E1) as well as a representation of the Δ5nsP3 attenuated Chikungunya virus used to exemplify the purification process of the current invention (labeled "Δ5nsP3"). The black triangle indicates the approximate location of the deletion in the nsP3 coding region. (Figure adapted from Hallengard et al. 2014, supra.)
Figure 10:
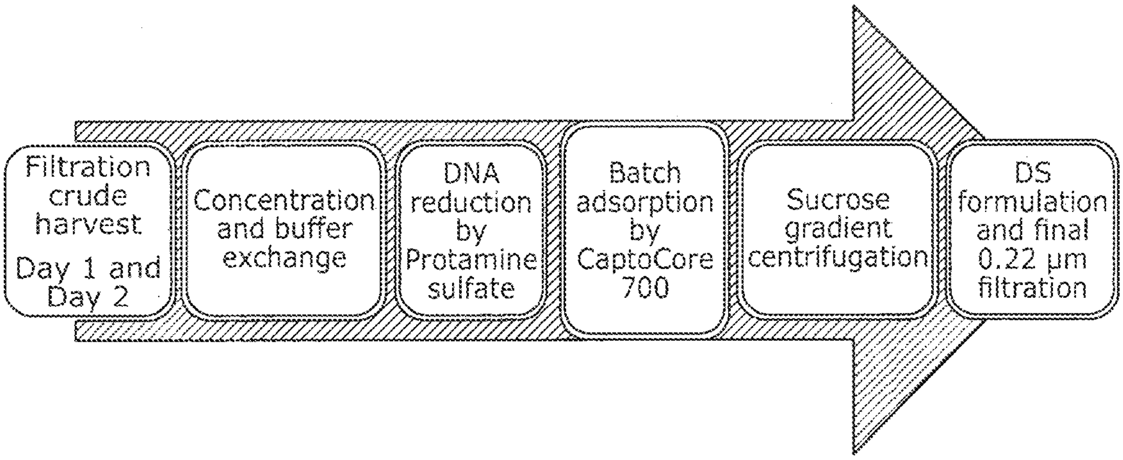
FIG. 10: Flow-chart showing an exemplary downstream Δ5nsP3 ChikV virus purification process from the crude harvest to formulation of the (vaccine) drug substance, a preferred embodiment of the process of the invention.
Figure 11A:
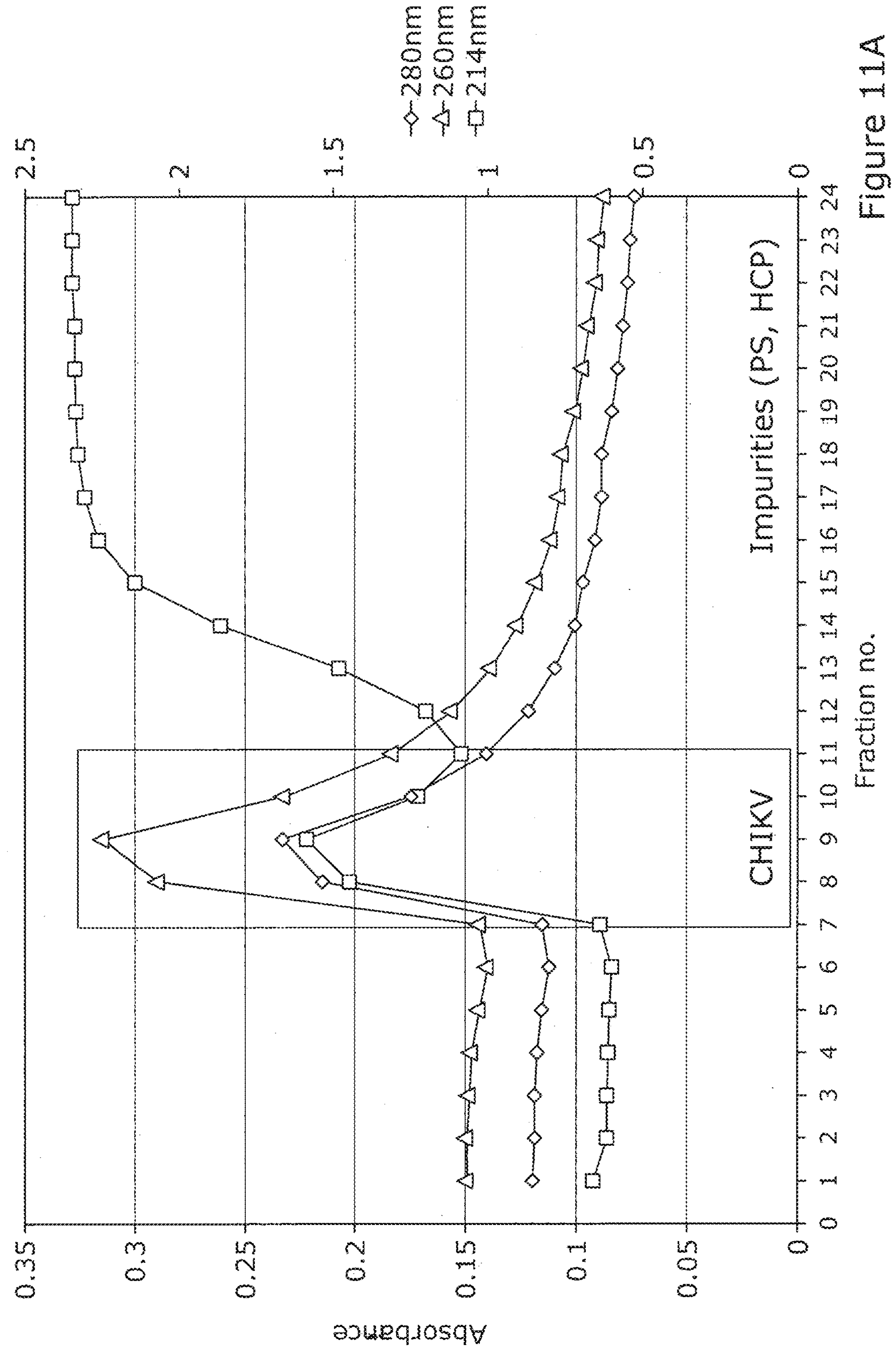
FIG. 11: Absorbance at 214 nm, 260 nm and 280 nm of individual sucrose gradient centrifugation (SGC) fractions of a representative purification run of the process of the invention (A); SEC-HPLC analysis of the final pooled fractions containing purified infectious attenuated Δ5nsP3 ChikV virus particles (B); and a silver-stained SDS-PAGE gel showing the protein content of the virus preparation following different steps of the process of the invention (defined in the table below the figure) (C).

UV absorbance measurement was used as primary method for analysis of the sucrose gradient fractions. Absorbance at 214, 280 and 260 nm was tested immediately after fractionation was completed. Briefly, a 100 μL sample of each fraction was transferred into a 96 well plate and absorbance at 214, 260 and 280 nm was measured using a plate reader. The absorbance values were plotted against the fraction number. A representative profile is shown in FIG. 11A. The Δ5nsP3 ChikV containing fractions were indicated by a peak in all three measured wavelengths (FIG. 11A, grey shaded area). The presence of impurities was indicated by an increase of the UV214 signal after the main peak. The fractions comprising the main peak were pooled from the peak start to the valley of the 214 nm curve. This method can be used as single method for pooling Δ5nsP3 ChikV fractions.

After identification of the virus containing fractions, the respective fractions were pooled. Pooling criteria for SGC fractions were based on UV 260 nm data, e.g. start of pooling at ~10% of peak maximum, end of pooling at ~30% of peak maximum. (Final pooling criteria at a manufacturing scale may need to be determined empirically.) The sucrose gradient pool was either stored at <~65° C. or immediately further formulated to drug substance (DS).

Size Exclusion Chromatography

The final pooled SGC fractions containing purified infectious Δ5nsP3 ChikV particles were analyzed for purity by SEC-HPLC. In brief, SEC was performed as follows: a Superose 6 10/300 Increase column (GE Healthcare) equilibrated with PBS+250 mM NaCl, pH 7.4 at 1 ml/min and 25° C., was used to detect ChikV particles at 214 nm detection wavelength in the pooled samples. SEC-HPLC is a semi-quantitative (relative yield) and qualitative (purity) method that separates intact virus particles from virus aggregates and host cell proteins (HCPs). The method cannot distinguish between infectious and non-infectious virus particles due to their identical retention time.

Figure 11B:
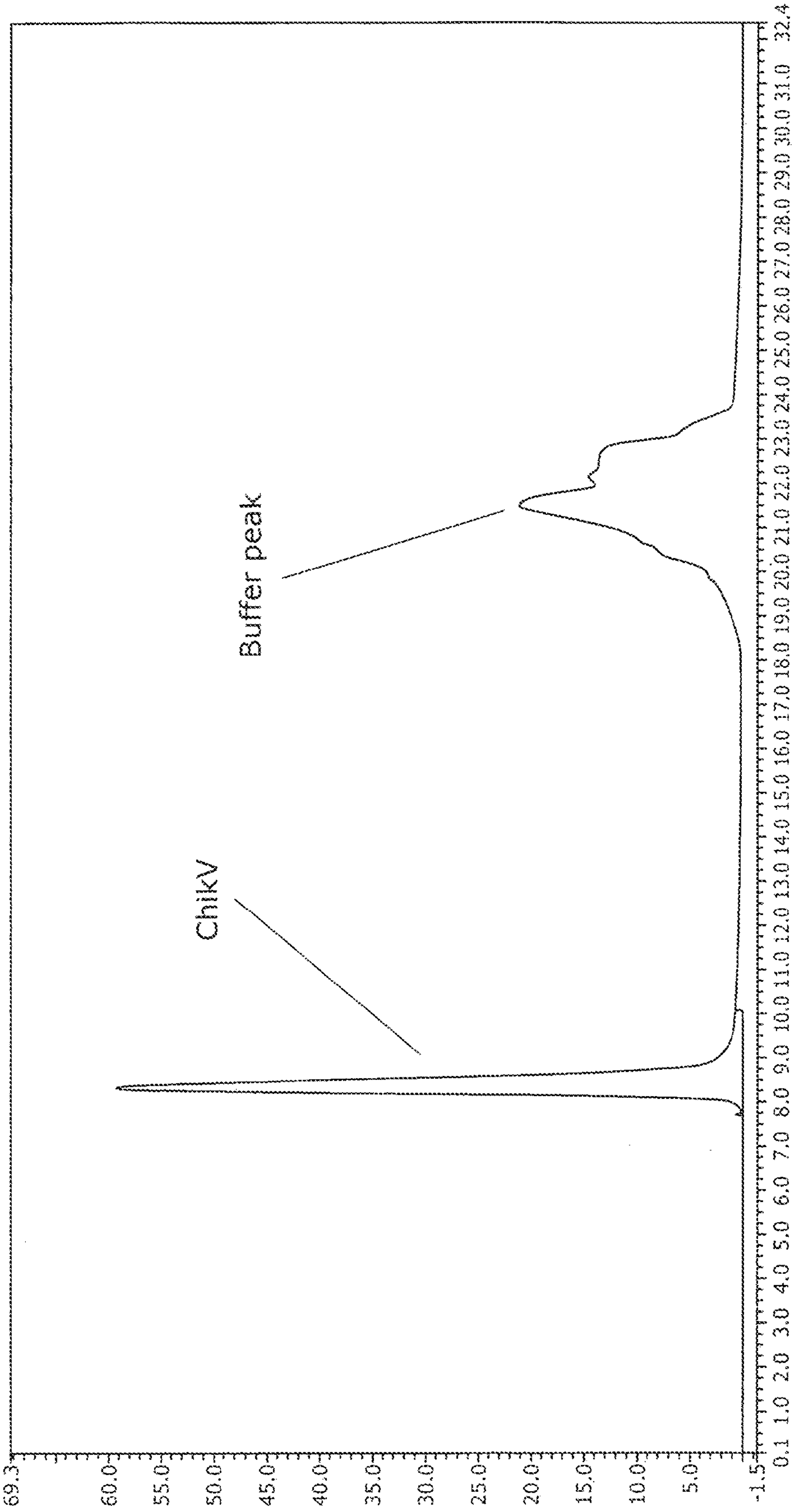

As shown in FIG. 11B, there were two defined peaks identified by SEC: the Δ5nsP3 ChikV peak and a peak corresponding to buffer components. The SGC step yield based on SEC-HPLC data for pooled fractions F6-F11 was estimated at ~70%. The final purity of the Δ5nsP3 ChikV SGC pool, based on SEC-HPLC analysis, was estimated at >95%.

SDS-PAGE and Silver Stain

SDS-PAGE silver stain was performed in order to qualitatively assess sample purity throughout the purification process from the first crude harvest through SGC. Briefly, ChikV process samples analyzed by SDS-PAGE/silver stain were diluted 1:1.33 with LDS buffer and were heated to 70° C. for 5 minutes. The samples were loaded onto 4-12% Bis-Tris Gels (NuPAGE). Silver staining was done using the Silver Express staining kit (Invitrogen).

A silver-stained gel of a representative ChikV Δ5nsP3 purification is shown in FIG. 11C. The viral proteins E1, E2 and C are marked on the right-hand side of the gel. The final SGC pool (fraction 7-fraction 11) is shown in lane 12. Note that a defined HCP band migrating between ChikV protein E2 and C still appears after CaptoCore700 treatment that has been identified as a single band in SDS-PAGE. This impurity is removed by sucrose gradient centrifugation, but can still be seen in fractions 13 and 14 (corresponding to lanes 14 and 15 of FIG. 11C).

Enrichment of Infectious Δ5nsP3 ChikV Particles by PS Treatment

Although generally used as a method of removing contaminating hcDNA, it was observed in the course of the present invention that PS treatment also removes virus aggregates and HCPs. Size exclusion chromatography (SEC-HPLC, as described above) was used throughout the purification process to determine the purity of the ChikV virus relative to impurities which also generate UV absorption.

Figure 12A:
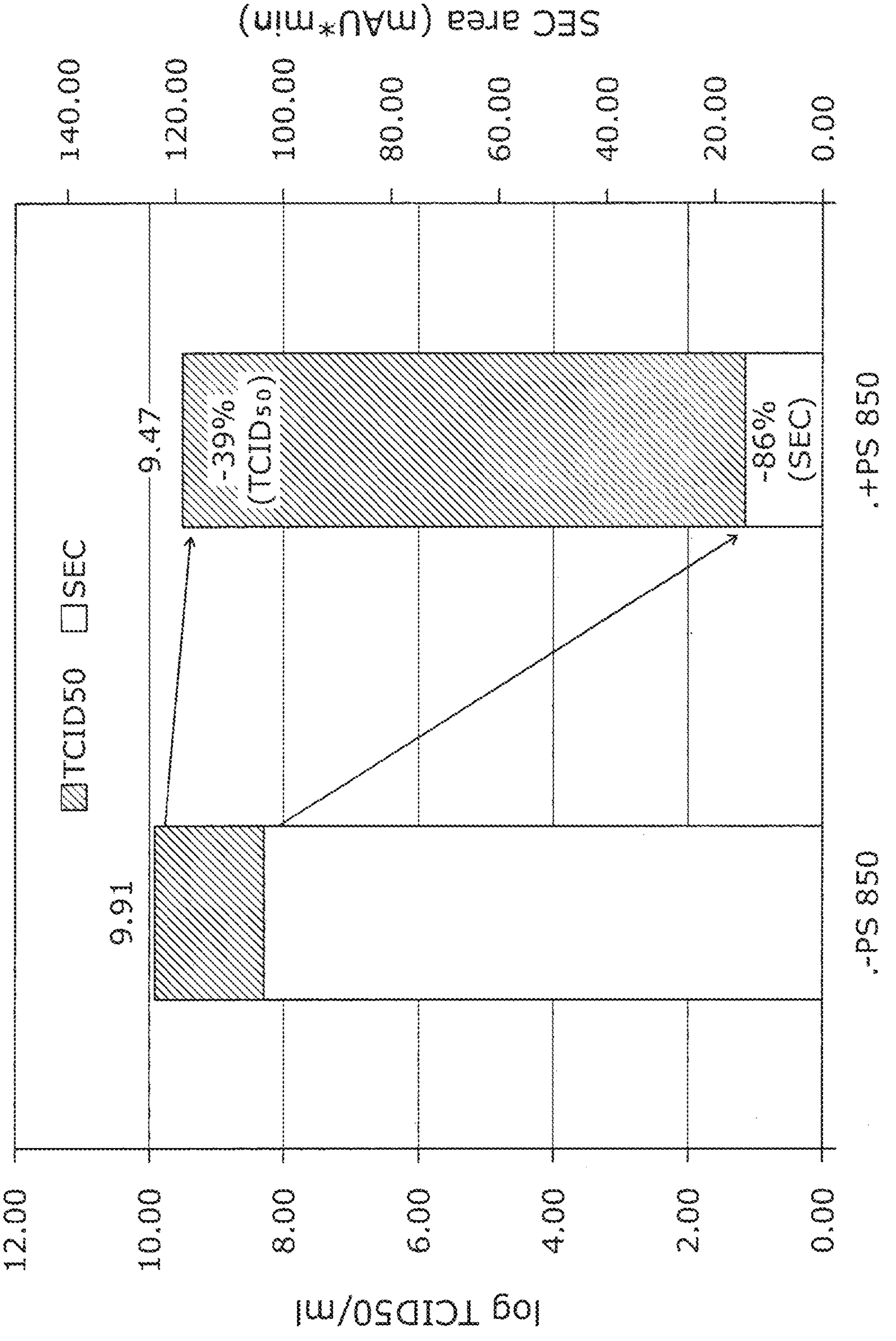
Figure 12B:
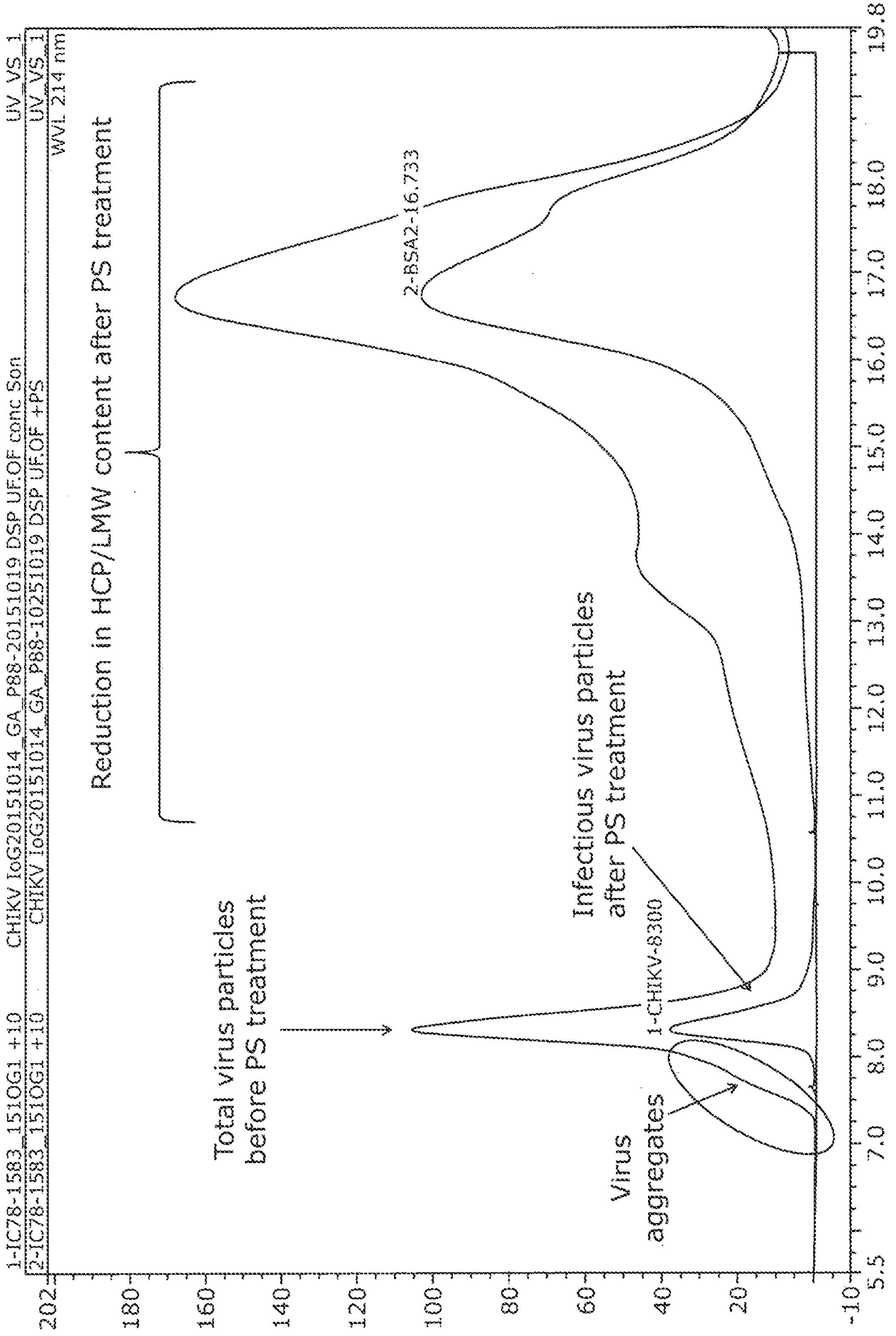

As can be seen in FIG. 12B, treatment with PS reduces not only host cell proteins and low molecular weight contaminants of the Δ5nsP3 ChikV preparation, but also reduces the SEC area corresponding to virus products, including aggregates as indicated. A surprising finding, however, was that even a reduction of the total SEC area by 86% (in a representative experiment shown in FIG. 12A, grey portion of bars) did not result in a concomitant reduction in infectious virus particles as measured by TCID50 (FIG. 12A, left axis). Instead, even though a large percentage of virus particles were removed by PS treatment, the majority of infectious particles remained. This observation indicates that PS treatment selectively enriches infectious virus particles from a larger pool of total virus particles present in the crude harvest.

TCID50 was performed to quantify infectious virus particles during the course of the purification process and to assign an active virus titer to final drug substance and drug product samples. Briefly, Vero cells were seeded at $2\times10^4$ cells per well in 100 μL medium (EMEM with 2 mM L-Glutamine+5% FBS+1% antibiotic/antimycotic) in 96-well TC-treated flat-bottom plates and incubated overnight at 35° C./5% $CO_2$. On day two, Vero cell monolayers were infected by adding 100 μL of 1:10 serial dilutions of test samples to each of quintuplicate wells seeded with Vero cells and incubated at 35° C./5% $CO_2$. On day seven, plaques were counted by visualization under a microscope. The TCID50 was calculated according to the Reed & Munch endpoint calculation method (Reed, L. J.; Muench, H. (1938) A simple method of estimating fifty percent endpoints, The American Journal of Hygiene 27: 493-497).

Furthermore, electron microscopy of Δ5nsP3 ChikV samples before and after PS treatment showed that not only large aggregates but also smaller non-infectious virus-like particles (essentially not fully assembled particles lacking the RNA genome) were effectively removed by PS (FIG. 13).

This enrichment of infectious virus particles was also observed when analyzing day one and day two crude harvests separately. As presented in Table 4, the SEC area (total virus particles) of the day 1 harvest remains roughly the same after PS treatment; whereas a large decrease in virus peak area is seen for the day 2 harvest after PS treatment. This observation was confirmed by MALLS analysis of the virus preparation, wherein it was seen that a higher percentage of virus particles were of the correct size following PS treatment. Similarly to the results shown in FIG. 12, day 1 and day 2 harvests showed no reduction in infectious particles as measured by TCID50 following PS treatment, indicating that mainly non-infectious, immature and/or aggregated virus particles are removed during the PS treatment and infectious particles are enriched in the preparation.

Figure 15A:
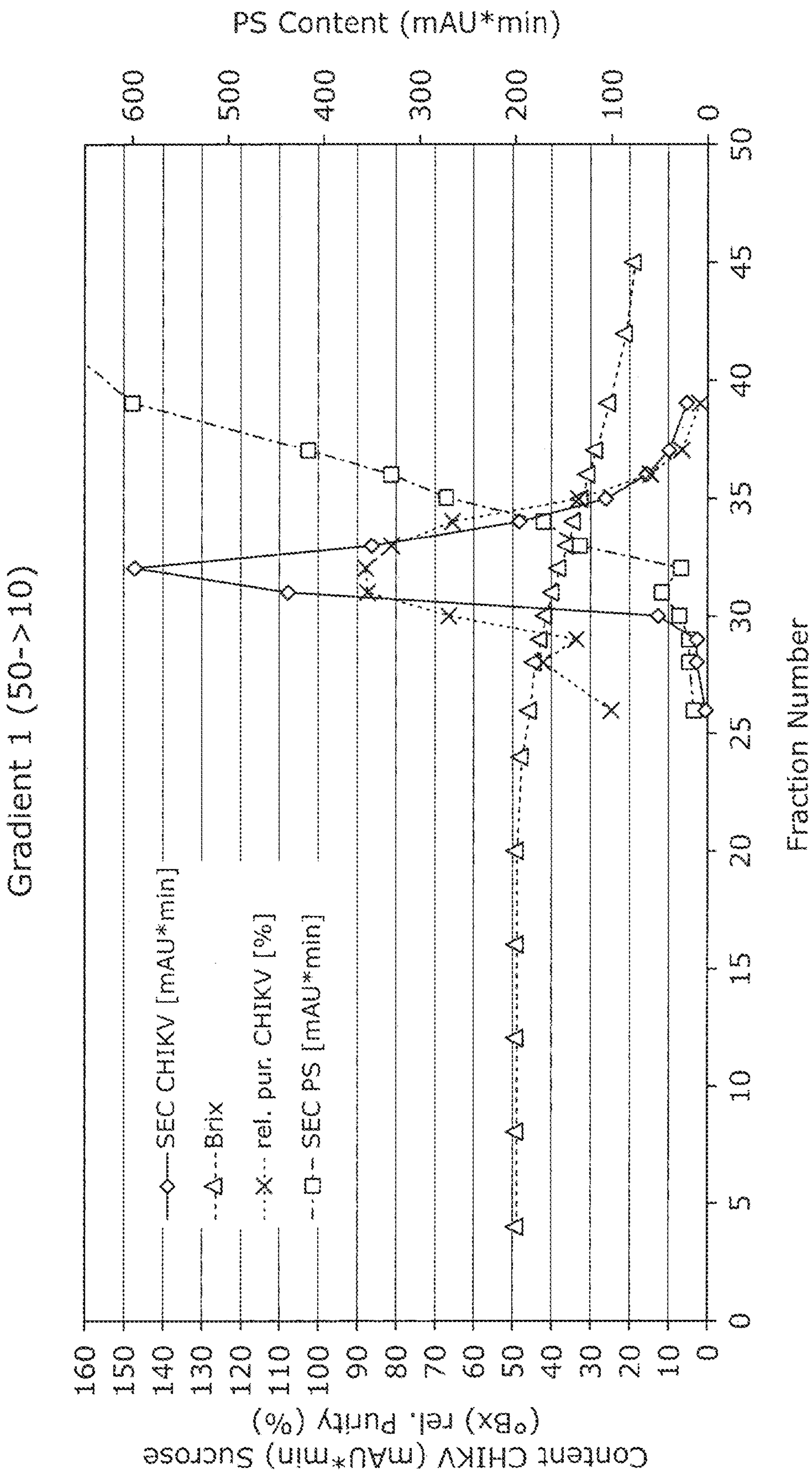
Figure 15B:
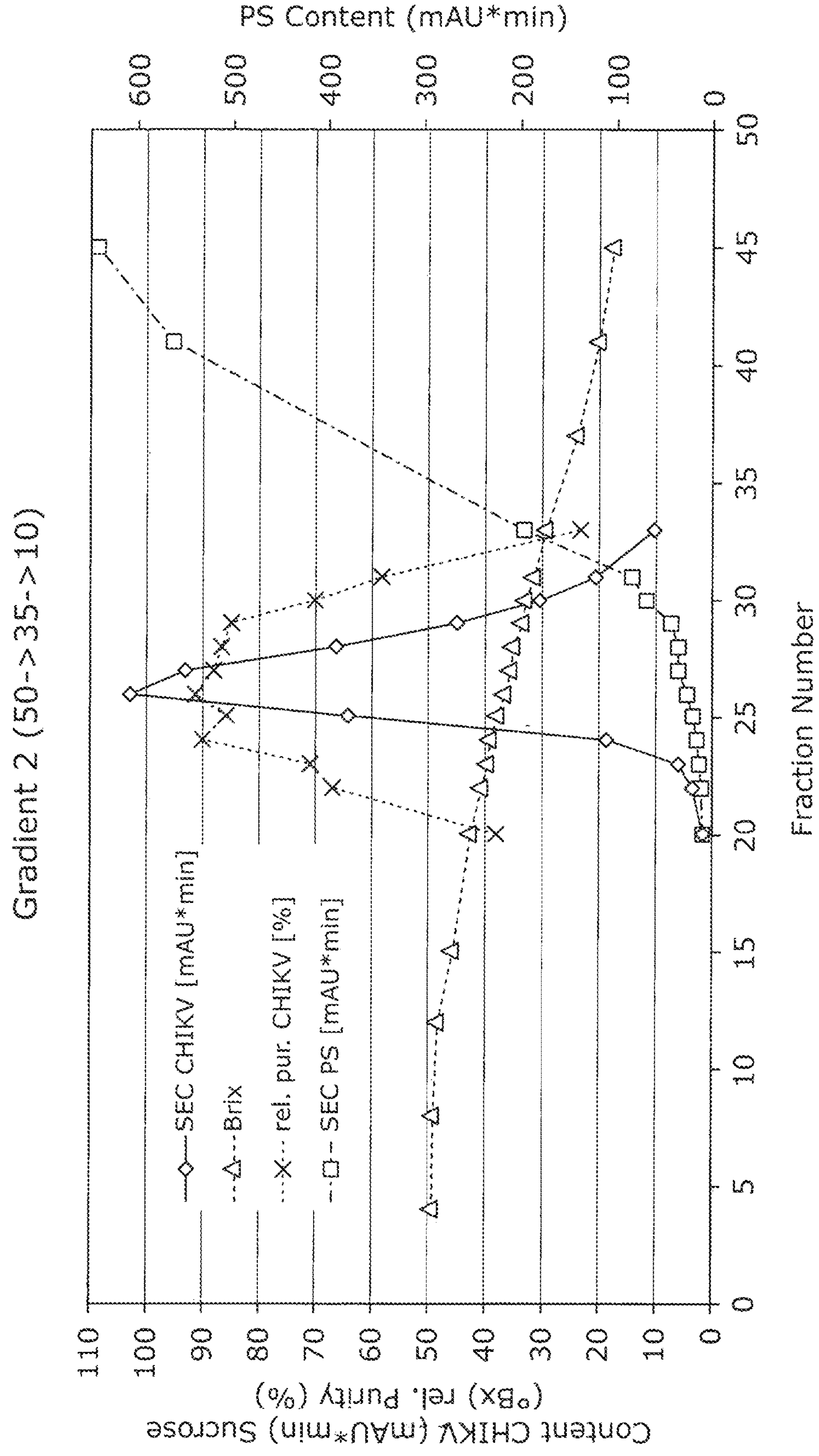
Figure 15C:
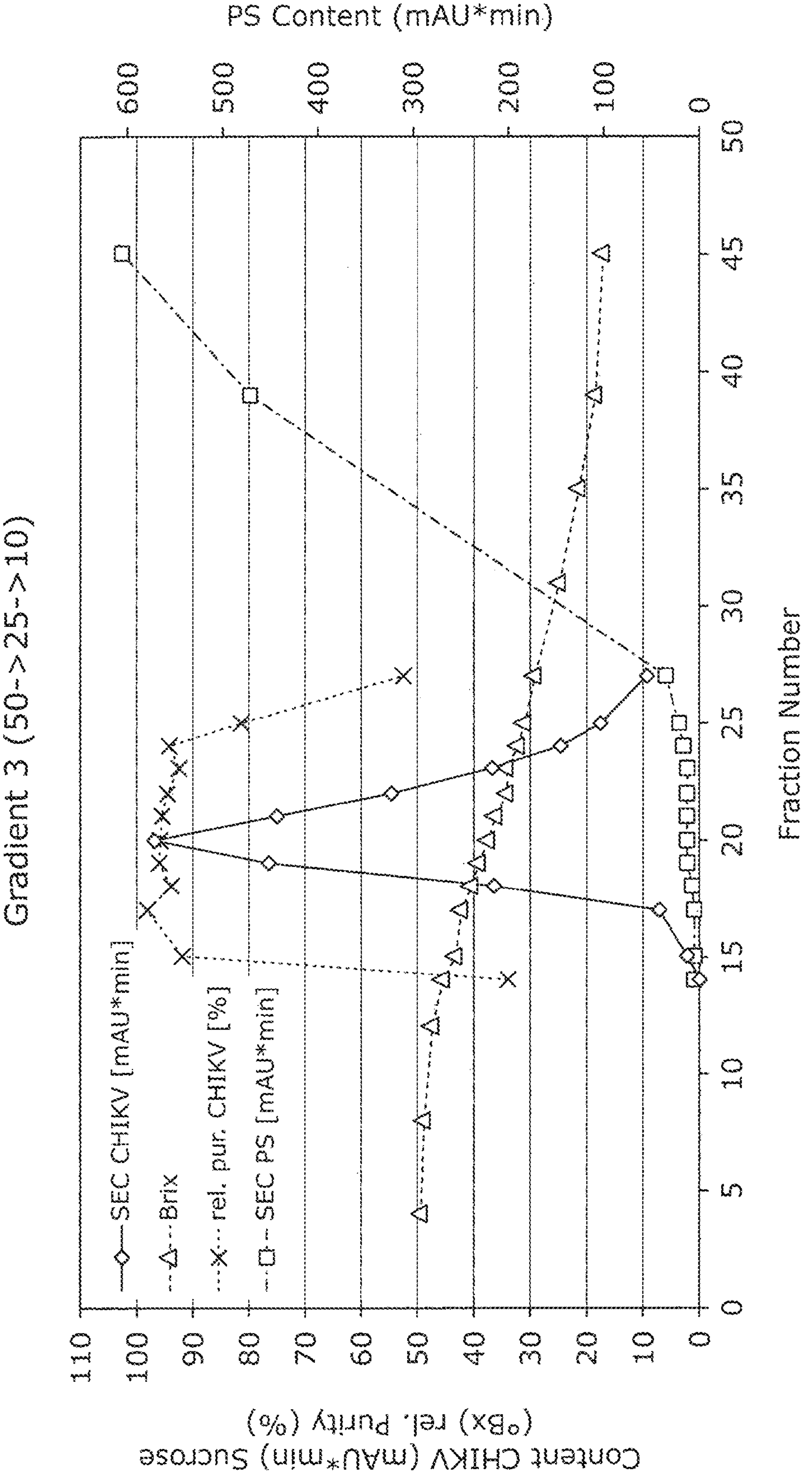
Figure 15D:
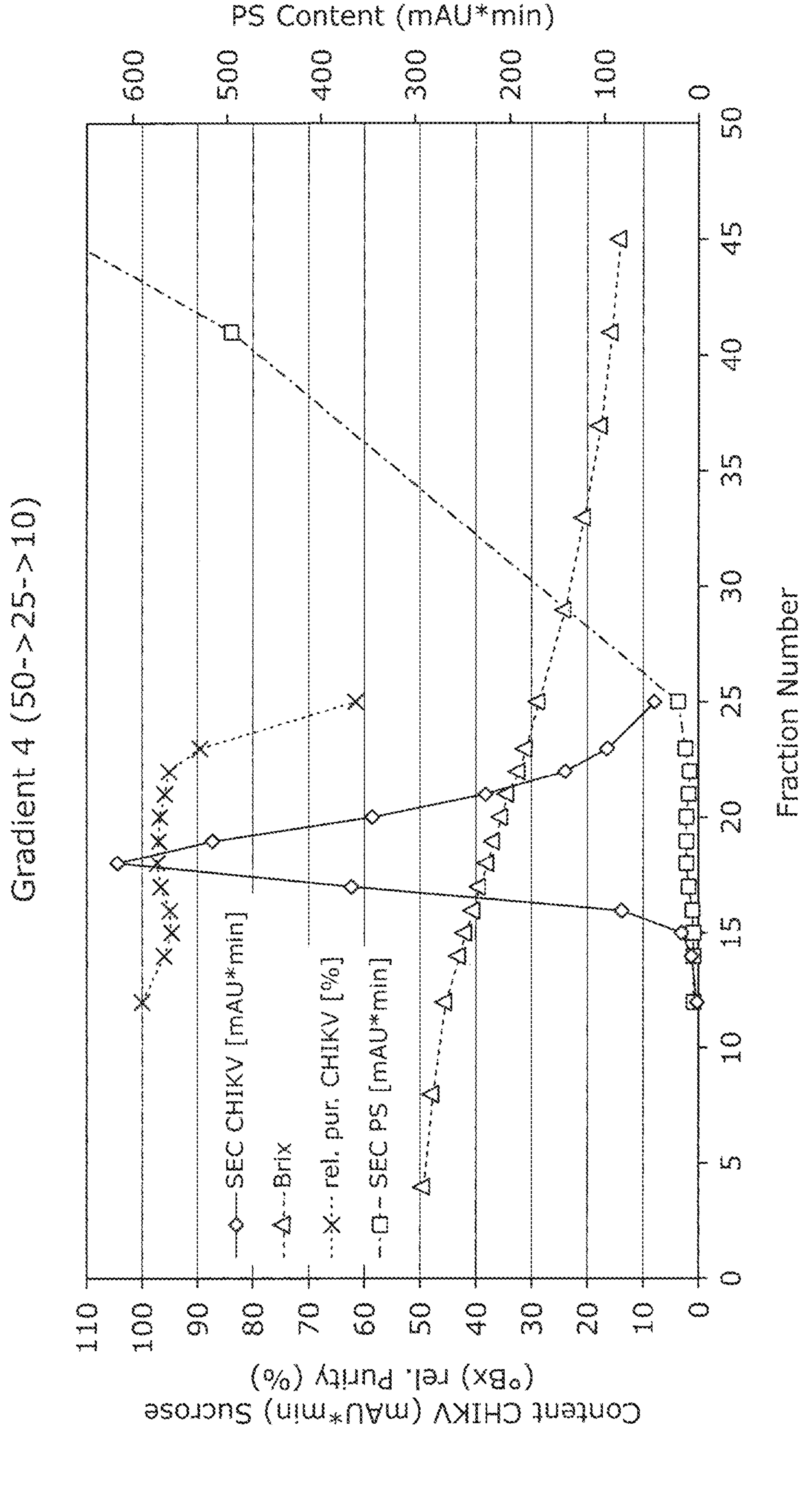

The PS-treated samples were further purified by sucrose gradient centrifugation (see FIG. 14 for a schematic preparation of an optimized sucrose gradient). An optimal sucrose gradient was determined experimentally as shown in FIG. 15. Results of the further purification of PS-treated ChikV on the optimized sucrose gradient of the invention are shown in FIG. 15D.

TABLE 4

Overview of the process of Δ5nsP3 ChikV purification as described in Example 1. SEC-MALLS analysis of harvests before and after PS treatment shows the removal of larger virus particles (aggregates), an effect that is particularly pronounced for day 2 harvests.

| | SEC | MALLS | | Infectious |
|---|---|---|---|---|
| | Area [mAU * min] | Total particles/ mL | % correct size (20-40 nm) | particles TCID50 log 10 |
| Harvest 1 (H1) | 57 | 1.17E+11 | 49% | 10.2 |
| H1 + protamine sulphate | 53 | 1.33E+11 | 81% | 10.0 |
| Harvest 2 (H2) | 36 | 4.60E+09 | 3% | 7.9 |
| H2 + protamine sulphate | 2 | 8.80E+09 | 59% | 7.9 |
| Combined Harvests (C) | 67 | 2.60E+10 | 14% | 9.9 |
| C + protamine sulphate | 24 | 8.00E+10 | 72% | 10.1 |

Finally, an overview of the relative amounts of Δ5nsP3 ChikV particles and other components as measured by SEC-HPLC at various steps throughout the entire virus purification process from crude harvest (a) to the final SGC purified pool is presented in FIG. 16. In sum, not only are the vast majority of contaminants and undesired products removed by the process, infectious ChikV particles are highly purified. As shown by the previously presented data, the final preparation is a highly enriched preparation of infectious ChikV particles.

Drug Substance (DS) Formulation

The pooled SGC fractions are diluted with DS formulation buffer M (10 mM Tris, 5% Sucrose (w/w), 1% (10 mg/mL) rHSA, pH 7.4±0.2). The final target volume of DS should be in the range of approximately 2 L. Based on current data the estimated range of the dilution factor might be 1:20 to 1:50.

Final DS Sterile Filtration

The final DS was filtered under aseptic conditions in a laminar flow hood using a sterility grade 0.2 μm syringe filter (e.g. 0.2 μm Mini Kleenpak EKV filter capsule with 220 $cm^2$ filter surface, Pall).

Quantification of Host Cell DNA (hcDNA) Host Cell Protein (HCP) and Endotoxin

The residual host cell DNA content of the sucrose gradient pool samples was determined by using the qPCR based assay. The DNA content in SGC pool was determined to be ≤0.002 ng/mL. The presence of residual host cell protein (HCP) from Vero cells was determined by ELISA. Residual host cell proteins present in the sucrose gradient pool samples were quantified using the Vero Cell HCP ELISA kit (Cygnus, F500). The residual host cell protein content in SGC pool was determined to be ≤200 ng/mL.

Endotoxin content of the SGC pool and DS was measured by Endosafe®-PTS™ system (Charles River). The system uses Limulus Amembocyte Lysate (LAL) reagents by a kinetic chromogenic methodology to measure color intensity directly related to the endotoxin content in a sample. Each cartridge contains precise amounts of a licensed LAL reagent, chromogenic substrate and an endotoxin control standard. Samples were diluted 1:100 in WFI. The SGC Pool F7-F11 was determined to be <5.00 EU/mL; likewise, the Drug Substance was also determined to have <5.00 EU/mL.

The following specifications for impurities in final Drug product were proposed: hcDNA <10 ng/dose; Endotoxins <50 EU/dose; HCP <200 ng/dose. These residual specifications would already be met in the highly concentrated SGC pool (~10 log TCID50/mL), which provides a high margin of safety considering the high dilution factor of SGC pool to final DP of >1:1000.

Example 2: Production of a Zika Drug Substance Suitable for Application as a Vaccine in Humans and Animals Materials and Methods:

For the production of ZikaV the JEV process platform (Srivastava et al., Vaccine 19 (2001) 4557-4565; U.S. Pat. No. 6,309,650B1) was used as a basis. Small changes of certain process steps were adapted to ZikaV properties and to improve purity. A short summary of the process steps is outlined below (see also FIGS. 17A and B). Briefly, the unexpected and novel purification properties of protamine sulphate (PS) were evaluated in purification processes for Zika Virus similarly as found above. Again non-infectious virus particle aggregates, HCP and other LMW impurities were removed by PS precipitation as shown by removal of aggregate shoulder in SEC-HPLC and no loss of infectious virus titer by PS treatment (FIG. 18). Further optimization of the Zika purification protocol is provided below.

Upstream:

Roller Bottle based Vero cell expansion (25×850 cm2 CellBind):

5% $CO_2$, 35° C., MEM+2 mM L-Glutamine+10% FBS

Infection with ZikaV research Master Seed Bank (rMSB) at MOI 0.01

Virus Production without serum

5% $CO_2$, 35° C., MEM+2 mM L-Glutamine

Multiple harvests (days 2, 3, 5 and 7) with re-feed

Sterile filtration of harvests and storage at 2-8° C. until further processing

Downstream:

Pooling of harvests and concentration by ultrafiltration (100 kDa)

Stabilization of concentrated harvest (Tris/10% sucrose) for storage if required (−80° C.)

Removal of hcDNA by Protamine Sulphate (2 mg/mL)

Sucrose Gradient Purification (optimized three layered gradient)

Formaldehyde Inactivation (0.02%, 22° C., 10 days), neutralization with Na-metabisulfite Dilution to DS antigen target content and formulation with Aluminium hydroxide (0.5 mg Al/mL)

Zika Virus Strain H/PF/2013 was originally isolated from a 51-year-old woman (accession number KJ776791.1, also SEQ ID NO: 13 herein) from French Polynesia. A sample was obtained from the European Virus Archive (EVAg; Ref-SKU: 001v-EVA1545). Based on this material, a research master seed bank (rMSB) was prepared on Vero cells as the cell substrate and the genomic sequence was checked by sequencing. Because the genomic sequence at the 5' and 3' flanking sequences of Zika virus strain H/PF/2013 was unknown, primers for sequencing were designed in those regions based on other Zika virus strains whereas the internal primers were designed from the published sequence (SEQ ID NOs: 80 to 123, see also Table A). The sequence obtained from the rMSB by use of these primers is provided by SEQ ID NO: 78. There was 100% overlap of the sequence with the published sequence of Zika Virus Strain H/PF/2013 (SEQ ID NO: 13). However, we sequenced additional regions 5' (an additional 40 bp) and 3 (an additional 160 bp) represented in SEQ ID NO: 78. In a preferred embodiment, the Zika virus of the invention comprises SEQ ID NO: 78. The genomic RNA is somewhat longer than the sequence according to SEQ ID NO: 78 (perhaps an additional 200 bp). Additionally, a Zika virus adapted to a host cell such as e.g. Vero cells may be expected to contain one or more mutations. For these reasons, the Zika virus of the current invention comprises the sequence of SEQ ID NO: 78 or, preferably, a sequence with at least 95%, 96%, 97%, 98%, or at least 99% sequence identity to the sequence provided by SEQ ID NO: 78. Furthermore, because the viral genome is likely to contain even further flanking regions to SEQ ID NO: 78; in one embodiment, the Zika virus of the invention contains the sequence of SEQ ID NO: 78 and optionally further comprises extensions at the 5' and/or 3' ends of at least 10, at least 20, at least 30, at least 40, at least 50, at least 60, at least 70, at least 80, at least 90, at least 100, at least 110, at least 120 or at least 130 nucleotides. In a preferred embodiment, the Zika virus comprises at least the coding sequence for the entire polyprotein of Zika Virus Strain H/PF/2013 of the invention i.e. the amino acid sequence of SEQ ID NO: 79 or a polyprotein with at least 95%, 96%, 97%, 98%, or at least 99% sequence identity to the sequence provided by SEQ ID NO: 79. Furthermore, the Zika virus comprises at least the coding sequence for the E-protein of Zika Virus Strain H/PF/2013 of the invention SEQ ID NO: 47 or an E-protein thereof with at least 95%, 96%, 97%, 98%, or at least 99% sequence identity to the sequence provided by SEQ ID NO: 47.

Virus Growth on Vero Cells

Vero cells were grown in Eagle's minimal essential medium (EMEM) containing 10% fetal bovine serum (FBS). Roller bottle cultures of Vero cell monolayers were infected with Zika Virus Strain H/PF/2013 at a multiplicity of infection (moi) of 0.01 plaque forming units (pfu) per cell. After 2 hours of virus adsorption, the cultures were washed 3 times with PBS and fed with EMEM without FBS and incubated at +35° C. with 5% $CO_2$. Infected Vero cell cultures were incubated until the virus titer reaches a desired level.

The culture medium was harvested at days 2, 3, 5 and 7 and were pooled from those harvest days and then centrifuged in a standard centrifuge. The supernatants were then filtered. Virus culture supernatants were concentrated by TFF ultrafiltration to remove cell culture media components and to reduce batch volume.

Evaluation of Harvest Procedure

The current JEV harvest process has scheduled harvests on days 3, 5, 7 and 9 post infection. To mimic the JEV process roller bottles were infected with ZIKV bank P4-FBS at an MOI of 0.01 in infection medium (MEM with 2% FBS+2 mM L-glutamine) for 2 hours. After removing the inoculum the cells were washed twice with PBS and 200 mL production medium (MEM+2 mM L-glutamine) was added. After taking a sample on day 2 the first virus harvest was conducted on day 3 after infection. At this point significantly higher CPE could be observed compared to cells where virus was removed on day 2. Plaque assay analysis showed that the viral titers on day 2 were in the same range as for the standard harvesting schedule. However, starting with the day 3 harvest, the observed titers were significantly lower correlating with the increased CPE observed compared to the standard harvest schedule. On day 5 post infection no more living cells could be observed at all and the experiment was terminated with a final day 5 harvest.

TABLE 5

The calculated titers per plaque assay are summarized in the list below.

| | Log 10 PFU/mL |
|---|---|
| sample day 2 | 7.02 |
| harvest day 3 | 6.66 |
| harvest day 5 | 6.26 |

This finding led to an optimized harvest schedule to better control of CPE and allow additional harvest day 5 and 7, see FIG. 23. For both harvest days the optimized ZikaV protocol yield significant higher virus titers compared to the modified protocol showing that the time of the first harvest is crucial for production yields. Additionally first harvesting at day 3 results in maximum 2 harvest points whereas first harvesting at day 2 allows for 4 harvest points further increasing the yield gain.

Downstream Purification of Zika Virus

The purification process was carried out at room temperature (18-22° C.) unless stated otherwise. Virus purification started with concentration of filtered combined harvest using 100 kDa cut-off TFF ultrafiltration modules to remove cell culture media components and reduce batch volume. After concentration, the pooled filtered harvest material was adjusted to a final concentration of 25 mM Tris pH 7.5 and 10% sucrose (w/w) using stock solution of both components (see FIG. 19 for SEC-HPLC of different harvests prior to PS treatment). This allowed for freezing the concentrated harvest at <−65° C. if required.

Host cell DNA and protein reduction as well reduction of non-infectious virus aggregates in the concentrated material was achieved by precipitation with protamine sulphate (2 mg/mL) followed by sucrose density centrifugation (2-8° C.) as final polishing step (see FIG. 20 for SEC-HPLC of different harvests post PS treatment). The purification process was designed to be completed within 2 working days with SGC starting on end of day 1 followed by fractionation and SDS-PAGE analysis on day 2. The sucrose gradient fractions were stored at 2-8° C. during the SDS-PAGE analysis (Silver staining) to identify the pure fractions containing ZikaV (see FIG. 21). After pooling the relevant fractions, the pool was diluted and inactivated by Formalin. After pooling the relevant fractions of sucrose gradient centrifugation, the pool was diluted 1:3 in PBS and inactivated by Formalin (0.02% v/v, 200 ppm). Fractions were subjected to analysis by SDS-PAGE.

Effect of PS Treatment on Virus Recovery

Samples of individual 30× concentrated harvests days 2, 3, 5 and 7 were analysed before (FIG. 19) and after PS (FIG. 20) treatment by SEC-HPLC and plaque assay. SEC-HPLC was used for determination of relative total ZikaV content (active+inactive) expressed as peak area, whereas the rel. ZikaV peak purity is given as relative content of virus monomer population to total virus peak. Plaque assay states the content of total active virus particles in each sample. Experimental results are summarized in Table 1. The virus peak recovery by SEC-HPLC was only between 12 to 36% with peak purity after PS treatment in the range of >90% (no virus aggregates detected). The recovery of active virus particles by plaque assay was all >100% (130-700%, range within the variability of the assay) showing that no active virus particles were lost during PS treatment. These results show that during PS treatment only non-infective (immature and/or aggregated virus) particles were removed.

TABLE 6

ZikaV recovery by SEC-HPLC and plaque assay before and after PS treatment.

| SEC-HPLC | | | | |
|---|---|---|---|---|
| | Peak area mAU * min | | | |
| Harvest day | 30x conc | 30x + PS | SEC Recovery (%) | rel. virus monomer content after PS (%) |
| Day 2 | 101.36 | 18.63 | 18 | 89% |
| Day 3 | 144.51 | 17.48 | 12 | 90% |
| Day 5 | 19.97 | 5.92 | 30 | 96% |
| Day 7 | 68.80 | 24.43 | 36 | 99% |

| Plaque Assay | | | |
|---|---|---|---|
| | PFU/mL | | |
| Harvest day | 30x conc | 30x + PS | Plaque Recovery (%) |
| Day 2 | 3E+08 | 5E+08 | 179 |
| Day 3 | 2E+08 | 4E+08 | 193 |
| Day 5 | 1E+08 | 9E+08 | 700 |
| Day 7 | 3E+08 | 4E+08 | 132 |

Sucrose Gradient Centrifugation

The PS treated harvest was split in two parts and loaded on two centrifuge bottles. Sucrose density gradient centrifugation (SGC) was used for final concentration and polishing of the ZikaV material. The ZikaV PS treated concentrated harvest was loaded on top of a solution consisting of three layers of sucrose with different densities. The three sucrose layers were selected based on a preliminary study which showed the formation of a linear sucrose gradient and complete separation of the virus particles from residual contaminants as demonstrated for ChikV (FIG. 15D). The optimal volumes of the sucrose solutions were determined empirically. The volumes of individual layers for a centrifugation in 100 mL bottle scale are shown in Table 2.

TABLE 7

Individual layers/volumes for a centrifugation in bottle.

| Solution | Volume (mL) |
|---|---|
| PS treated harvest in 10% sucrose (L) | 40 |
| 15% sucrose (J) | 15 |
| 35% sucrose (I) | 15 |
| 50% sucrose (H) | 20 |
| Total volume | 90 |

The sucrose gradient bottles were prepared by stratifying the individual sucrose layers. A plastic tube was attached to peristaltic pump tubing. The plastic tube was mounted on a laboratory stand using a clamp and placed into the centrifuge bottle. The nozzle of the plastic tube was touching the bottom of the bottle. Using a peristaltic pump the ZikaV material and the sucrose solutions were pumped into the cylinder. A measuring cylinder was used as feed vessel. The first solution pumped was the ZikaV material as it represented the solution of lowest density (10% sucrose (w/w)). After the ZikaV material the sucrose solutions were pumped in ascending order starting with the 15% (w/w) solution J, followed by 35% sucrose solution I and finishing with the highest density sucrose solution H (50% (w/w)). The described setup is shown in FIG. 14. After all sucrose solutions were transferred the plastic tubing was carefully removed in order not to disturb the layers.

Prior to centrifugation the centrifuge was pre-cooled to 4° C. The prepared SG bottles were carefully transferred into the pre-cooled rotor. (Note: Sudden movement of the bottles during transfer to the rotor must be avoided in order not to disturb the sucrose layers.) The bottles were centrifuged at ~11.000 RCF max at 4° C. for at least 20 hours, no brake/deceleration activated. In case a different centrifuge system with a different rotor is used the necessary speed and centrifugation times need to be calculated based on the k-factor in order to achieve comparable centrifugation efficiency.

Harvesting of the sucrose gradient was done manually using a peristaltic pump. A plastic tube attached to peristaltic pump tubing was used for harvesting the sucrose gradient. The bottle containing the gradient was mounted onto a laboratory stand in a tilted position (~12°) using a clamp. The plastic tubing was then placed into the bottle touching the bottom edge of the bottle and was fastened in position using a clamp. This resulted in a small gap of 1-2 mm between the tubing inlet and the bottom of the bottle (see FIG. 14).

Using a peristaltic pump set to a flow rate of 30 mL per minute the gradient was harvested and manually split into 2 mL fractions. A total number of 32 fractions per bottle were harvested (~64 mL) and the remaining volume was discarded. The fractions were immediately tested by SDS-PAGE/silver stain to identify the virus containing fractions with sufficient high purity. Representative SDS-PAGE is shown in FIG. 21. Fraction 10-14 were pooled and further processed.

The purified viral solution was inactivated by incubation with 0.02% formaldehyde over a period of ten days in a 22° C. controlled-temperature incubator. The formaldehyde is neutralized by addition of sodium metabisulphite on the tenth day.

The sucrose gradient pool (~17 mL after sampling) was further diluted 3-fold with PBS to a final volume of 51 mL in a PETG container. A volume of 1% formaldehyde (10,000 ppm) solution equivalent to 1/50 of the final volume of the pre-formaldehyde pool was added to this pool resulting in an effective concentration of 200 ppm. The formaldehyde-treated solution was mixed on a magnetic stirrer for 10 minutes. After sampling, the formaldehyde-treated viral solution was placed within a cooled incubator at 22° C.±2° C. On Day 5 post addition of formaldehyde, the formaldehyde-treated viral solution was filtered through a 0.2 μm filter and then placed in the incubator at 22° C.±2° C. again. On Day 10, after removing the 10-Day inactivation final sample, a volume of 1% (of the weight of the final formaldehyde-treated viral solution) of 200 mM-sodium metabisulphite solution (2 mM final concentration) was aseptically transferred into the PETG container containing the formaldehyde-treated viral solution. After mixing for 5 minutes on a magnetic stirrer, the neutralized inactivated viral solution is held at room temperature (20 to 25° C.) for a minimum of 30 minutes. After sampling, the neutralized inactivated viral solution is stored at 5° C.±3° C. until further processing.

Inactivation by Formaldehyde

Critical parameters for this step are final formalin concentration, temperature, mixing and transfer into a new container. A preliminary acceptance criterion for maximum pfu/mL (determined by plaque assay) has been set on the diluted pool pre formaldehyde treatment.

The quality of the neutralized inactivated viral solution was monitored by the following parameters: Plaque assay on Day 10, SEC-HPLC, SDS-PAGE/Western Blot.

Interestingly, SEC-HPLC analysis of samples taken during the inactivation period followed by neutralization with bisulfite showed more or less constant peak area throughout the inactivation period. This is in contrast to JEV where losses of viral particles up to 60% are observed using the process disclosed by Srivastava et al. Vaccine 19 (2001) 4557-4565. In a scale-down model the viral losses were even much higher due to surface/area ratio at smaller scale and high losses due to unspecific adsorption. Differences of the ZikaV inactivation experiment and JEV inactivation were noticed as follows:

A) Much higher purity of ZikaV SGP pool with regard to residual PS (<2 μg/mL) compared to JEV. The 3-fold ZikaV inactivated sample contained therefore <<1 μg/mL of residual PS. Commercial JEV SGP pool contains on average ~120 μg/mL (up to 152 μg/mL possible). The average dilution to inactivation solution of ~14-fold results in a residual PS content up to ~11 μg/mL. It may be that higher amount of residual PS could cause virus precipitation due to cross-linking/reaction with formalin.

B) ZikaV inactivation sample contained ~10% sucrose (3-fold dilution of SGP pool containing ~30-35% sucrose). Sucrose might have stabilizing effect of viral ZikaV particles during treatment with formalin.

Dilution to DS and Formulation with Aluminium Hydroxide (DP)

For preparation of ZikaV drug substance used in mouse potency assay an antigen content (expressed as total viral particles or SEC peak area) of 5 times higher compared to Ixiaro was targeted. The basis for determination of antigen content was SEC-HPLC. Briefly, a Superose 6 10/300 Increase column (GE Healthcare) equilibrated with PBS+250 mM NaCl, pH 7.4 at 1 ml/min and 25° C., was used to detect ZikaV at 214 nm detection wavelength in harvest samples and throughout the downstream process. In the current JEV process the antigen content in NIV is determined by a specific ELISA. A good correlation was observed between antigen content determined by ELISA and SEC-HPLC. On average, the antigen content in commercial NIV samples is in the range of 33 AU/mL corresponding to ~5.2 mAU JEV peak area, see FIG. 22.

ZikaV NIV day 10 (Zika peak ~36 mAU, analysed on Waters HPLC/Superose6 Increase column) was diluted with PBS to a target of 6.3 (~5.7× dilution). Aluminium hydroxide was added to a final concentration of 0.5 mg/mL Aluminium (1/20 v/v Alum 2% stock solution added) to prepare ZikaV Drug Product (DP). The DP was gently mixed for 5 min. An aliquot of the DP was removed, Alum sedimented by centrifugation and the clear supernatant analysed by SEC-HPLC. No ZikaV peak was detected in the supernatant indicating complete adsorption (estimated as >95%) of viral particles on the mineral adjuvant. Formulated ZikaV DP was stored at 2-8° C.

The impurity profile of the inactivated Zika virus DS is comparable to the profile of JEV DS with the exception of a lower PS content (Table 8).

TABLE 8

Determination of impurity profile in Zika and JEV DS samples:

| | Specification (JEV DS) | JEV | Zika |
|---|---|---|---|
| HCP (ng/mL) | <100<br>LOQ 12 ng/mL | <LOQ | <LOQ |
| DNA (pg/mL) | <200<br>LOQ 40 pg/mL | <40 | <40 |

TABLE 8-continued

Determination of impurity profile in Zika and JEV DS samples:

| | Specification (JEV DS) | JEV | Zika |
|---|---|---|---|
| Aggregates by SEC-MALLS (%) | Not specified, part of characterization LOQ 5% | <LOQ | <LOQ |
| PS (μg/mL) | Specification only at SGP pool to demonstrate consistent process performance (19-152 μg/mL), *PS content in DS calculated based on PS content in SGP pool (~100 μg/mL) and average dilution factor (~28x) to DS; LOQ 2 μg/mL | ~4* | <<LOQ |

*Typical PS impurity in a JEV sample produced in accordance with protocol disclosed in Srivastava et al. Vaccine 19 (2001) 4557-4565.

SEC-MALLS Results

A representative SEC-HPLC elution profile of ZikaV NIV at 214 nm detection wave length is shown in FIG. 24. Note that BSA (50 μg/mL) was added to the sample to minimize losses in HPLC glass vial due to unspecific surface adsorption. ZikaV monomer content was estimated as ~98% with a multimer content of ~2%.

SEC-MALLS analysis (FIG. 25) of the sample confirmed the radius Rz of the monomer ZikaV population peak 1 as 21.6 nm and ~49 nm for the multimer peak 2. Cumulative particle size distribution showed that 89% of all viral particles are within a radius range between 18 to 25 nm (FIG. 26).

Results confirm purity and homogeneity of ZikaV NIV.

Viral Titer by Plaque Assay

TABLE 9

Active ZikaV pfus were quantified by plaque assay throughout the process.

| Sample | Pfu/mL |
|---|---|
| Harvest day 2 (filtered) | $6.4 \times 10^7$ |
| Harvest day 3 (filtered) | $1.0 \times 10^8$ |
| Harvest day 5 (filtered) | $1.5 \times 10^8$ |
| Harvest day 7 (filtered) | $1.1 \times 10^8$ |
| PS treated harvest 300x concentrate (=SGP load) | $9.0 \times 10^8$ |
| SGP pool | $8.9 \times 10^8$ |
| Inactivation start (SGP pool 1:3 diluted) | $3.4 \times 10^8$ |
| Inactivation day 5 | <LOD |
| Inactivation day 10 | <LOD |

Comparison of PS and Benzonase on Process Performance

A direct comparison of DNA removal method of concentrated ZikaV harvest pool was done. One aliquot was treated with PS (2 mg/mL, 15 min at room temperature), the other aliquot was treated with Benzonase (50 U/mL, 2 mM MgCl2, 4 h RT, 48 h 2-8° C.). Both samples were further purified by sucrose gradient as described in this report. Interestingly, the Benzonase treated samples did not yield any pure fractions after sucrose gradient centrifugation of the treated ZikaV harvest. In those fractions where the specific virus bands were detected, a high amount of host cell protein was detected throughout the collected fractions. The PS treated material resulted in pure ZikaV containing fractions as expected. This finding may suggest that PS is not only effective for DNA removal by precipitation; in addition it improves the recovery of virus particles in the gradient by disrupting interaction of DNA (fragments) and virus particles. Benzonase treatment does not remove DNA, it only results in its fragmentation. Residual DNA fragments might still interact with virus particles and residual HCPs resulting in cross-contamination and co-purification in the sucrose gradient. Pooled SGP fractions were also analysed by SEC-HPLC. Although a large peak was detected, SDS-PAGE confirmed that this sample was highly contaminated with HCPs. A large peak might be detected at UV214 and 280 nm after SEC-HPLC analysis due to possible interaction of HCPs with large virus particles, changing the UV absorbance.

Immunogenicity of Vero Grown Zika Virus

Immunization of Mice

Prior to immunization, groups of ten 6-week-old female CD1 mice were bled via vena facialis and pre-immune sera were prepared. One intraperitoneal immunizations of 200 µL were administered. A dose titration (12 µg, 3 µg, 1 µg, 0.33 µg, 0.11 µg, 0.037 µg and 0.012 µg, equivalent to the protein amount in IXIARO) of inactivated Zika virus formulated with aluminium hydroxide (Al(OH)3) at a final concentration of 0.7%. Three weeks after immunization, blood was collected and immune sera were prepared. All animal experiments were conducted in accordance with Austrian law (BGB1 Nr. 501/1989) and approved by “Magistratsabteilung 58”.

Plaque Reduction Neutralization Test (PRNT)

Twelve well plates were used for PRNT. Each well was seeded with 1 mL medium containing $4\times10^5$ Vero cells and incubated 35° C. with 5% CO2 overnight. Pools of heat inactivated sera from each dose group were tested in triplicate. The target viruses (H/PF/2013 (SEQ ID NO: 13) or MR766 (SEQ ID NO: 11)) were diluted to 100 pfu/165 µL. Equal volumes of target virus and serum dilution were incubated at 35° C. with 5% $CO_2$ for 1 hour. The cell culture medium was aspirated from the Vero cells and 330 µL of the mixture target virus/serum dilution were added to each well and the plates were rocked back and forth 5 times before incubating for 2 hours at 35° C. with 5% $CO_2$. To each well 1 mL of a 2% methylcellulose solution containing EMEM and nutrients was added, the plates were then incubated for 5 days at 35° C. with 5% $CO_2$ before staining the cells for 1 hour with crystal violet/5% formaldehyde and subsequently washed 3 times with deionized water. The plates were air dried and the numbers of plaques in each well were manually counted.

Results

Neutralization was observed with serum pools from mice immunized with inactivated Zika virus vaccine (H/PF/2013) down to 37 ng (dosing equivalent to the amount protein in IXIARO®) against Zika viruses of both the Asian (H/PF/2013) and African (MR766) lineages (FIGS. 27 and 28, respectively). Complete inhibition was seen at the 1:20 serum dilution with an immunization dose down to 110 ng (dosing equivalent to the amount protein in IXIARO®). The neutralization of both the Asian (H/PF/2013) and African (MR766) lineages of the Zika virus was equivalent, which indicates high cross-neutralization between different Zika virus strains of the inactivated Zika virus vaccine (H/PF/2013).

Another neutralization assay was performed using the microneutralization assay as described by Larocca, et al. (2016, Nature doi:10.1038/nature18952). It was found that the inactivated Zika virus of the current invention had an MN50 (microneutralization) titer of 90 at 1 µg of inactivated purified virus.

Further methods: The immunogenicity of inactivated Zika virus preparations is assessed using a mouse model of Zika infection. Groups of adult mice are immunized subcutaneously (s.c.) with 500, 50, or 5 ng of inactivated Zika virus with adjuvant (e.g. aluminium hydroxide with or without IC310), or without adjuvant. An additional group of mice receive PBS as a negative control. Each group is administered the indicated inoculum at t=0 and in some cases also at three to four weeks later (t=3/4). Beginning approximately three weeks after administration of the last immunization, serum samples are obtained from each of the mice at regular intervals. The serum samples are tested for the presence of neutralizing antibodies using PRNT.

The in vivo protective efficacy of the inactivated Zika virus preparations is also assessed using a mouse model of Zika infection, i.e. IFN-alpha/beta receptor knock-out mice (A129) (see e.g. Dowall et al., 4 Mar. 2016, http://dx.doi.org/10.1101/042358) or blocking of the IFN-alpha/beta receptor by administration of anti-IFN-alpha/beta receptor monoclonal antibodies to C57BL/6 or BALB/c mice (see e.g. Pinto et al., 7 Dec. 2011, DOI: 10.1371/journal.ppat.1002407). For protection assays, groups of 10 three- to eight-weeks-old A129, C57BL/6 of BALB/c mice are inoculated subcutaneously in the hindquarters with inactivated Zika virus with adjuvant (aluminium hydroxide) or without adjuvant at t=0. Age-matched controls are inoculated with PBS or non-specific antigens in alum. Mice are optionally boosted with a second administration of the indicated inoculation three to four weeks later. The mice are then challenged subcutaneously at three to eight weeks post immunization by inoculation with a deadly dose of live Zika virus. One day prior to challenge of C57BL/6 and BALB/c mice, they are passively administered (intraperitoneally) anti-IFN-alpha/beta receptor monoclonal antibodies. Challenged mice are monitored daily for morbidity and mortality for up to twenty-one days. Another alternative is to challenge intracranially adult vaccinated/non-vaccinated adult mice and observe protection.

It is expected that the Zika virus produced by the process of the invention will provide very similar functional read-outs in in vitro, in vivo and finally human trials as the currently licensed JEV vaccine in the EU and US and elsewhere, IXIARO®. The dosage may alter but due to the very similar impurity profile and almost identical manufacture, a very similar efficacy and safety result will be expected as was determined for the currently licensed JEV vaccine (licensed in the EU and US and elsewhere).

Discussion & Conclusion

The existing manufacturing platform for production of inactivated JEV vaccine IXIARO® was used as a basis for a manufacturing feasibility study of inactivated ZikaV vaccine candidate (Asian strain H/PF/2013). The virus was produced on Vero cells cultivated in roller bottles. The virus was purified by PS treatment followed by an optimized sucrose gradient. Inactivation was done by formalin treat (0.02%, 10 days at 22° C.). For exploratory immunization studies in mice, a DP formulated with Alum was prepared with an estimated 5-fold higher virus particle content compared to IXIARO®, the commercial JEV Vaccine. The impurity profile of the DS met all criteria as defined in the specification for IXIARO®, the commercial JEV vaccine. The neutralization of both the Asian (H/PF/2013) and African (MR766) lineages of the Zika virus was equivalent, which indicates high cross-neutralization between different Zika virus strains of the inactivated Zika virus vaccine (H/PF/2013).

The in vivo data regarding immunogenicity of the inactivated Zika virus vaccine of the current invention indicates that the virus is surprisingly potently immunogenic and also highly cross-protective (very similar immunogenicity in African and Asian strains). Data indicate that immunogenicity was higher than the recently reported inactivated Zika virus vaccine candidate (Larocca, et. al, 2016, supra.). Inactivated viruses are among the safest vaccines and especially preferred for deliver to populations where safety is especially concerning, such as pregnant women, children and immunocompromised individuals, which makes the herein disclosed inactivated Zika virus particularly suitable. Obtaining a high titer of inactivated virus is a challenge in the field. The herein disclosed process for purifying inactivated Zika virus results in not only a high yield, but also a very pure drug substance.

Example 3: Development of a Purification Process for Yellow Fever Virus Vaccine Produced in Vero Cells A downstream process was developed for the purification of infectious yellow fever virus particles whereby host cell nucleic acids, non-infectious virus particles and aggregates are removed by the addition of protamine sulphate as described in Examples 1 and 2. The unexpected and novel purification properties of protamine sulphate (PS) were evaluated in purification processes for yellow fever (YF) as follows:

As before the treatment of YF-harvest with PS significantly reduces the amount of aggregates as seen with SEC for two vaccine strains currently in development (FIG. 29).

Further more detailed aspects of the invention:

A1. A Zika virus vaccine comprising an optimally inactivated Zika virus particle, wherein the Zika virus particle is able to seroconvert a subject that is administered the Zika virus vaccine with at least a 70% probability.

A2. The Zika virus vaccine of A1, wherein the Zika virus particle is able to seroconvert the subject that is administered the Zika virus vaccine with at least a 80%, 85%, 90%, or 95% probability.

A3. The vaccine of A1 or A2, wherein the Zika virus particle has a RNA genome corresponding to the DNA sequence provided by any one of the nucleic acid sequences of SEQ ID NOs: 2-13 or 78, or a variant nucleic acid sequence that is at least 88% identical to any one of SEQ ID NOs: 2-13 or 78 and able to pack a virulent Zika virus.

A4. The vaccine of any one of A1-A3, wherein the Zika virus particle has an E protein selected from the amino acid sequences provided by any one of SEQ ID NOs: 14-69, or a variant amino acid sequence that is at least 95% identical to any one of SEQ ID NOs: 14-69 and able to pack a virulent Zika virus.

A5. The vaccine of any one of A1-A4, wherein the Zika virus is inactivated by chemical inactivation, thermal inactivation, pH inactivation, or UV inactivation.

A6. The vaccine of A5, wherein the chemical inactivation comprises contacting the Zika virus with a chemical inactivation agent to completely inactivate the Zika virus as measured by plaque assay.

A7. The vaccine of A6, wherein the chemical inactivation comprises contacting the Zika virus with formaldehyde.

A8. The vaccine of A7, wherein the formaldehyde inactivation comprises contacting the Zika virus with formaldehyde for between 2-10 days.

A9. The vaccine of any one of A5-A8, wherein the chemical activation is performed at about +4° C. or about +22° C.

A10. The vaccine of any one of A1-A9, further comprising an adjuvant.

A11. The vaccine of A10, wherein the adjuvant is an aluminum salt adjuvant.

A12. The vaccine of A11, wherein the aluminum salt adjuvant is aluminium hydroxide or aluminium phosphate salt.

A13. The vaccine of any one of A10-A12, wherein the vaccine comprises or further comprises an adjuvant comprising a peptide and a deoxyinosine-containing immunostimulatory oligodeoxynucleic acid molecule (I-ODN).

A14. The vaccine of A13, wherein the peptide comprises the sequence KLKL5KLK (SEQ ID NO: 71) and the I-ODN comprises oligo-d(IC)13 (SEQ ID NO: 70).

A15. The vaccine of any one of A1-A14, further comprising one or more pharmaceutically acceptable excipient.

B1. A kit comprising a Zika virus vaccine of any one of A1-A15.

B2. The kit of B1, further comprising a second vaccine.

B3. The kit of B2, wherein the second vaccine is a West Nile virus vaccine, a Japanese Encephalitis virus vaccine, a yellow fever virus vaccine, a Dengue virus vaccine or a Chikungunya virus vaccine.

C1. A method, comprising administering a first dose of a therapeutically effective amount of the Zika virus vaccine of any one of A1-A15 to a subject in need thereof.

C2. The method of C1, further comprising administering a second dose of a therapeutically effective amount of the Zika virus vaccine.

C3. The method of C1 or C2, wherein the second dose of the Zika virus vaccine is administered about 7 days after the first dose of the Zika virus vaccine.

C4. The method of C1 or C2, wherein the second dose of the Zika virus vaccine is administered about 14 days after the first dose of the Zika virus vaccine.

C5. The method of C1 or C2, wherein the second dose of the Zika virus vaccine is administered about 28 days after the first dose of the Zika virus vaccine.

C6. The method of any one of C1-05, wherein the administering results in production of Zika virus neutralizing antibodies.

D1. A method of producing a Zika virus vaccine, comprising (i) passaging a Zika virus on Vero cells, thereby producing a culture supernatant comprising the Zika virus;
(ii) harvesting the culture medium of (i);
(iii) precipitating the harvested culture medium of (ii), thereby producing a Zika virus supernatant; and
(iv) optimally inactivating the Zika virus in the Zika virus supernatant of (iii) thereby producing an inactivated Zika virus.

D2. The method of D1, further comprising concentrating the culture medium of (ii) prior to step (iii).

D3. The method of D1 or D2, wherein the precipitating of (iii) comprises contacting the culture medium of (ii) with protamine sulfate or benzonase.

D4. The method of any one of D1-D3, further comprising (v) dialyzing the inactivated Zika virus of (iv), thereby producing a dialyzed Zika virus.

D5. The method of D4, further comprising (vi) filtering the dialyzed Zika virus of (v).

D6. The method of any one of D1-D5, wherein the inactivating is by chemical inactivation, thermal inactivation, pH inactivation, or UV inactivation.

D7. The method of D6, wherein the chemical inactivation comprises contacting the Zika virus with a chemical inactivation agent for at least 4 days.

D8. The method of D6 or D7, wherein the chemical inactivation agent comprises formaldehyde.

D9. The method of any one of D6-D8, wherein the chemical activation is performed at about +4° C. or about +22° C.

D10. The method of D8 or D9, further comprising neutralizing the formaldehyde.

D11. The method of D10, wherein the neutralizing is performed with sodium metabisulfite.

E1. The use of the optimally inactivated Zika virus vaccine of any one of A1-A15 for the treatment and prevention of a Zika virus infection.

E2. The use of E1, wherein the inactivated Zika virus vaccine is administered in a first dose of a therapeutically effective amount to a subject in need thereof.

E3. The use of E2, wherein the inactivated Zika virus vaccine is administered in a second dose of a therapeutically effective amount to the subject.

E4. The use of E3, wherein the second dose of the inactivated Zika virus vaccine is administered about 7 days after the first dose of the Zika virus vaccine.

E5. The use of E3, wherein the second dose of the Zika virus vaccine is administered about 14 days after the first dose of the Zika virus vaccine.

E6. The use of E3, wherein the second dose of the Zika virus vaccine is administered about 28 days after the first dose of the Zika virus vaccine.

E7. The use of any one of E1-E6, wherein the vaccine administration results in production of Zika virus neutralizing antibodies.

F1. A pharmaceutical composition for use in the treatment and prevention of a Zika virus infection, wherein said pharmaceutical composition comprises the optimally inactivated Zika virus vaccine of any one of A1-A15.

F2. The pharmaceutical composition of F1, wherein the inactivated Zika virus vaccine is administered in a first dose of a therapeutically effective amount to a subject in need thereof.

F3. The use of F2, wherein the inactivated Zika virus vaccine is administered in a second dose of a therapeutically effective amount to the subject.

F4. The use of F3, wherein the second dose of the inactivated Zika virus vaccine is administered about 7 days after the first dose of the Zika virus vaccine.

F5. The use of F3, wherein the second dose of the Zika virus vaccine is administered about 14 days after the first dose of the Zika virus vaccine.

F6. The use of F3, wherein the second dose of the Zika virus vaccine is administered about 28 days after the first dose of the Zika virus vaccine.

F7. The use of any one of F1-F6, wherein the vaccine administration results in production of Zika virus neutralizing antibodies.

G1. A Chikungunya virus vaccine comprising a live attenuated Chikungunya virus particle, wherein the Chikungunya virus particle is able to seroconvert a subject that is administered the Chikungunya virus vaccine with at least a 70% probability.

G2. The Chikungunya virus vaccine of G1, wherein the Chikungunya virus particle is able to seroconvert the subject that is administered the Chikungunya virus vaccine with at least a 80%, 85%, 90%, or 95% probability.

G3. The vaccine of G1 or G2, wherein the Chikungunya virus particle has an RNA genome corresponding to the DNA sequence provided by the nucleic acid sequences of SEQ ID NOs: 77, or a variant nucleic acid sequence that is at least 88% identical to SEQ ID NO: 77 and able to pack a Chikungunya virus.

G4. The vaccine of any one of G1-G3, wherein the Chikungunya virus is inactivated by chemical inactivation, thermal inactivation, pH inactivation, or UV inactivation.

G5. The vaccine of any one of G1-G4, further comprising an adjuvant.

G6. The vaccine of G5, wherein the adjuvant is an aluminum salt adjuvant.

G7. The vaccine of G6, wherein the aluminum salt adjuvant is aluminium hydroxide or aluminium phosphate salt.

G8. The vaccine of any one of G5-G7, wherein the vaccine comprises or further comprises an adjuvant comprising a peptide and a deoxyinosine-containing immunostimulatory oligodeoxynucleic acid molecule (I-ODN).

G9. The vaccine of any one of G1-G8, further comprising one or more pharmaceutically acceptable excipient(s).

H1. A kit comprising a Chikungunya virus vaccine of any one of G1-G9.

H2. The kit of H1, further comprising a second vaccine.

H3. The kit of H2, wherein the second vaccine is a West Nile virus vaccine, a Japanese Encephalitis virus vaccine, a Yellow Fever virus vaccine, a Dengue virus vaccine or a Zika virus vaccine.

I1. A method, comprising administering a first dose of a therapeutically effective amount of the Chikungunya virus vaccine of any one of G1-G9 to a subject in need thereof.

I2. The method of I1, further comprising administering a second dose of a therapeutically effective amount of the Chikungunya virus vaccine.

I3. The method of I1, wherein a single shot is sufficient for eliciting an effective immune protection in a subject such as a human.

J1. A method of producing a Chikungunya virus vaccine, comprising (i) passaging a Chikungunya virus on Vero cells, thereby producing a culture supernatant comprising the Chikungunya virus;

(ii) harvesting the culture medium of (i);

(iii) precipitating the harvested culture medium of (ii), thereby producing a Chikungunya virus supernatant.

J2. The method of J1, further comprising concentrating the culture medium of (ii) prior to step (iii).

J3. The method of J1 or J2, wherein said precipitation of (iii) comprises contacting the culture medium of (ii) with protamine sulfate or benzonase.

K1. The use of the Chikungunya virus vaccine of any one of G1-G9 for the treatment and prevention of a Zika virus infection.

K2. The use of K1, wherein the vaccine is administered in a single shot of a therapeutically effective amount to a subject in need thereof.

K3. The use of any one of K1-K2, wherein the vaccine administration results in production of Chikungunya virus neutralizing antibodies.

L1. A pharmaceutical composition for use in the treatment and prevention of a Chikungunya virus infection, wherein said pharmaceutical composition comprises the Chikungunya virus vaccine of any one of G1-G9.

L2. The pharmaceutical composition of L1, wherein the Chikungunya virus vaccine is administered in a single shot dose of a therapeutically effective amount to a subject in need thereof.

M1. Use of protamine, preferably a protamine salt, to separate infectious virus particles from non-infectious virus particles.

M2. The use according to M1, wherein the protamine salt also facilitates the separation of infectious virus particles from host cell proteins and/or low molecular weight materials.

M3. A process of purification of infectious virus particles, comprising the steps of:

a) providing a crude harvest (a) comprising virus particles and impurities, wherein the impurities are generated from growing said virus particles on a cell substrate;

b) reducing impurities from said crude harvest (a) by precipitation with an agent comprising protamine, preferably a protamine salt, more preferably a protamine sulphate, even more preferably a recombinant protamine sulphate, to obtain a virus preparation (b), wherein the enrichment of infectious virus particles in the virus preparation (b) relative to total virus products in the crude harvest (a) is in the range of at least 50% to 95%, preferably at least 80%.

M4. The use of M1 or M2 or the process of M3, wherein the virus particles are selected from the group consisting of flaviviruses, e.g. yellow fever virus, Dengue virus, Japanese encephalitis virus or Zika virus, and alphaviruses, e.g. Chikungunya virus.

M5. A process of purification of infectious virus particles, comprising the steps of:

a) providing a crude harvest (a) comprising virus particles and impurities, wherein the impurities are generated from growing said virus particles on a cell substrate;

b) reducing impurities from said crude harvest (a) by precipitation with an agent comprising protamine, preferably a protamine salt, more preferably a protamine sulphate, even more preferably a recombinant protamine sulphate, to obtain a virus preparation (b);

c) further purifying said virus preparation (b) by one or more size exclusion methods such as (i) a sucrose density gradient centrifugation, (ii) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cutoff of the pores can enter the ligand-activated core and collecting the virus particles, and/or (iii) size exclusion chromatography to obtain a virus preparation (c) comprising the infectious virus particles, wherein the residual host cell DNA of the virus preparation (c) is less than 100 ng/mL and the residual host cell protein and the residual aggregates of infectious virus particles of the final virus preparation (c) is less than 1 μg/mL.

M6. The process of M5, wherein the residual host cell DNA of the virus preparation (c) is less than 10 ng/mL and the residual host cell protein of the final virus preparation (c) is less than 100 ng/mL.

M7. The process of any of M3 to M6, wherein the crude harvest (a) comprising virus particles and impurities is subjected to one or more pre-purification step(s) prior to step (b).

M8. The process of M7, wherein the one or more pre-purification step(s) comprises a) filtration using a filter having a pore size equal to or less than 0.2 μm; and/or b) digestion of host cell genomic DNA by enzymatic treatment; and/or c) ultra/diafiltration using a hollow fiber membrane having a pore size equal to or greater than 300 kDa, preferably equal to or greater than 100 kDa.

M9. The process of any one of M3 to M8, wherein the concentration of protamine sulphate is 0.5 to 3 mg/ml, more preferably 1 to 2 mg/ml, more preferably 1.2 to 1.8 mg/ml, more preferably 1.4 to 1.6 mg/ml, most preferably 1.6 mg/ml.

M10. The process of any one of M3 to M9, wherein the enrichment of infectious virus particles in the virus preparation (c) or any final virus preparation relative to total virus products in the crude harvest (a) is in the range from at least 50% to 95%, preferably at least 80%.

M11. The process of any one of M7 to M10, wherein the one or more pre-purification step(s) prior to step (b) of any of M7 to M10 is performed using a filter having a pore size equal to or less than 1 μm, preferably 0.2 μm.

M12. The process of any one of M3 to M11, wherein the residual impurity of the virus preparation (c) is less than 10%.

M13. The process of any one of M3 to M12, wherein the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

M14. The process of M13, wherein said cell line is a Vero cell line.

M15. The process of any one of M3 to M14, wherein said virus is a live virus, an attenuated live virus, a chimeric virus, a modified live virus, or a recombinant live virus.

M16. The process of any one of M3 to M15, wherein said virus is selected from the group of viruses consisting of a Zika virus, preferably a Zika virus strain of the Asian lineage or an immunogenic variant thereof; an attenuated Chikungunya virus, preferably a Chikungunya virus with a deletion mutation in the non-structural protein 3; a yellow fever virus, a Dengue virus and a Japanese Encephalitis virus.

M17. The process of any one of M3 to M16, wherein said process resulting in final virus preparation (c) is followed by an inactivation step, wherein the virus is inactivated preferably by formaldehyde.

M18. A composition comprising the virus particles obtainable or obtained by the process of any one of M3 to M17, wherein the composition contains protamine at levels below detection in size exclusion chromatography.

M19. The composition according to M18, wherein the composition contains trace amounts of protamine or fragments thereof detectable by mass spectroscopy or other sensitive methods.

M20. The composition according to M18 or M19 for treating and/or protecting from an infection.

M21. Use of the process according to any one of M3 to M17 for manufacturing a composition for immunization against a virus infection.

M22. The use according to M21, wherein said virus infection is an infection caused by the group of viruses consisting of yellow fever virus, Chikungunya virus and Zika virus.

N1. A process of purification of infectious alphavirus particles, preferably Chikungunya virus particles, comprising the steps of:

(a) providing a crude harvest (a) comprising virus particles and impurities, wherein the impurities are generated from growing said virus particles on a cell substrate;

(b) reducing impurities from the crude harvest (a) by precipitation with an agent comprising a protamine salt, preferably a protamine sulphate, even more preferably a recombinant protamine sulphate, to obtain a virus preparation (b);

(c) contacting the virus preparation (b) with (i) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cut-off of the pores can enter the ligand-activated core and collecting the virus particles to obtain a virus preparation (d), or (ii) a solid-phase matrix comprising a ligand-activated core and an inactive shell comprising pores, wherein the molecular weight cut off of the pores excludes the virus particles from entering the ligand-activated core, and wherein a molecule smaller than the molecular weight cut-off of the pores can enter the ligand-activated core and separating the solid-phase matrix from the virus particles by filtration to produce a virus preparation (c); and (d) further purifying the virus preparation (c) by sucrose density gradient centrifugation to obtain a virus preparation (d) comprising the infectious virus particles, wherein the residual host cell DNA of the virus preparation (d) is less than 100 ng/mL and the residual host cell protein of the final virus preparation (d) is less than 1 μg/mL.

N2. The process of N1, wherein the residual host cell DNA of the virus preparation (d) is less than 10 ng/mL and the residual host cell protein of the final virus preparation (d) is less than 100 ng/mL.

N3. The process of N1 or 2, wherein the crude harvest (a) comprising virus particles and impurities is subjected to one or more pre-purification step(s) prior to step (b).

N4. The process of any one of N1 to 3, wherein the one or more pre-purification step(s) comprises (a) filtration using a filter having a pore size equal to or less than 0.2 μm; and/or (b) digestion of host cell genomic DNA by enzymatic treatment; and/or (c) ultra/diafiltration using a hollow fiber membrane having a pore size equal to or greater than 300 kDa, preferably equal to or greater than 100 kDa.

N5. The process of any one of N1 to 4, wherein the concentration of protamine sulphate is 1 to 2 mg/ml, more preferably 1.2 to 1.8 mg/ml, more preferably 1.4 to 1.6 mg/ml, most preferably 1.6 mg/ml.

N6. The process of any one of N1 to 5, wherein the molecule entering the core of the solid-phase matrix has a molecular weight less than 700 kDa.

N7. The process of any one of N1 to 6, wherein the ligand of the ligand-activated core of the solid-phase matrix is capable of binding the molecule that enters the ligand-activated core via cationic-, anionic-, hydrophobic- or mixed interactions.

N8. The process of any one of N1 to 7, wherein the ligand of the ligand-activated core of the solid-phase matrix is octylamine.

N9. The process of any one of N1 to 8, wherein the solid-phase matrix is used as a slurry and at a final concentration between 0.5% (v/v) and 10% (v/v), preferably 0.6%, 0.7%, 0.9%, 1%, 2%, 3%, 4%, 5%, 6%, 7%, 8%, 9%, 10%, most preferably 1%.

N10. The process of any one of N1 to 9, wherein the solid-phase matrix is incubated with the protamine-treated virus preparation (b) at refrigerated temperatures (2° C. to 8° C.) with a stirring for at least 10 minutes, preferably 15 minutes, 30 minutes or 1 hour, most preferably 15 minutes.

N11. The process of any one of N1 to 10, wherein the enrichment of infectious virus particles in the final virus preparation relative to total virus products in the crude harvest (a) is in the range from at least 50% to 95%, preferably at least 80%.

N12. The process of any one of N1 to 11, wherein the filtration of step (c) of N1 is performed using a filter having a pore size equal to or less than 1 μm, preferably 0.2 μm.

N13. The process of any one of N1 to 12, wherein the residual impurity of the final virus preparation is less than 10%.

N14. The process of any one of N1 to 13, wherein the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

N15. The process of N14, wherein said cell line is a Vero cell line.

N16. The process of any one of N1 to 15, wherein the Chikungunya virus is a live virus, an attenuated live virus, a chimeric virus, a modified live virus, or a recombinant live virus.

N17. The process of any one of N1 to 16, wherein the Chikungunya virus is the Δ5nsP3 attenuated mutant or an immunogenic variant thereof.

N18. The process of any one of N1 to 17, wherein said process resulting in final virus preparation (d) is followed by an inactivation step, wherein the virus is inactivated preferably by formaldehyde.

N19. Use of the process according to any one of N1 to 18 for manufacturing a composition for immunization against a Chikungunya virus infection.

N20. The use according to N19, wherein the composition for immunization against a Chikungunya virus infection is a vaccine.

N21. A composition comprising the virus particles obtainable by the process of any one of N1 to 18 for treating and/or preventing a Chikungunya virus infection.

P1. A Zika virus vaccine comprising an optimally inactivated Zika virus particle, wherein the Zika virus particle is able to seroconvert a subject that is administered the Zika virus vaccine with at least a 70% probability.

P2. The Zika virus vaccine of P1, wherein the Zika virus particle is able to seroconvert the subject that is administered the Zika virus vaccine with at least a 80%, 85%, 90%, or 95% probability, preferably a 80% probability.

P3. The vaccine of P1 or 2, wherein the Zika virus particle has a RNA genome corresponding to the DNA sequence provided by any one of the nucleic acid sequences of SEQ ID NOs: 1-11, or a variant nucleic acid sequence that is at least 88% identical to any one of SEQ ID NOs: 1-11 and able to pack a virulent Zika virus.

P4. The vaccine of any one of P1-3, wherein the Zika virus particle has an E protein selected from the amino acid sequences provided by any one of SEQ ID NOs: 12-67, or a variant amino acid sequence that is at least 95% identical to any one of SEQ ID NOs: 12-67 and able to pack a virulent Zika virus.

P5. The vaccine of any one of P1-4, wherein the Zika virus is inactivated by chemical inactivation, thermal inactivation, pH inactivation, or UV inactivation.

P6. The vaccine of P5, wherein the chemical inactivation comprises contacting the Zika virus with a chemical inactivation agent for longer than is required to completely inactivate the Zika virus as measured by plaque assay.

P7. The vaccine of P6, wherein the chemical inactivation comprises contacting the Zika virus with formaldehyde.

P8. The vaccine of P7, wherein the formaldehyde inactivation comprises contacting the Zika virus with formaldehyde for between 2-10 days.

P9. The vaccine of any one of P5-8, wherein the chemical activation is performed at about +4° C. or about +22° C.

P10. The vaccine of any one of P1-9, further comprising an adjuvant.

P11. The vaccine of P10, wherein the adjuvant is an aluminum salt adjuvant.

P12. The vaccine of P11, wherein the aluminum salt adjuvant is aluminium hydroxide or aluminium phosphate salt.

P13. The vaccine of any one of P10-12, wherein the vaccine comprises or further comprises an adjuvant comprising a peptide and a deoxyinosine-containing immunostimulatory oligodeoxynucleic acid molecule (I-ODN).

P14. The vaccine of P13, wherein the peptide comprises the sequence KLKLSKLK (SEQ ID NO: 71) and the I-ODN comprises oligo-d(IC)13 (SEQ ID NO: 70).

P15. The vaccine of any one of P1-14, further comprising one or more pharmaceutically acceptable excipient.

Q1. A process of purification of infectious virus particles, comprising the steps of:

(a) providing a crude harvest (a) comprising virus particles and impurities, wherein the impurities are generated from growing said virus particles on a cell substrate;

(b) reducing impurities from the crude harvest (a) by precipitation with an agent comprising protamine, preferably a protamine salt, more preferably a protamine sulphate, even more preferably a recombinant protamine sulphate, to obtain a virus preparation (b);

(c) further purifying the virus preparation (b) by an optimized sucrose density gradient centrifugation, wherein the optimized sucrose gradient is provided such that the protamine can be completely or almost completely separated from the virus fraction; and wherein the protamine concentration is reduced by this step to the extent that the protamine concentration in the final drug substance is below 1 μg/ml, preferably below 0.5 μg/mL, more preferably below 0.1 μg/mL, most preferably below 0.05 μg/mL.

Q2. The process of Q2, wherein the virus particles are selected from the group consisting of flaviviruses, e.g. yellow fever virus or Zika virus and alphaviruses, e.g. Chikungunya.

Q3. The process of Q1 or Q2, additionally comprising the step of:

(d) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cutoff of the pores can enter the ligand-activated core and collecting the virus particles.

Q4. The process of any of Q1 to 3, wherein the residual host cell DNA of the virus preparation (c) is less than 10 ng/mL and the residual host cell protein of the final virus preparation (c) is less than 100 ng/mL.

Q5. The process of any of Q1 to 4, wherein the crude harvest (a) comprising virus particles and impurities is subjected to one or more pre-purification step(s) prior to step (b).

Q6. The process of Q5, wherein the one or more pre-purification step(s) comprises (a) filtration using a filter having a pore size equal to or less than 0.2 μm; and/or (b) digestion of host cell genomic DNA by enzymatic treatment; and/or (c) ultra/diafiltration using a hollow fiber membrane having a pore size equal to or greater than 300 kDa, preferably equal to or greater than 100 kDa.

Q7. The process of any one of Q1 to 6, wherein the concentration of protamine sulphate is 0.5 to 3 mg/ml, more preferably 1 to 2 mg/ml, more preferably 1.2 to 1.8 mg/ml, more preferably 1.4 to 1.6 mg/ml, most preferably 1.6 mg/ml or 2 mg/ml.

Q8. The process of any one of Q1 to 7, wherein the enrichment of infectious virus particles in the virus preparation (c) or any final virus preparation relative to total virus products in the crude harvest (a) is in the range from at least 50% to 95%, preferably at least 80%.

Q9. The process of any one of Q5 to 8, wherein the one or more pre-purification step(s) prior to step (b) of any of Q5 to 8 is performed using a filter having a pore size equal to or less than 1 μm, preferably 0.2 μm.

Q10. The process of any one of Q1 to 9, wherein the residual impurity of the virus preparation (c) is less than 10%.

Q11. The process of any one of Q1 to 10, wherein the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

Q12. The process of Q11, wherein said cell line is a Vero cell line.

Q13. The process of any one of Q1 to 12, wherein the infectious virus particles is an infectious Zika virus particle that is a live virus, an attenuated live virus, a chimeric virus, a modified live virus, or a recombinant live virus.

Q14. The process of any one of Q1 to 13, wherein the Zika virus is a Zika virus strain of the Asian lineage or an immunogenic variant thereof.

Q15. The process of any one of Q1 to 14, wherein said process resulting in final virus preparation (c) or (d) is followed by an inactivation step, wherein the virus is inactivated preferably by formaldehyde.

Q16. Use of the process according to any one of Q1 to 15 for manufacturing a composition for immunization against a virus infection.

Q17. The use according to Q16, wherein the composition for immunization against a virus infection is an infection caused by a group of viruses consisting of yellow fever virus, Chikungunya virus and Zika virus.

Q18. A composition comprising the virus particles obtainable or obtained by the process of any one of Q1 to 17 for treating and/or preventing an infection, such as e.g. a Zika virus infection.

Q19. A Zika virus vaccine comprising an inactivated Zika virus particle grown on vero cells, wherein the Zika virus particle is able to seroconvert a subject that is administered the Zika virus vaccine with at least a 70% probability and comprises minor amounts of protamine sulphate, preferably below the detection limit.

Q20. The Zika virus vaccine of Q19, wherein the Zika virus particle is able to seroconvert the subject that is administered the Zika virus vaccine with at least a 80%, 85%, 90%, or 95% probability, preferably a 80% probability.

Q21. The vaccine of Q19 or 20, wherein the Zika virus particle has a RNA genome corresponding to the DNA sequence provided by any one of the nucleic acid sequences of SEQ ID NOs: 2-13, or a variant nucleic acid sequence that is at least 88% identical to any one of SEQ ID NOs: 2-13 and able to pack a virulent Zika virus.

Q22. The vaccine of any one of Q19, 20 and 21, wherein the Zika virus particle has an E protein selected from the amino acid sequences provided by any one of SEQ ID NOs: 14-69, or a variant amino acid sequence that is at least 95% identical to any one of SEQ ID NOs: 14-69 and able to pack a virulent Zika virus.

Q23. The vaccine of any one of Q19, 20 to 22, wherein the Zika virus obtained by culturing on Vero cells is purified by protamine sulfate precipitation and sucrose gradient centrifugation.

Q24. The vaccine of Q23, wherein the sucrose gradient centrifugation is an optimized sucrose gradient centrifugation.

Q25. The vaccine of Q24, wherein the optimized sucrose gradient centrifugation comprises a virus comprising fraction in a 10% (w/w) sucrose solution and three layers of sucrose with different densities, i.e. a first sucrose solution with 15% (w/w) sucrose solution, a second sucrose solution with 35% (w/w) sucrose solution, and a third sucrose solution with a 50% (w/w) sucrose solution.

Q26. The vaccine of any one of Q19, 20 to 25, wherein the Zika virus is inactivated by chemical inactivation, thermal inactivation, pH inactivation, or UV inactivation.

Q27. The vaccine of Q26, wherein the chemical inactivation comprises contacting the Zika virus with a chemical inactivation agent for longer than is required to completely inactivate the Zika virus as measured by plaque assay.

Q28. The vaccine of Q27, wherein the chemical inactivation comprises contacting the Zika virus with formaldehyde.

Q29. The vaccine of Q28, wherein the formaldehyde inactivation comprises contacting the Zika virus with formaldehyde for between 2-10 days.

Q30. The vaccine of any one of Q27-29, wherein the chemical activation is performed at about +4° C. or about +22° C.

Q31. The vaccine of any one of Q19 to 30, further comprising an adjuvant.

Q32. The vaccine of Q31, wherein the adjuvant is an aluminum salt adjuvant.

Q33. The vaccine of Q32, wherein the aluminum salt adjuvant is aluminium hydroxide or aluminium phosphate salt.

Q34. The vaccine of Q32, wherein the aluminum salt adjuvant is aluminium hydroxide with less than 1.25 ppb Cu based on the final pharmaceutical composition comprising the Zika virus, preferably the inactivated Zika virus.

Q35. The vaccine of any one of Q19 to 34, further comprising one or more pharmaceutically acceptable excipient.

R1. Use of protamine, preferably a protamine salt, to separate infectious and non-infectious virus particles, host cell proteins and/or undefined low molecular weight materials.

R2. A process of purification of infectious virus particles, comprising the steps of:

(a) providing a crude harvest (a) comprising virus particles and impurities, wherein the impurities are generated from growing said virus particles on a cell substrate;

(b) reducing impurities from the crude harvest (a) by precipitation with an agent comprising protamine, preferably a protamine salt, more preferably a protamine sulphate, even more preferably a recombinant protamine sulphate, to obtain a virus preparation (b), wherein the enrichment of infectious virus particles in the virus preparation (b) relative to total virus products in the crude harvest (a) is in the range from at least 50% to 95%, preferably at least 80%.

R3. The use of R1 or the process of R2, wherein the virus particles are selected from the group consisting of flaviviruses, e.g. yellow fever virus or Zika virus and alphaviruses, e.g. Chikungunya.

R4. A process of purification of infectious virus particles, comprising the steps of:

(a) providing a crude harvest (a) comprising virus particles and impurities, wherein the impurities are generated from growing said virus particles on a cell substrate;

(b) reducing impurities from the crude harvest (a) by precipitation with an agent comprising protamine, preferably a protamine salt, more preferably a protamine sulphate, even more preferably a recombinant protamine sulphate, to obtain a virus preparation (b);

(c) further purifying the virus preparation (b) by one or more size exclusion methods such as (i) a sucrose density gradient centrifugation, (ii) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cutoff of the pores can enter the ligand-activated core and collecting the virus particles, and/or (iii) size exclusion chromatography to obtain a virus preparation (c) comprising the infectious virus particles, wherein the residual host cell DNA of the virus preparation (c) is less than 100 ng/mL and the residual host cell protein and the residual aggregates of infectious virus particles of the final virus preparation (c) is less than 1 μg/mL.

R5. The process of R4, wherein the residual host cell DNA of the virus preparation (c) is less than 10 ng/mL and the residual host cell protein of the final virus preparation (c) is less than 100 ng/mL.

R6. The process of any of R2 to 5, wherein the crude harvest (a) comprising virus particles and impurities is subjected to one or more pre-purification step(s) prior to step (b).

R7. The process of R6, wherein the one or more pre-purification step(s) comprises (a) filtration using a filter having a pore size equal to or less than 0.2 μm; and/or (b) digestion of host cell genomic DNA by enzymatic treatment; and/or (c) ultra/diafiltration using a hollow fiber membrane having a pore size equal to or greater than 300 kDa, preferably equal to or greater than 100 kDa.

R8. The process of any one of R2 to 7, wherein the concentration of protamine sulphate is 0.5 to 3 mg/ml, more preferably 1 to 2 mg/ml, more preferably 1.2 to 1.8 mg/ml, more preferably 1.4 to 1.6 mg/ml, most preferably 1.6 mg/ml.

R9. The process of any one of R2 to 8, wherein the enrichment of infectious virus particles in the virus preparation (c) or any final virus preparation relative to total virus products in the crude harvest (a) is in the range from at least 50% to 95%, preferably at least 80%.

R10. The process of any one of R6 to 9, wherein the one or more pre-purification step(s) prior to step (b) of any of R6 to 9 is performed using a filter having a pore size equal to or less than 1 μm, preferably 0.2 μm.

R11. The process of any one of R2 to 10, wherein the residual impurity of the virus preparation (c) is less than 10%.

R12. The process of any one of R2 to 11, wherein the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

R13. The process of R12, wherein said cell line is a Vero cell line.

R14. The process of any one of R2 to 13, wherein the Zika virus is a live virus, an attenuated live virus, a chimeric virus, a modified live virus, or a recombinant live virus.

R15. The process of any one of R2 to 14, wherein the Zika virus is a Zika virus strain of the Asian lineage or an immunogenic variant thereof.

R16. The process of any one of R2 to 15, wherein said process resulting in final virus preparation (c) is followed by an inactivation step, wherein the virus is inactivated preferably by formaldehyde.

R17. Use of the process according to any one of R1 to 16 for manufacturing a composition for immunization against a virus infection.

R18. The use according to R17, wherein the composition for immunization against a virus infection is an infection caused by a group of viruses consisting of yellow fever virus, Chikungunya virus and Zika virus.

R19. A composition comprising the virus particles obtainable or obtained by the process of any one of R2 to 16 for treating and/or preventing an infection.

What is claimed is:

1. A method for removal of protamine from purified infectious virus particles, comprising a step of sucrose gradient centrifugation, wherein the sucrose gradient comprises a virus comprising fraction in a 10%+/−1% (w/w) sucrose solution and three further layers of sucrose solutions with different densities, wherein the three further layers of sucrose solutions comprise a first sucrose solution with 15%+/−1% (w/w) sucrose, a second sucrose solution with 35%+/−1% (w/w) sucrose, and a third sucrose solution with 50%+/−1% (w/w) sucrose.

2. A method for purification of infectious virus particles, comprising the steps of a) providing a crude harvest (a) comprising virus particles and impurities, wherein the impurities are generated from growing said virus particles on a cell substrate;

b) reducing impurities from said crude harvest (a) by precipitation with an agent comprising protamine to obtain a virus preparation (b);

c) further purifying said virus preparation (b) by sucrose density gradient centrifugation to obtain a virus preparation (c), wherein the sucrose gradient is provided such that the protamine can be completely or almost completely separated from the virus fraction; and wherein the protamine concentration is reduced by this step to the extent that the protamine concentration in the final drug substance is below 1 μg/ml, and wherein said sucrose density gradient comprises a virus comprising fraction in a 10%+/−1% (w/w) sucrose solution and three layers of sucrose with different densities, wherein the three further layers of sucrose solutions comprise a first sucrose solution with 15%+/−1% (w/w) sucrose, a second sucrose solution with 35%+/−1% (w/w) sucrose, and a third sucrose solution with 50%+/−1% (w/w) sucrose.

3. The method according to claim 2, wherein said virus particles are selected from the group consisting of flaviviruses.

4. The method according to claim 2, additionally comprising a further purification step of (d) further purifying said virus preparation (c) on a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cut-off of the pores can enter the ligand-activated core, to obtain virus preparation (d).

5. The method according to claim 2, wherein said crude harvest (a) comprising virus particles and impurities is subjected to one or more pre-purification step(s) prior to step (b), wherein said one or more pre-purification step(s) comprise a) filtration using a filter having a pore size equal to or less than 0.2 μm; and/or b) digestion of host cell genomic DNA by enzymatic treatment; and/or c) ultra/diafiltration using a hollow fiber membrane having a pore size equal to or greater than 100 kDa.

6. The method according to claim 2, wherein the concentration of protamine is from 0.5 mg/ml to 3 mg/ml.

7. The method according to claim 2, wherein the enrichment of infectious virus particles in the virus preparation (c) or any final virus preparation relative to total virus products in the crude harvest (a) is in the range from at least 50% to 95%.

8. The method according to claim 2, wherein said infectious virus particles are propagated in a cell line selected from the group consisting of an EB66 cell line, a Vero cell line, a Vero-aHis cell line, a HeLa cell line, a HeLa-S3 cell line, a 293 cell line, a PC12 cell line, a CHO cell line, a 3T3 cell line, a PerC6 cell line, an MDSK cell line, a chicken embryonic fibroblast cell line, a duck cell line and a diploid avian cell line.

9. The method according to claim 2, wherein said infectious virus particles are selected from the group consisting of a live virus, a live attenuated virus, a chimeric virus, a modified live virus or a recombinant live virus.

10. The method according to claim 2, wherein said step resulting in final virus preparation (c) or (d) is followed by an inactivation step.

11. The method according to claim 2, wherein said protamine is selected from the group consisting of a protamine salt, a protamine sulphate and a recombinant protamine sulphate.

12. The method according to claim 10, wherein said inactivation step is a formaldehyde inactivation step.

* * * * *

SEQUENCE LISTING

```
<160> NUMBER OF SEQ ID NOS: 123

<210> SEQ ID NO 1
<211> LENGTH: 32
<212> TYPE: PRT
<213> ORGANISM: Artificial Sequence
<220> FEATURE:
<223> OTHER INFORMATION: synthetic peptide

<400> SEQUENCE: 1

Pro Arg Arg Arg Arg Ser Ser Ser Arg Pro Val Arg Arg Arg Arg Arg
1               5                   10                  15

Pro Arg Val Ser Arg Arg Arg Arg Arg Arg Gly Gly Arg Arg Arg Arg
            20                  25                  30


<210> SEQ ID NO 2
<211> LENGTH: 10676
<212> TYPE: DNA
<213> ORGANISM: Zika virus

<400> SEQUENCE: 2

gttgttactg ttgctgactc agactgcgac agttcgagtt tgaagcgaaa gctagcaaca      60

gtatcaacag gttttatttg gatttggaaa cgagagtttc tggtcatgaa aaacccaaaa     120

aagaaatccg gaggattccg gattgtcaat atgctaaaac gcggagtagc ccgtgtgagc     180

ccctttgggg gcttgaagag gctgccagcc ggacttctgc tgggtcatgg gcccatcagg     240

atggtcttgg caattctagc ctttttgaga ttcacggcaa tcaagccatc actgggtctc     300

atcaatagat ggggttcagt ggggaaaaaa gaggctatgg aaataataaa gaagttcaag     360

aaagatctgg ctgccatgct gagaataatc aatgctagga aggagaagaa gagacggggc     420

gcagatacta gtgtcggaat tgttggcctc ctgctgacca cagctatggc agcggaggtc     480

actagacgtg ggagtgcata ctatatgtac ttggacagaa acgatgctgg ggaggccata     540

tcttttccaa ccacattggg gatgaataag tgttatatac agatcatgga tcttggacac     600

atgtgtgatg ccaccatgag ctatgaatgc cctatgctgg atgagggggt ggaaccagat     660

gacgtcgatt gttggtgcaa cacgacgtca acttgggttg tgtacggaac ctgccatcac     720

aaaaaaggtg aagcacggag atctagaaga gctgtgacgc tcccctccca ttccactagg     780

aagctgcaaa cgcggtcgca aacctggttg gaatcaagag aatacacaaa gcacttgatt     840

agagtcgaaa attggatatt caggaaccct ggcttcgcgt tagcagcagc tgccatcgct     900

tggcttttgg gaagctcaac gagccaaaaa gtcatatact tggtcatgat actgctgatt     960
```

-continued gccccggcat acagcatcag gtgcatagga gtcagcaata gggactttgt ggaaggtatg 1020
tcaggtggga cttgggttga tattgtcttg gaacatggag gttgtgtcac cgtaatggca 1080
caggacaaac cgactgtcga catagagctg gttacaacaa cagtcagcaa catggcggag 1140
gtaagatcct actgctatga ggcatcaata tcagacatgg cttcggacag ccgctgccca 1200
acacaaggtg aagcctacct tgacaagcaa tcagacactc aatatgtctg caaaagaacg 1260
ttagtggaca gaggctgggg aaatggatgt ggactttttg gcaaagggag tctggtgaca 1320
tgcgctaagt ttgcatgctc caagaaaatg accgggaaga gcatccagcc agagaatctg 1380
gagtaccgga taatgctgtc agttcatggc tcccagcaca gtgggatgat cgttaatgac 1440
acaggacatg aaactgatga gaatagagcg aaggttgaga taacgcccaa ttcaccaaga 1500
gccgaagcca ccctgggggg ttttggaagc ctaggacttg attgtgaacc gaggacaggc 1560
cttgactttt cagatttgta ttacttgact atgaataaca agcactggtt ggttcacaag 1620
gagtggttcc acgacattcc attaccttgg cacgctgggg cagacaccgg aactccacac 1680
tggaacaaca aagaagcact ggtagagttc aaggacgcac atgccaaaag gcaaactgtc 1740
gtggttctag ggagtcaaga aggagcagtt cacacggccc ttgctggagc tctggaggct 1800
gagatggatg gtgcaaaggg aaggctgtcc tctggccact tgaaatgtcg cctgaaaatg 1860
gataaactta gattgaaggg cgtgtcatac tccttgtgta ccgcagcgtt cacattcacc 1920
aagatcccgg ctgaaacact gcacgggaca gtcacagtgg aggtacagta cgcagggaca 1980
gatggacctt gcaaggttcc agctcagatg gcggtggaca tgcaaactct gaccccagtt 2040
gggaggttga taaccgctaa ccccgtaatc actgaaagca ctgagaactc taagatgatg 2100
ctggaacttg atccaccatt tggggactct tacattgtca taggagtcgg ggagaagaag 2160
atcacccacc actggcacag gagtggcagc accattggaa aagcatttga agccactgtg 2220
agaggtgcca agagaatggc agtcttggga gacacagcct gggactttgg atcagttgga 2280
ggcgctctca actcattggg caagggcatc catcaaattt ttggagcagc tttcaaatca 2340
ttgtttggag gaatgtcctg gttctcacaa attctcattg gaacgttgct gatgtggttg 2400
ggtctgaaca caaagaatgg atctatttcc cttatgtgct tggccttagg gggagtgttg 2460
atcttcttat ccacagccgt ctctgctgat gtggggtgct cggtggactt ctcaaagaag 2520
gagacgagat gcggtacagg ggtgttcgtc tataacgacg ttgaagcctg gagggacagg 2580
tacaagtacc atcctgactc cccccgtaga ttggcagcag cagtcaagca agcctgggaa 2640
gatggtatct gcgggatctc ctctgtttca agaatggaaa acatcatgtg gagatcagta 2700
gaaggggagc tcaacgcaat cctggaagag aatggagttc aactgacggt cgttgtggga 2760
tctgtaaaaa accccatgtg gagaggtcca cagagattgc ccgtgcctgt gaacgagctg 2820
ccccacggct ggaaggcttg gggggaaatcg cacttcgtca gagcagcaaa gacaaataac 2880
agctttgtcg tggatggtga cacactgaag gaatgcccac tcaaacatag agcatggaac 2940
agctttcttg tggaggatca tgggttcggg gtatttcaca ctagtgtctg gctcaaggtt 3000
agagaagatt attcattaga gtgtgatcca gccgttattg gaacagctgt taagggaaag 3060
gaggctgtac acagtgatct aggctactgg attgagagtg agaagaatga cacatggagg 3120
ctgaagaggg cccatctgat cgagatgaaa acatgtgaat ggccaaagtc ccacacattg 3180
tggacagatg gaatagaaga gagtgatctg atcataccca agtctttagc tgggccactc 3240
agccatcaca ataccagaga gggctacagg acccaaatga aagggccatg gcacagtgaa 3300

-continued gagcttgaaa ttcggtttga ggaatgccca ggcactaagg tccacgtgga ggaaacatgt 3360
ggaacaagag gaccatctct gagatcaacc actgcaagcg gaagggtgat cgaggaatgg 3420
tgctgcaggg agtgcacaat gcccccactg tcgttccggg ctaaagatgg ctgttggtat 3480
ggaatggaga taaggcccag gaaagaacca gaaagcaact tagtaaggtc aatggtgact 3540
gcaggatcaa ctgatcacat ggatcacttc tcccttggag tgcttgtgat tctgctcatg 3600
gtgcaggaag ggctgaagaa gagaatgacc acaaagatca tcataagcac atcaatggca 3660
gtgctggtag ctatgatcct gggaggattt tcaatgagtg acctggctaa gcttgcaatt 3720
ttgatgggtg ccaccttcgc ggaaatgaac actggaggag atgtagctca tctggcgctg 3780
atagcggcat tcaaagtcag accagcgttg ctggtatctt tcatcttcag agctaattgg 3840
acaccccgtg aaagcatgct gctggccttg gcctcgtgtc ttttgcaaac tgcgatctcc 3900
gccttggaag gcgacctgat ggttctcatc aatggttttg ctttggcctg gttggcaata 3960
cgagcgatgg ttgttccacg cactgataac atcaccttgg caatcctggc tgctctgaca 4020
ccactggccc ggggcacact gcttgtggcg tggagagcag gccttgctac ttgcgggggg 4080
tttatgctcc tctctctgaa gggaaaaggc agtgtgaaga agaacttacc atttgtcatg 4140
gccctgggac taaccgctgt gaggctggtc gaccccatca acgtggtggg gctgctgttg 4200
ctcacaagga gtgggaagcg gagctggccc cctagcgaag tactcacagc tgttggcctg 4260
atatgcgcat tggctggagg gttcgccaag gcagatatag agatggctgg gcccatggcc 4320
gcggtcggtc tgctaattgt cagttacgtg gtctcaggaa agagtgtgga catgtacatt 4380
gaaagagcag gtgacatcac atgggaaaaa gatgcggaag tcactggaaa cagtccccgg 4440
ctcgatgtgg cgctagatga gagtggtgat ttctccctgg tggaggatga cggtcccccc 4500
atgagagaga tcatactcaa ggtggtcctg atgaccatct gtggcatgaa cccaatagcc 4560
ataccctttg cagctggagc gtggtacgta tacgtgaaga ctggaaaaag gagtggtgct 4620
ctatgggatg tgcctgctcc caaggaagta aaaaaggggg agaccacaga tggagtgtac 4680
agagtaatga ctcgtagact gctaggttca acacaagttg gagtgggagt tatgcaagag 4740
ggggtctttc acactatgtg gcacgtcaca aaaggatccg cgctgagaag cggtgaaggg 4800
agacttgatc catactgggg agatgtcaag caggatctgg tgtcatactg tggtccatgg 4860
aagctagatg ccgcctggga cgggcacagc gaggtgcagc tcttggccgt gccccccgga 4920
gagagagcga ggaacatcca gactctgccc ggaatattta agacaaagga tggggacatt 4980
ggagcggttg cgctggatta cccagcagga acttcaggat ctccaatcct agacaagtgt 5040
gggagagtga taggacttta tggcaatggg gtcgtgatca aaaatgggag ttatgttagt 5100
gccatcaccc aagggaggag ggaggaagag actcctgttg agtgcttcga gccttcgatg 5160
ctgaagaaga agcagctaac tgtcttagac ttgcatcctg gagctgggaa aaccaggaga 5220
gttcttcctg aaatagtccg tgaagccata aaaacaagac tccgtactgt gatcttagct 5280
ccaaccaggg ttgtcgctgc tgaaatggag gaagccctta gagggcttcc agtgcgttat 5340
atgacaacag cagtcaatgt cacccactct ggaacagaaa tcgtcgactt aatgtgccat 5400
gccaccttca cttcacgtct actacagcca atcagagtcc ccaactataa tctgtatatt 5460
atggatgagg cccacttcac agatccctca agtatagcag caagaggata catttcaaca 5520
agggttgaga tgggcgaggc ggctgccatc ttcatgaccg ccacgccacc aggaacccgt 5580
gacgcatttc cggactccaa ctcaccaatt atggacaccg aagtggaagt cccagagaga 5640
gcctggagct caggctttga ttgggtgacg gattattctg gaaaaacagt ttggtttgtt 5700

-continued ccaagcgtga ggaacggcaa tgagatcgca gcttgtctga caaaggctgg aaaacgggtc 5760
atacagctca gcagaaagac ttttgagaca gagttccaga aaacaaaaca tcaagagtgg 5820
gactttgtcg tgacaactga catttcagag atgggcgcca actttaaagc tgaccgtgtc 5880
atagattcca ggagatgcct aaagccggtc atacttgatg gcgagagagt cattctggct 5940
ggacccatgc ctgtcacaca tgccagcgct gcccagagga gggggcgcat aggcaggaat 6000
cccaacaaac ctggagatga gtatctgtat ggaggtgggt gcgcagagac tgacgaagac 6060
catgcacact ggcttgaagc aagaatgctc cttgacaata tttacctcca agatggcctc 6120
atagcctcgc tctatcgacc tgaggccgac aaagtagcag ccattgaggg agagttcaag 6180
cttaggacgg agcaaaggaa gacctttgtg gaactcatga aaagaggaga tcttcctgtt 6240
tggctggcct atcaggttgc atctgccgga ataacctaca cagatagaag atggtgcttt 6300
gatggcacga ccaacaacac cataatggaa gacagtgtgc cggcagaggt gtggaccaga 6360
cacggagaga aaagagtgct caaaccgagg tggatggacg ccagagtttg ttcagatcat 6420
gcggccctga agtcattcaa ggagtttgcc gctgggaaaa gaggagcggc ttttggagtg 6480
atggaagccc tgggaacact gccaggacac atgacagaga gattccagga agccattgac 6540
aacctcgctg tgctcatgcg ggcagagact ggaagcaggc cttacaaagc cgcggcggcc 6600
caattgccgg agaccctaga gaccattatg cttttggggt tgctgggaac agtctcgctg 6660
ggaatctttt tcgtcttgat gaggaacaag ggcataggga agatgggctt tggaatggtg 6720
actcttgggg ccagcgcatg gctcatgtgg ctctcggaaa ttgagccagc cagaattgca 6780
tgtgtcctca ttgttgtgtt cctattgctg gtggtgctca tacctgagcc agaaaagcaa 6840
agatctcccc aggacaacca aatggcaatc atcatcatgg tagcagtagg tcttctgggc 6900
ttgattaccg ccaatgaact cggatggttg gagagaacaa agagtgacct aagccatcta 6960
atgggaagga gagaggaggg ggcaaccatg ggattctcaa tggacattga cctgcggcca 7020
gcctcagctt gggccatcta tgctgccttg acaactttca ttaccccagc cgtccaacat 7080
gcagtgacca cttcatacaa caactactcc ttaatggcga tggccacgca agctggagtg 7140
ttgtttggta tgggcaaagg gatgccattc tacgcatggg actttggagt cccgctgcta 7200
atgataggtt gctactcaca attaacgccc ctgaccctaa tagtggccat cattttgctc 7260
gtggcgcact acatgtactt gatcccaggg ctgcaggcag cagctgcgcg tgctgcccag 7320
aagagaacgg cagctggcat catgaagaac cctgttgtgg atggaatagt ggtgactgac 7380
attgacacaa tgacaattga cccccaagtg gagaaaaaga tgggacaggt gctactcatg 7440
gcagtagccg tctccagcgc catactgtcg cggaccgcct gggggtgggg ggaggctggg 7500
gccctgatca cagccgcaac ttccactttg tgggaaggct ctccgaacaa gtactggaac 7560
tcctctacag ccacttcact gtgtaacatt tttaggggaa gttacttggc tggagcttct 7620
ctaatctaca cagtaacaag aaacgctggc ttggtcaaga gacgtggggg tggaacagga 7680
gagaccctgg gagagaaatg gaaggcccgc ttgaaccaga tgtcggccct ggagttctac 7740
tcctacaaaa agtcaggcat caccgaggtg tgcagagaag aggcccgccg cgccctcaag 7800
gacggtgtgg caacgggagg ccatgctgtg tcccgaggaa gtgcaaagct gagatggttg 7860
gtggagcggg gatacctgca gccctatgga aaggtcattg atcttggatg tggcagaggg 7920
ggctggagtt actacgccgc caccatccgc aaagttcaag aagtgaaagg atacacaaaa 7980
ggaggccctg gtcatgaaga acccgtgttg gtgcaaagct atgggtggaa catagtccgt 8040

-continued

```
cttaagagtg gggtggacgt ctttcatatg gcggctgagc cgtgtgacac gttgctgtgt   8100
gacataggtg agtcatcatc tagtcctgaa gtggaagaag cacggacgct cagagtcctc   8160
tccatggtgg gggattggct tgaaaaaaga ccaggagcct tttgtataaa agtgttgtgc   8220
ccatacacca gcactatgat ggaaaccctg gagcgactgc agcgtaggta tgggggagga   8280
ctggtcagag tgccactctc ccgcaactct acacatgaga tgtactgggt ctctggagcg   8340
aaaagcaaca ccataaaaag tgtgtccacc acgagccagc tcctcttggg gcgcatggac   8400
gggcctagga ggccagtgaa atatgaggag gatgtgaatc tcggctctgg cacgcgggct   8460
gtggtaagct gcgctgaagc tcccaacatg aagatcattg gtaaccgcat tgaaaggatc   8520
cgcagtgagc acgcggaaac gtggttcttt gacgagaacc acccatatag gacatgggct   8580
taccatggaa gctatgaggc ccccacacaa gggtcagcgt cctctctaat aaacggggtt   8640
gtcaggctcc tgtcaaaacc ctgggatgtg gtgactggag tcacaggaat agccatgacc   8700
gacaccacac cgtatggtca gcaaagagtt ttcaaggaaa aagtggacac tagggtgcca   8760
gacccccaag aaggtactcg tcaggttatg agcatggtct cttcctggtt gtggaaagag   8820
ctaggcaaac acaaacggcc acgagtctgt accaaagaag agttcatcaa caaggttcgt   8880
agcaatgcag cattaggggc aatatttgaa gaggaaaaag agtggaagac tgcagtggaa   8940
gctgtgaacg atccaaggtt ctgggctcta gtggacaagg aaagagagca ccacctgaga   9000
ggagagtgcc agagttgtgt gtacaacatg atgggaaaaa gagaaaagaa acaaggggaa   9060
tttggaaagg ccaagggcag ccgcgccatc tggtatatgt ggctaggggc tagatttcta   9120
gagttcgaag cccttggatt cttgaacgag gatcactgga tggggagaga gaactcagga   9180
ggtggtgttg aagggctggg attacaaaga ctcggatatg tcctagaaga gatgagtcgc   9240
ataccaggag gaaggatgta tgcagatgac actgctggct gggacacccg catcagcagg   9300
tttgatctgg agaatgaagc tctaatcacc aaccaaatgg agaaagggca cagggccttg   9360
gcattggcca taatcaagta cacataccaa aacaaagtgg taaaggtcct tagaccagct   9420
gaaaaaggga aaacagttat ggacattatt tcgagacaag accaaagggg gagcggacaa   9480
gttgtcactt acgctcttaa cacatttacc aacctagtgg tgcaactcat tcggaatatg   9540
gaggctgagg aagtcctaga gatgcaagac ttgtggctgc tgcggaggtc agagaaagtg   9600
accaactggt tgcagagcaa cggatgggat aggctcaaac gaatggcagt cagtggagat   9660
gattgcgttg tgaagccaat tgatgatagg tttgcacatg ccctcaggtt cttgaatgat   9720
atgggaaaag ttaggaagga cacacaagag tggaaaccct caactggatg ggacaactgg   9780
gaagaagttc cgttttgctc ccaccacttc aacaagctcc atctcaagga cgggaggtcc   9840
attgtggttc cctgccgcca ccaagatgaa ctgattggcc gggcccgcgt ctctccaggg   9900
gcgggatgga gcatccggga gactgcttgc ctagcaaaat catatgcgca aatgtggcag   9960
ctcctttatt tccacagaag ggacctccga ctgatggcca atgccatttg ttcatctgtg  10020
ccagttgact gggttccaac tgggagaact acctggtcaa tccatggaaa gggagaatgg  10080
atgaccactg aagacatgct tgtggtgtgg aacagagtgt ggattgagga gaacgaccac  10140
atggaagaca agaccccagt tacgaaatgg acagacattc cctatttggg aaaaagggaa  10200
gacttgtggt gtggatctct catagggcac agaccgcgca ccacctgggc tgagaacatt  10260
aaaaacacag tcaacatggt gcgcaggatc ataggtgatg aagaaaagta catggactac  10320
ctatccaccc aagttcgcta cttgggtgaa gaagggtcta cacctggagt gctgtaagca  10380
ccaatcttaa tgttgtcagg cctgctagtc agccacagct tggggaaagc tgtgcagcct  10440
```

gtgacccccc caggagaagc tgggaaacca agcctatagt caggccgaga acgccatggc 10500
acggaagaag ccatgctgcc tgtgagcccc tcagaggaca ctgagtcaaa aaaccccacg 10560
cgcttggagg cgcaggatgg gaaaagaagg tggcgacctt ccccaccctt caatctgggg 10620
cctgaactgg agatcagctg tggatctcca gaagagggac tagtggttag aggaga 10676

<210> SEQ ID NO 3
<211> LENGTH: 10793
<212> TYPE: DNA
<213> ORGANISM: Zika virus

<400> SEQUENCE: 3
ccaatctgtg aatcagactg cgacagttcg agtttgaagc gaaagctagc aacagtatca 60
acaggtttta ttttggattt ggaaacgaga gtttctggtc atgaaaaacc caaaaaagaa 120
atccggagga ttccggattg tcaatatgct aaaacgcgga gtagcccgtg tgagcccctt 180
tgggggcttg aagaggctgc cagccggact tctgctgggt catgggccca tcaggatggt 240
cttggcgatt ctagcctttt tgagattcac ggcaatcaag ccatcactgg gtctcatcaa 300
tagatggggt tcagtgggga aaaaagaggc tatggaaata ataaagaagt tcaagaaaga 360
tctggctgcc atgctgagaa taatcaatgc caggaaggag aagaagagac gaggcgcaga 420
tactagtgtc ggaatcgttg gcctcctgct gaccacagct atggcagcgg aggtcactag 480
acgtgggagt gcatactata tgtacttgga cagaaacgat gctggggagg ccatatcttt 540
tccaaccaca ttggggatga ataagtgtta tatacagatc atggatcttg gacacatgtg 600
tgatgccacc atgagctatg aatgccctat gctggatgag ggggtggaac cagatgacgt 660
cgattgttgg tgcaacacga cgtcaacttg ggttgtgtac ggaacctgcc atcacaaaaa 720
aggtgaagca cggagatcta gaagagctgt gacgctcccc tcccattcca ctaggaagct 780
gcaaacgcgg tcgcaaacct ggttggaatc aagagaatac acaaagcact tgattagagt 840
cgaaaattgg atattcagga accctggctt cgcgttagca gcagctgcca tcgcttggct 900
tttgggaagc tcaacgagcc aaaaagtcat atacttggtc atgatactgc tgattgcccc 960
ggcatacagc atcaggtgca taggagtcag caatagggac tttgtggaag gtatgtcagg 1020
tgggacttgg gttgatgttg tcttggaaca tgggggttgt gtcaccgtaa tggcacagga 1080
caaaccgact gtcgacatag agctggttac aacaacagtc agcaacatgg cggaggtaag 1140
atcctactgc tatgaggcat caatatcaga catggcttcg gacagccgct gcccaacaca 1200
aggtgaagcc taccttgaca agcaatcaga cactcaatat gtctgcaaaa gaacgttagt 1260
ggacagaggc tggggaaatg gatgtggact tttggcaaa gggagcctgg tgacatgcgc 1320
taagtttgca tgctccaaga aaatgaccgg gaagagcatc cagccagaga atctggagta 1380
ccggataatg ctgtcagttc atggctccca gcacagtggg atgatcgtta atgacacagg 1440
acatgaaact gatgagaata gagcgaaggt tgagataacg cccaattcac caagagccga 1500
agccaccctg gggggttttg gaagcttagg acttgattgt gaaccgagga caggccttga 1560
cttttcagat ttgtattact tgactatgaa taacaagcac tggttggttc acaaggagtg 1620
gttccacgac attccattac cttggcacgc tggggcagac accggaactc cacactggaa 1680
caacaaagaa gcactggtag agttcaagga cgcacatgcc aaaaggcaaa ctgtcgtggt 1740
tctagggact caagaaggag cagttcacac ggcccttgct ggagctctgg aggctgagat 1800
ggatggtgca aagggaaggc tgtcctctgg ccacttgaaa tgtcgcctga aaatggataa 1860

```
acttagattg aagggcgtgt catactcctt gtgtaccgca gcgttcacat tcaccaagat   1920
cccggctgaa acactgcacg ggacagtcac agtggaggta cagtacgcag ggacagatgg   1980
accttgcaag gttccagctc agatggcggt ggacatgcaa actctgaccc cagttgggag   2040
gttgataacc gctaaccccg taatcactga aagcactgag aactctaaga tgatgctgga   2100
acttgatcca ccatttgggg actcttacat tgtcatagga gtcggggaga agaagatcac   2160
ccaccactgg cacaggagtg gcagcaccat tggaaaagca tttgaagcca ctgtgagagg   2220
tgccaagaga atggcagtct tgggagacac agcctgggac tttggatcag ttggaggcgc   2280
tctcaactca ttgggcaagg gcatccatca aatttttgga gcagctttca aatcattgtt   2340
tggaggaatg tcctggttct cacaaattct cattggaacg ttgctgatgt ggttgggtct   2400
gaacacaaag aatggatcta tttcccttat gtgcttggcc ttagggggag tgttgatctt   2460
cttatccaca gccgtctctg ctgatgtggg gtgctcggtg gacttctcaa agaaggagac   2520
gagatgtggt acaggggtgt tcgtctataa cgacgttgaa gcctggaggg acaggtacaa   2580
gtaccatcct gactctcccc gtagattggc agcagcagtc aagcaagcct gggaagatgg   2640
tatctgcggg atctcctctg tttcaagaat ggaaaacatc atgtggagat cagtagaagg   2700
ggagcttaac gcaatcctgg aagagaatgg agttcaactg acggtcgttg tgggatctgt   2760
aaaaaacccc atgtggagag gtccacagag attgcccgtg cctgtgaacg agctgcccca   2820
cggctggaag gcttggggga aatcgtactt cgtcagagca gcaaagacaa ataacagctt   2880
tgtcgtggat ggtgacacac tgaaggaatg cccactcaaa catagagcat ggaacagctt   2940
tcttgtggag gatcatgggt tcggggtatt tcacactagt gtctggctca aggttagaga   3000
agattattca ttagagtgtg atccagccgt tattggaaca gctgttaagg gaaaggaggc   3060
tgtacacagt gatctaggct actggattga gagtgagaag aatgacacat ggaggctgaa   3120
gagggcccat ctgatcgaga tgaaaacatg tgaatggcca aagtcccaca cattgtggac   3180
agatggaata gaagagagtg atctgatcat acccaagtct ttagctgggc cactcagcca   3240
tcacaatacc agagagggct acaggaccca aatgaaaggg ccatggcaca gtgaagagct   3300
tgaaattcgg tttgaggaat gcccaggcac taaggtccac gtggaggaaa catgtggaac   3360
aagaggacca tctctgagat caaccactgc aagcggaagg gtgatcgagg aatggtgctg   3420
cagggagtgc acaatgcccc cactgtcgtt ccgggctaaa gatggctgtt ggtatggaat   3480
ggagataagg cccaggaaag aaccagaaag caacttagta aggtcaatgg tgactgcagg   3540
atcaactgat cacatggatc acttctccct tggagtgctt gtgattctgc tcatggtgca   3600
ggaagggctg aagaagagaa tgaccacaaa gatcatcata agcacatcaa tggcagtgct   3660
ggtagctatg atcctgggag gattttcaat gagtgacctg gctaagcttg caattttgat   3720
gggtgccacc ttcgcggaaa tgaacactgg aggagatgta gctcatctgg cgctgatagc   3780
ggcattcaaa gtcagaccag cgttgctggt atctttcatc ttcagagcta attggacacc   3840
ccgtgaaagc atgctgctgg ccttggcctc gtgtttttg caaactgcga tctccgcctt   3900
ggaaggcgac ctgatggttc tcatcaatgg ttttgctttg gcctggttgg caatacgagc   3960
gatggttgtt ccacgcactg acaacatcac cttggcaatc ctggctgctc tgacaccact   4020
ggcccggggc acactgcttg tggcgtggag agcaggcctt gctacttgcg gggggtttat   4080
gctcctctct ctgaagggaa aaggcagtgt gaagaagaac ttaccatttg tcatggccct   4140
gggactaacc gctgtgaggc tggtcgaccc catcaacgtg gtgggactgc tgttgctcac   4200
aaggagtggg aagcggagct ggccccctag cgaagtactc acagctgttg gcctgatatg   4260
```

cgcattggct ggagggttcg ccaaggcaga tatagagatg gctgggccca tggccgcggt 4320
cggtctgcta attgtcagtt acgtggtctc aggaaagagt gtggacatgt acattgaaag 4380
agcaggtgac atcacatggg aaaaagatgc ggaagtcact ggaaacagtc cccggctcga 4440
tgtggcgcta gatgagagtg gtgacttctc cctggtggag gatgacggtc cccccatgag 4500
agagatcata ctcaaggtgg tcctgatgac catctgtggc atgaacccaa tagccatacc 4560
ctttgcagct ggagcgtggt acgtatacgt gaagactgga aaaaggagtg gtgctctatg 4620
ggatgtgcct gctcccaagg aagtaaaaaa gggggagacc acagatggag tgtacagagt 4680
aatgactcgt agactgctag gttcaacaca agttggagtg ggagttatgc aagagggggt 4740
ctttcacact atgtggcacg tcacaaaagg atccgcgctg agaagcggtg aagggagact 4800
tgatccatac tggggagatg tcaagcagga tctggtgtca tactgtggtc catggaagct 4860
agatgccgcc tgggacgggc acagcgaggt gcagctcttg gccgtgcccc ccggagagag 4920
agcgaggaac atccagactc tgcccggaat atttaagaca aaggatgggg acattggagc 4980
ggttgcgctg gattacccag caggaacttc aggatctcca atcctagaca agtgtgggag 5040
agtgatagga ctttatggca atggggtcgt gataaaaaat gggagttatg ttagtgccat 5100
cacccaaggg aggagggagg aagagactcc tgttgagtgc ttcgagcctt cgatgctgaa 5160
gaagaagcag ctaactgtct tagacttgca tcctggagct gggaaaacca ggagagttct 5220
tcctgaaata gtccgtgaag ccataaaaac aagactccgt actgtgatct tagctccaac 5280
cagggttgtc gctgctgaaa tggaggaagc ccttagaggg cttccagtgc gttatatgac 5340
aacagcagtc aatgtcaccc actctggaac agaaatcgtc gacttaatgt gccatgccac 5400
cttcacttca cgtctactac agccaatcag agtccccaac tataatctgt atattatgga 5460
tgaggcccac ttcacagatc cctcaagcat agcagcaaga ggatacattt caacaagggt 5520
tgagatgggc gaggcggctg ccatcttcat gaccgccacg ccaccaggaa cccgtgacgc 5580
atttccggac tccaactcac caattatgga caccgaagtg gaagtcccag agagagcctg 5640
gagctcaggc tttgattggg tgacggatca ttctggaaaa acagtttggt ttgttccaag 5700
cgtgaggaac ggcaatgaga tcgcagcttg tctgacaaag gctggaaaac gggtcataca 5760
gctcagcaga aagacttttg agacagagtt ccagaaaaca aaacatcaag agtgggactt 5820
tgtcgtgaca actgacattt cagagatggg cgccaacttt aaagctgacc gtgtcataga 5880
ttccaggaga tgcctaaagc cggtcatact tgatggcgag agagtcattc tggctggacc 5940
catgcctgtc acacatgcca gcgctgccca gaggaggggg cgcataggca ggaatcccaa 6000
caaacctgga gatgagtacc tgtatggagg tgggtgcgca gagactgacg aagaccatgc 6060
acactggctt gaagcaagaa tgctccttga caatatttac ctccaagatg gcctcatagc 6120
ctcgctctat cgacctgagg ccgacaaagt agcagccatt gagggagagt tcaagcttag 6180
gacggagcaa aggaagacct ttgtggaact catgaaaaga ggagatcttc ctgtttggct 6240
ggcctatcag gttgcatctg ccggaataac ctacacagat agaagatggt gctttgatgg 6300
cacgaccaac aacaccataa tggaagacag tgtgccggca gaggtgtgga ccagacacgg 6360
agagaaaaga gtgctcaaac cgaggtggat ggacgccaga gtttgttcag atcatgcggc 6420
cctgaagtca ttcaaggagt ttgccgctgg gaaaagagga gcggcttttg gagtgatgga 6480
agccctggga acactgccag gacacatgac agagagattc caggaagcca ttgacaacct 6540
cgctgtgctc atgcgggcag agactggaag caggccttac aaagccgcgg cggcccaatt 6600

```
gccggagacc ctagagacca ttatgctttt ggggttgctg ggaacagtct cgctgggaat   6660
ctttttcgtc ttgatgagga acaagggcat agggaagatg ggctttggaa tggtgactct   6720
tggggccagc gcatggctca tgtggctctc ggaaattgag ccagccagaa ttgcatgtgt   6780
cctcattgtt gtgttcctat tgctggtggt gctcatacct gagccagaaa agcaaagatc   6840
tccccaggac aaccaaatgg caatcatcat catggtagca gtaggtcttc tgggcttgat   6900
taccgccaat gaactcggat ggttggagag aacaaagagt gacctaagcc atctaatggg   6960
aaggagagag gagggggcaa ccataggatt ctcaatggac attgacctgc ggccagcctc   7020
agcttgggcc atctatgctg ccttgacaac tttcattacc ccagccgtcc aacatgcagt   7080
gaccacttca tacaacaact actccttaat ggcgatggcc acgcaagctg gagtgttgtt   7140
tggtatgggc aaagggatgc cattctacgc atgggacttt ggagtcccgc tgctaatgat   7200
aggttgctac tcacaattaa cacccctgac cctaatagtg gccatcattt tgctcgtggc   7260
gcactacatg tacttgatcc cagggctgca ggcagcagct gcgcgtgctg cccagaagag   7320
aacggcagct ggcatcatga agaaccctgt tgtggatgga atagtggtga ctgacattga   7380
cacaatgaca attgaccccc aagtggagaa aaagatggga caggtgctac tcatagcagt   7440
agccgtctcc agcgccatac tgtcgcggac cgcctggggg tgggggggagg ctggggccct   7500
gatcacagcc gcaacttcca ctttgtggga aggctctccg aacaagtact ggaactcctc   7560
tacagccact tcactgtgta acatttttag ggaagttac ttggctggag cttctctaat   7620
ctacacagta acaagaaacg ctggcttggt caagagacgt gggggtggaa caggagagac   7680
cctgggagag aaatggaagg cccgcttgaa ccagatgtcg gccctggagt tctactccta   7740
caaaaagtca ggcatcaccg aggtgtgcag agaagaggcc cgccgcgccc tcaaggacgg   7800
tgtggcaacg ggaggccatg ctgtgtcccg aggaagtgca aagctgagat ggttggtgga   7860
gcggggatac ctgcagccct atggaaaggt cattgatctt ggatgtggca gagggggctg   7920
gagttactac gccgccacca tccgcaaagt tcaagaagtg aaaggataca caaaaggagg   7980
ccctggtcat gaagaacccg tgttggtgca aagctatggg tggaacatag tccgtcttaa   8040
gagtggggtg gacgtctttc atatggcggc tgagccgtgt gacacgttgc tgtgtgacat   8100
aggtgagtca tcatctagtc ctgaagtgga agaagcacgg acgctcagag tcctctccat   8160
ggtgggggat tggcttgaaa aaagaccagg agccttttgc ataaaagtgt tgtgcccata   8220
caccagcact atgatggaaa ccctggagcg actgcagcgt aggtatgggg gaggactggt   8280
cagagtgcca ctctcccgca actctacaca tgagatgtac tgggtctctg gagcgaaaag   8340
caacaccata aaaagtgtgt ccaccacgag ccagctcctc ttggggcgca tggacgggcc   8400
taggaggcca gtgaaatatg aggaggatgt gaatctcggc tctggcacgc gggctgtggt   8460
aagctgcgct gaagctccca acatgaagat cattggtaac cgcattgaaa ggatccgcag   8520
tgagcacgcg gaaacgtggt tctttgacga aaaccaccca tataggacat gggcttacca   8580
tggaagctat gtggccccca cacaagggtc agcgtcctct ctaataaacg gggttgtcag   8640
gctcctgtca aaaccctggg atgtggtgac tggagtcaca ggaatagcca tgaccgacac   8700
cacaccgtat ggtcagcaaa gagttttcaa ggaaaaagtg gacactaggg tgccagaccc   8760
ccaagaaggc actcgtcagg ttatgagcat ggtctcttcc tggttgtgga aagagctagg   8820
caaacacaaa cgaccacgag tctgtaccaa agaagagttc atcaacaagg ttcgtagcaa   8880
tgcagcatta ggggcaatat ttgaagagga aaaagagtgg aagactgcag tggaagctgt   8940
gaacgatcca aggttctggg ctctagtgga caaggaaaga gagcaccacc tgagaggaga   9000
```

-continued gtgccagagt tgtgtgtaca acatgatggg aaaaagagaa aagaaacaag gggaatttgg 9060
aaaggccaag ggcagccgcg ccatctggta tatgtggcta ggggctagat ttctagagtt 9120
cgaagccctt ggattcttga acgaggatca ctggatgggg agagagaact caggaggtgg 9180
tgttgaaggg ctgggattac aaagactcgg atatgtccta gaagagatga gtcgcatacc 9240
aggaggaagg atgtatgcag atgacactgc tggctgggac acccgcatca gcaggtttga 9300
tctggagaat gaagctctaa tcaccaacca aatggagaaa gggcacaggg ccttggcatt 9360
ggccataatc aagtacacat accaaaacaa agtggtaaag gtccttagac cagctgaaaa 9420
agggaaaaca gttatggaca ttatttcgag acaagaccaa agggggagcg gacaagttgt 9480
cacttacgct cttaacacat ttaccaacct agtggtgcaa ctcattcgga atatggaggc 9540
tgaggaagtt ctagagatgc aagacttgtg gctgctgcgg aggtcagaga aagtgaccaa 9600
ctggttgcag agcaacggat gggataggct caaacgaatg gcagtcagtg gagatgattg 9660
cgttgtgaag ccaattgatg ataggtttgc acatgccctc aggttcttga atgatatggg 9720
aaaagttagg aaggacacac aagagtggaa accctcaact ggatgggaca actgggaaga 9780
agttccgttt tgctcccacc acttcaacaa gctccatctc aaggacggga ggtccattgt 9840
ggttccctgc cgccaccaag atgaactgat tggccgggcc cgcgtctctc caggggcggg 9900
atggagcatc cgggagactg cttgcctagc aaaatcatat gcgcaaatgt ggcagctcct 9960
ttatttccac agaagggacc tccgactgat ggccaatgcc atttgttcat ctgtgccagt 10020
tgactgggtt ccaactggga gaactacctg gtcaatccat ggaaagggag aatggatgac 10080
cactgaagac atgcttgtgg tgtggaacag agtgtggatt gaggagaacg accacatgga 10140
agacaagacc ccagttacga aatggacaga cattccctat ttgggaaaaa gggaagactt 10200
gtggtgtgga tctctcatag ggcacagacc gcgcaccacc tgggctgaga acattaaaaa 10260
tacagtcaac atggtgcgca ggatcatagg tgatgaagaa aagtacatgg actacctatc 10320
cacccaagtt cgctacttgg gtgaagaagg gtctacacct ggagtgctgt gagcaccaat 10380
cttaatgttg tcaggcctgc tagtcagcca cagcttgggg aaagctgtgc agcctgtgac 10440
ccctccagga gaagctgggt aaccaagcct atagtcaggc cgagaacgcc atggcacgga 10500
agaagccatg ctgcctgtga gcccctcaga ggacactgag tcaaaaaacc ccacgcgctt 10560
ggaggcgcag gatgggaaaa gaaggtggcg accttcccca cccttcaatc tggggcctga 10620
actggagatc agctgtggat ctccagaaga gggactagtg gttagaggag accccccgga 10680
aaacgcaaaa cagcatattg acgctgggaa agaccagaga ctccatgagt ttccaccacg 10740
ctggccgcca ggcacagatc gccgaatagc ggcggccggt gtggggaaat cca 10793

<210> SEQ ID NO 4
<211> LENGTH: 10675
<212> TYPE: DNA
<213> ORGANISM: Zika virus

<400> SEQUENCE: 4
gttgttgatc tgtgtgaatc agactgcgac agttcgagtt tgaagcgaaa gctagcaaca 60
gtatcaacag gttttatttt ggatttggaa acgagagttt ctggtcatga aaaacccaaa 120
aaagaaatcc ggaggattcc ggattgtcaa tatgctaaaa cgcggagtag cccgtgtgag 180
cccctttggg ggcttgaaga ggctgccagc cggacttctg ctgggtcatg ggcccatcag 240
gatggtcttg gcgattctag cctttttgag attcacggca atcaagccat cactgggtct 300

-continued

```
catcaataga tggggttcag tggggaaaaa agaggctatg gaaacaataa agaagttcaa    360
gaaagatctg gctgccatgc tgagaataat caatgctagg aaggagaaga agagacgagg    420
cgcagatact agtgtcggaa ttgttggcct cctgctgacc acagctatgg cagcggaggt    480
cactagacgt gggagtgcat actatatgta cttggacaga aacgatgctg gggaggccat    540
atcttttcca accacattgg ggatgaataa gtgttatata cagatcatgg atcttggaca    600
catgtgtgat gccaccatga gctatgaatg ccctatgctg gatgaggggg tggaaccaga    660
tgacgtcgat tgttggtgca acacgacgtc aacttgggtt gtgtacggaa cctgccatca    720
caaaaaaggt gaagcacgga gatctagaag agctgtgacg ctcccctccc attccaccag    780
gaagctgcaa acgcggtcgc aaacctggtt ggaatcaaga gaatacacaa agcacttgat    840
tagagtcgaa aattggatat tcaggaaccc tggcttcgcg ttagcagcag ctgccatcgc    900
ttggcttttg ggaagctcaa cgagccaaaa agtcatatac ttggtcatga tactgctgat    960
tgccccggca tacagcatca ggtgcatagg agtcagcaat agggactttg tggaaggtat   1020
gtcaggtggg acttgggttg atgttgtctt ggaacatgga ggttgtgtca ccgtaatggc   1080
acaggacaaa ccgactgtcg acatagagct ggttacaaca acagtcagca acatggcgga   1140
ggtaagatcc tactgctatg aggcatcaat atcagacatg gcttctgaca gccgctgccc   1200
aacacaaggt gaagcctacc ttgacaagca atcagacact caatatgtct gcaaaagaac   1260
gttagtggac agaggctggg gaaatggatg tggacttttt ggcaaaggga gcctggtgac   1320
atgcgctaag tttgcatgct ccaagaaaat gaccgggaag agcatccagc cagagaatct   1380
ggagtaccgg ataatgctgt cagttcatgg ctcccagcac agtgggatga tcgttaatga   1440
cacaggacat gaaactgatg agaatagagc gaaagttgag ataacgccca attcaccgag   1500
agccgaagcc accctggggg gttttggaag cctaggactt gattgtgaac cgaggacagg   1560
ccttgacttt tcagatttgt attacttgac tatgaataac aagcactggt tggttcacaa   1620
ggagtggttc cacgacattc cattaccttg gcacgctggg gcagacaccg gaactccaca   1680
ctggaacaac aaagaagcac tggtagagtt caaggacgca catgccaaaa ggcaaactgt   1740
cgtggttcta gggagtcaag aaggagcagt tcacacggcc cttgctggag ctctggaggc   1800
tgagatggat ggtgcaaagg gaaggctgtc ctctggccac ttgaaatgtc gcctgaaaat   1860
ggataaactt agattgaagg gcgtgtcata ctccttgtgt actgcagcgt tcacattcac   1920
caagatcccg gctgaaacac tgcacgggac agtcacagtg gaggtacagt acgcagggac   1980
agatggacct tgcaaggttc cagctcagat ggcggtggac atgcaaactc tgaccccagt   2040
tgggaggttg ataaccgcta accccgtaat cactgaaagc actgagaact ctaagatgat   2100
gctggaactt gatccaccat ttggggactc ttacattgtc ataggagtcg gggagaagaa   2160
gatcacccac cactggcaca ggagtggcag caccattgga aaagcatttg aagccactgt   2220
gagaggtgcc aagagaatgg cagtcttggg agacacagcc tgggactttg gatcagttgg   2280
aggcgctctc aactcattgg gcaagggcat ccatcaaatt tttggagcag ctttcaaatc   2340
attgtttgga ggaatgtcct ggttctcaca aattctcatt ggaacgttgc tgatgtggtt   2400
gggtctgaac acaaagaatg gatctatttc ccttatgtgc ttggccttag ggggagtgtt   2460
gatcttctta tccacagccg tctctgctga tgtggggtgc tcggtggact tctcaaagaa   2520
ggagacgaga tgcggtacag ggtgtgttcgt ctataacgac gttgaagcct ggagggacag   2580
gtacaagtac catcctgact ccccccgtag attggcagca gcagtcaagc aagcctggga   2640
agatggtatc tgcgggatct cctctgtttc aagaatggaa aacatcatgt ggagatcagt   2700
```

-continued

```
agaaggggag ctcaacgcaa tcctggaaga gaatggagtt caactgacgg tcgttgtggg   2760
atctgtaaaa aaccccatgt ggagaggtcc acagagattg cccgtgcctg tgaacgagct   2820
gccccacggc tggaaggctt gggggaaatc gtatttcgtc agagcagcaa agacaaataa   2880
cagctttgtc gtggatggtg acacactgaa ggaatgccca ctcaaacata gagcatggaa   2940
cagctttctt gtggaggatc atgggttcgg ggtatttcac actagtgtct ggctcaaggt   3000
tagagaagat tattcattag agtgtgatcc agccgttatt ggaacagctg ttaagggaaa   3060
ggaggctgta cacagtgatc taggctactg gattgagagt gagaagaatg acacatggag   3120
gctgaagagg gcccatctga tcgagatgaa aacatgtgaa tggccaaagt cccacacatt   3180
gtggacagat ggaatagaag agagtgatct gatcataccc aagtctttag ctgggccact   3240
cagccatcac aataccagag agggctacag gacccaaatg aaagggccat ggcacagtga   3300
agagcttgaa attcggtttg aggaatgccc aggcactaag gtccacgtgg aggaaacatg   3360
tggaacaaga ggaccatctc tgagatcaac cactgcaagc ggaagggtga tcgaggaatg   3420
gtgctgcagg gagtgcacaa tgcccccact gtcgttccgg gctaaagatg gctgttggta   3480
tggaatggag ataaggccca ggaaagaacc agaaagcaac ttagtaaggt caatggtgac   3540
tgcaggatca actgatcaca tggaccactt ctcccttgga gtgcttgtga tcctgctcat   3600
ggtgcaggaa gggctgaaga agagaatgac cacaaagatc atcataagca catcaatggc   3660
agtgctggta gctatgatcc tgggaggatt ttcaatgagt gacctggcta agcttgcaat   3720
tttgatgggt gccaccttcg cggaaatgaa cactggagga gatgtagctc atctggcgct   3780
gatagcggca ttcaaagtca gaccagcgtt gctggtatct ttcatcttca gagctaattg   3840
gacaccccgt gaaagcatgc tgctggcctt ggcctcgtgt cttttgcaaa ctgcgatctc   3900
cgccttggaa ggcgacctga tggttctcat caatggtttt gctttggcct ggttggcaat   3960
acgagcgatg gttgttccac gcactgataa catcaccttg gcaatcctgg ctgctctgac   4020
accactggcc cggggcacac tgcttgtggc gtggagagca ggccttgcta cttgcggggg   4080
gtttatgctc ctctctctga agggaaaagg cagtgtgaag aagaacttac catttgtcat   4140
ggccctggga ctaaccgctg tgaggctggt cgaccccatc aacgtggtgg gactgctgtt   4200
gctcacaagg agtgggaagc ggagctggcc ccctagcgaa gtactcacag ctgttggcct   4260
gatatgcgca ttggctggag ggttcgccaa ggcagatata gagatggctg ggcccatggc   4320
cgcggtcggt ctgctaattg tcagttacgt ggtctcagga aagagtgtgg acatgtacat   4380
tgaaagagca ggtgacatca catgggaaaa agatgcggaa gtcactggaa acagtccccg   4440
gctcgatgtg gcgctagatg agagtggtga tttctccctg gtggaggatg acggtccccc   4500
catgagagag atcatactca aggtggtcct gatgaccatc tgtggcatga acccaatagc   4560
cataccottt gcagctggag cgtggtacgt atacgtgaag actggaaaaa ggagtggtgc   4620
tctatgggat gtgcctgctc ccaaggaagt aaaaaagggg gagaccacag atggagtgta   4680
cagagtaatg actcgtagac tgctaggttc aacacaagtt ggagtgggag ttatgcaaga   4740
gggggtcttt cacactatgt ggcacgtcac aaaaggatcc gcgctgagaa gcggtgaagg   4800
gagacttgat ccatactggg gagatgtcaa gcaggatctg gtgtcatact gtggtccatg   4860
gaagctagat gccgcctggg atgggcacag cgaggtgcag ctcttggccg tgccccccgg   4920
agagagagcg aggaacatcc agactctgcc cggaatattt aagacaaagg atggggacat   4980
tggagcggtt gcgctggatt acccagcagg aacttcagga tctccaatcc tagacaagtg   5040
```

-continued

```
tgggagagtg ataggacttt atggcaatgg ggtcgtgatc aaaaacggga gttatgttag   5100
tgccatcacc caagggagga gggaggaaga gactcctgtt gagtgcttcg agccctcgat   5160
gctgaagaag aagcagctaa ctgtcttaga cttgcatcct ggagctggga aaaccaggag   5220
agttcttcct gaaatagtcc gtgaagccat aaaaacaaga ctccgtactg tgatcttagc   5280
tccaaccagg gttgtcgctg ctgaaatgga ggaggccctt agagggcttc cagtgcgtta   5340
tatgacaaca gcagtcaatg tcacccactc tggaacagaa atcgtcgact taatgtgcca   5400
tgccaccttc acttcacgtc tactacagcc aatcagagtc cccaactata atctgtatat   5460
tatggatgag gcccacttca cagatccctc aagtatagca gcaagaggat acatttcaac   5520
aagggttgag atgggcgagg cggctgccat cttcatgacc gccacgccac caggaacccg   5580
tgacgcattt ccggactcca actcaccaat tatggacacc gaagtggaag tcccagagag   5640
agcctggagc tcaggctttg attgggtgac ggatcattct ggaaaaacag tttggtttgt   5700
tccaagcgtg aggaacggca atgagatcgc agcttgtctg acaaaggctg gaaaacgggt   5760
catacagctc agcagaaaga cttttgagac agagttccag aaaacaaaac atcaagagtg   5820
ggactttgtc gtgacaactg acatttcaga gatgggcgcc aactttaaag ctgaccgtgt   5880
catagattcc aggagatgcc taaagccggt catacttgat ggcgagagag tcattctggc   5940
tggacccatg cctgtcacac atgccagcgc tgcccagagg agggggcgca taggcaggaa   6000
tcccaacaaa cctggagatg agtatctgta tggaggtggg tgcgcagaga ctgacgaaga   6060
ccatgcacac tggcttgaag caagaatgct ccttgacaat atttacctcc aagatggcct   6120
catagcctcg ctctatcgac ctgaggccga caaagtagca gccattgagg gagagttcaa   6180
gcttaggacg gagcaaagga agacctttgt ggaactcatg aaaagaggag atcttcctgt   6240
ttggctggcc tatcaggttg catctgccgg aataacctac acagatagaa gatggtgctt   6300
tgatggcacg accaacaaca ccataatgga agacagtgtg ccggcagagg tgtggaccag   6360
acacggagag aaaagagtgc tcaaaccgag gtggatggac gccagagttt gttcagatca   6420
tgcggccctg aagtcattca aggagtttgc cgctgggaaa agaggagcgg cttttggagt   6480
gatggaagcc ctgggaacac tgccaggaca catgacagag agattccagg aagccattga   6540
caacctcgct gtgctcatgc gggcagagac tggaagcagg ccttacaaag ccgcggcggc   6600
ccaattgccg gagaccctag agaccataat gcttttgggg ttgctgggaa cagtctcgct   6660
gggaatcttc ttcgtcttga tgaggaacaa gggcataggg aagatgggct ttggaatggt   6720
gactcttggg gccagcgcat ggctcatgtg gctctcggaa attgagccag ccagaattgc   6780
atgtgtcctc attgttgtgt tcctattgct ggtggtgctc atacctgagc cagaaaagca   6840
aagatctccc caggacaacc aaatggcaat catcatcatg gtagcagtag gtcttctggg   6900
cttgattacc gccaatgaac tcggatggtt ggagagaaca aagagtgacc taagccatct   6960
aatgggaagg agagaggagg gggcaaccat aggattctca atggacattg acctgcggcc   7020
agcctcagct tgggccatct atgctgcctt gacaactttc attaccccag ccgtccaaca   7080
tgcagtgacc acctcataca acaactactc cttaatggcg atggccacgc aagctggagt   7140
gttgtttggc atgggcaaag ggatgccatt ctacgcatgg gactttggag tcccgctgct   7200
aatgataggt tgctactcac aattaacacc cctgacccta atagtggcca tcattttgct   7260
cgtggcgcac tacatgtact tgatcccagg gctgcaggca gcagctgcgc gtgctgccca   7320
gaagagaacg gcagctggca tcatgaagaa ccctgttgtg gatggaatag tggtgactga   7380
cattgacaca atgacaattg acccccaagt ggagaaaaag atgggacagg tgctactcat   7440
```

-continued

```
agcagtagcc gtctccagcg ccatactgtc gcggaccgcc tgggggtggg gggaggctgg   7500
ggctctgatc acagccgcaa cttccacttt gtgggaaggc tctccgaaca agtactggaa   7560
ctcctctaca gccacttcac tgtgtaacat ttttagggga agttacttgg ctggagcttc   7620
tctaatctac acagtaacaa gaaacgctgg cttggtcaag agacgtgggg gtggaacagg   7680
agagaccctg ggagagaaat ggaaggcccg cttgaaccag atgtcggccc tggagttcta   7740
ctcctacaaa aagtcaggca tcaccgaggt gtgcagagaa gaggcccgcc gcgccctcaa   7800
ggacggtgtg gcaacgggag gccatgctgt gtcccgagga agtgcaaagc tgagatggtt   7860
ggtggagcgg ggatacctgc agccctatgg aaaggtcatt gatcttggat gtggcagagg   7920
gggctggagt tactacgtcg ccaccatccg caaagttcaa gaagtgaaag gatacacaaa   7980
aggaggccct ggtcatgaag aacccgtgtt ggtgcaaagc tatgggtgga acatagtccg   8040
tcttaagagt ggggtggacg tctttcatat ggcggctgag ccgtgtgaca cgttgctgtg   8100
tgacataggt gagtcatcat ctagtcctga agtggaagaa gcacggacgc tcagagtcct   8160
ctccatggtg gggggattggc ttgaaaaaag accaggagcc ttttgtataa aagtgttgtg   8220
cccatacacc agcactatga tggaaaccct ggagcgactg cagcgtaggt atggggggagg   8280
actggtcaga gtgccactct cccgcaactc tacacatgag atgtactggg tctctggagc   8340
gaaaagcaac accataaaaa gtgtgtccac cacgagccag ctcctcttgg ggcgcatgga   8400
cgggcctagg aggccagtga aatatgagga ggatgtgaat ctcggctctg gcacgcgggc   8460
tgtggtaagc tgcgctgaag ctcccaacat gaagatcatt ggtaaccgca ttgaaaggat   8520
ccgcagtgag cacgcggaaa cgtggttctt tgacgagaac cacccatata ggacatgggc   8580
ttaccatgga agctatgagg cccccacaca agggtcagcg tcctctctaa taaacggggt   8640
tgtcaggctc ctgtcaaaac cctgggatgt ggtgactgga gtcacaggaa tagccatgac   8700
cgacaccaca ccgtatggtc agcaaagagt tttcaaggaa aaagtggaca ctagggtgcc   8760
agacccccaa gaaggcactc gtcaggttat gagcatggtc tcttcctggt tgtggaaaga   8820
gctaggcaaa cacaaacggc cacgagtctg caccaaagaa gagttcatca acaaggttcg   8880
tagcaatgca gcattagggg caatatttga agaggaaaaa gagtggaaga ctgcagtgga   8940
agctgtgaac gatccaaggt tctgggctct agtggacaag gaaagagagc accacctgag   9000
aggagagtgc cagagctgtg tgtacaacat gatgggaaaa agagaaaaga aacaagggga   9060
atttggaaag gccaagggca gccgcgccat ctggtatatg tggctagggg ctagatttct   9120
agagttcgaa gcccttggat tcttgaacga ggatcactgg atggggagag agaactcagg   9180
aggtggtgtt gaagggctgg gattacaaag actcggatat gtcctagaag agatgagtcg   9240
tataccagga ggaaggatgt atgcagatga cactgctggc tgggacaccc gcattagcag   9300
gtttgatctg gagaatgaag ctctaatcac caaccaaatg gagaaagggc acagggcctt   9360
ggcattggcc ataatcaagt acacatacca aaacaaagtg gtaaaggtcc ttagaccagc   9420
tgaaaaaggg aaaacagtta tggacattat ttcgagacaa gaccaaaggg ggagcggaca   9480
agttgtcact tacgctctta acacatttac caacctagtg gtgcaactca ttcggaatat   9540
ggaggctgag gaagttctag agatgcaaga cttgtggctg ctgcggaggt cagagaaagt   9600
gaccaactgg ttgcagagca acggatggga taggctcaaa cgaatggcag tcagtggaga   9660
tgattgcgtt gtgaagccaa ttgatgatag gtttgcacat gccctcaggt tcttgaatga   9720
tatgggaaaa gttaggaagg acacacaaga gtggaaaccc tcaactggat gggacaactg   9780
```

```
ggaagaagtt ccgttttgct cccaccactt caacaagctc catctcaagg acgggaggtc   9840

cattgtggtt ccctgccgcc accaagatga actgattggc cgggcccgcg tctctccagg   9900

ggcgggatgg agcatccggg agactgcttg cctagcaaaa tcatatgcgc aaatgtggca   9960

gctcctttat ttccacagaa gggacctccg actgatggcc aatgccattt gttcatctgt  10020

gccagttgac tgggttccaa ctgggagaac tacctggtca atccatggaa agggagaatg  10080

gatgaccact gaagacatgc ttgtggtgtg gaacagagtg tggattgagg agaacgacca  10140

catggaagac aagaccccag ttacgaaatg gacagacatt ccctatttgg gaaaaaggga  10200

agacttgtgg tgtggatctc tcatagggca cagaccgcgc accacctggg ctgagaacat  10260

taaaaacaca gtcaacatgg tgcgcaggat cataggtgat gaagaaaagt acatggacta  10320

cctatccacc caagttcgct acttgggtga agaagggtct acacctggag tgctgtaagc  10380

accaatctta atgttgtcag gcctgctagt cagccacagc ttggggaaag ctgtgcagcc  10440

tgtgaccccc ccaggagaag ctgggaaacc aagcctatag tcaggccgag aacgccatgg  10500

cacggaagaa gccatgctgc ctgtgagccc ctcagaggac actgagtcaa aaaaccccac  10560

gcgcttggag gcgcaggatg ggaaaagaag gtggcgacct tccccaccct tcaatctggg  10620

gcctgaactg gagatcagct gtggatctcc agaagaggga ctagtggtta gagga       10675
```

<210> SEQ ID NO 5
<211> LENGTH: 10676
<212> TYPE: DNA
<213> ORGANISM: Zika virus

<400> SEQUENCE: 5

```
gttgttactg ttgctgactc agactgcgac agttcgagtt tgaagcgaaa gctagcaaca     60

gtatcaacag gttttatttg gatttggaaa cgagagtttc tggtcatgaa aaacccaaaa    120

aagaaatccg gaggattccg gattgtcaat atgctaaaac gcggagtagc ccgtgtgagc    180

ccctttgggg gcttgaagag gctgccagcc ggacttctgc tgggtcatgg gcccatcagg    240

atggtcttgg caattctagc ctttttgaga ttcacggcaa tcaagccatc actgggtctc    300

atcaatagat ggggttcagt ggggaaaaaa gaggctatgg aaataataaa gaagttcaag    360

aaagatctgg ctgccatgct gagaataatc aatgctagga aggagaagaa gagacgaggc    420

gcagatacta gtgtcggaat tgttggcctc ctgctgacca cagctatggc agcggaggtc    480

actagacgtg ggagtgcata ctatatgtac ttggacagaa acgatgctgg ggaggccata    540

tcttttccaa ccacattggg gatgaataag tgttatatac agatcatgga tcttggacac    600

atgtgtgatg ccaccatgag ctatgaatgc cctatgctgg atgagggggt ggaaccagat    660

gacgtcgatt gttggtgcaa cacgacgtca acttgggttg tgtacggaac ctgccatcac    720

aaaaaaggtg aagcacggag atctagaaga gctgtgacgc tcccctccca ttccactagg    780

aagctgcaaa cgcggtcgca aacctggttg gaatcaagag aatacacaaa gcacttgatt    840

agagtcgaaa attggatatt caggaaccct ggcttcgcgt tagcagcagc tgccatcgct    900

tggcttttgg gaagctcaac gagccaaaaa gtcatatact tggtcatgat actgctgatt    960

gccccggcat acagcatcag gtgcatagga gtcagcaata gggactttgt ggaaggtatg   1020

tcaggtggga cttgggttga tgttgtcttg gaacatggag gttgtgtcac cgtaatggca   1080

caggacaaac cgactgtcga catagagctg gttacaacaa cagtcagcaa catggcggag   1140

gtaagatcct actgctatga ggcatcaata tcagacatgg cttcggacag ccgctgccca   1200

acacaaggtg aagcctacct tgacaagcaa tcagacactc aatatgtctg caaaagaacg   1260
```

```
ttagtggaca gaggctgggg aaatggatgt ggactttttg gcaaagggag tctggtgaca   1320
tgcgctaagt ttgcatgctc caagaaaatg accgggaaga gcatccagcc agagaatctg   1380
gagtaccgga taatgctgtc agttcatggc tcccagcaca gtgggatgat cgttaatgac   1440
acaggacatg aaactgatga gaatagagcg aaggttgaga taacgcccaa ttcaccaaga   1500
gccgaagcca ccctgggggg ttttggaagc ctaggacttg attgtgaacc gaggacaggc   1560
cttgactttt cagatttgta ttacttgact atgaataaca agcactggtt ggttcacaag   1620
gagtggttcc acgacattcc attaccttgg cacgctgggg cagacaccgg aactccacac   1680
tggaacaaca aagaagcact ggtagagttc aaggacgcac atgccaaaag gcaaactgtc   1740
gtggttctag ggagtcaaga aggagcagtt cacacggccc ttgctggagc tctggaggct   1800
gagatggatg gtgcaaaggg aaggctgtcc tctggccact tgaaatgtcg cctgaaaatg   1860
gataaactta gattgaaggg cgtgtcatac tccttgtgta ccgcagcgtt cacattcacc   1920
aagatcccgg ctgaaacact gcacgggaca gtcacagtgg aggtacagta cgcagggaca   1980
gatggacctt gcaaggttcc agctcagatg gcggtggaca tgcaaactct gaccccagtt   2040
gggaggttga taaccgctaa ccccgtaatc actgaaagca ctgagaactc taagatgatg   2100
ctggaacttg atccaccatt tggggactct tacattgtca taggagtcgg ggagaagaag   2160
atcacccacc actggcacag gagtggcagc accattggaa aagcatttga agccactgtg   2220
agaggtgcca agagaatggc agtcttggga gacacagcct gggactttgg atcagttgga   2280
ggcgctctca actcattggg caagggcatc catcaaattt ttggagcagc tttcaaatca   2340
ttgtttggag gaatgtcctg gttctcacaa attctcattg gaacgttgct gatgtggttg   2400
ggtctgaaca caaagaatgg atctatttcc cttatgtgct tggccttagg gggagtgttg   2460
atcttcttat ccacagccgt ctctgctgat gtggggtgct cggtggactt ctcaaagaag   2520
gagacgagat gcggtacagg ggtgttcgtc tataacgacg ttgaagcctg gagggacagg   2580
tacaagtacc atcctgactc cccccgtaga ttggcagcag cagtcaagca agcctgggaa   2640
gatggtatct gcgggatctc ctctgtttca agaatggaaa acatcatgtg gagatcagta   2700
gaaggggagc tcaacgcaat cctggaagag aatggagttc aactgacggt cgttgtggga   2760
tctgtaaaaa accccatgtg gagaggtcca cagagattgc ccgtgcctgt gaacgagctg   2820
ccccacggct ggaaggcttg gggggaaatcg cacttcgtca gagcagcaaa gacaaataac   2880
agctttgtcg tggatggtga cacactgaag gaatgcccac tcaaacatag agcatggaac   2940
agctttcttg tggaggatca tgggttcggg gtatttcaca ctagtgtctg gctcaaggtt   3000
agagaagatt attcattaga gtgtgatcca gccgttattg gaacagctgt taagggaaag   3060
gaggctgtac acagtgatct aggctactgg attgagagtg agaagaatga cacatggagg   3120
ctgaagaggg cccatctgat cgagatgaaa acatgtgaat ggccaaagtc ccacacattg   3180
tggacagatg gaatagaaga gagtgatctg atcataccca agtctttagc tgggccactc   3240
agccatcaca ataccagaga gggctacagg acccaaatga aagggccatg gcacagtgaa   3300
gagcttgaaa ttcggtttga ggaatgccca ggcactaagg tccacgtgga ggaaacatgt   3360
ggaacaagag gaccatctct gagatcaacc actgcaagcg gaagggtgat cgaggaatgg   3420
tgctgcaggg agtgcacaat gcccccactg tcgttccggg ctaaagatgg ctgttggtat   3480
ggaatggaga taaggcccag gaaagaacca gaaagcaact tagtaaggtc aatggtgact   3540
gcaggatcaa ctgatcacat ggatcacttc tcccttggag tgcttgtgat tctgctcatg   3600
```

-continued

```
gtgcaggaag ggctgaagaa gagaatgacc acaaagatca tcataagcac atcaatggca   3660
gtgctggtag ctatgatcct gggaggattt tcaatgagtg acctggctaa gcttgcaatt   3720
ttgatgggtg ccaccttcgc ggaaatgaac actggaggag atgtagctca tctggcgctg   3780
atagcggcat tcaaagtcag accagcgttg ctggtatctt tcatcttcag agctaattgg   3840
acaccccgtg aaagcatgct gctggccttg gcctcgtgtc ttttgcaaac tgcgatctcc   3900
gccttggaag gcgacctgat ggttctcatc aatggttttg ctttggcctg gttggcaata   3960
cgagcgatgg ttgttccacg cactgataac atcaccttgg caatcctggc tgctctgaca   4020
ccactggccc ggggcacact gcttgtggcg tggagagcag gccttgctac ttgcgggggg   4080
tttatgctcc tctctctgaa gggaaaaggc agtgtgaaga agaacttacc atttgtcatg   4140
gccctgggac taaccgctgt gaggctggtc gaccccatca acgtggtggg gctgctgttg   4200
ctcacaagga gtgggaagcg gagctggccc cctagcgaag tactcacagc tgttggcctg   4260
atatgcgcat tggctggagg gttcgccaag gcagatatag agatggctgg gcccatggcc   4320
gcggtcggtc tgctaattgt cagttacgtg gtctcaggaa agagtgtgga catgtacatt   4380
gaaagagcag gtgacatcac atgggaaaaa gatgcggaag tcactggaaa cagtccccgg   4440
ctcgatgtgg cgctagatga gagtggtgat ttctccctgg tggaggatga cggtcccccc   4500
atgagagaga tcatactcaa ggtggtcctg atgaccatct gtggcatgaa cccaatagcc   4560
ataccctttg cagctggagc gtggtacgta tacgtgaaga ctggaaaaag gagtggtgct   4620
ctatgggatg tgcctgctcc caaggaagta aaaaaggggg agaccacaga tggagtgtac   4680
agagtaatga ctcgtagact gctaggttca acacaagttg gagtgggagt tatgcaagag   4740
ggggtctttc acactatgtg gcacgtcaca aaaggatccg cgctgagaag cggtgaaggg   4800
agacttgatc catactgggg agatgtcaag caggatctgg tgtcatactg tggtccatgg   4860
aagctagatg ccgcctggga cgggcacagc gaggtgcagc tcttggccgt gcccccccgga   4920
gagagagcga ggaacatcca gactctgccc ggaatattta agacaaagga tggggacatt   4980
ggagcggttg cgctggatta cccagcagga acttcaggat ctccaatcct agacaagtgt   5040
gggagagtga taggacttta tggcaatggg gtcgtgatca aaaatgggag ttatgttagt   5100
gccatcaccc aagggaggag ggaggaagag actcctgttg agtgcttcga gccttcgatg   5160
ctgaagaaga agcagctaac tgtcttagac ttgcatcctg gagctgggaa aaccaggaga   5220
gttcttcctg aaatagtccg tgaagccata aaaacaagac tccgtactgt gatcttagct   5280
ccaaccaggg ttgtcgctgc tgaaatggag gaagccctta gagggcttcc agtgcgttat   5340
atgacaacag cagtcaatgt cacccactct ggaacagaaa tcgtcgactt aatgtgccat   5400
gccaccttca cttcacgtct actacagcca atcagagtcc ccaactataa tctgtatatt   5460
atggatgagg cccacttcac agatccctca agtatagcag caagaggata catttcaaca   5520
agggttgaga tgggcgaggc ggctgccatc ttcatgaccg ccacgccacc aggaacccgt   5580
gacgcatttc cggactccaa ctcaccaatt atggacaccg aagtggaagt cccagagaga   5640
gcctggagct caggctttga ttgggtgacg gattattctg gaaaaacagt ttggtttgtt   5700
ccaagcgtga ggaacggcaa tgagatcgca gcttgtctga caaaggctgg aaaacgggtc   5760
atacagctca gcagaaagac ttttgagaca gagttccaga aaacaaaaca tcaagagtgg   5820
gactttgtcg tgacaactga catttcagag atgggcgcca actttaaagc tgaccgtgtc   5880
atagattcca ggagatgcct aaagccggtc atacttgatg gcgagagagt cattctggct   5940
ggacccatgc ctgtcacaca tgccagcgct gcccagagga gggggcgcat aggcaggaat   6000
```

```
cccaacaaac ctggagatga gtatctgtat ggaggtgggt gcgcagagac tgacgaagac   6060
catgcacact ggcttgaagc aagaatgctc cttgacaata tttacctcca agatggcctc   6120
atagcctcgc tctatcgacc tgaggccgac aaagtagcag ccattgaggg agagttcaag   6180
cttaggacgg agcaaaggaa gacctttgtg gaactcatga aaagaggaga tcttcctgtt   6240
tggctggcct atcaggttgc atctgccgga ataacctaca cagatagaag atggtgcttt   6300
gatggcacga ccaacaacac cataatggaa gacagtgtgc cggcagaggt gtggaccaga   6360
cacggagaga aaagagtgct caaaccgagg tggatggacg ccagagtttg ttcagatcat   6420
gcggccctga agtcattcaa ggagtttgcc gctgggaaaa gaggagcggc ttttggagtg   6480
atggaagccc tgggaacact gccaggacac atgacagaga gattccagga agccattgac   6540
aacctcgctg tgctcatgcg ggcagagact ggaagcaggc cttacaaagc cgcggcggcc   6600
caattgccgg agaccctaga gaccattatg cttttggggt tgctgggaac agtctcgctg   6660
ggaatctttt tcgtcttgat gaggaacaag ggcataggga agatgggctt tggaatggtg   6720
actcttgggg ccagcgcatg gctcatgtgg ctctcggaaa ttgagccagc cagaattgca   6780
tgtgtcctca ttgttgtgtt cctattgctg gtggtgctca tacctgagcc agaaaagcaa   6840
agatctcccc aggacaacca aatggcaatc atcatcatgg tagcagtagg tcttctgggc   6900
ttgattaccg ccaatgaact cggatggttg gagagaacaa agagtgacct aagccatcta   6960
atgggaagga gagaggaggg ggcaaccatg ggattctcaa tggacattga cctgcggcca   7020
gcctcagctt gggccatcta tgctgccttg acaactttca ttaccccagc cgtccaacat   7080
gcagtgacca cttcatacaa caactactcc ttaatggcga tggccacgca agctggagtg   7140
ttgtttggta tgggcaaagg gatgccattc tacgcatggg actttggagt cccgctgcta   7200
atgataggtt gctactcaca attaacgccc ctgaccctaa tagtggccat cattttgctc   7260
gtggcgcact acatgtactt gatcccaggg ctgcaggcag cagctgcgcg tgctgcccag   7320
aagagaacgg cagctggcat catgaagaac cctgttgtgg atggaatagt ggtgactgac   7380
attgacacaa tgacaattga cccccaagtg gagaaaaaga tgggacaggt gctactcatg   7440
gcagtagccg tctccagcgc catactgtcg cggaccgcct gggggtgggg ggaggctggg   7500
gccctgatca cagccgcaac ttccactttg tgggaaggct ctccgaacaa gtactggaac   7560
tcctctacag ccacttcact gtgtaacatt tttaggggaa gttacttggc tggagcttct   7620
ctaatctaca cagtaacaag aaacgctggc ttggtcaaga gacgtggggg tggaacagga   7680
gagaccctgg gagagaaatg gaaggcccgc ttgaaccaga tgtcggccct ggagttctac   7740
tcctacaaaa agtcaggcat caccgaggtg tgcagagaag aggcccgccg cgccctcaag   7800
gacggtgtgg caacgggagg ccatgctgtg tcccgaggaa gtgcaaagct gagatggttg   7860
gtggagcggg gatacctgca gccctatgga aaggtcattg atcttggatg tggcagaggg   7920
ggctggagtt actacgccgc caccatccgc aaagttcaag aagtgaaagg atacacaaaa   7980
ggaggccctg gtcatgaaga acccgtgttg gtgcaaagct atgggtggaa catagtccgt   8040
cttaagagtg ggtggacgt ctttcatatg gcggctgagc cgtgtgacac gttgctgtgt   8100
gacataggtg agtcatcatc tagtcctgaa gtggaagaag cacggacgct cagagtcctc   8160
tccatggtgg gggattggct tgaaaaaaga ccaggagcct tttgtataaa agtgttgtgc   8220
ccatacacca gcactatgat ggaaaccctg gagcgactgc agcgtaggta tgggggagga   8280
ctggtcagag tgccactctc ccgcaactct acacatgaga tgtactgggt ctctggagcg   8340
```

-continued

```
aaaagcaaca ccataaaaag tgtgtccacc acgagccagc tcctcttggg gcgcatggac   8400
gggcctagga ggccagtgaa atatgaggag gatgtgaatc tcggctctgg cacgcgggct   8460
gtggtaagct gcgctgaagc tcccaacatg aagatcattg gtaaccgcat tgaaaggatc   8520
cgcagtgagc acgcggaaac gtggttcttt gacgagaacc acccatatag gacatgggct   8580
taccatggaa gctatgaggc ccccacacaa gggtcagcgt cctctctaat aaacggggtt   8640
gtcaggctcc tgtcaaaacc ctgggatgtg gtgactggag tcacaggaat agccatgacc   8700
gacaccacac cgtatggtca gcaaagagtt ttcaaggaaa aagtggacac tagggtgcca   8760
gacccccaag aaggcactcg tcaggttatg agcatggtct cttcctggtt gtggaaagag   8820
ctaggcaaac acaaacggcc acgagtctgt accaaagaag agttcatcaa caaggttcgt   8880
agcaatgcag cattaggggc aatatttgaa gaggaaaaag agtggaagac tgcagtggaa   8940
gctgtgaacg atccaaggtt ctgggctcta gtggacaagg aaagagagca ccacctgaga   9000
ggagagtgcc agagttgtgt gtacaacatg atgggaaaaa gagaaaagaa acaaggggaa   9060
tttggaaagg ccaagggcag ccgcgccatc tggtatatgt ggctaggggc tagatttcta   9120
gagttcgaag cccttggatt cttgaacgag gatcactgga tggggagaga gaactcagga   9180
ggtggtgttg aagggctggg attacaaaga ctcggatatg tcctagaaga gatgagtcgc   9240
ataccaggag gaaggatgta tgcagatgac actgctggct gggacacccg catcagcagg   9300
tttgatctgg agaatgaagc tctaatcacc aaccaaatgg agaaagggca cagggccttg   9360
gcattggcca taatcaagta cacataccaa aacaaagtgg taaaggtcct tagaccagct   9420
gaaaaaggga agacagttat ggacattatt tcgagacaag accaaagggg gagcggacaa   9480
gttgtcactt acgctcttaa cacatttacc aacctagtgg tgcaactcat tcggaatatg   9540
gaggctgagg aagttctaga gatgcaagac ttgtggctgc tgcggaggtc agagaaagtg   9600
accaactggt tgcagagcaa cggatgggat aggctcaaac gaatggcagt cagtggagat   9660
gattgcgttg tgaagccaat tgatgatagg tttgcacatg ccctcaggtt cttgaatgat   9720
atgggaaaag ttaggaagga cacacaagag tggaaaccct caactggatg ggacaactgg   9780
gaagaagttc cgttttgctc ccaccacttc aacaagctcc atctcaagga cgggaggtcc   9840
attgtggttc cctgccgcca ccaagatgaa ctgattggcc gggcccgcgt ctctccaggg   9900
gcgggatgga gcatccggga gactgcttgc ctagcaaaat catatgcgca aatgtggcag   9960
ctcctttatt tccacagaag ggacctccga ctgatggcca atgccatttg ttcatctgtg  10020
ccagttgact gggttccaac tgggagaact acctggtcaa tccatggaaa gggagaatgg  10080
atgaccactg aagacatgct tgtggtgtgg aacagagtgt ggattgagga gaacgaccac  10140
atggaagaca agaccccagt tacgaaatgg acagacattc cctatttggg aaaaagggaa  10200
gacttgtggt gtggatctct catagggcac agaccgcgca ccacctgggc tgagaacatt  10260
aaaaacacag tcaacatggt gcgcaggatc ataggtgatg aagaaaagta catggactac  10320
ctatccaccc aagttcgcta cttgggtgaa gaagggtcta cacctggagt gctgtaagca  10380
ccaatcttaa tgttgtcagg cctgctagtc agccacagct tggggaaagc tgtgcagcct  10440
gtgacccccc caggagaagc tgggaaacca agcctatagt caggccgaga acgccatggc  10500
acggaagaag ccatgctgcc tgtgagcccc tcagaggaca ctgagtcaaa aaaccccacg  10560
cgcttggagg cgcaggatgg gaaaagaagg tggcgacctt ccccaccctt caatctgggg  10620
cctgaactgg agatcagctg tggatctcca gaagagggac tagtggttag aggaga      10676
```

-continued

<210> SEQ ID NO 6
<211> LENGTH: 10808
<212> TYPE: DNA
<213> ORGANISM: Zika virus

<400> SEQUENCE: 6
agttgttgat ctgtgtgaat cagactgcga cagttcgagt ttgaagcgaa agctagcaac 60
agtatcaaca ggttttattt tggatttgga aacgagagtt tctggtcatg aaaaacccaa 120
aaaagaaatc cggaggattc cggattgtca atatgctaaa acgcggagta gcccgtgtga 180
gcccctttgg gggcttgaag aggctgccag ccggacttct gctgggtcat gggcccatca 240
ggatggtctt ggcaattcta gcctttttga gattcacggc aatcaagcca tcactgggtc 300
tcatcaatag atggggttca gtggggaaaa aagaggctat ggaaataata aagaagttca 360
agaaagatct ggctgccatg ctgagaataa tcaatgctag gaaggagaag aagagacgag 420
gcgcagatac tagtgtcgga attgttggcc tcctgctgac cacagctatg gcagcggagg 480
tcactagacg tgggagtgca tactatatgt acttggacag aaacgatgct ggggaggcca 540
tatcttttcc aaccacattg gggatgaata agtgttatat acagatcatg gatcttggac 600
acatgtgtga tgccaccatg agctatgaat gccctatgct ggatgagggg gtggaaccag 660
atgacgtcga ttgttggtgc aacacgacgt caacttgggt tgtgtacgga acctgccatc 720
acaaaaaagg tgaagcacgg agatctagaa gagctgtgac gctcccctcc cattccacta 780
ggaagctgca aacgcggtcg caaacctggt tggaatcaag agaatacaca aagcacttga 840
ttagagtcga aaattggata ttcaggaacc ctggcttcgc gttagcagca gctgccatcg 900
cttggctttt gggaagctca acgagccaaa aagtcatata cttggtcatg atactgctga 960
ttgccccggc atacagcatc aggtgcatag gagtcagcaa tagggacttt gtggaaggta 1020
tgtcaggtgg gacttgggtt gatgttgtct tggaacatgg aggttgtgtc accgtaatgg 1080
cacaggacaa accgactgtc gacatagagc tggttacaac aacagtcagc aacatggcgg 1140
aggtaagatc ctactgctat gaggcatcaa tatcagacat ggcttcggac agccgctgcc 1200
caacacaagg tgaagcctac cttgacaagc aatcagacac tcaatatgtc tgcaaaagaa 1260
cgttagtgga cagaggctgg ggaaatggat gtggactttt tggcaaaggg agcctggtga 1320
catgcgctaa gtttgcatgc tccaagaaaa tgaccgggaa gagcatccag ccagagaatc 1380
tggagtaccg gataatgctg tcagttcatg gctcccagca cagtgggatg atcgttaatg 1440
acacaggaca tgaaactgat gagaatagag cgaaggttga gataacgccc aattcaccaa 1500
gagccgaagc caccctgggg ggttttggaa gcctaggact tgattgtgaa ccgaggacag 1560
gccttgactt ttcagatttg tattacttga ctatgaataa caagcactgg ttggtccaca 1620
aggagtggtt ccacgacatt ccattacctt ggcacgctgg ggcagacacc ggaactccac 1680
actggaacaa caaagaagca ctggtagagt tcaaggacgc acatgccaaa aggcaaactg 1740
tcgtggttct agggagtcaa gaaggagcag ttcacacggc ccttgctgga gctctggagg 1800
ctgagatgga tggtgcaaag ggaaggctgt cctctggcca cttgaaatgt cgcctgaaaa 1860
tggataaact tagattgaag ggcgtgtcat actccttgtg taccgcagcg ttcacattca 1920
ccaagatccc ggctgaaaca ctgcacggga cagtcacagt ggaggtacag tacgcaggga 1980
cagatggacc ttgcaaggtt ccagctcaga tggcggtgga catgcaaact ctgaccccag 2040
ttgggaggtt gataaccgct aaccccgtaa tcactgaaag cactgagaac tctaagatga 2100
tgctggaact tgatccacca tttggggact cttacattgt cataggagtc ggggagaaga 2160
agatcaccca ccactggcac aggagtggca gcaccattgg aaaagcattt gaagccactg 2220
tgagaggtgc caagagaatg gcagtcttgg gagacacagc ctgggacttt ggatcagttg 2280
gaggcgctct caactcattg ggcaagggca tccatcaaat ttttggagca gctttcaaat 2340
cattgtttgg aggaatgtcc tggttctcac aaatcctcat tggaacgttg ctgatgtggt 2400
tgggtctgaa cacaaagaat ggatctattt cccttatgtg cttggcctta gggggagtgt 2460
tgatcttctt atccacagcc gtctctgctg atgtggggtg ctcggtggac ttctcaaaga 2520
aggagacgag atgcggtaca ggggtgttcg tctataacga cgttgaagcc tggagggaca 2580
ggtacaagta ccatcctgac tccccccgta gattggcagc agcagtcaag caagcctggg 2640
aagatggtat ctgcgggatc tcctctgttt caagaatgga gaacatcatg tggagatcag 2700
tagaagggga gctcaacgca atcttggaag agaatggagt tcaactgacg gtcgttgtgg 2760
gatctgtaaa aaaccccatg tggagaggtc cacagagatt gcccgtgcct gtgaacgagc 2820
tgccccacgg ctggaaggct tgggggaaat cgtacttcgt cagagcagca aagacaaata 2880
acagctttgt cgtggatggt gacacactga aggaatgccc actcgaacat agagcatgga 2940
acagctttct tgtggaggat catgggttcg ggtatttca cactagtgtc tggctcaagg 3000
ttagagaaga ttattcatta gagtgtgatc cagccgttat tggaacagct gttaagggga 3060
aggaggctgt acacagtgat ctaggctact ggattgagag tgagaagaat gacacatgga 3120
ggctgaagag ggcccatcta atcgagatga aaacatgtga atggccaaag tcccacacat 3180
tgtgggcaga tggaatagaa gagagtgatc tgatcattcc caagtcttta gctgggccac 3240
tcagccatca caataccaga gagggctaca ggacccaaat gaaagggcca tggcacagtg 3300
aagagcttga aattcggttt gaggaatgcc cgggcactaa ggtccacgtg gaggaaacat 3360
gtggaacaag aggaccatct ctgagatcaa ccactgcaag cggaagggtg atcgaggaat 3420
ggtgctgcag ggagtgcaca atgcccccac tgtcgttccg ggctaaagat ggctgttggt 3480
atggaatgga gataaggccc aggaaagaac cagaaagcaa cttagtaagg tcagtggtga 3540
ctgcaggatc aactgatcac atggatcact tctcccttgg agtgcttgtg attctgctca 3600
tggtgcagga agggctgaag aagagaatga ccacaaagat catcataagc acatcaatgg 3660
cagtgctggt agctatgatc ctgggaggat tttcaatgag tgacctggct aagcttgcaa 3720
ttttgatggg cgccaccttc gcggaaatga acactggagg agatgtagct catctggcgc 3780
tgatagcggc attcaaagtc agaccagcgt tgctggtatc tttcatcttc agagctaatt 3840
ggacaccccg tgaaagcatg ctgctggcct tggcctcgtg tcttttgcaa actgcgatct 3900
ccgccttgga aggcgacctg atggttctca tcaatggttt tgctttggcc tggttggcaa 3960
tacgagcgat ggttgttcca cgcactgata acatcacctt ggcaatcctg gctgctctga 4020
caccactggc ccggggcaca ctgcttgtgg cgtggagagc aggccttgct acttgcgggg 4080
ggtttatgct cctctctctg aagggaaaag gcagtgtgaa gaagaactta ccatttgtca 4140
tggccctggg actaaccgct gtgaggctgg tcgaccccat caacgtggtg ggactgctgt 4200
tgctcacaag gagtgggaag cggagctggc cccctagcga agtactcaca gctgttggcc 4260
tgatatgcgc attggctgga gggttcgcca aggcagatat agagatggct gggcccatgg 4320
ccgcggtcgg tctgctaatt gtcagttacg tggtctcagg aaagagtgtg gacatgtaca 4380
ttgaaagagc aggtgacatc acatgggaaa aagatgcgga agtcactgga aacagtcccc 4440
ggctcgatgt ggcgctagat gagagtggtg atttctccct ggtggaggat gacggtcccc 4500
ccatgagaga gatcatactc aaggtggtcc tgatgaccat ctgtggcatg aacccaatag 4560
ccataccctt tgcagctgga gcgtggtacg tatacgtgaa gactggaaaa aggagtggtg 4620
ctctatggga tgtgcctgct cccaaggaag taaaaaaggg ggagaccaca gatggagtgt 4680
acagagtaat gactcgtaga ctgctaggtt caacacaagt tggagtggga gttatgcaag 4740
agggggtctt tcacactatg tggcacgtca caaaaggatc cgcgctgaga agcggtgaag 4800
ggagacttga tccatactgg ggagatgtca agcaggatct ggtgtcatac tgtggtccat 4860
ggaagctaga tgccgcctgg gacgggcaca gcgaggtgca gctcttggcc gtgccccccg 4920
gagagagagc gaggaacatc cagactctgc ccggaatatt taagacaaag gatggggaca 4980
ttggagcggt tgcgctggat tacccagcag gaacttcagg atctccaatc ctagacaagt 5040
gtgggagagt gataggactt tatggcaatg ggtcgtgat caaaaatggg agttatgtta 5100
gtgccatcac ccaagggagg agggaggaag agactcctgt tgagtgcttc gagccttcga 5160
tgctgaagaa gaagcagcta actgtcttag acttgcatcc tggagctggg aaaaccagga 5220
gagttcttcc tgaaatagtc cgtgaagcca taaaaacaag actccgtact gtgatcttag 5280
ctccaaccag ggttgtcgct gctgaaatgg aggaagccct tagagggctt ccagtgcgtt 5340
atatgacaac agcagtcaat gtcacccact ctggaacaga aatcgtcgac ttaatgtgcc 5400
atgccacctt cacttcacgt ctactacagc caatcagagt ccccaactat aatctgtata 5460
ttatggatga ggcccacttc acagatccct caagtatagc agcaagagga tacatttcaa 5520
caagggttga gatgggcgag gcggctgcca tcttcatgac cgccacgcca ccaggaaccc 5580
gtgacgcatt tccggactcc aactcaccaa ttatggacac cgaagtggaa gtcccagaga 5640
gagcctggag ctcaggcttt gattgggtga cggatcattc tggaaaaaca gtttggtttg 5700
ttccaagcgt gaggaacggc aatgagatcg cagcttgtct gacaaaggct ggaaaacggg 5760
tcatacagct cagcagaaag acttttgaga cagagttcca gaaaacaaaa catcaagagt 5820
gggactttgt cgtgacaact gacatttcag agatgggcgc caactttaaa gctgaccgtg 5880
tcatagattc caggagatgc ctaaagccgg tcatacttga tggcgagaga gtcattttgg 5940
ctggacccat gcctgtcaca catgccagcg ctgcccagag gagggggcgc ataggcagga 6000
atcccaacaa acctggagat gagtatctgt atggaggtgg gtgcgcagag actgacgaag 6060
accatgcaca ctggcttgaa gcaagaatgc tccttgacaa tatttacctc caagatggcc 6120
tcatagcctc gctctatcga cctgaggccg acaaagtagc agccattgag ggagagttca 6180
agcttaggac ggagcaaagg aagacctttg tggaactcat gaaaagagga gatcttcctg 6240
tttggctggc ctatcaggtt gcatctgccg gaataaccta cacagataga agatggtgct 6300
ttgatggcac gaccaacaac accataatgg aagacagtgt gccggcagag gtgtggacca 6360
gacacggaga gaaaagagtg ctcaaaccga ggtggatgga cgccagagtt tgttcagatc 6420
atgcggccct gaagtcattc aaggagtttg ccgctgggaa aagaggagcg gcttttggag 6480
tgatggaagc cctgggaaca ctgccaggac acatgacaga gagattccag gaagccattg 6540
acaacctcgc tgtgctcatg cgggcagaga ctggaagcag gccttacaaa gccgcggcgg 6600
cccaattgcc ggagacccta gagaccatta tgcttttggg gttgctggga acagtctcgc 6660
tgggaatctt tttcgtcttg atgaggaaca agggcatagg gaagatgggc tttggaatgg 6720
tgactcttgg ggccagcgca tggctcatgt ggctctcgga aattgagcca gccagaattg 6780
catgtgtcct cattgttgtg ttcctattgc tggtggtgct catacctgag ccagaaaagc 6840
aaagatctcc ccaggacaac caaatggcaa tcatcatcat ggtagcagta ggtcttctgg 6900

-continued

```
gcttgattac cgccaatgaa ctcggatggt tggagagaac aaagagtgac ctaagccatc   6960
taatgggaag gagagaggag ggagcaacca taggattctc aatggacatt gacctgcggc   7020
cagcctcagc ttgggccatc tatgctgcct tgacaacttt cattacccca gccgtccaac   7080
atgcagtgac cacttcatac aacaactact ccttaatggc gatggccacg caagctggag   7140
tgttgtttgg tatgggcaaa gggatgccat tctacgcatg ggactttgga gtcccgctgc   7200
taatgatagg ttgctactca caattaacac ccctgaccct aatagtggcc atcattttgc   7260
tcgtggcgca ctacatgtac ttgatcccag ggctgcaggc agcagctgcg cgtgctgccc   7320
agaagagaac ggcagctggc atcatgaaga accctgttgt ggatggaata gtggtgactg   7380
acattgacac aatgacaatt gacccccaag tggagaaaaa gatgggacag gtgctactca   7440
tagcagtagc agtctccagc gccatactgt cgcggaccgc ctgggggtgg ggggaggctg   7500
gggccctgat cacagccgca acttccactt tgtgggaagg ctctccgaac aagtactgga   7560
actcctctac agccacttca ctgtgtaaca tttttagggg aagttacttg gctggagctt   7620
ctctaatcta catagtaaca agaaacgctg gcttggtcaa gagacgtggg ggtggaacag   7680
gagagaccct gggagagaaa tggaaggccc gcttgaacca gatgtcggcc ctggagttct   7740
actcctacaa aaagtcaggc atcaccgagg tgtgcagaga agaggcccgc cgcgccctca   7800
aggatggtgt ggcaacggga ggccatgctg tgtcccgagg aagtgcaaag ctgagatggt   7860
tggtggagcg gggatacctg cagccctatg gaaaggtcat tgatcttgga tgtggcagag   7920
ggggctggag ttactacgcc gccaccatcc gcaaagttca agaagtgaaa ggatacacaa   7980
aaggaggccc tggtcatgaa gaacccgtgt tggtgcaaag ctatgggtgg aacatagtcc   8040
gtcttaagag tggggtggac gtctttcata tggcggctga gccgtgtgac acgttgctgt   8100
gtgacatagg tgagtcatca tctagtcctg aagtggaaga agcacggacg ctcagagtcc   8160
tctccatggt gggggattgg cttgaaaaaa gaccaggagc cttttgtata aaagtgttgt   8220
gcccatacac cagcactatg atggaaaccc tggagcgact gcagcgtagg tatgggggag   8280
gactggtcag agtgccactc tcccgcaact ctacacatga gatgtactgg gtctctggag   8340
cgaaaagcaa caccataaaa agtgtgtcca ccacgagcca gctcctcttg gggcgcatgg   8400
acgggcctag gaggccagtg aaatatgagg aggatgtgaa tctcggctct ggcacgcggg   8460
ctgtggtaag ctgcgctgaa gctcccaaca tgaagatcat tggtaaccgc attgaaagga   8520
tccgcagtga gcacgcggaa acgtggttct ttgacgagaa ccacccatat aggacatggg   8580
cttaccatgg aagctatgag gcccccacac aagggtcagc gtcctctcta ataaacgggg   8640
ttgtcaggct cctgtcaaaa ccctgggatg tggtgactgg agtcacagga atagccatga   8700
ccgacaccac accgtatggt cagcaaagag ttttcaagga aaaagtggac actagggtgc   8760
cagaccccca agaaggcact cgtcaggtta tgagcatggt ctcttcctgg ttgtggaaag   8820
agctaggcaa acacaaacgg ccacgagtct gtaccaaaga agagttcatc aacaaggttc   8880
gtagcaatgc agcattaggg gcaatatttg aagaggaaaa agagtggaag actgcagtgg   8940
aagctgtgaa cgatccaagg ttctgggctc tagtggacaa ggaaagagag caccacctga   9000
gaggagagtg ccagagttgt gtgtacaaca tgatgggaaa aagagaaaag aaacaagggg   9060
aatttggaaa ggccaagggc agccgcgcca tctggtatat gtggctaggg gctagatttc   9120
tagagttcga agcccttgga ttcttgaacg aggatcactg gatggggaga gagaactcag   9180
gaggtggtgt tgaagggctg ggattacaaa gactcggata tgtcctagaa gagatgagtc   9240
gcataccagg aggaaggatg tatgcagatg acactgctgg ctgggacacc cgcatcagca   9300
```

```
ggttcgatct ggagaatgaa gctctaatca ccaaccaaat ggagaaaggg catagggcct   9360
tggcattggc cataatcaag tacacatacc aaaacaaagt ggtaaaggtc cttagaccag   9420
ctgaaaaagg gaaaacagtt atggacatta tttcgagaca agaccaaagg gggagcggac   9480
aagttgtcac ttacgctctt aacacattta ccaacctagt ggtgcaactc attcggaata   9540
tggaggctga ggaagttcta gagatgcaag acttgtggct gctgcggagg tcagagaaag   9600
tgaccaactg gttgcagagc aacggatggg ataggctcaa acgaatggca gtcagtggag   9660
atgattgcgt tgtgaagcca attgatgata ggtttgcaca tgccctcagg ttcttgaatg   9720
atatgggaaa agttaggaag gacacacaag agtggaaacc ctcaactgga tgggacaact   9780
gggaagaagt tccgttttgc tcccaccact tcaacaagct ccatctcaag gacgggaggt   9840
ccattgtggt tccctgccgc caccaagatg aactgattgg ccgggcccgc gtctctccag   9900
gggcgggatg gagcatccgg gagactgctt gcctagcaaa atcatatgcg caaatgtggc   9960
agctccttta tttccacaga agggacctcc gactgatggc caatgccatt tgttcatctg  10020
tgccagttga ctgggttcca actgggagaa ctacctggtc aatccatgga aagggagaat  10080
ggatgaccac tgaagacatg cttgtggtgt ggaacagagt gtggattgag gagaacgacc  10140
acatggaaga caagacccca gttacgaaat ggacagacat tccctatttg ggaaaaaggg  10200
aagacttgtg gtgtggatct ctcatagggc acagaccgcg caccacctgg gctgagaaca  10260
ttaaaaacac agtcaacatg gtgcgcagga tcataggtga tgaagaaaag tacatggact  10320
acctatccac ccaagttcgc tacttgggtg aagaagggtc tacacctgga gtgctgtaag  10380
caccaatctt aatgttgtca ggcctgctag tcagccacag cttggggaaa gctgtgcagc  10440
ctgtgacccc cccaggagaa gctgggaaac caagcctata gtcaggccga gaacgccatg  10500
gcacggaaga agccatgctg cctgtgagcc cctcagagga cactgagtca aaaaacccca  10560
tgcgcttgga ggcgcaggat gggaaaagaa ggtggcgacc ttccccaccc ttcaatctgg  10620
ggcctgaact ggagatcagc tgtggatctc cagaagaggg actagtggtt agaggagacc  10680
ccccggaaaa cgcaaaacag catattgacg ctgggaaaga ccagagactc catgagtttc  10740
caccacgctg gccgccaggc acagatcgcc gaatagcggc ggccggtgtg gggaaatcca  10800
tgggtctt                                                           10808
```

```
<210> SEQ ID NO 7
<211> LENGTH: 10807
<212> TYPE: DNA
<213> ORGANISM: Zika virus

<400> SEQUENCE: 7

agttgttgat ctgtgtgaat cagactgcga cagttcgagt ttgaagcgaa agctagcaac     60
agtatcaaca ggttttattt tggatttgga aacgagagtt tctggtcatg aaaaacccaa    120
aaaagaaatc cggaggattc cggattgtca atatgctaaa acgcggagta gcccgtgtga    180
gcccctttgg gggcttgaag aggctgccag ccggacttct gctgggtcat gggcccatca    240
ggatggtctt ggcgattcta gcctttttga gattcacggc aatcaagcca tcactgggtc    300
tcatcaatag atggggttca gtgggaaaaa aagaggctat ggaaataata aagaagttca    360
agaaagatct ggctgccatg ctgagaataa tcaatgctag gaaggagaag aagagacgag    420
gcacagatac tagtgtcgga attgttggcc tcctgctgac cacagctatg gcagcggagg    480
tcactagacg tgggagtgca tactatatgt acttggacag aagcgatgct ggggaggcca    540
```

```
tatcttttcc aaccacactg gggatgaata agtgttatat acagatcatg gatcttggac    600
acatgtgtga tgccaccatg agctatgaat gccctatgct ggatgagggg gtagaaccag    660
atgacgtcga ttgttggtgc aacacgacgt caacttgggt tgtgtacgga acctgccatc    720
acaaaaaagg tgaagcacgg agatccagaa gagctgtgac gctcccctcc cattccacta    780
ggaagctgca aacgcggtcg cagacctggt tggaatcaag agaatacaca aagcacttga    840
ttagagtcga aaattggata ttcaggaacc ctggcttcgc gttagcagca gctgccatcg    900
cttggctttt gggaagctca acgagccaaa aagtcatata cttggtcatg atactgctga    960
ttgccccggc atacagcatc aggtgcatag gagtcagtaa tagggacttt gtggaaggta   1020
tgtcaggtgg gacttgggtt gatgttgtct tggaacatgg aggttgtgtc accgtaatgg   1080
cacaggacaa accgactgtc gacatagagc tggttacaac aacagtcagc aacatggcgg   1140
aggtaagatc ctactgctat gaggcatcaa tatcggacat ggcttcggac agccgctgcc   1200
caacacaagg tgaagcctac cttgacaagc aatcagacac tcaatatgtc tgcaaaagaa   1260
cgttagtgga cagaggctgg ggaaatggat gtggactttt tggcaaaggg agcctggtga   1320
catgcgctaa gtttgcatgc tccaagaaaa tgaccgggaa gagcatccag ccagagaatc   1380
tggagtaccg gataatgctg tcagttcatg gctcccagca cagtgggatg atcgttaatg   1440
acacaggaca tgaaactgat gagaatagag cgaaggttga gataacgccc aattcaccaa   1500
gagccgaagc caccctgggg ggttttggaa gcctaggact tgattgtgaa ccgaggacag   1560
gccttgactt ttcagatttg tattacttga ctatgaacaa caagcactgg ttggttcaca   1620
aggagtggtt ccacgacatt ccattacctt ggcacactgg ggcagacacc ggaactccac   1680
actggaacaa caaagaagca ctggtagagt tcaaggacgc acatgccaaa aggcaaactg   1740
tcgtggttct agggagtcaa gaaggagcag ttcacacggc ccttgctgga gctctggagg   1800
ctgagatgga tggtgcaaag ggaaggctgt cctctggcca cttgaaatgt cgcctgaaaa   1860
tggataaact tagattgaag ggcgtgtcat actccttgtg taccgcagcg ttcacattca   1920
ccaagatccc ggctgaaaca ctgcacggga cagtcacagt ggaggtacag tacgcaggga   1980
cagatggacc ttgcaaggtt ccagctcaga tggcggtgga catgcaaact ctgaccccag   2040
ttgggaggtt gataaccgct aaccccgtaa tcactgaagg cactgagaac tctaagatga   2100
tgctggaact tgatccacca tttggggact cttacattgt cataggagtc ggggagaaga   2160
agatcaccca ccactggcac aggagtggca gcaccattgg aaaagcattt gaagccactg   2220
tgagaggtgc caagagaatg gcagtcttgg gagacacagc ctgggacttt ggatcagttg   2280
gaggcgttct taactcattg ggcaagggca tccatcaaat ttttggagca gctttcaaat   2340
cattgtttgg aggaatgtcc tggttctcac aaattctcat tggaacgttg ctgatgtggt   2400
tgggtctgaa tacaaagaat ggatctattt cccttatgtg cttggcctta gggggagtgt   2460
tgatcttctt atccacagcc gtctccgctg atgtggggtg ctcggtggac ttctcaaaga   2520
aggaaacgag atgcggtaca ggggtgttcg tctataacga cgttgaagcc tggagggaca   2580
ggtacaagta ccatcctgac tcccctcgta gattggcagc agtagtcaag caagcctggg   2640
aagatggtat ctgtgggatc tcctctgttt caagaatgga aaacatcatg tggagatcag   2700
tagaagggga gctcaacgca atcctggaag agaatggagt tcaactgacg gtcgttgtgg   2760
gatctgtaaa aaaccccatg tggagaggtc cacagagatt gcccgtgcct gtgaacgagc   2820
tgccccacgg ctggaaggct tgggggaaat cgtacttcgt cagagcagca aagacaaata   2880
acagctttgt cgtggatggt gacacactga aggaatgccc actcaaacat agagcatgga   2940
```

```
acagctttct tgtggaggat catgggttcg gggtatttca cactagtgtc tggctcaagg   3000

ttagagaaga ttattcacta gagtgtgatc cagccgtcat tggaacagct gttaagggaa   3060

aggaggctgt acacagtgat ctaggctact ggattgagag tgagaagaac gacacatgga   3120

ggctgaggag ggcccacctg atcgagatga aaacatgtga atggccaaag tcccacacat   3180

tgtggacaga tggaatagaa gagagtgatc tgatcatacc caagtcttta gctgggccac   3240

tcagccatca caacaccaga gagggctaca ggacccaaat gaaagggcca tggcacagtg   3300

aagagcttga aattcggttt gaggaatgcc caggcactaa ggtccacgtg gaggaaacat   3360

gtggaacaag aggaccatct ctgagatcaa ccactgcaag cggaagggtg atcgaggaat   3420

ggtgctgcag ggagtgcaca atgcccccac tgtcgttccg ggctaaagat ggctgttggt   3480

atggaatgga gataaggccc aggaaagaac cagaaagtaa cttagtaagg tcaatggtga   3540

ctgcaggatc aactgatcac atggatcact tttcccttgg agtgcttgtg attctgctca   3600

tggtgcagga agggctgaag aagagaatga ccacaaagat catcataagc acatcaatgg   3660

cagtgctggt agctatgatc ctgggaggat tttcaatgag tgatctggct aagcttgcaa   3720

ttttgatggg tgccaccttt gcggaaatga acactggagg agatgtagct catctggcgc   3780

tggtagcggc attcaaagtc agaccagcgt tgctggtatc tttcatcttc agagctaatt   3840

ggacaccccg tgaaagcatg ctgctggcct tggcctcgtg tcttttgcaa actgcgatct   3900

ccgccttgga aggcgacctg atggttctca tcaatggttt tgctttggcc tggttggcaa   3960

tacgagcgat ggttgttcca cgcactgaca atatcacctt ggcaatcctg gctgctctga   4020

caccactggc ccggggcaca ctgcttgtgg cgtggagagc aggccttgct acttgcgggg   4080

ggttcatgct cctctctctg aaggggaaag gcagtgtgaa gaagaactta ccatttgtca   4140

tggccctggg actaaccgct gtgaggctgg tcgaccccat caacgtggtg ggactgctgt   4200

tgctcacaag gagtgggaag cggagctggc cccctagcga agtactcaca gctgttggcc   4260

tgatatgcgc attggctgga gggttcgcca aggcagatat agagatggct gggcccatgg   4320

ccgcggtcgg tctgctaatt gtcagttacg tggtctcagg aaagagtgtg gacatgtaca   4380

ttgaaagagc aggtgacatc acatgggaaa aagatgcgga agttactgga aacagtcccc   4440

ggctcgatgt ggcactagat gagagtggtg atttctccct ggtggaggat gacggtcccc   4500

ccatgagaga gatcatactc aaagtggtcc tgatgaccat ctgtggcatg aacccaatag   4560

ccataccctt tgcagctgga gcgtggtacg tatacgtgaa aactggaaaa aggagtggtg   4620

ctctatggga tgtgcctgct cccaaggaag taaaaaaggg ggagaccaca gatggagtgt   4680

acagagtaat gactcgtaga ctgctaggtt caacacaagt tggagtggga gttatgcaag   4740

agggggtctt tcacactatg tggcatgtca caaaaggatc cgcgctgaga agcggtgaag   4800

ggagacttga tccatactgg ggagatgtca agcaggatct ggtgtcatac tgtggtccat   4860

ggaagctaga tgccgcctgg gacgggcaca gcgaggtgca gctcttggcc gtgccccccg   4920

gagagagagc gaggaacatc cagactctgc ccggaatatt taagacaaag gatggggaca   4980

ttggagcggt tgcgctggac tatccagcag gaacttcagg atctccaatc ctagacaagt   5040

gtgggagagt gataggactc tatggcaatg gggtcgtgat caagaatggg agttatgtca   5100

gtgccatcac ccaagggagg agggaggaag agactcctgt tgagtgcttc gagccttcga   5160

tgctgaagaa gaagcagcta actgtcttag acttgcatcc tggagctggg aaaaccagga   5220

gagttcttcc tgaaatagtc cgtgaagcca taaaaacgag actccgtact gtgatcttag   5280
```

-continued

```
ctccaaccag ggttgtcgct gctgaaatgg aggaagccct tagagggctt ccagtgcgtt   5340
atatgacaac agcagtcaat gtcacccatt ctgggacaga aatcgttgac ttaatgtgcc   5400
atgccacctt cacttcacgt ctactacagc caatcagagt ccccaactat aatctgtata   5460
ttatggatga ggcccacttc acagatccct caagtatagc agcaagagga tacatttcaa   5520
caagggttga gatgggcgag gcagctgcca tcttcatgac cgccacgcca ccaggaaccc   5580
gtgacgcatt cccggactcc aactcaccaa ttatggacac cgaagtggaa gtcccagaga   5640
gagcctggag ctcaggcttt gattgggtga cggatcattc tggaaaaaca gtttggtttg   5700
tcccaagcgt gaggaacggc aatgagatcg cagcttgtct gacaaaggct ggaaaacggg   5760
tcatacagct cagcagaaag acttttgaga cagagttcca gaaaacaaaa catcaagagt   5820
gggacttcgt cgtgacaact gacatttcag agatgggcgc caactttaaa gctgaccgtg   5880
tcatagattc caggagatgc ctaaagccgg tcatacttga tggcgagaga gtcattctgg   5940
ctggacccat gcctgtcaca catgccagcg ctgcccagag gagggggcgc ataggcagga   6000
atcccaacaa acctggagat gagtatctgt atggaggtgg gtgcgcagag actgatgaag   6060
accatgcaca ctggcttgaa gcaagaatgc tccttgacaa tatttacctc caagatggcc   6120
tcatagcctc gctctatcga cctgaggccg acaaagtagc agccattgag ggagagttca   6180
agcttaggac ggagcaaagg aagacctttg tggaactcat gaaaagagga gatcttcctg   6240
tttggctggc ctatcaggtt gcatctgccg gaataaccta cacagataga agatggtgct   6300
ttgatggcat gaccaacaac accataatgg aagacagtgt gccggcagag gtgtggacca   6360
gacacggaga gaaaagagtg ctcaaaccga ggtggatgga cgccagagtt tgttcagatc   6420
atgcggccct gaagtcattc aaggagtttg ccgctgggaa aagaggagcg gcttttggag   6480
tgatggaagc cctgggaaca ctgccaggac acatgacgga gagattccag gaagccattg   6540
acaacctcgc tgtgctcatg cgggcagaga ctggaagcag gccttacaaa gccgcggcgg   6600
cccaattgcc ggagacccta gagaccatta tgcttttggg gttgctggga acagtctcgc   6660
tgggaatctt tttcgtcttg atgcggaaca agggcatagg gaagatgggc tttggaatgg   6720
tgactcttgg ggccagcgca tggctcatgt ggctctcgga aattgagcca gccagaattg   6780
catgcgtcct cattgttgtg ttcctattgc tggtggtgct catacctgag ccagaaaagc   6840
aaagatcccc ccaggacaac caaatggcaa tcatcatcat ggtagcagta ggtcttctgg   6900
gcttgattac cgccaatgaa ctcggatggt tggagagaac aaagagtgac ctaagccatc   6960
taatgggaag gagagaggag ggggcaacca taggattctc aatggacatt gacctgcggc   7020
cagcctcggc ctgggccatc tatgctgccc tgacaacttt cattacccca gccgtccaac   7080
atgcagtgac cacttcatac aacaactact ccttaatggc gatggccacg caagctggag   7140
tgttgtttgg tatgggcaaa gggatgccat tctacgcatg ggactttgga gtcccgctgc   7200
taatgatagg ttgctactca caattaacac ccctgaccct aatagtggct atcattttgc   7260
tcgtggcgca ctacatgtac ttgatcccag ggctgcaggc agcagctgcg cgtgctgccc   7320
agaagagaac ggcagctggc atcatgaaga accctgttgt ggatggaata gtggtgactg   7380
acattgacac aatgactatt gacccccaag tggagaaaaa gatgggacag gtgctactca   7440
tagcagtagc cgtctccagc gccatactgt cgcggaccgc ctgggggtgg ggggaagctg   7500
gggccctgat cacagctgca acttccactt tgtgggaagg ctctccgaac aagtactgga   7560
actcctctac agccacttca ctgtgcaaca tttttagggg aagttacttg gctggagctt   7620
ctctaatcta cacagtaaca agaaacgctg gcttggtcaa gagacgtggg ggtggaacag   7680
```

-continued

```
gagagaccct gggagagaaa tggaaggccc gcttgaacca gatgtcggcc ctggagttct   7740
actcctacaa aaagtcaggc atcaccgagg tgtgcagaga agaggcccgc cgcgccctca   7800
aggacggtgt ggcaacggga ggccatgctg tgtcccgagg aagtgcaaag ctgagatggt   7860
tggtggagcg gggatacctg cagccctatg gaaaggtcat tgatcttgga tgtggcagag   7920
ggggctggag ttactacgcc gccaccatcc gcaaagttca agaagtgaaa ggatacacaa   7980
aaggaggccc tggtcatgaa gaacccatgt tggtgcaaag ctatgggtgg aacatagtcc   8040
gtcttaagag tggggtggac gtctttcata tggcggctga gccgtgtgac acgttgctgt   8100
gtgacatagg tgagtcatca tctagtcctg aagtggaaga agcacggacg ctcagagtcc   8160
tctccatggt gggggattgg cttgaaaaaa gaccaggagc cttttgtgta aaagtgttgt   8220
gcccatacac cagcactatg atggaaaccc tggagcgact gcagcgtagg tatgggggag   8280
gactggtcag agtgccactc tcccgcaact ctacacatga gatgtactgg gtctctggag   8340
cgaaaagcaa caccataaaa agtgtgtcca ccacgagcca gctcctcttg ggcgcatgg    8400
acgggcccag gaggccagtg aaatatgagg aggatgtgaa tctcggctct ggcacgcggg   8460
ctgtggtaag ctgcgctgaa gctcccaaca tgaagatcat tggtaaccgc attgaaagga   8520
tccgcagtga gcacgcggaa acgtggttct ttgacgagaa ccacccatat aggacatggg   8580
cttaccatgg aagctatgag gcccctacac aagggtcagc gtcctctcta ataaacgggg   8640
ttgtcaggct cctgtcaaaa ccctgggatg tggtgactgg agtcacagga atagccatga   8700
ccgacaccac accgtatggt cagcaaagag ttttcaagga aaaagtggac accagggtgc   8760
cagaccccca agaaggcact cgtcaggtta tgagcatggt ctcttcctgg ttgtggaaag   8820
agctaggcaa acacaaacgg ccacgagtct gtaccaaaga agagttcatc aacaaggttc   8880
gtagcaatgc agcattaggg gcaatatttg aagaggaaaa agagtggaag accgcagtgg   8940
aagctgtgaa cgatccaagg ttctgggctc tagtggacaa ggaaagagag caccacctga   9000
gaggagagtg ccagagctgt gtgtacaaca tgatgggaaa aagagaaaag aaacaagggg   9060
aatttggaaa ggccaagggc agccgcgcca tctggtatat gtggctaggg gctagatttc   9120
tagagttcga agcccttgga ttcttaaatg aggatcactg gatggggaga gagaactcag   9180
gaggtggtgt tgaagggctg ggattacaaa gactcggata tgtcctagaa gagatgagtc   9240
gcataccagg aggaaggatg tatgcagatg acactgctgg ctgggacacc cgcatcagca   9300
ggtttgatct ggagaatgaa gctttaatca ccaaccaaat ggagaaaggg cacagggcct   9360
tagcattggc cataatcaag tacacatacc aaaacaaagt ggtaaaggtc cttagaccag   9420
ctgaaaaagg gaagacagtt atggacatta tttcaagaca agaccaaagg gggagcggac   9480
aagttgtcac ttacgctctt aacacattta ccaacctagt ggtgcaactc attcggaata   9540
tggaggctga ggaagttcta gagatgcaag acttgtggct gctgcggagg tcagagaaag   9600
tgaccaactg gttgcagagc aacggatggg ataggctcaa acgaatggca gtcagtggag   9660
atgattgcgt tgtgaagcca attgatgata ggtttgcaca tgccctcagg ttcttgaatg   9720
atatgggaaa agttaggaag gacacacaag agtggaaacc ctcaactgga tgggacaact   9780
gggaagaagt tccgttttgt tcccaccact tcaacaagct ccatctcaag gacgggaggt   9840
ccattgtggt tccctgccgc caccaagatg aactgattgg ccgggcccgt gtctctccag   9900
gggcgggatg gagcatccgg gagactgctt gcctagcaaa gtcatatgcg caaatgtggc   9960
agctccttta tttccacaga agggacctcc gactgatggc caatgccatc tgttcatctg  10020
```

-continued

```
tgccagttga ctgggttcca actgggagaa ctacctggtc aatccatgga aagggagaat  10080

ggatgaccac tgaagacatg cttgtggtgt ggaacagagt gtggattgag gagaacgacc  10140

acatggaaga caagacccca gttacgaaat ggacagacat tccctatctg ggaaaaaggg  10200

aagacttgtg gtgtggatct ctcatagggc acagaccgcg caccacctgg gctgagaaca  10260

ttaaaaacac agtcaacatg gtgcgcagga tcataggtga tgaagaaaag tacatggact  10320

acctatccac ccaagttcgc tacttgggtg aagaagggtc tacacctgga gtgctataag  10380

caccaatctt agtgttgtca ggcctgctag tcagccacag cttggggaaa gctgtgcagc  10440

ctgtgacccc cccaggagag gctgggaaac caagcccata gtcaggccga gaacgccatg  10500

gcacggaaga agccatgctg cctgtgagcc cctcagagga cactgagtca aaaaacccca  10560

cgcgcttgga ggcgcaggat gggaaaagaa ggtggcgacc ttccccaccc ttcaatctgg  10620

ggcctgaact ggagatcagc tgtggatctc cagaagaggg actagtggtt agaggagacc  10680

ccccggaaaa cgcaaaacag catattgacg ctgggaaaga ccagagactc catgagtttc  10740

caccacgctg gccgccaggc acagatcgcc gaatagcggc ggccggtgtg gggaaatcca  10800

tgggtct                                                           10807
```

<210> SEQ ID NO 8
<211> LENGTH: 10807
<212> TYPE: DNA
<213> ORGANISM: Zika virus

<400> SEQUENCE: 8

```
agttgttgat ctgtgtgaat cagactgcga cagttcgagt ttgaagcgaa agctagcaac     60

agtatcaaca ggttttattt tggatttgga aacgagagtt tctggtcatg aaaaacccaa    120

aaaagaaatc cggaggattc cggattgtca atatgctaaa acgcggagta gcccgtgtga    180

gcccctttgg gggcttgaag aggctgccag ccggacttct gctgggccat gggcccatca    240

ggatggtctt ggcgatacta gcctttttga gattcacggc aatcaagcca tcactgggtc    300

tcatcaatag atggggttca gtggggaaaa aagaggctat ggaaataata aagaagttca    360

agaaagatct ggctgccatg ctgagaataa tcaatgctag gaaggagaag aagagacgag    420

gcgcagatac tagcgtcgga attgttggcc tcctcctgac cacagccatg gcagtagagg    480

tcactagacg tgggagtgca tactatatgt acttggacag aagcgatgct ggggaggcca    540

tatcttttcc aaccacactg gggatgaata agtgttacat acaaatcatg gatcttggac    600

acatgtgtga tgccaccatg agctatgaat gccctatgtt ggatgagggg gtagaaccag    660

atgacgtcga ttgctggtgc aacacgacat caacttgggt tgtgtatgga acctgccacc    720

acaaaaaagg tgaagcacgg agatctagaa gagctgtgac gctcccctcc cattccacta    780

ggaagctgca aacgcggtcg cagacctggt tggaatcaag agaatacaca aagcacctga    840

ttagagttga aaattggata ttcaggaacc ctggcttcgc gttagcagca gctgtcatcg    900

cttggctttt gggaagttca acgagccaaa aagtcatata tctggtcatg atactgctga    960

ttgccccggc atacagcatc aggtgcatag gagtcagcaa tagggacttt gtggaaggta   1020

tgtcaggtgg gacttgggtt gatgttgtct tggaacatgg aggttgtgtt accgtaatgg   1080

cacaggacaa accgactgtc gacatagagc tggttacaac aacagtcagc aacatggcgg   1140

aggtaagatc ctactgctat gaggcatcaa tatcggatat ggcttcggac agccgctgcc   1200

caacacaagg tgaggcctac cttgacaagc agtcagacac tcaatatgtc tgcaaaagaa   1260

cgttagtgga cagaggctgg ggaaatggat gtggactttt tggcaaaggg agcctggtga   1320
```

```
catgcgctaa gtttgcatgc tccaagaaaa tgaccgggaa gagcatccag ccagagaatc   1380
tggagtaccg gataatgctg tcagttcatg gctcccagca cagtgggatg atcgttaatg   1440
acacaggaca tgaaactgat gagaatagag cgaaggttga gataacgccc aattcaccaa   1500
gagccgaagc caccctgggg ggttttggga gcctaggact tgattgtgaa ccgaggacag   1560
gccttgactt ttcagatttg tattacctga ctatgaataa caagcactgg ttggttcaca   1620
aggagtggtt ccacgacatt ccattacctt ggcatgctgg ggcagacact ggaactccac   1680
attggaacaa caaagaagca ctggtagagt tcaaggacgc acatgcaaaa aggcaaactg   1740
tcgtggttct agggagtcaa gaaggagcag ttcacacggc ccttgctgga gctctggagg   1800
ctgagatgga tggagccaag ggaaggctgt cctctggcca cttgaaatgt cgcctgaaaa   1860
tggataaact tagattgaag ggcgtgtcat actccttgtg cactgcagcg ttcacattca   1920
ccaagatccc ggctgaaaca ctgcacggga cagtcacagt ggaggtacag tacgcaggga   1980
cagatggacc ttgcaaggtt ccagctcaga tggcggtgga tatgcaaact ctgaccccag   2040
ttgggaggtt gataaccgct aaccctgtaa tcactgaaag caccgagaac tctaagatga   2100
tgctggaact tgatccacca tttggggact cttacattgt cataggagtc ggggagaaga   2160
agatcaccca tcactggcac aggagtggca gcaccattgg aaaagcattt gaagccactg   2220
tgagaggtgc caagagaatg gcagtcttgg gagacacagc ctgggacttt ggatcagttg   2280
ggggtgctct caactcattg ggcaagggca tccatcaaat ttttggagca gctttcaaat   2340
cattgttcgg aggaatgtcc tggttctcac aaattctcat tggaacgttg ctggtgtggt   2400
tgggtctgaa tacaaagaat ggatctattt cccttacgtg cttggcctta gggggagtgt   2460
tgatcttctt atccacagcc gtttctgctg atgtggggtg ctcggtggac ttctcaaaga   2520
aggaaacgag atgcggtaca ggggtgttcg tctataacga cgttgaagcc tggagggaca   2580
ggtacaagta ccatcctgac tcccctcgta gattggcagc agcagtcaag caagcctggg   2640
aagatgggat ctgtgggatc tcctctgtct caagaatgga aaacatcatg tggagatcag   2700
tagaagggga gctcaacgca atcctggaag agaatggagt tcaactgacg gtcgttgtgg   2760
gatctgtaaa aaaccccatg tggagaggtc cacagagatt gcccgtgcct gtgaacgagc   2820
tgccccacgg ctggaaggct tgggggaaat cgtacttcgt cagagcagca aagacaaata   2880
acagctttgt cgtggatggt gacacactga aggaatgccc actcaaacat agagcatgga   2940
acagctttct tgtggaggat catgggtttg ggggtatttca cactagtgtc tggctcaagg   3000
ttagagaaga ttattcatta gagtgtgatc cagccgtcat tggaacagct gctaagggaa   3060
aggaggctgt gcacagcgat ctaggctact ggattgagag tgagaagaac gacacatgga   3120
ggctgaagag ggcccacctg atcgagatga aaacatgtga atggccaaag tcccacacat   3180
tgtggacaga tggagtagaa gaaagtgatc tgatcatacc caagtcttta gctgggccac   3240
tcagccatca caacaccaga gagggctaca ggactcaaat gaaagggcca tggcacagtg   3300
aagagcttga aattcggttt gaggaatgcc caggcactaa ggtccacgtg gaggaaacat   3360
gtgggacaag aggaccatcc ctgagatcaa ccactgcaag cggaagggtg atcgaggaat   3420
ggtgctgcag ggaatgcaca atgcccccac tgtcgttccg agctaaagat ggctgttggt   3480
atggaatgga gataaggccc aggaaagaac cagaaagtaa cttagtaagg tcaatggtga   3540
ctgcaggatc aactgatcac atggatcact tctctcttgg agtgcttgtg attttgctca   3600
tggtgcagga agggctgaag aagagaatga ccacaaagat catcataagc acatcaatgg   3660
```

-continued cagtgctggt agccatgatc ctgggaggat tttcaatgag tgacctggct aagcttgcaa 3720
ttttgatggg tgccaccttc gcggaaatga acactggagg agatgtagct catttggcgc 3780
tgatagcggc attcaaagtc agacctgcgt tgctggtatc tttcatcttc agagctaatt 3840
ggacaccccg tgagagcatg ctgctggcct tggcctcgtg tcttctgcaa actgcgatct 3900
ccgccttgga aggcgacctg atggttctca tcaatggttt tgctttggcc tggttggcaa 3960
tacgagcgat ggttgttcca cgcactgaca acatcacctt ggcaatcctg gctgctctga 4020
caccactggc ccggggcaca ctgcttgtgg cgtggagagc aggccttgct acttgcgggg 4080
ggttcatgct cctctctctg aaggggaaag gcagtgtgaa gaagaaccta ccatttgtca 4140
tggccttggg actaactgct gtgaggctgg tcgaccccat caacgtggtg ggactgctgt 4200
tgctcacaag gagtgggaag cggagctggc cccctagtga agtactcaca gctgttggcc 4260
tgatatgcgc attggctgga gggttcgcca aggcggatat agagatggct gggcccatgg 4320
ccgcggtcgg tctgctaatt gtcagttacg tggtctcagg aaagagtgtg gacatgtaca 4380
ttgaaagagc aggtgacatc acatgggaaa aagatgcgga aatcactgga aacagtcccc 4440
ggctcgatgt ggcactagat gagagtggtg atttctccct agtggaggat gatggtccac 4500
ccatgagaga gatcatactc aaagtggtcc tgatgaccat ctgcggcatg aacccaatag 4560 ccatacccttt tgcagctgga gcgtggtacg tgtatgtgaa gactggaaaa aggagtggtg 4620
ctctatggga tgtgcctgct cccaaggaag taaaaaaggg ggagaccaca gatggagtgt 4680
acagagtaat gactcgtaga ctgcttggtt caacacaagt tggagtggga gtcatgcaag 4740
agggggtctt ccacactatg tggcacgtca caaaaggatc cgcgctgaga agcggtgaag 4800
ggagacttga tccatactgg ggagatgtca agcaggatct ggtgtcatac tgtggtccgt 4860
ggaagctaga cgccgcctgg gacgggcaca gcgaggtgca gctcttggcc gtgccccccg 4920
gagagagagc gaggaacatc cagactctgc ccggaacatt taagacaaag gatggggaca 4980
ttggagcagt tgcgctggac tacccagcag gaacttcagg atctccaatc ctagacaagt 5040
gtgggagagt gataggactc tatggtaatg gggtcgtgat aaaaaatggg agttatgtta 5100
gtgccatcac ccaagggagg agggaggaag agactcctgt tgagtgcttc gagccttcga 5160
tgctgaagaa gaagcagcta actgtcttag acctgcatcc tggagccggg aaaaccagga 5220
gagttcttcc tgaaatagtc cgtgaagcca taaaaacaag actccgtact gtgatcttag 5280
ctccaaccag ggtcgtcgct gctgaaatgg aggaagccct tagagggctt ccagttcgtt 5340
atatgacaac agcagtcaat gtcacccatt ctgggacaga aatcgttgac ttaatgtgcc 5400
atgctacctt cacttcacgc ctactacaac caatcagagt ccccaactat aatttgtata 5460
ttatggatga ggcccacttc acagatccct caagtatagc agcaagagga tacatttcaa 5520
caagggttga gatgggcgag gcggctgcca tcttcatgac cgccacgcca ccaggaaccc 5580
gtgacgcatt cccggactcc aactcaccaa ttatggacac cgaggtggaa gtcccagaga 5640
gagcctggag cacaggcttt gattgggtga cggatcattc tgggaaaaca gtctggtttg 5700
ttccaagcgt gaggaacggc aatgagatcg cagcttgtct gacaaaggct ggaaaacggg 5760
tcatacagct cagcagaaag acttttgaga cagagttcca gaaaacgaaa aatcaagagt 5820
gggacttcgt cgtgacaacc gacatttcag agatgggcgc caactttaaa gctgaccgtg 5880
tcatagattc caggagatgc ttaaagccgg tcatacttga tggcgagaga gtcattttgg 5940
ctggacccat gcctgtcaca catgccagcg ctgctcagag gagggggcgc ataggcagga 6000
atcccaacaa acctggagat gagtatctgt atggaggtgg gtgcgcagag actgatgaag 6060

```
atcacgcaca ctggcttgaa gcaagaatgc ttcttgacaa catttacctc caagatggcc   6120
tcatagcttc gctctatcga cctgaggccg acaaagtagc agctattgag ggagagttca   6180
agcttaggac ggagcaaagg aagacctttg tggaactcat gaaaagagga gatcttccgg   6240
tttggttggc ctatcaggtt gcatctgccg gaataaccta cacagataga agatggtgct   6300
ttgatggcat gaccaacaac accataatgg aagacagtgt gccggcagag gtgtggacca   6360
gatacggaga gaaaagagtg ctcaaaccga ggtggatgga cgccagagtt tgttcagatc   6420
atgcggccct gaagtcattc aaagagtttg ccgctgggaa aagaggagcg gcctttggag   6480
tgatagaagc cctgggaaca ctgccaggac acatgacaga gagattccag gaagccattg   6540
acaacctcgc tgtgctcatg cgggcagaga ctggaagcag gccttacaaa gccgcggcgg   6600
cccaattgcc ggagacccta gagaccatta tgcttttggg gttgctggga acagtctcgc   6660
tgggaatctt tttcgtcttg atgcggaaca agggcatggg gaagatgggc tttggaatgg   6720
tgactcttgg ggccagcgca tggcttatgt ggctctcgga aattgagcca gccagaattg   6780
catgtgtcct cattgtcgtg ttcctattgc tggtggtgct catacctgag ccagaaaagc   6840
aaagatctcc tcaggacaac caaatggcaa tcatcatcat ggtagcagtg ggtcttctgg   6900
gcttgattac cgccaatgaa ctcggatggt tggagagaac aaaaagtgac ctaagccatc   6960
taatgggaag gagagaggag gggcaacca caggattctc aatggacatt gacctgcggc   7020
cagcctcagc ttgggctatc tatgctgctc tgacaacttt catcacccca gccgtccaac   7080
atgcggtgac cacttcatac aacaactact ccttaatggc gatggccacg caagctgggg   7140
tgttgtttgg tatgggcaaa gggatgccat tctacgcatg ggactttgga gtcccgctgc   7200
taatgatggg ttgctactca caattaacac ctctgaccct aatagtggcc atcattttgc   7260
tcgtggcgca ctacatgtac ttgatcccag ggctgcaggc agcagctgcg cgggctgccc   7320
agaagagaac ggcagctggc atcatgaaga accctgttgt ggatggaata gtggtgactg   7380
acattgacac aatgacaatt gacccccaag tggaaaaaaa gatggggcag gtgctactca   7440
tagcagtagc cgtctccagc gccatactgt cgcggaccgc ctgggggtgg ggggaggctg   7500
gggccctgat cacagctgca acttccacct tgtgggaagg ctctccgaac aagtactgga   7560
actcctccac agccacttca ctgtgtaaca tttttagggg aagttacttg gctggagctt   7620
ctctaatcta cacagtaaca agaaacgctg gcttggtcaa gagacgtggg ggtggaacgg   7680
gagagaccct gggagagaaa tggaaggccc gcctgaacca gatgtcggcc ctggagttct   7740
actcctacaa aaagtcaggc atcaccgagg tgtgcagaga agaggcccgc cgtgccctca   7800
aggacggtgt ggcaacagga ggccatgctg tgtcccgagg aagtgcaaag cttagatggc   7860
tggtggagag aggatacctg cagccctatg gaaaggtcat tgatcttgga tgtggcagag   7920
ggggctggag ttactatgcc gccaccatcc gcaaagttca ggaagtgaaa ggatacacaa   7980
aaggaggccc tggtcatgaa gaacccatgt tggtgcaaag ctatgggtgg aacatagtcc   8040
gtcttaagag tggggtggac gtctttcaca tggcggctga gccgtgtgac actttgctgt   8100
gtgatatagg tgagtcatca tctagtcctg aagtggaaga agcacggacg ctcagagtcc   8160
tctccatggt gggggattgg cttgaaaaaa gaccaggagc cttttgtata aaagtgttgt   8220
gcccatacac cagcactatg atggaaaccc tggagcgact gcagcgtagg tatgggggag   8280
gactggtcag ggtgccactc tcccgcaact ctacacatga gatgtactgg gtctctggag   8340
cgaaaagcaa caccataaaa agtgtgtcca ccacgagcca gctcctcttg ggcgcatgg   8400
```

-continued

```
acgggcccag gaggccagtg aaatatgagg aggatgtgaa tctcggctct ggcacgcggg   8460
ctgtggtaag ctgcgctgaa gctcccaaca tgaagatcat tggtaaccgc attgagagga   8520
tccgcagtga gcacgcggaa acgtggttct ttgacgagaa ccacccatat aggacatggg   8580
cttaccatgg aagctatgag gcccctacac aagggtcagc gtcctctcta ataaacgggg   8640
ttgtcaggct cctgtcaaaa ccctgggatg tggtgactgg agtcacagga atagccatga   8700
ctgacaccac accgtatggt cagcaaagag ttttcaagga aaaagtggac actagggtgc   8760
cagaccccca agaaggcact cgtcaggtta tgagcatggt ctcttcctgg ttatggaagg   8820
agctaggcaa acacaaacgg ccacgagtct gtaccaaaga agagttcatc aacaaggttc   8880
gtagcaatgc agcattaggg gcaatatttg aagaggaaaa agagtggaag actgcagtgg   8940
aagctgtgaa tgatccaagg ttctgggctc tagtggacaa ggaaagagag catcacctga   9000
gaggagagtg tcagagctgt gtgtacaaca tgatgggaaa aagagaaaag aaacaagggg   9060
aatttggaaa ggccaagggc agccgcgcca tctggtatat gtggctaggg gctagattcc   9120
tagagttcga agcccttgga ttcttgaatg aggatcattg gatggggaga gagaattcag   9180
gaggtggtgt tgaaggactg ggattacaaa gactcggata tgtcctagaa gagatgagtc   9240
gcataccagg aggaaggatg tatgcagatg atactgctgg ctgggacacc cgcatcagca   9300
ggtttgatct ggagaatgaa gctctaatca ccaaccaaat ggagaaaggg cacagggcct   9360
tggcattggc cataatcaag tacacatacc aaaacaaagt ggtaaaggtc cttagaccag   9420
ctgaaaaagg gaagacagtt atggacatta tttcaagaca agaccaaagg gggagcggac   9480
aagttgtcac ttacgctctt aatacattca ccaacctggt ggtgcagctc attcggaata   9540
tggaggctga ggaagttcta gagatgcaag acttgtggct gctgcggagg ccagagaaag   9600
tgaccaactg gttgcaaagc aacggatggg ataggctcaa aagaatggca gtcagtggag   9660
atgattgcgt tgtgaaacca attgatgata ggtttgcaca tgccctcagg ttcttgaatg   9720
atatgggaaa agttaggaag gacacacaag agtggaaacc ctcaactgga tgggacaact   9780
gggaagaagt tccgttttgc tcccaccact tcaacaaact ccatcttaag gacgggaggt   9840
ccattgtggt tccctgccgc caccaagatg aactgattgg ccgagcccgc gtatcaccag   9900
gggcgggatg gagcatccgg gagactgctt gcctagcaaa atcatatgcg caaatgtggc   9960
agctccttta tttccacaga agggacctcc gactgatggc caatgccatt tgttcatctg  10020
tgccagttga ttgggttcca actgggagaa ctacctggtc aatccatgga aagggagaat  10080
ggatgaccac tgaagacatg cttgtggtat ggaacagagt gtggattgag gaaaacgacc  10140
acatggaaga caagacccca gttacaaaat ggacagacat tccctatttg ggaaaaagag  10200
aagacttgtg gtgtggatct ctcatagggc acagaccgcg tactacctgg gctgagaaca  10260
tcaaaaatac agtcaacatg atgcgcagga tcataggtga tgaagaaaag tacatggact  10320
acctatccac ccaggttcgc tacttgggtg aagaagggtc cacacctgga gtgctgtaag  10380
caccaatctt agtgttgtca ggcctgctag tcagccacag cttggggaaa gctgtgcagc  10440
ctgtgacccc cccaggagaa gctgggaaac caagcctata gtcaggccga gaacgccatg  10500
gcacggaaga agccatgctg cctgtgagcc cctcagagga cactgagtca aaaaacccca  10560
cgcgcttgga ggcgcaggat gggaaaagaa ggtggcgacc ttccccaccc ttcaatctgg  10620
ggcctgaact ggagatcagc tgtggatctc cagaagaggg actagtggtt agaggagacc  10680
ccccggaaaa cgcaaaacag catattgacg ctgggaaaga ccagagactc catgagtttc  10740
caccacgctg gccgccaggc acagatcgcc gaatagcggc ggccggtgtg gggaaatcca  10800
```

-continued tgggtct 10807

<210> SEQ ID NO 9
<211> LENGTH: 10648
<212> TYPE: DNA
<213> ORGANISM: Zika virus

<400> SEQUENCE: 9
gacagttcga gtttgaagcg aaagctagca acagtatcaa caggttttat ttggatttgg 60
aaacgagagt ttctggtcat gaaaaaccca aaaaagaaat ccggaggatt ccggattgtc 120
aatatgctaa aacgcggagt agcccgtgtg agcccctttg ggggcttgaa gaggctgcca 180
gccggacttc tgctgggtca tgggcccatc aggatggtct tggcgattct agccttttg 240 agattcacgg caatcaagcc atcactgggt ctcatcaata gatggggttc agtggggaaa 300
aaagaggcta tggaaataat aaagaagttc aagaaagatc tggctgccat gctgagaata 360
atcaatgcta ggaaggagaa gaagagacga ggcgcagata ctagtgtcgg aattgttggc 420
ctcctgctga ccacagctat ggcagcggag gtcactagac gtgggagtgc atactatatg 480
tacttggaca gaaacgatgc tggggaggcc atatcttttc caaccacatt ggggatgaat 540
aagtgttata tacagatcat ggatcttgga cacatgtgtg atgccaccat gagctatgaa 600
tgccctatgc tggatgaggg ggtggaacca gatgacgtcg attgttggtg caacacgacg 660
tcaacttggg ttgtgtacgg aacctgccat cacaaaaaag gtgaagcacg gagatctaga 720
agagctgtga cgctcccctc ccattccact aggaagctgc aaacgcggtc gcaaacctgg 780
ttggaatcaa gagaatacac aaagcacttg attagagtcg aaaattggat attcaggaac 840
cctggcttcg cgttagcagc agctgccatc gcttggcttt tgggaagctc aacgagccaa 900
aaagtcatat acttggtcat gatactgctg attgccccgg catacagcat caggtgcata 960
ggagtcagca atagggactt tgtggaaggt atgtcaggtg ggacctgggt tgatgttgtc 1020
ttggaacatg gaggttgtgt caccgtaatg gcacaggaca aaccgactgt cgacatagag 1080
ctggttacaa caacagtcag caacatggcg gaggtaagat cctactgcta tgaggcatca 1140
atatcagaca tggcttcgga cagccgctgc ccaacacaag gtgaagccta ccttgacaag 1200
caatcagaca ctcaatatgt ctgcaaaaga acgttagtgg acagaggctg gggaaatgga 1260
tgtggacttt ttggcaaagg gagcctggtg acatgcgcta agtttgcatg ctccaagaaa 1320
atgaccggga agagcatcca gccagagaat ctggagtacc ggataatgct gtcagttcat 1380
ggctcccagc acagtgggat gattgttaat gacacaggac atgaaactga tgagaataga 1440
gcgaaagttg agataacgcc caattcacca agagccgaag ccaccctggg gggttttgga 1500
agcctaggac ttgattgtga accgaggaca ggccttgact tttcagattt gtattacttg 1560
actatgaata acaagcactg gttggttcac aaggagtggt tccacgacat tccattacct 1620
tggcacgctg gggcagacac cggaactcca cactggaaca acaaagaagc actggtagag 1680
ttcaaggacg cacatgccaa aaggcaaact gtcgtggttc tagggagtca agaaggagca 1740
gttcacacgg cccttgctgg agctctggag gctgagatgg atggtgcaaa gggaaggctg 1800
tcctctggcc acttgaaatg tcgcctgaaa atggataaac ttagattgaa gggcgtgtca 1860
tactccttgt gtactgcagc gttcacattc accaagatcc cggctgaaac actgcacggg 1920
acagtcacag tggaggtaca gtacgcaggg acagatggac cttgcaaggt tccagctcag 1980
atggcggtgg acatgcaaac tctgacccca gttgggaggt tgataaccgc taaccccgta 2040

-continued

```
atcactgaaa gcactgagaa ctctaagatg atgctggaac ttgatccacc atttggggac   2100
tcttacattg tcataggagt cggggagaag aagatcaccc accactggca caggagtggc   2160
agcaccattg gaaaagcatt tgaagccact gtgagaggtg ccaagagaat ggcagtcttg   2220
ggagacacag cctgggactt tggatcagtt ggaggcgctc tcaactcatt gggcaagggc   2280
atccatcaaa tttttggagc agctttcaaa tcattgtttg gaggaatgtc ctggttctca   2340
caaattctca ttggaacgtt gctgatgtgg ttgggtctga acacaaagaa tggatctatt   2400
tcccttatgt gcttggcctt agggggagtg ttgatcttct tatccacagc cgtctctgct   2460
gatgtggggt gctcggtgga cttctcaaag aaggagacga gatgcggtac aggggtgttc   2520
gtctataacg acgttgaagc ctggagggac aggtacaagt accatcctga ctccccccgt   2580
agattggcag cagcagtcaa gcaagcctgg gaagatggta tctgcgggat ctcctctgtt   2640
tcaagaatgg aaaacatcat gtggagatca gtagaagggg agctcaacgc aatcctggaa   2700
gagaatggag ttcaactgac ggtcgttgtg ggatctgtaa aaaaccccat gtggagaggt   2760
ccacagagat tgcccgtgcc tgtgaacgag ctgccccacg gctggaaggc ttgggggaaa   2820
tcgtacttcg tcagagcagc aaagacaaat aacagctttg tcgtggatgg tgacacactg   2880
aaggaatgcc cactcaaaca tagagcatgg aacagctttc ttgtggagga tcatgggttc   2940
ggggtatttc acactagtgt ctggctcaag gttagagaag attattcatt agagtgtgat   3000
ccagccgtta ttggaacagc tgttaaggga aaggaggctg tacacagtga tctaggctac   3060
tggattgaga gtgagaagaa tgacacatgg aggctgaaga gggcccatct gatcgagatg   3120
aaaacatgtg aatggccaaa gtcccacaca ttgtggacag atggaataga agagagtgat   3180
ctgatcatac ccaagtcttt agctgggcca ctcagccatc acaataccag agagggctac   3240
aggacccaaa tgaaagggcc atggcacagt gaagagcttg aaattcggtt tgaggaatgc   3300
ccaggcacta aggtccacgt ggaggaaaca tgtggaacaa gaggaccatc tctgagatca   3360
accactgcaa gcggaagggt gatcgaggaa tggtgctgca gggagtgcac aatgccccca   3420
ctgtcgttcc gggctaaaga tggctgttgg tatggaatgg agataaggcc caggaaagaa   3480
ccagaaagca acttagtaag gtcaatggtg actgcaggat caactgatca catggaccac   3540
ttctcccttg gagtgcttgt gattctgctc atggtgcagg aagggctgaa gaagagaatg   3600
accacaaaga tcatcataag cacatcaatg gcagtgctgg tagctatgat cctgggagga   3660
ttttcaatga gtgacctggc taagcttgca attttgatgg gtgccacctt cgcggaaatg   3720
aacactggag gagatgtagc tcatctggcg ctgatagcgg cattcaaagt cagaccagcg   3780
ttgctggtat ctttcatctt cagagctaat tggacacccc gtgaaagcat gctgctggcc   3840
ttggcctcgt gtcttttgca aactgcgatc tccgccttgg aaggcgacct gatggttctc   3900
atcaatggtt ttgctttggc ctggttggca atacgagcga tggttgttcc acgcactgat   3960
aacatcacct tggcaatcct ggctgctctg acaccactgg cccggggcac actgcttgtg   4020
gcgtggagag caggccttgc tacttgcggg gggtttatgc tcctctctct gaagggaaaa   4080
ggcagtgtga agaagaactt accatttgtc atggccctgg gactaaccgc tgtgaggctg   4140
gtcgacccca tcaacgtggt gggactgctg ttgctcacaa ggagtgggaa gcggagctgg   4200
ccccctagcg aagtactcac agctgttggc ctgatatgcg cattggctgg agggttcgcc   4260
aaggcagata tagagatggc tgggcccatg gccgcggtcg gtctgctaat tgtcagttac   4320
gtggtctcag gaaagagtgt ggacatgtac attgaaagag caggtgacat cacatgggaa   4380
aaagatgcgg aagtcactgg aaacagtccc cggctcgatg tggcgctaga tgagagtggt   4440
```

```
gatttctccc tggtggagga tgacggtccc cccatgagag agatcatact caaggtggtc   4500
ctgatgacca tctgtggcat gaacccaata gccataccct ttgcagctgg agcgtggtac   4560
gtatacgtga agactggaaa aaggagtggt gctctatggg atgtgcctgc tcccaaggaa   4620
gtaaaaaagg gggagaccac agatggagtg tacagagtaa tgactcgtag actgctaggt   4680
tcaacacaag ttggagtggg agttatgcaa gagggggtct ttcacactat gtggcacgtc   4740
acaaaaggat ccgcgctgag aagcggtgaa gggagacttg atccatactg gggagatgtc   4800
aagcaggatc tggtgtcata ctgtggtcca tggaagctag atgccgcctg ggacgggcac   4860
agcgaggtgc agctcttggc cgtgcccccc ggagagagag cgaggaacat ccagactctg   4920
cccggaatat ttaagacaaa ggatggggac attggagcgg ttgcgctgga ttacccagca   4980
ggaacttcag gatctccaat cctagacaag tgtgggagag tgataggact ttatggcaat   5040
ggggtcgtga tcaaaaatgg gagttatgtt agtgccatca cccaagggag gagggaggaa   5100
gagactcctg ttgagtgctt cgagccttcg atgctgaaga agaagcagct aactgtctta   5160
gacttgcatc ctggagctgg gaaaaccagg agagttcttc ctgaaatagt ccgtgaagcc   5220
ataaaaacaa gactccgtac tgtgatctta gctccaacca gggttgtcgc tgctgaaatg   5280
gaggaggccc ttagagggct tccagtgcgt tatatgacaa cagcagtcaa tgtcacccac   5340
tctggaacag aaatcgtcga cttaatgtgc catgccacct tcacttcacg tctactacag   5400
ccaatcagag tccccaacta taatctgtat attatggatg aggcccactt cacagatccc   5460
tcaagtatag cagcaagagg atacatttca acaagggttg agatgggcga ggcggctgcc   5520
atcttcatga ccgccacgcc accaggaacc cgtgacgcat ttccggactc caactcacca   5580
attatggaca ccgaagtgga agtcccagag agagcctgga gctcaggctt tgattgggtg   5640
acggatcatt ctggaaaaac agtttggttt gttccaagcg tgaggaacgg caatgagatc   5700
gcagcttgtc tgacaaaggc tggaaaacgg gtcatacagc tcagcagaaa gacttttgag   5760
acagagttcc agaaaacaaa acatcaagag tgggactttg tcgtgacaac tgacatttca   5820
gagatgggcg ccaactttaa agctgaccgt gtcatagatt ccaggagatg cctaaagccg   5880
gtcatacttg atggcgagag agtcattctg gctggaccca tgcctgtcac acatgccagc   5940
gctgcccaga ggagggggcg cataggcagg aatcccaaca aacctggaga tgagtatctg   6000
tatggaggtg ggtgcgcaga gactgacgaa gaccatgcac actggcttga agcaagaatg   6060
ctccttgaca atatttacct ccaagatggc ctcatagcct cgctctatcg acctgaggcc   6120
gacaaagtag cagccattga gggagagttc aagcttagga cggagcaaag gaagaccttt   6180
gtggaactca tgaaaagagg agatcttcct gtttggctgg cctatcaggt tgcatctgcc   6240
ggaataacct acacagatag aagatggtgc tttgatggca cgaccaacaa caccataatg   6300
gaagacagtg tgccggcaga ggtgtggacc agacacggag agaaaagagt gctcaaaccg   6360
aggtggatgg acgccagagt ttgttcagat catgcggccc tgaagtcatt caaggagttt   6420
gccgctggga aaagaggagc ggcttttgga gtgatggaag ccctgggaac actgccagga   6480
cacatgacag agagattcca ggaagccatt gacaacctcg ctgtgctcat gcgggcagag   6540
actggaagca ggccttacaa agccgcggcg gcccaattgc cggagaccct agagaccatt   6600
atgcttttgg ggttgctggg aacagtctcg ctgggaatct tcttcgtctt gatgaggaac   6660
aagggcatag ggaagatggg ctttggaatg gtgactcttg ggccagcgc atggctcatg    6720
tggctctcgg aaattgagcc agccagaatt gcatgtgtcc tcattgttgt gtttctattg   6780
```

-continued ctggtggtgc tcatacctga gccagaaaag caaagatctc cccaggacaa ccaaatggca 6840
atcatcatca tggtagcagt aggtcttctg ggcttgatta ccgccaatga actcggatgg 6900
ttggagagaa caaagagtga cctaagccat ctaatgggaa ggagagagga gggggcaacc 6960
ataggattct caatggacat tgacctgcgg ccagcctcag cttgggccat ctatgctgcc 7020
ttgacaactt tcattacccc agccgtccaa catgcagtga ccacttcata caacaactac 7080
tccttaatgg cgatggccac gcaagctgga gtgttgtttg gtatgggcaa agggatgcca 7140
ttctacgcat gggactttgg agtcccgctg ctaatgatag gttgctactc acaattaaca 7200
cccctgaccc taatagtggc catcattttg ctcgtggcgc actacatgta cttgatccca 7260
gggctgcagg cagcagctgc gcgtgctgcc cagaagagaa cggcagctgg catcatgaag 7320
aaccctgttg tggatggaat agtggtgact gacattgaca caatgacaat tgacccccaa 7380
gtggagaaaa agatgggaca ggtgctactc atagcagtag ccgtctccag cgccatactg 7440
tcgcggaccg cctgggggtg gggggaggct ggggccctga tcacagccgc aacttccact 7500
ttgtgggaag gctctccgaa caagtactgg aactcctcta cagccacttc actgtgtaac 7560
atttttaggg gaagttactt ggctggagct tctctaatct acacagtaac aagaaacgct 7620
ggcttggtca agagacgtgg gggtggaaca ggagagaccc tgggagagaa atggaaggcc 7680
cgcttgaacc agatgtcggc cctggagttc tactcctaca aaaagtcagg catcaccgag 7740
gtgtgcagag aagaggcccg ccgcgccctc aaggacggtg tggcaacggg aggccatgct 7800
gtgtcccgag gaagtgcaaa gctgagatgg ttggtggagc ggggatacct gcagccctat 7860
ggaaaggtca ttgatcttgg atgtggcaga gggggctgga gttactacgc cgccaccatc 7920
cgcaaagttc aagaagtgaa aggatacaca aaaggaggcc ctggtcatga agaacccgtg 7980
ttggtgcaaa gctatgggtg gaacatagtc cgtcttaaga gtggggtgga cgtctttcat 8040
atggcggctg agccgtgtga cacgttgctg tgtgacatag gtgagtcatc atctagtcct 8100
gaagtggaag aagcacggac gctcagagtc ctctccatgg tgggggattg gcttgaaaaa 8160
agaccaggag ccttttgtat aaaggtgttg tgcccataca ccagcactat gatggaaacc 8220
ctggagcgac tgcagcgtag gtatgggggga ggactggtca gagtgccact ctcccgcaac 8280
tctacacatg agatgtattg ggtctctgga gcgaaaagca acaccataaa aagtgtgtcc 8340
accacgagcc agctcctctt ggggcgcatg gacgggccta ggaggccagt gaaatatgag 8400
gaggatgtga atctcggctc tggcacgcgg gctgtggtaa gctgcgctga agctcccaac 8460
atgaagatca ttggtaaccg cattgaaagg atccgcagtg agcacgcgga aacgtggttc 8520
tttgacgaga accacccata taggacatgg gcttaccatg gaagctatga ggcccccaca 8580
caagggtcag cgtcctctct aataaacggg gttgtcaggc tcctgtcaaa accctgggat 8640
gtggtgactg gagtcacagg aatagccatg accgacacca caccgtatgg tcagcaaaga 8700
gttttcaagg aaaaagtgga cactagggtg ccagaccccc aagaaggcac tcgtcaggtt 8760
atgagcatgg tctcttcctg gttgtggaaa gagctaggca aacacaaacg gccacgagtc 8820
tgtaccaaag aagagttcat caacaaggtt cgtagcaatg cagcattagg ggcaatattt 8880
gaagaggaaa aagagtggaa gactgcagtg gaagctgtga acgatccaag gttctgggct 8940
ctagtggata aggaaagaga gcaccacctg agaggagagt gccagagttg tgtgtacaac 9000
atgatgggaa aaagagaaaa gaaacaaggg gaatttggaa aggccaaggg cagccgcgcc 9060
atctggtata tgtggctagg ggctagattt ctagagttcg aagcccttgg attcttgaac 9120
gaggatcact ggatggggag agagaactca ggaggtggtg ttgaagggct gggattacaa 9180

```
agactcggat atgtcctaga agagatgagt cgtataccag gaggaaggat gtatgcagat   9240
gacactgctg gctgggacac ccgcatcagc aggtttgatc tggagaatga agctctaatc   9300
accaaccaaa tggaaaaagg gcacagggcc ttggcattgg ccataatcaa gtacacatac   9360
caaaacaaag tggtaaaggt ccttagacca gctgaaaaag ggaaaacagt tatggacatt   9420
atttcgagac aagaccaaag ggggagcgga caagttgtca cttacgctct taacacattt   9480
accaacctag tggtgcaact cattcggaat atggaggctg aggaagttct agagatgcaa   9540
gacttgtggc tgctgcggag gtcagagaaa gtgaccaact ggttgcagag caacggatgg   9600
gataggctca aacgaatggc agtcagtgga gatgattgcg ttgtgaagcc aattgatgat   9660
aggtttgcac atgccctcag gttcttgaat gatatgggaa aagttaggaa ggacacacaa   9720
gagtggaaac cctcaactgg atgggacaac tgggaagaag ttccgttttg ctcccaccac   9780
ttcaacaagc tccatctcaa ggacgggagg tccattgtgg ttccctgccg ccaccaagat   9840
gaactgattg gccgggcccg cgtctctcca ggggcgggat ggagcatccg ggagactgct   9900
tgcctagcaa aatcatatgc gcaaatgtgg cagctccttt atttccacag aagggacctc   9960
cgactgatgg ccaatgccat ttgttcatct gtgccagttg actgggttcc aactgggaga  10020
actacctggt caatccatgg aaagggagaa tggatgacca ctgaagacat gcttgtggtg  10080
tggaacagag tgtggattga ggagaacgac cacatggaag acaagacccc agttacgaaa  10140
tggacagaca tcccctattt gggaaaaagg gaagacttgt ggtgtggatc tctcataggg  10200
cacagaccgc gcaccacctg ggctgagaac attaaaaaca cagtcaacat ggtgcgcagg  10260
atcataggtg atgaagaaaa gtacatggac tacctatcca cccaagttcg ctacttgggt  10320
gaagaagggt ctacacctgg agtgctgtaa gcaccagtct taatgttgtc aggcctgcta  10380
gtcagccaca gcttggggaa agctgtgcag cctgtgaccc cccaggaga agctgggaaa    10440
ccaagcctat agtcaggccg agaacgccat ggcacggaag aagccatgct gcctgtgagc  10500
ccctcagagg acactgagtc aaaaaacccc acgcgcttgg aggcgcagga tgggaaaaga  10560
aggtggcgac cttccccacc cttcaatctg gggcctgaac tggagatcag ctgtggatct  10620
ccagaagagg gactagtggt tagaggag                                     10648
```

<210> SEQ ID NO 10
<211> LENGTH: 10676
<212> TYPE: DNA
<213> ORGANISM: Zika virus

<400> SEQUENCE: 10

```
gttgttactg ttgctgactc agactgcgac agttcgagtt tgaagcgaaa gctagcaaca     60
gtatcaacag gttttatttg gatttggaaa cgagagtttc tggtcatgaa aaacccaaaa    120
aagaaatccg gaggattccg gattgtcaat atgctaaaac gcggagtagc ccgtgtgagc    180
ccctttgggg gcttgaagag gctgccagcc ggacttctgc tgggtcatgg gcccatcagg    240
atggtcttgg caattctagc ctttttgaga ttcacggcaa tcaagccatc actgggtctc    300
atcaatagat ggggttcagt ggggaaaaaa gatgctatgg aaataataaa gaagttcaag    360
aaagatctgg ctgccatgct gagaataatc aatgctagga aggagaagaa gagacgaggc    420
gcagatacta gtgtcggaat tgttggcctc ctgctgacca cagctatggc agcggaggtc    480
actagacgtg ggagtgcata ctatatgtac ttggacagaa acgatgctgg ggaggccata    540
tcttttccaa ccacattggg gatgaataag tgttatatac agatcatgga tcttggacac    600
```

-continued

```
atgtgtgatg ccaccatgag ctatgaatgc cctatgctgg atgagggggt ggaaccagat    660
gacgtcgatt gttggtgcaa cacgacgtca acttgggttg tgtacggaac ctgccatcac    720
aaaaaaggtg aagcacggag atctagaaga gctgtgacgc tcccttccca ttccactagg    780
aagctgcaaa cgcggtcgca aacctggttg gaatcaagag aatacacaaa gcacttgatt    840
agagtcgaaa attggatatt caggaaccct ggcttcgcgt tagcagcagc tgccatcgct    900
tggcttttgg gaagctcaac gagccaaaaa gtcatatact tggtcatgat actgctgatt    960
gccccggcat acagcatcag gtgcatagga gtcagcaata gggactttgt ggaaggtatg   1020
tcaggtggga cttgggttga tgttgtcttg gaacatggag gttgtgtcac cgcaatggca   1080
caggacaaac cgactgtcga catagagctg gttacaacaa cagtcagcaa catggcggag   1140
gtaagatcct actgctatga ggcatcaata tcagacatgg cttcggacag ccgctgccca   1200
acacaaggtg aagcctacct tgacaagcaa tcagacactc aatatgtttg caaaagaacg   1260
ttagtggaca gaggctgggg aaatggatgt ggactttttg gcaaagggag tctggtgaca   1320
tgcgctaagt ttgcatgctc caagaaaatg accgggaaga gcatccagcc agagaatctg   1380
gagtaccgga taatgctgtc agttcatggc tcccagcaca gtgggatgct cgttaatgac   1440
acaggacatg aaactgatga gaatagagcg aaggttgaga taacgcccaa ttcaccaaga   1500
gccgaagcca ccctgggggg ttttggaagc ctaggacttg attgtgaacc gaggacaggc   1560
cttgactttt cagatttgta ttacttgact atgaataaca agcactggtt ggctcacaag   1620
gagtggttcc acgacattcc attaccttgg cacgctgggg cagccaccgg aactccacac   1680
tggaacaaca aagaagcact ggtagagttc aaggacgcac atgccaaaag gcaaactgtc   1740
gtggttctag ggagtcaaga aggagcagtt cacacggccc ttgctggagc tctggaggct   1800
gagatggatg gtgcaaaggg aaggctgtcc tctggccact tgaaatgtcg cctgaaaatg   1860
gataaactta gattgaaggg cgtgtcatac tccttgtgta ccgcagcgtt cacattcacc   1920
aagatcccgg ctgaaacagt ggacgggaca gtcacagtgg agggacagta cggagggaca   1980
gatggacctt gcaaggttcc agctcagatg gcggtggaca tgcagactct gaccccagtt   2040
gggaggttga taaccgctaa ccccgtaatc actgaaagca ctgagaactc taagatgatg   2100
ctggaacttg atccaccatt tggggactct tacattgtca taggagtcgg ggagaagaag   2160
atcacccacc actggcacag gagtggcagc accattggaa aagcatttga agccactgtg   2220
agaggtgcca agagaatggc agtcttggga gacacagcct gggactttgg atcagttgga   2280
ggcgctctca actcattggg caagggcatc catcaaatta ttggagcagc tttcaaatca   2340
ttgtttggag gaatgtcctg gttctcacaa attctcattg ggacgttgct gatgtggttg   2400
ggtctgaaca caaagaatgg atctatttcc cttatgtgct tggccttagg gggagtgttg   2460
atcttcttat ccacagccgt ctcaggtggt gtggggtgct cggtggactt ctcaaagaag   2520
gagacgagat gcggtacagg ggtgttcgtc tataacgatg ttgaagcctg gagggacagg   2580
tacaagtacc atcctgactc cccccgtaga ttggcagcag cagtcaagca agcctgggaa   2640
gatggtatct gcgggatctc ctctgtttca agaatggaaa acatcatgtg gagatcagta   2700
gaaggggagc tcaacgcaat cctggaagag aatggagttc aactgacggt cgttgtggga   2760
tctgtaaaaa accccatgtg gagaggtcca cagagattgc ccgtgcctgt gaacgagctg   2820
ccccacggct ggaaggcttg gggggaaatcg tacttcgtca gagcagcaaa gacaaataac   2880
agctttgtcg tggatggtga cacactgaag gaatgcccac tcaaacatag agcatggaac   2940
agctttcttg tggaggatca tgggttcggg gtatttcaca ctagtgtctg gctcaaggtt   3000
```

agagaagact attggttaga gtgtgatcca gccgttattg gaacagctgt taagggaaag 3060
gaggctgtac acagtgatct aggctactgg attgagagtg agaagaatga cacatggtgg 3120
ctgaagaggg cccatctgat cgagatgaaa acatgtgaat ggccaaagtc ccacacattg 3180
tggacagatg gaatagaaga gagtgatctg atcataccca agtctttagc tgggccactc 3240
agccatcaca atgccagaga gggctacagg acccaaatga aagggccatg gcacagtgaa 3300
gagcttgaaa ttcggtttga ggaatgccca ggcactaagg tccacgtgga ggaaacatgt 3360
ggaacaagag gaccatctct gagatcaacc actgcaagcg gaagggtgat cgaggaatgg 3420
tgctccaggg agtgcacaat gcccccactg tccttccagg ctaaagatgg ctgttggtat 3480
ggaatggaga taaggcccag gaaagaacca gaaagcaact tagtaaggtc aatggtgact 3540
gcaggatcaa ctgatcacat ggatcacttc tcccttggag tgcttgtgat tctgctcatg 3600
gtgcaggaag ggctgaagaa gagaatgacc acaaagatca tcataagcac atcaatggca 3660
gtgctggtag ctatgatcct gggaggattt tcaatgagtg acctggctaa gcttgcaatt 3720
ttgatgggtg ccaccttcgc ggaaatgaac actggaggag atgtagctca tctggcgctg 3780
atagcggcat tcaaagtcag accagcgttg ctggtatctt tcatcttcag agctaattgg 3840
acaccccgtg aaagcatgct gctggccttg gcctcgtgtc ttttgcaaac tgcgatctcc 3900
gccttggaag gcgacctgat ggttctcatc aatggttttg ctttggcctg gttggcaata 3960
cgagcgatgg ttgttccacg cactgataac atcaccttag caatcctggc tgctctgaca 4020
ccactggccc ggggcacact gcttgtggcg tggagagcag gccttgctac ttgcgggggg 4080
tttatgctcc tctctctgaa gggaaaaggc agtgtgaaga agaacttacc atttgtcatg 4140
gccctgggac taaccgctgt gaggctggtc gaccccatca acgtggtggg actgctgttg 4200
ctcacaagga gtgggaagcg gagctggccc cctagcgaag tactcacagc tgttggcctg 4260
atatgcgcat tggctggagg gttcgccaag gcagatatag agatggctgg gcccatggcc 4320
gcggtcggtc tgctaattgt cagttacgtg gtctcaggaa agagtgtgga catgtacatt 4380
gaaagagcag gtgacatcac atgggaaaaa gatgcggaag tcactggaaa cagtccccgg 4440
ctcgatgtgg cgctagatga gagtggtgat ttctccctgg tggaggatga cggtcccccc 4500
atgagagaga tcatactcaa ggtggtcctg atgaccatct gtggcatgaa cccaatagcc 4560
ataccctttg cagctggagc gtggtacgta tacgtgaaga ctggaaaaag gagtggtgct 4620
ctatgggatg tgcctgctcc caaggaagta aaaaaggggg agaccacaga tggagtgtac 4680
agagtaatga ctcgcagact gctaggttca acacaagttg gagtgggagt tatgcaagag 4740
ggggtctttc acactatgtg gcacgtcaca aaaggatccg cgctgagaag cggtgaaggg 4800
agacttgatc catactgggg agatgtcaag caggatctgg tgtcatactg tggtccatgg 4860
aagctagatg ccgcctggga cgggcacagc gaggtgcagc tcttggccgt gccccccgga 4920
gagagagcga ggaacatcca gactctgccc ggaatattta agacaaagga tggggacatt 4980
ggagcggttg cactggatta cccagcagga acttcaggat ctccaatcct agacaagtgt 5040
gggagagtga taggacttta tggcaatggg gtcgtgatca aaaatgggag ttatgttagt 5100
gccatcaccc aagggaggag ggaggaagag actcctgttg agtgcttcga gccttcgatg 5160
ctgaagaaga agcagctaac tgtcttagac ttgcatcctg gagctgggaa aaccaggaga 5220
gttcttcctg aaatagtccg tgaagccata aaaacaagac tccgtactgt gatcttggct 5280
ccaaccaggg ttgtcgctgc tgaaatggag gaggccctta gagggcttcc agtgcgttat 5340

-continued

```
atgacaacag cagtcaatgt cacccactct ggaacagaaa tcgtcgactt aatgtgccat   5400
gccaccttca cttcacgtct actacagcca attagagtcc ccaactataa tctgtatatt   5460
atggatgagg cccacttcac agatccctca agtatagcag caagaggata catttcaaca   5520
agggttgaga tgggcgaggc ggctgccatc ttcatgaccg ccacgccacc aggaacccgt   5580
gacgcatttc cggactccaa ctcaccaatt atggacaccg aagtggaagt cccagagaga   5640
gcctggagct caggctttga ttgggtgacg gagtattctg gaaaaacagt ttggtttgtt   5700
ccacgcgtga ggaacggcaa tgagatcgca gcttgtctga caaaggctgg aaaacgggtc   5760
atacagctca gcagaaagac ttttgagaca gagttccaga aaacaaaaca tcaagagtgg   5820
gactttgtcg tgacaactga catttcagag atgggcgcca actttaaagc tgaccgtgtc   5880
atagattcca ggagatgcct aaagccggtc atacttggtg gcgagagagt cattctggct   5940
ggacccatgc ctgtcacaca tgccagcgct gcccagagga gggggcgcat aggcaggaat   6000
cccaacaaac ctggagatga gtatctgtat ggaggtgggt gcgcagagac tgacgaagac   6060
catgcacact ggcttgaagc aagaatgctc cttgacaata tttacctcca agatggcctc   6120
atagcctcgc tctatcgacc tgaggccgac aaagtagcag ccattgaggg agagttcaag   6180
cttaggacgg agcaaaggaa gacctttgtg gaactcatga aaagaggaga tcttcctgtt   6240
tggctggcct atcaggttgc atctgccgga ataacctaca cagatagaag atggtgcttt   6300
gatggcacga ccaacaacac cataatggaa gacagtgtgc cggcagaggt gtggaccaga   6360
cacggagaga aaagagtgct caaaccgagg tggatggacg ccagagtttg ttcagatcat   6420
gcggccctga agtcattcaa ggagtttgcc gctgggaaaa gaggagcggc ttttggagtg   6480
atggaagccc tgggaacact gccaggacac atgacagaga gattccagga agccattgac   6540
aacctcgctg tgctcatgcg ggcagagact ggaagcaggc cttacaaagc cgcggcggcc   6600
caattgccgg agaccctaga gaccattatg cttttggggt tgctgggaac agtctcgctg   6660
ggaatctttt tcgtcttgat gaggaacaag ggcataggga agatgggctt tggaatggtg   6720
actcttgggg ccagcgcatg gctcatgtgg ctctcggaaa ttgagccagc cagaattgca   6780
tgtgtcctca ttgttgtgtt cctattgctg gtggtgctca tacctgagcc agaaaagcaa   6840
agatctcccc aggacaacca aatggccatc atcatcatgg tagcagtagg tcttctgggc   6900
ttgattaccg ccaatgaact cggatggttg gagagaacaa agagtgacct aagccatcta   6960
atgggaagga gagaggaggg ggcaaccatg ggattctcaa tggacattga cctgcggcca   7020
gcctcagctt gggccatcta tcctgccttg acatctttca ttaccccagc cgtccaacat   7080
gcagtgacca cttcatacaa caactactcc ttaatggcga tggccacgca agctggagtg   7140
ttgtttggta tgggcaaagg gatgccattc tacgcatggg actttggagt cccgctgcta   7200
atgataggtt gctactcaca attaacgccc ctgaccctaa tagtggccat cattttgctc   7260
gtggcgcact acatgtactt gatcccaggg ctgcaggcag cagctgcgcg tgctgcccag   7320
aagagaacgg cagctggcat catgaagaac cctgttgtgg agggaatagt ggtgactgac   7380
attgacacaa tgacaattga cccccaagtg gagaaaaaga tgggacaggt gctactcatg   7440
gcagtagccg tctccagcgc catactgtcg aggaccgcct gggggtgggg ggaggctggg   7500
gccctgatca cagccgcaac ttccactttg tgggaaggct ctccgaacaa gtactggaac   7560
tcctctacag ccacctcact gtgtaacatt tttaggggaa gttacttggc tggagcttct   7620
ctaatctaca cagtaacaag aaacgctggc ttggtcaaga gacgtggggg tggaacagga   7680
gagaccctgg gagagaaatg gaaggcccgc ttgaaccaga tgtcggccct ggagttctac   7740
```

```
tcctacaaaa agtcaggcat caccgaggtg tgcagagaag aggcccgccg cgccctcaag   7800
gacggtgtgg caacgggagg ccatgctgtg tcccgaggaa gtgcaaagct gagatggttg   7860
gtggagcggg gatacctgca gccctatgga aaggtcattg atcttggatg tggcagaggg   7920
ggctggagtt actacgccgc caccatccgc aaagttcaag aagtgaaagg atacacaaaa   7980
ggaggccctg gtcatgaaga acccgtgttg gtgcaaagct atgggtggaa catagtccgt   8040
cttaagagtg gggtggacgt ctttcatatg gcggctgagc cgtgtgacac gttgctgtgt   8100
gacataggtg agtcatcatc tagtcctgaa gtggaagaag cacggacgct cagagtcctc   8160
tccatggtgg gggattggct tgaaaaaaga ccaggagcct tttgtataaa agtgttgtgc   8220
ccatacacca gcactatgat ggaaaccctg gagcgactgc agcgtaggta tgggggagga   8280
ctggtcagag tgccactctc ccgcaactct acacatgaga tgtactgggt ctctggagcg   8340
aaaagcaaca ccataaaaag tgtgtccacc acgagccagc tcctcttggg gcgcatggac   8400
gggcctagga ggccagtgaa atatgaggag gatgtgaatc tcggctctgg cacgcgggct   8460
gtggtaagct gcgctgaagc tcccaacatg aagatcattg gtaaccgcat tgaaaggatc   8520
cgcgctgaga aagcggaaac gtggttcttt gacgagaacc acccatatag gacatgggct   8580
taccatggaa gctatgatgc cgccacacaa gggtcagcgt cctctctaat aaacggggtt   8640
gtcaggctcc tgtcaaaacc ctgggatgtg gtgactggag tcacaggaat agccatgacc   8700
gacaccacac cgtatggtca gcaaagagtt ttcaaggaaa aagtggacac tagggtgcca   8760
gacccccaag aaggcactcg tcaggttatg agcatggtct cttcctggtt gtggaaagag   8820
ctaggcaaac acaaacggcc acgagtctgt accaaagaag agttcatcaa caaggttcgt   8880
agcaatgcag cattaggggc aatatttgaa gaggaaaaag agtggaagac tgcagtggaa   8940
gctgtgaacg atccaaggtt ctgggctcta gtggacaagg aaagagagca ccacctgaga   9000
ggagagtgcc agagttgtgt gtacatcaca atgggaaaaa gagaaaagaa acaaggggaa   9060
tttggaaagg ccaagggcag ccgcgccatc tggtatatgt ggctaggggc tagatttcta   9120
gagttcgaag cccttggatt cttgaacgag gatcactgga tggggagaga gaactcagga   9180
ggtggtgttg aagggctggg attacaaaga ctcggatatg tcctagaaga gatgagtcgc   9240
ataccaggag gaaggatgta tgcagatgac actgctggct gggacacccg catcagcagg   9300
tttgatctgg agaatgaagc tctaatcacc aaccaaatgg agaaagggca cagggccttg   9360
gcattggcca taatcaagta cacataccaa aacaaagtgg taaaggtcct tagaccagct   9420
gaaaaaggga agacagttat ggacattatt tcgagacaag accaaagggg gagcggacaa   9480
gttgtcactt acgctctcaa cacatttacc aacctagtgg tgcaactcat tcggaatatg   9540
gaggctgagg aagttctaga gatgcaagac ttgtggctgc tgcggaggtc agagaaagtg   9600
accaactggt tgcagagcaa cggatgggat aggctcaaac gaatggcggt cagtggagat   9660
gattgcgttg tgaaaccaat tgatgatagg tttgcacatg ccctcaggtt cttgaatgat   9720
atgggaaaag ttaggaagga cacacaagag tggaaaccct caactggatg ggacaactgg   9780
gaagaagttc ccttctgctc ccaccacttc aacaagctcc atctcaagga cgggaggtcc   9840
attgtggttc cctgccgcca ccaagatgaa ctgattggcc gggcccgcgt ctctccaggg   9900
gcgggatgga gcatccggga gactgcttgc ctagcaaaat catatgcgca aatgtggcag   9960
ctcctttatt tccacagaag ggacctccga ctgatggcca atgccatttg ttcatctgtg  10020
ccagttgact gggttccaac tgggagaact acctggtcaa tccatggaaa gggagaatgg  10080
```

-continued

```
atgaccactg aagacatgct tgtggcgtgg aacagagtgt ggattgagga gaacgaccac  10140

atggaagaca agaccccagt cacgaaatgg acagacattc cctatttggg aaaaagggaa  10200

gacttgtggt gtggatctct catagggcac agaccgcgca ccacctgggc tgagaacatt  10260

aaaaacacag tcaacatggt gcgcaggatc ataggtgatg aagaaaagta catggactac  10320

ctatccaccc aagttcgcta cttgggtgaa gaagggtcta cacctggagt gctgtaagca  10380

ccaatcttaa tgttgtcagg cctgctagtc agccacagct tggggaaagc tgtgcagcct  10440

gtgacccccc caggagaagc tgggaaacca agcctatagt caggccgaga acgccatggc  10500

acggaagaag ccatgctgcc tgtgagcccc tcagaggaca ctgagtcaaa aaaccccacg  10560

cgcttggagg cgcaggatgg gaaaagaagg tggcgacctt ccccaccctt caatctgggg  10620

cctgaactgg agatcagctg tggatctcca gaagagggac tagtggttag aggaga      10676
```

```
<210> SEQ ID NO 11
<211> LENGTH: 10807
<212> TYPE: DNA
<213> ORGANISM: Zika virus

<400> SEQUENCE: 11

agttgttgat ctgtgtgagt cagactgcga cagttcgagt ctgaagcgag agctaacaac     60

agtatcaaca ggtttaattt ggatttggaa acgagagttt ctggtcatga aaaacccaaa    120

gaagaaatcc ggaggattcc ggattgtcaa tatgctaaaa cgcggagtag cccgtgtaaa    180

ccccttggga ggtttgaaga ggttgccagc cggacttctg ctgggtcatg gacccatcag    240

aatggttttg gcgatactag cctttttgag atttacagca atcaagccat cactgggcct    300

tatcaacaga tggggttccg tggggaaaaa agaggctatg gaaataataa agaagttcaa    360

gaaagatctt gctgccatgt tgagaataat caatgctagg aaagagagga agagacgtgg    420

cgcagacacc agcatcggaa tcattggcct cctgctgact acagccatgg cagcagagat    480

cactagacgc gggagtgcat actacatgta cttggatagg agcgatgccg ggaaggccat    540

ttcgtttgct accacattgg gagtgaacaa gtgccacgta cagatcatgg acctcgggca    600

catgtgtgac gccaccatga gttatgagtg ccctatgctg gatgagggag tggaaccaga    660

tgatgtcgat tgctggtgca acacgacatc aacttgggtt gtgtacggaa cctgtcatca    720

caaaaaaggt gaggcacggc gatctagaag agccgtgacg ctcccttctc actctacaag    780

gaagttgcaa acgcggtcgc agacctggtt agaatcaaga gaatacacga agcacttgat    840

caaggttgaa aactggatat tcaggaaccc cgggtttgcg ctagtggccg ttgccattgc    900

ctggcttttg ggaagctcga cgagccaaaa agtcatatac ttggtcatga tactgctgat    960

tgccccggca tacagtatca ggtgcattgg agtcagcaat agagacttcg tggagggcat   1020

gtcaggtggg acctgggttg atgttgtctt ggaacatgga ggctgcgtta ccgtgatggc   1080

acaggacaag ccaacagttg acatagagtt ggtcacgacg acggttagta acatggccga   1140

ggtaagatcc tattgctacg aggcatcgat atcggacatg gcttcggaca gtcgttgccc   1200

aacacaaggt gaagcctacc ttgacaagca atcagacact caatatgtct gcaaaagaac   1260

attagtggac agaggttggg gaaacggttg tggacttttt ggcaaaggga gcttggtgac   1320

atgtgccaag tttacgtgtt ctaagaagat gaccgggaag agcattcaac cggaaaatct   1380

ggagtatcgg ataatgctat cagtgcatgg ctcccagcat agcgggatga ctgtcaatga   1440

tataggatat gaaactgacg aaaatagagc gaaagtcgag gttacgccta attcaccaag   1500

agcggaagca accttgggag gctttggaag cttaggactt gactgtgaac caaggacagg   1560
```

ccttgacttt tcagatctgt attacctgac catgaacaat aagcattggt tggtgcacaa 1620
agagtggttt catgacatcc cattgccttg gcatgctggg gcagacactg gaactccaca 1680
ctggaacaac aaagaggcat tggtagaatt caaggatgcc cacgccaaga ggcaaaccgt 1740
cgtcgttctg gggagccagg aaggagccgt tcacacggct ctcgctggag ctctagaggc 1800
tgagatggat ggtgcaaagg gaaagctgtt ctctggccat ttgaaatgcc gcctaaaaat 1860
ggacaagctt agattgaagg gcgtgtcata ttccttgtgc actgcggcat tcacattcac 1920
caaggtccca gctgaaacac tgcatggaac agtcacagtg gaggtgcagt atgcagggac 1980
agatggaccc tgcaagatcc cagtccagat ggcggtggac atgcagaccc tgaccccagt 2040
tggaaggctg ataaccgcca accccgtgat tactgaaagc actgagaact caaagatgat 2100
gttggagctt gacccaccat ttggggattc ttacattgtc ataggagttg gggacaagaa 2160
aatcacccac cactggcata ggagtggtag caccatcgga aaggcatttg aggccactgt 2220
gagaggcgcc aagagaatgg cagtcctggg ggatacagcc tgggacttcg gatcagtcgg 2280
gggtgtgttc aactcactgg gtaagggcat tcaccagatt tttggagcag ccttcaaatc 2340
actgtttgga ggaatgtcct ggttctcaca gatcctcata ggcacgctgc tagtgtggtt 2400
aggtttgaac acaaagaatg gatctatctc cctcacatgc ttggccctgg ggggagtgat 2460
gatcttcctc tccacggctg tttctgctga cgtggggtgc tcagtggact tctcaaaaaa 2520
ggaaacgaga tgtggcacgg gggtattcat ctataatgat gttgaagcct ggagggaccg 2580
gtacaagtac catcctgact ccccccgcag attggcagca gcagtcaagc aggcctggga 2640
agaggggatc tgtgggatct catccgtttc aagaatggaa aacatcatgt ggaaatcagt 2700
agaaggggag ctcaatgcta tcctagagga gaatggagtt caactgacag ttgttgtggg 2760
atctgtaaaa aaccccatgt ggagaggtcc acaaagattg ccagtgcctg tgaatgagct 2820
gccccatggc tggaaagcct gggggaaatc gtattttgtt agggcggcaa agaccaacaa 2880
cagttttgtt gtcgacggtg acacactgaa ggaatgtccg cttgagcaca gagcatggaa 2940
tagttttctt gtggaggatc acgggtttgg agtcttccac accagtgtct ggcttaaggt 3000
cagagaagat tactcattag aatgtgaccc agccgtcata ggaacagctg ttaagggaag 3060
ggaggccgcg cacagtgatc tgggctattg gattgaaagt gaaaagaatg acacatggag 3120
gctgaagagg gcccacctga ttgagatgaa aacatgtgaa tggccaaagt ctcacacatt 3180
gtggacagat ggagtagaag aaagtgatct tatcataccc aagtctttag ctggtccact 3240
cagccaccac aacaccagag agggttacag aacccaagtg aaagggccat ggcacagtga 3300
agagcttgaa atccggtttg aggaatgtcc aggcaccaag gtttacgtgg aggagacatg 3360
cggaactaga ggaccatctc tgagatcaac tactgcaagt ggaagggtca ttgaggaatg 3420
gtgctgtagg gaatgcacaa tgcccccact atcgtttcga gcaaaagacg gctgctggta 3480
tggaatggag ataaggccca ggaaagaacc agagagcaac ttagtgaggt caatggtgac 3540
agcggggtca accgatcata tggaccactt ctctcttgga gtgcttgtga ttctactcat 3600
ggtgcaggag gggttgaaga agagaatgac cacaaagatc atcatgagca catcaatggc 3660
agtgctggta gtcatgatct tgggaggatt ttcaatgagt gacctggcca agcttgtgat 3720
cctgatgggt gctactttcg cagaaatgaa cactggagga gatgtagctc acttggcatt 3780
ggtagcggca tttaaagtca gaccagcctt gctggtctcc ttcattttca gagccaattg 3840
gacaccccgt gagagcatgc tgctagccct ggcttcgtgt cttctgcaaa ctgcgatctc 3900

-continued

```
tgctcttgaa ggtgacttga tggtcctcat taatggattt gctttggcct ggttggcaat   3960
tcgagcaatg gccgtgccac gcactgacaa catcgctcta ccaatcttgg ctgctctaac   4020
accactagct cgaggcacac tgctcgtggc atggagagcg ggcctggcta cttgtggagg   4080
gatcatgctc ctctccctga aagggaaagg tagtgtgaag aagaacctgc catttgtcat   4140
ggccctggga ttgacagctg tgagggtagt agaccctatt aatgtggtag gactactgtt   4200
actcacaagg agtgggaagc ggagctggcc ccctagtgaa gttctcacag ccgttggcct   4260
gatatgtgca ctggccggag ggtttgccaa ggcagacatt gagatggctg gacccatggc   4320
tgcagtaggc ttgctaattg tcagctatgt ggtctcggga aagagtgtgg acatgtacat   4380
tgaaagagca ggtgacatca catgggaaaa ggacgcggaa gtcactggaa acagtcctcg   4440
gcttgacgtg gcactggatg agagtggtga tttctccttg gtagaggaag atggtccacc   4500
catgagagag atcatactta aggtggtcct gatggccatc tgtggcatga acccaatagc   4560
tatacctttt gctgcaggag cgtggtatgt gtatgtgaag actgggaaaa ggagtggcgc   4620
cctctgggac gtgcctgctc ccaaagaagt gaagaaagga gagaccacag atggagtgta   4680
cagagtgatg actcgcagac tgctaggttc aacacaggtt ggagtgggag tcatgcaaga   4740
gggagtcttc cacaccatgt ggcacgttac aaaaggagcc gcactgagga gcggtgaggg   4800
aagacttgat ccatactggg gggatgtcaa gcaggacttg gtgtcatact gtgggccttg   4860
gaagttggat gcagcttggg atggactcag cgaggtacag cttttggccg tacctcccgg   4920
agagagggcc agaaacattc agaccctgcc tggaatattc aagacaaagg acggggacat   4980
cggagcagtt gctctggact accctgcagg gacctcagga tctccgatcc tagacaaatg   5040
tggaagagtg ataggactct atggcaatgg ggttgtgatc aagaatggaa gctatgttag   5100
tgctataacc cagggaaaga gggaggagga gactccggtt gaatgtttcg aaccctcgat   5160
gctgaagaag aagcagctaa ctgtcttgga tctgcatcca ggagccggaa aaaccaggag   5220
agttcttcct gaaatagtcc gtgaagccat aaaaaagaga ctccggacag tgatcttggc   5280
accaactagg gttgtcgctg ctgagatgga ggaggccttg agaggacttc cggtgcgtta   5340
catgacaaca gcagtcaacg tcacccattc tgggacagaa atcgttgatt tgatgtgcca   5400
tgccactttc acttcacgct tactacaacc catcagagtc cctaattaca atctctacat   5460
catggatgaa gcccacttca cagacccctc aagtatagct gcaagaggat atatatcaac   5520
aagggttgaa atgggcgagg cggctgccat ttttatgact gccacaccac caggaacccg   5580
tgatgcgttt cctgactcta actcaccaat catggacaca gaagtggaag tcccagagag   5640
agcctggagc tcaggctttg attgggtgac agaccattct gggaaaacag tttggttcgt   5700
tccaagcgtg agaaacggaa atgaaatcgc agcctgtctg acaaaggctg gaaagcgggt   5760
catacagctc agcaggaaga cttttgagac agaatttcag aaaacaaaaa atcaagagtg   5820
ggactttgtc ataacaactg acatctcaga gatgggcgcc aacttcaagg ctgaccgggt   5880
catagactct aggagatgcc taaaaccagt catacttgat ggtgagagag tcatcttggc   5940
tgggcccatg cctgtcacgc atgctagtgc tgctcagagg agaggacgta taggcaggaa   6000
ccctaacaaa cctggagatg agtacatgta tggaggtggg tgtgcagaga ctgatgaagg   6060
ccatgcacac tggcttgaag caagaatgct tcttgacaac atctacctcc aggatggcct   6120
catagcctcg ctctatcggc ctgaggccga taaggtagcc gccattgagg gagagtttaa   6180
gctgaggaca gagcaaagga agaccttcgt ggaactcatg aagagaggag accttcccgt   6240
ctggctagcc tatcaggttg catctgccgg aataacttac acagacagaa gatggtgctt   6300
```

```
tgatggcaca accaacaaca ccataatgga agacagcgta ccagcagagg tgtggacaaa   6360
gtatggagag aagagagtgc tcaaaccgag atggatggat gctagggtct gttcagacca   6420
tgcggccctg aagtcgttca aagaattcgc cgctggaaaa agaggagcgg ctttgggagt   6480
aatggaggcc ctgggaacac tgccaggaca catgacagag aggtttcagg aagccattga   6540
caacctcgcc gtgctcatgc gagcagagac tggaagcagg ccttataagg cagcggcagc   6600
ccaactgccg gagaccctag agaccattat gctcttaggt ttgctgggaa cagtttcact   6660
ggggatcttc ttcgtcttga tgcggaataa gggcatcggg aagatgggct ttggaatggt   6720
aaccettggg gccagtgcat ggctcatgtg gctttcggaa attgaaccag ccagaattgc   6780
atgtgtcctc attgttgtgt ttttattact ggtggtgctc atacccgagc cagagaagca   6840
aagatctccc caagataacc agatggcaat tatcatcatg gtggcagtgg gccttctagg   6900
tttgataact gcaaacgaac ttggatggct ggaaagaaca aaaaatgaca tagctcatct   6960
aatgggaagg agagaagaag gagcaaccat gggattctca atggacattg atctgcggcc   7020
agcctccgcc tgggctatct atgccgcatt gacaactctc atcaccccag ctgtccaaca   7080
tgcggtaacc acttcataca acaactactc cttaatggcg atggccacac aagctggagt   7140
gctgtttggc atgggcaaag ggatgccatt ttatgcatgg gaccttggag tcccgctgct   7200
aatgatgggt tgctattcac aattaacacc cctgactctg atagtagcta tcattctgct   7260
tgtggcgcac tacatgtact tgatcccagg cctacaagcg gcagcagcgc gtgctgccca   7320
gaaaaggaca gcagctggca tcatgaagaa tcccgttgtg gatggaatag tggtaactga   7380
cattgacaca atgacaatag acccccaggt ggagaagaag atgggacaag tgttactcat   7440
agcagtagcc atctccagtg ctgtgctgct gcggaccgcc tggggatggg gggaggctgg   7500
agctctgatc acagcagcga cctccacctt gtgggaaggc tctccaaaca aatactggaa   7560
ctcctctaca gccacctcac tgtgcaacat cttcagagga agctatctgg caggagcttc   7620
ccttatctat acagtgacga gaaacgctgg cctggttaag agacgtggag gtgggacggg   7680
agagactctg ggagagaagt ggaaagctcg tctgaatcag atgtcggccc tggagttcta   7740
ctcttataaa aagtcaggta tcactgaagt gtgtagagag gaggctcgcc gtgccctcaa   7800
ggatggagtg gccacaggag gacatgccgt atcccgggga agtgcaaagc tcagatggtt   7860
ggtggagaga ggatatctgc agccctatgg gaaggttgtt gacctcggat gtggcagagg   7920
gggctggagc tattatgccg ccaccatccg caaagtgcag gaggtgagag gatacacaaa   7980
gggaggtccc ggtcatgaag aacccatgct ggtgcaaagc tatgggtgga acatagttcg   8040
tctcaagagt ggagtggacg tcttccacat ggcggctgag ccgtgtgaca ctctgctgtg   8100
tgacataggt gagtcatcat ctagtcctga agtggaagag acacgaacac tcagagtgct   8160
ctctatggtg ggggactggc ttgaaaaaag accaggggcc ttctgtataa aggtgctgtg   8220
cccatacacc agcactatga tggaaaccat ggagcgactg caacgtaggc atgggggagg   8280
attagtcaga gtgccattgt ctcgcaactc cacacatgag atgtactggg tctctggggc   8340
aaagagcaac atcataaaaa gtgtgtccac cacaagtcag ctcctcctgg gacgcatgga   8400
tggccccagg aggccagtga aatatgagga ggatgtgaac ctcggctcgg gtacacgagc   8460
tgtggcaagc tgtgctgagg ctcctaacat gaaaatcatc ggcaggcgca ttgagagaat   8520
ccgcaatgaa catgcagaaa catggtttct tgatgaaaac cacccataca ggacatgggc   8580
ctaccatggg agctacgaag cccccacgca aggatcagcg tcttccctcg tgaacggggt   8640
```

-continued

```
tgttagactc ctgtcaaagc cttgggacgt ggtgactgga gttacaggaa tagccatgac   8700
tgacaccaca ccatacggcc aacaaagagt cttcaaagaa aaagtggaca ccagggtgcc   8760
agatccccaa gaaggcactc gccaggtaat gaacatagtc tcttcctggc tgtggaagga   8820
gctggggaaa cgcaagcggc cacgcgtctg caccaaagaa gagtttatca acaaggtgcg   8880
cagcaatgca gcactgggag caatatttga agaggaaaaa gaatggaaga cggctgtgga   8940
agctgtgaat gatccaaggt tttgggccct agtggatagg gagagagaac accacctgag   9000
aggagagtgt cacagctgtg tgtacaacat gatgggaaaa agagaaaaga agcaaggaga   9060
gttcgggaaa gcaaaaggta gccgcgccat ctggtacatg tggttgggag ccagattctt   9120
ggagtttgaa gcccttggat tcttgaacga ggaccattgg atgggaagag aaaactcagg   9180
aggtggagtc gaagggttag gattgcaaag acttggatac attctagaag aaatgaatcg   9240
ggcaccagga ggaaagatgt acgcagatga cactgctggc tgggacaccc gcattagtaa   9300
gtttgatctg gagaatgaag ctctgattac caaccaaatg gaggaagggc acagaactct   9360
ggcgttggcc gtgattaaat acacatacca aaacaaagtg gtgaaggttc tcagaccagc   9420
tgaaggagga aaaacagtta tggacatcat ttcaagacaa gaccagagag ggagtggaca   9480
agttgtcact tatgctctca acacattcac caacttggtg gtgcagctta tccggaacat   9540
ggaagctgag gaagtgttag agatgcaaga cttatggttg ttgaggaagc cagagaaagt   9600
gaccagatgg ttgcagagca atggatggga tagactcaaa cgaatggcgg tcagtggaga   9660
tgactgcgtt gtgaagccaa tcgatgatag gtttgcacat gccctcaggt tcttgaatga   9720
catgggaaaa gttaggaaag acacacagga gtggaaaccc tcgactggat ggagcaattg   9780
ggaagaagtc ccgttctgct cccaccactt caacaagctg tacctcaagg atgggagatc   9840
cattgtggtc ccttgccgcc accaagatga actgattggc cgagctcgcg tctcaccagg   9900
ggcaggatgg agcatccggg agactgcctg tcttgcaaaa tcatatgcgc agatgtggca   9960
gctcctttat ttccacagaa gagaccttcg actgatggct aatgccattt gctcggctgt  10020
gccagttgac tgggtaccaa ctgggagaac cacctggtca atccatggaa agggagaatg  10080
gatgaccact gaggacatgc tcatggtgtg gaatagagtg tggattgagg agaacgacca  10140
tatggaggac aagactcctg taacaaaatg gacagacatt ccctatctag gaaaaaggga  10200
ggacttatgg tgtggatccc ttatagggca cagaccccgc accacttggg ctgaaaacat  10260
caaagacaca gtcaacatgg tgcgcaggat cataggtgat gaagaaaagt acatggacta  10320
tctatccacc caagtccgct acttgggtga ggaagggtcc acacccggag tgttgtaagc  10380
accaatttta gtgttgtcag gcctgctagt cagccacagt ttggggaaag ctgtgcagcc  10440
tgtaaccccc ccaggagaag ctgggaaacc aagctcatag tcaggccgag aacgccatgg  10500
cacggaagaa gccatgctgc ctgtgagccc ctcagaggac actgagtcaa aaaaccccac  10560
gcgcttggaa gcgcaggatg ggaaaagaag gtggcgacct tccccaccct tcaatctggg  10620
gcctgaactg gagactagct gtgaatctcc agcagaggga ctagtggtta gaggagaccc  10680
cccggaaaac gcaaaacagc atattgacgc tgggaaagac cagagactcc atgagtttcc  10740
accacgctgg ccgccaggca cagatcgccg aacagcggcg gccggtgtgg ggaaatccat  10800
ggtttct                                                             10807
```

<210> SEQ ID NO 12
<211> LENGTH: 10794
<212> TYPE: DNA
<213> ORGANISM: Zika virus -continued

<400> SEQUENCE: 12

```
agttgttgat ctgtgtgagt cagactgcga cagttcgagt ctgaagcgag agctaacaac     60
agtatcaaca ggtttaattt ggatttggaa acgagagttt ctggtcatga aaaaccccaa    120
agaagaaatc cggaggatcc ggattgtcaa tatgctaaaa cgcggagtag cccgtgtaaa    180
ccccttggga ggtttgaaga ggttgccagc cggacttctg ctgggtcatg gacccatcag    240
aatggttttg gcgatactag ccttttttgag atttacagca atcaagccat cactgggcct    300
tatcaacaga tggggttccg tggggaaaaa agaggctatg gaaataataa agaagttcaa    360
gaaagatctt gctgccatgt tgagaataat caatgctagg aaagagagga agagacgtgg    420
cgcagacacc agcatcggaa tcattggcct cctgctgact acagccatgg cagcagagat    480
cactagacgc gggagtgcat actacatgta cttggatagg agcgatgccg ggaaggccat    540
ttcgtttgct accacattgg gagtgaacaa gtgccacgta cagatcatgg acctcgggca    600
catgtgtgac gccaccatga gttatgagtg ccctatgctg gatgagggag tggaaccaga    660
tgatgtcgat tgctggtgca acacgacatc aacttgggtt gtgtacggaa cctgtcatca    720
caaaaaaggt gaggcacggc gatctagaag agccgtgacg ctcccttctc actctacaag    780
gaagttgcaa acgcggtcgc agacctggtt agaatcaaga gaatacacga agcacttgat    840
caaggttgaa aactggatat tcaggaaccc cgggtttgcg ctagtggccg ttgccattgc    900
ctggcttttg ggaagctcga cgagccaaaa agtcatatac ttggtcatga tactgctgat    960
tgccccggca tacagtatca ggtgcattgg agtcagcaat agagacttcg tggagggcat   1020
gtcaggtggg acctgggttg atgttgtctt ggaacatgga ggctgcgtta ccgtgatggc   1080
acaggacaag ccaacagtcg acatagagtt ggtcacgacg acggttagta acatggccga   1140
ggtaagatcc tattgctacg aggcatcgat atcggacatg gcttcggaca gtcgttgccc   1200
aacacaaggt gaagcctacc ttgacaagca atcagacact caatatgtct gcaaaagaac   1260
attagtggac agaggttggg gaaacggttg tggacttttt ggcaaaggga gcttggtgac   1320
atgtgccaag tttacgtgtt ctaagaagat gaccgggaag agcattcaac cggaaaatct   1380
ggagtatcgg ataatgctat cagtgcatgg ctcccagcat agcgggatga ttggatatga   1440
aactgacgaa gatagagcga aagtcgaggt tacgcctaat tcaccaagag cggaagcaac   1500
cttgggaggc tttggaagct taggacttga ctgtgaacca aggacaggcc ttgacttttc   1560
agatctgtat tacctgacca tgaacaataa gcattggttg gtgcacaaag agtggtttca   1620
tgacatccca ttgccttggc atgctggggc agacaccgga actccacact ggaacaacaa   1680
agaggcattg gtagaattca aggatgccca cgccaagagg caaaccgtcg tcgttctggg   1740
gagccaggaa ggagccgttc acacggctct cgctggagct ctagaggctg agatggatgg   1800
tgcaaaggga aggctgttct ctggccattt gaaatgccgc ctaaaaatgg acaagcttag   1860
attgaagggc gtgtcatatt ccttgtgcac tgcggcattc acattcacca aggtcccagc   1920
tgaaacactg catggaacag tcacagtgga ggtgcagtat gcagggacag atggaccctg   1980
caagatccca gtccagatgg cggtggacat gcagaccctg accccagttg gaaggctgat   2040
aaccgccaac cccgtgatta ctgaaagcac tgagaactca aagatgatgt tggagcttga   2100
cccaccattt ggggattctt acattgtcat aggagttggg gacaagaaaa tcacccacca   2160
ctggcatagg agtggtagca ccatcggaaa ggcatttgag gccactgtga gaggcgccaa   2220
gagaatggca gtcctggggg atacagcctg ggacttcgga tcagtcgggg gtgtgttcaa   2280
```

-continued

```
ctcactgggt aagggcattc accagatttt tggagcagcc ttcaaatcac tgtttggagg   2340
aatgtcctgg ttctcacaga tcctcatagg cacgctgcta gtgtggttag gtttgaacac   2400
aaagaatgga tctatctccc tcacatgctt ggccctgggg ggagtgatga tcttcctctc   2460
cacggctgtt tctgctgacg tggggtgctc agtggacttc tcaaaaaagg aaacgagatg   2520
tggcacgggg gtattcatct ataatgatgt tgaagcctgg agggaccggt acaagtacca   2580
tcctgactcc ccccgcagat tggcagcagc agtcaagcag gcctgggaag aggggatctg   2640
tgggatctca tccgtttcaa gaatggaaaa catcatgtgg aaatcagtag aaggggagct   2700
caatgctatc ctagaggaga atggagttca actgacagtt gttgtgggat ctgtaaaaaa   2760
ccccatgtgg agaggtccac aaagattgcc agtgcctgtg aatgagctgc cccatggctg   2820
gaaagcctgg gggaaatcgt attttgttag ggcggcaaag accaacaaca gttttgttgt   2880
cgacggtgac acactgaagg aatgtccgct tgagcacaga gcatggaata gttttcttgt   2940
ggaggatcac gggtttggag tcttccacac cagtgtctgg cttaaggtca gagaagatta   3000
ctcattagaa tgtgacccag ccgtcatagg aacagctgtt aagggaaggg aggccgcgca   3060
cagtgatctg ggctattgga ttgaaagtga aaagaatgac acatggaggc tgaagagggc   3120
ccacctgatt gagatgaaaa catgtgaatg gccaaagtct cacacattgt ggacagatgg   3180
agtagaagaa agtgatctta tcatacccaa gtctttagct ggtccactca gccaccacaa   3240
caccagagag ggttacagaa cccaagtgaa agggccatgg cacagtgaag agcttgaaat   3300
ccggtttgag gaatgtccag gcaccaaggt ttacgtggag gagacatgcg gaactagagg   3360
accatctctg agatcaacta ctgcaagtgg aagggtcatt gaggaatggt gctgtaggga   3420
atgcacaatg cccccactat cgtttcgagc aaaagacggc tgctggtatg gaatggagat   3480
aaggcccagg aaagaaccag agagcaactt agtgaggtca atggtgacag cggggtcaac   3540
cgatcatatg gaccacttct ctcttggagt gcttgtgatt ctactcatgg tgcaggaggg   3600
gttgaagaag agaatgacca caaagatcat catgagcaca tcaatggcag tgctggtagt   3660
catgatcttg ggaggatttt caatgagtga cctggccaag cttgtgatcc tgatgggtgc   3720
tactttcgca gaaatgaaca ctggaggaga tgtagctcac ttggcattgg tagcggcatt   3780
taaagtcaga ccagccttgc tggtctcctt cattttcaga gccaattgga caccccgtga   3840
gagcatgctg ctagccctgg cttcgtgtct tctgcaaact gcgatctctg ctcttgaagg   3900
tgacttgatg gtcctcatta atggatttgc tttggcctgg ttggcaattc gagcaatggc   3960
cgtgccacgc actgacaaca tcgctctacc aatcttggct gctctaacac cactagctcg   4020
aggcacactg ctcgtggcat ggagagcggg cctggctact tgtggaggga tcatgctcct   4080
ctccctgaaa gggaaaggta gtgtgaagaa gaacctgcca tttgtcatgg ccctgggatt   4140
gacagctgtg agggtagtag accctattaa tgtggtagga ctactgttac tcacaaggag   4200
tgggaagcgg agctggcccc ctagtgaagt tctcacagcc gttggcctga tatgtgcact   4260
ggccggaggg tttgccaagg cagacattga gatggctgga cccatggctg cagtaggctt   4320
gctaattgtc agctatgtgg tctcgggaaa gagtgtggac atgtacattg aaagagcagg   4380
tgacatcaca tgggaaaagg acgcggaagt cactggaaac agtcctcggc ttgacgtggc   4440
actggatgag agtggtgact tctccttggt agaggaagat ggtccaccca tgagagagat   4500
catactcaag gtggtcctga tggccatctg tggcatgaac ccaatagcta taccttttgc   4560
tgcaggagcg tggtatgtgt atgtgaagac tgggaaaagg agtggcgccc tctgggacgt   4620
gcctgctccc aaagaagtga agaaaggaga gaccacagat ggagtgtaca gagtgatgac   4680
```

```
tcgcagactg ctaggttcaa cacaggttgg agtgggagtc atgcaagagg gagtcttcca   4740
caccatgtgg cacgttacaa aaggagccgc actgaggagc ggtgagggaa gacttgatcc   4800
atactggggg gatgtcaagc aggacttggt gtcatactgt gggccttgga agttggatgc   4860
agcttgggat ggactcagcg aggtacagct tttggccgta cctcccggag agagggccag   4920
aaacattcag accctgcctg gaatattcaa gacaaaggac ggggacatcg gagcagttgc   4980
tctggactac cctgcaggga cctcaggatc tccgatccta gacaaatgtg gaagagtgat   5040
aggactctat ggcaatgggg ttgtgatcaa gaatggaagc tatgttagtg ctataaccca   5100
gggaaagagg gaggaggaga ctccggttga atgtttcgaa ccctcgatgc tgaagaagaa   5160
gcagctaact gtcttggatc tgcatccagg agccggaaaa accaggagag ttcttcctga   5220
aatagtccgt gaagccataa aaaagagact ccggacagtg atcttggcac caactagggt   5280
tgtcgctgct gagatggagg aggccttgag aggacttccg gtgcgttaca tgacaacagc   5340
agtcaacgtc acccattctg ggacagaaat cgttgatttg atgtgccatg ccactttcac   5400
ttcacgctta ctacaaccca tcagagtccc taattacaat ctcaacatca tggatgaagc   5460
ccacttcaca gacccctcaa gtatagctgc aagaggatac atatcaacaa gggttgaaat   5520
gggcgaggcg gctgccattt ttatgactgc cacaccacca ggaacccgtg atgcgtttcc   5580
tgactctaac tcaccaatca tggacacaga agtggaagtc ccagagagag cctggagctc   5640
aggctttgat tgggtgacag accattctgg gaaaacagtt tggttcgttc caagcgtgag   5700
aaacggaaat gaaatcgcag cctgtctgac aaaggctgga aagcgggtca tacagctcag   5760
caggaagact tttgagacag aatttcagaa aacaaaaaat caagagtggg actttgtcat   5820
aacaactgac atctcagaga tgggcgccaa cttcaaggct gaccgggtca tagactctag   5880
gagatgccta aaaccagtca tacttgatgg tgagagagtc atcttggctg ggcccatgcc   5940
tgtcacgcat gctagtgctg ctcagaggag aggacgtata ggcaggaacc ctaacaaacc   6000
tggagatgag tacatgtatg gaggtgggtg tgcagagact gatgaaggcc atgcacactg   6060
gcttgaagca agaatgcttc ttgacaacat ctacctccag gatggcctca tagcctcgct   6120
ctatcggcct gaggccgata aggtagccgc cattgaggga gagtttaagc tgaggacaga   6180
gcaaaggaag accttcgtgg aactcatgaa gagaggagac cttcccgtct ggctagccta   6240
tcaggttgca tctgccggaa taacttacac agacagaaga tggtgctttg atggcacaac   6300
caacaacacc ataatggaag acagtgtacc agcagaggtt tggacaaagt atggagagaa   6360
gagagtgctc aaaccgagat ggatggatgc tagggtctgt tcagaccatg cggccctgaa   6420
gtcgttcaaa gaattcgccg ctggaaaaag aggagcggct ttgggagtaa tggaggccct   6480
gggaacactg ccaggacaca tgacagagag gtttcaggaa gccattgaca acctcgccgt   6540
gctcatgcga gcagagactg gaagcaggcc ttataaggca gcggcagccc aactgccgga   6600
gaccctagag accattatgc tcttaggttt gctgggaaca gtttcactgg ggatcttctt   6660
cgtcttgatg cggaataagg gcatcgggaa gatgggcttt ggaatggtaa cccttggggc   6720
cagtgcatgg ctcatgtggc tttcggaaat tgaaccagcc agaattgcat gtgtcctcat   6780
tgttgtgttt ttattactgg tggtgctcat acccgagcca gagaagcaaa gatctcccca   6840
agataaccag atggcaatta tcatcatggt ggcagtgggc cttctaggtt tgataactgc   6900
aaacgaactt ggatggctgg aaagaacaaa aaatgacata gctcatctaa tgggaaggag   6960
agaagaagga gcaaccatgg gattctcaat ggacattgat ctgcggccag cctccgcctg   7020
```

-continued

```
ggctatctat gccgcattga caactctcat caccccagct gtccaacatg cggtaaccac   7080
ttcatacaac aactactcct taatggcgat ggccacacaa gctggagtgc tgtttggcat   7140
gggcaaaggg atgccattta tgcatgggga ccttggagtc ccgctgctaa tgatgggttg   7200
ctattcacaa ttaacacccc tgactctgat agtagctatc attctgcttg tggcgcacta   7260
catgtacttg atcccaggcc tacaagcggc agcagcgcgt gctgcccaga aaaggacagc   7320
agctggcatc atgaagaatc ccgttgtgga tggaatagtg gtaactgaca ttgacacaat   7380
gacaatagac ccccaggtgg agaagaagat gggacaagtg ttactcatag cagtagccat   7440
ctccagtgct gtgctgctgc ggaccgcctg ggatggggg gaggctggag ctctgatcac   7500
agcagcgacc tccaccttgt gggaaggctc tccaaacaaa tactggaact cctctacagc   7560
cacctcactg tgcaacatct tcagaggaag ctatctggca ggagcttccc ttatctatac   7620
agtgacgaga aacgctggcc tggttaagag acgtggaggt gggacgggag agactctggg   7680
agagaagtgg aaagctcgtc tgaatcagat gtcggccctg gagttctact cttataaaaa   7740
gtcaggtatc actgaagtgt gtagagagga ggctcgccgt gccctcaagg atggagtggc   7800
cacaggagga catgccgtat cccggggaag tgcaaagatc agatggttgg aggagagagg   7860
atatctgcag ccctatggga aggttgttga cctcggatgt ggcagagggg gctggagcta   7920
ttatgccgcc accatccgca aagtgcagga ggtgagagga tacacaaagg gaggtcccgg   7980
tcatgaagaa cccatgctgg tgcaaagcta tgggtggaac atagttcgtc tcaagagtgg   8040
agtggacgtc ttccacatgg cggctgagcc gtgtgacact ctgctgtgtg acataggtga   8100
gtcatcatct agtcctgaag tggaagagac acgaacactc agagtgctct ctatggtggg   8160
ggactggctt gaaaaaagac caggggcctt ctgtataaag gtgctgtgcc catacaccag   8220
cactatgatg gaaaccatgg agcgactgca acgtaggcat gggggaggat tagtcagagt   8280
gccattgtgt cgcaactcca cacatgagat gtactgggtc tctggggcaa agagcaacat   8340
cataaaaagt gtgtccacca caagtcagct cctcctggga cgcatggatg gccccaggag   8400
gccagtgaaa tatgaggagg atgtgaacct cggctcgggt acacgagctg tggcaagctg   8460
tgctgaggct cctaacatga aaatcatcgg caggcgcatt gagagaatcc gcaatgaaca   8520
tgcagaaaca tggtttcttg atgaaaacca cccatacagg acatgggcct accatgggag   8580
ctacgaagcc cccacgcaag gatcagcgtc ttccctcgtg aacggggttg ttagactcct   8640
gtcaaagcct tgggacgtgg tgactggagt tacaggaata gccatgactg acaccacacc   8700
atacggccaa caaagagtct tcaaagaaaa agtggacacc agggtgccag atccccaaga   8760
aggcactcgc caggtaatga acatagtctc ttcctggctg tggaaggagc tggggaaacg   8820
caagcggcca cgcgtctgca ccaaagaaga gtttatcaac aaggtgcgca gcaatgcagc   8880
actgggagca atatttgaag aggaaaaaga atggaagacg gctgtggaag ctgtgaatga   8940
tccaaggttt tgggccctag tggataggga gagagaacac cacctgagag gagagtgtca   9000
cagctgtgtg tacaacatga tgggaaaaag agaaaagaag caaggagagt tcgggaaagc   9060
aaaaggtagc cgcgccatct ggtacatgtg gttgggagcc agattcttgg agtttgaagc   9120
ccttggattc ttgaacgagg accattggat gggaagagaa aactcaggag gtggagtcga   9180
agggttagga ttgcaaagac ttggatacat tctagaagaa atgaatcggg caccaggagg   9240
aaagatgtac gcagatgaca ctgctggctg ggacacccgc attagtaagt ttgatctgga   9300
gaatgaagct ctgattacca accaaatgga ggaagggcac agaactctgg cgttggccgt   9360
gattaaatac acataccaaa acaaagtggt gaaggttctc agaccagctg aaggaggaaa   9420
```

```
aacagttatg gacatcattt caagacaaga ccagagaggg agtggacaag ttgtcactta   9480
tgctctcaac acattcacca acttggtggt gcagcttatc cggaacatgg aagctgagga   9540
agtgttagag atgcaagact tatggttgtt gaggaagcca gagaaagtga ccagatggtt   9600
gcagagcaat ggatgggata gactcaaacg aatggcggtc agtggagatg actgcgttgt   9660
gaagccaatc gatgataggt ttgcacatgc cctcaggttc ttgaatgaca tgggaaaagt   9720
taggaaagac acacaggagt ggaaaccctc gactggatgg agcaattggg aagaagtccc   9780
gttctgctcc caccacttca acaagctgta cctcaaggat gggagatcca ttgtggtccc   9840
ttgccgccac caagatgaac tgattggccg agctcgcgtc tcaccagggg caggatggag   9900
catccgggag actgcctgtc ttgcaaaatc atatgcgcag atgtggcagc tcctttattt   9960
ccacagaaga gaccttcgac tgatggctaa tgccatttgc tcggctgtgc cagttgactg  10020
ggtaccaact gggagaacca cctggtcaat ccatggaaag ggagaatgga tgaccactga  10080
ggacatgctc atggtgtgga atagagtgtg gattgaggag aacgaccata tggaggacaa  10140
gactcctgta acaaaatgga cagacattcc ctatctagga aaaagggagg acttatggtg  10200
tggatccctt atagggcaca gaccccgcac cacttgggct gaaaacatca aagacacagt  10260
caacatggtg cgcaggatca taggtgatga agaaaagtac atggactatc tatccaccca  10320
agtccgctac ttgggtgagg aagggtccac acccggagtg ttgtaagcac caattttagt  10380
gttgtcaggc ctgctagtca gccacagttt ggggaaagct gtgcagcctg taaccccccc  10440
aggagaagct gggaaaccaa gctcatagtc aggccgagaa cgccatggca cggaagaagc  10500
catgctgcct gtgagcccct cagaggacac tgagtcaaaa aaccccacgc gcttggaagc  10560
gcaggatggg aaaagaaggt ggcgaccttc cccacccttc aatctggggc ctgaactgga  10620
gactagctgt gaatctccag cagagggact agtggttaga ggagaccccc cggaaaacgc  10680
aaaacagcat attgacgtgg gaaagaccag agactccatg agtttccacc acgctggccg  10740
ccaggcacag atcgccgaac ttcggcggcc ggtgtgggga aatccatggt ttct        10794
```

<210> SEQ ID NO 13
<211> LENGTH: 10617
<212> TYPE: DNA
<213> ORGANISM: Zika virus

<400> SEQUENCE: 13

```
agtatcaaca ggttttattt tggatttgga aacgagagtt tctggtcatg aaaaacccaa     60
aaaagaaatc cggaggattc cggattgtca atatgctaaa acgcggagta gcccgtgtga    120
gcccctttgg gggcttgaag aggctgccag ccggacttct gctgggtcat gggcccatca    180
ggatggtctt ggcgattcta gcctttttga gattcacggc aatcaagcca tcactgggtc    240
tcatcaatag atggggttca gtggggaaaa aagaggctat ggaaataata aagaagttca    300
agaaagatct ggctgccatg ctgagaataa tcaatgctag gaaggagaag aagagacgag    360
gcgcagatac tagtgtcgga attgttggcc tcctgctgac cacagctatg gcagcggagg    420
tcactagacg tgggagtgca tactatatgt acttggacag aaacgacgct ggggaggcca    480
tatcttttcc aaccacattg ggatgaata agtgttatat acagatcatg gatcttggac     540
acatgtgtga tgccaccatg agctatgaat gccctatgct ggatgagggg gtggaaccag    600
atgacgtcga ttgttggtgc aacacgacgt caacttgggt tgtgtacgga acctgccatc    660
acaaaaaagg tgaagcacgg agatctagaa gagctgtgac gctcccctcc cattccacta    720
```

-continued

```
ggaagctgca aacgcggtcg caaacctggt tggaatcaag agaatacaca aagcacttga    780
ttagagtcga aaattggata ttcaggaacc ctggcttcgc gttagcagca gctgccatcg    840
cttggctttt gggaagctca acgagccaaa aagtcatata cttggtcatg atactgctga    900
ttgccccggc atacagcatc aggtgcatag gagtcagcaa tagggacttt gtggaaggta    960
tgtcaggtgg gacttgggtt gatgttgtct tggaacatgg aggttgtgtc accgtaatgg   1020
cacaggacaa accgactgtc gacatagagc tggttacaac aacagtcagc aacatggcgg   1080
aggtaagatc ctactgctat gaggcatcaa tatcggacat ggcttcggac agccgctgcc   1140
caacacaagg tgaagcctac cttgacaagc aatcagacac tcaatatgtc tgcaaaagaa   1200
cgttagtgga cagaggctgg ggaaatggat gtggactttt tggcaaaggg agcctggtga   1260
catgcgctaa gtttgcatgc tccaagaaaa tgaccgggaa gagcatccag ccagagaatc   1320
tggagtaccg gataatgctg tcagttcatg gctcccagca cagtgggatg atcgttaatg   1380
acacaggaca tgaaactgat gagaatagag cgaaggttga gataacgccc aattcaccaa   1440
gagccgaagc caccctgggg ggttttggaa gcctaggact tgattgtgaa ccgaggacag   1500
gccttgactt ttcagatttg tattacttga ctatgaataa caagcactgg ttggttcaca   1560
aggagtggtt ccacgacatt ccattacctt ggcacgctgg ggcagacacc ggaactccac   1620
actggaacaa caaagaagca ctggtagagt tcaaggacgc acatgccaaa aggcaaactg   1680
tcgtggttct agggagtcaa gaaggagcag ttcacacggc ccttgctgga gctctggagg   1740
ctgagatgga tggtgcaaag ggaaggctgt cctctggcca cttgaaatgt cgcctgaaaa   1800
tggataaact tagattgaag ggcgtgtcat actccttgtg taccgcagcg ttcacattca   1860
ccaagatccc ggctgaaaca ctgcacggga cagtcacagt ggaggtacag tacgcaggga   1920
cagatggacc ttgcaaggtt ccagctcaga tggcggtgga catgcaaact ctgaccccag   1980
ttgggaggtt gataaccgct aaccccgtaa tcactgaaag cactgagaac tctaagatga   2040
tgctggaact tgatccacca tttggggact cttacattgt cataggagtc ggggagaaga   2100
agatcaccca ccactggcac aggagtggca gcaccattgg aaaagcattt gaagccactg   2160
tgagaggtgc caagagaatg gcagtcttgg gagacacagc ctgggacttt ggatcagttg   2220
gaggcgctct caactcattg ggcaagggca tccatcaaat ttttggagca gctttcaaat   2280
cattgtttgg aggaatgtcc tggttctcac aaattctcat tggaacgttg ctgatgtggt   2340
tgggtctgaa cacaaagaat ggatctattt ccccttatgtg cttggcctta gggggagtgt   2400
tgatcttctt atccacagct gtctctgctg atgtggggtg ctcggtggac ttctcaaaga   2460
aggagacgag atgcggtaca ggggtgttcg tctataacga cgttgaagcc tggagggaca   2520
ggtacaagta ccatcctgac tccccccgta gattggcagc agcagtcaag caagcctggg   2580
aagatggtat ctgtgggatc tcctctgttt caagaatgga aaacatcatg tggagatcag   2640
tagaagggga gctcaacgca atcctggaag agaatggagt tcaactgacg gtcgttgtgg   2700
gatctgtaaa aaaccccatg tggagaggtc cacagagatt gcccgtgcct gtgaacgagc   2760
tgccccacgg ctggaaggct tgggggaaat cgtacttcgt cagagcagca aagacaaata   2820
acagctttgt cgtggatggt gacacactga aggaatgccc actcaaacat agagcatgga   2880
acagctttct tgtggaggat catgggttcg gggtatttca cactagtgtc tggctcaagg   2940
ttagagaaga ttattcatta gagtgtgatc cagccgttat tggaacagct gttaagggaa   3000
aggaggctgt acacagtgat ctaggctact ggattgagag tgagaagaat gacacatgga   3060
ggctgaagag ggcccatctg atcgagatga aaacatgtga atggccaaag tcccacacat   3120
```

-continued tgtggacaga tggaatagaa gagagtgatc tgatcatacc caagtcttta gctgggccac 3180
tcagccatca caataccaga gagggctaca ggacccaaat gaaagggcca tggcacagtg 3240
aagagcttga aattcggttt gaggaatgcc caggcactaa ggtccacgtg gaggaaacat 3300
gtggaacaag aggaccatct ctgagatcaa ccactgcaag cggaagggtg atcgaggaat 3360
ggtgctgcag ggagtgcaca atgcccccac tgtcgttccg ggctaaagat ggctgttggt 3420
atggaatgga gataaggccc aggaaagaac cagaaagtaa cttagtaagg tcaatggtga 3480
ctgcaggatc aactgatcac atggatcact tctcccttgg agtgcttgtg attctgctca 3540
tggtgcagga agggctgaag aagagaatga ccacaaagat catcataagc acatcgatgg 3600
cagtgctggt agctatgatc ctgggaggat tttcaatgag tgacctggct aagcttgcaa 3660
ttttgatggg tgccaccttc gcggaaatga acactggagg agatgtagct catctggcgc 3720
tgatagcggc attcaaagtc agaccagcgt tgctggtatc tttcatcttc agagctaatt 3780
ggacaccccg tgaaagcatg ctgctggcct tggcctcgtg tcttttgcaa actgcgatct 3840
ccgccttgga aggcgacctg atggttctca tcaatggttt tgctttggcc tggttggcaa 3900
tacgagcgat ggttgttcca cgcactgata acatcacctt ggcaatcctg gctgctctga 3960
caccactggc ccggggcaca ctgcttgtgg cgtggagagc aggccttgct acttgcgggg 4020
ggtttatgct cctctctctg aagggaaaag gcagtgtgaa gaagaactta ccatttgtca 4080
tggccctggg actaaccgct gtgaggctgg tcgaccccat caacgtggtg ggactgctgt 4140
tgctcacaag gagtgggaag cggagctggc cccctagcga agtactcaca gctgttggcc 4200
tgatatgcgc attggctgga gggttcgcca aggcagatat agagatggct gggcccatgg 4260
ccgcggtcgg tctgctaatt gtcagttacg tggtctcagg aaagagtgtg gacatgtaca 4320
ttgaaagagc aggtgacatc acatgggaaa aagatgcgga agtcactgga aacagtcccc 4380
ggctcgatgt ggcgctagat gagagtggtg atttctccct ggtggaggat gacggtcccc 4440
ccatgagaga gatcatactc aaggtggtcc tgatgaccat ctgtggcatg aacccaatag 4500
ccataccctt tgcagctgga gcgtggtacg tatacgtgaa gactggaaaa aggagtggtg 4560
ctctatggga tgtgcctgct cccaaggaag taaaaaaggg ggagaccaca gatggagtgt 4620
acagagtaat gactcgtaga ctgctaggtt caacacaagt tggagtggga gttatgcaag 4680
agggggtctt tcacactatg tggcacgtca caaaaggatc cgcgctgaga agcggtgaag 4740
ggagacttga tccatactgg ggagatgtca agcaggatct ggtgtcatac tgtggtccat 4800
ggaagctaga tgccgcctgg gacgggcaca gcgaggtgca gctcttggcc gtgccccccg 4860
gagagagagc gaggaacatc cagactctgc ccggaatatt taagacaaag gatggggaca 4920
ttggagcggt tgcgctggat tacccagcag gaacttcagg atctccaatc ctagacaagt 4980
gtgggagagt gataggactt tatggcaatg gggtcgtgat caaaaatggg agttatgtta 5040
gtgccatcac ccaagggagg agggaggaag agactcctgt tgagtgcttc gagccttcga 5100
tgctgaagaa gaagcagcta actgtcttag acttgcatcc tggagctggg aaaaccagga 5160
gagttcttcc tgaaatagtc cgtgaagcca taaaaacaag actccgtact gtgatcttag 5220
ctccaaccag ggttgtcgct gctgaaatgg aggaagccct tagagggctt ccagtgcgtt 5280
atatgacaac agcagtcaat gtcacccact ctggaacaga aatcgtcgac ttaatgtgcc 5340
atgccacctt cacttcacgt ctactacagc caatcagagt ccccaactat aatctgtata 5400
ttatggatga ggcccacttc acagatccct caagtatagc agcaagagga tacatttcaa 5460

```
caagggttga gatgggcgag gcggctgcca tcttcatgac cgccacgcca ccaggaaccc   5520
gtgacgcatt tccggactcc aactcaccaa ttatggacac cgaagtggaa gtcccagaga   5580
gagcctggag ctcaggcttt gattgggtga cggatcattc tggaaaaaca gtttggtttg   5640
ttccaagcgt gaggaacggc aatgagatcg cagcttgtct gacaaaggct ggaaaacggg   5700
tcatacagct cagcagaaag acttttgaga cagagttcca gaaaacaaaa catcaagagt   5760
gggactttgt cgtgacaact gacatttcag agatgggcgc caactttaaa gctgaccgtg   5820
tcatagattc caggagatgc ctaaagccgg tcatacttga tggcgagaga gtcattctgg   5880
ctggacccat gcctgtcaca catgccagcg ctgcccagag gagggggcgc ataggcagga   5940
atcccaacaa acctggagat gagtatctgt atggaggtgg gtgcgcagag actgacgaag   6000
accatgcaca ctggcttgaa gcaagaatgc tccttgacaa tatttacctc caagatggcc   6060
tcatagcctc gctctatcga cctgaggccg acaaagtagc agccattgag ggagagttca   6120
agcttaggac ggagcaaagg aagacctttg tggaactcat gaaaagagga gatcttcctg   6180
tttggctggc ctatcaggtt gcatctgccg gaataaccta cacagataga agatggtgct   6240
ttgatggcac gaccaacaac accataatgg aagacagtgt gccggcagag gtgtggacca   6300
gacacggaga gaaaagagtg ctcaaaccga ggtggatgga cgccagagtt tgttcagatc   6360
atgcggccct gaagtcattc aaggagtttg ccgctgggaa aagaggagcg gcttttggag   6420
tgatggaagc cctgggaaca ctgccaggac acatgacaga gagattccag gaagccattg   6480
acaacctcgc tgtgctcatg cgggcagaga ctggaagcag gccttacaaa gccgcggcgg   6540
cccaattgcc ggagacccta gagaccatta tgcttttggg gttgctggga acagtctcgc   6600
tgggaatctt tttcgtcttg atgaggaaca agggcatagg gaagatgggc tttggaatgg   6660
tgactcttgg ggccagcgca tggctcatgt ggctctcgga aattgagcca gccagaattg   6720
catgtgtcct cattgttgtg ttcctattgc tggtggtgct catacctgag ccagaaaagc   6780
aaagatctcc ccaggacaac caaatggcaa tcatcatcat ggtagcagta ggtcttctgg   6840
gcttgattac cgccaatgaa ctcggatggt tggagagaac aaagagtgac ctaagccatc   6900
taatgggaag gagagaggag ggggcaacca taggattctc aatggacatt gacctgcggc   6960
cagcctcagc ttgggccatc tatgctgcct tgacaacttt cattacccca gccgtccaac   7020
atgcagtgac cacttcatac aacaactact ccttaatggc gatggccacg caagctggag   7080
tgttgtttgg tatgggcaaa gggatgccat tctacgcatg ggactttgga gtcccgctgc   7140
taatgatagg ttgctactca caattaacac ccctgaccct aatagtggcc atcattttgc   7200
tcgtggcgca ctacatgtac ttgatcccag ggctgcaggc agcagctgcg cgtgctgccc   7260
agaagagaac ggcagctggc atcatgaaga accctgttgt ggatggaata gtggtgactg   7320
acattgacac aatgacaatt gacccccaag tggagaaaaa gatgggacag gtgctactca   7380
tagcagtagc cgtctccagc gccatactgt cgcggaccgc ctgggggtgg ggggaggctg   7440
gggccctgat cacagcggca acttccactt tgtgggaagg ctctccgaac aagtactgga   7500
actcctctac agccacttca ctgtgtaaca tttttagggg aagttacttg gctggagctt   7560
ctctaatcta cacagtaaca agaaacgctg gcttggtcaa gagacgtggg ggtggaacag   7620
gagagaccct gggagagaaa tggaaggccc gcttgaacca gatgtcggcc ctggagttct   7680
actcctacaa aaagtcaggc atcaccgagg tgtgcagaga agaggcccgc cgcgccctca   7740
aggacggtgt ggcaacggga ggccatgctg tgtcccgagg aagtgcaaag ctgagatggt   7800
tggtggagcg gggatacctg cagccctatg gaaaggtcat tgatcttgga tgtggcagag   7860
```

```
ggggctggag ttactacgcc gccaccatcc gcaaagttca agaagtgaaa ggatacacaa   7920
aaggaggccc tggtcatgaa gaacccatgt tggtgcaaag ctatgggtgg aacatagtcc   7980
gtcttaagag tggggtggac gtctttcata tggcggctga gccgtgtgac acgttgctgt   8040
gtgacatagg tgagtcatca tctagtcctg aagtggaaga agcacggacg ctcagagtcc   8100
tctccatggt gggggattgg cttgaaaaaa gaccaggagc cttttgtata aaagtgttgt   8160
gcccatacac cagcactatg atggaaaccc tggagcgact gcagcgtagg tatgggggag   8220
gactggtcag agtgccactc tcccgcaact ctacacatga gatgtactgg gtctctggag   8280
cgaaaagcaa caccataaaa agtgtgtcca ccacgagcca gctcctcttg ggcgcatgg    8340
acgggcccag gaggccagtg aaatatgagg aggatgtgaa tctcggctct ggcacgcggg   8400
ctgtggtaag ctgcgctgaa gctcccaaca tgaagatcat tggtaaccgc attgaaagga   8460
tccgcagtga gcacgcggaa acgtggttct ttgacgagaa ccacccatat aggacatggg   8520
cttaccatgg aagctatgag gcccccacac aagggtcagc gtcctctcta ataaacgggg   8580
ttgtcaggct cctgtcaaaa ccctgggatg tggtgactgg agtcacagga atagccatga   8640
ccgacaccac accgtatggt cagcaaagag ttttcaagga aaaagtggac actagggtgc   8700
cagaccccca agaaggcact cgtcaggtta tgagcatggt ctcttcctgg ttgtggaaag   8760
agctaggcaa acacaaacgg ccacgagtct gtaccaaaga agagttcatc aacaaggttc   8820
gtagcaatgc agcattaggg gcaatatttg aagaggaaaa agagtggaag actgcagtgg   8880
aagctgtgaa cgatccaagg ttctgggctc tagtggacaa ggaaagagag caccacctga   8940
gaggagagtg ccagagttgt gtgtacaaca tgatgggaaa aagagaaaag aaacaagggg   9000
aatttggaaa ggccaagggc agccgcgcca tctggtatat gtggctaggg gctagatttc   9060
tagagttcga agcccttgga ttcttgaacg aggatcactg gatggggaga gagaactcag   9120
gaggtggtgt tgaagggctg ggattacaaa gactcggata tgtcctagaa gagatgagtc   9180
gcataccagg aggaaggatg tatgcagatg acactgctgg ctgggacacc cgcatcagca   9240
ggtttgatct ggagaatgaa gctctaatca ccaaccaaat ggagaaaggg cacagggcct   9300
tggcattggc cataatcaag tacacatacc aaaacaaagt ggtaaaggtc cttagaccag   9360
ctgaaaaagg gaagacagtt atggacatta tttcgagaca agaccaaagg gggagcggac   9420
aagttgtcac ttacgctctt aacacattta ccaacctagt ggtgcaactc attcggaata   9480
tggaggctga ggaagttcta gagatgcaag acttgtggct gctgcggagg tcagagaaag   9540
tgaccaactg gttgcagagc aacggatggg ataggctcaa acgaatggca gtcagtggag   9600
atgattgcgt tgtgaagcca attgatgata ggtttgcaca tgccctcagg ttcttgaatg   9660
atatgggaaa agttaggaag gacacacaag agtggaaacc ctcaactgga tgggacaact   9720
gggaagaagt tccgttttgc tcccaccact tcaacaagct ccatctcaag gacgggaggt   9780
ccattgtggt tccctgccgc caccaagatg aactgattgg ccgggcccgc gtctctccag   9840
gggcgggatg gagcatccgg gagactgctt gcctagcaaa atcatatgcg caaatgtggc   9900
agctccttta tttccacaga agggacctcc gactgatggc caatgccatt tgttcatctg   9960
tgccagttga ctgggttcca actgggagaa ctacctggtc aatccatgga aagggagaat  10020
ggatgaccac tgaagacatg cttgtggtgt ggaacagagt gtggattgag gagaacgacc  10080
acatggaaga caagacccca gttacgaaat ggacagacat tccctatttg ggaaaaaggg  10140
aagacttgtg gtgtggatct ctcatagggc acagaccgcg caccacctgg gctgagaaca  10200
```

-continued

```
ttaaaaacac agtcaacatg gtgcgcagga tcataggtga tgaagaaaag tacatggact  10260

acctatccac ccaagttcgc tacttgggtg aagaagggtc tacacctgga gtgctgtaag  10320

caccaatctt agtgttgtca ggcctgctag tcagccacag cttggggaaa gctgtgcagc  10380

ctgtgacccc cccaggagaa gctgggaaac caagcctata gtcaggccga gaacgccatg  10440

gcacggaaga agccatgctg cctgtgagcc cctcagagga cactgagtca aaaaacccca  10500

cgcgcttgga ggcgcaggat gggaaaagaa ggtggcgacc ttccccaccc ttcaatctgg  10560

ggcctgaact ggagatcagc tgtggatctc cagaagaggg actagtggtt agaggag     10617


<210> SEQ ID NO 14
<211> LENGTH: 498
<212> TYPE: PRT
<213> ORGANISM: Zika virus

<400> SEQUENCE: 14

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Glu Asn Arg Ala Lys
145                 150                 155                 160

Val Glu Val Thr Pro Asn Ser Pro Arg Ala Glu Ala Thr Leu Gly Gly
                165                 170                 175

Phe Gly Ser Leu Gly Leu Asp Cys Glu Pro Arg Thr Gly Leu Asp Phe
            180                 185                 190

Ser Asp Leu Tyr Tyr Leu Thr Met Asn Asn Lys His Trp Leu Val His
        195                 200                 205

Lys Glu Trp Phe His Asp Ile Pro Leu Pro Trp His Ala Gly Ala Asp
    210                 215                 220

Thr Gly Thr Pro His Trp Asn Asn Lys Glu Ala Leu Val Glu Phe Lys
225                 230                 235                 240

Asp Ala His Ala Lys Arg Gln Thr Val Val Val Leu Gly Ser Gln Glu
                245                 250                 255

Gly Ala Val His Thr Ala Leu Ala Gly Ala Leu Glu Ala Glu Met Asp
            260                 265                 270

Gly Ala Lys Gly Arg Leu Phe Ser Gly His Leu Lys Cys Arg Leu Lys
        275                 280                 285

Met Asp Lys Leu Arg Leu Lys Gly Val Ser Tyr Ser Leu Cys Thr Ala
    290                 295                 300
```

```
Ala Phe Thr Phe Thr Lys Val Pro Ala Glu Thr Leu His Gly Thr Val
305                 310                 315                 320

Thr Val Glu Val Gln Tyr Ala Gly Thr Asp Gly Pro Cys Lys Val Pro
                325                 330                 335

Ala Gln Met Ala Val Asp Met Gln Thr Leu Thr Pro Val Gly Arg Leu
            340                 345                 350

Ile Thr Ala Asn Pro Val Ile Thr Glu Ser Thr Glu Asn Ser Lys Met
        355                 360                 365

Met Leu Glu Leu Asp Pro Pro Phe Gly Asp Ser Tyr Ile Val Ile Gly
    370                 375                 380

Val Gly Asp Lys Lys Ile Thr His His Trp His Arg Ser Gly Ser Thr
385                 390                 395                 400

Ile Gly Lys Ala Phe Glu Ala Thr Val Arg Gly Ala Lys Arg Met Ala
                405                 410                 415

Val Leu Gly Asp Thr Ala Trp Asp Phe Gly Ser Val Gly Gly Val Phe
            420                 425                 430

Asn Ser Leu Gly Lys Gly Ile His Gln Ile Phe Gly Ala Ala Phe Lys
        435                 440                 445

Ser Leu Phe Gly Gly Met Ser Trp Phe Ser Gln Ile Leu Ile Gly Thr
    450                 455                 460

Leu Leu Val Trp Leu Gly Leu Asn Thr Lys Asn Gly Ser Ile Ser Leu
465                 470                 475                 480

Thr Cys Leu Ala Leu Gly Gly Val Met Ile Phe Leu Ser Thr Ala Val
                485                 490                 495

Ser Ala


<210> SEQ ID NO 15
<211> LENGTH: 498
<212> TYPE: PRT
<213> ORGANISM: Zika virus

<400> SEQUENCE: 15

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Glu Asn Arg Ala Lys
145                 150                 155                 160

Val Glu Val Thr Pro Asn Ser Pro Arg Ala Glu Ala Thr Leu Gly Gly
                165                 170                 175
```

```
Phe Gly Ser Leu Gly Leu Asp Cys Glu Pro Arg Thr Gly Leu Asp Phe
            180                 185                 190

Ser Asp Leu Tyr Tyr Leu Thr Met Asn Asn Lys His Trp Leu Val His
        195                 200                 205

Lys Glu Trp Phe His Asp Ile Pro Leu Pro Trp His Ser Gly Ala Asp
    210                 215                 220

Thr Glu Thr Pro His Trp Asn Asn Lys Glu Ala Leu Val Glu Phe Lys
225                 230                 235                 240

Asp Ala His Ala Lys Arg Gln Thr Val Val Val Leu Gly Ser Gln Glu
                245                 250                 255

Gly Ala Val His Thr Ala Leu Ala Gly Ala Leu Glu Ala Glu Met Asp
            260                 265                 270

Gly Ala Lys Gly Arg Leu Ser Ser Gly His Leu Lys Cys Arg Leu Lys
        275                 280                 285

Met Asp Lys Leu Arg Leu Lys Gly Val Ser Tyr Ser Leu Cys Thr Ala
    290                 295                 300

Ala Phe Thr Phe Thr Lys Val Pro Ala Glu Thr Leu His Gly Thr Val
305                 310                 315                 320

Thr Val Glu Val Gln Tyr Ala Gly Arg Asp Gly Pro Cys Lys Val Pro
                325                 330                 335

Ala Gln Met Ala Val Asp Met Gln Thr Leu Thr Pro Val Gly Arg Leu
            340                 345                 350

Ile Thr Ala Asn Pro Val Ile Thr Glu Ser Thr Glu Asn Ser Lys Met
        355                 360                 365

Met Leu Glu Leu Asp Pro Pro Phe Gly Asp Ser Tyr Ile Val Ile Gly
    370                 375                 380

Val Gly Asp Lys Lys Ile Thr His His Trp His Arg Ser Gly Ser Ile
385                 390                 395                 400

Ile Gly Lys Ala Phe Glu Ala Thr Val Arg Gly Ala Lys Arg Met Ala
                405                 410                 415

Val Leu Gly Asp Thr Ala Trp Asp Phe Gly Ser Val Gly Gly Val Phe
            420                 425                 430

Asn Ser Leu Gly Lys Gly Ile His Gln Ile Phe Gly Ala Ala Phe Lys
        435                 440                 445

Ser Leu Phe Gly Gly Met Ser Trp Phe Ser Gln Ile Leu Ile Gly Thr
    450                 455                 460

Leu Leu Val Trp Leu Gly Leu Asn Thr Lys Asn Gly Ser Ile Ser Leu
465                 470                 475                 480

Thr Cys Leu Ala Leu Gly Gly Val Met Ile Phe Leu Ser Thr Ala Val
                485                 490                 495

Ser Ala


<210> SEQ ID NO 16
<211> LENGTH: 504
<212> TYPE: PRT
<213> ORGANISM: Zika virus
<220> FEATURE:
<221> NAME/KEY: misc_feature
<222> LOCATION: (156)..(162)
<223> OTHER INFORMATION: X=any amino acid

<400> SEQUENCE: 16

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30
```

-continued

```
Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Xaa Xaa Xaa Xaa Xaa
145                 150                 155                 160

Xaa Xaa Asn Arg Ala Glu Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445
```

```
Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500


<210> SEQ ID NO 17
<211> LENGTH: 504
<212> TYPE: PRT
<213> ORGANISM: Zika virus
<220> FEATURE:
<221> NAME/KEY: misc_feature
<222> LOCATION: (152)..(156)
<223> OTHER INFORMATION: X=any amino acid

<400> SEQUENCE: 17

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Xaa Xaa Xaa Xaa Xaa Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Arg Leu Val Arg Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
```

```
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

Leu Lys Lys Gly Ser Ser Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Val His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500


<210> SEQ ID NO 18
<211> LENGTH: 504
<212> TYPE: PRT
<213> ORGANISM: Zika virus

<400> SEQUENCE: 18

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Ile Gly His Glu Thr
145                 150                 155                 160
```

-continued

```
Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500


<210> SEQ ID NO 19
<211> LENGTH: 504
<212> TYPE: PRT
<213> ORGANISM: Zika virus

<400> SEQUENCE: 19

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30
```

-continued

```
Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445
```

```
Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500


<210> SEQ ID NO 20
<211> LENGTH: 504
<212> TYPE: PRT
<213> ORGANISM: Zika virus

<400> SEQUENCE: 20

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320
```

-continued

```
Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Val His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500


<210> SEQ ID NO 21
<211> LENGTH: 504
<212> TYPE: PRT
<213> ORGANISM: Zika virus

<400> SEQUENCE: 21

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
```

```
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Val His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500


<210> SEQ ID NO 22
<211> LENGTH: 504
<212> TYPE: PRT
<213> ORGANISM: Zika virus

<400> SEQUENCE: 22

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45
```

-continued

```
Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
```

```
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500


<210> SEQ ID NO 23
<211> LENGTH: 504
<212> TYPE: PRT
<213> ORGANISM: Zika virus

<400> SEQUENCE: 23

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Thr Val Asn Asp Ile Gly Tyr Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Lys Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335
```

```
Gly Pro Cys Lys Ile Pro Val Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500


<210> SEQ ID NO 24
<211> LENGTH: 504
<212> TYPE: PRT
<213> ORGANISM: Zika virus

<400> SEQUENCE: 24

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Thr Val Asn Asp Ile Gly Tyr Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205
```

```
Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Lys Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Ile Pro Val Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500
```

<210> SEQ ID NO 25
<211> LENGTH: 504
<212> TYPE: PRT
<213> ORGANISM: Zika virus

<400> SEQUENCE: 25

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
```

```
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly Tyr Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Lys Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Ile Pro Val Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495
```

```
Phe Leu Ser Thr Ala Val Ser Ala
            500


<210> SEQ ID NO 26
<211> LENGTH: 504
<212> TYPE: PRT
<213> ORGANISM: Zika virus

<400> SEQUENCE: 26

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Val Cys Thr Ala Ala Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
```

-continued

```
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500


<210> SEQ ID NO 27
<211> LENGTH: 500
<212> TYPE: PRT
<213> ORGANISM: Zika virus

<400> SEQUENCE: 27

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Gly Tyr Glu Thr Asp Glu Asp Arg
145                 150                 155                 160

Ala Lys Val Glu Val Thr Pro Asn Ser Pro Arg Ala Glu Ala Thr Leu
                165                 170                 175

Gly Gly Phe Gly Ser Leu Gly Leu Asp Cys Glu Pro Arg Thr Gly Leu
            180                 185                 190

Asp Phe Ser Asp Leu Tyr Tyr Leu Thr Met Asn Asn Lys His Trp Leu
        195                 200                 205

Val His Lys Glu Trp Phe His Asp Ile Pro Leu Pro Trp His Ala Gly
    210                 215                 220
```

-continued

```
Ala Asp Thr Gly Thr Pro His Trp Asn Asn Lys Glu Ala Leu Val Glu
225                 230                 235                 240

Phe Lys Asp Ala His Ala Lys Arg Gln Thr Val Val Val Leu Gly Ser
                245                 250                 255

Gln Glu Gly Ala Val His Thr Ala Leu Ala Gly Ala Leu Glu Ala Glu
            260                 265                 270

Met Asp Gly Ala Lys Gly Arg Leu Phe Ser Gly His Leu Lys Cys Arg
        275                 280                 285

Leu Lys Met Asp Lys Leu Arg Leu Lys Gly Val Ser Tyr Ser Leu Cys
    290                 295                 300

Thr Ala Ala Phe Thr Phe Thr Lys Val Pro Ala Glu Thr Leu His Gly
305                 310                 315                 320

Thr Val Thr Val Glu Val Gln Tyr Ala Gly Thr Asp Gly Pro Cys Lys
                325                 330                 335

Ile Pro Val Gln Met Ala Val Asp Met Gln Thr Leu Thr Pro Val Gly
            340                 345                 350

Arg Leu Ile Thr Ala Asn Pro Val Ile Thr Glu Ser Thr Glu Asn Ser
        355                 360                 365

Lys Met Met Leu Glu Leu Asp Pro Pro Phe Gly Asp Ser Tyr Ile Val
    370                 375                 380

Ile Gly Val Gly Asp Lys Lys Ile Thr His His Trp His Arg Ser Gly
385                 390                 395                 400

Ser Thr Ile Gly Lys Ala Phe Glu Ala Thr Val Arg Gly Ala Lys Arg
                405                 410                 415

Met Ala Val Leu Gly Asp Thr Ala Trp Asp Phe Gly Ser Val Gly Gly
            420                 425                 430

Val Phe Asn Ser Leu Gly Lys Gly Ile His Gln Ile Phe Gly Ala Ala
        435                 440                 445

Phe Lys Ser Leu Phe Gly Gly Met Ser Trp Phe Ser Gln Ile Leu Ile
    450                 455                 460

Gly Thr Leu Leu Val Trp Leu Gly Leu Asn Thr Lys Asn Gly Ser Ile
465                 470                 475                 480

Ser Leu Thr Cys Leu Ala Leu Gly Gly Val Met Ile Phe Leu Ser Thr
                485                 490                 495

Ala Val Ser Ala
            500


<210> SEQ ID NO 28
<211> LENGTH: 500
<212> TYPE: PRT
<213> ORGANISM: Zika virus

<400> SEQUENCE: 28

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95
```

-continued

```
Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Gly Tyr Glu Thr Asp Glu Asp Arg
145                 150                 155                 160

Ala Lys Val Glu Val Thr Pro Asn Ser Pro Arg Ala Glu Ala Thr Leu
                165                 170                 175

Gly Gly Phe Gly Ser Leu Gly Leu Asp Cys Glu Pro Arg Thr Gly Leu
            180                 185                 190

Asp Phe Ser Asp Leu Tyr Tyr Leu Thr Met Asn Asn Lys His Trp Leu
        195                 200                 205

Val His Lys Glu Trp Phe His Asp Ile Pro Leu Pro Trp His Ala Gly
    210                 215                 220

Ala Asp Thr Gly Thr Pro His Trp Asn Asn Lys Glu Ala Leu Val Glu
225                 230                 235                 240

Phe Lys Asp Ala His Ala Lys Arg Gln Thr Val Val Val Leu Gly Ser
                245                 250                 255

Gln Glu Gly Ala Val His Thr Ala Leu Ala Gly Ala Leu Glu Ala Glu
            260                 265                 270

Met Asp Gly Ala Lys Gly Arg Leu Phe Ser Gly His Leu Lys Cys Arg
        275                 280                 285

Leu Lys Met Asp Lys Leu Arg Leu Lys Gly Val Ser Tyr Ser Leu Cys
    290                 295                 300

Thr Ala Ala Phe Thr Phe Thr Lys Val Pro Ala Glu Thr Leu His Gly
305                 310                 315                 320

Thr Val Thr Val Glu Val Gln Tyr Ala Gly Thr Asp Gly Pro Cys Lys
                325                 330                 335

Ile Pro Val Gln Met Ala Val Asp Met Gln Thr Leu Thr Pro Val Gly
            340                 345                 350

Arg Leu Ile Thr Ala Asn Pro Val Ile Thr Glu Ser Thr Glu Asn Ser
        355                 360                 365

Lys Met Met Leu Glu Leu Asp Pro Pro Phe Gly Asp Ser Tyr Ile Val
    370                 375                 380

Ile Gly Val Gly Asp Lys Lys Ile Thr His His Trp His Arg Ser Gly
385                 390                 395                 400

Ser Thr Ile Gly Lys Ala Phe Glu Ala Thr Val Arg Gly Ala Lys Arg
                405                 410                 415

Met Ala Val Leu Gly Asp Thr Ala Trp Asp Phe Gly Ser Val Gly Gly
            420                 425                 430

Val Phe Asn Ser Leu Gly Lys Gly Ile His Gln Ile Phe Gly Ala Ala
        435                 440                 445

Phe Lys Ser Leu Phe Gly Gly Met Ser Trp Phe Ser Gln Ile Leu Ile
    450                 455                 460

Gly Thr Leu Leu Val Trp Leu Gly Leu Asn Thr Lys Asn Gly Ser Ile
465                 470                 475                 480

Ser Leu Thr Cys Leu Ala Leu Gly Gly Val Met Ile Phe Leu Ser Thr
                485                 490                 495

Ala Val Ser Ala
            500
```

<210> SEQ ID NO 29
<211> LENGTH: 500
<212> TYPE: PRT
<213> ORGANISM: Zika virus

<400> SEQUENCE: 29

Ile Arg Cys Ile Gly Val Ser Asn Arg Asp Phe Val Glu Gly Met Ser
1 5 10 15

Gly Gly Thr Trp Val Asp Val Val Leu Glu His Gly Gly Cys Val Thr
20 25 30

Val Met Ala Gln Asp Lys Pro Thr Val Asp Ile Glu Leu Val Thr Thr
35 40 45

Thr Val Ser Asn Met Ala Glu Val Arg Ser Tyr Cys Tyr Glu Ala Ser
50 55 60

Ile Ser Asp Met Ala Ser Asp Ser Arg Cys Pro Thr Gln Gly Glu Ala
65 70 75 80

Tyr Leu Asp Lys Gln Ser Asp Thr Gln Tyr Val Cys Lys Arg Thr Leu
85 90 95

Val Asp Arg Gly Trp Gly Asn Gly Cys Gly Leu Phe Gly Lys Gly Ser
100 105 110

Leu Val Thr Cys Ala Lys Phe Thr Cys Ser Lys Lys Met Thr Gly Lys
115 120 125

Ser Ile Gln Pro Glu Asn Leu Glu Tyr Arg Ile Met Leu Ser Val His
130 135 140

Gly Ser Gln His Ser Gly Met Ile Gly Tyr Glu Thr Asp Glu Asp Arg
145 150 155 160

Ala Lys Val Glu Val Thr Pro Asn Ser Pro Arg Ala Glu Ala Thr Leu
165 170 175

Gly Gly Phe Gly Ser Leu Gly Leu Asp Cys Glu Pro Arg Thr Gly Leu
180 185 190

Asp Phe Ser Asp Leu Tyr Tyr Leu Thr Met Asn Asn Lys His Trp Leu
195 200 205

Val His Lys Glu Trp Phe His Asp Ile Pro Leu Pro Trp His Ala Gly
210 215 220

Ala Asp Thr Gly Thr Pro His Trp Asn Asn Lys Glu Ala Leu Val Glu
225 230 235 240

Phe Lys Asp Ala His Ala Lys Arg Gln Thr Val Val Val Leu Gly Ser
245 250 255

Gln Glu Gly Ala Val His Thr Ala Leu Ala Gly Ala Leu Glu Ala Glu
260 265 270

Met Asp Gly Ala Lys Gly Arg Leu Phe Ser Gly His Leu Lys Cys Arg
275 280 285

Leu Lys Met Asp Lys Leu Arg Leu Lys Gly Val Ser Tyr Ser Leu Cys
290 295 300

Thr Ala Ala Phe Thr Phe Thr Lys Val Pro Ala Glu Thr Leu His Gly
305 310 315 320

Thr Val Thr Val Glu Val Gln Tyr Ala Gly Thr Asp Gly Pro Cys Lys
325 330 335

Ile Pro Val Gln Met Ala Val Asp Met Gln Thr Leu Thr Pro Val Gly
340 345 350

Arg Leu Ile Thr Ala Asn Pro Val Ile Thr Glu Ser Thr Glu Asn Ser
355 360 365

Lys Met Met Leu Glu Leu Asp Pro Pro Phe Gly Asp Ser Tyr Ile Val
370 375 380

```
Ile Gly Val Gly Asp Lys Lys Ile Thr His His Trp His Arg Ser Gly
385                 390                 395                 400

Ser Thr Ile Gly Lys Ala Phe Glu Ala Thr Val Arg Gly Ala Lys Arg
                405                 410                 415

Met Ala Val Leu Gly Asp Thr Ala Trp Asp Phe Gly Ser Val Gly Gly
            420                 425                 430

Val Phe Asn Ser Leu Gly Lys Gly Ile His Gln Ile Phe Gly Ala Ala
        435                 440                 445

Phe Lys Ser Leu Phe Gly Gly Met Ser Trp Phe Ser Gln Ile Leu Ile
    450                 455                 460

Gly Thr Leu Leu Val Trp Leu Gly Leu Asn Thr Lys Asn Gly Ser Ile
465                 470                 475                 480

Ser Leu Thr Cys Leu Ala Leu Gly Gly Val Met Ile Phe Leu Ser Thr
                485                 490                 495

Ala Val Ser Ala
            500


<210> SEQ ID NO 30
<211> LENGTH: 504
<212> TYPE: PRT
<213> ORGANISM: Zika virus

<400> SEQUENCE: 30

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Thr Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
```

-continued

```
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Gly
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 31
<211> LENGTH: 504
<212> TYPE: PRT
<213> ORGANISM: Zika virus

<400> SEQUENCE: 31

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110
```

```
Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Thr Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Gly
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 32
<211> LENGTH: 504
<212> TYPE: PRT

<213> ORGANISM: Zika virus

<400> SEQUENCE: 32

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400
```

```
His Arg Ser Gly Ser Thr Ile Gly Lys Ala Phe Glu Ala Thr Val Arg
            405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 33
<211> LENGTH: 504
<212> TYPE: PRT
<213> ORGANISM: Zika virus

<400> SEQUENCE: 33

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270
```

Leu Glu Ala Glu Met Asp Gly Ala Lys Gly Arg Leu Ser Ser Gly His
275 280 285

Leu Lys Cys Arg Leu Lys Met Asp Lys Leu Arg Leu Lys Gly Val Ser
290 295 300

Tyr Ser Leu Cys Thr Ala Ala Phe Thr Phe Thr Lys Ile Pro Ala Glu
305 310 315 320

Thr Leu His Gly Thr Val Thr Val Glu Val Gln Tyr Ala Gly Thr Asp
325 330 335

Gly Pro Cys Lys Val Pro Ala Gln Met Ala Val Asp Met Gln Thr Leu
340 345 350

Thr Pro Val Gly Arg Leu Ile Thr Ala Asn Pro Val Ile Thr Glu Ser
355 360 365

Thr Glu Asn Ser Lys Met Met Leu Glu Leu Asp Pro Pro Phe Gly Asp
370 375 380

Ser Tyr Ile Val Ile Gly Val Gly Glu Lys Lys Ile Thr His His Trp
385 390 395 400

His Arg Ser Gly Ser Thr Ile Gly Lys Ala Phe Glu Ala Thr Val Arg
405 410 415

Gly Ala Lys Arg Met Ala Val Leu Gly Asp Thr Ala Trp Asp Phe Gly
420 425 430

Ser Val Gly Gly Ala Leu Asn Ser Leu Gly Lys Gly Ile His Gln Ile
435 440 445

Phe Gly Ala Ala Phe Lys Ser Leu Phe Gly Gly Met Ser Trp Phe Ser
450 455 460

Gln Ile Leu Ile Gly Thr Leu Leu Met Trp Leu Gly Leu Asn Thr Lys
465 470 475 480

Asn Gly Ser Ile Ser Leu Met Cys Leu Ala Leu Gly Gly Val Leu Ile
485 490 495

Phe Leu Ser Thr Ala Val Ser Ala
500

<210> SEQ ID NO 34
<211> LENGTH: 504
<212> TYPE: PRT
<213> ORGANISM: Zika virus

<400> SEQUENCE: 34

Ile Arg Cys Ile Gly Val Ser Asn Arg Asp Phe Val Glu Gly Met Ser
1 5 10 15

Gly Gly Thr Trp Val Asp Val Val Leu Glu His Gly Gly Cys Val Thr
20 25 30

Val Met Ala Gln Asp Lys Pro Thr Val Asp Ile Glu Leu Val Thr Thr
35 40 45

Thr Val Ser Asn Met Ala Glu Val Arg Ser Tyr Cys Tyr Glu Ala Ser
50 55 60

Ile Ser Asp Met Ala Ser Asp Ser Arg Cys Pro Thr Gln Gly Glu Ala
65 70 75 80

Tyr Leu Asp Lys Gln Ser Asp Thr Gln Tyr Val Cys Lys Arg Thr Leu
85 90 95

Val Asp Arg Gly Trp Gly Asn Gly Cys Gly Leu Phe Gly Lys Gly Ser
100 105 110

Leu Val Thr Cys Ala Lys Phe Ala Cys Ser Lys Lys Met Thr Gly Lys
115 120 125

Ser Ile Gln Pro Glu Asn Leu Glu Tyr Arg Ile Met Leu Ser Val His

-continued

```
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 35
<211> LENGTH: 504
<212> TYPE: PRT
<213> ORGANISM: Zika virus

<400> SEQUENCE: 35

-continued

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
```

```
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 36
<211> LENGTH: 504
<212> TYPE: PRT
<213> ORGANISM: Zika virus

<400> SEQUENCE: 36

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285
```

```
Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 37
<211> LENGTH: 504
<212> TYPE: PRT
<213> ORGANISM: Zika virus

<400> SEQUENCE: 37

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160
```

```
Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 38
<211> LENGTH: 504
<212> TYPE: PRT
<213> ORGANISM: Zika virus

<400> SEQUENCE: 38

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
```

-continued

```
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445
```

```
Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 39
<211> LENGTH: 504
<212> TYPE: PRT
<213> ORGANISM: Zika virus

<400> SEQUENCE: 39

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
```

-continued 305 310 315 320

Thr Leu His Gly Thr Val Thr Val Glu Val Gln Tyr Ala Gly Thr Asp
325 330 335

Gly Pro Cys Lys Val Pro Ala Gln Met Ala Val Asp Met Gln Thr Leu
340 345 350

Thr Pro Val Gly Arg Leu Ile Thr Ala Asn Pro Val Ile Thr Glu Ser
355 360 365

Thr Glu Asn Ser Lys Met Met Leu Glu Leu Asp Pro Pro Phe Gly Asp
370 375 380

Ser Tyr Ile Val Ile Gly Val Gly Glu Lys Lys Ile Thr His His Trp
385 390 395 400

His Arg Ser Gly Ser Thr Ile Gly Lys Ala Phe Glu Ala Thr Val Arg
405 410 415

Gly Ala Lys Arg Met Ala Val Leu Gly Asp Thr Ala Trp Asp Phe Gly
420 425 430

Ser Val Gly Gly Ala Leu Asn Ser Leu Gly Lys Gly Ile His Gln Ile
435 440 445

Phe Gly Ala Ala Phe Lys Ser Leu Phe Gly Gly Met Ser Trp Phe Ser
450 455 460

Gln Ile Leu Ile Gly Thr Leu Leu Met Trp Leu Gly Leu Asn Thr Lys
465 470 475 480

Asn Gly Ser Ile Ser Leu Met Cys Leu Ala Leu Gly Gly Val Leu Ile
485 490 495

Phe Leu Ser Thr Ala Val Ser Ala
500

<210> SEQ ID NO 40
<211> LENGTH: 504
<212> TYPE: PRT
<213> ORGANISM: Zika virus

<400> SEQUENCE: 40

Ile Arg Cys Ile Gly Val Ser Asn Arg Asp Phe Val Glu Gly Met Ser
1 5 10 15

Gly Gly Thr Trp Val Asp Val Val Leu Glu His Gly Gly Cys Val Thr
20 25 30

Val Met Ala Gln Asp Lys Pro Thr Val Asp Ile Glu Leu Val Thr Thr
35 40 45

Thr Val Ser Asn Met Ala Glu Val Arg Ser Tyr Cys Tyr Glu Ala Ser
50 55 60

Ile Ser Asp Met Ala Ser Asp Ser Arg Cys Pro Thr Gln Gly Glu Ala
65 70 75 80

Tyr Leu Asp Lys Gln Ser Asp Thr Gln Tyr Val Cys Lys Arg Thr Leu
85 90 95

Val Asp Arg Gly Trp Gly Asn Gly Cys Gly Leu Phe Gly Lys Gly Ser
100 105 110

Leu Val Thr Cys Ala Lys Phe Ala Cys Ser Lys Lys Met Thr Gly Lys
115 120 125

Ser Ile Gln Pro Glu Asn Leu Glu Tyr Arg Ile Met Leu Ser Val His
130 135 140

Gly Ser Gln His Ser Gly Met Ile Val Asn Asp Thr Gly His Glu Thr
145 150 155 160

Asp Glu Asn Arg Ala Lys Val Glu Ile Thr Pro Asn Ser Pro Arg Ala
165 170 175

-continued

```
Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 41
<211> LENGTH: 504
<212> TYPE: PRT
<213> ORGANISM: Zika virus

<400> SEQUENCE: 41

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45
```

-continued

```
Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460
```

```
Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 42
<211> LENGTH: 504
<212> TYPE: PRT
<213> ORGANISM: Zika virus

<400> SEQUENCE: 42

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335
```

```
Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 43
<211> LENGTH: 504
<212> TYPE: PRT
<213> ORGANISM: Zika virus

<400> SEQUENCE: 43

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
```

```
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 44
<211> LENGTH: 504
<212> TYPE: PRT
<213> ORGANISM: Zika virus

<400> SEQUENCE: 44

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60
```

-continued

```
Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
```

```
                485                 490                 495

Phe Leu Ser Thr Ala Val Ser Ala
            500


<210> SEQ ID NO 45
<211> LENGTH: 504
<212> TYPE: PRT
<213> ORGANISM: Zika virus

<400> SEQUENCE: 45

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350
```

-continued

```
Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 46
<211> LENGTH: 504
<212> TYPE: PRT
<213> ORGANISM: Zika virus

<400> SEQUENCE: 46

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220
```

```
Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 47
<211> LENGTH: 504
<212> TYPE: PRT
<213> ORGANISM: Zika virus

<400> SEQUENCE: 47

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
```

-continued

```
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 48
<211> LENGTH: 504
<212> TYPE: PRT
<213> ORGANISM: Zika virus

<400> SEQUENCE: 48

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
```

```
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 49
<211> LENGTH: 504
<212> TYPE: PRT
<213> ORGANISM: Zika virus

<400> SEQUENCE: 49

```
Ile Arg Cys Ile Gly Val Ser Asn Arg Asp Phe Val Glu Gly Met Ser
1               5                   10                  15

Gly Gly Thr Trp Val Asp Ile Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240
```

```
Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 50
<211> LENGTH: 504
<212> TYPE: PRT
<213> ORGANISM: Zika virus

<400> SEQUENCE: 50

```
Ile Arg Cys Ile Gly Val Ser Asn Arg Asp Phe Val Glu Gly Met Ser
1               5                   10                  15

Gly Gly Thr Trp Val Asp Ile Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110
```

```
Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 51
<211> LENGTH: 504

<212> TYPE: PRT
<213> ORGANISM: Zika virus

<400> SEQUENCE: 51

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Ile Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400
```

```
His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 52
<211> LENGTH: 504
<212> TYPE: PRT
<213> ORGANISM: Zika virus

<400> SEQUENCE: 52

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Thr Gln Glu Gly Ala Val His Thr Ala Leu Ala Gly Ala
```

```
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 53
<211> LENGTH: 504
<212> TYPE: PRT
<213> ORGANISM: Zika virus

<400> SEQUENCE: 53

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125
```

```
Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Thr Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 54
<211> LENGTH: 504
<212> TYPE: PRT
<213> ORGANISM: Zika virus

<400> SEQUENCE: 54

-continued

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415
```

```
Gly Ala Arg Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 55
<211> LENGTH: 504
<212> TYPE: PRT
<213> ORGANISM: Zika virus

<400> SEQUENCE: 55

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285
```

```
Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 56
<211> LENGTH: 504
<212> TYPE: PRT
<213> ORGANISM: Zika virus

<400> SEQUENCE: 56

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
```

145 150 155 160

Asp Glu Asn Arg Ala Lys Val Glu Ile Thr Pro Asn Ser Pro Arg Ala
165 170 175

Glu Ala Thr Leu Gly Gly Phe Gly Ser Leu Gly Leu Asp Cys Glu Pro
180 185 190

Arg Thr Gly Leu Asp Phe Ser Asp Leu Tyr Tyr Leu Thr Met Asn Asn
195 200 205

Lys His Trp Leu Val His Lys Glu Trp Phe His Asp Ile Pro Leu Pro
210 215 220

Trp His Ala Gly Ala Asp Thr Gly Thr Pro His Trp Asn Asn Lys Glu
225 230 235 240

Ala Leu Val Glu Phe Lys Asp Ala His Ala Lys Arg Gln Thr Val Val
245 250 255

Val Leu Gly Ser Gln Glu Gly Ala Val His Thr Ala Leu Ala Gly Ala
260 265 270

Leu Glu Ala Glu Met Asp Gly Ala Lys Gly Arg Leu Ser Ser Gly His
275 280 285

Leu Lys Cys Arg Leu Lys Met Asp Lys Leu Arg Leu Lys Gly Val Ser
290 295 300

Tyr Ser Leu Cys Thr Ala Ala Phe Thr Phe Thr Lys Ile Pro Ala Glu
305 310 315 320

Thr Leu His Gly Thr Val Thr Val Glu Val Gln Tyr Ala Gly Thr Asp
325 330 335

Gly Pro Cys Lys Val Pro Ala Gln Met Ala Val Asp Met Gln Thr Leu
340 345 350

Thr Pro Val Gly Arg Leu Ile Thr Ala Asn Pro Val Ile Thr Glu Ser
355 360 365

Thr Glu Asn Ser Lys Met Met Leu Glu Leu Asp Pro Pro Phe Gly Asp
370 375 380

Ser Tyr Ile Val Ile Gly Val Gly Glu Lys Lys Ile Thr His His Trp
385 390 395 400

His Arg Ser Gly Ser Thr Ile Gly Lys Ala Phe Glu Ala Thr Val Arg
405 410 415

Gly Ala Lys Arg Met Ala Val Leu Gly Asp Thr Ala Trp Asp Phe Gly
420 425 430

Ser Val Gly Gly Ala Leu Asn Ser Leu Gly Lys Gly Ile His Gln Ile
435 440 445

Phe Gly Ala Ala Phe Lys Ser Leu Phe Gly Gly Met Ser Trp Phe Ser
450 455 460

Gln Ile Leu Ile Gly Thr Leu Leu Met Trp Leu Gly Leu Asn Ala Lys
465 470 475 480

Asn Gly Ser Ile Ser Leu Met Cys Leu Ala Leu Gly Gly Val Leu Ile
485 490 495

Phe Leu Ser Thr Ala Val Ser Ala
500

<210> SEQ ID NO 57
<211> LENGTH: 504
<212> TYPE: PRT
<213> ORGANISM: Zika virus

<400> SEQUENCE: 57

Ile Arg Cys Ile Gly Val Ser Asn Arg Asp Phe Val Glu Gly Met Ser
1 5 10 15

```
Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
```

435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Ala Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 58
<211> LENGTH: 504
<212> TYPE: PRT
<213> ORGANISM: Zika virus

<400> SEQUENCE: 58

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

```
Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Thr Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 59
<211> LENGTH: 504
<212> TYPE: PRT
<213> ORGANISM: Zika virus

<400> SEQUENCE: 59

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Gly Thr Gly His Glu Thr
145                 150                 155                 160

Asp Glu Asn Arg Ala Lys Val Glu Ile Thr Pro Asn Ser Pro Arg Ala
                165                 170                 175
```

```
Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 60
<211> LENGTH: 504
<212> TYPE: PRT
<213> ORGANISM: Zika virus

<400> SEQUENCE: 60

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
```

-continued

```
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Leu Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460
```

Gln Ile Leu Ile Gly Thr Leu Leu Met Trp Leu Gly Leu Asn Thr Lys
465 470 475 480

Asn Gly Ser Ile Ser Leu Met Cys Leu Ala Leu Gly Gly Val Leu Ile
485 490 495

Phe Leu Ser Thr Ala Val Ser Ala
500

<210> SEQ ID NO 61
<211> LENGTH: 504
<212> TYPE: PRT
<213> ORGANISM: Zika virus

<400> SEQUENCE: 61

Ile Arg Cys Ile Gly Val Ser Asn Arg Asp Phe Val Glu Gly Met Ser
1 5 10 15

Gly Gly Thr Trp Val Asp Val Val Leu Glu His Gly Gly Cys Val Thr
20 25 30

Val Met Ala Gln Asp Lys Pro Ala Val Asp Ile Glu Leu Val Thr Thr
35 40 45

Thr Val Ser Asn Met Ala Glu Val Arg Ser Tyr Cys Tyr Glu Ala Ser
50 55 60

Ile Ser Asp Met Ala Ser Asp Ser Arg Cys Pro Thr Gln Gly Glu Ala
65 70 75 80

Tyr Leu Asp Lys Gln Ser Asp Thr Gln Tyr Val Cys Lys Arg Thr Leu
85 90 95

Val Asp Arg Gly Trp Gly Asn Gly Cys Gly Leu Phe Gly Lys Gly Ser
100 105 110

Leu Val Thr Cys Ala Lys Phe Ala Cys Ser Lys Lys Met Thr Gly Lys
115 120 125

Ser Ile Gln Pro Glu Asn Leu Glu Tyr Arg Ile Met Leu Ser Val His
130 135 140

Gly Ser Gln His Ser Gly Met Ile Val Asn Asp Thr Gly His Glu Thr
145 150 155 160

Asp Glu Asn Arg Ala Lys Val Glu Ile Thr Pro Asn Ser Pro Arg Ala
165 170 175

Glu Ala Thr Leu Gly Gly Phe Gly Ser Leu Gly Leu Asp Cys Glu Pro
180 185 190

Arg Thr Gly Leu Asp Phe Ser Asp Leu Tyr Tyr Leu Thr Met Asn Asn
195 200 205

Lys His Trp Leu Val His Lys Glu Trp Phe His Asp Ile Pro Leu Pro
210 215 220

Trp His Ala Gly Ala Asp Thr Gly Thr Pro His Trp Asn Asn Lys Glu
225 230 235 240

Ala Leu Val Glu Phe Lys Asp Ala His Ala Lys Arg Gln Thr Val Val
245 250 255

Val Leu Gly Ser Gln Glu Gly Ala Val His Thr Ala Leu Ala Gly Ala
260 265 270

Leu Glu Ala Glu Met Asp Gly Ala Lys Gly Arg Leu Ser Ser Gly His
275 280 285

Leu Lys Cys Arg Leu Lys Met Asp Lys Leu Arg Leu Lys Gly Val Ser
290 295 300

Tyr Ser Leu Cys Thr Ala Ala Phe Thr Phe Thr Lys Ile Pro Ala Glu
305 310 315 320

Thr Leu His Gly Thr Val Thr Val Glu Val Gln Tyr Ala Gly Thr Asp

```
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Leu Ile
                485                 490                 495

Phe Leu Ser Thr Ala Val Ser Ala
            500


<210> SEQ ID NO 62
<211> LENGTH: 504
<212> TYPE: PRT
<213> ORGANISM: Zika virus

<400> SEQUENCE: 62

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190
```

```
Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Leu Ile
                485                 490                 495

Phe Leu Ser Thr Ala Val Ser Ala
            500


<210> SEQ ID NO 63
<211> LENGTH: 504
<212> TYPE: PRT
<213> ORGANISM: Zika virus

<400> SEQUENCE: 63

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60
```

```
Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480
```

```
Asn Gly Ser Ile Ser Leu Thr Cys Leu Ala Leu Gly Gly Val Leu Ile
                485                 490                 495

Phe Leu Ser Thr Ala Val Ser Ala
            500


<210> SEQ ID NO 64
<211> LENGTH: 504
<212> TYPE: PRT
<213> ORGANISM: Zika virus

<400> SEQUENCE: 64

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Ser Thr
        35                  40                  45

Thr Val Ser Asn Met Ala Glu Val Arg Ser Tyr Cys Tyr Glu Ala Thr
    50                  55                  60

Ile Ser Asp Ile Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Ala Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350
```

```
Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 65
<211> LENGTH: 504
<212> TYPE: PRT
<213> ORGANISM: Zika virus
<220> FEATURE:
<221> NAME/KEY: misc_feature
<222> LOCATION: (1)..(504)
<223> OTHER INFORMATION: X=any amino acid

<400> SEQUENCE: 65

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Xaa Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190
```

```
Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

Xaa Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Leu Ile
                485                 490                 495

Phe Leu Ser Thr Ala Val Ser Ala
            500


<210> SEQ ID NO 66
<211> LENGTH: 504
<212> TYPE: PRT
<213> ORGANISM: Zika virus

<400> SEQUENCE: 66

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Ala Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60
```

```
Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Leu Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Ala His Lys Glu Trp Phe His Asp Ile Pro Leu Pro
    210                 215                 220

Trp His Ala Gly Ala Ala Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Val Asp Gly Thr Val Thr Val Glu Gly Gln Tyr Gly Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Ile Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480
```

```
Asn Gly Ser Ile Ser Leu Met Cys Leu Ala Leu Gly Gly Val Leu Ile
                485                 490                 495

Phe Leu Ser Thr Ala Val Ser Gly
            500


<210> SEQ ID NO 67
<211> LENGTH: 504
<212> TYPE: PRT
<213> ORGANISM: Zika virus

<400> SEQUENCE: 67

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Ala Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Leu Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Ala His Lys Glu Trp Phe His Asp Ile Pro Leu Pro
    210                 215                 220

Trp His Ala Gly Ala Ala Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Val Asp Gly Thr Val Thr Val Glu Gly Gln Tyr Gly Gly Thr Asp
                325                 330                 335

Gly Pro Cys Lys Val Pro Ala Gln Met Ala Val Asp Met Gln Thr Leu
            340                 345                 350
```

```
Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Ile Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Gly
            500


<210> SEQ ID NO 68
<211> LENGTH: 504
<212> TYPE: PRT
<213> ORGANISM: Zika virus

<400> SEQUENCE: 68

Ile Ser Cys Ile Gly Val Ser Asn Arg Asp Leu Val Glu Gly Met Ser
1               5                   10                  15

Gly Gly Thr Trp Val Asp Val Val Leu Glu His Gly Gly Cys Val Thr
            20                  25                  30

Glu Met Ala Gln Asp Lys Pro Thr Val Asp Ile Glu Leu Val Thr Met
        35                  40                  45

Thr Val Ser Asn Met Ala Glu Val Arg Ser Tyr Cys Tyr Glu Ala Ser
    50                  55                  60

Leu Ser Asp Met Ala Ser Ala Ser Arg Cys Pro Thr Gln Gly Glu Pro
65                  70                  75                  80

Ser Leu Asp Lys Gln Ser Asp Thr Gln Ser Val Cys Lys Arg Thr Leu
                85                  90                  95

Gly Asp Arg Gly Trp Gly Asn Gly Cys Gly Ile Phe Gly Lys Gly Ser
            100                 105                 110

Leu Val Thr Cys Ser Lys Phe Thr Cys Cys Lys Lys Met Pro Gly Lys
        115                 120                 125

Ser Ile Gln Pro Glu Asn Leu Glu Tyr Arg Ile Met Leu Pro Val His
    130                 135                 140

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
```

```
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Ser Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500


<210> SEQ ID NO 69
<211> LENGTH: 498
<212> TYPE: PRT
<213> ORGANISM: Zika virus

<400> SEQUENCE: 69

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80
```

-continued

```
Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Glu Asn Arg Ala Lys
145                 150                 155                 160

Val Glu Val Thr Pro Asn Ser Pro Arg Ala Glu Ala Thr Leu Gly Gly
                165                 170                 175

Phe Gly Ser Leu Gly Leu Asp Cys Glu Pro Arg Thr Gly Leu Asp Phe
            180                 185                 190

Ser Asp Leu Tyr Tyr Leu Thr Met Asn Asn Lys His Trp Leu Val His
        195                 200                 205

Lys Glu Trp Phe His Asp Ile Pro Leu Pro Trp His Ala Gly Ala Asp
    210                 215                 220

Thr Gly Thr Pro His Trp Asn Asn Lys Glu Ala Leu Val Glu Phe Lys
225                 230                 235                 240

Asp Ala His Ala Lys Arg Gln Thr Val Val Val Leu Gly Ser Gln Glu
                245                 250                 255

Gly Ala Val His Thr Ala Leu Ala Gly Ala Leu Glu Ala Glu Met Asp
            260                 265                 270

Gly Ala Lys Gly Arg Leu Phe Ser Gly His Leu Lys Cys Arg Leu Lys
        275                 280                 285

Met Asp Lys Leu Arg Leu Lys Gly Val Ser Tyr Ser Leu Cys Thr Ala
    290                 295                 300

Ala Phe Thr Phe Thr Lys Val Pro Ala Glu Thr Leu His Gly Thr Val
305                 310                 315                 320

Thr Val Glu Val Gln Tyr Ala Gly Thr Asp Gly Pro Cys Lys Val Pro
                325                 330                 335

Ala Gln Met Ala Val Asp Met Gln Thr Leu Thr Pro Val Gly Arg Leu
            340                 345                 350

Ile Thr Ala Asn Pro Val Ile Thr Glu Ser Thr Glu Asn Ser Lys Met
        355                 360                 365

Met Leu Glu Leu Asp Pro Pro Phe Gly Asp Ser Tyr Ile Val Ile Gly
    370                 375                 380

Val Gly Asp Lys Lys Ile Thr His His Trp His Arg Ser Gly Ser Thr
385                 390                 395                 400

Ile Gly Lys Ala Phe Glu Ala Thr Val Arg Gly Ala Lys Arg Met Ala
                405                 410                 415

Val Leu Gly Asp Thr Ala Trp Asp Phe Gly Ser Val Gly Gly Val Phe
            420                 425                 430

Asn Ser Leu Gly Lys Gly Ile His Gln Ile Phe Gly Ala Ala Phe Lys
        435                 440                 445

Ser Leu Phe Gly Gly Met Ser Trp Phe Ser Gln Ile Leu Ile Gly Thr
    450                 455                 460

Leu Leu Val Trp Leu Gly Leu Asn Thr Lys Asn Gly Ser Ile Ser Leu
465                 470                 475                 480

Thr Cys Leu Ala Leu Gly Gly Val Met Ile Phe Leu Ser Thr Ala Val
                485                 490                 495

Ser Ala
```

<210> SEQ ID NO 70
<211> LENGTH: 26
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(26)
<223> OTHER INFORMATION: n=inosine

<400> SEQUENCE: 70
ncncncncnc ncncncncnc ncncnc 26

<210> SEQ ID NO 71
<211> LENGTH: 11
<212> TYPE: PRT
<213> ORGANISM: Artificial Sequence
<220> FEATURE:
<223> OTHER INFORMATION: synthetic peptide

<400> SEQUENCE: 71

Lys Leu Lys Leu Leu Leu Leu Leu Lys Leu Lys
1 5 10

<210> SEQ ID NO 72
<211> LENGTH: 11840
<212> TYPE: DNA
<213> ORGANISM: Chikungunya virus

<400> SEQUENCE: 72
atggctgcgt gagacacacg tagcctacca gtttcttact gctctactct gcaaagcaag 60
agattaataa cccatcatgg atcctgtgta cgtggacata gacgctgaca gcgccttttt 120
gaaggccctg caacgtgcgt accccatgtt tgaggtggaa ccaaggcagg tcacaccgaa 180
tgaccatgct aatgctagag cgttctcgca tctagctata aaactaatag agcaggaaat 240
tgaccccgac tcaaccatcc tggatatcgg cagtgcgcca gcaaggagga tgatgtcgga 300
caggaagtac cactgcgtct gcccgatgcg cagtgcggaa gatcccgaga gactcgccaa 360
ttatgcgaga aagctagcat ctgccgcagg aaaagtcctg gacagaaaca tctctggaaa 420
gatcggggac ttacaagcag taatggccgt gccagacacg gagacgccaa cattctgctt 480
acacacagac gtctcatgta gacagagagc agacgtcgct atataccaag acgtctatgc 540
tgtacacgca cccacgtcgc tataccacca ggcgattaaa ggggtccgag tggcgtactg 600
ggttgggttc gacacaaccc cgttcatgta caatgccatg gcgggtgcct acccctcata 660
ctcgacaaac tgggcagatg agcaggtact gaaggctaag aacataggat tatgttcaac 720
agacctgacg gaaggtagac gaggcaagtt gtctattatg agagggaaaa agctaaaacc 780
gtgcgaccgt gtgctgttct cagtagggtc aacgctctac ccggaaagcc gcaagctact 840
taagagctgg cacctgccat cggtgttcca tttaaagggc aaactcagct tcacatgccg 900
ctgtgataca gtggtttcgt gtgagggcta cgtcgttaag agaataacga tgagcccagg 960
cctttatgga aaaaccacag ggtatgcggt aacccaccac gcagacggat tcctgatgtg 1020
caagactacc gacacggttg acggcgaaag artgtcattc tcggtgtgca catacgtgcc 1080
ggcgaccatt tgtgatcaaa tgaccggcat ccttgctaca gaagtcacgc cggaggatgc 1140
acagaagctg ttggtggggc tgaaccagag aatagtggtt aacggcagaa cgcaacggaa 1200
tacgaacacc atgaaaaatt atctgcttcc cgtggtcgcc caagccttca gtaagtgggc 1260
aaaggagtgc cggaaagaca tggaagatga aaaactcctg ggggtcagag aaagaacact 1320
gacctgctgc tgtctatggg cattcaagaa gcagaaaaca cacacggtct acaagaggcc 1380
tgatacccag tcaattcaga aggttcaggc cgagtttgac agctttgtgg taccgagtct 1440
gtggtcgtcc gggttgtcaa tccctttgag gactagaatc aaatggttgt taagcaaggt 1500
gccaaaaacc gacctgatcc catacagcgg agacgcccga gaagcccggg acgcagaaaa 1560
agaagcagag gaagaacgag aagcagaact gactcgcgaa gccctaccac ctctacaggc 1620
agcacaggaa gatgttcagg tcgaaatcga cgtggaacag cttgaggaca gagcgggcgc 1680
aggaataata gagactccga gaggagctat caaagttact gcccaaccaa cagaccacgt 1740
cgtgggagag tacctggtac tctccccgca gaccgtacta cgtagccaga agctcagtct 1800
gattcacgct ttggcggagc aagtgaagac gtgcacgcac aacggacgag cagggaggta 1860
tgcggtcgaa gcgtacgacg gccgagtcct agtgccctca ggctatgcaa tctcgcctga 1920
agacttccag agtctaagcg aaagcgcaac gatggtgtat aacgaaagag agttcgtaaa 1980
cagaaagcta caccatattg cgatgcacgg accagccctg aacaccgacg aagagtcgta 2040
tgagctggtg agggcagaga ggacagaaca cgagtacgtc tacgacgtgg atcagagaag 2100
atgctgtaag aaggaagaag ccgcaggact ggtactggtg ggcgacttga ctaatccgcc 2160
ctaccacgaa ttcgcatatg aagggctaaa aatccgccct gcctgcccat acaaaattgc 2220
agtcatagga gtcttcggag taccgggatc tggcaagtca gctattatca agaacctagt 2280
taccaggcag gacctggtga ctagcggaaa gaaagaaaac tgccaagaaa tcaccaccga 2340
cgtgatgaga cagagaggtc tagagatatc tgcacgtacg gttgactcgc tgctcttgaa 2400
tggatgcaac agaccagtcg acgtgttgta cgtagacgag gcgtttgcgt gccactctgg 2460
aacgctactt gctttgatcg ccttggtgag accaaggcag aaagttgtac tttgtggtga 2520
cccgaagcag tgcggcttct tcaatatgat gcagatgaaa gtcaactata atcacaacat 2580
ctgcacccaa gtgtaccaca aaagtatctc caggcggtgt acactgcctg tgaccgccat 2640
tgtgtcatcg ttgcattacg aaggcaaaat gcgcactacg aatgagtaca acaagccgat 2700
tgtagtggac actacaggct caacaaaacc tgaccctgga gacctcgtgt taacgtgctt 2760
cagagggtgg gttaaacaac tgcaaattga ctatcgtgga tacgaggtca tgacagcagc 2820
cgcatcccaa gggttaacca gaaaaggagt ttacgcagtt agacaaaaag ttaatgaaaa 2880
cccgctctat gcatcaacgt cagagcacgt caacgtactc ctaacgcgta cggaaggtaa 2940
actggtatgg aagacacttt ccggcgaccc gtggataaag acgctgcaga acccaccgaa 3000
aggaaacttc aaagcaacta ttaaggagtg ggaggtggag catgcatcaa taatggcggg 3060
catctgcagt caccaaatga ccttcgatac attccaaaat aaagccaacg tttgttgggc 3120
taagagcttg gtccctatcc tcgaaacagc ggggataaaa ctaaatgata ggcagtggtc 3180
tcagataatt caagccttca aagaagacaa agcatactca cctgaagtag ccctgaatga 3240
aatatgtacg cgcatgtatg ggtggatct agacagcggg ctattttcta aaccgttggt 3300
gtctgtgtat tacgcggata accactggga taataggcct ggagggaaaa tgttcggatt 3360
taaccccgag gcagcatcca ttctagaaag aaagtatcca ttcacaaaag ggaagtggaa 3420
catcaacaag cagatctgcg tgactaccag gaggatagaa gactttaacc ctaccaccaa 3480
catcataccg gccaacagga gactaccaca ctcattagtg gccgaacacc gcccagtaaa 3540
aggggaaaga atggaatggc tggttaacaa gataaacggc caccacgtgc tcctggtcag 3600

-continued

```
tggctataac cttgcactgc ctactaagag agtcacttgg gtagcgccgt taggtgtccg   3660
cggagcggac tacacataca acctagagtt gggtctgcca gcaacgcttg gtaggtatga   3720
cctagtggtc ataaacatcc acacaccttt tcgcatacac cattaccaac agtgcgtcga   3780
ccacgcaatg aaactgcaaa tgctcggggg tgactcattg agactgctca aaccgggcgg   3840
ctctctattg atcagagcat atggttacgc agatagaacc agtgaacgag tcatctgcgt   3900
attgggacgc aagtttagat cgtctagagc gttgaaacca ccatgtgtca ccagcaacac   3960
tgagatgttt ttcctattca gcaactttga caatggcaga aggaatttca caactcatgt   4020
catgaacaat caactgaatg cagccttcgt aggacaggtc acccgagcag gatgtgcacc   4080
gtcgtaccgg gtaaaacgca tggacatcgc gaagaacgat gaagagtgcg tagtcaacgc   4140
cgctaaccct cgcgggttac cgggtgrcgg tgtttgcaag gcagtataca aaaaatggcc   4200
ggagtccttt aagaacagtg caacaccagt gggaaccgca aaaacagtta tgtgcggtac   4260
gtatccagta atccacgctg ttggaccaaa cttctctaat tattcggagt ctgaagggga   4320
ccgggaattg gcagctgcct atcgagaagt cgcaaaggaa gtaactaggc tgggagtaaa   4380
tagtgtagct atacctctcc tctccacagg tgtatactca ggagggaaag acaggctgac   4440
ccagtcactg aaccacctct ttacagccat ggactcgacg gatgcagacg tggtcatcta   4500
ctgccgcgac aaagaatggg agaagaaaat atctgaggcc atacagatgc ggacccaagt   4560
agagctgctg gatgagcaca tctccataga ctgcgatatt gttcgcgtgc accctgacag   4620
cagcttggca ggcagaaaag gatacagcac cacggaaggc gcactgtact catatctaga   4680
agggacccgt tttcatcaga cggctgtgga tatggcggag atacatacta tgtggccaaa   4740
gcaaacagag gccaatgagc aagtctgcct atatgccctg gggaaagta ttgaatcgat    4800
caggcagaaa tgcccggtgg atgatgcaga cgcatcatct ccccccaaaa ctgtcccgtg   4860
cctttgccgt tacgctatga ctccagaacg cgtcacccgg cttcgcatga accacgtcac   4920
aagcataatt gtgtgttctt cgtttcccct cccaaagtac aaaatagaag gagtgcaaaa   4980
agtcaaatgc tctaaggtaa tgctatttga ccacaacgtg ccatcgcgcg taagtccaag   5040
ggaatataka tcttcccagg agtctgcaca ggaggcgagt acaatcacgt cactgacgca   5100
tagtcaattc gacctaagcg ttgatggcga gatactgccc gtcccgtcag acctggatgc   5160
tgacgcccca gccctagaac cagcactaga cgacggggcg acacacacgc tgccatccac   5220
aaccggaaac cttgcggccg tgtctgattg ggtaatgagc accgtacctg tcgcgccgcc   5280
cagaagaagg cgagggagaa acctgactgt gacatgtgac gagagagaag ggaatataac   5340
acccatggct agcgtccgat tctttagggc agagctgtgt ccggtcgtac aagaaacagc   5400
ggagacgcgt gacacagcaa tgtctcttca ggcaccaccg agtaccgcca cggaaccgaa   5460
tcatccgccg atctccttcg gagcatcaag cgagacgttc cccattacat ttggggactt   5520
caacgaagga gaaatcgaaa gcttgtcttc tgagctacta actttcggag acttcttacc   5580
aggagaagtg gatgacttga cagacagcga ctggtccacg tgctcagaca cggacgacga   5640
gttatgacta gacagggcag gtgggtatat attctcgtcg gacaccggtc caggtcattt   5700
acaacagaag tcagtacgcc agtcagtgct gccggtgaac accctggagg aagtccacga   5760
ggagaagtgt tacccaccta agctggatga agcaaaggag caactattac ttaagaaact   5820
ccaggagagt gcatccatgg ccaacagaag caggtatcag tcgcgcaaag tagaaaacat   5880
gaaagcagca atcatccaga gactaaagag aggctgtaga ctatacttaa tgtcagagac   5940
cccaaaagtc cctacttacc ggactacata tccggcgcct gtgtactcgc ctccgatcaa   6000
```

-continued

```
cgtccgattg tccaatcccg agtccgcagt ggcagcatgc aatgagttct tagctagaaa   6060
ctatccaact gtctcatcat accaaattac cgacgagtat gatgcatatc tagacatggt   6120
ggacgggtcg gagagttgcc tggaccgagc gacattcaat ccgtcaaaac tcaggagcta   6180
cccgaaacag cacgcttacc acgcgccctc catcagaagc gctgtaccgt ccccattcca   6240
gaacacacta cagaatgtac tggcagcagc cacgaaaaga aactgcaacg tcacacagat   6300
gagggaatta cccactttgg actcagcagt attcaacgtg gagtgtttca aaaaattcgc   6360
atgcaaccaa gaatactggg aagaatttgc tgccagccct attaggataa caactgagaa   6420
tttagcaacc tatgttacta aactaaaagg gccaaaagca gcagcgctat tcgcaaaaac   6480
ccataatcta ctgccactac aggaagtacc aatggatagg ttcacagtag atatgaaaag   6540
ggacgtaaag gtgactcctg gtacaaagca tacagaggaa agacctaagg tgcaggttat   6600
acaggcggct gaacccttgg cgacagcata cctatgtggg attcacagag agctggttag   6660
gaggctgaac gccgtcctcc tacccaatgt acatacacta tttgacatgt ctgccgagga   6720
tttcgatgcc atcatagccg cacactttaa gccaggagac actgttttgg aaacggacat   6780
agcctccttt gataagagcc aagatgattc acttgcgctt actgctttga tgctgttaga   6840
ggatttaggg gtggatcact ccctgctgga cttgatagag gctgctttcg gagagatttc   6900
cagctgtcac ctaccgacag gtacgcgctt caagttcggc gccatgatga aatcaggtat   6960
gttcctaact ctgttcgtca acacattgtt aaacatcacc atcgccagcc gagtgctgga   7020
agatcgtctg acaaaatccg cgtgcgcggc cttcatcggc gacgacaaca taatacatgg   7080
agtcgtctcc gatgaattga tggcagccag atgtgccact tggatgaaca tggaagtgaa   7140
gatcatagat gcagttgtat ccttgaaagc cccttacttt tgtggagggt ttatactgca   7200
cgatactgtg acaggaacag cttgcagagt ggcagacccg ctaaaaaggc tttttaaact   7260
gggcaaaccg ctagcggcag gtgacgaaca agatgaagat agaagacgag cgctggctga   7320
cgaagtgatc agatggcaac gaacagggct aattgatgag ctggagaaag cggtatactc   7380
taggtacgaa gtgcagggta tatcagttgt ggtaatgtcc atggccacct ttgcaagctc   7440
cagatccaac ttcgagaagc tcagaggacc cgtcataact ttgtacggcg gtcctaaata   7500
ggtacgcact acagctacct attttgcaga agccgacagc aagtatctaa acactaatca   7560
gctacaatgg agttcatccc aacccaaact ttttacaata ggaggtacca gcctcgaccc   7620
tggactccgc gccctactat ccaagtcatc aggcccagac cgcgccctca gaggcaagct   7680
gggcaacttg cccagctgat ctcagcagtt aataaactga caatgcgcgc ggtaccccaa   7740
cagaagccac gcaggaatcg gaagaataag aagcaaaagc aaaaacaaca ggcgccacaa   7800
aacaacacaa atcaaaagaa gcagccacct aaaaagaaac cggctcaaaa gaaaaagaag   7860
ccgggccgca gagagaggat gtgcatgaaa atcgaaaatg attgtatttt cgaagtcaag   7920
cacgaaggta aggtaacagg ttacgcgtgc ctggtggggg acaaagtaat gaaaccagca   7980
cacgtaaagg ggaccatcga taacgcggac ctggccaaac tggcctttaa gcggtcatct   8040
aagtatgacc ttgaatgcgc gcagataccc gtgcacatga agtccgacgc ttcgaagttc   8100
acccatgaga aaccggaggg gtactacaac tggcaccacg gagcagtaca gtactcagga   8160
ggccggttca ccatccctac aggtgctggc aaaccagggg acagcggcag accgatcttc   8220
gacaacaagg gacgcgtggt ggccatagtc ttaggaggag ctaatgaagg agcccgtaca   8280
gccctctcgg tggtgacctg gaataaagac attgtcacta aaatcacccc cgagggggcc   8340
```

```
gaagagtgga gtcttgccat cccagttatg tgcctgttgg caaacaccac gttcccctgc   8400
tcccagcccc cttgcacgcc ctgctgctac gaaaaggaac cggaggaaac cctacgcatg   8460
cttgaggaca acgtcatgag acctgggtac tatcagctgc tacaagcatc cttaacatgt   8520
tctccccacc gccagcgacg cagcaccaag gacaacttca atgtctataa agccacaaga   8580
ccatacttag ctcactgtcc cgactgtgga gaagggcact cgtgccatag tcccgtagca   8640
ctagaacgca tcagaaatga agcgacagac gggacgctga aaatccaggt ctccttgcaa   8700
atcggaataa agacggatga cagccacgat tggaccaagc tgcgttatat ggacaaccac   8760
atgccagcag acgcagagag ggcggggcta tttgtaagaa catcagcacc gtgtacgatt   8820
actggaacaa tgggacactt catcctggcc cgatgtccaa aaggggaaac tctgacggtg   8880
ggattcactg acagtaggaa gattagtcac tcatgtacgc acccatttca ccacgaccct   8940
cctgtgatag gtcgggaaaa attccattcc cgaccgcagc acggtaaaga gctaccttgc   9000
agcacgtacg tgcagagcac cgccgcaact accgaggaga tagaggtaca catgcccca    9060
gacacccctg atcgcacatt aatgtcacaa cagtccggca acgtaaagat cacagtcaat   9120
ggccagacgg tgcggtacaa gtgtaattgc ggtggctcaa atgaaggact aacaactaca   9180
gacaaagtga ttaataactg caaggttgat caatgtcatg ccgcggtcac caatcacaaa   9240
aagtggcagt ataactcccc tctggtcccg cgtaatgctg aacttgggga ccgaaaagga   9300
aaaattcaca tcccgtttcc gctggcaaat gtaacatgca gggtgcctaa agcaaggaac   9360
cccaccgtga cgtacgggaa aaaccaagtc atcatgctac tgtatcctga ccacccaaca   9420
ctcctgtcct accggaatat gggagaagaa ccaaactatc aagaagagtg ggtgatgcat   9480
aagaaggaag tcgtgctaac cgtgccgact gaagggctcg aggtcacgtg gggcaacaac   9540
gagccgtata agtattggcc gcagttatct acaaacggta cagcccatgg ccacccgcat   9600
gagataattc tgtattatta tgagctgtac cccactatga ctgtagtagt tgtgtcagtg   9660
gccacgttca tactcctgtc gatggtgggt atggcagcgg ggatgtgcat gtgtgcacga   9720
cgcagatgca tcacaccgta tgaactgaca ccaggagcta ccgtcccttt cctgcttagc   9780
ctaatatgct gcatcagaac agctaaagcg gccacatacc aagaggctgc gatatacctg   9840
tggaacgagc agcaaccttt gttttggcta caagccctta ttccgctggc agccctgatt   9900
gttctatgca actgtctgag actcttacca tgctgctgta aaacgttggc tttttagcc    9960
gtaatgagcg tcggtgccca cactgtgagc gcgtacgaac acgtaacagt gatcccgaac  10020
acggtgggag taccgtataa gactctagtc aatagacctg gctacagccc catggtattg  10080
gagatggaac tactgtcagt cactttggag ccaacactat cgcttgatta catcacgtgc  10140
gagtacaaaa ccgtcatccc gtctccgtac gtgaagtgct gcggtacagc agagtgcaag  10200
gacaaaaacc tacctgacta cagctgtaag gtcttcaccg gcgtctaccc atttatgtgg  10260
ggcggcgcct actgcttctg cgacgctgaa aacacgcagt tgagcgaagc acacgtggag  10320
aagtccgaat catgcaaaac agaatttgca tcagcataca gggctcatac cgcatctgca  10380
tcagctaagc tccgcgtcct ttaccaagga aataacatca ctgtaactgc ctatgcaaac  10440
ggcgaccatg ccgtcacagt taaggacgcc aaattcattg tggggccaat gtcttcagcc  10500
tggacacctt tcgacaacaa aattgtggtg tacaaaggtg acgtctataa catggactac  10560
ccgccctttg gcgcaggaag accaggacaa tttggcgata tccaaagtcg cacacctgag  10620
agtaaagacg tctatgctaa tacacaactg gtactgcaga gaccggctgt gggtacggta  10680
cacgtgccat actctcaggc accatctggc tttaagtatt ggctaaaaga acgcggggcg  10740
```

tcgctgcagc acacagcacc atttggctgc caaatagcaa caaacccggt aagagcggtg 10800
aactgcgccg tagggaacat gcccatctcc atcgacatac cggaagcggc cttcactagg 10860
gtcgtcgacg cgccctcttt aacggacatg tcgtgcgagg taccagcctg cacccattcc 10920
tcagactttg gggcgtcgc cattattaaa tatgcagcca gcaagaaagg caagtgtgcg 10980
gtgcattcga tgactaacgc cgtcactatt cgggaagctg agatagaagt tgaagggaat 11040
tctcagctgc aaatctcttt ctcgacggcc ttagccagcg ccgaattccg cgtacaagtc 11100
tgttctacac aagtacactg tgcagccgag tgccaccccc cgaaggacca catagtcaac 11160
tacccggcgt cacataccac cctcggggtc caggacatct ccgctacggc gatgtcatgg 11220
gtgcagaaga tcacgggagg tgtgggactg gttgttgctg ttgccgcact gattctaatc 11280
gtggtgctat gcgtgtcgtt cagcaggcac taacttgaca attaagtatg aaggtatatg 11340
tgtcccctaa gagacacact gtacatagca aataatctat agatcaaagg gctacgcaac 11400
ccctgaatag taacaaaata caaaatcact aaaaattata aaaacagaaa aatacataaa 11460
taggtatacg tgtcccctaa gagacacatt gtatgtaggt gataagtata gatcaaaggg 11520
ccgaataacc cctgaatagt aacaaaatat gaaaatcaat aaaaatcata aaatagaaaa 11580
accataaaca gaagtagttc aaagggctat aaaacccctg aatagtaaca aaacataaaa 11640
ttaataaaaa tcaaatgaat accataattg gcaaacggaa gagatgtagg tacttaagct 11700
tcctaaaagc agccgaactc actttgagaa gtaggcatag cataccgaac tcttccacga 11760
ttctccgaac ccacagggac gtaggagatg ttattttgtt tttaatattt caaaaaaaaa 11820
aaaaaaaaaa aaaaaaaaaa 11840

<210> SEQ ID NO 73
<211> LENGTH: 10863
<212> TYPE: DNA
<213> ORGANISM: Japanese encephalitis virus

<400> SEQUENCE: 73
tttaaacagt tttttagaac ggaagataac catgactaaa aaaccaggag ggcccggtaa 60
aaaccgggct atcaatatgc tgaaacgcgg cctaccccgc gtattcccac tagtgggagt 120
gaagagggta gtaatgagct tgttggacgg cagagggcca gtacgtttcg tgctggctct 180
tatcacgttc ttcaagttta cagcattagc cccgaccaag gcgcttttag gccgatggaa 240
agcagtggaa aagagtgtgg caatgaaaca tcttactagt ttcaaacgag aacttggaac 300
actcattgac gccgtgaaca agcggggcag aaagcaaaac aaaagaggag gaaatgaagg 360
ctcaatcatg tggctcgcga gcttggcagt tgtcatagct tgtgcaggag ccatgaagtt 420
gtcgaatttc caggggaagc ttttgatgac catcaacaac acggacattg cagacgttat 480
cgtgattccc acctcaaaag gagagaacag atgctgggtc cgggcaatcg acgtcggcta 540
catgtgtgag gacactatca cgtacgaatg tcctaagctt accatgggca atgatccaga 600
ggatgtggat tgctggtgtg acaaccaaga agtctacgtc caatatggac ggtgcacgcg 660
gaccaggcat tccaagcgaa gcaggagatc cgtgtcggtc caaacacatg gggagagttc 720
actagtgaat aaaaaagagg cttggctgga ttcaacgaaa gccacacgat atctcatgaa 780
aactgagaac tggatcataa ggaatcctgg ctatgctttc ctggcggcgg tacttggctg 840
gatgcttggc agtaacaacg gtcaacgcgt ggtatttacc atcctcctgc tgttggtcgc 900
tccggcttac agttttaatt gtctgggaat gggcaatcgt gacttcatag aaggagccag 960

-continued

```
tggagccact tgggtggact tggtgctaga aggagatagc tgcttgacaa tcatggcaaa   1020
cgacaaacca acattggacg tccgcatgat taacatcgaa gctagccaac ttgctgaggt   1080
cagaagttac tgctatcatg cttcagtcac tgacatctcg acggtggctc ggtgccccac   1140
gactggagaa gcccacaacg agaagcgagc tgatagtagc tatgtgtgca aacaaggctt   1200
cactgaccgt gggtggggca acggatgtgg acttttcggg aagggaagca ttgacacatg   1260
tgcaaaattc tcctgcacca gtaaagcgat tgggagaaca atccagccag aaaacatcaa   1320
atacgaagtt ggcatttttg tgcatggaac caccacttcg gaaaaccatg ggaattattc   1380
agcgcaagtt ggggcgtccc aggcggcaaa gtttacagta acacccaatg ctccttcgat   1440
aaccctcaaa cttggtgact acggagaagt cacactggac tgtgagccaa ggagtggact   1500
gaacactgaa gcgttttacg tcatgaccgt ggggtcaaag tcatttctgg tccataggga   1560
gtggtttcat gacctcgctc tcccctggac gtccccttcg agcacagcgt ggagaaacag   1620
agaactcctc atggaatttg aaggggcgca cgccacaaaa cagtccgttg ttgctcttgg   1680
gtcacaggaa ggaggcctcc atcaggcgtt ggcaggagcc atcgtggtgg agtactcaag   1740
ctcagtgaag ttaacatcag gccacctgaa atgtaggctg aaaatggaca aactggctct   1800
gaaaggcaca acctatggca tgtgtacaga aaaattctcg ttcgcgaaaa atccggcgga   1860
cactggtcac ggaacagttg tcattgaact ctcctactct gggagtgatg gcccctgcaa   1920
aattccgatt gtttccgttg cgagcctcaa tgacatgacc cccgttgggc ggctggtgac   1980
agtgaacccc ttcgtcgcga cttccagtgc caactcaaag gtgctggtcg agatggaacc   2040
ccccttcgga gactcctaca tcgtagttgg aaggggagac aagcagatca accaccattg   2100
gcacaaagct ggaagcacgc tgggcaaggc cttttcaaca actttgaagg gagctcaaag   2160
actggcagcg ttgggcgaca cagcctggga ctttggctct attggagggg tcttcaactc   2220
cataggaaaa gccgttcacc aagtgtttgg tggtgccttc agaacactct ttgggggaat   2280
gtcttggatc acacaagggc taatgggtgc cctactgctc tggatgggcg tcaacgcacg   2340
agaccgatca attgctttgg ccttcttagc cacagggggt gtgctcgtgt tcttagcgac   2400
caatgtgcat gctgacactg gatgtgccat tgacatcaca agaaaagaga tgagatgtgg   2460
aagtggcatc ttcgtgcaca acgacgtgga agcctgggtg gataggtata aatatttgcc   2520
agaaacgccc agatccctag cgaagatcgt ccacaaagcg cacaaggaag gcgtgtgcgg   2580
agtcagatct gtcactagac tggagcacca aatgtgggaa gccgtacggg acgaattgaa   2640
cgtcctgctc aaagagaatg cagtggacct cagtgtggtt gtgaacaagc ccgtgggaag   2700
atatcgctca gcccctaaac gcctatccat gacgcaagag aagtttgaaa tgggctggaa   2760
agcatgggga aaaagcattc tctttgcccc ggaattggct aactccacat ttgtcgtaga   2820
tggacctgag acaaaggaat gccctgatga gcacagagct tggaacagca tgcaaatcga   2880
agacttcggc tttggcatca catcaacccg tgtgtggctg aaaattagag aggagagcac   2940
tgacgagtgt gatggagcga tcataggcac ggctgtcaaa ggacatgtgg cagtccatag   3000
tgacttgtcg tactggattg agagtcgcta caacgacaca tggaaacttg agagggcagt   3060
ctttggagag gtcaaatctt gcacttggcc agagacacac accctttggg gagatgatgt   3120
tgaggaaagt gaactcatca ttccgcacac catagccgga ccaaaaagca agcacaatcg   3180
gagggaaggg tataagacac aaaaccaggg accttgggat gagaatggca tagtcttgga   3240
ctttgattat tgcccaggga caaaagtcac cattacagag gattgtggca agagaggccc   3300
ttcggtcaga accactactg acagtggaaa gttgatcact gactggtgct gtcgcagttg   3360
```

ctcccttccg cccctacgat tccggacaga aaatggctgc tggtacggaa tggaaatcag 3420
acctgttagg catgatgaaa caacactcgt cagatcacag gttgatgctt tcaatggtga 3480
aatggttgac ccttttcagc tgggccttct ggtgatgttt ctggccaccc aggaggtcct 3540
tcgcaagagg tggacggcca gattgaccat tcctgcggtt ttgggggccc tacttgtgct 3600
gatgcttggg ggcatcactt acactgattt ggcgaggtat gtggtgctag tcgctgctgc 3660
tttcgcagag gccaacagtg gaggagacgt cctgcacctt gctttgattg ccgtttttaa 3720
gatccaacca gcatttctag tgatgaacat gcttagcacg agatggacga accaagaaaa 3780
cgtggttctg gtcctagggg ctgccttttt ccaattggcc tcagtagatc tgcaaatagg 3840
agtccacgga atcctgaatg ccgccgctat agcatggatg attgtccgag cgatcacctt 3900
ccccacaacc tcctccgtca ccatgccagt cttagcgctt ctaactccgg ggatgagggc 3960
tctataccta gacacttaca gaatcatcct cctcgtcata gggatttgct ccctgctgca 4020
cgagaggaaa aagaccatgg caaaaaagaa aggagctgta ctcttgggct tagcgctcac 4080
atccactgga tggttctcgc ccaccactat agctgccgga ctaatggtct gcaacccaaa 4140
caagaagaga gggtggccag ctactgagtt tttgtcggca gttggattga tgtttgccat 4200
cgtaggtggt ttggccgagt tggatattga atccatgtca atacccttca tgctggcagg 4260
tctcatggca gtgtcctacg tggtgtcagg aaaagcaaca gatatgtggc ttgaacgggc 4320
cgccgacatc agctgggaga tggatgctgc aatcacagga agcagtcgga ggctggatgt 4380
gaaactggat gatgacggag attttcactt gattgatgat cccggtgttc catggaaggt 4440
ctgggtcctg cgcatgtctt gcattggctt agccgccctc acgccttggg ccatcgttcc 4500
cgccgctttc ggttattggc tcactttaaa aacaacaaaa agagggggcg tgttttggga 4560
cacgccatcc ccaaaacctt gctcaaaagg agacaccact acaggagtct accgaattat 4620
ggctagaggg attcttggca cttaccaggc cggcgtcgga gtcatgtacg agaatgtttt 4680
ccacacacta tggcacacaa ctagaggagc agccattatg agtggagaag gaaaattgac 4740
gccatactgg ggtagtgtga gagaagaccg catagcttac ggaggcccat ggaggtttga 4800
ccgaaaatgg aatggaacag atgacgtgca agtgatcgtg gtagaaccgg ggaaggctgc 4860
agtaaacatc cagacaaaac caggagtgtt tcggactccc ttcggggagg ttggggctgt 4920
tagtctggat tacccgcgag gaacatccgg ctcacccatt ctggattcca atggagacat 4980
tataggccta tacggcaatg gagttgagct tggcgatggc tcatacgtca gcgccatcgt 5040
gcagggtgac cgtcaggagg aaccagtccc agaagcttac accccaaaca tgttgagaaa 5100
gagacagatg actgtgctag atttgcaccc tggttcaggg aaaaccagga aaattctgcc 5160
acaaataatt aaggacgcta tccagcagcg cctaagaaca gctgtgttgg caccgacgcg 5220
ggtggtagca gcagaaatgg cagaagcttt gagagggctc ccagtacgat atcaaacttc 5280
agcagtgcag agagagcacc aagggaatga aatagtggat gtgatgtgcc acgccactct 5340
gacccataga ctgatgtcac cgaacagagt gcccaactac aacctatttg tcatggatga 5400
agctcatttc accgacccag ccagtatagc cgcacgagga tacattgcta ccaaggtgga 5460
attaggggag gcagcagcca tctttatgac agcgaccccg cctggaacca cggatccttt 5520
tcctgactca aatgccccaa tccatgattt gcaagatgag ataccagaca gggcatggag 5580
cagtggatac gaatggatca cagaatatgc gggtaaaacc gtgtggtttg tggcgagcgt 5640
aaaaatgggg aatgagattg caatgtgcct ccaaagagcg gggaaaaagg tcatccaact 5700

```
caaccgcaag tcctatgaca cagaataccc aaaatgtaag aatggagact gggattttgt   5760
cattaccacc gacatctctg aaatgggggc caacttcggt gcgagcaggg tcatcgactg   5820
tagaaagagc gtgaaaccca ccatcttaga agagggagaa ggcagagtca tcctcggaaa   5880
cccatctccc ataaccagtg caagcgcagc tcaacggagg ggcagagtag gcagaaaccc   5940
caaccaagtt ggagatgaat accactatgg gggggctacc agtgaagatg acagtaacct   6000
agcccattgg acagaggcaa agatcatgtt agacaacata cacatgccca atggactggt   6060
ggcccagctc tatggaccag agagggaaaa ggctttcaca atggatggcg aataccgtct   6120
cagaggtgaa gaaaagaaaa acttcttaga gctgcttagg acggctgacc tcccggtgtg   6180
gctggcctac aaggtggcgt ccaatggcat tcagtacacc gacagaaagt ggtgttttga   6240
tgggccgcgt acgaatgcca tactggagga caacaccgag gtagagatag tcacccggat   6300
gggtgagagg aaaatcctca agccgagatg gcttgatgca agagtttatg cagatcacca   6360
agccctcaag tggttcaaag actttgcagc agggaagaga tcagccgtta gcttcataga   6420
ggtgctcggt cgcatgcctg agcatttcat gggaaagacg cgggaagctt tagacaccat   6480
gtacttggtt gcaacggctg agaaaggtgg gaaagcacac cgaatggctc tcgaagagct   6540
gccagatgca ctggaaacca tcacacttat tgtcgccatt actgtgatga caggaggatt   6600
cttcctacta atgatgcagc gaaagggtat agggaagatg ggtcttggag ctctagtgct   6660
cacgctagct accttcttcc tgtgggcggc agaggttcct ggaaccaaaa tagcagggac   6720
cctgctgatc gccctgctgc tgatggtggt tctcatccca gaaccggaaa aacagaggtc   6780
acagacagat aaccaactgg cggtgtttct catctgtgtc ttgaccgtgg ttggagtggt   6840
ggcagcaaac gagtacggga tgctagaaaa aaccaaagca gatctcaaga gcatgtttgg   6900
cggaaagacg caggcatcag gactgactgg attgccaagc atggcactgg acctgcgtcc   6960
agccacagcc tgggcactgt atgggggggag cacagtcgtg ctaacccctc ttctgaagca   7020
cctgatcacg tcggaatacg tcaccacatc gctagcctca attaactcac aagctggctc   7080
attattcgtc ttgccacgag gcgtgccttt taccgaccta gacttgaccg ttggcctcgt   7140
cttccttggc tgttggggtc aaatcaccct cacaacgttt ctgacagcca tggttctggc   7200
gacacttcac tatgggtaca tgctccctgg atggcaagca gaagcactca gggctgccca   7260
gagaaggaca gcggctggaa taatgaagaa tgccgttgtt gacggaatgg tcgccactga   7320
tgtgcctgaa ctggaaagga ctactcctct gatgcaaaag aaagtcggac aggtgctcct   7380
cataggggta agcgtggcag cgttcctcgt caaccctaat gtcaccactg tgagagaagc   7440
aggggtgttg gtgacggcgg ctacgcttac tttgtgggac aatggagcca gtgccgtttg   7500
gaattccacc acagccacgg gactctgcca tgtcatgcga ggtagctacc tggctggagg   7560
ctccattgct tggactctca tcaagaacgc tgataagccc tccttgaaaa ggggaaggcc   7620
tgggggcagg acgctagggg agcagtggaa ggaaaaacta aatgccatga gcagagaaga   7680
gttttttaaa taccggagag aggccataat cgaggtggac cgcactgaag cacgcagggc   7740
cagacgtgaa aataacatag tgggaggaca tccggtttcg cgaggctcag caaaactccg   7800
ttggctcgtg gagaaaggat ttgtctcgcc aataggaaaa gtcattgatc tagggtgtgg   7860
gcgtggagga tggagctact acgcagcaac cctgaagaag gtccaggaag tcagaggata   7920
cacgaaaggt ggggcgggac atgaagaacc gatgctcatg cagagctacg gctggaacct   7980
ggtctccctg aagagtggag tggacgtgtt ttacaaacct tcagagccca gtgacaccct   8040
gttctgtgac ataggggaat cctccccaag tccagaagta gaagaacaac gcacactacg   8100
```

```
cgtcctagag atgacatctg actggttgca ccgaggacct agagagttct gcattaaagt   8160
tctctgccct tacatgccca aggttataga aaaaatggaa gttctgcagc gccgcttcgg   8220
aggtgggcta gtgcgtctcc ccctgtcccg aaactccaat cacgagatgt attgggttag   8280
tggagccgct ggcaatgtgg tgcacgctgt gaacatgacc agccaggtac tactggggcg   8340
aatggatcgc acagtgtgga gagggccaaa gtatgaggaa gatgtcaacc tagggagcgg   8400
aacaagagcc gtgggaaagg gagaagtcca tagcaatcag gagaaaatca agaagagaat   8460
ccagaagctt aaagaagaat tcgccacaac gtggcacaaa gaccctgagc atccataccg   8520
cacttggaca taccacggaa gctatgaagt gaaggctact ggctcagcca gctctctcgt   8580
caacggagtg gtgaagctca tgagcaaacc ttgggacgcc attgccaacg tcaccaccat   8640
ggccatgact gacaccaccc cttttggaca gcaaagagtt ttcaaggaga aagttgacac   8700
gaaggctcct gagccaccag ctggagccaa ggaagtgctc aacgagacca ccaactggct   8760
gtgggcccac ttgtcacggg aaaaaagacc ccgcttgtgc accaaggaag aattcataaa   8820
gaaagtcaac agcaacgcgg ctcttggagc agtgttcgct gaacagaatc aatggagcac   8880
ggcgcgtgag gctgtggatg acccgcggtt ttgggagatg gttgatgaag agagggaaaa   8940
ccatctgcga ggagagtgtc acacatgtat ctacaacatg atgggaaaaa gagagaagaa   9000
gcctggagag tttggaaaag ctaaaggaag cagggccatt tggttcatgt ggcttggagc   9060
acggtatcta gagtttgaag ctttggggtt cctgaatgaa gaccattggc tgagccgaga   9120
gaattcagga ggtggagtgg aaggctcagg cgtccaaaag ctgggataca tcctccgtga   9180
catagcagga aagcaaggag ggaaaatgta cgctgatgat accgccgggt gggacactag   9240
aattaccaga actgatttag aaaatgaagc taaggtactg gagctcctag acggtgaaca   9300
ccgcatgctc gcccgagcca taattgaact gacttacagg cacaaagtgg tcaaggtcat   9360
gagacctgca gcagaaggaa agaccgtgat ggacgtgata tcaagagaag atcaaagggg   9420
gagtggacag gtggtcactt atgctcttaa cactttcacg aacatcgctg tccagctcgt   9480
caggctgatg gaggctgagg gggtcattgg accacaacac ttggaacagc tacctaggaa   9540
aaacaagata gctgtcagga cctggctctt tgagaatgga gaggagagag tgaccaggat   9600
ggcgatcagc ggagacgact gtgtcgtcaa gccgctggac gacagattcg ccacagccct   9660
ccacttcctc aacgcaatgt caaaggtcag aaaagacatc caggaatgga agccttcgca   9720
tggctggcac gattggcagc aagttccctt ctgctctaac cattttcagg agattgtgat   9780
gaaagatgga aggagtatag ttgtcccgtg cagaggacag gatgagctga taggcagggc   9840
tcgcatctct ccaggagctg gatggaatgt gaaggacaca gcttgcctgg ccaaagcata   9900
tgcacagatg tggctactcc tatacttcca tcgcagggac ttgcgtctca tggcaaatgc   9960
gatttgctca gcagtgccag tggattgggt gcccacaggc aggacatcct ggtcaataca  10020
ctcgaaagga gagtggatga ccacggaaga catgctgcag gtctggaaca gagtctggat  10080
tgaagaaaat gaatggatga tggacaagac tccaatcaca agctggacag acgttccgta  10140
tgtgggaaag cgtgaggaca tctggtgtgg cagcctcatc ggaacgcgat ccagagcaac  10200
ctgggctgag aacatctatg cggcgataaa ccaggttaga gctgtcattg ggaaagaaaa  10260
ttatgttgac tacatgacct cactcaggag atacgaagac gtcttgatcc aggaagacag  10320
ggtcatctag tgtgatttaa ggtagaaaag tagactatgt aaataatgta aatgagaaaa  10380
tgcatgcata tggagtcagg ccagcaaaag ctgccaccgg atactgggta gacggtgctg  10440
```

cctgcgtctc agtcccagga ggactgggtt aacaaatctg acaacagaaa gtgagaaagc 10500
cctcagaacc gtctcggaag taggtccctg ctcactggaa gttgaaagac caacgtcagg 10560
ccacaaattt gtgccactcc gctagggagt gcggcctgcg cagccccagg aggactgggt 10620
taccaaagcc gttgaggccc ccacggccca agcctcgtct aggatgcaat agacgaggtg 10680
taaggactag aggttagagg agaccccgtg gaaacaacaa catgcggccc aagccccctc 10740
gaagctgtag aggaggtgga aggactagag gttagaggag accccgcatt tgcatcaaac 10800
agcatattga cacctgggaa tagactggga gatcttctgc tctatctcaa catcagctac 10860
tag 10863

<210> SEQ ID NO 74
<211> LENGTH: 10977
<212> TYPE: DNA
<213> ORGANISM: Japanese encephalitis virus

<400> SEQUENCE: 74
agaagtttat ctgtgtgaac ttcttggctt agtatcgtag agaagaatcg agagattagt 60
gcagtttaaa cagtttttta gaacggaaga taaccatgac taaaaaacca ggagggcccg 120
gtaaaaaccg ggctatcaat atgctgaaac gcggcctacc ccgcgtattc ccactagtgg 180
gagtgaagag ggtagtaatg agcttgttgg acggcagagg gccagtacgt ttcgtgctgg 240
ctcttatcac gttcttcaag tttacagcat tagccccgac caaggcgctt tcaggccgat 300
ggaaagcagt ggaaaagagt gtggcaatga aacatcttac tagtttcaaa cgagaacttg 360
gaacactcat tgacgccgtg aacaagcggg gcagaaagca aaacaaaaga ggaggaaatg 420
aaggctcaat catgtggctc gcgagcttgg cagttgtcat agcttgtgca ggagccatga 480
agttgtcgaa tttccagggg aagcttttga tgaccatcaa caacacggac attgcagacg 540
ttatcgtgat tcccacctca aaaggagaga acagatgctg ggtccgggca atcgacgtcg 600
gctacatgtg tgaggacact atcacgtacg aatgtcctaa gcttaccatg ggcaatgatc 660
cagaggatgt ggattgctgg tgtgacaacc aagaagtcta cgtccaatat ggacggtgca 720
cgcggaccag gcattccaag cgaagcagga gatccgtgtc ggtccaaaca catggggaga 780
gttcactagt gaataaaaaa gaggcttggc tggattcaac gaaagccaca cgatatctca 840
tgaaaactga gaactggatc ataaggaatc ctggctatgc tttcctggcg gcggtacttg 900
gctggatgct tggcagtaac aacggtcaac gcgtggtatt taccatcctc ctgctgttgg 960
tcgctccggc ttacagtttt aattgtctgg gaatgggcaa tcgtgacttc atagaaggag 1020
ccagtggagc cacttgggtg gacttggtgc tagaaggaga cagctgcttg acaatcatgg 1080
caaacgacaa accaacattg gacgtccgca tgattaacat cgaagctagc caacttgctg 1140
aggtcagaag ttactgctat catgcttcag tcactgacat ctcgacggtg gctcggtgcc 1200
ccacgactgg agaagcccac aacgagaagc gagctgatag tagctatgtg tgcaaacaag 1260
gcttcactga ccgtgggtgg ggcaacggat gtggattttt cgggaaggga agcattgaca 1320
catgtgcaaa attctcctgc accagtaaag cgattgggag aacaatccag ccagaaaaca 1380
tcaaatacaa agttggcatt tttgtgcatg gaaccaccac ttcggaaaac catgggaatt 1440
attcagcgca agttggggcg tcccaggcgg caaagtttac agtaacaccc aatgctcctt 1500
cggtagccct caaacttggt gactacggag aagtcacact ggactgtgag ccaaggagtg 1560
gactgaacac tgaagcgttt tacgtcatga ccgtggggtc aaagtcattt ctggtccata 1620
gggagtggtt tcatgacctc gctctcccct ggacgtcccc ttcgagcaca gcgtggagaa 1680

-continued

```
acagagaact cctcatggaa tttgaagggg cgcacgccac aaaacagtcc gttgttgctc   1740
ttgggtcaca ggaaggaggc ctccatcatg cgttggcagg agccatcgtg gtggagtact   1800
caagctcagt gatgttaaca tcaggccacc tgaaatgtag gctgaaaatg gacaaactgg   1860
ctctgaaagg cacaacctat ggcatgtgta cagaaaaatt ctcgttcgcg aaaaatccgg   1920
tggacactgg tcacggaaca gttgtcattg aactctccta ctctgggagt gatggcccct   1980
gcaaaattcc gattgtttcc gttgcgagcc tcaatgacat gacccccgtt gggcggctgg   2040
tgacagtgaa ccccttcgtc gcgacttcca gtgccaactc aaaggtgctg gtcgagatgg   2100
aacccccctt cggagactcc tacatcgtag ttggaagggg agacaagcag atcaaccacc   2160
attggcacaa agctggaagc acgctgggca aggccttttc aacaactttg aagggagctc   2220
aaagactggc agcgttgggc gacacagcct gggactttgg ctctattgga ggggtcttca   2280
actccatagg aagagccgtt caccaagtgt ttggtggtgc cttcagaaca ctctttgggg   2340
gaatgtcttg gatcacacaa gggctaatgg gtgccctact gctctggatg ggcgtcaacg   2400
cacgagaccg atcaattgct ttggccttct tagccacagg aggtgtgctc gtgttcttag   2460
cgaccaatgt gcatgctgac actggatgtg ccattgacat cacaagaaaa gagatgagat   2520
gtggaagtgg catcttcgtg cacaacgacg tggaagcctg ggtggatagg tataaatatt   2580
tgccagaaac gcccagatcc ctagcgaaga tcgtccacaa agcgcacaag gaaggcgtgt   2640
gcggagtcag atctgtcact agactggagc accaaatgtg ggaagccgta agggacgaat   2700
tgaacgtcct gctcaaagag aatgcagtgg acctcagtgt ggttgtgaac aagcccgtgg   2760
gaagatatcg ctcagcccct aaacgcctat ccatgacgca agagaagttt gaaatgggct   2820
ggaaagcatg ggaaaaaagc atcctctttg ccccggaatt ggctaactcc acatttgtcg   2880
tagatggacc tgagacaaag gaatgccctg atgagcacag agcttggaac agcatgcaaa   2940
tcgaagactt cggctttggc atcacatcaa cccgtgtgtg gctgaaaatt agagaggaga   3000
gcactgacga gtgtgatgga gcgatcatag gcacggctgt caaaggacat gtggcagtcc   3060
atagtgactt gtcgtactgg attgagagtc gctacaacga cacatggaaa cttgagaggg   3120
cagtctttgg agaggtcaaa tcttgcactt ggccagagac acacaccctt tggggagatg   3180
atgttgagga aagtgaactc atcattccgc acaccatagc cggaccaaaa agcaagcaca   3240
atcggaggga agggtataag acacaaaacc agggaccttg ggatgagaat ggcatagtct   3300
tggactttga ttattgccca gggacaaaag tcaccattac agaggattgt agcaagagag   3360
gcccttcggt cagaaccact actgacagtg gaaagttgat cactgactgg tgctgtcgca   3420
gttgctccct tccgccccta cgattccgga cagaaaatgg ctgctggtac ggaatggaaa   3480
tcagacctgt tatgcatgat gaaacaacac tcgtcagatc acaggttcat gctttcaaag   3540
gtgaaatggt tgaccctttt cagctgggcc ttctggtgat gtttctggcc acccaggaag   3600
tccttcgcaa gaggtggacg gccagattga ccattcctgc ggttttgggg gtcctacttg   3660
tgctgatgct tgggggtatc acttacactg atttggcgag gtatgtggtg ctagtcgctg   3720
ctgctttcgc agaggccaac agtggaggag acgtcctgca ccttgctttg attgctgttt   3780
ttaagatcca accagcattt ttagtgatga acatgcttag cacgagatgg acgaaccaag   3840
aaaacgtggt tctggtccta ggggctgcct ttttccaatt ggcctcagta gatctgcaaa   3900
taggagtcca cggaatcctg aatgccgccg ctatagcatg gatgattgtc cgagcgatca   3960
ccttccccac aacctcctcc gtcaccatgc cagtcttagc gcttctaact ccggggatga   4020
```

gggctctata cctagacact tacagaatca tcctcctcgt catagggatt tgctccctgc 4080
tgcacgagag gaaaaagacc atggcgaaaa agaaaggagc tgtactcttg ggcttagcgc 4140
tcacatccac tggatggttc tcgcccacca ctatagctgc cggactaatg gtctgcaacc 4200
caaacaagaa gagagggtgg ccagctactg agtttttgtc ggcagttgga ttgatgtttg 4260
ccatcgtagg tggtttggcc gagttggata ttgaatccat gtcaataccc ttcatgctgg 4320
caggtctcat ggcagtgtcc tacgtggtgt caggaaaagc aacagatatg tggcttgaac 4380
gggccgccga catcagctgg gatatgggtg ctgcaatcac aggaagcagt cggaggctgg 4440
atgtgaaact ggatgatgac ggagattttc acttgattga tgatcccggt gttccatgga 4500
aggtctgggt cctgcgcatg tcttgcattg gcttagccgc cctcacgcct tgggccatcg 4560
ttcccgccgc tttcggttat tggctcactt taaaaacaac aaaaagaggg ggcgtgtttt 4620
gggacacgcc atccccaaaa ccttgctcaa aaggagacac cactacagga gtctaccgaa 4680
ttatggctag agggattctt ggcacttacc aggccggcgt cggagtcatg tacgagaatg 4740
ttttccacac actatggcac acaactagag gagcagccat tgtgagtgga gaaggaaaat 4800
tgacgccata ctggggtagt gtgaaagaag accgcatagc ttacggaggc ccatggaggt 4860
ttgaccgaaa atggaatgga acagatgacg tgcaagtgat cgtggtagaa ccggggaagg 4920
gcgcagtaaa catccagaca aaaccaggag tgtttcggac tcccttcggg gaggttgggg 4980
ctgttagtct ggattacccg cgaggaacat ccggctcacc cattctggat tccaatggag 5040
acattatagg cctatacggc aatggagttg agcttggcga tggctcatac gtcagcgcca 5100
tcgtgcaggg tgaccgtcag gaggaaccag tcccagaagc ttacacccca aacatgttga 5160
gaaagagaca gatgactgtg ctagatttgc accctggttc agggaaaacc aggaaaattc 5220
tgccacaaat aattaaggac gctatccagc agcgcctaag aacagctgtg ttggcaccga 5280
cgcgggtggt agcagcagaa atggcagaag ctttgagagg gctcccagta cgatatcaaa 5340
cttcagcagt gcagagagag caccaaggga atgaaatagt ggatgtgatg tgccacgcca 5400
ctctgaccca tagactgatg tcaccgaaca gagtgcccaa ctacaaccta tttgtcatgg 5460
atgaagctca tttcaccgac ccagccagta tagccgcacg aggatacatt gctaccaagg 5520
tggaattagg ggaggcagca gccatcttta tgacagcgac cccgcctgga accacggatc 5580
cttttcctga ctcaaatgcc ccaatccatg atttgcaaga tgagatacca gacagggcat 5640
ggagcagtgg atacgaatgg atcacagaat atgcgggtaa aaccgtgtgg tttgtggcga 5700
gcgtaaaaat ggggaatgag attgcaatgt gcctccaaag agcggggaaa aaggtcatcc 5760
aactcaaccg caagtcctat gacacagaat acccaaaatg taagaatgga gactgggatt 5820
ttgtcattac caccgacatc tctgaaatgg gggccaactt cggtgcgagc agggtcatcg 5880
actgtagaaa gagcgtgaaa cccaccatct tagaagaggg agaaggcaga gtcatcctcg 5940
gaaacccatc tcccataacc agtgcaagcg cagctcaacg gaggggcaga gtaggcagaa 6000
accccaatca agttggagat gaataccact atgggggggc taccagtgaa gatgacagta 6060
acctagccca ttggacagag gcaaagatca tgttagacaa catacacatg cccaatggac 6120
tggtggccca gctctatgga ccagagaggg aaaaggcttt cacaatggat ggcgaatacc 6180
gtctcagagg tgaagaaaag aaaaacttct tagagctgct taggacggct gacctcccgg 6240
tgtggctggc ctacaaggtg gcgtccaatg gcattcagta caccgacaga aagtggtgtt 6300
ttgatgggcc gcgtacgaat gccatactgg aggacaacac cgaggtagag atagtcaccc 6360
ggatgggtga gaggaaaatc ctcaagccga gatggcttga tgcaagagtt tatgcagatc 6420
accaggccct caagtggttc aaagactttg cagcagggaa gagatcagcc gttagcttca 6480
tagaggtgct cggtcgcatg cctgagcatt tcatgggaaa gacgcgggaa gctttagaca 6540
ccatgtactt ggttgcaacg gctgagaaag gtgggaaagc acaccgaatg gctctcgaag 6600
agctgccaga tgcactggaa accatcacac ttattgtcgc cattactgtg atgacaggag 6660
gattcttcct actaatgatg cagcgaaagg gtatagggaa gatgggtctt ggagctctag 6720
tgctcacact agctaccttc ttcctgtggg cggcagaggt tcctggaacc aaaatagcag 6780
ggaccctgct gatcgccctg ctgctgatgg tggttctcat cccagaaccg gaaaaacaga 6840
ggtcacagac agataaccaa ctggcggtgt ttctcatctg tgtcttgacc gtggttggag 6900
tggtggcagc aaacgagtac gggatgctag aaaaaaccaa agcggatctc aagagcatgt 6960
ttggcggaaa gacgcaggca tcaggactga ctggattgcc aagcatggca ctggacctgc 7020
gtccagccac agcctgggca ctgtatgggg ggagcacagt cgtgctaacc cctcttctga 7080
agcacctgat cacgtcggaa tacgtcacca catcgctagc ttcaattaac tcacaagctg 7140
gctcattatt cgtcttgcca cgaggcgtgc cttttaccga cctagacttg actgttggcc 7200
tcgtcttcct tggctgttgg ggtcaagtca ccctcacaac gtttctgaca gccatggttc 7260
tggcgacact tcactatggg tacatgctcc ctggatggca agcagaagca ctcagggctg 7320
cccagagaag gacagcggct ggaataatga agaatgccgt tgttgacgga atggtcgcca 7380
ctgatgtgcc tgaactggaa aggactactc ctctgatgca aaagaaagtc ggacaggtgc 7440
tcctcatagg ggtaagcgtg gcagcgttcc tcgtcaaccc taatgtcacc actgtgagag 7500
aagcaggggt gttggtgacg gcggctacgc ttactttgtg ggacaatgga gccagtgccg 7560
tttggaattc caccacagcc acgggactct gccatgtcat gcgaggtagc tacctggctg 7620
gaggctccat tgcttggact ctcatcaaga acgctgataa gccctccttg aaaaggggaa 7680
ggcctggggg caggacgcta ggggagcagt ggaaggaaaa actaaatgcc atgagtagag 7740
aagagttttt taaataccgg agagaggcca taatcgaggt ggaccgcact gaagcacgca 7800
gggccagacg tgaaaataac atagtgggag gacatccggt ttcgcgaggc tcagcaaaac 7860
tccgttggct cgtggagaaa ggatttgtct cgccaatagg aaaagtcatt gatctagggt 7920
gtgggcgtgg aggatggagc tactacgcag caaccctgaa gaaggtccag gaagtcagag 7980
gatacacgaa aggtggggcg ggacatgaag aaccgatgct catgcagagc tacggctgga 8040
acctggtctc cctgaagagt ggagtggacg tgttttacaa accttcagag cccagtgata 8100
ccctgttctg tgacataggg gaatcctccc caagtccaga agtagaagaa caacgcacac 8160
tacgcgtcct agagatgaca tctgactggt tgcaccgagg acctagagag ttctgcatta 8220
aagttctctg cccttacatg cccaaggtta tagaaaaaat ggaagttctg cagcgtcgct 8280
tcggaggtgg gctagtgcgt ctccccctgt cccgaaactc caatcacgag atgtattggg 8340
ttagtggagc cgctggcaat gtggtgcacg ctgtgaacat gaccagccag gtattactgg 8400
ggcgaatgga tcgcacagtg tggagagggc caaagtatga ggaagatgtc aacctaggga 8460
gcggaacaag agccgtggga aagggagaag tccatagcaa tcaggagaaa atcaagaaga 8520
gaatccagaa gcttaaagaa gaattcgcca caacgtggca caaagaccct gagcatccat 8580
accgcacttg gacataccac ggaagctatg aagtgaaggc tactggctca gccagctctc 8640
tcgtcaacgg agtggtgaag ctcatgagca aaccttggga cgccattgcc aacgtcacca 8700
ccatggccat gactgacacc accccttttg gacagcaaag agttttcaag gagaaagttg 8760

-continued

```
acacgaaggc tcctgagcca ccagctggag ccaaggaagt gctcaacgag accaccaact   8820
ggctgtgggc ctacttgtca cgggaaaaaa gaccccgctt gtgcaccaag gaagaattca   8880
ttaagaaagt taacagcaac gcggctcttg gagcagtgtt cgctgaacag aatcaatgga   8940
gcacggcgcg tgaggctgtg gatgacccgc ggttttggga gatggttgat gaagagaggg   9000
aaaaccatct gcgaggagag tgtcacacat gtatctacaa catgatggga aaaagagaga   9060
agaagcctgg agagtttgga aaagctaaag gaagcagggc catttggttc atgtggcttg   9120
gagcacggta tctagagttt gaagctttgg ggttcctgaa tgaagaccat tggctgagcc   9180
gagagaattc aggaggtgga gtggaaggct caggcgtcca aaagctggga tacatcctcc   9240
gtgacatagc aggaaagcaa ggagggaaaa tgtacgctga tgataccgcc gggtgggaca   9300
ctagaattac cagaactgat ttagaaaatg aagctaaggt actggagctc ctagacggtg   9360
aacaccgcat gctcgcccga gccataattg aactgactta caggcacaaa gtggtcaagg   9420
tcatgagacc tgcagcagaa ggaaagaccg tgatggacgt gatatcaaga gaagatcaaa   9480
gggggagtgg acaggtggtc acttatgctc ttaacacttt cacgaacatc gctgtccagc   9540
tcgtcaggct gatggaggct gagggggtca ttggaccaca acacttggaa catctaccta   9600
ggaaaaacaa gatagctgtc aggacctggc tctttgagaa tggagaggag agagtgacca   9660
ggatggcgat cagcggagac gactgtgccg tcaaaccgct ggacgacaga ttcgccacag   9720
ccctccactt cctcaacgca atgtcaaagg tcagaaaaga catccaggaa tggaagcctt   9780
cgcatggctg gcacgattgg cagcaagttc ccttctgttc taaccatttt caggagattg   9840
tgatgaaaga tggaaggagt atagttgtcc cgtgcagagg acaggatgag ctgataggca   9900
gggctcgcat ctctcctgga gctggatgga atgtgaagga cacagcttgc ctggccaaag   9960
catatgcaca gatgtggcta ctcctatact tccatcgcag ggacttgcgt ctcatggcaa  10020
atgcgatttg ctcagcagtg ccagtagatt gggtgcccac aggcaggaca tcctggtcaa  10080
tacactcgaa aggagagtgg atgaccacgg aagacatgct gcaggtctgg aacagagttt  10140
ggattgaaga aaatgaatgg atgatggaca agactccaat cacaagctgg acagacgttc  10200
cgtatgtggg aaagcgcgag gacatctggt gtggcagcct catcggaacg cgatccagag  10260
caacctgggc tgagaacatc tatgcggcga taaaccaggt tagagctgtc attgggaaag  10320
aaaattatgt tgactacatg acctcactca ggagatacga agacgtcttg atccaggaag  10380
acagggtcat ctagtgtgat ttaaggtaga aaagtagact atgtaaacaa tgtaaatgag  10440
aaaatgcatg catatggagt caggccagca aaagctgcca ccggatactg ggtagacggt  10500
gctgcctgcg tctcagtccc aggaggactg ggttaacaaa tctgacaaca gaaagtgaga  10560
aagccctcag aaccgtctcg gaagtaggtc cctgctcact ggaagttgaa agaccaacgt  10620
caggccacaa atttgtgcca ctccgctagg gagtgcggcc tgcgcagccc caggaggact  10680
gggttaccaa agccgttgag gcccccacgg cccaagcctc gtctaggatg caatagacga  10740
ggtgtaagga ctagaggtta gaggagaccc cgtggaaaca acaacatgcg gcccaagccc  10800
cctcgaagct gtagaggagg tggaaggact agaggttaga ggagaccccg catttgcatc  10860
aaacagcata ttgacacctg ggaatagact gggagatctt ctgctctatc tcaacatcag  10920
ctactaggca cagagcgccg aagtatgtag ctggtggtga ggaagaacac aggatct     10977
```

<210> SEQ ID NO 75
<211> LENGTH: 10976
<212> TYPE: DNA
<213> ORGANISM: Japanese encephalitis virus

<400> SEQUENCE: 75

```
agaagtttat ctgtgtgaac ttcttggctt agtatcgtag agaagaatcg agagattagt     60
gcagtttaaa cagtttttta gaacggaaga taaccatgac taaaaaacca ggagggcccg    120
gtaaaaaccg ggctatcaat atgctgaaac gcggcctacc ccgcgtattc ccactagtgg    180
gagtgaagag ggtagtaatg agcttgttgg acggcagagg gccagtacgt ttcgtgctgg    240
ctcttatcac gttcttcaag tttacagcat tagccccgac caaggcgctt tcaggccgat    300
ggaaagcagt ggaaaagagt gtggcaatga aacatcttac tagtttcaaa cgagaacttg    360
gaacactcat tgacgccgtg aacaagcggg gcagaaagca aaacaaaaga ggaggaaatg    420
aaggctcaat catgtggctc gcgagcttgg cagttgtcat agcttgtgca ggagccatga    480
agttgtcgaa tttccagggg aagcttttga tgaccatcaa caacacggac attgcagacg    540
ttatcgtgat tcccacctca aaaggagaga acagatgctg ggtccgggca atcgacgtcg    600
gctacatgtg tgaggacact atcacgtacg aatgtcctaa gcttaccatg ggcaatgatc    660
cagaggatgt ggattgctgg tgtgacaacc aagaagtcta cgtccaatat ggacggtgca    720
cgcggaccag gcattccaag cgaagcagga gatccgtgtc ggtccaaaca catggggaga    780
gttcactagt gaataaaaaa gaggcttggc tggattcaac gaaagccaca cgatatctca    840
tgaaaactga gaactggatc ataaggaatc ctggctatgc tttcctggcg gcggtacttg    900
gctggatgct tggcagtaac aacggtcaac gcgtggtatt taccatcctc ctgctgttgg    960
tcgctccggc ttacagtttt aattgtctgg gaatgggcaa tcgtgacttc atagaaggag   1020
ccagtggagc cacttgggtg gacttggtgc tagaaggaga cagctgcttg acaatcatgg   1080
caaacgacaa accaacattg gacgtccgca tgattaacat cgaagctagc caacttgctg   1140
aggtcagaag ttactgctat catgcttcag tcactgacat ctcgacggtg gctcggtgcc   1200
ccacgactgg agaagcccac aacgagaagc gagctgatag tagctatgtg tgcaaacaag   1260
gcttcactga ccgtgggtgg ggcaacggat gtggattttt cgggaaggga agcattgaca   1320
catgtgcaaa attctcctgc accagtaaag cgattgggag aacaatccag ccagaaaaca   1380
tcaaatacaa agttggcatt tttgtgcatg gaaccaccac ttcggaaaac catgggaatt   1440
attcagcgca agttggggcg tcccaggcgg caaagtttac agtaacaccc aatgctcctt   1500
cggtagccct caaacttggt gactacggag aagtcacact ggactgtgag ccaaggagtg   1560
gactgaacac tgaagcgttt tacgtcatga ccgtggggtc aaagtcattt ctggtccata   1620
gggagtggtt tcatgacctc gctctcccct ggacgtcccc ttcgagcaca gcgtggagaa   1680
acagagaact cctcatggaa tttgaagggg cgcacgccac aaaacagtcc gttgttgctc   1740
ttgggtcaca ggaaggaggc ctccatcatg cgttggcagg agccatcgtg gtggagtact   1800
caagctcagt gatgttaaca tcaggccacc tgaaatgtag gctgaaaatg gacaaactgg   1860
ctctgaaagg cacaacctat ggcatgtgta cagaaaaatt ctcgttcgcg aaaaatccgg   1920
tggacactgg tcacggaaca gttgtcattg aactctccta ctctgggagt gatggcccct   1980
gcaaaattcc gattgtttcc gttgcgagcc tcaatgacat gacccccgtt gggcggctgg   2040
tgacagtgaa ccccttcgtc gcgacttcca gtgccaactc aaaggtgctg gtcgagatgg   2100
aacccccctt cggagactcc tacatcgtag ttggaagggg agacaagcag atcaaccacc   2160
attggcacaa agctggaagc acgctgggca aggccttttc aacaactttg aagggagctc   2220
aaagactggc agcgttgggc gacacagcct gggactttgg ctctattgga ggggtcttca   2280
```

actccatagg aagagccgtt caccaagtgt ttggtgatgc cttcagaaca ctctttgggg 2340
gaatgtcttg gatcacacaa gggctaatgg gtgccctact gctctggatg ggcgtcaacg 2400
cacgagaccg atcaattgct ttggccttct tagccacagg aggtgtgctc gtgttcttag 2460
cgaccaatgt gcatgctgac actggatgtg ccattgacat cacaagaaaa gagatgagat 2520
gtggaagtgg catcttcgtg cacaacgacg tggaagcctg ggtggatagg tataaatatt 2580
tgccagaaac gcccagatcc ctagcgaaga tcgtccacaa agcgcacaag gaaggcgtgt 2640
gcggagtcag atctgtcact agactggagc accaaatgtg ggaagccgta agggacgaat 2700
tgaacgtcct gctcaaagag aatgcagtgg acctcagtgt ggttgtgaac aagcccgtgg 2760
gaagatatcg ctcagcccct aaacgcctat ccatgacgca agagaagttt gaaatgggct 2820
ggaaagcatg ggaaaaaagc atcctctttg ccccggaatt ggctaactcc acatttgtcg 2880
tagatggacc tgagacaaag gaatgccctg atgagcacag agcttggaac agcatgcaaa 2940
tcgaagactt cggctttggc atcacatcaa cccgtgtgtg gctgaaaatt agagaggaga 3000
gcactgacga gtgtgatgga gcgatcatag gcacggctgt caaaggacat gtggcagtcc 3060
atagtgactt gtcgtactgg attgagagtc gctacaacga cacatggaaa cttgagaggg 3120
cagtctttgg agaggtcaaa tcttgcactt ggccagagac acacaccctt tggggagatg 3180
atgttgagga aagtgaactc atcattccgc acaccatagc cggaccaaaa agcaagcaca 3240
atcggaggga agggtataag acacaaaacc agggaccttg ggatgagaat ggcatagtct 3300
tggactttga ttattgccca gggacaaaag tcaccattac agaggattgt agcaagagag 3360
gcccttcggt cagaaccact actgacagtg gaaagttgat cactgactgg tgctgtcgca 3420
gttgctccct tccgccccta cgattccgga cagaaaatgg ctgctggtac ggaatggaaa 3480
tcagacctgt tatgcatgat gaaacaacac tcgtcagatc acaggttcat gctttcaaag 3540
gtgaaatggt tgaccctttt cagctgggcc ttctggtgat gtttctggcc acccaggaag 3600
tccttcgcaa gaggtggacg gccagattga ccattcctgc ggttttgggg gtcctacttg 3660
tgctgatgct tgggggtatc acttacactg atttggcgag gtatgtggtg ctagtcgctg 3720
ctgctttcgc agaggccaac agtggaggag acgtcctgca ccttgctttg attgctgttt 3780
ttaagatcca accagcattt ttagtgatga acatgcttag cacgagatgg acgaaccaag 3840
aaaacgtggt tctggtccta ggggctgcct tttccaatt ggcctcagta gatctgcaaa 3900
taggagtcca cggaatcctg aatgccgccg ctatagcatg gatgattgtc cgagcgatca 3960
ccttccccac aacctcctcc gtcaccatgc cagtcttagc gcttctaact ccggggatga 4020
gggctctata cctagacact tacagaatca tcctcctcgt catagggatt tgctccctgc 4080
tgcacgagag gaaaaagacc atggcgaaaa agaaaggagc tgtactcttg ggcttagcgc 4140
tcacatccac tggatggttc tcgcccacca ctatagctgc cggactaatg gtctgcaacc 4200
caaacaagaa gagagggtgg ccagctactg agtttttgtc ggcagttgga ttgatgtttg 4260
ccatcgtagg tggtttggcc gagttggata ttgaatccat gtcaataccc ttcatgctgg 4320
caggtctcat ggcagtgtcc tacgtggtgt caggaaaagc aacagatatg tggcttgaac 4380
gggccgccga catcagctgg gatatgggtg ctgcaatcac aggaagcagt cggaggctgg 4440
atgtgaaact ggatgatgac ggagattttc acttcattga tgatcccggt gttccatgga 4500
aggtctgggt cctgcgcatg tcttgcattg gcttagccgc cctcacgcct tgggccatcg 4560
ttcccgccgc tttcggttat tggctcactt taaaaacaac aaaaagaggg ggcgtgtttt 4620
gggacacgcc atccccaaaa ccttgctcaa aaggagacac cactacagga gtctaccgaa 4680
ttatggctag agggattctt ggcacttacc aggccggcgt cggagtcatg tacgagaatg 4740
ttttccacac actatggcac acaactagag gagcagccat tgtgagtgga gaaggaaaat 4800
tgacgccata ctggggtagt gtgaaagaag accgcatagc ttacggaggc ccatggaggt 4860
ttgaccgaaa atggaatgga acagatgacg tgcaagtgat cgtggtagaa ccggggaagg 4920
gcgcagtaaa catccagaca aaaccaggag tgtttcggac tcccttcggg gaggttgggg 4980
ctgttagtct ggattacccg cgaggaacat ccggctcacc cattctggat tccaatggag 5040
acattatagg cctatacggc aatggagttg agcttggcga tggctcatac gtcagcgcca 5100
tcgtgcaggg tgaccgtcag gaggaaccag tcccagaagc ttacacccca aacatgttga 5160
gaaagagaca gatgactgtg ctagatttgc accctggttc agggaaaacc aggaaaattc 5220
tgccacaaat aattaaggac gctatccagc agcgcctaag aacagctgtg ttggcaccga 5280
cgcgggtggt agcagcagaa atggcagaag ttttgagagg gctcccagta cgatatcaaa 5340
cttcagcagt gcagagagag caccaaggga atgaaatagt ggatgtgatg tgccacgcca 5400
ctctgaccca tagactgatg tcaccgaaca gagtgcccaa ctacaaccta tttgtcatgg 5460
atgaagctca tttcaccgac ccagccagta tagccgcacg aggatacatt gctaccaagg 5520
tggaattagg ggaggcagca gccatcttta tgacagcgac cccgcctgga accacggatc 5580
cttttcctga ctcaaatgcc ccaatccatg atttgcaaga tgagatacca gacagggcat 5640
ggagcagtgg atacgaatgg atcacagaat atgcgggtaa aaccgtgtgg tttgtggcga 5700
gcgtaaaaat ggggaatgag attgcaatgt gcctccaaag agcggggaaa aaggtcatcc 5760
aactcaaccg caagtcctat gacacagaat acccaaaatg taagaatgga gactgggatt 5820
ttgtcattac caccgacatc tctgaaatgg gggccaactt cggtgcgagc agggtcatcg 5880
actgtagaaa gagcgtgaaa cccaccatct tagaagaggg agaaggcaga gtcatcctcg 5940
gaaacccatc tcccataacc agtgcaagcg cagctcaacg gaggggcaga gtaggcagaa 6000
accccaatca agttggagat gaataccact atgggggggc taccagtgaa gatgacagta 6060
acctagccca ttggacagag gcaaagatca tgttagacaa catacacatg cccaatggac 6120
tggtggccca gctctatgga ccagagaggg aaaaggcttt cacaatggat ggcgaatacc 6180
gtctcagagg tgaagaaaag aaaaacttct tagagctgct taggacggct gacctcccgg 6240
tgtggctggc ctacaaggtg gcgtccaatg gcattcagta caccgacaga aagtggtgtt 6300
ttgatgggcc gcgtacgaat gccatactgg aggacaacac cgaggtagag atagtcaccc 6360
ggatgggtga gaggaaaatc ctcaagccga gatggcttga tgcaagagtt tatgcagatc 6420
accaggccct caagtggttc aaagactttg cagcagggaa gagatcagcc gttagcttca 6480
tagaggtgct cggtcgcatg cctgagcatt tcatgggaaa gacgcgggaa gctttagaca 6540
ccatgtactt ggttgcaacg gctgagaaag gtgggaaagc acaccgaatg gctctcgaag 6600
agctgccaga tgcactggaa accatcacac ttattgtcgc cattactgtg atgacaggag 6660
gattcttcct actaatgatg cagcgaaagg gtatagggaa gatgggtctt ggagctctag 6720
tgctcacact agctaccttc ttcctgtggg cggcagaggt tcctggaacc aaaatagcag 6780
ggaccctgct gatcgccctg ctgctgatgg tggttctcat cccagaaccg gaaaaacaga 6840
ggtcacagac agataaccaa ctggcggtgt ttctcatctg tgtcttgacc gtggttggag 6900
tggtggcagc aaacgagtac gggatgctag aaaaaaccaa agcggatctc aagagcatgt 6960
ttggcggaaa gacgcaggca tcaggactga ctggattgcc aagcatggca ctggacctgc 7020

-continued

```
gtccagccac agcctgggca ctgtatgggg ggagcacagt cgtgctaacc cctcttctga   7080
agcacctgat cacgtcggaa tacgtcacca catcgctagc ttcaattaac tcacaagctg   7140
gctcattatt cgtcttgcca cgaggcgtgc cttttaccga cctagacttg actgttggcc   7200
tcgtcttcct tggctgttgg ggtcaagtca ccctcacaac gtttctgaca gccatggttc   7260
tggcgacact tcactatggg tacatgctcc ctggatggca agcagaagca ctcagggctg   7320
cccagagaag gacagcggct ggaataatga agaatgccgt tgttgacgga atggtcgcca   7380
ctgatgtgcc tgaactggaa aggactactc ctctgatgca aaagaaagtc ggacaggtgc   7440
tcctcatagg ggtaagcgtg gcagcgttcc tcgtcaaccc taatgtcacc actgtgagag   7500
aagcaggggt gttggtgacg gcggctacgc ttactttgtg ggacaatgga gccagtgccg   7560
tttggaattc caccacagcc acgggactct gccatgtcat gcgaggtagc tacctggctg   7620
gaggctccat tgcttggact ctcatcaaga acgctgataa gccctccttg aaaaggggaa   7680
ggcctggggg caggacgcta ggggagcagt ggaaggaaaa actaaatgcc atgagtagag   7740
aagagttttt taaataccgg agagagggca taatcgaggt ggaccgcact gaagcacgca   7800
gggccagaag tgaaaataac atagtgggag gacatccggt ttcgcgaggc tcagcaaaac   7860
tccgttggct tgtggagaaa ggatttgtct cgccaatagg aaaagtcatt gatctagggt   7920
gtgggcgtgg aggatggagc tactacgcag caaccctgaa gaaggtccag gaagtcagag   7980
gatacacgaa aggtggggcg ggacatgaag aaccgatgct catgcagagc tacggctgga   8040
acctggtctc cctgaagagt ggagtggacg tgttttacaa accttcagag cccagtgata   8100
ccctgttctg tgacataggg gaatcctccc caagtccaga agtagaagaa caacgcacac   8160
tacgcgtcct agagatgaca tctgactggt tgcaccgagg acctagagag ttctgcatta   8220
aagttctctg cccttacatg cccaaggtta tagaaaaaat tgaagttctg cagcgccgct   8280
tcggaggtgg gctagtgcgt ctccccctgt cccgaaactc caatcacgag atgtattggg   8340
ttagtggagc cgctggcaat gtggtgcacg ctgtgaacat gaccagccag gtattactgg   8400
ggcgaatgga tcgcacagtg tggagagggc caaagtatga ggaagatgtc aacctaggga   8460
gcggaacaag agccgtggga aagggagaag tccatagcaa tcaggagaaa atcaagaaga   8520
gaatccagaa gcttaaagaa gaattcgcca caacgtggca caaagaccct gagcatccat   8580
accgcacttg gacataccac ggaagctatg aagtgaaggc tactggctca gccagctctc   8640
tcgtcaacgg agtggtgaag ctcatgagca aaccttggga cgccattgcc aacgtcacca   8700
ccatggccat gactgacacc acccctttttg gacagcaaag agttttcaag gagaaagttg   8760
acacgaaggc tcctgagcca ccagctggag ccaaggaagt gctcaacgag accaccaact   8820
ggctgtgggc ctacttgtca cgggaaaaaa gaccccgctt gtgcaccaag gaagaattca   8880
ttaagaaagt taacagcaac gcggctcttg gagcagtgtt cgctgaacag aatcaatgga   8940
gcacggcgcg tgaggctgtg gatgacccgc ggttttggga gatggttgat gaagagaggg   9000
aaaaccatct gcgaggagag tgtcacacat gtatctacaa catgatggga aaaagagaga   9060
agaagcctgg agagtttgga aaagctaaag gaagcagggc catttggttc atgtggcttg   9120
gagcacggta tctagagttt gaagctttgg ggttcctgaa tgaagaccat tggctgagcc   9180
gagagaattc aggaggtgga gtggaaggct caggcgtcca aaagctggga tacatcctcc   9240
gtgacatagc aggaaagcaa ggagggaaaa tgtacgctga tgataccgcc gggtgggaca   9300
ctagaattac cagaactgat ttagaaaatg aagctaaggt actggagctc ctagacggtg   9360
aacaccgcat gctcgcccga gccataattg aactgactta caggcacaaa gtggtcaagg   9420
```

```
tcatgagacc tgcagcagaa ggaaagaccg tgatggacgt gatatcaaga gaagatcaaa   9480

gggggagtgg acaggtggtc acttatgctc ttaacacttt cacgaacatc gctgtccagc   9540

tcgtcaggct gatggaggct gagggggtca ttggaccaca acacttggaa catctaccta   9600

ggaaaaacaa gatagctgtc aggacctggc tctttgagaa tggagaggag agagtgacca   9660

ggatggcgat cagcggagac gactgtgccg tcaaaccgct ggacgacaga ttcgccacag   9720

ccctccactt cctcaacgca atgtcaaagg tcagaaaaga catccaggaa tggaagcctt   9780

cgcatggctg gcacgattgg cagcaagttc ccttctgttc taaccatttt caggagattg   9840

tgatgaaaga tggaaggagt atagttgtcc cgtgcagagg acaggatgag ctgataggca   9900

gggctcgcat ctctccagga gctggatgga atgtgaagga cacagcttgc ctgcccaaag   9960

catatgcaca aatgtgggta ctcctatact tccaccgcag ggacttgcgt ctcatggcaa  10020

atgcgatttg ctcagcagtg ccagtagatt gggtgcccac aggcaggaca tcctggtcaa  10080

tacactcgaa aggagagtgg atgaccacgg aagacatgct gcaggtctgg aacagagttt  10140

ggattgaaga aaatgaatgg atgatggaca agactccaat cacaagctgg acagacgttc  10200

cgtatgtggg aaagcgcgag gacatctggt gtggcagcct catcggaacg cgatccagag  10260

caacctgggc tgagaacatc tatgcggcga taaaccaggt tagagctgtc attgggaaag  10320

aaaattatgt tgactacatg acctcactca ggagatacga agacgtcttg atccaggaag  10380

acagggtcat ctagtgtgat ttaaggtaga aaagtagact atgtaaacaa tgtaaatgag  10440

aaaatgcatg catatggagt caggccagca aaagctgcca ccggatactg ggtagacggt  10500

gctgcctgcg tctcagtccc aggaggactg ggttaacaaa tctgacaaca gaaagtgaga  10560

aagccctcag aactgtctcg gaagtaggtc cctgctcact ggaagttgaa agaccaacgt  10620

caggccacaa atttgtgcca ctccgctagg gagtgcggcc tgcgcagccc caggaggact  10680

gggttaccaa agccgttgag cccccacggc ccaagcctcg tctaggatgc aatagacgag  10740

gtgtaaggac tagaggttag aggagacccc gtggaaacaa caacatgcgg cccaagcccc  10800

ctcgaagctg tagaggaggt ggaaggacta gaggttagag gagaccccgc atttgcatca  10860

aacagcatat tgacacctgg gaatagactg ggagatcttc tgctctatct caacatcagc  10920

tactaggcac agagcgccga agtatgtacg tggtggtgag gaagaacaca ggatct      10976
```

<210> SEQ ID NO 76
<211> LENGTH: 10838
<212> TYPE: DNA
<213> ORGANISM: Yellow fever virus

<400> SEQUENCE: 76

```
gtgctaattg aggtgcattg gtctgcaaat cgagttgcta ggcaataaac acatttggat     60

taattttaat cgttcgttga gcgattagca gagaactgac cagaacatgt ctggtcgtaa    120

agctcaggga aaaaccctgg gcgtcaatat ggtacgacga ggagttcgct ccttgtcaaa    180

caaaataaaa caaaaaacaa aacaaattgg aaacagacct ggaccttcaa gaggtgttca    240

aggatttatc tttttctttt tgttcaacat tttgactgga aaaaagatca cagcccacct    300

aaagaggttg tggaaaatgc tggacccaag acaaggcttg gctgttctaa ggaaagtcaa    360

gagagtggtg gccagtttga tgagaggatt gtcctcaagg aaacgccgtt cccatgatgt    420

tctgactgtg caattcctaa ttttgggaat gctgttgatg acgggtggag tgaccttggt    480

gcggaaaaac agatggttgc tcctaaatgt gacatctgag gacctcggga aaacattctc    540
```

```
tgtgggcaca ggcaactgca caacaaacat tttggaagcc aagtactggt gcccagactc    600
aatggaatac aactgtccca atctcagtcc aagagaggag ccagatgaca ttgattgctg    660
gtgctatggg gtggaaaacg ttagagtcgc atatggtaag tgtgactcag caggcaggtc    720
taggaggtca agaagggcca ttgacttgcc tacgcatgaa aaccatggtt tgaagacccg    780
gcaagaaaaa tggatgactg gaagaatggg tgaaaggcaa ctccaaaaga ttgagagatg    840
gttcgtgagg aacccctttt ttgcagtgac ggctctgacc attgcctacc ttgtgggaag    900
caacatgacg caacgagtcg tgattgccct actggtcttg gctgttggtc cggcctactc    960
agctcactgc attggaatta ctgacaggga tttcattgag ggggtgcatg gaggaacttg   1020
ggtttcagct accctggagc aagacaagtg tgtcactgtt atggcccctg acaagccttc   1080
attggacatc tcactagaga cagtagccat tgatagacct gctgaggtga ggaaagtgtg   1140
ttacaatgca gttctcactc atgtgaagat taatgacaag tgccccagca ctggagaggc   1200
ccacctagct gaagagaacg aaggggacaa tgcgtgcaag cgcacttatt ctgatagagg   1260
ctggggcaat ggctgtggcc tatttgggaa agggagcatt gtggcatgcg ccaaattcac   1320
ttgtgccaaa tccatgagtt tgtttgaggt tgatcagacc aaaattcagt atgtcatcag   1380
agcacaattg catgtagggg ccaagcagga aaattggact accgacatta agactctcaa   1440
gtttgatgcc ctgtcaggct cccaggaagt cgagttcatt gggtatggaa aagctacact   1500
ggaatgccag gtgcaaactg cggtggactt tggtaacagt tacatcgctg agatggaaac   1560
agagagctgg atagtggaca gacagtgggc ccaggacttg accctgccat ggcagagtgg   1620
aagtggcggg gtgtggagag agatgcatca tcttgtcgaa tttgaacctc cgcatgccgc   1680
cactatcaga gtactggccc tgggaaacca ggaaggctcc ttgaaaacag ctcttactgg   1740
cgcaatgagg gttacaaagg acacaaatga caacaacctt tacaaactac atggtggaca   1800
tgtttcttgc agagtgaaat tgtcagcttt gacactcaag ggacatcct acaaaaatatg   1860
cactgacaaa atgttttttg tcaagaaccc aactgacact ggccatggca ctgttgtgat   1920
gcaggtgaaa gtgtcaaaag gagccccctg caggattcca gtgatagtag ctgatgatct   1980
tacagcggca atcaataaag gcattttggt tacagttaac cccatcgcct caaccaatga   2040
tgatgaagtg ctgattgagg tgaacccacc ttttggagac agctacatta tcgttgggag   2100
aggagattca cgtctcactt accagtggca caaagaggga agctcaatag gaaagttgtt   2160
cactcagacc atgaaaggcg tggaacgcct ggccgtcatg ggagacaccg cctgggattt   2220
cagctccgct ggagggttct tcacttcggt tgggaaagga attcatacgg tgtttggctc   2280
tgcctttcag gggctatttg gcggcttgaa ctggataaca aaggtcatca tgggggcggt   2340
acttatatgg gttggcatca acacaagaaa catgacaatg tccatgagca tgatcttggt   2400
aggagtgatc atgatgtttt tgtctctagg agttggggcg gatcaaggat gcgccatcaa   2460
ctttggcaag agagagctca agtgcggaga tggtatcttc atatttagag actctgatga   2520
ctggctgaac aagtactcat actatccaga agatcctgtg aagcttgcat caatagtgaa   2580
agcctctttt gaagaaggga agtgtggcct aaattcagtt gactcccttg agcatgagat   2640
gtggagaagc agggcagatg agatcaatgc catttttgag gaaaacgagg tggacatttc   2700
tgttgtcgtg caggatccaa agaatgttta ccagagagga actcatccat tttccagaat   2760
tcgggatggt ctgcagtatg gttggaagac ttggggtaag aaccttgtgt tctccccagg   2820
gaggaagaat ggaagcttca tcatagatgg aaagtccagg aaagaatgcc cgttttcaaa   2880
ccgggtctgg aattctttcc agatagagga gtttgggacg ggagtgttca ccacacgcgt   2940
```

gtacatggac gcagtctttg aatacaccat agactgcgat ggatctatct tgggtgcagc 3000
ggtgaacgga aaaaagagtg cccatggctc tccaacattt tggatgggaa gtcatgaagt 3060
aaatgggaca tggatgatcc acaccttgga ggcattagat tacaaggagt gtgagtggcc 3120
actgacacat acgattggaa catcagttga agagagtgaa atgttcatgc cgagatcaat 3180
cggaggccca gttagctctc acaatcatat ccctggatac aaggttcaga cgaacggacc 3240
ttggatgcag gtaccactag aagtgaagag agaagcttgc ccagggacta gcgtgatcat 3300
tgatggcaac tgtgatggac ggggaaaatc aaccagatcc accacggata gcgggaaagt 3360
tattcctgaa tggtgttgcc gctcctgcac aatgccgcct gtgagcttcc atggtagtga 3420
tgggtgttgg tatcccatgg aaattaggcc aaggaaaacg catgaaagcc atctggtgcg 3480
ctcctgggtt acagctggag aaatacatgc tgtccctttt ggtttggtga gcatgatgat 3540
agcaatggaa gtggtcctaa ggaaaagaca gggaccaaag caaatgttgg ttggaggagt 3600
agtgctcttg ggagcaatgc tggtcgggca agtaactctc cttgatttgc tgaaactcac 3660
agtggctgtg ggattgcatt tccatgagat gaacaatgga ggagacgcca tgtatatggc 3720
gttgattgct gccttttcaa tcagaccagg gctgctcatc ggctttgggc tcaggaccct 3780
atggagccct cgggaacgcc ttgtgctgac cctaggagca gccatggtgg agattgcctt 3840
gggtggcgtg atgggcggcc tgtggaagta tctaaatgca gtttctctct gcatcctgac 3900
aataaatgct gttgcttcta ggaaagcatc aaataccatc ttgcccctca tggctctgtt 3960
gacacctgtc actatggctg aggtgagact tgccgcaatg ttcttttgtg ccgtggttat 4020 catagggtc cttcaccaga atttcaagga cacctccatg cagaagacta tacctctggt 4080
ggccctcaca ctcacatctt acctgggctt gacacaacct tttttgggcc tgtgtgcatt 4140
tctggcaacc cgcatatttg ggcgaaggag tatcccagtg aatgaggcac tcgcagcagc 4200
tggtctagtg ggagtgctgg caggactggc ttttcaggag atggagaact tccttggtcc 4260
gattgcagtt ggaggactcc tgatgatgct ggttagcgtg gctgggaggg tggatgggct 4320
agagctcaag aagcttggtg aagtttcatg ggaagaggag gcggagatca gcgggagttc 4380
cgcccgctat gatgtggcac tcagtgaaca aggggagttc aagctgcttt ctgaagagaa 4440
agtgccatgg gaccaggttg tgatgacctc gctggccttg gttggggctg ccctccatcc 4500
atttgctctt ctgctggtcc ttgctgggtg gctgtttcat gtcaggggag ctaggagaag 4560
tggggatgtc ttgtgggata ttcccactcc taagatcatc gaggaatgtg aacatctgga 4620
ggatgggatt tatggcatat tccagtcaac cttcttgggg gcctcccagc gaggagtggg 4680
agtggcacag ggaggggtgt tccacacaat gtggcatgtc acaagaggag ctttccttgt 4740
caggaatggc aagaagttga ttccatcttg ggcttcagta aaggaagacc ttgtcgccta 4800
tggtggctca tggaagttgg aaggcagatg ggatggagag gaagaggtcc agttgatcgc 4860
ggctgttcca ggaaagaacg tggtcaacgt ccagacaaaa ccgagcttgt tcaaagtgag 4920
gaatggggga gaaatcgggg ctgtcgctct tgactatccg agtggcactt caggatctcc 4980
tattgttaac aggaacggag aggtgattgg gctgtacggc aatggcatcc ttgtcggtga 5040
caactccttc gtgtccgcca tatcccagac tgaggtgaag gaagaaggaa aggaggagct 5100
ccaagagatc ccgacaatgc taaagaaagg aatgacaact gtccttgatt ttcatcctgg 5160
agctgggaag acaagacgtt tcctcccaca gatcttggcc gagtgcgcac ggagacgctt 5220
gcgcactctt gtgttggccc ccaccagggt tgttctttct gaaatgaagg aggcttttca 5280

```
cggcctggac gtgaaattcc acacacaggc tttttccgct cacggcagcg ggagagaagt   5340
cattgatgct atgtgccatg ccaccctaac ttacaggatg ttggaaccaa ctagggttgt   5400
taactgggaa gtgatcatta tggatgaagc ccattttttg gatccagcta gcatagccgc   5460
tagaggttgg gcagcgcaca gagctagggc aaatgaaagt gcaacaatct tgatgacagc   5520
cacaccgcct gggactagtg atgaatttcc acattcaaat ggtgaaatag aagatgttca   5580
aacggacata cccagtgagc cctggaacac agggcatgac tggatcctgg ctgacaaaag   5640
gcccacggca tggttccttc catccatcag agctgcaaat gtcatggctg cctctttgcg   5700
taaggctgga aagagtgtgg tggtcctgaa caggaaaacc tttgagagag aataccccac   5760
gataaagcag aagaaacctg actttatatt ggccactgac atagctgaaa tgggagccaa   5820
cctttgcgtg gagcgagtgc tggattgcag gacggctttt aagcctgtgc ttgtggatga   5880
agggaggaag gtggcaataa aagggccact tcgtatctcc gcatcctctg ctgctcaaag   5940
gagggggcgc attgggagaa atcccaacag agatggagac tcatactact attctgagcc   6000
tacaagtgaa aataatgccc accacgtctg ctggttggag gcctcaatgc tcttggacaa   6060
catggaggtg aggggtggaa tggtcgcccc actctatggc gttgaaggaa ctaaaacacc   6120
agtttcccct ggtgaaatga gactgaggga tgaccagagg aaagtcttca gagaactagt   6180
gaggaattgt gacctgcccg tttggctttc gtggcaagtg gccaaggctg gtttgaagac   6240
gaatgatcgt aagtggtgtt ttgaaggccc tgaggaacat gagatcttga atgacagcgg   6300
tgaaacagtg aagtgcaggg ctcctggagg agcaaagaag cctctgcgcc caaggtggtg   6360
tgatgaaagg gtgtcatctg accagagtgc gctgtctgaa tttattaagt ttgctgaagg   6420
taggagggga gctgctgaag tgctagttgt gctgagtgaa ctccctgatt tcctggctaa   6480
aaaaggtgga gaggcaatgg ataccatcag tgtgtttctc cactctgagg aaggctctag   6540
ggcttaccgc aatgcactat caatgatgcc tgaggcaatg acaatagtca tgctgtttat   6600
actggctgga ctactgacat cgggaatggt catctttttc atgtctccca aaggcatcag   6660
tagaatgtct atggcgatgg gcacaatggc cggctgtgga tatctcatgt tccttggagg   6720
cgtcaaaccc actcacatct cctatatcat gctcatattc tttgtcctga tggtggttgt   6780
gatccccgag ccagggcaac aaaggtccat ccaagacaac caagtggcat acctcattat   6840
tggcatcctg acgctggttt cagcggtggc agccaacgag ctaggcatgc tggagaaaac   6900
caaagaggac ctctttggga agaagaactt aattccatct agtgcttcac cctggagttg   6960
gccggatctt gacctgaagc caggagctgc ctggacagtg tacgttggca ttgttacaat   7020
gctctctcca atgttgcacc actggatcaa agtcgaatat ggcaacctgt ctctgtctgg   7080
aatagcccag tcagcctcag tcctttcttt catggacaag ggataccat tcatgaagat   7140
gaatatctcg gtcataatgc tgctggtcag tggctggaat tcaataacag tgatgcctct   7200
gctctgtggc atagggtgcg ccatgctcca ctggtctctc attttacctg gaatcaaagc   7260
gcagcagtca aagcttgcac agagaagggt gttccatggc gttgccaaga accctgtggt   7320
tgatgggaat ccaacagttg acattgagga agctcctgaa atgcctgccc tttatgagaa   7380
gaaactggct ctatatctcc ttcttgctct cagcctagct tctgttgcca tgtgcagaac   7440
gcccttttca ttggctgaag gcattgtcct agcatcagct gccctagggc cgctcataga   7500
gggaaacacc agccttcttt ggaatggacc catggctgtc tccatgacag gagtcatgag   7560
ggggaatcac tatgcttttg tgggagtcat gtacaatcta tggaagatga aaactggacg   7620
ccgggggagc gcgaatggaa aaactttggg tgaagtctgg aagagggaac tgaatctgtt   7680
```

-continued

```
ggacaagcga cagtttgagt tgtataaaag gaccgacatt gtggaggtgg atcgtgatac   7740
ggcacgcagg catttggccg aagggaaggt ggacaccggg gtggcggtct ccagggggac   7800
cgcaaagtta aggtggttcc atgagcgtgg ctatgtcaag ctggaaggta gggtgattga   7860
cctggggtgt ggccgcggag gctggtgtta ctacgctgct gcgcaaaagg aagtgagtgg   7920
ggtcaaagga tttactcttg gaagagacgg ccatgagaaa cccatgaatg tgcaaagtct   7980
gggatggaac atcatcacct tcaaggacaa aactgatatc caccgcctag aaccagtgaa   8040
atgtgacacc cttttgtgtg acattggaga gtcatcatcg tcatcggtca cagaggggga   8100
aaggaccgtg agagttcttg atactgtaga aaaatggctg gcttgtgggg ttgacaactt   8160
ctgtgtgaag gtgttagctc catacatgcc agatgttctc gagaaactgg aattgctcca   8220
aaggaggttt ggcggaacag tgatcaggaa ccctctctcc aggaattcca ctcatgaaat   8280
gtactacgtg tctggagccc gcagcaatgt cacatttact gtgaaccaaa catcccgcct   8340
cctgatgagg agaatgaggc gtccaactgg aaaagtgacc ctggaggctg acgtcatcct   8400
cccaattggg acacgcagtg ttgagacaga caagggaccc ctggacaaag aggccataga   8460
agaaagggtt gagaggataa aatctgagta catgacctct tggttttatg acaatgacaa   8520
cccctacagg acctggcact actgtggctc ctatgtcaca aaaacctcag gaagtgcggc   8580
gagcatggta aatggtgtta ttaaaattct gacatatcca tgggacagga tagaggaggt   8640
cacaagaatg gcaatgactg acacaacccc ttttggacag caaagagtgt ttaaagaaaa   8700
agttgacacc agagcaaagg atccaccagc gggaactagg aagatcatga aagttgtcaa   8760
caggtggctg ttccgccacc tggccagaga aaagaacccc agactgtgca caaaggaaga   8820
atttattgca aaagtccgaa gtcatgcagc cattggagct tacctggaag aacaagaaca   8880
gtggaagact gccaatgagg ctgtccaaga cccaaagttc tgggaactgg tggatgaaga   8940
aaggaagctg caccaacaag gcaggtgtcg gacttgtgtg tacaacatga tggggaaaag   9000
agagaagaag ctgtcagagt ttgggaaagc aaagggaagc cgtgccatat ggtatatgtg   9060
gctgggagcg cggtatcttg agtttgaggc cctgggattc ctgaatgagg accattgggc   9120
ttccagggaa aactcaggag gaggagtgga aggcattggc ttacaatacc taggatatgt   9180
gatcagagac ctggctgcaa tggatggtgg tggattctac gcggatgaca ccgctggatg   9240
ggacacgcgc atcacagagg cagaccttga tgatgaacag gagatcttga actacatgag   9300
cccacatcac aaaaaactgg cacaagcagt gatggaaatg acatacaaga acaaagtggt   9360
gaaagtgttg agaccagccc caggagggaa agcctacatg gatgtcataa gtcgacgaga   9420
ccagagagga tccgggcagg tagtgactta tgctctgaac accatcacca acttgaaagt   9480
ccaattgatc agaatggcag aagcagagat ggtgatacat caccaacatg ttcaagattg   9540
tgatgaatca gttctgacca ggctggaggc atggctcact gagcacggat gtaacagact   9600
gaagaggatg gcggtgagtg gagacgactg tgtggtccgg cccatcgatg acaggttcgg   9660
cctggccctg tcccatctca acgccatgtc caaggttaga aaggacatat ctgaatggca   9720
gccatcaaaa gggtggaatg attgggagaa tgtgcccttc tgttcccacc acttccatga   9780
actacagctg aaggatggca ggaggattgt ggtgccttgc cgagaacagg acgagctcat   9840
tgggagagga agggtgtctc caggaaacgg ctggatgatc aaggaaacag cttgcctcag   9900
caaagcctat gccaacatgt ggtcactgat gtattttcac aaaagggaca tgaggctact   9960
gtcattggct gtttcctcag ctgttcccac ctcatgggtt ccacaaggac gcacaacatg  10020
```

-continued

```
gtcgattcat gggaaagggg agtggatgac cacggaagac atgcttgagg tgtggaacag  10080
agtatggata accaacaacc cacacatgca ggacaagaca atggtgaaaa aatggagaga  10140
tgtcccttat ctaaccaaga gacaagacaa gctgtgcgga tcactgattg gaatgaccaa  10200
tagggccacc tgggcctccc acatccattt ggtcatccat cgtatccgaa cgctgattgg  10260
acaggagaaa tacactgact acctaacagt catggacagg tattctgtgg atgctgacct  10320
gcaactgggt gagcttatct gaaacaccat ctaacaggaa taaccgggat acaaaccacg  10380
ggtggagaac cggactcccc acaacctgaa accgggatat aaaccacggc tggagaaccg  10440
gactccgcac ttaaaatgaa acagaaaccg ggataaaaac tacggatgga gaaccggact  10500
ccacacattg agacagaaga agttgtcagc ccagaacccc acacgagttt tgccactgct  10560
aagctgtgag gcagtgcagg ctgggacagc cgacctccag gttgcgaaaa acctggtttc  10620
tgggacctcc caccccagag taaaaagaac ggagcctccg ctaccaccct cccacgtggt  10680
ggtagaaaga cggggtctag aggttagagg agaccctcca gggaacaaat agtgggacca  10740
tattgacgcc agggaaagac cggagtggtt ctctgctttt cctccagagg tctgtgagca  10800
cagtttgctc aagaataagc agacctttgg atgacaaa                          10838
```

<210> SEQ ID NO 77
<211> LENGTH: 11674
<212> TYPE: DNA
<213> ORGANISM: Chikungunya virus

<400> SEQUENCE: 77

```
gatggctgcg tgagacacac gtagcctacc agtttcttac tgctctactc tgcaaagcaa     60
gagattaata acccatcatg gatcctgtgt acgtggacat agacgctgac agcgcctttt    120
tgaaggccct gcaacgtgcg taccccatgt ttgaggtgga accaaggcag gtcacaccga    180
atgaccatgc taatgctaga gcgttctcgc atctagctat aaaactaata gagcaggaaa    240
ttgaccccga ctcaaccatc ctggatatcg gcagtgcgcc agcaaggagg atgatgtcgg    300
acaggaagta ccactgcgtc tgcccgatgc gcagtgcgga agatcccgag agactcgcca    360
attatgcgag aaagctagca tctgccgcag gaaaagtcct ggacagaaac atctctggaa    420
agatcgggga cttacaagca gtaatggccg tgccagacac ggagacgcca acattctgct    480
tacacacaga cgtctcatgt agacagagag cagacgtcgc tatataccaa gacgtctatg    540
ctgtacacgc acccacgtcg ctataccacc aggcgattaa aggggtccga gtggcgtact    600
gggttgggtt cgacacaacc ccgttcatgt acaatgccat ggcgggtgcc taccccctcat   660
actcgacaaa ctgggcagat gagcaggtac tgaaggctaa gaacatagga ttatgttcaa    720
cagacctgac ggaaggtaga cgaggcaagt tgtctattat gagagggaaa aagctaaaac    780
cgtgcgaccg tgtgctgttc tcagtagggt caacgctcta cccggaaagc cgcaagctac    840
ttaagagctg gcacctgcca tcggtgttcc atttaaaggg caaactcagc ttcacatgcc    900
gctgtgatac agtggtttcg tgtgagggct acgtcgttaa gagaataacg atgagcccag    960
gcctttatgg aaaaaccaca gggtatgcgg taacccacca cgcagacgga ttcctgatgt   1020
gcaagactac cgacacggtt gacggcgaaa gaatgtcatt ctcggtgtgc acatacgtgc   1080
cggcgaccat ttgtgatcaa atgaccggca tccttgctac agaagtcacg ccggaggatg   1140
cacagaagct gttggtgggg ctgaaccaga gaatagtggt taacggcaga acgcaacgga   1200
atacgaacac catgaaaaat tatctgcttc ccgtggtcgc ccaagccttc agtaagtggg   1260
caaaggagtg ccggaaagac atggaagatg aaaaactcct gggggtcaga gaaagaacac   1320
```

-continued

```
tgacctgctg ctgtctatgg gcattcaaga agcagaaaac acacacggtc tacaagaggc   1380
ctgataccca gtcaattcag aaggttcagg ccgagtttga cagctttgtg gtaccgagtc   1440
tgtggtcgtc cgggttgtca atccctttga ggactagaat caaatggttg ttaagcaagg   1500
tgccaaaaac cgacctgatc ccatacagcg gagacgcccg agaagcccgg gacgcagaaa   1560
aagaagcaga ggaagaacga gaagcagaac tgactcgcga agccctacca cctctacagg   1620
cagcacagga agatgttcag gtcgaaatcg acgtggaaca gcttgaggac agagcgggcg   1680
caggaataat agagactccg agaggagcta tcaaagttac tgcccaacca acagaccacg   1740
tcgtgggaga gtacctggta ctctccccgc agaccgtact acgtagccag aagctcagtc   1800
tgattcacgc tttggcggag caagtgaaga cgtgcacgca caacggacga gcagggaggt   1860
atgcggtcga agcgtacgac ggccgagtcc tagtgccctc aggctatgca atctcgcctg   1920
aagacttcca gagtctaagc gaaagcgcaa cgatggtgta taacgaaaga gagttcgtaa   1980
acagaaagct acaccatatt gcgatgcacg gaccagccct gaacaccgac gaagagtcgt   2040
atgagctggt gagggcagag aggacagaac acgagtacgt ctacgacgtg gatcagagaa   2100
gatgctgtaa gaaggaagaa gccgcaggac tggtactggt gggcgacttg actaatccgc   2160
cctaccacga attcgcatat gaagggctaa aaatccgccc tgcctgccca tacaaaattg   2220
cagtcatagg agtcttcgga gtaccgggat ctggcaagtc agctattatc aagaacctag   2280
ttaccaggca ggacctggtg actagcggaa agaaagaaaa ctgccaagaa atcaccaccg   2340
acgtgatgag acagagaggt ctagagatat ctgcacgtac ggttgactcg ctgctcttga   2400
atggatgcaa cagaccagtc gacgtgttgt acgtagacga ggcgtttgcg tgccactctg   2460
gaacgctact tgctttgatc gccttggtga gaccaaggca gaaagttgta ctttgtggtg   2520
acccgaagca gtgcggcttc ttcaatatga tgcagatgaa agtcaactat aatcacaaca   2580
tctgcaccca agtgtaccac aaaagtatct ccaggcggtg tacactgcct gtgaccgcca   2640
ttgtgtcatc gttgcattac gaaggcaaaa tgcgcactac gaatgagtac aacaagccga   2700
ttgtagtgga cactacaggc tcaacaaaac ctgaccctgg agacctcgtg ttaacgtgct   2760
tcagagggtg ggttaaacaa ctgcaaattg actatcgtgg atacgaggtc atgacagcag   2820
ccgcatccca agggttaacc agaaaaggag tttacgcagt tagacaaaaa gttaatgaaa   2880
acccgctcta tgcatcaacg tcagagcacg tcaacgtact cctaacgcgt acggaaggta   2940
aactggtatg gaagacactt tccggcgacc cgtggataaa gacgctgcag aacccaccga   3000
aaggaaactt caaagcaact attaaggagt gggaggtgga gcatgcatca ataatggcgg   3060
gcatctgcag tcaccaaatg accttcgata cattccaaaa taaagccaac gtttgttggg   3120
ctaagagctt ggtccctatc ctcgaaacag cggggataaa actaaatgat aggcagtggt   3180
ctcagataat tcaagccttc aaagaagaca aagcatactc acctgaagta gccctgaatg   3240
aaatatgtac gcgcatgtat ggggtggatc tagacagcgg gctattttct aaaccgttgg   3300
tgtctgtgta ttacgcggat aaccactggg ataataggcc tggagggaaa atgttcggat   3360
ttaaccccga ggcagcatcc attctagaaa gaaagtatcc attcacaaaa gggaagtgga   3420
acatcaacaa gcagatctgc gtgactacca ggaggataga agactttaac cctaccacca   3480
acatcatacc ggccaacagg agactaccac actcattagt ggccgaacac cgcccagtaa   3540
aaggggaaag aatggaatgg ctggttaaca agataaacgg ccaccacgtg ctcctggtca   3600
gtggctataa ccttgcactg cctactaaga gagtcacttg ggtagcgccg ttaggtgtcc   3660
```

```
gcggagcgga ctacacatac aacctagagt tgggtctgcc agcaacgctt ggtaggtatg   3720
acctagtggt cataaacatc cacacacctt ttcgcataca ccattaccaa cagtgcgtcg   3780
accacgcaat gaaactgcaa atgctcgggg gtgactcatt gagactgctc aaaccgggcg   3840
gctctctatt gatcagagca tatggttacg cagatagaac cagtgaacga gtcatctgcg   3900
tattgggacg caagtttaga tcgtctagag cgttgaaacc accatgtgtc accagcaaca   3960
ctgagatgtt tttcctattc agcaactttg acaatggcag aaggaatttc acaactcatg   4020
tcatgaacaa tcaactgaat gcagccttcg taggacaggt cacccgagca ggatgtgcac   4080
cgtcgtaccg ggtaaaacgc atggacatcg cgaagaacga tgaagagtgc gtagtcaacg   4140
ccgctaaccc tcgcgggtta ccgggtggcg gtgtttgcaa ggcagtatac aaaaaatggc   4200
cggagtcctt taagaacagt gcaacaccag tgggaaccgc aaaaacagtt atgtgcggta   4260
cgtatccagt aatccacgct gttggaccaa acttctctaa ttattcggag tctgaagggg   4320
accgggaatt ggcagctgcc tatcgagaag tcgcaaagga agtaactagg ctgggagtaa   4380
atagtgtagc tatacctctc ctctccacag gtgtatactc aggagggaaa gacaggctga   4440
cccagtcact gaaccacctc tttacagcca tggactcgac ggatgcagac gtggtcatct   4500
actgccgcga caaagaatgg gagaagaaaa tatctgaggc catacagatg cggacccaag   4560
tagagctgct ggatgagcac atctccatag actgcgatat tgttcgcgtg caccctgaca   4620
gcagcttggc aggcagaaaa ggatacagca ccacggaagg cgcactgtac tcatatctag   4680
aagggacccg ttttcatcag acggctgtgg atatggcgga gatacatact atgtggccaa   4740
agcaaacaga ggccaatgag caagtctgcc tatatgccct gggggaaagt attgaatcga   4800
tcaggcagaa atgcccggtg gatgatgcag acgcatcatc tccccccaaa actgtcccgt   4860
gcctttgccg ttacgctatg actccagaac gcgtcacccg gcttcgcatg aaccacgtca   4920
caagcataat tgtgtgttct tcgtttcccc tcccaaagta caaaatagaa ggagtgcaaa   4980
aagtcaaatg ctctaaggta atgctatttg accacaacgt gccatcgcgc gtaagtccaa   5040
gggcttatag aggtgccgct gccggtaacc ttgcggccgt gtctgattgg gtaatgagca   5100
ccgtacctgt cgcgccgccc agaagaaggc gagggagaaa cctgactgtg acatgtgacg   5160
agagagaagg gaatataaca cccatggcta gcgtccgatt ctttagggca gagctgtgtc   5220
cggtcgtaca agaaacagcg gagacgcgtg acacagcaat gtctcttcag gcaccaccga   5280
gtaccgccac ggaaccgaat catccgccga tctccttcgg agcatcaagc gagacgttcc   5340
ccattacatt tggggacttc aacgaaggag aaatcgaaag cttgtcttct gagctactaa   5400
ctttcggaga cttcttacca ggagaagtgg atgacttgac agacagcgac tggtccacgt   5460
gctcagacac ggacgacgag ttaagactag acagggcagg tgggtatata ttctcgtcgg   5520
acaccggtcc aggtcattta caacagaagt cagtacgcca gtcagtgctg ccggtgaaca   5580
ccctggagga agtccacgag gagaagtgtt acccacctaa gctggatgaa gcaaaggagc   5640
aactattact taagaaactc caggagagtg catccatggc caacagaagc aggtatcagt   5700
cgcgcaaagt agaaaacatg aaagcagcaa tcatccagag actaaagaga ggctgtagac   5760
tatacttaat gtcagagacc ccaaaagtcc ctacttaccg gactacatat ccggcgcctg   5820
tgtactcgcc tccgatcaac gtccgattgt ccaatcccga gtccgcagtg gcagcatgca   5880
atgagttctt agctagaaac tatccaactg tctcatcata ccaaattacc gacgagtatg   5940
atgcatatct agacatggtg gacgggtcgg agagttgcct ggaccgagcg acattcaatc   6000
cgtcaaaact caggagctac ccgaaacagc acgcttacca cgcgccctcc atcagaagcg   6060
```

```
ctgtaccgtc cccattccag aacacactac agaatgtact ggcagcagcc acgaaaagaa   6120
actgcaacgt cacacagatg agggaattac ccactttgga ctcagcagta ttcaacgtgg   6180
agtgtttcaa aaaattcgca tgcaaccaag aatactggga agaatttgct gccagcccta   6240
ttaggataac aactgagaat ttagcaacct atgttactaa actaaaaggg ccaaaagcag   6300
cagcgctatt cgcaaaaacc cataatctac tgccactaca ggaagtacca atggataggt   6360
tcacagtaga tatgaaaagg gacgtaaagg tgactcctgg tacaaagcat acagaggaaa   6420
gacctaaggt gcaggttata caggcggctg aacccttggc gacagcatac ctatgtggga   6480
ttcacagaga gctggttagg aggctgaacg ccgtcctcct acccaatgta catacactat   6540
ttgacatgtc tgccgaggat ttcgatgcca tcatagccgc acactttaag ccaggagaca   6600
ctgttttgga aacggacata gcctcctttg ataagagcca agatgattca cttgcgctta   6660
ctgctttgat gctgttagag gatttagggg tggatcactc cctgctggac ttgatagagg   6720
ctgctttcgg agagatttcc agctgtcacc taccgacagg tacgcgcttc aagttcggcg   6780
ccatgatgaa atcaggtatg ttcctaactc tgttcgtcaa cacattgtta aacatcacca   6840
tcgccagccg agtgctggaa gatcgtctga caaaatccgc gtgcgcggcc ttcatcggcg   6900
acgacaacat aatacatgga gtcgtctccg atgaattgat ggcagccaga tgtgccactt   6960
ggatgaacat ggaagtgaag atcatagatg cagttgtatc cttgaaagcc ccttactttt   7020
gtggagggtt tatactgcac gatactgtga caggaacagc ttgcagagtg gcagacccgc   7080
taaaaaggct ttttaaactg ggcaaaccgc tagcggcagg tgacgaacaa gatgaagata   7140
gaagacgagc gctggctgac gaagtgatca gatggcaacg aacagggcta attgatgagc   7200
tggagaaagc ggtatactct aggtacgaag tgcagggtat atcagttgtg gtaatgtcca   7260
tggccacctt tgcaagctcc agatccaact tcgagaagct cagaggaccc gtcataactt   7320
tgtacggcgg tcctaaatag gtacgcacta cagctaccta ttttgcagaa gccgacagca   7380
agtatctaaa cactaatcag ctacaatgga gttcatccca acccaaactt tttacaatag   7440
gaggtaccag cctcgaccct ggactccgcg ccctactatc caagtcatca ggcccagacc   7500
gcgccctcag aggcaagctg ggcaacttgc ccagctgatc tcagcagtta ataaactgac   7560
aatgcgcgcg gtaccacaac agaagccacg caggaatcgg aagaataaga agcaaaagca   7620
aaaacaacag gcgccacaaa acaacacaaa tcaaaagaag cagccaccta aaaagaaacc   7680
ggctcaaaag aaaaagaagc cgggccgcag agagaggatg tgcatgaaaa tcgaaaatga   7740
ttgtattttc gaagtcaagc acgaaggtaa ggtaacaggt tacgcgtgcc tggtggggga   7800
caaagtaatg aaaccagcac acgtaaaggg gaccatcgat aacgcggacc tggccaaact   7860
ggcctttaag cggtcatcta agtatgacct tgaatgcgcg cagatacccg tgcacatgaa   7920
gtccgacgct tcgaagttca cccatgagaa accggagggg tactacaact ggcaccacgg   7980
agcagtacag tactcaggag gccggttcac catccctaca ggtgctggca aaccagggga   8040
cagcggcaga ccgatcttcg acaacaaggg acgcgtggtg gccatagtct taggaggagc   8100
taatgaagga gcccgtacag ccctctcggt ggtgacctgg aataaagaca ttgtcactaa   8160
aatcaccccc gagggggccg aagagtggag tcttgccatc ccagttatgt gcctgttggc   8220
aaacaccacg ttcccctgct cccagccccc ttgcacgccc tgctgctacg aaaaggaacc   8280
ggaggaaacc ctacgcatgc ttgaggacaa cgtcatgaga cctgggtact atcagctgct   8340
acaagcatcc ttaacatgtt ctccccaccg ccagcgacgc agcaccaagg acaacttcaa   8400
```

-continued

```
tgtctataaa gccacaagac catacttagc tcactgtccc gactgtggag aagggcactc   8460
gtgccatagt cccgtagcac tagaacgcat cagaaatgaa gcgacagacg ggacgctgaa   8520
aatccaggtc tccttgcaaa tcggaataaa gacggatgac agccacgatt ggaccaagct   8580
gcgttatatg gacaaccaca tgccagcaga cgcagagagg gcggggctat ttgtaagaac   8640
atcagcaccg tgtacgatta ctggaacaat gggacacttc atcctggccc gatgtccaaa   8700
aggggaaact ctgacggtgg gattcactga cagtaggaag attagtcact catgtacgca   8760
cccatttcac cacgaccctc ctgtgatagg tcgggaaaaa ttccattccc gaccgcagca   8820
cggtaaagag ctaccttgca gcacgtacgt gcagagcacc gccgcaacta ccgaggagat   8880
agaggtacac atgcccccag acacccctga tcgcacatta atgtcacaac agtccggcaa   8940
cgtaaagatc acagtcaatg gccagacggt gcggtacaag tgtaattgcg gtggctcaaa   9000
tgaaggacta acaactacag acaaagtgat taataactgc aaggttgatc aatgtcatgc   9060
cgcggtcacc aatcacaaaa agtggcagta taactcccct ctggtcccgc gtaatgctga   9120
acttggggac cgaaaaggaa aaattcacat cccgtttccg ctggcaaatg taacatgcag   9180
ggtgcctaaa gcaaggaacc ccaccgtgac gtacgggaaa aaccaagtca tcatgctact   9240
gtatcctgac cacccaacac tcctgtccta ccggaatatg ggagaagaac caaactatca   9300
agaagagtgg gtgatgcata agaaggaagt cgtgctaacc gtgccgactg aagggctcga   9360
ggtcacgtgg ggcaacaacg agccgtataa gtattggccg cagttatcta caaacggtac   9420
agcccatggc cacccgcatg agataattct gtattattat gagctgtacc ccactatgac   9480
tgtagtagtt gtgtcagtgg ccacgttcat actcctgtcg atggtgggta tggcagcggg   9540
gatgtgcatg tgtgcacgac gcagatgcat cacaccgtat gaactgacac caggagctac   9600
cgtccctttc ctgcttagcc taatatgctg catcagaaca gctaaagcgg ccacatacca   9660
agaggctgcg atatacctgt ggaacgagca gcaacctttg ttttggctac aagcccttat   9720
tccgctggca gccctgattg ttctatgcaa ctgtctgaga ctcttaccat gctgctgtaa   9780
aacgttggct tttttagccg taatgagcgt cggtgcccac actgtgagcg cgtacgaaca   9840
cgtaacagtg atcccgaaca cggtgggagt accgtataag actctagtca atagacctgg   9900
ctacagcccc atggtattgg agatggaact actgtcagtc actttggagc caacactatc   9960
gcttgattac atcacgtgcg agtacaaaac cgtcatcccg tctccgtacg tgaagtgctg  10020
cggtacagca gagtgcaagg acaaaaacct acctgactac agctgtaagg tcttcaccgg  10080
cgtctaccca tttatgtggg gcggcgccta ctgcttctgc gacgctgaaa acacgcagtt  10140
gagcgaagca cacgtggaga agtccgaatc atgcaaaaca gaatttgcat cagcatacag  10200
ggctcatacc gcatctgcat cagctaagct ccgcgtcctt taccaaggaa ataacatcac  10260
tgtaactgcc tatgcaaacg gcgaccatgc cgtcacagtt aaggacgcca aattcattgt  10320
ggggccaatg tcttcagcct ggacaccttt cgacaacaaa attgtggtgt acaaaggtga  10380
cgtctataac atggactacc cgccctttgg cgcaggaaga ccaggacaat ttggcgatat  10440
ccaaagtcgc acacctgaga gtaaagacgt ctatgctaat acacaactgg tactgcagag  10500
accggctgtg ggtacggtac acgtgccata ctctcaggca ccatctggct ttaagtattg  10560
gctaaaagaa cgcggggcgt cgctgcagca cacagcacca tttggctgcc aaatagcaac  10620
aaacccggta agagcggtga actgcgccgt agggaacatg cccatctcca tcgacatacc  10680
ggaagcggcc ttcactaggg tcgtcgacgc gccctcttta acggacatgt cgtgcgaggt  10740
accagcctgc acccattcct cagactttgg gggcgtcgcc attattaaat atgcagccag  10800
```

```
caagaaaggc aagtgtgcgg tgcattcgat gactaacgcc gtcactattc gggaagctga  10860

gatagaagtt gaagggaatt ctcagctgca aatctctttc tcgacggcct tagccagcgc  10920

cgaattccgc gtacaagtct gttctacaca agtacactgt gcagccgagt gccacccccc  10980

gaaggaccac atagtcaact acccggcgtc acataccacc ctcggggtcc aggacatctc  11040

cgctacggcg atgtcatggg tgcagaagat cacgggaggt gtgggactgg ttgttgctgt  11100

tgccgcactg attctaatcg tggtgctatg cgtgtcgttc agcaggcact aacttgacaa  11160

ttaagtatga aggtatatgt gtcccctaag agacacactg tacatagcaa ataatctata  11220

gatcaaaggg ctacgcaacc cctgaatagt aacaaaatac aaaatcacta aaaattataa  11280

aaacagaaaa atacataaat aggtatacgt gtcccctaag agacacattg tatgtaggtg  11340

ataagtatag atcaaagggc cgaataaccc ctgaatagta acaaaatatg aaaatcaata  11400

aaaatcataa aatagaaaaa ccataaacag aagtagttca aagggctata aaacccctga  11460

atagtaacaa aacataaaat taataaaaat caaatgaata ccataattgg caaacggaag  11520

agatgtaggt acttaagctt cctaaaagca gccgaactca ctttgagaag taggcatagc  11580

ataccgaact cttccacgat tctccgaacc cacagggacg taggagatgt tattttgttt  11640

ttaatatttc aaaaaaaaaa aaaaaaaaaa aaaa                             11674
```

<210> SEQ ID NO 78
<211> LENGTH: 10773
<212> TYPE: DNA
<213> ORGANISM: Zika virus

<400> SEQUENCE: 78

```
cagactgcga cagttcgagt ttgaagcgaa agctagcaac agtatcaaca ggttttattt     60

tggatttgga aacgagagtt tctggtcatg aaaaacccaa aaaagaaatc cggaggattc    120

cggattgtca atatgctaaa acgcggagta gcccgtgtga gcccctttgg gggcttgaag    180

aggctgccag ccggacttct gctgggtcat gggcccatca ggatggtctt ggcgattcta    240

gcctttttga gattcacggc aatcaagcca tcactgggtc tcatcaatag atggggttca    300

gtggggaaaa aagaggctat ggaaataata aagaagttca agaaagatct ggctgccatg    360

ctgagaataa tcaatgctag gaaggagaag aagagacgag gcgcagatac tagtgtcgga    420

attgttggcc tcctgctgac cacagctatg gcagcggagg tcactagacg tgggagtgca    480

tactatatgt acttggacag aaacgacgct ggggaggcca tatcttttcc aaccacattg    540

gggatgaata agtgttatat acagatcatg gatcttggac acatgtgtga tgccaccatg    600

agctatgaat gccctatgct ggatgagggg gtggaaccag atgacgtcga ttgttggtgc    660

aacacgacgt caacttgggt tgtgtacgga acctgccatc acaaaaaagg tgaagcacgg    720

agatctagaa gagctgtgac gctcccctcc cattccacta ggaagctgca aacgcggtcg    780

caaacctggt tggaatcaag agaatacaca aagcacttga ttagagtcga aaattggata    840

ttcaggaacc ctggcttcgc gttagcagca gctgccatcg cttggctttt gggaagctca    900

acgagccaaa aagtcatata cttggtcatg atactgctga ttgccccggc atacagcatc    960

aggtgcatag gagtcagcaa tagggacttt gtggaaggta tgtcaggtgg gacttgggtt   1020

gatgttgtct tggaacatgg aggttgtgtc accgtaatgg cacaggacaa accgactgtc   1080

gacatagagc tggttacaac aacagtcagc aacatggcgg aggtaagatc ctactgctat   1140

gaggcatcaa tatcggacat ggcttcggac agccgctgcc caacacaagg tgaagcctac   1200
```

```
cttgacaagc aatcagacac tcaatatgtc tgcaaaagaa cgttagtgga cagaggctgg   1260
ggaaatggat gtggactttt tggcaaaggg agcctggtga catgcgctaa gtttgcatgc   1320
tccaagaaaa tgaccgggaa gagcatccag ccagagaatc tggagtaccg gataatgctg   1380
tcagttcatg gctcccagca cagtgggatg atcgttaatg acacaggaca tgaaactgat   1440
gagaatagag cgaaggttga gataacgccc aattcaccaa gagccgaagc caccctgggg   1500
ggttttggaa gcctaggact tgattgtgaa ccgaggacag gccttgactt ttcagatttg   1560
tattacttga ctatgaataa caagcactgg ttggttcaca aggagtggtt ccacgacatt   1620
ccattacctt ggcacgctgg ggcagacacc ggaactccac actggaacaa caaagaagca   1680
ctggtagagt tcaaggacgc acatgccaaa aggcaaactg tcgtggttct agggagtcaa   1740
gaaggagcag ttcacacggc ccttgctgga gctctggagg ctgagatgga tggtgcaaag   1800
ggaaggctgt cctctggcca cttgaaatgt cgcctgaaaa tggataaact tagattgaag   1860
ggcgtgtcat actccttgtg taccgcagcg ttcacattca ccaagatccc ggctgaaaca   1920
ctgcacggga cagtcacagt ggaggtacag tacgcaggga cagatggacc ttgcaaggtt   1980
ccagctcaga tggcggtgga catgcaaact ctgaccccag ttgggaggtt gataaccgct   2040
aaccccgtaa tcactgaaag cactgagaac tctaagatga tgctggaact tgatccacca   2100
tttggggact cttacattgt cataggagtc ggggagaaga agatcaccca ccactggcac   2160
aggagtggca gcaccattgg aaaagcattt gaagccactg tgagaggtgc caagagaatg   2220
gcagtcttgg gagacacagc ctgggacttt ggatcagttg gaggcgctct caactcattg   2280
ggcaagggca tccatcaaat ttttggagca gctttcaaat cattgtttgg aggaatgtcc   2340
tggttctcac aaattctcat tggaacgttg ctgatgtggt tgggtctgaa cacaaagaat   2400
ggatctattt cccttatgtg cttggcctta gggggagtgt tgatcttctt atccacagct   2460
gtctctgctg atgtggggtg ctcggtggac ttctcaaaga aggagacgag atgcggtaca   2520
ggggtgttcg tctataacga cgttgaagcc tggagggaca ggtacaagta ccatcctgac   2580
tccccccgta gattggcagc agcagtcaag caagcctggg aagatggtat ctgtgggatc   2640
tcctctgttt caagaatgga aaacatcatg tggagatcag tagaagggga gctcaacgca   2700
atcctggaag agaatggagt tcaactgacg gtcgttgtgg gatctgtaaa aaaccccatg   2760
tggagaggtc cacagagatt gcccgtgcct gtgaacgagc tgccccacgg ctggaaggct   2820
tgggggaaat cgtacttcgt cagagcagca aagacaaata acagctttgt cgtggatggt   2880
gacacactga aggaatgccc actcaaacat agagcatgga acagctttct tgtggaggat   2940
catgggttcg ggtatttcca cactagtgtc tggctcaagg ttagagaaga ttattcatta   3000
gagtgtgatc cagccgttat tggaacagct gttaagggaa aggaggctgt acacagtgat   3060
ctaggctact ggattgagag tgagaagaat gacacatgga ggctgaagag ggcccatctg   3120
atcgagatga aaacatgtga atggccaaag tcccacacat tgtggacaga tggaatagaa   3180
gagagtgatc tgatcatacc caagtcttta gctgggccac tcagccatca caataccaga   3240
gagggctaca ggacccaaat gaaagggcca tggcacagtg aagagcttga aattcggttt   3300
gaggaatgcc caggcactaa ggtccacgtg gaggaaacat gtggaacaag aggaccatct   3360
ctgagatcaa ccactgcaag cggaagggtg atcgaggaat ggtgctgcag ggagtgcaca   3420
atgcccccac tgtcgttccg ggctaaagat ggctgttggt atggaatgga gataaggccc   3480
aggaaagaac cagaaagtaa cttagtaagg tcaatggtga ctgcaggatc aactgatcac   3540
atggatcact tctcccttgg agtgcttgtg attctgctca tggtgcagga agggctgaag   3600
```

-continued

```
aagagaatga ccacaaagat catcataagc acatcgatgg cagtgctggt agctatgatc   3660
ctgggaggat tttcaatgag tgacctggct aagcttgcaa ttttgatggg tgccaccttc   3720
gcggaaatga acactggagg agatgtagct catctggcgc tgatagcggc attcaaagtc   3780
agaccagcgt tgctggtatc tttcatcttc agagctaatt ggacaccccg tgaaagcatg   3840
ctgctggcct tggcctcgtg tcttttgcaa actgcgatct ccgccttgga aggcgacctg   3900
atggttctca tcaatggttt tgctttggcc tggttggcaa tacgagcgat ggttgttcca   3960
cgcactgata acatcacctt ggcaatcctg gctgctctga caccactggc ccggggcaca   4020
ctgcttgtgg cgtggagagc aggccttgct acttgcgggg ggtttatgct cctctctctg   4080
aagggaaaag gcagtgtgaa gaagaactta ccatttgtca tggccctggg actaaccgct   4140
gtgaggctgg tcgaccccat caacgtggtg ggactgctgt tgctcacaag gagtgggaag   4200
cggagctggc cccctagcga agtactcaca gctgttggcc tgatatgcgc attggctgga   4260
gggttcgcca aggcagatat agagatggct gggcccatgg ccgcggtcgg tctgctaatt   4320
gtcagttacg tggtctcagg aaagagtgtg gacatgtaca ttgaaagagc aggtgacatc   4380
acatgggaaa aagatgcgga agtcactgga aacagtcccc ggctcgatgt ggcgctagat   4440
gagagtggtg atttctccct ggtggaggat gacggtcccc ccatgagaga gatcatactc   4500
aaggtggtcc tgatgaccat ctgtggcatg aacccaatag ccatacccct tgcagctgga   4560
gcgtggtacg tatacgtgaa gactggaaaa aggagtggtg ctctatggga tgtgcctgct   4620
cccaaggaag taaaaaaggg ggagaccaca gatggagtgt acagagtaat gactcgtaga   4680
ctgctaggtt caacacaagt tggagtggga gttatgcaag agggggtctt tcacactatg   4740
tggcacgtca caaaaggatc cgcgctgaga agcggtgaag ggagacttga tccatactgg   4800
ggagatgtca agcaggatct ggtgtcatac tgtggtccat ggaagctaga tgccgcctgg   4860
gacgggcaca gcgaggtgca gctcttggcc gtgccccccg gagagagagc gaggaacatc   4920
cagactctgc ccggaatatt taagacaaag gatggggaca ttggagcggt tgcgctggat   4980
tacccagcag gaacttcagg atctccaatc ctagacaagt gtgggagagt gataggactt   5040
tatggcaatg gggtcgtgat caaaaatggg agttatgtta gtgccatcac ccaagggagg   5100
agggaggaag agactcctgt tgagtgcttc gagccttcga tgctgaagaa gaagcagcta   5160
actgtcttag acttgcatcc tggagctggg aaaaccagga gagttcttcc tgaaatagtc   5220
cgtgaagcca taaaaacaag actccgtact gtgatcttag ctccaaccag ggttgtcgct   5280
gctgaaatgg aggaagccct tagagggctt ccagtgcgtt atatgacaac agcagtcaat   5340
gtcacccact ctggaacaga aatcgtcgac ttaatgtgcc atgccacctt cacttcacgt   5400
ctactacagc caatcagagt ccccaactat aatctgtata ttatggatga ggcccacttc   5460
acagatccct caagtatagc agcaagagga tacatttcaa caagggttga gatgggcgag   5520
gcggctgcca tcttcatgac cgccacgcca ccaggaaccc gtgacgcatt tccggactcc   5580
aactcaccaa ttatggacac cgaagtggaa gtcccagaga gagcctggag ctcaggcttt   5640
gattgggtga cggatcattc tggaaaaaca gtttggtttg ttccaagcgt gaggaacggc   5700
aatgagatcg cagcttgtct gacaaaggct ggaaaacggg tcatacagct cagcagaaag   5760
acttttgaga cagagttcca gaaaacaaaa catcaagagt gggactttgt cgtgacaact   5820
gacatttcag agatgggcgc caactttaaa gctgaccgtg tcatagattc caggagatgc   5880
ctaaagccgg tcatacttga tggcgagaga gtcattctgg ctggacccat gcctgtcaca   5940
```

-continued

```
catgccagcg ctgcccagag gagggggcgc ataggcagga atcccaacaa acctggagat   6000
gagtatctgt atggaggtgg gtgcgcagag actgacgaag accatgcaca ctggcttgaa   6060
gcaagaatgc tccttgacaa tatttacctc caagatggcc tcatagcctc gctctatcga   6120
cctgaggccg acaaagtagc agccattgag ggagagttca agcttaggac ggagcaaagg   6180
aagacctttg tggaactcat gaaaagagga gatcttcctg tttggctggc ctatcaggtt   6240
gcatctgccg gaataaccta cacagataga agatggtgct ttgatggcac gaccaacaac   6300
accataatgg aagacagtgt gccggcagag gtgtggacca gacacggaga gaaaagagtg   6360
ctcaaaccga ggtggatgga cgccagagtt tgttcagatc atgcggccct gaagtcattc   6420
aaggagtttg ccgctgggaa aagaggagcg gcttttggag tgatggaagc cctgggaaca   6480
ctgccaggac acatgacaga gagattccag gaagccattg acaacctcgc tgtgctcatg   6540
cgggcagaga ctggaagcag gccttacaaa gccgcggcgg cccaattgcc ggagacccta   6600
gagaccatta tgcttttggg gttgctggga acagtctcgc tgggaatctt tttcgtcttg   6660
atgaggaaca agggcatagg gaagatgggc tttggaatgg tgactcttgg ggccagcgca   6720
tggctcatgt ggctctcgga aattgagcca gccagaattg catgtgtcct cattgttgtg   6780
ttcctattgc tggtggtgct catacctgag ccagaaaagc aaagatctcc ccaggacaac   6840
caaatggcaa tcatcatcat ggtagcagta ggtcttctgg gcttgattac cgccaatgaa   6900
ctcggatggt tggagagaac aaagagtgac ctaagccatc taatgggaag gagagaggag   6960
ggggcaacca taggattctc aatggacatt gacctgcggc cagcctcagc ttgggccatc   7020
tatgctgcct tgacaacttt cattacccca gccgtccaac atgcagtgac cacttcatac   7080
aacaactact ccttaatggc gatggccacg caagctggag tgttgtttgg tatgggcaaa   7140
gggatgccat tctacgcatg ggactttgga gtcccgctgc taatgatagg ttgctactca   7200
caattaacac ccctgaccct aatagtggcc atcattttgc tcgtggcgca ctacatgtac   7260
ttgatcccag ggctgcaggc agcagctgcg cgtgctgccc agaagagaac ggcagctggc   7320
atcatgaaga accctgttgt ggatggaata gtggtgactg acattgacac aatgacaatt   7380
gacccccaag tggagaaaaa gatgggacag gtgctactca tagcagtagc cgtctccagc   7440
gccatactgt cgcggaccgc ctgggggtgg ggggaggctg gggccctgat cacagcggca   7500
acttccactt tgtgggaagg ctctccgaac aagtactgga actcctctac agccacttca   7560
ctgtgtaaca tttttagggg aagttacttg gctggagctt ctctaatcta cacagtaaca   7620
agaaacgctg gcttggtcaa gagacgtggg ggtggaacag gagagaccct gggagagaaa   7680
tggaaggccc gcttgaacca gatgtcggcc ctggagttct actcctacaa aaagtcaggc   7740
atcaccgagg tgtgcagaga agaggcccgc cgcgccctca aggacggtgt ggcaacggga   7800
ggccatgctg tgtcccgagg aagtgcaaag ctgagatggt tggtggagcg gggatacctg   7860
cagccctatg gaaaggtcat tgatcttgga tgtggcagag gggctggag ttactacgcc   7920
gccaccatcc gcaaagttca agaagtgaaa ggatacacaa aaggaggccc tggtcatgaa   7980
gaacccatgt tggtgcaaag ctatgggtgg aacatagtcc gtcttaagag tggggtggac   8040
gtctttcata tggcggctga gccgtgtgac acgttgctgt gtgacatagg tgagtcatca   8100
tctagtcctg aagtggaaga agcacggacg ctcagagtcc tctccatggt gggggattgg   8160
cttgaaaaaa gaccaggagc cttttgtata aaagtgttgt gcccatacac cagcactatg   8220
atggaaaccc tggagcgact gcagcgtagg tatgggggag gactggtcag agtgccactc   8280
tcccgcaact ctacacatga gatgtactgg gtctctggag cgaaaagcaa caccataaaa   8340
```

agtgtgtcca ccacgagcca gctcctcttg gggcgcatgg acgggcccag gaggccagtg 8400
aaatatgagg aggatgtgaa tctcggctct ggcacgcggg ctgtggtaag ctgcgctgaa 8460
gctcccaaca tgaagatcat tggtaaccgc attgaaagga tccgcagtga gcacgcggaa 8520
acgtggttct ttgacgagaa ccacccatat aggacatggg cttaccatgg aagctatgag 8580
gcccccacac aagggtcagc gtcctctcta ataaacgggg ttgtcaggct cctgtcaaaa 8640
ccctgggatg tggtgactgg agtcacagga atagccatga ccgacaccac accgtatggt 8700
cagcaaagag ttttcaagga aaaagtggac actagggtgc cagaccccca agaaggcact 8760
cgtcaggtta tgagcatggt ctcttcctgg ttgtggaaag agctaggcaa acacaaacgg 8820
ccacgagtct gtaccaaaga agagttcatc aacaaggttc gtagcaatgc agcattaggg 8880
gcaatatttg aagaggaaaa agagtggaag actgcagtgg aagctgtgaa cgatccaagg 8940
ttctgggctc tagtggacaa ggaaagagag caccacctga gaggagagtg ccagagttgt 9000
gtgtacaaca tgatgggaaa aagagaaaag aaacaagggg aatttggaaa ggccaagggc 9060
agccgcgcca tctggtatat gtggctaggg gctagatttc tagagttcga agcccttgga 9120
ttcttgaacg aggatcactg gatggggaga gagaactcag gaggtggtgt tgaagggctg 9180
ggattacaaa gactcggata tgtcctagaa gagatgagtc gcataccagg aggaaggatg 9240
tatgcagatg acactgctgg ctgggacacc cgcatcagca ggtttgatct ggagaatgaa 9300
gctctaatca ccaaccaaat ggagaaaggg cacagggcct tggcattggc cataatcaag 9360
tacacatacc aaaacaaagt ggtaaaggtc cttagaccag ctgaaaaagg gaagacagtt 9420
atggacatta tttcgagaca agaccaaagg gggagcggac aagttgtcac ttacgctctt 9480
aacacattta ccaacctagt ggtgcaactc attcggaata tggaggctga ggaagttcta 9540
gagatgcaag acttgtggct gctgcggagg tcagagaaag tgaccaactg gttgcagagc 9600
aacggatggg ataggctcaa acgaatggca gtcagtggag atgattgcgt tgtgaagcca 9660
attgatgata ggtttgcaca tgccctcagg ttcttgaatg atatgggaaa agttaggaag 9720
gacacacaag agtggaaacc ctcaactgga tgggacaact gggaagaagt tccgttttgc 9780
tcccaccact tcaacaagct ccatctcaag gacgggaggt ccattgtggt tccctgccgc 9840
caccaagatg aactgattgg ccgggcccgc gtctctccag ggcgggatg gagcatccgg 9900
gagactgctt gcctagcaaa atcatatgcg caaatgtggc agctccttta tttccacaga 9960
agggacctcc gactgatggc caatgccatt tgttcatctg tgccagttga ctgggttcca 10020
actgggagaa ctacctggtc aatccatgga aagggagaat ggatgaccac tgaagacatg 10080
cttgtggtgt ggaacagagt gtggattgag gagaacgacc acatggaaga caagacccca 10140
gttacgaaat ggacagacat tccctatttg ggaaaaaggg aagacttgtg gtgtggatct 10200
ctcatagggc acagaccgcg caccacctgg gctgagaaca ttaaaaacac agtcaacatg 10260
gtgcgcagga tcataggtga tgaagaaaag tacatggact acctatccac ccaagttcgc 10320
tacttgggtg aagaagggtc tacacctgga gtgctgtaag caccaatctt agtgttgtca 10380
ggcctgctag tcagccacag cttggggaaa gctgtgcagc ctgtgacccc cccaggagaa 10440
gctgggaaac caagcctata gtcaggccga gaacgccatg gcacggaaga agccatgctg 10500
cctgtgagcc cctcagagga cactgagtca aaaaacccca cgcgcttgga ggcgcaggat 10560
gggaaaagaa ggtggcgacc ttccccaccc ttcaatctgg ggcctgaact ggagatcagc 10620
tgtggatctc cagaagaggg actagtggtt agaggagacc ccccggaaaa cgcaaaacag 10680

-continued

```
catattgacg ctgggaaaga ccagagactc catgagtttc caccacgctg gccgccaggc  10740

acagatcgcc gaatagcggc ggccggtgtg ggg                                10773


<210> SEQ ID NO 79
<211> LENGTH: 3423
<212> TYPE: PRT
<213> ORGANISM: Zika virus

<400> SEQUENCE: 79

Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
```

-continued

```
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780
```

```
Leu Ile Phe Leu Ser Thr Ala Val Ser Ala Asp Val Gly Cys Ser Val
785                 790                 795                 800

Asp Phe Ser Lys Lys Glu Thr Arg Cys Gly Thr Gly Val Phe Val Tyr
                805                 810                 815

Asn Asp Val Glu Ala Trp Arg Asp Arg Tyr Lys Tyr His Pro Asp Ser
            820                 825                 830

Pro Arg Arg Leu Ala Ala Ala Val Lys Gln Ala Trp Glu Asp Gly Ile
        835                 840                 845

Cys Gly Ile Ser Ser Val Ser Arg Met Glu Asn Ile Met Trp Arg Ser
    850                 855                 860

Val Glu Gly Glu Leu Asn Ala Ile Leu Glu Glu Asn Gly Val Gln Leu
865                 870                 875                 880

Thr Val Val Val Gly Ser Val Lys Asn Pro Met Trp Arg Gly Pro Gln
                885                 890                 895

Arg Leu Pro Val Pro Val Asn Glu Leu Pro His Gly Trp Lys Ala Trp
            900                 905                 910

Gly Lys Ser Tyr Phe Val Arg Ala Ala Lys Thr Asn Asn Ser Phe Val
        915                 920                 925

Val Asp Gly Asp Thr Leu Lys Glu Cys Pro Leu Lys His Arg Ala Trp
    930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
                965                 970                 975

Val Ile Gly Thr Ala Val Lys Gly Lys Glu Ala Val His Ser Asp Leu
            980                 985                 990

Gly Tyr Trp Ile Glu Ser Glu Lys  Asn Asp Thr Trp Arg  Leu Lys Arg
        995                 1000                1005

Ala His  Leu Ile Glu Met Lys  Thr Cys Glu Trp Pro  Lys Ser His
    1010                 1015                 1020

Thr Leu  Trp Thr Asp Gly Ile  Glu Glu Ser Asp Leu  Ile Ile Pro
    1025                 1030                 1035

Lys Ser  Leu Ala Gly Pro Leu  Ser His His Asn Thr  Arg Glu Gly
    1040                 1045                 1050

Tyr Arg  Thr Gln Met Lys Gly  Pro Trp His Ser Glu  Glu Leu Glu
    1055                 1060                 1065

Ile Arg  Phe Glu Glu Cys Pro  Gly Thr Lys Val His  Val Glu Glu
    1070                 1075                 1080

Thr Cys  Gly Thr Arg Gly Pro  Ser Leu Arg Ser Thr  Thr Ala Ser
    1085                 1090                 1095

Gly Arg  Val Ile Glu Glu Trp  Cys Cys Arg Glu Cys  Thr Met Pro
    1100                 1105                 1110

Pro Leu  Ser Phe Arg Ala Lys  Asp Gly Cys Trp Tyr  Gly Met Glu
    1115                 1120                 1125

Ile Arg  Pro Arg Lys Glu Pro  Glu Ser Asn Leu Val  Arg Ser Met
    1130                 1135                 1140

Val Thr  Ala Gly Ser Thr Asp  His Met Asp His Phe  Ser Leu Gly
    1145                 1150                 1155

Val Leu  Val Ile Leu Leu Met  Val Gln Glu Gly Leu  Lys Lys Arg
    1160                 1165                 1170

Met Thr  Thr Lys Ile Ile Ile  Ser Thr Ser Met Ala  Val Leu Val
    1175                 1180                 1185
```

```
Ala Met  Ile Leu Gly Gly Phe  Ser Met Ser Asp Leu  Ala Lys Leu
    1190                 1195                 1200

Ala Ile  Leu Met Gly Ala Thr  Phe Ala Glu Met Asn  Thr Gly Gly
    1205                 1210                 1215

Asp Val  Ala His Leu Ala Leu  Ile Ala Ala Phe Lys  Val Arg Pro
    1220                 1225                 1230

Ala Leu  Leu Val Ser Phe Ile  Phe Arg Ala Asn Trp  Thr Pro Arg
    1235                 1240                 1245

Glu Ser  Met Leu Leu Ala Leu  Ala Ser Cys Leu Leu  Gln Thr Ala
    1250                 1255                 1260

Ile Ser  Ala Leu Glu Gly Asp  Leu Met Val Leu Ile  Asn Gly Phe
    1265                 1270                 1275

Ala Leu  Ala Trp Leu Ala Ile  Arg Ala Met Val Val  Pro Arg Thr
    1280                 1285                 1290

Asp Asn  Ile Thr Leu Ala Ile  Leu Ala Ala Leu Thr  Pro Leu Ala
    1295                 1300                 1305

Arg Gly  Thr Leu Leu Val Ala  Trp Arg Ala Gly Leu  Ala Thr Cys
    1310                 1315                 1320

Gly Gly  Phe Met Leu Leu Ser  Leu Lys Gly Lys Gly  Ser Val Lys
    1325                 1330                 1335

Lys Asn  Leu Pro Phe Val Met  Ala Leu Gly Leu Thr  Ala Val Arg
    1340                 1345                 1350

Leu Val  Asp Pro Ile Asn Val  Val Gly Leu Leu Leu  Leu Thr Arg
    1355                 1360                 1365

Ser Gly  Lys Arg Ser Trp Pro  Pro Ser Glu Val Leu  Thr Ala Val
    1370                 1375                 1380

Gly Leu  Ile Cys Ala Leu Ala  Gly Gly Phe Ala Lys  Ala Asp Ile
    1385                 1390                 1395

Glu Met  Ala Gly Pro Met Ala  Ala Val Gly Leu Leu  Ile Val Ser
    1400                 1405                 1410

Tyr Val  Val Ser Gly Lys Ser  Val Asp Met Tyr Ile  Glu Arg Ala
    1415                 1420                 1425

Gly Asp  Ile Thr Trp Glu Lys  Asp Ala Glu Val Thr  Gly Asn Ser
    1430                 1435                 1440

Pro Arg  Leu Asp Val Ala Leu  Asp Glu Ser Gly Asp  Phe Ser Leu
    1445                 1450                 1455

Val Glu  Asp Asp Gly Pro Pro  Met Arg Glu Ile Ile  Leu Lys Val
    1460                 1465                 1470

Val Leu  Met Thr Ile Cys Gly  Met Asn Pro Ile Ala  Ile Pro Phe
    1475                 1480                 1485

Ala Ala  Gly Ala Trp Tyr Val  Tyr Val Lys Thr Gly  Lys Arg Ser
    1490                 1495                 1500

Gly Ala  Leu Trp Asp Val Pro  Ala Pro Lys Glu Val  Lys Lys Gly
    1505                 1510                 1515

Glu Thr  Thr Asp Gly Val Tyr  Arg Val Met Thr Arg  Arg Leu Leu
    1520                 1525                 1530

Gly Ser  Thr Gln Val Gly Val  Gly Val Met Gln Glu  Gly Val Phe
    1535                 1540                 1545

His Thr  Met Trp His Val Thr  Lys Gly Ser Ala Leu  Arg Ser Gly
    1550                 1555                 1560

Glu Gly  Arg Leu Asp Pro Tyr  Trp Gly Asp Val Lys  Gln Asp Leu
    1565                 1570                 1575

Val Ser  Tyr Cys Gly Pro Trp  Lys Leu Asp Ala Ala  Trp Asp Gly
```

1580 1585 1590

His Ser Glu Val Gln Leu Leu Ala Val Pro Pro Gly Glu Arg Ala
1595 1600 1605

Arg Asn Ile Gln Thr Leu Pro Gly Ile Phe Lys Thr Lys Asp Gly
1610 1615 1620

Asp Ile Gly Ala Val Ala Leu Asp Tyr Pro Ala Gly Thr Ser Gly
1625 1630 1635

Ser Pro Ile Leu Asp Lys Cys Gly Arg Val Ile Gly Leu Tyr Gly
1640 1645 1650

Asn Gly Val Val Ile Lys Asn Gly Ser Tyr Val Ser Ala Ile Thr
1655 1660 1665

Gln Gly Arg Arg Glu Glu Glu Thr Pro Val Glu Cys Phe Glu Pro
1670 1675 1680

Ser Met Leu Lys Lys Lys Gln Leu Thr Val Leu Asp Leu His Pro
1685 1690 1695

Gly Ala Gly Lys Thr Arg Arg Val Leu Pro Glu Ile Val Arg Glu
1700 1705 1710

Ala Ile Lys Thr Arg Leu Arg Thr Val Ile Leu Ala Pro Thr Arg
1715 1720 1725

Val Val Ala Ala Glu Met Glu Glu Ala Leu Arg Gly Leu Pro Val
1730 1735 1740

Arg Tyr Met Thr Thr Ala Val Asn Val Thr His Ser Gly Thr Glu
1745 1750 1755

Ile Val Asp Leu Met Cys His Ala Thr Phe Thr Ser Arg Leu Leu
1760 1765 1770

Gln Pro Ile Arg Val Pro Asn Tyr Asn Leu Tyr Ile Met Asp Glu
1775 1780 1785

Ala His Phe Thr Asp Pro Ser Ser Ile Ala Ala Arg Gly Tyr Ile
1790 1795 1800

Ser Thr Arg Val Glu Met Gly Glu Ala Ala Ala Ile Phe Met Thr
1805 1810 1815

Ala Thr Pro Pro Gly Thr Arg Asp Ala Phe Pro Asp Ser Asn Ser
1820 1825 1830

Pro Ile Met Asp Thr Glu Val Glu Val Pro Glu Arg Ala Trp Ser
1835 1840 1845

Ser Gly Phe Asp Trp Val Thr Asp His Ser Gly Lys Thr Val Trp
1850 1855 1860

Phe Val Pro Ser Val Arg Asn Gly Asn Glu Ile Ala Ala Cys Leu
1865 1870 1875

Thr Lys Ala Gly Lys Arg Val Ile Gln Leu Ser Arg Lys Thr Phe
1880 1885 1890

Glu Thr Glu Phe Gln Lys Thr Lys His Gln Glu Trp Asp Phe Val
1895 1900 1905

Val Thr Thr Asp Ile Ser Glu Met Gly Ala Asn Phe Lys Ala Asp
1910 1915 1920

Arg Val Ile Asp Ser Arg Arg Cys Leu Lys Pro Val Ile Leu Asp
1925 1930 1935

Gly Glu Arg Val Ile Leu Ala Gly Pro Met Pro Val Thr His Ala
1940 1945 1950

Ser Ala Ala Gln Arg Arg Gly Arg Ile Gly Arg Asn Pro Asn Lys
1955 1960 1965

Pro Gly Asp Glu Tyr Leu Tyr Gly Gly Gly Cys Ala Glu Thr Asp
1970 1975 1980

```
Glu Asp  His Ala His Trp Leu  Glu Ala Arg Met Leu  Leu Asp Asn
    1985                 1990                 1995

Ile Tyr  Leu Gln Asp Gly Leu  Ile Ala Ser Leu Tyr  Arg Pro Glu
    2000                 2005                 2010

Ala Asp  Lys Val Ala Ala Ile  Glu Gly Glu Phe Lys  Leu Arg Thr
    2015                 2020                 2025

Glu Gln  Arg Lys Thr Phe Val  Glu Leu Met Lys Arg  Gly Asp Leu
    2030                 2035                 2040

Pro Val  Trp Leu Ala Tyr Gln  Val Ala Ser Ala Gly  Ile Thr Tyr
    2045                 2050                 2055

Thr Asp  Arg Arg Trp Cys Phe  Asp Gly Thr Thr Asn  Asn Thr Ile
    2060                 2065                 2070

Met Glu  Asp Ser Val Pro Ala  Glu Val Trp Thr Arg  His Gly Glu
    2075                 2080                 2085

Lys Arg  Val Leu Lys Pro Arg  Trp Met Asp Ala Arg  Val Cys Ser
    2090                 2095                 2100

Asp His  Ala Ala Leu Lys Ser  Phe Lys Glu Phe Ala  Ala Gly Lys
    2105                 2110                 2115

Arg Gly  Ala Ala Phe Gly Val  Met Glu Ala Leu Gly  Thr Leu Pro
    2120                 2125                 2130

Gly His  Met Thr Glu Arg Phe  Gln Glu Ala Ile Asp  Asn Leu Ala
    2135                 2140                 2145

Val Leu  Met Arg Ala Glu Thr  Gly Ser Arg Pro Tyr  Lys Ala Ala
    2150                 2155                 2160

Ala Ala  Gln Leu Pro Glu Thr  Leu Glu Thr Ile Met  Leu Leu Gly
    2165                 2170                 2175

Leu Leu  Gly Thr Val Ser Leu  Gly Ile Phe Phe Val  Leu Met Arg
    2180                 2185                 2190

Asn Lys  Gly Ile Gly Lys Met  Gly Phe Gly Met Val  Thr Leu Gly
    2195                 2200                 2205

Ala Ser  Ala Trp Leu Met Trp  Leu Ser Glu Ile Glu  Pro Ala Arg
    2210                 2215                 2220

Ile Ala  Cys Val Leu Ile Val  Val Phe Leu Leu Leu  Val Val Leu
    2225                 2230                 2235

Ile Pro  Glu Pro Glu Lys Gln  Arg Ser Pro Gln Asp  Asn Gln Met
    2240                 2245                 2250

Ala Ile  Ile Ile Met Val Ala  Val Gly Leu Leu Gly  Leu Ile Thr
    2255                 2260                 2265

Ala Asn  Glu Leu Gly Trp Leu  Glu Arg Thr Lys Ser  Asp Leu Ser
    2270                 2275                 2280

His Leu  Met Gly Arg Arg Glu  Glu Gly Ala Thr Ile  Gly Phe Ser
    2285                 2290                 2295

Met Asp  Ile Asp Leu Arg Pro  Ala Ser Ala Trp Ala  Ile Tyr Ala
    2300                 2305                 2310

Ala Leu  Thr Thr Phe Ile Thr  Pro Ala Val Gln His  Ala Val Thr
    2315                 2320                 2325

Thr Ser  Tyr Asn Asn Tyr Ser  Leu Met Ala Met Ala  Thr Gln Ala
    2330                 2335                 2340

Gly Val  Leu Phe Gly Met Gly  Lys Gly Met Pro Phe  Tyr Ala Trp
    2345                 2350                 2355

Asp Phe  Gly Val Pro Leu Leu  Met Ile Gly Cys Tyr  Ser Gln Leu
    2360                 2365                 2370
```

Thr Pro Leu Thr Leu Ile Val Ala Ile Ile Leu Leu Val Ala His
2375 2380 2385

Tyr Met Tyr Leu Ile Pro Gly Leu Gln Ala Ala Ala Ala Arg Ala
2390 2395 2400

Ala Gln Lys Arg Thr Ala Ala Gly Ile Met Lys Asn Pro Val Val
2405 2410 2415

Asp Gly Ile Val Val Thr Asp Ile Asp Thr Met Thr Ile Asp Pro
2420 2425 2430

Gln Val Glu Lys Lys Met Gly Gln Val Leu Leu Ile Ala Val Ala
2435 2440 2445

Val Ser Ser Ala Ile Leu Ser Arg Thr Ala Trp Gly Trp Gly Glu
2450 2455 2460

Ala Gly Ala Leu Ile Thr Ala Ala Thr Ser Thr Leu Trp Glu Gly
2465 2470 2475

Ser Pro Asn Lys Tyr Trp Asn Ser Ser Thr Ala Thr Ser Leu Cys
2480 2485 2490

Asn Ile Phe Arg Gly Ser Tyr Leu Ala Gly Ala Ser Leu Ile Tyr
2495 2500 2505

Thr Val Thr Arg Asn Ala Gly Leu Val Lys Arg Arg Gly Gly Gly
2510 2515 2520

Thr Gly Glu Thr Leu Gly Glu Lys Trp Lys Ala Arg Leu Asn Gln
2525 2530 2535

Met Ser Ala Leu Glu Phe Tyr Ser Tyr Lys Lys Ser Gly Ile Thr
2540 2545 2550

Glu Val Cys Arg Glu Glu Ala Arg Arg Ala Leu Lys Asp Gly Val
2555 2560 2565

Ala Thr Gly Gly His Ala Val Ser Arg Gly Ser Ala Lys Leu Arg
2570 2575 2580

Trp Leu Val Glu Arg Gly Tyr Leu Gln Pro Tyr Gly Lys Val Ile
2585 2590 2595

Asp Leu Gly Cys Gly Arg Gly Gly Trp Ser Tyr Tyr Ala Ala Thr
2600 2605 2610

Ile Arg Lys Val Gln Glu Val Lys Gly Tyr Thr Lys Gly Gly Pro
2615 2620 2625

Gly His Glu Glu Pro Met Leu Val Gln Ser Tyr Gly Trp Asn Ile
2630 2635 2640

Val Arg Leu Lys Ser Gly Val Asp Val Phe His Met Ala Ala Glu
2645 2650 2655

Pro Cys Asp Thr Leu Leu Cys Asp Ile Gly Glu Ser Ser Ser Ser
2660 2665 2670

Pro Glu Val Glu Glu Ala Arg Thr Leu Arg Val Leu Ser Met Val
2675 2680 2685

Gly Asp Trp Leu Glu Lys Arg Pro Gly Ala Phe Cys Ile Lys Val
2690 2695 2700

Leu Cys Pro Tyr Thr Ser Thr Met Met Glu Thr Leu Glu Arg Leu
2705 2710 2715

Gln Arg Arg Tyr Gly Gly Gly Leu Val Arg Val Pro Leu Ser Arg
2720 2725 2730

Asn Ser Thr His Glu Met Tyr Trp Val Ser Gly Ala Lys Ser Asn
2735 2740 2745

Thr Ile Lys Ser Val Ser Thr Thr Ser Gln Leu Leu Leu Gly Arg
2750 2755 2760

Met Asp Gly Pro Arg Arg Pro Val Lys Tyr Glu Glu Asp Val Asn

```
    2765                2770                2775

Leu Gly  Ser Gly Thr Arg Ala  Val Val Ser Cys Ala  Glu Ala Pro
    2780                2785                2790

Asn Met  Lys Ile Ile Gly Asn  Arg Ile Glu Arg Ile  Arg Ser Glu
    2795                2800                2805

His Ala  Glu Thr Trp Phe Phe  Asp Glu Asn His Pro  Tyr Arg Thr
    2810                2815                2820

Trp Ala  Tyr His Gly Ser Tyr  Glu Ala Pro Thr Gln  Gly Ser Ala
    2825                2830                2835

Ser Ser  Leu Ile Asn Gly Val  Val Arg Leu Leu Ser  Lys Pro Trp
    2840                2845                2850

Asp Val  Val Thr Gly Val Thr  Gly Ile Ala Met Thr  Asp Thr Thr
    2855                2860                2865

Pro Tyr  Gly Gln Gln Arg Val  Phe Lys Glu Lys Val  Asp Thr Arg
    2870                2875                2880

Val Pro  Asp Pro Gln Glu Gly  Thr Arg Gln Val Met  Ser Met Val
    2885                2890                2895

Ser Ser  Trp Leu Trp Lys Glu  Leu Gly Lys His Lys  Arg Pro Arg
    2900                2905                2910

Val Cys  Thr Lys Glu Glu Phe  Ile Asn Lys Val Arg  Ser Asn Ala
    2915                2920                2925

Ala Leu  Gly Ala Ile Phe Glu  Glu Glu Lys Glu Trp  Lys Thr Ala
    2930                2935                2940

Val Glu  Ala Val Asn Asp Pro  Arg Phe Trp Ala Leu  Val Asp Lys
    2945                2950                2955

Glu Arg  Glu His His Leu Arg  Gly Glu Cys Gln Ser  Cys Val Tyr
    2960                2965                2970

Asn Met  Met Gly Lys Arg Glu  Lys Lys Gln Gly Glu  Phe Gly Lys
    2975                2980                2985

Ala Lys  Gly Ser Arg Ala Ile  Trp Tyr Met Trp Leu  Gly Ala Arg
    2990                2995                3000

Phe Leu  Glu Phe Glu Ala Leu  Gly Phe Leu Asn Glu  Asp His Trp
    3005                3010                3015

Met Gly  Arg Glu Asn Ser Gly  Gly Gly Val Glu Gly  Leu Gly Leu
    3020                3025                3030

Gln Arg  Leu Gly Tyr Val Leu  Glu Glu Met Ser Arg  Ile Pro Gly
    3035                3040                3045

Gly Arg  Met Tyr Ala Asp Asp  Thr Ala Gly Trp Asp  Thr Arg Ile
    3050                3055                3060

Ser Arg  Phe Asp Leu Glu Asn  Glu Ala Leu Ile Thr  Asn Gln Met
    3065                3070                3075

Glu Lys  Gly His Arg Ala Leu  Ala Leu Ala Ile Ile  Lys Tyr Thr
    3080                3085                3090

Tyr Gln  Asn Lys Val Val Lys  Val Leu Arg Pro Ala  Glu Lys Gly
    3095                3100                3105

Lys Thr  Val Met Asp Ile Ile  Ser Arg Gln Asp Gln  Arg Gly Ser
    3110                3115                3120

Gly Gln  Val Val Thr Tyr Ala  Leu Asn Thr Phe Thr  Asn Leu Val
    3125                3130                3135

Val Gln  Leu Ile Arg Asn Met  Glu Ala Glu Glu Val  Leu Glu Met
    3140                3145                3150

Gln Asp  Leu Trp Leu Leu Arg  Arg Ser Glu Lys Val  Thr Asn Trp
    3155                3160                3165
```

```
Leu Gln Ser Asn Gly Trp Asp Arg Leu Lys Arg Met Ala Val Ser
    3170                3175                3180

Gly Asp Asp Cys Val Val Lys Pro Ile Asp Asp Arg Phe Ala His
    3185                3190                3195

Ala Leu Arg Phe Leu Asn Asp Met Gly Lys Val Arg Lys Asp Thr
    3200                3205                3210

Gln Glu Trp Lys Pro Ser Thr Gly Trp Asp Asn Trp Glu Glu Val
    3215                3220                3225

Pro Phe Cys Ser His His Phe Asn Lys Leu His Leu Lys Asp Gly
    3230                3235                3240

Arg Ser Ile Val Val Pro Cys Arg His Gln Asp Glu Leu Ile Gly
    3245                3250                3255

Arg Ala Arg Val Ser Pro Gly Ala Gly Trp Ser Ile Arg Glu Thr
    3260                3265                3270

Ala Cys Leu Ala Lys Ser Tyr Ala Gln Met Trp Gln Leu Leu Tyr
    3275                3280                3285

Phe His Arg Arg Asp Leu Arg Leu Met Ala Asn Ala Ile Cys Ser
    3290                3295                3300

Ser Val Pro Val Asp Trp Val Pro Thr Gly Arg Thr Thr Trp Ser
    3305                3310                3315

Ile His Gly Lys Gly Glu Trp Met Thr Thr Glu Asp Met Leu Val
    3320                3325                3330

Val Trp Asn Arg Val Trp Ile Glu Glu Asn Asp His Met Glu Asp
    3335                3340                3345

Lys Thr Pro Val Thr Lys Trp Thr Asp Ile Pro Tyr Leu Gly Lys
    3350                3355                3360

Arg Glu Asp Leu Trp Cys Gly Ser Leu Ile Gly His Arg Pro Arg
    3365                3370                3375

Thr Thr Trp Ala Glu Asn Ile Lys Asn Thr Val Asn Met Val Arg
    3380                3385                3390

Arg Ile Ile Gly Asp Glu Glu Lys Tyr Met Asp Tyr Leu Ser Thr
    3395                3400                3405

Gln Val Arg Tyr Leu Gly Glu Glu Gly Ser Thr Pro Gly Val Leu
    3410                3415                3420
```

<210> SEQ ID NO 80
<211> LENGTH: 28
<212> TYPE: DNA
<213> ORGANISM: Artificial Sequence
<220> FEATURE:
<223> OTHER INFORMATION: primer

<400> SEQUENCE: 80
ttaggatccg ttgttgatct gtgtgaat 28

<210> SEQ ID NO 81
<211> LENGTH: 26
<212> TYPE: DNA
<213> ORGANISM: Artificial Sequence
<220> FEATURE:
<223> OTHER INFORMATION: primer

<400> SEQUENCE: 81
taactcgagc gtacacaacc caagtt 26

<210> SEQ ID NO 82
<211> LENGTH: 27

<212> TYPE: DNA
<213> ORGANISM: Artificial Sequence
<220> FEATURE:
<223> OTHER INFORMATION: primer

<400> SEQUENCE: 82
ttaggatcct cactagacgt gggagtg 27

<210> SEQ ID NO 83
<211> LENGTH: 29
<212> TYPE: DNA
<213> ORGANISM: Artificial Sequence
<220> FEATURE:
<223> OTHER INFORMATION: primer

<400> SEQUENCE: 83
taactcgaga agccatgtcy gatattgat 29

<210> SEQ ID NO 84
<211> LENGTH: 26
<212> TYPE: DNA
<213> ORGANISM: Artificial Sequence
<220> FEATURE:
<223> OTHER INFORMATION: primer

<400> SEQUENCE: 84
ttaggatccg catacagcat caggtg 26

<210> SEQ ID NO 85
<211> LENGTH: 27
<212> TYPE: DNA
<213> ORGANISM: Artificial Sequence
<220> FEATURE:
<223> OTHER INFORMATION: primer

<400> SEQUENCE: 85
taactcgagt gtggagttcc ggtgtct 27

<210> SEQ ID NO 86
<211> LENGTH: 31
<212> TYPE: DNA
<213> ORGANISM: Artificial Sequence
<220> FEATURE:
<223> OTHER INFORMATION: primer

<400> SEQUENCE: 86
ttaggatccg aatagagcga argttgagat a 31

<210> SEQ ID NO 87
<211> LENGTH: 28
<212> TYPE: DNA
<213> ORGANISM: Artificial Sequence
<220> FEATURE:
<223> OTHER INFORMATION: primer

<400> SEQUENCE: 87
taactcgagt ggtgggtgat cttcttct 28

<210> SEQ ID NO 88
<211> LENGTH: 31
<212> TYPE: DNA
<213> ORGANISM: Artificial Sequence
<220> FEATURE:
<223> OTHER INFORMATION: primer

<400> SEQUENCE: 88

-continued ttaggatcca gtcacagtgg aggtacagta c 31

<210> SEQ ID NO 89
<211> LENGTH: 27
<212> TYPE: DNA
<213> ORGANISM: Artificial Sequence
<220> FEATURE:
<223> OTHER INFORMATION: primer

<400> SEQUENCE: 89
taactcgagc rcagatacca tcttccc 27

<210> SEQ ID NO 90
<211> LENGTH: 28
<212> TYPE: DNA
<213> ORGANISM: Artificial Sequence
<220> FEATURE:
<223> OTHER INFORMATION: primer

<400> SEQUENCE: 90
ttaggatccc ttatgtgctt ggccttag 28

<210> SEQ ID NO 91
<211> LENGTH: 26
<212> TYPE: DNA
<213> ORGANISM: Artificial Sequence
<220> FEATURE:
<223> OTHER INFORMATION: primer

<400> SEQUENCE: 91
taactcgagt cttcagcctc catgtg 26

<210> SEQ ID NO 92
<211> LENGTH: 29
<212> TYPE: DNA
<213> ORGANISM: Artificial Sequence
<220> FEATURE:
<223> OTHER INFORMATION: primer

<400> SEQUENCE: 92
ttaggatcca atgcccactc aaacataga 29

<210> SEQ ID NO 93
<211> LENGTH: 30
<212> TYPE: DNA
<213> ORGANISM: Artificial Sequence
<220> FEATURE:
<223> OTHER INFORMATION: primer

<400> SEQUENCE: 93
taactcgagt cattctcttc ttcagccctt 30

<210> SEQ ID NO 94
<211> LENGTH: 26
<212> TYPE: DNA
<213> ORGANISM: Artificial Sequence
<220> FEATURE:
<223> OTHER INFORMATION: primer

<400> SEQUENCE: 94
ttaggatcca agggtgatcg aggaat 26

<210> SEQ ID NO 95
<211> LENGTH: 29
<212> TYPE: DNA
<213> ORGANISM: Artificial Sequence
<220> FEATURE:
<223> OTHER INFORMATION: primer

<400> SEQUENCE: 95
taactcgagt tcccttcaga gagaggagc 29

<210> SEQ ID NO 96
<211> LENGTH: 28
<212> TYPE: DNA
<213> ORGANISM: Artificial Sequence
<220> FEATURE:
<223> OTHER INFORMATION: primer

<400> SEQUENCE: 96
ttaggatcct cttttgcaaa ctgcgatc 28

<210> SEQ ID NO 97
<211> LENGTH: 27
<212> TYPE: DNA
<213> ORGANISM: Artificial Sequence
<220> FEATURE:
<223> OTHER INFORMATION: primer

<400> SEQUENCE: 97
taactcgagt ccagctgcaa agggtat 27

<210> SEQ ID NO 98
<211> LENGTH: 28
<212> TYPE: DNA
<213> ORGANISM: Artificial Sequence
<220> FEATURE:
<223> OTHER INFORMATION: primer

<400> SEQUENCE: 98
ttaggatccg tgtggacatg tacattga 28

<210> SEQ ID NO 99
<211> LENGTH: 26
<212> TYPE: DNA
<213> ORGANISM: Artificial Sequence
<220> FEATURE:
<223> OTHER INFORMATION: primer

<400> SEQUENCE: 99
taactcgagc ccattgccat aaagtc 26

<210> SEQ ID NO 100
<211> LENGTH: 28
<212> TYPE: DNA
<213> ORGANISM: Artificial Sequence
<220> FEATURE:
<223> OTHER INFORMATION: primer

<400> SEQUENCE: 100
ttaggatcct catactgtgg tccatgga 28

<210> SEQ ID NO 101
<211> LENGTH: 26
<212> TYPE: DNA
<213> ORGANISM: Artificial Sequence
<220> FEATURE:
<223> OTHER INFORMATION: primer

<400> SEQUENCE: 101
taactcgagg cccatctcaa cccttg 26

<210> SEQ ID NO 102
<211> LENGTH: 26
<212> TYPE: DNA
<213> ORGANISM: Artificial Sequence
<220> FEATURE:
<223> OTHER INFORMATION: primer

<400> SEQUENCE: 102
ttaggatcct agagggcttc cagtgc 26

<210> SEQ ID NO 103
<211> LENGTH: 31
<212> TYPE: DNA
<213> ORGANISM: Artificial Sequence
<220> FEATURE:
<223> OTHER INFORMATION: primer

<400> SEQUENCE: 103
taactcgaga tactcatctc caggtttgtt g 31

<210> SEQ ID NO 104
<211> LENGTH: 30
<212> TYPE: DNA
<213> ORGANISM: Artificial Sequence
<220> FEATURE:
<223> OTHER INFORMATION: primer

<400> SEQUENCE: 104
ttaggatccg aaaacaaaac atcaagagtg 30

<210> SEQ ID NO 105
<211> LENGTH: 31
<212> TYPE: DNA
<213> ORGANISM: Artificial Sequence
<220> FEATURE:
<223> OTHER INFORMATION: primer

<400> SEQUENCE: 105
taactcgagg aatctctctg tcatgtgtcc t 31

<210> SEQ ID NO 106
<211> LENGTH: 26
<212> TYPE: DNA
<213> ORGANISM: Artificial Sequence
<220> FEATURE:
<223> OTHER INFORMATION: primer

<400> SEQUENCE: 106
ttaggatcct tgatggcacg accaac 26

<210> SEQ ID NO 107
<211> LENGTH: 28
<212> TYPE: DNA
<213> ORGANISM: Artificial Sequence
<220> FEATURE:
<223> OTHER INFORMATION: primer

<400> SEQUENCE: 107
ttaggatccg ttgttgatct gtgtgaat 28

<210> SEQ ID NO 108
<211> LENGTH: 26
<212> TYPE: DNA
<213> ORGANISM: Artificial Sequence
<220> FEATURE:
<223> OTHER INFORMATION: primer

<400> SEQUENCE: 108
taactcgagc aggtcaatgt ccattg 26

<210> SEQ ID NO 109
<211> LENGTH: 30
<212> TYPE: DNA
<213> ORGANISM: Artificial Sequence
<220> FEATURE:
<223> OTHER INFORMATION: primer

<400> SEQUENCE: 109
ttaggatcct gttgtgttcc tattgctggt 30

<210> SEQ ID NO 110
<211> LENGTH: 25
<212> TYPE: DNA
<213> ORGANISM: Artificial Sequence
<220> FEATURE:
<223> OTHER INFORMATION: primer

<400> SEQUENCE: 110
taactcgagt gatcagrgcc ccagc 25

<210> SEQ ID NO 111
<211> LENGTH: 26
<212> TYPE: DNA
<213> ORGANISM: Artificial Sequence
<220> FEATURE:
<223> OTHER INFORMATION: primer

<400> SEQUENCE: 111
ttaggatcct gctgcccaga agagaa 26

<210> SEQ ID NO 112
<211> LENGTH: 26
<212> TYPE: DNA
<213> ORGANISM: Artificial Sequence
<220> FEATURE:
<223> OTHER INFORMATION: primer

<400> SEQUENCE: 112
taactcgagc accaacaygg gttctt 26

<210> SEQ ID NO 113
<211> LENGTH: 25
<212> TYPE: DNA
<213> ORGANISM: Artificial Sequence
<220> FEATURE:
<223> OTHER INFORMATION: primer

<400> SEQUENCE: 113
ttaggatcct caaggacggt gtggc 25

<210> SEQ ID NO 114
<211> LENGTH: 28
<212> TYPE: DNA
<213> ORGANISM: Artificial Sequence
<220> FEATURE:
<223> OTHER INFORMATION: primer

<400> SEQUENCE: 114
taactcgagc aatgatcttc atgttggg 28

<210> SEQ ID NO 115

<211> LENGTH: 26
<212> TYPE: DNA
<213> ORGANISM: Artificial Sequence
<220> FEATURE:
<223> OTHER INFORMATION: primer

<400> SEQUENCE: 115
ttaggatcct atgggggagg actggt 26

<210> SEQ ID NO 116
<211> LENGTH: 25
<212> TYPE: DNA
<213> ORGANISM: Artificial Sequence
<220> FEATURE:
<223> OTHER INFORMATION: primer

<400> SEQUENCE: 116
taactcgagc ccagaacctt ggatc 25

<210> SEQ ID NO 117
<211> LENGTH: 25
<212> TYPE: DNA
<213> ORGANISM: Artificial Sequence
<220> FEATURE:
<223> OTHER INFORMATION: primer

<400> SEQUENCE: 117
ttaggatcca gacccccaag aaggc 25

<210> SEQ ID NO 118
<211> LENGTH: 26
<212> TYPE: DNA
<213> ORGANISM: Artificial Sequence
<220> FEATURE:
<223> OTHER INFORMATION: primer

<400> SEQUENCE: 118
taactcgagc ccctttggtc ttgtct 26

<210> SEQ ID NO 119
<211> LENGTH: 29
<212> TYPE: DNA
<213> ORGANISM: Artificial Sequence
<220> FEATURE:
<223> OTHER INFORMATION: primer

<400> SEQUENCE: 119
ttaggatcca ggaaggatgt atgcagatg 29

<210> SEQ ID NO 120
<211> LENGTH: 30
<212> TYPE: DNA
<213> ORGANISM: Artificial Sequence
<220> FEATURE:
<223> OTHER INFORMATION: primer

<400> SEQUENCE: 120
taactcgaga catttgcgca tatgattttg 30

<210> SEQ ID NO 121
<211> LENGTH: 28
<212> TYPE: DNA
<213> ORGANISM: Artificial Sequence
<220> FEATURE:
<223> OTHER INFORMATION: primer

<400> SEQUENCE: 121

-continued

```
ttaggatcca ggaaggacac acaagagt                                    28


<210> SEQ ID NO 122
<211> LENGTH: 26
<212> TYPE: DNA
<213> ORGANISM: Artificial Sequence
<220> FEATURE:
<223> OTHER INFORMATION: primer

<400> SEQUENCE: 122

taactcgaga caggctgcac agcttt                                      26


<210> SEQ ID NO 123
<211> LENGTH: 28
<212> TYPE: DNA
<213> ORGANISM: Artificial Sequence
<220> FEATURE:
<223> OTHER INFORMATION: primer

<400> SEQUENCE: 123

ttaggatcct ctctcatagg gcacagac                                    28
```